US012365897B2

(12) United States Patent
Bush et al.

(10) Patent No.: US 12,365,897 B2
(45) Date of Patent: Jul. 22, 2025

(54) RNAI AGENTS FOR INHIBITING EXPRESSION OF MUCIN 5AC (MUC5AC), COMPOSITIONS THEREOF, AND METHODS OF USE

(71) Applicant: Arrowhead Pharmaceuticals, Inc., Pasadena, CA (US)

(72) Inventors: Erik W. Bush, Verona, WI (US); Anthony Nicholas, Oregon, WI (US); Casi M. Schienebeck, Deerfield, WI (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 203 days.

(21) Appl. No.: 17/824,841

(22) Filed: May 25, 2022

(65) Prior Publication Data

US 2023/0002767 A1 Jan. 5, 2023

Related U.S. Application Data

(60) Provisional application No. 63/194,370, filed on May 28, 2021.

(51) Int. Cl.
*C12N 15/113* (2010.01)
*A61P 11/12* (2006.01)

(52) U.S. Cl.
CPC ............ *C12N 15/113* (2013.01); *A61P 11/12* (2018.01); *C12N 2310/14* (2013.01); *C12N 2310/315* (2013.01); *C12N 2310/317* (2013.01); *C12N 2310/321* (2013.01)

(58) Field of Classification Search
CPC .............. C12N 15/113; C12N 2310/14; C12N 2310/315; C12N 2310/317; C12N 2310/321; A61P 11/12
See application file for complete search history.

(56) References Cited

U.S. PATENT DOCUMENTS

| | | | | |
|---|---|---|---|---|
| 5,998,203 | A | 12/1999 | Matulic-Adamic et al. | |
| 8,090,542 | B2 * | 1/2012 | Khvorova | C12N 15/1135 435/6.1 |
| 2011/0245325 | A1 | 10/2011 | Hoshi et al. | |
| 2015/0337023 | A1 | 11/2015 | Wang | |
| 2017/0037396 | A1 * | 2/2017 | Lee | C12N 15/113 |
| 2021/0025000 | A1 | 1/2021 | Huang et al. | |

FOREIGN PATENT DOCUMENTS

| | | | | |
|---|---|---|---|---|
| WO | 2000053722 | A1 | 9/2000 | |
| WO | 2008022309 | A2 | 2/2008 | |
| WO | WO-2010067882 | A1 * | 6/2010 | C12N 15/113 |
| WO | 2011104169 | A1 | 9/2011 | |
| WO | 2012083185 | A2 | 6/2012 | |
| WO | 2013032829 | A1 | 3/2013 | |
| WO | 2013158141 | A1 | 10/2013 | |
| WO | 2016003869 | A1 | 1/2016 | |
| WO | 2017214112 | A1 | 12/2017 | |
| WO | WO-2018027106 | A2 * | 2/2018 | A61K 31/675 |
| WO | 2018085415 | A1 | 5/2018 | |
| WO | 2019089765 | A1 | 5/2019 | |
| WO | 2019161213 | A1 | 8/2019 | |

OTHER PUBLICATIONS

Rao, D. D., Vorhies, J. S., Senzer, N., & Nemunaitis, J. (2009). siRNA vs. shRNA: similarities and differences. Advanced drug delivery reviews, 61(9), 746-759. (Year: 2009).*

Dong, Y., Zhou, L., Zhao, D., Li, K., Liu, Z., Che, N., & Liu, H. (2020). MUC5AC enhances tumor heterogeneity in lung adenocarcinoma with mucin production and is associated with poor prognosis. Japanese journal of clinical oncology, 50(6), 701-711. (Year: 2020).*

Pothuraju, R., Rachagani, S., Krishn, S. R., Chaudhary, S., Nimmakayala, R. K., Siddiqui, J. A., . . . & Batra, S. K. (2020). Molecular implications of MUC5AC-CD44 axis in colorectal cancer progression and chemoresistance. Molecular cancer, 19, 1-14. (Year: 2020).*

McKelvey, M. C., Brown, R., Ryan, S., Mall, M. A., Weldon, S., & Taggart, C. C. (2021). Proteases, mucus, and mucosal immunity in chronic lung disease. International journal of molecular sciences, 22(9), 5018. (Year: 2021).*

Bonser, L. R., & Erle, D. J. (2017). Airway mucus and asthma: the role of MUC5AC and MUC5B. Journal of clinical medicine, 6(12), 112. (Year: 2017).*

Bu, X. D., Li, N., Tian, X. Q., Li, L., Wang, J. S., Yu, X. J., & Huang, P. L. (2010). Altered expression of MUC2 and MUC5AC in progression of colorectal carcinoma. World Journal of Gastroenterology: WJG, 16(32), 4089. (Year: 2010).*

Graham, M. T., & Nadeau, K. C. (2014). Lessons learned from mice and man: mimicking human allergy through mouse models. Clinical Immunology, 155(1), 1-16. (Year: 2014).*

(Continued)

*Primary Examiner* — Richard A Schnizer
*Assistant Examiner* — Christina Tran
(74) *Attorney, Agent, or Firm* — Paul VanderVelde; Meibo Chen; Mitchell Porter

(57) ABSTRACT

Described are RNAi agents, compositions that include RNAi agents, and methods for inhibition of a Mucin 5AC (MUC5AC) gene. The MUC5AC RNAi agents and RNAi agent conjugates disclosed herein inhibit the expression of an MUC5AC gene. Pharmaceutical compositions that include one or more MUC5AC RNAi agents, optionally with one or more additional therapeutics, are also described. Delivery of the described MUC5AC RNAi agents to pulmonary epithelial cells, in vivo, provides for inhibition of MUC5AC gene expression and a reduction in MUC5AC production, which can provide a therapeutic benefit to subjects, including human subjects, for the treatment of various diseases including mucoobstructive lung disease such as severe asthma and various cancers.

18 Claims, 6 Drawing Sheets

Specification includes a Sequence Listing.

(56) References Cited

OTHER PUBLICATIONS

Livraghi-Butrico, Alessandra, et al. "Contribution of mucus concentration and secreted mucins Muc5ac and Muc5b to the pathogenesis of muco-obstructive lung disease." Mucosal immunology 10.2 (2017): 395-407. (Year: 2017).*
Li, J., & Ye, Z. (2020). The potential role and regulatory mechanisms of MUC5AC in chronic obstructive pulmonary disease. Molecules, 25(19), 4437. (Year: 2020).*
Morgan, L.E., Jaramillo, A.M., Shenoy, S.K. et al. Disulfide disruption reverses mucus dysfunction in allergic airway disease. Nat Commun 12, 249 (2021). https://doi.org/10.1038/s41467-020-20499-0 (Year: 2021).*
Morrison, C. B., Markovetz, M. R., & Ehre, C. (2019). Mucus, mucins, and cystic fibrosis. Pediatric pulmonology, 54, S84-S96. (Year: 2019).*
Abraham et al.; "Characterization of a late phase pulmonary response after antigen challenge in allergic sheep"; Amm Rev Respir Dis.; 128(5):839-44; 1983.
Adler et al.; "Regulated mucin secretion from airway epithelial cells"; Frontiers in Endocrinology; vol. 4; Article 129; doi: 10.3389/fendo.2013.00129; 2013.
Altenhofer et al.; "Synthesis of a novel cyclopropyl phosphonate nucleotide as a phosphate mimic"; Chem Commun (Camb); 57(55):6808-6811; 2021.
Altman et al.; "Inducible expression quantitative trait locus analysis of the MUC5AC gene in asthma in urban populations of children"; J Allergy Clin Immunol. Dec. 2021;148(6):1505-1514. doi: 10.1016/j.jaci.2021.04.035. Epub May 18, 2021. PMID: 34019912; PMCID: PMC8599524.
Bauer, et al.; "Requirement for MUC5AC in KRAS-dependent lung carcinogenesis"; JCI Insight; 2018; 3(15): e120941; https://doi.org/10.1172/jci.insight.120941.
Bonser et al.; "Epithelial tethering of MUC5AC-rich mucus impairs mucociliary transport in asthma"; J Clin Invest. Jun. 1, 2016;126(6):2367-71. doi: 10.1172/JCI84910. Epub May 16, 2016. PMID: 27183390; Pmcid: PMC4887179.
Bonser et al.; "Airway Mucus and Asthma: The Role of MUC5AC and MUC5B"; J. Clin. Med.; 6, 112; 2017.
Caniga, et.al.; "Assessment of multiple pharmacological mechanisms in the ascaris sensitive sheep model of allergic asthma"; Journal of Inflammation; 2013; 10(Suppl 1):P15; doi:10.1186/1476-9255-10-S1-P15.
Cohn, et al.; "Escalating Mucus Inhibition to the Top of Our Priorities"; American Journal of Respiratory Cell and Molecular Biology; vol. 61, No. 3; Sep. 2019.
Czauderna, et al.; "Structural variations and stablising modifications of synthetic siRNAs in mammalian cells"; Nucleic Acids Res.; 2003, 31(11), 2705-16.
Duncan et al.; "The Mucus Barrier to Inhaled Gene Therapy"; Molecular Therapy; vol. 24; No. 12; 2043-2053; 2016.
Dunican et al.; "Mucus plugs in patients with asthma linked to eosinophilia and airflow obstruction"; J. Clinic Invest.; 2018; 128(3):997-1009; https://doi.org/10.1172/JCI95693.
Evans et al.; "The polymeric mucin Muc5ac is required for allergic airway hyperreactivity"; Nat Commun. Feb. 17, 2015;6:6281. doi: 10.1038/ncomms7281. PMID: 25687754; PMCID: PMC4333679.
Evans et al.; "SPDEFending the lung through mucin expression"; American Journal of Respiratory Cell and Molecular Biology; vol. 59; No. 3; pp. 287-288; 2018.
Ha EV, Rogers DF.; "Novel Therapies to Inhibit Mucus Synthesis and Secretion in Airway Hypersecretory Diseases"; Pharmacology. 2016;97(1-2):84-100. doi: 10.1159/000442794. Epub Dec. 17, 2015. PMID: 26674354.
Hays et al.; "Central Role of Muc5ac Expression in Mucous Metaplasia and Its Regulation by Conserved 5' Elements"; Am. J. Respir. Cell Mol. Biol.; vol. 37; pp. 273-290; 2007.
Kamola et al.; "The siRNA Non-seed Region and Its Target Sequences are Auxiliary Determinants of Off-Target Effects"; PLOS Computational Biology; 11(12), Figure 1; 2015.
Kesimer et al.; "Airway Mucin Concentration as a Marker of Chronic Bronchitis"; N Engl J Med.; Sep. 7, 2017; 377(10): 911-922; doi.10.1056/NEJMoa1701632.
Kim et al.; "β2-Adrenergic Receptors Chaperone Trapped Bitter Taste Receptor 14 to the Cell Surface as a Heterodimer and Exert Unidirectional Desensitization of Taste Receptor Function"; The Journal of Biological Chemistry; vol. 291; No. 34; pp. 17616-17628; 2016.
Koeppen et al.; "Detrimental role of the airway mucin Muc5ac during ventilator-induced lung injury"; Mucosal Immunol.; Jul. 2013; 6(4): 762-775; doi:10.1038/mi.2012.114.
Lillehoj et al.; "Cellular and Molecular Biology of Airway Mucins"; Int Rev Cell Mol Biol.; 2013; 303:139-202; doi. 10.1016/B978-0-12-407697-6.00004-0.
Okuda et al.; "Localization of Secretory Mucins MUC5AC and MUC5B in Normal/Healthy Human Airways"; Am J Respir Crit Care Med; vol. 199; Issue 6; pp. 715-727; Mar. 15, 2019.
Ortelli et al.; "Translational Analysis of Moderate to Severe Asthma GWAS Signals Into Candidate Causal Genes and Their Functional, Tissue-Dependent and Disease-Related Associations"; Front Allergy. Oct. 18, 2021;2:738741. doi: 10.3389/falgy.2021.738741. PMID: 35386986; PMCID: PMC8974692.
Radicioni et al.; "Airway mucin MUC5AC and MUC5B concentrations and the initiation and progression of chronic obstructive pulmonary disease: an analysis of the SPIROMICS cohort"; Lancet Respir Med. Nov. 2021;9 (11):1241-1254. doi: 10.1016/S2213-2600(21)00079-5. Epub May 28, 2021. PMID: 34058148; PMCID: PMC8570975.
Rose et al.; "Respiratory Tract Mucin Genes and Mucin Glycoproteins in Health and Disease"; Physiol. Rev.; 86: 245-278; 2006; doi: 10.1152/physrev.00010.2005.
Roy et al.; "Muc5b Is Required for Airway Defense"; Nature; Jan. 16, 2024; 505(7483): 412-416; doi. 10.1038/nature12807.
Seibold et al.; "A Common MUC5B Promoter Polymorphism and Pulmonary Fibrosis"; N Engl J Med.; Apr. 21, 2011; 364(16): 1503-1512; doi:10.1056/NEJMoa1013660.
Tepper et al.; "Symposium Summary: Breathe In, Breathe Out, Its Easy: What you Need to Know About Developing Inhaled Drugs"; Int. J. Toxicol.; 35(4):376-92; 2016.
Wolff et al.; "Toxicologic Testing of Inhaled Pharmaceutical Aerosols"; Crit Rev Toxicol.; 23(4):343-369; 1993.
Wu et al.; "Discovery of Regulators of Receptor Internalization with High-Throughput Flow Cytometry"; Mol. Pharmacol.; 82: 645-657; 2012.
International Search Report and Written Opinion for corresponding International Application No. PCT/US2022/030969 with a completion date of Sep. 21, 2022 and a mailing date of Oct. 13, 2022.
Portelli MA, Rakkar K, Hu S, Guo Y, Adcock IM, Sayers I. Translational Analysis of Moderate to Severe Asthma GWAS Signals Into Candidate Causal Genes and Their Functional, Tissue-Dependent and Disease-Related Associations. Front Allergy. Oct. 18, 2021;2:738741. doi: 10.3389/falgy.2021.738741. PMID: 35386986; PMCID: PMC8974692.

* cited by examiner

RNAI AGENTS FOR INHIBITING EXPRESSION OF MUCIN 5AC (MUC5AC), COMPOSITIONS THEREOF, AND METHODS OF USE

CROSS REFERENCE TO RELATED APPLICATIONS

This application claims priority from U.S. Provisional Patent Application Ser. No. 63/194,370, filed on May 28, 2021, the contents of which are incorporated herein by reference in its entirety.

SEQUENCE LISTING

This application contains a Sequence Listing which has been submitted in ASCII format and is hereby incorporated by reference in its entirety. The ASCII copy is named SEQLIST_30659Amended_2024.04.01.txt, was created on Apr. 1, 2024, and is 461 kb in size.

FIELD OF THE INVENTION

The present disclosure relates to RNA interference (RNAi) agents, e.g., double stranded RNAi agents, for inhibition of Mucin 5AC ("MUC5AC") gene expression, compositions that include MUC5AC RNAi agents, and methods of use thereof.

BACKGROUND

MUC5AC is a transcriptionally regulated secreted mucin expressed in airway epithelia of the lung and in other mucosal tissues (for example, gastrointestinal, urogenital, eye, and ear) (Lillehoj et al, Int Rev Cell Mol Biol, 2013). In airways, MUC5AC and MUC5B are the major gel-forming mucins. MUC5B is constitutively expressed and is required for mucociliary clearance (Roy et al., Nature 2014). Normal subjects have a relatively higher expression of MUC5B versus MUC5AC in the trachea and proximal airways, with this ratio further increasing in distal airways with expression of MUC5AC almost undetectable in distal and terminal bronchioles (Okuda et al., AJRCCM 2019). Typically expressed at low levels in the airway, MUC5AC expression can be robustly induced by external stress stimuli like pro-inflammatory mediators (including, for example, type 2 cytokines: IL-4, IL-9, IL-17, IL-23 and IL-13), noxious inhaled substances (for example, cigarette smoke, acrolein, toxic gases), viral infections, and allergens. The resulting mucus hypersecretion and hyperconcentration is understood to be a common pathogenic mechanism linked to airway obstruction in severe asthma and other mucoobstructive lung diseases such as cystic fibrosis (CF), chronic obstructive pulmonary disease (COPD), non-CF bronchiectasis (NCFB), and primary ciliary dyskinesia (PCD) (Boucher, NEJM 2019). In asthma, COPD, and NCFB patients, exaggerated expression and secretion of MUC5AC results in a narrowing of airway lumen, airway obstruction, and exacerbations (Dunican et al., JCI 2017; Bonser et al., JCI 2016: Kesimer et al., NEJM 2017; Ramsey et al., AJRCCM 2019). A genome-wide association study (GWAS) identified a novel MUC5AC allele linked to increased MUC5AC expression and patients with moderate-to-severe asthma (Shrine et al., Lancet Respir Med 2019). Experimental evidence from MUC5AC-deficient mice demonstrated that MUC5AC-mediated airway plugging is a major contributor to airway hyperresponsiveness to allergens independent of inflammation and bronchoconstriction (Evans et al, Nat Commun, 2015). Current standard of care treatments for severe asthma and other mucoobstructive lung diseases include bronchodilators and anti-inflammatory therapeutics (such as corticosteroids and biologics), but currently available treatments do not directly address pathogenic mucin overexpression and hypersecretion. Alternative approaches that directly treat mucus hypersecretion and obstruction are needed.

Increased expression of MUC5AC has also been observed in malignancies such as lung adenocarcinomas, pancreatic cancer, salivary gland carcinoma, breast cancer, cholangiocarcinoma, ovarian cancer, and other tumors (Krishn et al., Carcinogenesis 2018), where it has been linked to migration and invasiveness of tumor cells. Loss-of-function mutations in MUC5AC and other mucin genes are significantly underrepresented in tumor cells, suggesting that mucin overexpression may shield tumors from recognition by immune cells (Gorlov et al., Cancer Genetics 2019). Tumor MUC5AC overexpression is associated with progression and poor survival in lung adenocarcinoma patients (Bauer et al., JCI Insight 2018). MUC5AC overexpression has also been linked to number of other conditions including: allergic rhinitis, chronic rhinosinusitis, otitis media, Barret's esophagus, pancreatitis, and inflammatory bowel disease (Krishn et al., Carcinogenesis 2018).

SUMMARY

There exists a need for novel RNA interference (RNAi) agents (termed RNAi agents, RNAi triggers, or triggers), e.g., double stranded RNAi agents, that are able to selectively and efficiently inhibit the expression of a MUC5AC gene, including for use as a therapeutic or medicament. Further, there exists a need for compositions of novel MUC5AC-specific RNAi agents for the treatment of diseases or disorders associated with mucus hypersecretion and obstruction (referred to herein as "mucoobstructive" lung diseases and disorders) such as for example cystic fibrosis (CF), chronic obstructive pulmonary disease (COPD), non-CF bronchiectasis (NCFB), primary ciliary dyskinesia (PCD), and asthma, and/or diseases or disorders that can be mediated at least in part by a reduction in MUC5AC gene expression and/or MUC5AC protein levels.

The nucleotide sequences and chemical modifications of the MUC5AC RNAi agents disclosed herein, as well as their combination with certain specific targeting ligands suitable for selectively and efficiently delivering the MUC5AC RNAi agents in vivo, differ from what is known in the art. The MUC5AC RNAi agents disclosed herein provide for highly potent and efficient inhibition of the expression of a MUC5AC gene and have sequences suitable for use as a therapeutic for the treatment of diseases and disorders.

In general, the present disclosure features MUC5AC gene-specific RNAi agents, compositions that include MUC5AC RNAi agents, and methods for inhibiting expression of a MUC5AC gene in vitro and/or in vivo using the MUC5AC RNAi agents and compositions that include MUC5AC RNAi agents described herein. The MUC5AC RNAi agents described herein are able to selectively and efficiently decrease expression of a MUC5AC gene, and thereby reduce the expression of the MUC5AC protein, which can lead to a therapeutic benefit such as, for example, a reduction in mucoobstruction in the lung.

The described MUC5AC RNAi agents can be used in methods for therapeutic treatment (including preventative or prophylactic treatment) of symptoms and diseases including, but not limited to, mucoobstructive lung diseases (such as asthma, CF, COPD, NCFB, PCD), allergic bronchopulmonary aspergillosis, interstitial lung diseases, cancer (such as lung adenocarcinomas, pancreatic cancer, salivary gland carcinoma, breast cancer, cholangiocarcinoma, ovarian cancer, and other tumors), respiratory infections (such as respiratory syncytial virus, influenza, rhinovirus), otitis media, inflammatory bowel disease, gallstone disease, allergic rhinitis, chronic rhinosinusitis and nasal polyposis.

In one aspect, the disclosure features RNAi agents for inhibiting expression of a MUC5AC gene, wherein the RNAi agent includes a sense strand (also referred to as a passenger strand) and an antisense strand (also referred to as a guide strand). The sense strand and the antisense strand can be partially, substantially, or fully complementary to each other. The length of the RNAi agent sense strands described herein each can be 15 to 49 nucleotides in length. The length of the RNAi agent antisense strands described herein each can be 18 to 49 nucleotides in length. In some embodiments, the sense and antisense strands are independently 18 to 26 nucleotides in length. The sense and antisense strands can be either the same length or different lengths. In some embodiments, the sense and antisense strands are independently 21 to 26 nucleotides in length. In some embodiments, the sense and antisense strands are independently 21 to 24 nucleotides in length. In some embodiments, both the sense strand and the antisense strand are 21 nucleotides in length. In some embodiments, the antisense strands are independently 18, 19, 20, 21, 22, 23, 24, 25, 26, 27, 28, 29, or 30 nucleotides in length. In some embodiments, the sense strands are independently 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides in length. The RNAi agents described herein, upon delivery to a cell expressing MUC5AC, inhibit the expression of one or more MUC5AC gene variants in vivo and/or in vitro.

The MUC5AC RNAi agents disclosed herein target a human MUC5AC gene (see, e.g., SEQ ID NO:1). In some embodiments, the MUC5AC RNAi agents disclosed herein target a portion of a MUC5AC gene having the sequence of any of the sequences disclosed in Table 1.

In another aspect, the disclosure features compositions, including pharmaceutical compositions, that include one or more of the disclosed MUC5AC RNAi agents that are able to selectively and efficiently decrease expression of a MUC5AC gene. The compositions that include one or more MUC5AC RNAi agents described herein can be administered to a subject, such as a human or animal subject, for the treatment (including prophylactic treatment or inhibition) of symptoms and diseases associated with MUC5AC gene expression and/or MUC5AC protein levels.

Examples of MUC5AC RNAi agent sense strands and antisense strands that can be used in a MUC5AC RNAi agent are provided in Tables 3, 4, 5, 6, and 7. Examples of MUC5AC RNAi agent duplexes are provided in Tables 8A, 8B, 8C, 9, 10A, 10B, and 11. Examples of 19-nucleotide core stretch sequences that may consist of or may be included in the sense strands and antisense strands of certain MUC5AC RNAi agents disclosed herein, are provided in Table 2.

In another aspect, the disclosure features methods for delivering MUC5AC RNAi agents to epithelial cells in a subject, such as a mammal, in vivo. Also described herein are compositions for use in such methods. In some embodiments, disclosed herein are methods for delivering MUC5AC RNAi agents to pulmonary cells (epithelial cells, macrophages, smooth muscle, endothelial cells) to a subject in vivo. In some embodiments, the subject is a human subject.

The methods disclosed herein include the administration of one or more MUC5AC RNAi agents to a subject, e.g., a human or animal subject, by any suitable means known in the art. The pharmaceutical compositions disclosed herein that include one or more MUC5AC RNAi agents can be administered in a number of ways depending upon whether local or systemic treatment is desired. Administration can be, but is not limited to, for example, intravenous, intraarterial, subcutaneous, intraperitoneal, subdermal (e.g., via an implanted device), and intraparenchymal administration. In some embodiments, the pharmaceutical compositions described herein are administered by inhalation (such as dry powder inhalation or aerosol inhalation), intranasal administration, intratracheal administration, or oropharyngeal aspiration administration.

In some embodiments, it is desired that the MUC5AC RNAi agents described herein inhibit the expression of an MUC5AC gene in the pulmonary epithelium, for which the administration is by inhalation (e.g., by an inhaler device, such as a metered-dose inhaler, or a nebulizer such as a jet or vibrating mesh nebulizer, or a soft mist inhaler).

The one or more MUC5AC RNAi agents can be delivered to target cells or tissues using any oligonucleotide delivery technology known in the art. In some embodiments, a MUC5AC RNAi agent is delivered to cells or tissues by covalently linking the RNAi agent to a targeting group. In some embodiments, the targeting group can include a cell receptor ligand, such as an integrin targeting ligand. Integrins are a family of transmembrane receptors that facilitate cell-extracellular matrix (ECM) adhesion. In particular, integrin alpha-v-beta-6 ($\alpha v\beta 6$) is an epithelial-specific integrin that is known to be a receptor for ECM proteins and the TGF-beta latency-associated peptide (LAP), and is expressed in various cells and tissues. Integrin $\alpha v\beta 6$ is known to be highly upregulated in injured pulmonary epithelium. In some embodiments, the MUC5AC RNAi agents described herein are linked to an integrin targeting ligand that has affinity for integrin $\alpha v\beta 6$. As referred to herein, an "$\alpha v\beta 6$ integrin targeting ligand" is a compound that has affinity for integrin $\alpha v\beta 6$, which can be utilized as a ligand to facilitate the targeting and delivery of an RNAi agent to which it is attached to the desired cells and/or tissues (i.e., to cells expressing integrin $\alpha v\beta 6$). In some embodiments, multiple $\alpha v\beta 6$ integrin targeting ligands or clusters of $\alpha v\beta 6$ integrin targeting ligands are linked to a MUC5AC RNAi agent. In some embodiments, the MUC5AC RNAi agent-$\alpha v\beta 6$ integrin targeting ligand conjugates are selectively internalized by lung epithelial cells, either through receptor-mediated endocytosis or by other means.

Examples of targeting groups useful for delivering MUC5AC RNAi agents that include $\alpha v\beta 6$ integrin targeting ligands are disclosed, for example, in International Patent Application Publication No. WO 2018/085415 and International Patent Application Publication No. WO 2019/089765, the contents of each of which are incorporated by reference herein in their entirety.

A targeting group can be linked to the 3' or 5' end of a sense strand or an antisense strand of a MUC5AC RNAi agent. In some embodiments, a targeting group is linked to the 3' or 5' end of the sense strand. In some embodiments, a targeting group is linked to the 5' end of the sense strand. In some embodiments, a targeting group is linked internally to a nucleotide on the sense strand and/or the antisense strand of the RNAi agent. In some embodiments, a targeting group is linked to the RNAi agent via a linker.

In another aspect, the disclosure features compositions that include one or more MUC5AC RNAi agents that have the duplex structures disclosed in Tables 8A, 8B, 8C, 9, 10A, 10B, and 11.

The use of MUC5AC RNAi agents provides methods for therapeutic (including prophylactic) treatment of diseases or disorders for which a reduction in MUC5AC gene expression and/or a reduction in MUC5AC protein levels can provide a therapeutic benefit. The MUC5AC RNAi agents disclosed herein can be used to treat various diseases, including mucoobstructive lung diseases (such as asthma, CF, COPD, NCFB, PCD), allergic bronchopulmonary aspergillosis, interstitial lung diseases, cancer (such as lung adenocarcinomas, pancreatic cancer, salivary gland carcinoma, breast cancer, cholangiocarcinoma, ovarian cancer, and other tumors), respiratory infections (such as respiratory syncytial virus, influenza, rhinovirus), otitis media, inflammatory bowel disease, gallstone disease, allergic rhinitis, chronic rhinosinusitis and nasal polyposis. In some embodiments, the MUC5AC RNAi agents disclosed herein can be used to treat a mucoobstructive lung disease, such as severe asthma or COPD. MUC5AC RNAi agents can further be used to treat, for example, various cancers. Such methods of treatment include administration of a MUC5AC RNAi agent to a human being or animal having elevated or enhanced MUC5AC gene expression and/or MUC5AC protein levels above what is desired.

One aspect described herein is an RNAi agent for inhibiting expression of a MUC5AC gene, comprising:

(i) an antisense strand that is between 18 and 49 nucleotides in length that includes a nucleotide sequence at least partially complementary to a corresponding stretch of contiguous nucleotides of the MUC5AC gene transcript (SEQ ID NO: 1); and (ii) a sense strand comprising a nucleotide sequence that is at least partially complementary to the antisense strand;

wherein the RNAi agent sense strand is optionally further linked to a targeting ligand, and wherein RNAi agent is capable of inhibiting expression of a MUC5AC gene.

Another aspect described herein is an RNAi agent for inhibiting expression of a MUC5AC gene, comprising:

(i) an antisense strand comprising at least 17 contiguous nucleotides differing by 0 or 1 nucleotides from any one of the sequences provided in Table 3; and (ii) a sense strand comprising a nucleotide sequence that is at least partially complementary to the antisense strand;

wherein the RNAi agent sense strand is optionally further linked to a targeting ligand, and wherein RNAi agent is capable of inhibiting expression of a MUC5AC gene.

In some embodiments, a MUC5AC RNAi agent disclosed herein includes an antisense strand that consists of, consists essentially of, or comprises a sequence differing by 0 or 1 nucleobases from the nucleotide sequence (5'→3') UUGUAGUAGUCGCAGAACAGC (SEQ ID NO: 1525). In some embodiments, a MUC5AC RNAi agent disclosed herein includes an antisense strand that consists of, consists essentially of, or comprises a nucleotide sequence differing by no more than 1 nucleotide from the nucleotide sequence (5'→3') UUGUAGUAGUCGCAGAACAGC (SEQ ID NO: 1525), wherein all or substantially all of the nucleotides are modified nucleotides. In some embodiments, a MUC5AC RNAi agent disclosed herein includes an antisense strand that consists of, consists essentially of, or comprises a nucleobase sequence differing by 0 or 1 nucleobases from the nucleotide sequence (5'→3') UUGUAGUAGUCGCAGAACAGC (SEQ ID NO: 1525), wherein SEQ ID NO: 1525 is located at positions 1-21 (5'→3') of the antisense strand.

In some embodiments, a MUC5AC RNAi agent disclosed herein includes an antisense strand that consists of, consists essentially of, or comprises a modified nucleotide sequence differing by no more than 1 nucleotide from the nucleotide sequence (5'→3') cPrpusUfsgsUfaGfuAfgUfcGfcAfgAfaCfaGfsc (SEQ ID NO: 1127), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; cPrpu represents a 5'-cyclopropyl phosphonate-2'-O-methyluridine; and s represents a phosphorothioate linkage, and wherein the sense strand is at least substantially complementary to the antisense strand. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 3A through 3J showing all internucleoside linkages). In some embodiments, a MUC5AC RNAi agent disclosed herein includes an antisense strand that consists of, consists essentially of, or comprises the nucleotide sequence (5'→3') cPrpusUfsgsUfaGfuAfgUfcGfcAfgAfaCfaGfsc (SEQ ID NO: 1127), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; cPrpu represents a 5'-cyclopropyl phosphonate-2'-O-methyluridine; and s represents a phosphorothioate linkage, and wherein the sense strand is at least substantially complementary to the antisense strand.

In some embodiments, a MUC5AC RNAi agent disclosed herein includes an antisense strand that consists of, consists essentially of, or comprises a modified nucleotide sequence differing by no more than 1 nucleotide from the nucleotide sequence (5'→3') usUfsgsUfaGfuAfgUfcGfcAfgAfaCfaGfsc (SEQ ID NO: 1065), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; and s represents a phosphorothioate linkage, and wherein the sense strand is at least substantially complementary to the antisense strand. In some embodiments, a MUC5AC RNAi agent disclosed herein includes an antisense strand that consists of, consists essentially of, or comprises the nucleotide sequence (5'→3') usUfsgsUfaGfuAfgUfcGfcAfgAfaCfaGfsc (SEQ ID NO: 1065), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; and s represents a phosphorothioate linkage, and wherein the sense strand is at least substantially complementary to the antisense strand.

In some embodiments, a MUC5AC RNAi agent disclosed herein includes an antisense strand that consists of, consists essentially of, or comprises a nucleobase sequence differing by 0 or 1 nucleobases from the nucleotide sequence (5'→3') UUCUUGUUCAGGCAAAUCAGC (SEQ ID NO: 1535). In some embodiments, a MUC5AC RNAi agent disclosed herein includes an antisense strand that consists of, consists essentially of, or comprises a nucleotide sequence differing by no more than 1 nucleotide from the nucleotide sequence (5'→3') UUCUUGUUCAGGCAAAUCAGC (SEQ ID NO:

1535), wherein all or substantially all of the nucleotides are modified nucleotides. In some embodiments, a MUC5AC RNAi agent disclosed herein includes an antisense strand that consists of, consists essentially of, or comprises a nucleobase sequence differing by 0 or 1 nucleobases from the nucleotide sequence (5'→3') UUCUU-GUUCAGGCAAAUCAGC (SEQ ID NO: 1535), wherein SEQ ID NO: 1535 is located at positions 1-21 (5'→3') of the antisense strand.

In some embodiments, a MUC5AC RNAi agent disclosed herein includes an antisense strand that consists of, consists essentially of, or comprises a modified nucleotide sequence differing by no more than 1 nucleotide from the nucleotide sequence (5'→3') usUfscsuuguucagGfcAfaAfucagsc (SEQ ID NO: 1166), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; and s represents a phosphorothioate linkage, and wherein the sense strand is at least substantially complementary to the antisense strand. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 3A through 3J showing all internucleoside linkages). In some embodiments, a MUC5AC RNAi agent disclosed herein includes an antisense strand that consists of, consists essentially of, or comprises the nucleotide sequence (5'→3') usUfscsuu-guucagGfcAfaAfucagsc (SEQ ID NO: 1166), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; and s represents a phosphorothioate linkage, and wherein the sense strand is at least substantially complementary to the antisense strand.

In some embodiments, a MUC5AC RNAi agent disclosed herein includes an antisense strand that consists of, consists essentially of, or comprises a modified nucleotide sequence differing by no more than 1 nucleotide from the nucleotide sequence (5'→3') cPrpuUfcuuguucagGfcAfaAfucagsc (SEQ ID NO: 1191), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; cPrpu represents a 5'-cyclopropyl phosphonate-2'-O-methyluridine; and s represents a phosphorothioate linkage, and wherein the sense strand is at least substantially complementary to the antisense strand. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 3A through 3J showing all internucleoside linkages). In some embodiments, a MUC5AC RNAi agent disclosed herein includes an antisense strand that consists of, consists essentially of, or comprises the nucleotide sequence (5'→3') cPrpuUfcuuguucagGfcAfaAfucagsc (SEQ ID NO: 1191), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; cPrpu represents a 5'-cyclopropyl phosphonate-2'-O-methyluridine; and s represents a phosphorothioate linkage, and wherein the sense strand is at least substantially complementary to the antisense strand.

In some embodiments, a MUC5AC RNAi agent disclosed herein includes an antisense strand that consists of, consists essentially of, or comprises a nucleotide sequence that differs by 0 or 1 nucleotides from one of the following nucleotide sequences (5'→3'):

```
                                    (SEQ ID NO: 1525)
UUGUAGUAGUCGCAGAACAGC;
or
                                    (SEQ ID NO: 1535)
UUCUUGUUCAGGCAAAUCAGC;
```

wherein the MUC5AC RNAi agent further includes a sense strand that is at least partially complementary to the antisense strand; and wherein all or substantially all of the nucleotides on both the antisense strand and the sense strand are modified nucleotides.

In some embodiments, a MUC5AC RNAi agent disclosed herein includes an antisense strand that consists of, consists essentially of, or comprises a nucleotide sequence that differs by 0 or 1 nucleotides from one of the following nucleotide sequences (5'→3'):

```
                                    (SEQ ID NO: 1525)
UUGUAGUAGUCGCAGAACAGC;
or
                                    (SEQ ID NO: 1535)
UUCUUGUUCAGGCAAAUCAGC;
```

wherein the MUC5AC RNAi agent further includes a sense strand that is at least partially complementary to the antisense strand; wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes a compound having affinity for an integrin receptor.

In some embodiments, a MUC5AC RNAi agent disclosed herein includes an antisense strand that consists of, consists essentially of, or comprises a nucleotide sequence that differs by 0 or 1 nucleotides from one of the following nucleotide sequences (5'→3'):

```
                                    (SEQ ID NO: 1525)
UUGUAGUAGUCGCAGAACAGC;
or
                                    (SEQ ID NO: 1535)
UUCUUGUUCAGGCAAAUCAGC;
```

wherein the MUC5AC RNAi agent further includes a sense strand that is at least partially complementary to the antisense strand; wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes a compound having affinity for an integrin receptor; and wherein the respective antisense strand sequence is located at positions 1-21 of the antisense strand.

In some embodiments, a MUC5AC RNAi agent disclosed herein includes an antisense strand and a sense strand, wherein the antisense strand and the sense strand consist of, consist essentially of, or comprise nucleotide sequences that differ by 0 or 1 nucleotides from one of the following nucleotide sequence (5'→3') pairs:

```
                                  (SEQ ID NO: 1525)
UUGUAGUAGUCGCAGAACAGC
and

                                  (SEQ ID NO: 1617)
GCUGUUCUGCGACUACUACAA;
or

                                  (SEQ ID NO: 1535)
UUCUUGUUCAGGCAAAUCAGC
and

                                  (SEQ ID NO: 1632)
GCUGAUUUGCCUGAACAAGAA;
```

or wherein all or substantially all of the nucleotides on both the antisense strand and the sense strand are modified nucleotides.

In some embodiments, a MUC5AC RNAi agent disclosed herein includes an antisense strand and a sense strand, wherein the antisense strand and the sense strand consist of, consist essentially of, or comprise nucleotide sequences that differ by 0 or 1 nucleotides from one of the following nucleotide sequences (5'→3') pairs:

```
                                  (SEQ ID NO: 1525)
UUGUAGUAGUCGCAGAACAGC
and

                                  (SEQ ID NO: 1617)
GCUGUUCUGCGACUACUACAA;
or

                                  (SEQ ID NO: 1535)
UUCUUGUUCAGGCAAAUCAGC
and

                                  (SEQ ID NO: 1632)
GCUGAUUUGCCUGAACAAGAA;
```

or wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes a compound with affinity for an integrin receptor.

In some embodiments, a MUC5AC RNAi agent disclosed herein includes an antisense strand that consists of, consists essentially of, or comprises a modified nucleotide sequence that differs by 0 or 1 nucleotides from one of the following nucleotide sequences (5'→3'):

```
                                  (SEQ ID NO: 1127)
cPrpusUfsgsUfaGfuAfgUfcGfcAfgAfaCfaGfsc;

                                  (SEQ ID NO: 1065)
usUfsgsUfaGfuAfgUfcGfcAfgAfaCfaGfsc;

                                  (SEQ ID NO: 1166)
usUfscsuuguucagGfcAfaAfucagsc;

                                  (SEQ ID NO: 1191)
cPrpuUfcuuguucagGfcAfaAfucagsc;
```

wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; cPrpu represents a 5'-cyclopropyl phosphonate-2'-O-methyluridine; s represents a phosphorothioate linkage; and wherein the MUC5AC RNAi agent further includes the sense strand that is at least partially complementary to the antisense strand; and wherein all or substantially all of the nucleotides of the sense strand are modified nucleotides.

In some embodiments, a MUC5AC RNAi agent disclosed herein includes an antisense strand that consists of, consists essentially of, or comprises a modified nucleotide sequence that differs by 0 or 1 nucleotides from one of the following nucleotide sequences (5'→3'):

```
                                  (SEQ ID NO: 1127)
cPrpusUfsgsUfaGfuAfgUfcGfcAfgAfaCfaGfsc;

                                  (SEQ ID NO: 1065)
usUfsgsUfaGfuAfgUfcGfcAfgAfaCfaGfsc;

                                  (SEQ ID NO: 1166)
usUfscsuuguucagGfcAfaAfucagsc;

                                  (SEQ ID NO: 1191)
cPrpuUfcuuguucagGfcAfaAfucagsc;
```

wherein the MUC5AC RNAi agent further includes the sense strand that is at least partially complementary to the antisense strand; wherein all or substantially all of the nucleotides of the sense strand are modified nucleotides; wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes a compound with affinity for an integrin receptor.

In some embodiments, a MUC5AC RNAi agent disclosed herein includes an antisense strand and a sense strand that consists of, consists essentially of, or comprises one of the following nucleotide sequence pairs (5'→3'):

```
                                  (SEQ ID NO: 1127)
cPrpusUfsgsUfaGfuAfgUfcGfcAfgAfaCfaGfsc
and

                                  (SEQ ID NO: 1265)
gscuguucuGfCfGfacuacuacaa;

                                  (SEQ ID NO: 1065)
usUfsgsUfaGfuAfgUfcGfcAfgAfaCfaGfsc
and

                                  (SEQ ID NO: 1265)
gscuguucuGfCfGfacuacuacaa;

                                  (SEQ ID NO: 1166)
usUfscsuuguucagGfcAfaAfucagsc
and

                                  (SEQ ID NO: 1315)
gscugauUfuGfcCfugaacaagaa;
and

                                  (SEQ ID NO: 1191)
cPrpuUfcuuguucagGfcAfaAfucagsc
and

                                  (SEQ ID NO: 1315)
gscugauUfuGfcCfugaacaagaa;
```

and wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; cPrpu represents a 5'-cyclopropyl phosphonate-2'-O-methyluridine; and s represents a phosphorothioate linkage; and wherein the sense strand also includes a targeting ligand having affinity for an integrin receptor, wherein the targeting ligand is optionally linked at the 5'-end of the sense strand.

In some embodiments, a MUC5AC RNAi agent disclosed herein includes an antisense strand and a sense strand that consists of, consists essentially of, or comprises modified nucleotide sequences that differs by 0 or 1 nucleotides from one of the following sequence pairs (5'→3'):

```
                                        (SEQ ID NO: 1127)
cPrpusUfsgsUfaGfuAfgUfcGfcAfgAfaCfaGfsc
and
                                        (SEQ ID NO: 1491)
Tri-SM6.1-avb6-(TA14)gscuguucuGfCfGfacuacua

caas(invAb);
                                        (SEQ ID NO: 1065)
usUfsgsUfaGfuAfgUfcGfcAfgAfaCfaGfsc
and
                                        (SEQ ID NO: 1491)
Tri-SM6.1-avb6-(TA14)gscuguucuGfCfGfacuacua

caas(invAb);
                                        (SEQ ID NO: 1166)
usUfscsuuguucagGfcAfaAfucagsc
and
                                        (SEQ ID NO: 1513)
Tri-SM6.1-avb6-(TA14)gscugauUfuGfcCfugaacaa

gaas(invAb);
                                        (SEQ ID NO: 1191)
cPrpuUfcuuguucagGfcAfaAfucagsc
and
                                        (SEQ ID NO: 1513)
Tri-SM6.1-avb6-(TA14)gscugauUfuGfcCfugaacaa

gaas(invAb);
```

wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; cPrpu represents a 5'-cyclopropyl phosphonate-2'-O-methyluridine; Tri-SM6.1-αvβ6-(TA14) represents the tridentate αvβ6 epithelial cell targeting ligand with the chemical structure as shown in FIG. 1; (invAb) represents an inverted abasic deoxyribonucleotide (see also Table 11), and s represents a phosphorothioate linkage.

In some embodiments, a MUC5AC RNAi agent disclosed herein includes an antisense strand that includes a nucleobase sequence that differs by 0 or 1 nucleobases from the nucleotide sequences selected from the group consisting of (5'→3'):

```
                      (SEQ ID NO: 79)
UUGUAGUAGUCGCAGAACA;
and
                      (SEQ ID NO: 83)
UUCUUGUUCAGGCAAAUCA.
```

In some embodiments, a MUC5AC RNAi agent disclosed herein includes an antisense strand that includes a nucleobase sequence that differs by 0 or 1 nucleobases from the nucleotide sequences selected from the group consisting of (5'→3'):

```
                      (SEQ ID NO: 79)
UUGUAGUAGUCGCAGAACA;
and
                      (SEQ ID NO: 83)
UUCUUGUUCAGGCAAAUCA;
```

wherein all or substantially all of the nucleotides are modified nucleotides.

In some embodiments, a MUC5AC RNAi agent disclosed herein includes an antisense strand that includes a nucleobase sequence that differs by 0 or 1 nucleobases from the nucleotide sequences selected from the group consisting of (5'→3'):

```
                      (SEQ ID NO: 79)
UUGUAGUAGUCGCAGAACA;
and
                      (SEQ ID NO: 83)
UUCUUGUUCAGGCAAAUCA;
```

wherein all or substantially all of the nucleotides are modified nucleotides, and wherein SEQ ID NO:79 and SEQ ID NO: 83, respectively, is located at nucleotide positions 1-19 (5'→3') of the antisense strand.

In some embodiments, a MUC5AC RNAi agent disclosed herein includes an antisense strand and a sense strand that each include a nucleobase sequences that differs by 0 or 1 nucleobases from the nucleotide sequence pairs selected from the group consisting of (5'→3'):

```
                      (SEQ ID NO: 79)
UUGUAGUAGUCGCAGAACA;
and
                     (SEQ ID NO: 568)
UGUUCUGCGACUACUACAA;
or
                      (SEQ ID NO: 83)
UUCUUGUUCAGGCAAAUCA
and
                     (SEQ ID NO: 572)
UGAUUUGCCUGAACAAGAA.
```

In some embodiments, a MUC5AC RNAi agent disclosed herein includes an antisense strand and a sense strand that each include a nucleobase sequences that differs by 0 or 1 nucleobases from the nucleotide sequence pairs selected from the group consisting of (5'→3'):

```
                      (SEQ ID NO: 79)
UUGUAGUAGUCGCAGAACA;
and
                     (SEQ ID NO: 568)
UGUUCUGCGACUACUACAA;
or
```

-continued (SEQ ID NO: 83)
UUCUUGUUCAGGCAAAUCA
and (SEQ ID NO: 572)
UGAUUUGCCUGAACAAGAA;

and wherein all or substantially all of the nucleotides are modified nucleotides.

Definitions

As used herein, the terms "oligonucleotide" and "polynucleotide" mean a polymer of linked nucleosides each of which can be independently modified or unmodified.

As used herein, an "RNAi agent" (also referred to as an "RNAi trigger") means a composition that contains an RNA or RNA-like (e.g., chemically modified RNA) oligonucleotide molecule that is capable of degrading or inhibiting (e.g., degrades or inhibits under appropriate conditions) translation of targeted messenger RNA (mRNA) transcripts in a sequence specific manner. As used herein, RNAi agents may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action. RNAi agents disclosed herein are comprised of a sense strand and an antisense strand, and include, but are not limited to: small (or short) interfering RNAs (siRNAs), double stranded RNAs (dsRNA), micro RNAs (miRNAs), short hairpin RNAs (shRNA), and dicer substrates. The antisense strand of the RNAi agents described herein is at least partially complementary to the mRNA being targeted (i.e., MUC5AC mRNA). RNAi agents can include one or more modified nucleotides and/or one or more non-phosphodiester linkages.

As used herein, the terms "silence," "reduce," "inhibit," "down-regulate," or "knockdown" when referring to expression of a given gene, mean that the expression of the gene, as measured by the level of RNA transcribed from the gene or the level of polypeptide, protein, or protein subunit translated from the mRNA in a cell, group of cells, tissue, organ, or subject in which the gene is transcribed, is reduced when the cell, group of cells, tissue, organ, or subject is treated with the RNAi agents described herein as compared to a second cell, group of cells, tissue, organ, or subject that has not or have not been so treated.

As used herein, the terms "sequence" and "nucleotide sequence" mean a succession or order of nucleobases or nucleotides, described with a succession of letters using standard nomenclature. Unless otherwise indicated, nucleotide sequences are written left to right in 5' to 3' orientation.

As used herein, a "base," "nucleotide base," or "nucleobase," is a heterocyclic pyrimidine or purine compound that is a component of a nucleotide, and includes the primary purine bases adenine and guanine, and the primary pyrimidine bases cytosine, thymine, and uracil. A nucleobase may further be modified to include, without limitation, universal bases, hydrophobic bases, promiscuous bases, size-expanded bases, and fluorinated bases. (See, e.g., Modified Nucleosides in Biochemistry, Biotechnology and Medicine, Herdewijn, P. ed. Wiley-VCH, 2008). The synthesis of such modified nucleobases (including phosphoramidite compounds that include modified nucleobases) is known in the art.

As used herein, the term "nucleotide" has the same meaning as commonly understood in the art. Thus, the term "nucleotide" as used herein, refers to a glycoside comprising a sugar moiety, a base moiety and a covalently linked group (linkage group), such as a phosphate or phosphorothioate internucleoside linkage group, and covers both naturally occurring nucleotides, such as DNA or RNA, and non-naturally occurring nucleotides comprising modified sugar and/or base moieties, which are also referred to as nucleotide analogs or modified nucleotides herein. A single nucleotide may be referred to here as a monomer or unit.

As used herein, and unless otherwise indicated, the term "complementary," when used to describe a first nucleobase or nucleotide sequence (e.g., RNAi agent sense strand or targeted mRNA) in relation to a second nucleobase or nucleotide sequence (e.g., RNAi agent antisense strand or a single-stranded antisense oligonucleotide), means the ability of an oligonucleotide or polynucleotide including the first nucleotide sequence to hybridize (form base pair hydrogen bonds under mammalian physiological conditions (or otherwise suitable in vivo or in vitro conditions)) and form a duplex or double helical structure under certain standard conditions with an oligonucleotide that includes the second nucleotide sequence. The person of ordinary skill in the art would be able to select the set of conditions most appropriate for a hybridization test. Complementary sequences include Watson-Crick base pairs or non-Watson-Crick base pairs and include natural or modified nucleotides or nucleotide mimics, at least to the extent that the above hybridization requirements are fulfilled. Sequence identity or complementarity is independent of modification. For example, a and Af, as defined herein, are complementary to U (or T) and identical to A for the purposes of determining identity or complementarity.

As used herein, "perfectly complementary" or "fully complementary" means that in a hybridized pair of nucleobase or nucleotide sequence molecules, all (100%) of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, "partially complementary" means that in a hybridized pair of nucleobase or nucleotide sequence molecules, at least 70%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, "substantially complementary" means that in a hybridized pair of nucleobase or nucleotide sequence molecules, at least 85%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, the terms "complementary," "fully complementary," "partially complementary," and "substantially complementary" are used with respect to the nucleobase or nucleotide matching between the sense strand and the antisense strand of an RNAi agent, or between the antisense strand of an RNAi agent and a sequence of an MUC5AC mRNA.

As used herein, the term "substantially identical" or "substantial identity," as applied to a nucleic acid sequence means the nucleotide sequence (or a portion of a nucleotide sequence) has at least about 85% sequence identity or more, e.g., at least 90%, at least 95%, or at least 99% identity, compared to a reference sequence. Percentage of sequence identity is determined by comparing two optimally aligned sequences over a comparison window. The percentage is calculated by determining the number of positions at which the same type of nucleic acid base occurs in both sequences to yield the number of matched positions, dividing the number of matched positions by the total number of positions in the window of comparison and multiplying the result by 100 to yield the percentage of sequence identity. The inventions disclosed herein encompass nucleotide sequences substantially identical to those disclosed herein.

As used herein, the terms "treat," "treatment," and the like, mean the methods or steps taken to provide relief from or alleviation of the number, severity, and/or frequency of one or more symptoms of a disease in a subject. As used herein, "treat" and "treatment" may include the prevention, management, prophylactic treatment, and/or inhibition or reduction of the number, severity, and/or frequency of one or more symptoms of a disease in a subject.

As used herein, the phrase "introducing into a cell," when referring to an RNAi agent, means functionally delivering the RNAi agent into a cell. The phrase "functional delivery," means delivering the RNAi agent to the cell in a manner that enables the RNAi agent to have the expected biological activity, e.g., sequence-specific inhibition of gene expression.

Unless stated otherwise, use of the symbol  as used herein means that any group or groups may be linked thereto that is in accordance with the scope of the inventions described herein.

As used herein, the term "isomers" refers to compounds that have identical molecular formulae, but that differ in the nature or the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images are termed "enantiomers," or sometimes optical isomers. A carbon atom bonded to four non-identical substituents is termed a "chiral center."

As used herein, unless specifically identified in a structure as having a particular conformation, for each structure in which asymmetric centers are present and thus give rise to enantiomers, diastereomers, or other stereoisomeric configurations, each structure disclosed herein is intended to represent all such possible isomers, including their optically pure and racemic forms. For example, the structures disclosed herein are intended to cover mixtures of diastereomers as well as single stereoisomers.

As used in a claim herein, the phrase "consisting of" excludes any element, step, or ingredient not specified in the claim. When used in a claim herein, the phrase "consisting essentially of" limits the scope of a claim to the specified materials or steps and those that do not materially affect the basic and novel characteristic(s) of the claimed invention.

The person of ordinary skill in the art would readily understand and appreciate that the compounds and compositions disclosed herein may have certain atoms (e.g., N, O, or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the environment (such as pH), as would be readily understood by the person of ordinary skill in the art. Correspondingly, compounds described herein with labile protons or basic atoms should also be understood to represent salt forms of the corresponding compound. Compounds described herein may be in a free acid, free base, or salt form. Pharmaceutically acceptable salts of the compounds described herein should be understood to be within the scope of the invention.

As used herein, the term "linked" or "conjugated" when referring to the connection between two compounds or molecules means that two compounds or molecules are joined by a covalent bond. Unless stated, the terms "linked" and "conjugated" as used herein may refer to the connection between a first compound and a second compound either with or without any intervening atoms or groups of atoms.

As used herein, the term "including" is used to herein mean, and is used interchangeably with, the phrase "including but not limited to." The term "or" is used herein to mean, and is used interchangeably with, the term "and/or," unless the context clearly indicates otherwise.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Where a value is explicitly recited, it is to be understood that values which are about the same quantity or amount as the recited value are also within the scope of the disclosure. Where a combination is disclosed, each sub-combination of the elements of that combination is also specifically disclosed and is within the scope of the disclosure. Conversely, where different elements or groups of elements are individually disclosed, combinations thereof are also disclosed. Where any element of a disclosure is disclosed as having a plurality of alternatives, examples of that disclosure in which each alternative is excluded singly or in any combination with the other alternatives are also hereby disclosed; more than one element of a disclosure can have such exclusions, and all combinations of elements having such exclusions are hereby disclosed.

Other objects, features, aspects, and advantages of the invention will be apparent from the following detailed description, accompanying figures, and from the claims.

The following abbreviations are used in FIGS. 3A to 3J: a, c, g, i, and u are 2'-O-methyl modified nucleotides; Af, Cf, Gf, and Uf are 2'-fluoro modified nucleotides; o is a phosphodiester linkage; s is a phosphorothioate linkage; invAb is an inverted abasic residue (see, e.g., Table 11); cPrpu is a 5'-cyclopropyl phosphonate-2'-O-methyluridine modified nucleotide (see, e.g., Table 11); Tri-SM6.1-αvβ6-(TA14) is the tridentate αvβ6 epithelial cell targeting ligand having the structure shown in FIG. 1; and (TriAlk14) is the linking group as shown in Table 11, which is suitable for subsequent coupling to targeting ligands (See also, Example 1 herein).

Figure 3A:
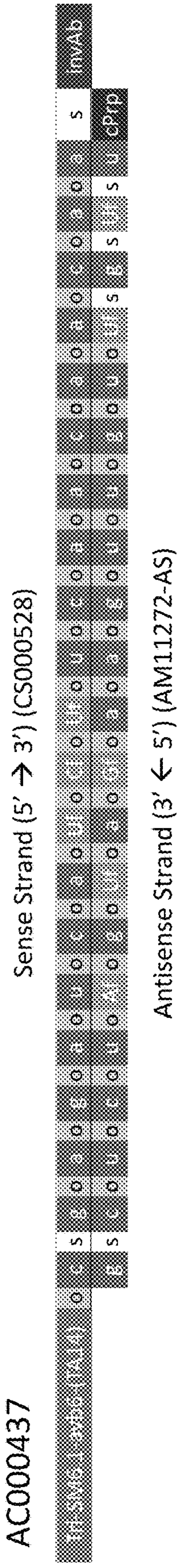

FIG. 3A. Schematic diagram of the modified sense and antisense strands (SEQ ID NOs: 1490 and 1116, respectively) of the MUC5AC RNAi agent conjugate having the structure of AC000437 (see, e.g., Tables 9, 10, and 11), having a tridentate αvβ6 epithelial cell targeting ligand linked at the 5' end of the sense strand.

Figure 3B:
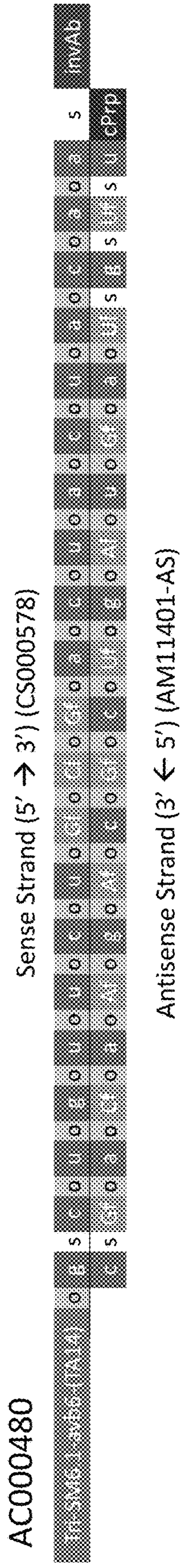

FIG. 3B. Schematic diagram of the modified sense and antisense strands (SEQ ID NOs: 1491 and 1127, respectively) of the MUC5AC RNAi agent conjugate having the structure of AC000480 (see, e.g., Tables 9, 10, and 11), having a tridentate αvβ6 epithelial cell targeting ligand linked at the 5' end of the sense strand.

Figure 3C:
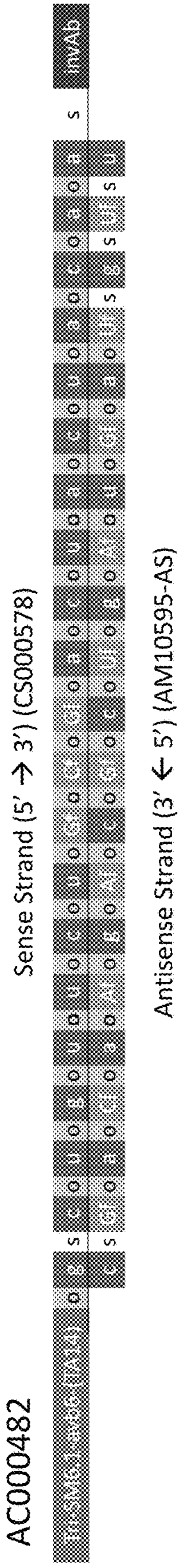

FIG. 3C. Schematic diagram of the modified sense and antisense strands (SEQ ID NOs: 1491 and 1065, respectively) of the MUC5AC RNAi agent conjugate having the structure of AC000482 (see, e.g., Tables 9, 10, and 11), having a tridentate αvβ6 epithelial cell targeting ligand linked at the 5' end of the sense strand.

Figure 3D:
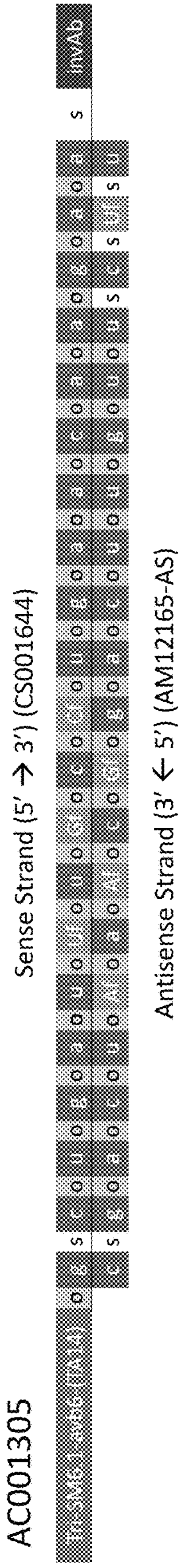

FIG. 3D. Schematic diagram of the modified sense and antisense strands (SEQ ID NOs: 1513 and 1166, respectively) of the MUC5AC RNAi agent conjugate having the structure of AC001305 (see, e.g., Tables 9, 10, and 11), having a tridentate αvβ6 epithelial cell targeting ligand linked at the 5' end of the sense strand.

Figure 3E:
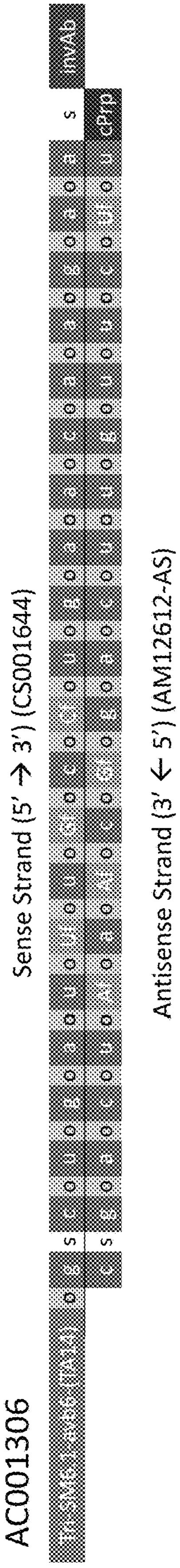

FIG. 3E. Schematic diagram of the modified sense and antisense strands (SEQ ID NOs: 1513 and 1191, respectively) of the MUC5AC RNAi agent conjugate having the structure of AC001306 (see, e.g., Tables 9, 10, and 11), having a tridentate αvβ6 epithelial cell targeting ligand linked at the 5' end of the sense strand.

Figure 3F:
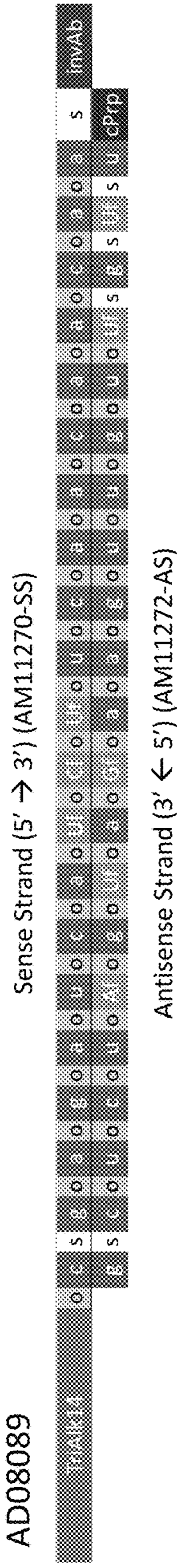

FIG. 3F. Schematic diagram of the modified sense and antisense strands (SEQ ID NOs: 1381 and 1116, respectively) of the MUC5AC RNAi agent duplex having the structure of AD08089 (see, e.g., Tables 8 and 10), having a (TriAlk14) linker at the 5' end of the sense strand.

Figure 3G:
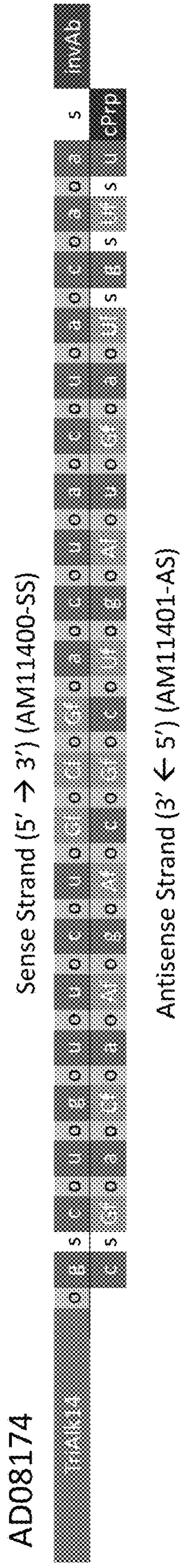

FIG. 3G. Schematic diagram of the modified sense and antisense strands (SEQ ID NOs: 1392 and 1127, respectively) of the MUC5AC RNAi agent duplex having the structure of AD08174 (see, e.g., Tables 8 and 10), having a (TriAlk14) linker at the 5' end of the sense strand.

Figure 3H:
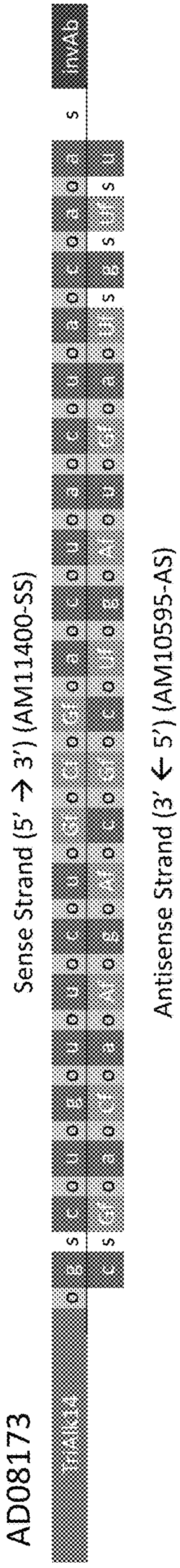

FIG. 3H. Schematic diagram of the modified sense and antisense strands (SEQ ID NOs: 1392 and 1065, respectively) of the MUC5AC RNAi agent duplex having the structure of AD08173 (see, e.g., Tables 8 and 10), having a (TriAlk14) linker at the 5' end of the sense strand.

Figure 3I:
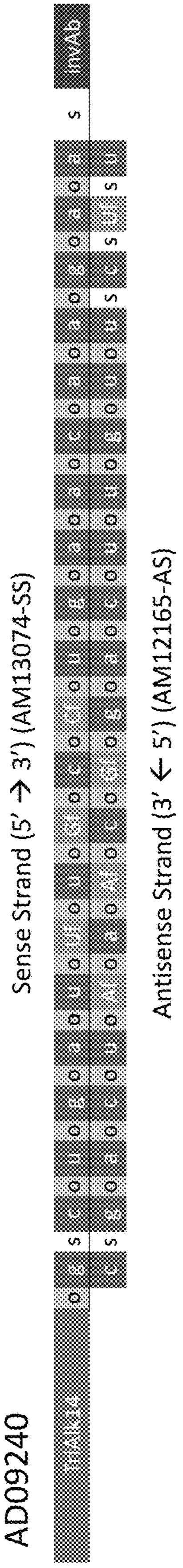

FIG. 3I. Schematic diagram of the modified sense and antisense strands (SEQ ID NOs: 1441 and 1166, respectively) of the MUC5AC RNAi agent duplex having the structure of AD09240 (see, e.g., Tables 8 and 10), having a (TriAlk14) linker at the 5' end of the sense strand.

Figure 3J:
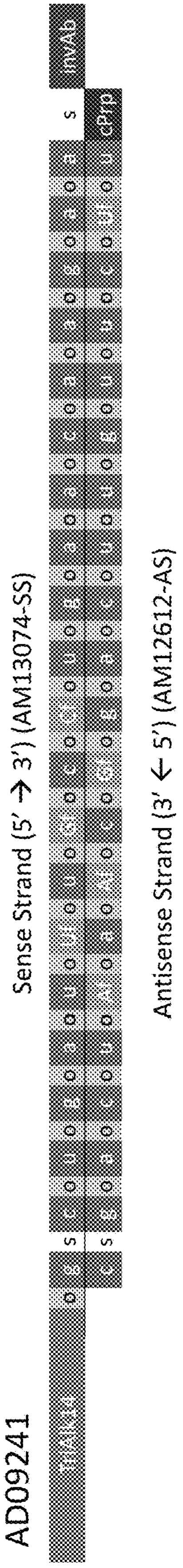

FIG. 3J. Schematic diagram of the modified sense and antisense strands (SEQ ID NOs: 1441 and 1191, respectively) of the MUC5AC RNAi agent duplex having the structure of AD09241 (see, e.g., Tables 8 and 10), having a (TriAlk14) linker at the 5' end of the sense strand.

DETAILED DESCRIPTION

RNAi Agents

Described herein are RNAi agents for inhibiting expression of a MUC5AC gene (referred to herein as MUC5AC RNAi agents or MUC5AC RNAi triggers). Each MUC5AC RNAi agent disclosed herein comprises a sense strand and an antisense strand. The sense strand can be 15 to 49 nucleotides in length. The antisense strand can be 18 to 49 nucleotides in length. The sense and antisense strands can be either the same length or they can be different lengths. In some embodiments, the sense and antisense strands are each independently 18 to 27 nucleotides in length. In some embodiments, both the sense and antisense strands are each 21-26 nucleotides in length. In some embodiments, the sense and antisense strands are each 21-24 nucleotides in length. In some embodiments, the sense and antisense strands are each independently 19-21 nucleotides in length. In some embodiments, the sense strand is about 19 nucleotides in length while the antisense strand is about 21 nucleotides in length. In some embodiments, the sense strand is about 21 nucleotides in length while the antisense strand is about 23 nucleotides in length. In some embodiments, a sense strand is 23 nucleotides in length and an antisense strand is 21 nucleotides in length. In some embodiments, both the sense and antisense strands are each 21 nucleotides in length. In some embodiments, the RNAi agent antisense strands are each independently 18, 19, 20, 21, 22, 23, 24, 25, 26, 27, 28, 29, or 30 nucleotides in length. In some embodiments, the RNAi agent sense strands are each independently 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides in length. The sense and antisense strands are annealed to form a duplex, and in some embodiments, a double-stranded RNAi agent has a duplex length of about 15, 16, 17, 18, 19, 20, 21, 22, 23 or 24 nucleotides.

Examples of nucleotide sequences used in forming MUC5AC RNAi agents are provided in Tables 2, 3, 4, 5, 6, 7, and 11. Examples of RNAi agent duplexes, that include the sense strand and antisense strand sequences in Tables 2, 3, 4, 5, 6, and 7 are shown in Tables 8A, 8B, 8C, 9, 10A, 10B, and 11.

In some embodiments, the region of perfect, substantial, or partial complementarity between the sense strand and the antisense strand is 15-26 (e.g., 15, 16, 17, 18, 19, 20, 21, 22, 23, 24, 25, or 26) nucleotides in length and occurs at or near the 5' end of the antisense strand (e.g., this region may be separated from the 5' end of the antisense strand by 0, 1, 2, 3, or 4 nucleotides that are not perfectly, substantially, or partially complementary).

A sense strand of the MUC5AC RNAi agents described herein includes at least 15 consecutive nucleotides that have at least 85% identity to a core stretch sequence (also referred to herein as a "core stretch" or "core sequence") of the same number of nucleotides in an MUC5AC mRNA. In some embodiments, a sense strand core stretch sequence is 100% (perfectly) complementary or at least about 85% (substantially) complementary to a core stretch sequence in the antisense strand, and thus the sense strand core stretch sequence is typically perfectly identical or at least about 85% identical to a nucleotide sequence of the same length (sometimes referred to, e.g., as a target sequence) present in the MUC5AC mRNA target. In some embodiments, this sense strand core stretch is 15, 16, 17, 18, 19, 20, 21, 22, 23, or 24 nucleotides in length. In some embodiments, this sense strand core stretch is 17 nucleotides in length. In some embodiments, this sense strand core stretch is 19 nucleotides in length.

An antisense strand of a MUC5AC RNAi agent described herein includes at least 18 consecutive nucleotides that have at least 85% complementarity to a core stretch of the same number of nucleotides in an MUC5AC mRNA and to a core stretch of the same number of nucleotides in the corresponding sense strand. In some embodiments, an antisense strand core stretch is 100% (perfectly) complementary or at least about 85% (substantially) complementary to a nucleotide sequence (e.g., target sequence) of the same length present in the MUC5AC mRNA target. In some embodiments, this antisense strand core stretch is 15, 16, 17, 18, 19, 20, 21, 22, 23, or 24 nucleotides in length. In some embodiments, this antisense strand core stretch is 19 nucleotides in length. In some embodiments, this antisense strand core stretch is 17 nucleotides in length. In some embodiments, this antisense strand core stretch is 21 nucleotides in length. A sense strand core stretch sequence can be the same length as a corresponding antisense core stretch sequence or it can be a different length.

The MUC5AC RNAi agent sense and antisense strands anneal to form a duplex. A sense strand and an antisense strand of a MUC5AC RNAi agent can be partially, substantially, or fully complementary to each other. Within the complementary duplex region, the sense strand core stretch sequence is at least 85% complementary or 100% complementary to the antisense core stretch sequence. In some embodiments, the sense strand core stretch sequence contains a sequence of at least 15, at least 16, at least 17, at least 18, at least 19, at least 20, at least 21, at least 22, or at least 23 nucleotides that is at least 85% or 100% complementary to a corresponding 15, 16, 17, 18, 19, 20, 21, 22, 23, or 24 nucleotide sequence of the antisense strand core stretch sequence (i.e., the sense and antisense core stretch sequences of a MUC5AC RNAi agent have a region of at least 15, at least 16, at least 17, at least 18, at least 19, at least 20, at least 21, at least 22, at least 23, or at least 24 nucleotides that is at least 85% base paired or 100% base paired.)

In some embodiments, the antisense strand of a MUC5AC RNAi agent disclosed herein differs by 0, 1, 2, or 3 nucleotides from any of the antisense strand sequences in Table 2, Table 3, or Table 11. In some embodiments, the sense strand of a MUC5AC RNAi agent disclosed herein differs by 0, 1, 2, or 3 nucleotides from any of the sense strand sequences in Table 2, Table 4, Table 5, Table 6, Table 7, or Table 11.

In some embodiments, the sense strand and/or the antisense strand can optionally and independently contain an additional 1, 2, 3, 4, 5, or 6 nucleotides (extension) at the 3' end, the 5' end, or both the 3' and 5' ends of the core stretch sequences. The antisense strand additional nucleotides, if present, may or may not be complementary to the corresponding sequence in the MUC5AC mRNA. The sense strand additional nucleotides, if present, may or may not be identical to the corresponding sequence in the MUC5AC mRNA. The antisense strand additional nucleotides, if present, may or may not be complementary to the corresponding sense strand's additional nucleotides, if present.

As used herein, an extension comprises 1, 2, 3, 4, 5, or 6 nucleotides at the 5' and/or 3' end of the sense strand core stretch sequence and/or antisense strand core stretch sequence. The extension nucleotides on a sense strand may or may not be complementary to nucleotides, either core stretch sequence nucleotides or extension nucleotides, in the corresponding antisense strand. Conversely, the extension nucleotides on an antisense strand may or may not be complementary to nucleotides, either core stretch nucleotides or extension nucleotides, in the corresponding sense strand. In some embodiments, both the sense strand and the antisense strand of an RNAi agent contain 3' and 5' extensions. In some embodiments, one or more of the 3' extension nucleotides of one strand base pairs with one or more 5' extension nucleotides of the other strand. In other embodiments, one or more of 3' extension nucleotides of one strand do not base pair with one or more 5' extension nucleotides of the other strand. In some embodiments, a MUC5AC RNAi agent has an antisense strand having a 3' extension and a sense strand having a 5' extension. In some embodiments, the extension nucleotide(s) are unpaired and form an overhang. As used herein, an "overhang" refers to an extension or stretch of one or more unpaired nucleotides located at a terminal end of either the sense strand or the antisense strand that does not form part of the hybridized or duplexed portion of an RNAi agent disclosed herein.

In some embodiments, a MUC5AC RNAi agent comprises an antisense strand having a 3' extension of 1, 2, 3, 4, 5, or 6 nucleotides in length. In other embodiments, a MUC5AC RNAi agent comprises an antisense strand having a 3' extension of 1, 2, or 3 nucleotides in length. In some embodiments, one or more of the antisense strand extension nucleotides comprise nucleotides that are complementary to the corresponding MUC5AC mRNA sequence. In some embodiments, one or more of the antisense strand extension nucleotides comprise nucleotides that are not complementary to the corresponding MUC5AC mRNA sequence.

In some embodiments, a MUC5AC RNAi agent comprises a sense strand having a 3' extension of 1, 2, 3, 4, or 5 nucleotides in length. In some embodiments, one or more of the sense strand extension nucleotides comprises adenosine, uracil, or thymidine nucleotides, AT dinucleotide, or nucleotides that correspond to or are the identical to nucleotides in the MUC5AC mRNA sequence. In some embodiments, the 3' sense strand extension includes or consists of one of the following sequences, but is not limited to: T, UT, TT, UU, UUT, TTT, or TTTT (each listed 5' to 3').

A sense strand can have a 3' extension and/or a 5' extension. In some embodiments, a MUC5AC RNAi agent comprises a sense strand having a 5' extension of 1, 2, 3, 4, 5, or 6 nucleotides in length. In some embodiments, one or more of the sense strand extension nucleotides comprise nucleotides that correspond to or are identical to nucleotides in the MUC5AC mRNA sequence.

Examples of sequences used in forming MUC5AC RNAi agents are provided in Tables 2, 3, 4, 5, 6, 7, and 11. In some embodiments, a MUC5AC RNAi agent antisense strand includes a sequence of any of the sequences in Tables 2, 3, or 11. In certain embodiments, a MUC5AC RNAi agent antisense strand comprises or consists of any one of the modified sequences in Table 3. In some embodiments, a MUC5AC RNAi agent antisense strand includes the sequence of nucleotides (from 5' end→3' end) 1-17, 2-17, 1-18, 2-18, 1-19, 2-19, 1-20, 2-20, 1-21, or 2-21, of any of the sequences in Table 2, Table 3, or Table 11. In some embodiments, a MUC5AC RNAi agent sense strand includes the sequence of any of the sequences in Tables 2, 4, 5, 6, or 7. In some embodiments, a MUC5AC RNAi agent sense strand includes the sequence of nucleotides (from 5' end→3' end) 1-18, 1-19, 1-20, 1-21, 2-19, 2-20, 2-21, 3-20, 3-21, or 4-21 of any of the sequences in Tables 2, 4, 5, 6, or 7. In certain embodiments, a MUC5AC RNAi agent sense strand comprises or consists of a modified sequence of any one of the modified sequences in Table 4, 5, 6, 7, or 11.

In some embodiments, the sense and antisense strands of the RNAi agents described herein contain the same number of nucleotides. In some embodiments, the sense and antisense strands of the RNAi agents described herein contain different numbers of nucleotides. In some embodiments, the sense strand 5' end and the antisense strand 3' end of an RNAi agent form a blunt end. In some embodiments, the sense strand 3' end and the antisense strand 5' end of an RNAi agent form a blunt end. In some embodiments, both ends of an RNAi agent form blunt ends. In some embodiments, neither end of an RNAi agent is blunt-ended. As used herein a "blunt end" refers to an end of a double stranded RNAi agent in which the terminal nucleotides of the two annealed strands are complementary (form a complementary base-pair).

In some embodiments, the sense strand 5' end and the antisense strand 3' end of an RNAi agent form a frayed end. In some embodiments, the sense strand 3' end and the antisense strand 5' end of an RNAi agent form a frayed end. In some embodiments, both ends of an RNAi agent form a frayed end. In some embodiments, neither end of an RNAi agent is a frayed end. As used herein a frayed end refers to an end of a double stranded RNAi agent in which the terminal nucleotides of the two annealed strands form a pair (i.e., do not form an overhang) but are not complementary (i.e. form a non-complementary pair). In some embodiments, one or more unpaired nucleotides at the end of one strand of a double stranded RNAi agent form an overhang. The unpaired nucleotides may be on the sense strand or the antisense strand, creating either 3' or 5' overhangs. In some embodiments, the RNAi agent contains: a blunt end and a frayed end, a blunt end and 5' overhang end, a blunt end and a 3' overhang end, a frayed end and a 5' overhang end, a frayed end and a 3' overhang end, two 5' overhang ends, two 3' overhang ends, a 5' overhang end and a 3' overhang end, two frayed ends, or two blunt ends. Typically, when present, overhangs are located at the 3' terminal ends of the sense strand, the antisense strand, or both the sense strand and the antisense strand.

The MUC5AC RNAi agents disclosed herein may also be comprised of one or more modified nucleotides. In some embodiments, substantially all of the nucleotides of the sense strand and substantially all of the nucleotides of the antisense strand of the MUC5AC RNAi agent are modified nucleotides. The MUC5AC RNAi agents disclosed herein may further be comprised of one or more modified internucleoside linkages, e.g., one or more phosphorothioate linkages or phosphorodithioate linkages. In some embodiments, a MUC5AC RNAi agent contains one or more modified nucleotides and one or more modified internucleoside linkages. In some embodiments, a 2'-modified nucleotide is combined with modified internucleoside linkage.

In some embodiments, a MUC5AC RNAi agent is prepared or provided as a salt, mixed salt, or a free-acid. In some embodiments, a MUC5AC RNAi agent is prepared as a pharmaceutically acceptable salt. In some embodiments, a MUC5AC RNAi agent is prepared as a pharmaceutically acceptable sodium salt. Such forms that are well known in the art are within the scope of the inventions disclosed herein.

Modified Nucleotides

Modified nucleotides, when used in various oligonucleotide constructs, can preserve activity of the compound in cells while at the same time increasing the serum stability of these compounds, and can also minimize the possibility of activating interferon activity in humans upon administration of the oligonucleotide construct.

In some embodiments, a MUC5AC RNAi agent contains one or more modified nucleotides. As used herein, a "modified nucleotide" is a nucleotide other than a ribonucleotide (2'-hydroxyl nucleotide). In some embodiments, at least 50% (e.g., at least 60%, at least 70%, at least 80%, at least 90%, at least 95%, at least 97%, at least 98%, at least 99%, or 100%) of the nucleotides are modified nucleotides. As used herein, modified nucleotides can include, but are not limited to, deoxyribonucleotides, nucleotide mimics, abasic nucleotides, 2'-modified nucleotides, inverted nucleotides, modified nucleobase-comprising nucleotides, bridged nucleotides, peptide nucleic acids (PNAs), 2',3'-seco nucleotide mimics (unlocked nucleobase analogues), locked nucleotides, 3'-O-methoxy (2' internucleoside linked) nucleotides, 2'-F-Arabino nucleotides, 5'-Me, 2'-fluoro nucleotide, morpholino nucleotides, vinyl phosphonate deoxyribonucleotides, vinyl phosphonate containing nucleotides, and cyclopropyl phosphonate containing nucleotides. 2'-modified nucleotides (i.e., a nucleotide with a group other than a hydroxyl group at the 2' position of the five-membered sugar ring) include, but are not limited to, 2'-O-methyl nucleotides (also referred to as 2'-methoxy nucleotides), 2'-fluoro nucleotides (also referred to herein as 2'-deoxy-2'-fluoro nucleotides), 2'-deoxy nucleotides, 2'-methoxyethyl (2'-O-2-methoxylethyl) nucleotides (also referred to as 2'-MOE), 2'-amino nucleotides, and 2'-alkyl nucleotides. It is not necessary for all positions in a given compound to be uniformly modified. Conversely, more than one modification can be incorporated in a single MUC5AC RNAi agent or even in a single nucleotide thereof. The MUC5AC RNAi agent sense strands and antisense strands can be synthesized and/or modified by methods known in the art. Modification at one nucleotide is independent of modification at another nucleotide.

Modified nucleobases include synthetic and natural nucleobases, such as 5-substituted pyrimidines, 6-azapyrimidines and N-2, N-6 and 0-6 substituted purines, (e.g., 2-aminopropyladenine, 5-propynyluracil, or 5-propynylcytosine), 5-methylcytosine (5-me-C), 5-hydroxymethyl cytosine, inosine, xanthine, hypoxanthine, 2-aminoadenine, 6-alkyl (e.g., 6-methyl, 6-ethyl, 6-isopropyl, or 6-n-butyl) derivatives of adenine and guanine, 2-alkyl (e.g., 2-methyl, 2-ethyl, 2-isopropyl, or 2-n-butyl) and other alkyl derivatives of adenine and guanine, 2-thiouracil, 2-thiothymine, 2-thiocytosine, 5-halouracil, cytosine, 5-propynyl uracil, 5-propynyl cytosine, 6-azo uracil, 6-azo cytosine, 6-azo thymine, 5-uracil (pseudouracil), 4-thiouracil, 8-halo, 8-amino, 8-sulfhydryl, 8-thioalkyl, 8-hydroxyl and other 8-substituted adenines and guanines, 5-halo (e.g., 5-bromo), 5-trifluoromethyl, and other 5-substituted uracils and cytosines, 7-methylguanine and 7-methyladenine, 8-azaguanine and 8-azaadenine, 7-deazaguanine, 7-deazaadenine, 3-deazaguanine, and 3-deazaadenine.

In some embodiments, the 5' and/or 3' end of the antisense strand can include abasic residues (Ab), which can also be referred to as an "abasic site" or "abasic nucleotide." An abasic residue (Ab) is a nucleotide or nucleoside that lacks a nucleobase at the 1' position of the sugar moiety. (See, e.g., U.S. Pat. No. 5,998,203). In some embodiments, an abasic residue can be placed internally in a nucleotide sequence. In some embodiments, Ab or AbAb can be added to the 3' end of the antisense strand. In some embodiments, the 5' end of the sense strand can include one or more additional abasic residues (e.g., (Ab) or (AbAb)). In some embodiments, UUAb, UAb, or Ab are added to the 3' end of the sense strand. In some embodiments, an abasic (deoxyribose) residue can be replaced with a ribitol (abasic ribose) residue.

In some embodiments, all or substantially all of the nucleotides of an RNAi agent are modified nucleotides. As used herein, an RNAi agent wherein substantially all of the nucleotides present are modified nucleotides is an RNAi agent having four or fewer (i.e., 0, 1, 2, 3, or 4) nucleotides in both the sense strand and the antisense strand being ribonucleotides (i.e., unmodified). As used herein, a sense strand wherein substantially all of the nucleotides present are modified nucleotides is a sense strand having two or fewer (i.e., 0, 1, or 2) nucleotides in the sense strand being unmodified ribonucleotides. As used herein, an antisense sense strand wherein substantially all of the nucleotides present are modified nucleotides is an antisense strand having two or fewer (i.e., 0, 1, or 2) nucleotides in the antisense strand being unmodified ribonucleotides. In some embodiments, one or more nucleotides of an RNAi agent is an unmodified ribonucleotide. Chemical structures for certain modified nucleotides are set forth in Table 12 herein.

Modified Internucleoside Linkages

In some embodiments, one or more nucleotides of a MUC5AC RNAi agent are linked by non-standard linkages or backbones (i.e., modified internucleoside linkages or modified backbones). Modified internucleoside linkages or backbones include, but are not limited to, phosphorothioate groups (represented herein as a lower case "s"), chiral phosphorothioates, thiophosphates, phosphorodithioates, phosphotriesters, aminoalkyl-phosphotriesters, alkyl phosphonates (e.g., methyl phosphonates or 3'-alkylene phosphonates), chiral phosphonates, phosphinates, phosphoramidates (e.g., 3'-amino phosphoramidate, aminoalkylphosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'. In some embodiments, a modified internucleoside linkage or backbone lacks a phosphorus atom. Modified internucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some embodiments, modified internucleoside backbones include, but are not limited to, siloxane backbones, sulfide backbones, sulfoxide backbones, sulfone backbones, formacetyl and thioformacetyl backbones, methylene formacetyl and thioformacetyl backbones, alkene-containing backbones, sulfamate backbones, methyleneimino and methylenehydrazino backbones, sulfonate and sulfonamide backbones, amide backbones, and other backbones having mixed N, O, S, and $CH_2$ components.

In some embodiments, a sense strand of a MUC5AC RNAi agent can contain 1, 2, 3, 4, 5, or 6 phosphorothioate linkages, an antisense strand of a MUC5AC RNAi agent can contain 1, 2, 3, 4, 5, or 6 phosphorothioate linkages, or both the sense strand and the antisense strand independently can contain 1, 2, 3, 4, 5, or 6 phosphorothioate linkages. In some embodiments, a sense strand of a MUC5AC RNAi agent can contain 1, 2, 3, or 4 phosphorothioate linkages, an antisense strand of a MUC5AC RNAi agent can contain 1, 2, 3, or 4 phosphorothioate linkages, or both the sense strand and the antisense strand independently can contain 1, 2, 3, or 4 phosphorothioate linkages.

In some embodiments, a MUC5AC RNAi agent sense strand contains at least two phosphorothioate internucleoside linkages. In some embodiments, the phosphorothioate internucleoside linkages are between the nucleotides at positions 1-3 from the 3' end of the sense strand. In some embodiments, one phosphorothioate internucleoside linkage is at the 5' end of the sense strand nucleotide sequence, and another phosphorothioate linkage is at the 3' end of the sense strand nucleotide sequence. In some embodiments, two phosphorothioate internucleoside linkage are located at the 5' end of the sense strand, and another phosphorothioate linkage is at the 3' end of the sense strand. In some embodiments, the sense strand does not include any phosphorothioate internucleoside linkages between the nucleotides, but contains one, two, or three phosphorothioate linkages between the terminal nucleotides on both the 5' and 3' ends and the optionally present inverted abasic residue terminal caps. In some embodiments, the targeting ligand is linked to the sense strand via a phosphorothioate linkage.

In some embodiments, a MUC5AC RNAi agent antisense strand contains four phosphorothioate internucleoside linkages. In some embodiments, the four phosphorothioate internucleoside linkages are between the nucleotides at positions 1-3 from the 5' end of the antisense strand and between the nucleotides at positions 19-21, 20-22, 21-23, 22-24, 23-25, or 24-26 from the 5' end. In some embodiments, three phosphorothioate internucleoside linkages are located between positions 1-4 from the 5' end of the antisense strand, and a fourth phosphorothioate internucleoside linkage is located between positions 20-21 from the 5' end of the antisense strand. In some embodiments, a MUC5AC RNAi agent contains at least three or four phosphorothioate internucleoside linkages in the antisense strand.

Capping Residues or Moieties

In some embodiments, the sense strand may include one or more capping residues or moieties, sometimes referred to in the art as a "cap," a "terminal cap," or a "capping residue." As used herein, a "capping residue" is anon-nucleotide compound or other moiety that can be incorporated at one or more termini of a nucleotide sequence of an RNAi agent disclosed herein. A capping residue can provide the RNAi agent, in some instances, with certain beneficial properties, such as, for example, protection against exonuclease degradation. In some embodiments, inverted abasic residues (invAb) (also referred to in the art as "inverted abasic sites") are added as capping residues (see Table 12). (See, e.g., F. Czauderna, Nucleic Acids Res., 2003, 31(11), 2705-16). Capping residues are generally known in the art, and include, for example, inverted abasic residues as well as carbon chains such as a terminal $C_3H_7$ (propyl), $C_6H_{13}$ (hexyl), or $C_{12}H_{25}$ (dodecyl) groups. In some embodiments, a capping residue is present at either the 5' terminal end, the 3' terminal end, or both the 5' and 3' terminal ends of the sense strand. In some embodiments, the 5' end and/or the 3' end of the sense strand may include more than one inverted abasic deoxyribose moiety as a capping residue.

In some embodiments, one or more inverted abasic residues (invAb) are added to the 3' end of the sense strand. In some embodiments, one or more inverted abasic residues (invAb) are added to the 5' end of the sense strand. In some embodiments, one or more inverted abasic residues or inverted abasic sites are inserted between the targeting ligand and the nucleotide sequence of the sense strand of the RNAi agent. In some embodiments, the inclusion of one or more inverted abasic residues or inverted abasic sites at or near the terminal end or terminal ends of the sense strand of an RNAi agent allows for enhanced activity or other desired properties of an RNAi agent.

In some embodiments, one or more inverted abasic residues (invAb) are added to the 5' end of the sense strand. In some embodiments, one or more inverted abasic residues can be inserted between the targeting ligand and the nucleotide sequence of the sense strand of the RNAi agent. The inverted abasic residues may be linked via phosphate, phosphorothioate (e.g., shown herein as (invAb)s)), or other internucleoside linkages. In some embodiments, the inclusion of one or more inverted abasic residues at or near the terminal end or terminal ends of the sense strand of an RNAi agent may allow for enhanced activity or other desired properties of an RNAi agent. In some embodiments, an inverted abasic (deoxyribose) residue can be replaced with an inverted ribitol (abasic ribose) residue. In some embodiments, the 3' end of the antisense strand core stretch sequence, or the 3' end of the antisense strand sequence, may include an inverted abasic residue. The chemical structures for inverted abasic deoxyribose residues are shown in Table 12 below.

MUC5AC RNAi Agents

The MUC5AC RNAi agents disclosed herein are designed to target specific positions on a MUC5AC gene (e.g., SEQ ID NO:1 (NM_001304359.2)). As defined herein, an antisense strand sequence is designed to target a MUC5AC gene at a given position on the gene when the 5' terminal nucleobase of the antisense strand is aligned with a position that is 19 nucleotides downstream (towards the 3' end) from the position on the gene when base pairing to the gene. For example, as illustrated in Tables 1 and 2 herein, an antisense strand sequence designed to target a MUC5AC gene at position 3535 requires that when base pairing to the gene, the 5' terminal nucleobase of the antisense strand is aligned with position 3553 of a MUC5AC gene.

As provided herein, a MUC5AC RNAi agent does not require that the nucleobase at position 1 (5'→3') of the antisense strand be complementary to the gene, provided that there is at least 85% complementarity (e.g., at least 85, 86, 87, 88, 89, 90, 91, 92, 93, 94, 95, 96, 97, 98, 99, or 100% complementarity) of the antisense strand and the gene across a core stretch sequence of at least 16 consecutive nucleotides. For example, for a MUC5AC RNAi agent disclosed herein that is designed to target position 3535 of a MUC5AC gene, the 5' terminal nucleobase of the antisense strand of the of the MUC5AC RNAi agent must be aligned with position 3553 of the gene; however, the 5' terminal nucleobase of the antisense strand may be, but is not required to be, complementary to position 3553 of a MUC5AC gene, provided that there is at least 85% complementarity (e.g., at least 85, 86, 87, 88, 89, 90, 91, 92, 93, 94, 95, 96, 97, 98, 99, or 100% complementarity) of the antisense strand and the gene across a core stretch sequence of at least 16 consecutive nucleotides. As shown by, among other things, the various examples disclosed herein, the specific site of binding of the gene by the antisense strand of the MUC5AC RNAi agent (e.g., whether the MUC5AC RNAi agent is designed to target a MUC5AC gene at position 3535, at position 4993, at position 15051, or at some other position) is an important factor to the level of inhibition achieved by the MUC5AC RNAi agent. (See also, Kamola et al., The siRNA Non-seed Region and Its Target Sequences are Auxiliary Determinants of Off-Target Effects, PLOS Computational Biology, 11(12), FIG. 1 (2015)).

In some embodiments, the MUC5AC RNAi agents disclosed herein target a MUC5AC gene at or near the positions of the MUC5AC sequence shown in Table 1. In some embodiments, the antisense strand of a MUC5AC RNAi agent disclosed herein includes a core stretch sequence that is fully, substantially, or at least partially complementary to a target MUC5AC 19-mer sequence disclosed in Table 1.

TABLE 1

MUC5AC 19-mer mRNA Target Sequences (taken from *homo sapiens* mucin 5AC, oligomeric mucus/gel-forming (MUC5AC) gene transcript, GenBank NM_001304359.2 (SEQ ID NO: 1))

| SEQ ID No. | MUC5AC 19-mer Target Sequences (5' → 3') | Corresponding Positions of Sequence on SEQ ID NO: 1 | Targeted Gene Position (as referred to herein) |
|---|---|---|---|
| 2 | GCUUCCACUACAAGACCUU | 304-322 | 304 |
| 3 | UGUGGAACCACGAUGACAG | 610-628 | 610 |
| 4 | GCAAGACCUCUGCUUCUGU | 923-941 | 923 |
| 5 | CACAGACUGCACCAACUGC | 1277-1295 | 1277 |
| 6 | CAGUGCCUUCACUGUACUG | 1445-1463 | 1445 |
| 7 | AGUGCCUUCACUGUACUGC | 1446-1464 | 1446 |
| 8 | CAGCGAGACCUGCCUGAAG | 1493-1511 | 1493 |
| 9 | GGGAAGUGUUCCUGAACCA | 1567-1585 | 1567 |
| 10 | AACGUCACCAUCUUCAGAC | 1617-1635 | 1617 |
| 11 | ACGUCACCAUCUUCAGACC | 1618-1636 | 1618 |
| 12 | UGUGGGAACUUCAACAGCA | 1758-1776 | 1758 |
| 13 | GGGAACUUCAACAGCAUCC | 1761-1779 | 1761 |
| 14 | UCCAGGCCGAUGACUUCCG | 1777-1795 | 1777 |
| 15 | CUUCUUCAACACCUUCAAG | 1832-1850 | 1832 |
| 16 | UUCAACACCUUCAAGACCC | 1836-1854 | 1836 |
| 17 | CCAACAUCAGGAACAGCUU | 1867-1885 | 1867 |
| 18 | CAUCAGGAACAGCUUCGAG | 1871-1889 | 1871 |
| 19 | AGUAUGCUCAGCACUGGUG | 1921-1939 | 1921 |
| 20 | ACCUACUACUCGAACUGCA | 2001-2019 | 2001 |
| 21 | UACUACUCGAACUGCAUGU | 2004-2022 | 2004 |
| 22 | ACAUCACCUGCAGUGUUGG | 2230-2248 | 2230 |
| 23 | CACCUGCAGUGUUGGCUUC | 2234-2252 | 2234 |
| 24 | UGGACAUGACCUGUUACAG | 2536-2554 | 2536 |
| 25 | AGAGCUACAGCUUCAACGG | 2797-2815 | 2797 |
| 26 | AGGGACCACCUGCUCCAAG | 2915-2933 | 2915 |
| 27 | CUGCUCCAAGGCCAUCAAG | 2924-2942 | 2924 |
| 28 | UGCUCCAAGGCCAUCAAGA | 2925-2943 | 2925 |
| 29 | CUCCAAGGCCAUCAAGAUU | 2927-2945 | 2927 |
| 30 | GACAAGAAGACCAGCAUCU | 3090-3108 | 3090 |
| 31 | AGACCAGCAUCUUCAUCAA | 3097-3115 | 3097 |
| 32 | ACCAGCAUCUUCAUCAACC | 3099-3117 | 3099 |
| 33 | CCUCAGCCCCGAGUUCAAG | 3116-3134 | 3116 |
| 34 | UGGGAACUUCGACGACAUC | 3155-3173 | 3155 |
| 35 | CAGAAGCAGUGCAGCAUCC | 3321-3339 | 3321 |
| 36 | CAGGCCUGCCAUGAAGUUU | 3475-3493 | 3475 |

TABLE 1-continued

MUC5AC 19-mer mRNA Target Sequences (taken from *homo sapiens* mucin 5AC, oligomeric mucus/gel-forming (MUC5AC) gene transcript, GenBank NM_001304359.2 (SEQ ID NO: 1))

| SEQ ID No. | MUC5AC 19-mer Target Sequences (5' → 3') | Corresponding Positions of Sequence on SEQ ID NO: 1 | Targeted Gene Position (as referred to herein) |
|---|---|---|---|
| 37 | CCCUCUGUUCUGCGACUAC | 3530-3548 | 3530 |
| 38 | CCUCUGUUCUGCGACUACU | 3531-3549 | 3531 |
| 39 | UCUGUUCUGCGACUACUAC | 3533-3551 | 3533 |
| 40 | CUGUUCUGCGACUACUACA | 3534-3552 | 3534 |
| 41 | UGUUCUGCGACUACUACAA | 3535-3553 | 3535 |
| 42 | UCUUUGAUGAGGACAAGAU | 3694-3712 | 3694 |
| 43 | CUUUGAUGAGGACAAGAUG | 3695-3713 | 3695 |
| 44 | UUUGAUGAGGACAAGAUGC | 3696-3714 | 3696 |
| 45 | ACGUCAUCUACCACACGAC | 3910-3928 | 3910 |
| 46 | UGCUACAACUACCAGAUCA | 4443-4461 | 4443 |
| 47 | UACAACUACCAGAUCAGGG | 4446-4464 | 4446 |
| 48 | CUGAUUUGCCUGAACAAGA | 4992-5010 | 4992 |
| 49 | UGAUUUGCCUGAACAAGAA | 4993-5011 | 4993 |
| 50 | CACCCAUCUGCUACAACUA | 5020-5038 | 5020 |
| 51 | ACCCAUCUGCUACAACUAU | 5021-5039 | 5021 |
| 52 | UGCUACAACUAUGAGAUCC | 5028-5046 | 5028 |
| 53 | GCUACAACUAUGAGAUCCG | 5029-5047 | 5029 |
| 54 | GAUCCGCAUCCAGUGUUGC | 5042-5060 | 5042 |
| 55 | AAAGUGGUUCGACGUGGAC | 5297-5315 | 5297 |
| 56 | GUGGUUCGACGUGGACUUC | 5300-5318 | 5300 |
| 57 | GGUUCGACGUGGACUUCCC | 5302-5320 | 5302 |
| 58 | AAGGAAACCUACAACAACA | 5346-5364 | 5346 |
| 59 | AGGAAACCUACAACAACAU | 5347-5365 | 5347 |
| 60 | AAACCUACAACAACAUCAU | 5350-5368 | 5350 |
| 61 | AGAGGUGAGCAUCGAACAC | 5441-5459 | 5441 |
| 62 | GCAGGGACCCUUCAAGAUG | 5519-5537 | 5519 |
| 63 | AGAUGUGCCUCAACUACGA | 5533-5551 | 5533 |
| 64 | AUGUGCCUCAACUACGAGG | 5535-5553 | 5535 |
| 65 | ACCUCCUCUUGGCAGAAAU | 6777-6795 | 6777 |
| 66 | AGGACAACCACUUUGGUGA | 6798-6816 | 6798 |
| 67 | CUCUGCUCCUACAACUAGC | 6998-7016 | 6998 |
| 68 | ACCUCUGCUUCUACAACUA | 7980-7998 | 7980 |
| 69 | AUAACCAGCACAACUUCUG | 8448-8466 | 8448 |
| 70 | ACCAGAACAACCUCUGCUC | 8739-8757 | 8739 |
| 71 | CUACAACCAGCACAAUCUC | 9310-9328 | 9310 |
| 72 | UGGACCAAGUGGUUUGACA | 9729-9747 | 9729 |
| 73 | ACAACCAGCACAACUUCUG | 10206-10224 | 10206 |
| 74 | CAACCACUUUGGUGACAAG | 11014-11032 | 11014 |
| 75 | ACAACCAACACAACUUCUG | 11361-11379 | 11361 |
| 76 | CUCUGCUCCUACAACUAGC | 12965-12983 | 12965 |
| 77 | GAGAUCAUCUUCAACAACA | 15051-15069 | 15051 |
| 78 | AGAUCAUCUUCAACAACAA | 15052-15070 | 15052 |

*Homo sapiens* mucin 5AC, oligomeric mucus/gel-forming (MUC5AC) gene transcript, GenBank NM_001304359.2 (SEQ ID NO:1) (17,448 bases):

```
  1 ctcagaggct gctgagggac agggcactct tccccgccgt ccacacaatg agtgttggcc
 61 ggaggaagct ggccctgctc tgggccctgg ctctcgctct ggcctgcacc cggcatacag
121 gccatgccca ggatggctcc tccgaatcca gctacaagca ccaccctgcc ctctctccta
181 tcgcccgggg gcccagcggg gtcccgctcc gtggggcgac tgtcttccca tctctgagga
241 ccatccctgt ggtacgagcc tccaacccgg cgcacaacgg gcgggtgtgc agcacctggg
301 gcagcttcca ctacaagacc ttcgacggcg acgtcttccg cttccccggc ctctgcaact
361 acgtgttctc cgagcactgc ggtgccgcct acgaggattt taacatccag ctacgccgca
421 gccaggagtc agcggccccc acgctgagca gggtcctcat gaaggtggat ggcgtggtca
481 tccagctgac caagggctcc gtcctggtca acggccaccc ggtcctgctg cccttcagcc
541 agtctggggt cctcattcag cagagcagca gctacaccaa ggtggaggcc aggctgggcc
601 ttgtcctcat gtggaaccac gatgacagcc tgctgctgga gctggacacc aaatacgcca
```

-continued

```
661   acaagacctg tgggctctgt ggggacttca acgggatgcc cgtggtcagc gagctcctct
721   cccacaacac caagctgaca cccatggaat tcgggaacct gcagaagatg gacgacccca
781   cggaccagtg tcaggaccct gtccctgaac cccgaggaa ctgctccact ggctttggca
841   tctgtgagga gctcctgcac ggccagctgt tctctggctg cgtggccctg gtggacgtcg
901   gcagctacct ggaggcttgc aggcaagacc tctgcttctg tgaagacacc gacctgctca
961   gctgcgtctg ccacaccctt gccgagtact cccggcagtg cacccatgca ggggggttgc
1021  cccaggactg gcggggccct gacttctgcc cccagaagtg ccccaacaac atgcagtacc
1081  acgagtgccg ctccccctgc gcagacacct gctccaacca ggagcactcc cgggcctgtg
1141  aggaccactg tgtggccggc tgcttctgcc ctgaggggac ggtgcttgac gacatcggcc
1201  agaccggctg tgtccctgtg tcaaagtgtg cctgcgtcta caacggggct gcctatgccc
1261  caggggccac ctactccaca gactgcacca actgcacctg ctccggaggc cggtggagct
1321  gccaggaggt tccatgcccg ggtacctgct ctgtgcttgg aggtgcccac ttctcaacgt
1381  ttgacgggaa gcaatacacg gtgcacggcg actgcagcta tgtgctgacc aagccctgtg
1441  acagcagtgc cttcactgta ctggctgagc tgcgcaggtg cgggctgacg gacagcgaga
1501  cctgcctgaa gagcgtgaca ctgagcctgg atggggcgca gacggtggtg gtgatcaagg
1561  ccagtgggga agtgttcctg aaccagatct acacccagct gcccatctct gcagccaacg
1621  tcaccatctt cagaccctca accttcttca tcatcgccca gaccagcctg ggcctgcagc
1681  tgaacctgca gctggtgccc accatgcagc tgttcatgca gctggcgccc aagctccgtg
1741  ggcagacctg cggtctctgt gggaacttca acagcatcca ggccgatgac ttccggaccc
1801  tcagtggggt ggtggaggcc accgctgcgg ccttcttcaa caccttcaag acccaggccg
1861  cctgccccaa catcaggaac agcttcgagg acccctgctc tctgagcgtg gagaatgaga
1921  agtatgctca gcactggtgc tcgcagctga ccgatgccga cggccccttc ggccggtgcc
1981  atgctgccgt gaagccggga acctactact cgaactgcat gtttgacacc tgcaactgtg
2041  agcggagcga ggactgcctg tgcgccgcgc tgtcctccta cgtgcacgcc tgtgccgcca
2101  agggcgtgca gctcggcggc tggagggacg gcgtctgcac gaagcctatg accacttgcc
2161  ccaagtcaat gacgtaccac taccatgtca gcacctgcca gcccacctgc cgctccctga
2221  gcgaggggga catcacctgc agtgttggct tcatccccgt ggatggctgc atctgtccca
2281  agggcacctt cctggacgac acgggcaagt gtgtgcaggc cagcaactgt ccctgctacc
2341  acagaggctc catgatcccc aatggggagt cggtgcacga cagcggggct atctgcacct
2401  gcacacatgg gaagctgagc tgcatcggag gccaagcccc cgccccagtg tgtgctgcgc
2461  ccatggtgtt ctttgactgc cgaaatgcca cgcccgggga cacaggggct ggctgtcaga
2521  agagctgcca cacactggac atgacctgtt acagccccca gtgtgtgcct ggctgcgtgt
2581  gccccgacgg gctggtggcg gacggcgagg gcggctgcat cactgcggag gactgcccct
2641  gcgtgcacaa tgaggccagc taccgggccg gccagaccat ccgggtgggc tgcaacacct
2701  gcacctgtga cagcaggatg tggcggtgca cagatgaccc ctgcctggcc acctgcgccg
2761  tgtacgggga cggccactac ctcaccttcg acggacagag ctacagcttc aacggagact
2821  gcgagtacac gctggtgcag aaccactgtg gcgggaaaga cagcacccag gactcctttc
2881  gtgttgtcac cgagaacgtc ccctgcggca ccacagggac cacctgctcc aaggccatca
2941  agatttttcct ggggggcttc gagctgaagc taagccatgg gaaggtggag gtgatcggga
3001  cggacgagag ccaggaggtg ccatacacca tccggcagat gggcatctac ctggtggtgg
3061  acaccgacat tggcctggtg ctgctgtggg acaagaagac cagcatcttc atcaacctca
```

-continued

```
3121  gccccgagtt caagggcagg gtctgcggcc tgtgtgggaa cttcgacgac atcgccgtta
3181  atgactttgc cacgcggagc cggtctgtgg tgggggacgt gctggagttt gggaacagct
3241  ggaagctctc ccctcctgc ccagatgccc tggcgcccaa ggacccctgc acggccaacc
3301  ccttccgcaa gtcctgggcc cagaagcagt gcagcatcct ccacggcccc accttcgccg
3361  cctgccacgc acacgtggag ccggccaggt actacgaggc ctgcgtgaac gacgcgtgcg
3421  cctgcgactc cgggggtgac tgcgagtgct tctgcacggc tgtggccgcc tacgcccagg
3481  cctgccatga agtaggcctg tgtgtgtcct ggcggacccc gagcatctgc cctctgttct
3541  gcgactacta caaccccgaa ggccagtgcg agtggcacta ccagccctgc ggggtgccct
3601  gcctgcgcac ctgccggaac ccccgtggag actgcctgcg ggacgtccgg ggcctggaag
3661  gctgctaccc caagtgccca ccagaggctc ccatctttga tgaggacaag atgcagtgtg
3721  tggccacctg cccaaccccg cctctgccac cacggtgcca cgtccatggg aagtcctacc
3781  ggccaggtgc agtggtgccc tcggacaaga actgccagtc ctgccttgt acggagcgcg
3841  gcgtggagtg cacctacaaa gctgaggcct gtgtctgcac ctacaatgga cagcgcttcc
3901  acccagggga cgtcatctac cacacgacgg atggcacggg tggctgcatc tccgcccgct
3961  gcggggccaa cggcaccatt gagaggaggg tctacccctg cagccccacc acccctgtcc
4021  ccccaaccac cttctccttc tccacacccc cgcttgtcgt gagctccacg cacaccccca
4081  gcaatggccc aagcagcgcg cacacaggcc ctccgagcag cgcctggccc accacagcag
4141  gcacttctcc caggacgagg ctgcccacag cctctgcctc actgccgccg gtctgtgggg
4201  aaaagtgcct gtggtcgcca tggatggatg tcagccgccc tggacggggc acggacagcg
4261  gtgacttcga cacactggag aacctccgcg cccatgggta ccgggtgtgc gaatcaccca
4321  ggtcggtgga gtgccgagct gaggacgccc ccggagtgcc gctccgagcc ctggggcagc
4381  gtgtgcagtg cagcccggat gtggggctga cctgtcgtaa cagggagcag gcatcggggc
4441  tctgctacaa ctaccagatc agggtccagt gctgcacgcc cctaccctgc tccacctcta
4501  gcagtccagc ccagaccact cctccaacta cctccaagac cactgaaacc cgggcctcag
4561  gctcctcagc tcccagcagc acacctggca ccgtgtctct ctctacagcc aggacgacac
4621  ctgccccagg taccgctacc tctgtcaaaa aaactttctc aactcccagc cctccgccag
4681  tgccggcaac atcaacatca tccatgtcga ccacggcccc ggggacctct gtggtctcca
4741  gcaagcccac ccccacggag cccagcacat cctcctgcct gcaggagctt tgcacctgga
4801  ccgagtggat cgatggcagc taccctgctc ctggaataaa tggtggagat tttgacacat
4861  ttcaaaattt gagagacgaa ggatacacat tctgtgaaag tcctcgaagc gtgcagtgcc
4921  gggcagagag cttccccaac acgccgctgg cagacctggg gcaggacgtc atctgcagcc
4981  acacagaggg gctgatttgc ctgaacaaga accagctccc acccatctgc tacaactatg
5041  agatccgcat ccagtgttgc gagacggtga acgtgtgcag agacatcacc agactgccaa
5101  agaccgtcgc aacgacacgg ccgactccac atccaaccgg agctcagacc cagaccacct
5161  tcaccacaca catgccctcg gcctccacag agcaacccac ggcaacctcc aggggtgggc
5221  ccacagcaac cagcgtcaca cagggcaccc acaccacact agtcaccaga aactgtcatc
5281  cccggtgcac ctggacaaag tggttcgacg tggacttccc gtcccccgga ccccatggtg
5341  gagacaagga aacctacaac aacatcatca ggagtgggga aaaaatctgc cgccgacctg
5401  aggagatcac caggctccag tgccgagcca agagccaccc agaggtgagc atcgaacacc
5461  tgggccaggt ggtgcagtgc agccgggaag agggcctggt gtgccggaac caggaccagc
```

-continued

```
5521 agggaccctt caagatgtgc ctcaactacg aggtgcgtgt gctctgctgc gagacccccca
5581 gaggctgcca catgacctcc acacctggct ccacctctag cagtccagcc cagaccactc
5641 cttcaacaac ctccaagacc actgaaaccc aggcctcagg ctcctcagcc cccagcagca
5701 cacctggcac cgtgtctctc tctacagcca ggacgacacc tgccccaggt accgctacct
5761 ctgtcaaaaa aactttctca actcccagcc ctccgccagt gccggcaaca tcaacatcat
5821 ccatgtcgac cacggccccg gggacctctg tggtctccag caagcccacc cccacggagc
5881 ccagcacatc ctcctgcctg caggagcttt gcacctggac cgagtggatt gatggcagct
5941 accctgctcc tggaataaat ggtggagatt ttgacacatt tcaaaatttg agagacgaag
6001 gatacacatt ctgtgaaagt cctcgaagcg tgcagtgccg ggcagagagc ttccccaaca
6061 cgccgctggc agacctgggg caggacgtca tctgcagcca cacagagggg ctgatttgcc
6121 tgaacaagaa ccagctccca cccatctgct acaactatga gatccgcatc cagtgttgcg
6181 agacggtgaa cgtgtgcaga gacatcacca gaccgccaaa gaccgtcgca acgacacggc
6241 cgactccaca tccaaccgga gctcagaccc agaccacctt caccacacac atgccctcgg
6301 cctccacaga gcaacccacg gcaacctcca ggggtgggcc cacagcaacc agcgtcacac
6361 agggcaccca caccacacca gtcaccagaa actgtcatcc ccggtgcacc tggacaacgt
6421 ggttcgacgt ggacttcccg tcccccggac cccatggtgg agacaaggaa acctacaaca
6481 acatcatcag gagtggggaa aaaatctgcc gccgacctga ggagatcacc aggctccagt
6541 gccgagccaa gagccaccca gaggtgagca tcgaacacct gggccaggtg gtgcagtgca
6601 gccgggaaga gggcctggtg tgccggaacc aggaccagca gggacccttc aagatgtgcc
6661 tcaactacga ggtgcgtgtg ctctgctgcg agacccccaa aggctgcccc gtgacctcca
6721 cacctgtgac agctcctagc accccctagtg ggagagccac cagcccaact cagagcacct
6781 cctcttggca gaaatccagg acaaccactt tggtgacaac cagcacaacc tccactccac
6841 agaccagtac aacctatgcc catacaacca gcacaacctc tgctcctaca gccagaacaa
6901 cctctgctcc tacaaccaga acaacctctg cctctccagc cagcacaacc tctggtcctg
6961 gaaatactcc cagccctgtt cctaccacca gcacaatctc tgctcctaca actagcataa
7021 cctctgcccc tacaaccagc acaacctctg cccctacaag cagcacaacc tctggtcctg
7081 gaactactcc cagccctgtt cctaccacca gcataacctc tgcccctaca accagcacaa
7141 cctctgctcc tacaaccagc acaacctctg cccgtacaag cagcacaacc tctgccacta
7201 ccaccagcag aatctctggt cctgaaacta ctcccagccc tgttcctacc accagcacaa
7261 cctctgccac tacaaccagc acaacctcag ctcctacaac cagcacaacc tctgccccta
7321 caagcagcac aacctccagt ccacagacca gcacaacctc ggctcctaca accagcacaa
7381 cttctggtcc tggaactacc ccaagccctg ttcccacgac cagcacaacc tctgccccta
7441 caacaagaac aacttctgct cctaaaagca gcacaacctc tgccgctaca accagcacaa
7501 cctctggtcc tgaaactact cctagacctg ttcctaccac cagcacaacc tcttctccta
7561 caaccagcac aacctctgct cctacaacca gcacaacctc tgcttctaca accagcacaa
7621 cctctggtgc tggaactact cccagccctg ttcccaccac cagcacaacc tctgctccta
7681 caaccagcac aacctctgcc cctataagca gcacaacctc tgccactaca accagcacaa
7741 cctctggtcc tggaactact cccagccctg ttcctaccac gagcacaacc tctgctccta
7801 caaccagcac aacctctggt cctggaacta ctcccagtgc tgttcccacc accagcataa
7861 cctctgcacc tacaaccagc acaaactctg cccctataag cagcacaacc tctgccacta
7921 caaccagcag aatctctggt cctgaaacta ctcccagccc tgttcctacc gccagcacaa
```

-continued

```
7981   cctctgcttc tacaactagc acaacctctg gtcctggaac tactcccagc cctgttccta
8041   ccaccagcac aatctctgtt cctaccacca gcacaacttc tgcttctaca accagcacaa
8101   cctctgcttc tacaaccagc acaacctctg gtcctggaac tactcccagc cctgttccca
8161   ccaccagcac aacctctgct cccacaacaa gcacaacctc tgcccctaca accagcacaa
8221   tctcggcccc aacaaccagc acaacctctg ccactacaac cagcacgacc tctgctccta
8281   cacccagaag aacctcagcc cctacaacca gcacaatctc tgcctctacc accagcacaa
8341   cctctgcgac tacaaccagc acaacctctg ctactacaac cagcacaatc tctgccccta
8401   caaccagcac aactttgtct cctacaacca gcacaacctc tactactata accagcacaa
8461   cttctgcccc tataagcagc acaacttcca caccacagac cagcacaact tcggctccta
8521   caaccagcac aacttctggt cctggaacta cttcaagccc tgttcccacc accagcacaa
8581   cctctgcccc tacaaccagc acaacctctg cccctacaac cagaacaacc tctgtcccta
8641   caagcagcac aacctccact gctacaacca gcacaacctc tggccctgga actactccca
8701   gccctgttcc caccaccagt acaacctctg ctcctacaac cagaacaacc tctgctccta
8761   caaccagcac aacctctgcc cctacaacca gcacaacctc tgcccctaca agcagcacaa
8821   cctcagctac tacaaccagc acaatctctg ttcctacaac cagcacaact tctgttcctg
8881   gaactactcc cagccctgtt cctaccacca gcacaatctc tgttcctacc accagcacaa
8941   cttctgcttc tacaaccagc acaacctctg gtcctggaac tactcccagc cctgttccca
9001   ccaccagcac aacctctgct cccacaacaa gcacaacctc tgcccctaca accagcacaa
9061   tctcggcccc aacaaccagc acaccctctg cccctacaac cagcacaacc ttagctccta
9121   caaccagcac aacctctgcc cctacaacca gcacaacctc taccccctaca agcagcacaa
9181   cctcctctcc acagaccagc acaacctcgg cttctaccac cagcataact tctggtcctg
9241   gaactacccc aagccctgtt cccaccacca gcacaacctc tgctcctaca accagcacaa
9301   cctctgccgc tacaaccagc acaatctcgg ccccaacaac cagcacaacg tctgctccta
9361   caaccagcac aacctctgcc tctacagcca gcaaaacctc tggtcttgga actactccca
9421   gccctattcc taccaccagc acaacctctc ctcctacaac cagcacaact tctgcctcta
9481   cagccagcaa aacctctggt cctggaacca ctcccagccc tgttcccacc accagcacaa
9541   tctttgctcc tagaaccagc accacttctg cctctacaac cagcacaacc cctggtcctg
9601   gaaccactcc cagccccgtt cccaccacca gcacagcctc tgtttcaaag accagcacaa
9661   gccatgtttc catatccaag acaacccact cccaaccagt caccagagac tgtcatctcc
9721   ggtgcacctg gaccaagtgg tttgacatag acttcccatc ccctggaccc cacggcgggg
9781   acaaggaaac ctacaacaac atcatcagga gtggggaaaa aatctgccgc cgacctgagg
9841   agatcaccag gctccagtgc cgagccgaga gccacccgga ggtgagcatt gaacacctgg
9901   gccaggtggt gcagtgcagc cgtgaagagg gcctggtgtg ccggaaccag gaccagcagg
9961   gacccttcaa gatgtgcctc aactacgagg tgcgtgtgct ctgctgcgag acccctaaag
10021  gttgccccgt gacctccaca cctgtgacag ctcctagcac ccctagtggg agagccacca
10081  gcccaactca gagcacttcc tcttggcaga aatccaggac aaccactttg gtgacaacca
10141  gcacaacctc cactccacag accagcacaa cctctgctcc tacaaccagc acaacctctg
10201  ctcccacaac cagcacaact tctgccccta caaccagcac aacctccact ccacagacca
10261  gcatatcctc tgcccctaca agcagcacaa cctcggctcc tacaagcagc acaatctctg
10321  ctcgtacaac cagcataatc tctgccccta caaccagcac aacctcttcc cctacaacca
```

-continued 10381 gcacaacctc tgctactaca accagcacaa cctctgcccc tacaagcagc acaacctcca 10441 ctccacagac cagcaaaacc tcagctgcta caagcagcac aacctccggt tctggaacta 10501 ctcccagccc tgttaccacc accagcacag cctctgtttc aaagaccagc acaagccatg 10561 tttctgtatc caagacaacc cactcccaac cagtcaccag agactgtcat ccccggtgca 10621 cctggaccaa atggtttgat gtggactttc catcccctgg accccacggt ggggacaagg 10681 aaacctacaa caacatcatc aggagtgggg aaaaaatctg ccgccgacct gaggagatca 10741 ccaggctcca gtgccgagcc aagagccacc cggaggtgag catcgaacac ctgggccagg 10801 tggtgcagtg cagccgcgaa gagggcctgg tgtgccggaa ccaggaccag cagggaccct 10861 tcaagatgtg cctcaactac gaggtgcgtg tgctttgctg cgagaccccc aaaggctgcc 10921 ccgtgacctc cacatctgtg acagctccta gcacccctag tgggagagcc accagcccaa 10981 ctcagagcac ctcctcttgg cagaaatcca ggacaaccac tttggtgaca agcagcataa 11041 cctccactac acagaccagc acaacctctg cccctacaac tagcacaacc cctgcttcta 11101 tacccagcac aacctctgcc ccaacaacca gcacaacctc tgctcccaca acgagcacaa 11161 cttctgcccc tacaaccagc acaacctcca ctccacagac caccacatcc tctgccccta 11221 caagcagcac aacctcggct cctaccacca gcacaatctc tgcccctaca accagcacaa 11281 tctctgcccc tacaaccagc acaacctctg ctcccacagc cagcacaacg tcagctccta 11341 cgagcacttc ctcggctcct acaaccaaca caacctctgc ccctacaact agcactacct 11401 ctgctcccat aaccagcaca atctctgccc ctacaaccag cacaacctcc actccacaga 11461 ccagcacaat ctcttcccct acaaccagca caacctccac tccgcagacc agcacaacct 11521 cttcccctac aactagcaca acctcagctc ctacaaccag cacaacttct gcccctacaa 11581 ccagcacaac ctccactcca cagaccagca tatcctctgc ccctacaagc agcacaacct 11641 ctgctcctac agccagcaca atctctgccc ctacaaccag cacaacctct ttccatacaa 11701 ccagcacaac ctctccccct acaagcagca caagctccac tccacagacc agcaaaacct 11761 cagctgctac aagcagcaca acctccggtt ctggaactac tcccagcccc gttcccacca 11821 ccagcacagc ctctgtttca aagaccagca caagccatgt ttctgtatcc aagacaaccc 11881 actcccaacc agtcaccaga gactgtcatc cccggtgcac ctggaccaag tggtttgacg 11941 tggactttcc atcccctgga ccccacggtg gggacaagga aacctacaac aacatcatca 12001 ggagtgggga aaaaatctgc cgccgacctg aggagatcac caggctccag tgccgagccg 12061 agagccaccc ggaggtgagc atcgaacacc tgggccaggt ggtgcagtgc agccgggaag 12121 agggcctggt gtgccggaac caggaccagc agggaccctt caagatgtgc ctcaactacg 12181 aggtgcgtgt gctctgctgc gagaccccca aaggctgccc cgtgacctcc acacctgtga 12241 cagctcctag cacccctagt gggagagcca ccagcccaac tcagagcact tcctcttggc 12301 agaaatccag gacaaccact ttggtgacaa ccagcacaac ctccactcca cagaccagca 12361 caacctctgc ccctacaacc agcacaatcc ctgcttctac acccagcaca acctctgccc 12421 ctacaaccag cacaacctct gcccctacaa ccagcacgac ctcagctcct acacacagaa 12481 cgacttctgg tcctacaacc agcacaacct tggctcctac aaccagcaca acctctgctc 12541 caacaaccag cacaaactct gctcctacaa ccagcacaat ctctgcctct acaaccagca 12601 caatctctgc ccctacaacc agcacaatct cttcccctac aagcagcaca acctccactc 12661 cacagaccag caaaacctca gctgctacaa gcagcacaac ctccggttct ggaactactc 12721 caagccctgt tcccaccacc agcacaacct ctgcctctac aaccagcaca acttctgctc 12781 ctacaaccag cacaacctct ggtcctggaa ctactccaag ccctgttccc agcaccagta -continued

```
12841   caacctctgc tgctacaacc agcacaacct ctgctcctac aaccagaaca acatctgctc
12901   ctacaagcag catgacctct ggtcctggaa ctactcccag ccctgttccc accaccagca
12961   caacctctgc tcctacaact agcacaacct ctggtcctgg aactactccc agccctgttc
13021   ccaccaccag cacaacctct gctcctataa ccagcacaac ctctggtcct ggaagtactc
13081   ccagccctgt tcccaccacc agcacaacct ctgctcctac aaccagcaca acctctgcct
13141   ctacagccag cacaacctct ggtcctggaa ctactcccag ccctgttccc accaccagca
13201   caacctctgc tcctacaacc agaacaacct ctgcctctac agccagcaca acctctggtc
13261   ctggaagtac tcccagccct gttcccacca ccagcacaac ctctgctcct acaaccagaa
13321   caacccctgc ctctacagcc agcacaacct ctggtcctgg aactactccc agccctgttc
13381   ccaccacaag cacaacctct gcttctacaa ccagcacaat ctctctccct acaaccagca
13441   caacctctgc tcctataacc agcatgacct ctggtcctgg aactactccc agccctgttc
13501   ccaccaccag cacaacctct gctcctacaa ccagcacaac ctctgcctct acagccagca
13561   caacctctgg tcctggaact actcccagcc ctgttcccac caccagcaca acctctgctc
13621   ctacaaccag cacaacctct gcctctacag ccagcacaac ctctggtcct ggaacttctc
13681   tcagccctgt tcccaccacg agcacaacct ctgctcctac aactagcaca acctctggtc
13741   ctggaactac tcccagccct gttcccacca ccagcacaac ctctgctcct acaaccagca
13801   cgacctctgg tcctggaact actcccagcc ccgttcccac caccagcaca acccctgttt
13861   caaagaccag cacaagccat ctttctgtat ccaagacaac ccactcccaa ccagtcacca
13921   gtgactgtca tcctctgtgc gcctggacaa agtggttcga cgtggacttc ccatcccctg
13981   gaccccacgg cggggacaag gaaacctaca acaacatcat caggagtggg gaaaaaatct
14041   gccgccgacc tgaggagatc accaggctcc agtgccgagc cgagagccac ccggaggtga
14101   acattgaaca cctgggtcag gtggtgcagt gcagccgtga agagggcctg gtgtgccgga
14161   accaggacca gcagggaccc ttcaagatgt gcctcaacta cgaggtgcgc gtgctctgct
14221   gcgagacccc cagaggctgc ccggtgacct ctgtgacccc atatgggact tctcctacca
14281   atgctctgta tccttccctg tctacttcca tggtatccgc ctccgtggca tccacctctg
14341   tggcatccag ctctgtggca tccagctctg tggcttactc cacccaaacc tgcttctgca
14401   acgtggctga ccggctctac cctgcaggat ccaccatata ccgccacaga gacctcgctg
14461   gccattgcta ttatgccctg tgtagccagg actgccaagt ggtcagaggg gttgacagtg
14521   actgtccgtc caccacgctg cctcctgccc cagccacgtc cccttcaata tccacctccg
14581   agcccgtcac tgagctggga tgcccaaatg cggttccccc cagaaagaaa ggtgagacct
14641   gggccacacc caactgctcc gaggccacct gtgagggcaa caacgtcatc tccctgcgcc
14701   cgcgcacgtg cccgagggtg gagaagccca cttgtgccaa cggctacccg gctgtgaagg
14761   tggctgacca agatggctgc tgccatcact accagtgcca gtgtgtgtgc agcggctggg
14821   gtgaccccca ctacatcacc ttcgacggca cctactacac cttcctggac aactgcacgt
14881   acgtgctggt gcagcagatt gtgcccgtgt atggccactt ccgcgtgctc gtcgacaact
14941   acttctgcgg tgcggaggac gggctctcct gcccgaggtc catcatcctg gagtaccacc
15001   aggaccgcgt ggtgctgacc cgcaagccag tccacggggt gatgacaaac gagatcatct
15061   tcaacaacaa ggtggtcagc cccggcttcc ggaaaaacgg catcgtggtc tcgcgcatcg
15121   gcgtcaagat gtacgcgacc atcccggagc tgggagtcca ggtcatgttc tccggcctca
15181   tcttctccgt ggaggtgccc ttcagcaagt ttgccaacaa caccgagggc cagtgcggca
```

-continued

```
15241   cttgcaccaa cgacaggaag gatgagtgcc gcacgcctag gggacggtg gtcgcttcct
15301   gctccgagat gtccggcctc tggaacgtga gcatacccga ccagccagcc tgccaccggc
15361   ctcacccgac gcccaccacg gtcgggccca ccacagttgg gtctaccacg gtcgggccca
15421   ccacagttgg gtctaccacg gtcgggccca ccacaccgcc tgctccgtgc ctgccatcac
15481   ccatctgcca gctgattctg agcaaggtct ttgagccgtg ccacactgtg atcccccccac
15541   tgctgttcta tgagggctgc gtctttgacc ggtgccacat gacggacctg gatgtggtgt
15601   gctccagcct ggagctgtac gcggcactct gtgcgtccca cgacatctgc atcgattgga
15661   gaggccggac cggccacatg tgcccattca cctgcccagc cgacaaggtg taccagccct
15721   gcggcccgag caacccctcc tactgctacg ggaatgacag cgccagcctc ggggctctgc
15781   cggaggccgg ccccatcacc gaaggctgct tctgtccgga gggcatgacc ctcttcagca
15841   ccagtgccca agtctgcgtg cccacgggct gccccaggtg tctggggccc cacggagagc
15901   cggtgaaggt gggccacacc gtcggcatgg actgccagga gtgcacgtgt gaggcggcca
15961   cgtggacgct gacctgccga cccaagctct gcccgctgcc ccctgcctgc cccctgcccg
16021   gcttcgtgcc tgtgcctgca gccccacagg ccggccagtg ctgcccccag tacagctgcg
16081   cctgcaacac cagccgctgc cccgcgcccg tgggctgtcc tgagggcgcc cgcgcgatcc
16141   cgacctacca ggagggggcc tgctgcccag tccaaaactg cagctggaca gtgtgcagca
16201   tcaacgggac cctgtaccag cccggcgccg tggtctcctc gagcctgtgc gaaacctgca
16261   ggtgtgagct gccgggtggc cccccatcgg acgcgtttgt ggtcagctgt gagacccaga
16321   tctgcaacac acactgccct gtgggcttcg agtaccagga gcagagcggg cagtgctgtg
16381   gcacctgtgt gcaggtcgcc tgtgtcacca acaccagcaa gagccccgcc cacctcttct
16441   accccggcga gacctggtca gacgcaggga accactgtgt gacccaccag tgtgagaagc
16501   accaggatgg gctcgtggtg gtcaccacga agaaggcgtg cccccccgctc agctgttctc
16561   tggacgaggc ccgcatgagc aaggacggct gctgccgctt ctgcccgccg cccccgcccc
16621   cgtaccagaa ccagtcgacc tgtgctgtgt accataggag cctgatcatc cagcagcagg
16681   gctgcagctc ctcggagccc gtgcgcctgg cttactgccg gggggaactgt ggggacagct
16741   cttccatgta ctcgctcgag ggcaacacgg tggagcacag gtgccagtgc tgccaggagc
16801   tgcggacctc gctgaggaat gtgaccctgc actgcaccga cggctccagc cgggccttca
16861   gctacaccga ggtggaagag tgcggctgca tgggccggcg gtgccctgcg ccgggcgaca
16921   cccagcactc ggaggaggcg gaacccgagc ccagccagga ggcagagagt gggagctggg
16981   agagaggcgt cccagtgtcc cccatgcact gaccagcact gccgccctcc tgacctccaa
17041   ggagaacctc ccatatgtcc tctgagctcg gcttccaagg ccagtggaac ttgtgcccct
17101   gtccaggcgg ctgcagcttt gaacacactg tccacgcccg ctttcttgtg gagggtgtgg
17161   gctatgggtc acctgctgcc tggaggaggg gcccttaccc accccgcctg cagccacctc
17221   tcaggaccag ccccggggct ggccgagctc ctctggccat gcatccagcc tgctgttctg
17281   gggacgtgag catcacctga gggtctcagg aatgacgctt ggacatggtg atcagctgcc
17341   tggtggctgc aggaggaaga acctcactcc tacctcagcc ctcagcctgc gctcccctcc
17401   tcagtacacg gccaatctgt tgcataaata cacttgagca ttttgcaa
```

In some embodiments, a MUC5AC RNAi agent includes an antisense strand wherein position 19 of the antisense strand (5'→3') is capable of forming a base pair with position 1 of a 19-mer target sequence disclosed in Table 1. In some embodiments, a MUC5AC agent includes an antisense strand wherein position 1 of the antisense strand (5'→3') is capable of forming a base pair with position 19 of a 19-mer target sequence disclosed in Table 1.

In some embodiments, a MUC5AC agent includes an antisense strand wherein position 2 of the antisense strand (5'→3') is capable of forming a base pair with position 18 of a 19-mer target sequence disclosed in Table 1. In some embodiments, a MUC5AC agent includes an antisense strand wherein positions 2 through 18 of the antisense strand (5'→3') are capable of forming base pairs with each of the respective complementary bases located at positions 18 through 2 of the 19-mer target sequence disclosed in Table 1.

For the RNAi agents disclosed herein, the nucleotide at position 1 of the antisense strand (from 5' end→3' end) can be perfectly complementary to a MUC5AC gene, or can be non-complementary to a MUC5AC gene. In some embodiments, the nucleotide at position 1 of the antisense strand (from 5' end→3' end) is a U, A, or dT. In some embodiments, the nucleotide at position 1 of the antisense strand (from 5' end→3' end) forms an A:U or U:A base pair with the sense strand.

In some embodiments, a MUC5AC RNAi agent antisense strand comprises the sequence of nucleotides (from 5' end→3' end) 2-18 or 2-19 of any of the antisense strand sequences in Table 2, Table 3, or Table 11. In some embodiments, a MUC5AC RNAi sense strand comprises the sequence of nucleotides (from 5' end→3' end) 1-17, 1-18, or 2-18 of any of the sense strand sequences in Table 2, Table 4, Table 5, Table 6, or Table 7.

In some embodiments, a MUC5AC RNAi agent is comprised of (i) an antisense strand comprising the sequence of nucleotides (from 5' end→3' end) 1-18, 1-19, or 2-19 of any of the antisense strand sequences in Table 2 or Table 3, and (ii) a sense strand comprising the sequence of nucleotides (from 5' end→3' end) 2-19, 1-19, 1-18, or 2-18 of any of the sense strand sequences in Table 2, Table 4, Table 5, Table 6, or Table 7.

In some embodiments, the MUC5AC RNAi agents include core 19-mer nucleotide sequences shown in the following Table 2.

TABLE 2

MUC5AC RNAi Agent Antisense Strand and Sense Strand Core Stretch Base Sequences (N = any nucleobase; I = inosine (hypoxanthine nucleobase)

| SEQ ID NO:. | Antisense Strand Base Sequence (5' → 3') (Shown as an Unmodified Nucleotide Sequence) | SEQ ID NO:. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 79 | UUGUAGUAGUCGCAGAACA | 568 | UGUUCUGCGACUACUACAA | 3535-3553 | 3535 |
| 80 | NUGUAGUAGUCGCAGAACA | 569 | UGUUCUGCGACUACUACAN | 3535-3553 | 3535 |
| 81 | UUGUAGUAGUCGCAGAACN | 570 | NGUUCUGCGACUACUACAA | 3535-3553 | 3535 |
| 82 | NUGUAGUAGUCGCAGAACN | 571 | NGUUCUGCGACUACUACAN | 3535-3553 | 3535 |
| 83 | UUCUUGUUCAGGCAAAUCA | 572 | UGAUUUGCCUGAACAAGAA | 4993-5011 | 4993 |
| 84 | NUCUUGUUCAGGCAAAUCA | 573 | UGAUUUGCCUGAACAAGAN | 4993-5011 | 4993 |
| 85 | UUCUUGUUCAGGCAAAUCN | 574 | NGAUUUGCCUGAACAAGAA | 4993-5011 | 4993 |
| 86 | NUCUUGUUCAGGCAAAUCN | 575 | NGAUUUGCCUGAACAAGAN | 4993-5011 | 4993 |
| 87 | CUUGAUGGCCUUGGAGCAG | 576 | CUGCUCCAAGGCCAUCAAG | 2924-2942 | 2924 |
| 88 | UUUGAUGGCCUUGGAGCAG | 577 | CUGCUCCAAGGCCAUCAAA | 2924-2942 | 2924 |
| 89 | NUUGAUGGCCUUGGAGCAG | 578 | CUGCUCCAAGGCCAUCAAN | 2924-2942 | 2924 |
| 90 | UUUGAUGGCCUUGGAGCAN | 579 | NUGCUCCAAGGCCAUCAAA | 2924-2942 | 2924 |
| 91 | NUUGAUGGCCUUGGAGCAN | 580 | NUGCUCCAAGGCCAUCAAN | 2924-2942 | 2924 |
| 92 | AAUCUUGAUGGCCUUGGAG | 581 | CUCCAAGGCCAUCAAGAUU | 2927-2945 | 2927 |
| 93 | AAUCUUGAUGGCCUUGGAN | 582 | NUCCAAGGCCAUCAAGAUU | 2927-2945 | 2927 |
| 94 | UAUCUUGAUGGCCUUGGAG | 583 | CUCCAAGGCCAUCAAGAUA | 2927-2945 | 2927 |
| 95 | UAUCUUGAUGGCCUUGGAN | 584 | NUCCAAGGCCAUCAAGAUA | 2927-2945 | 2927 |
| 96 | NAUCUUGAUGGCCUUGGAG | 585 | CUCCAAGGCCAUCAAGAUN | 2927-2945 | 2927 |
| 97 | NAUCUUGAUGGCCUUGGAN | 586 | NUCCAAGGCCAUCAAGAUN | 2927-2945 | 2927 |
| 98 | CUUGAACUCGGGGCUGAGG | 587 | CCUCAGCCCCGAGUUCAAG | 3116-3134 | 3116 |
| 99 | UUUGAACUCGGGGCUGAGG | 588 | CCUCAGCCCCGAGUUCAAA | 3116-3134 | 3116 |
| 100 | NUUGAACUCGGGGCUGAGG | 589 | CCUCAGCCCCGAGUUCAAN | 3116-3134 | 3116 |
| 101 | UUUGAACUCGGGGCUGAGN | 590 | NCUCAGCCCCGAGUUCAAA | 3116-3134 | 3116 |
| 102 | NUUGAACUCGGGGCUGAGN | 591 | NCUCAGCCCCGAGUUCAAN | 3116-3134 | 3116 |

TABLE 2-continued

MUC5AC RNAi Agent Antisense Strand and Sense Strand Core Stretch Base Sequences (N = any nucleobase; I = inosine (hypoxanthine nucleobase))

| SEQ ID NO:. | Antisense Strand Base Sequence (5' → 3') (Shown as an Unmodified Nucleotide Sequence) | SEQ ID NO:. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 103 | GGAUGCUGCACUGCUUCUG | 592 | CAGAAGCAGUGCAGCAUCC | 3321-3339 | 3321 |
| 104 | UGAUGCUGCACUGCUUCUG | 593 | CAGAAGCAGUGCAGCAUCA | 3321-3339 | 3321 |
| 105 | NGAUGCUGCACUGCUUCUG | 594 | CAGAAGCAGUGCAGCAUCN | 3321-3339 | 3321 |
| 106 | UGAUGCUGCACUGCUUCUN | 595 | NAGAAGCAGUGCAGCAUCA | 3321-3339 | 3321 |
| 107 | NGAUGCUGCACUGCUUCUN | 596 | NAGAAGCAGUGCAGCAUCN | 3321-3339 | 3321 |
| 108 | UGAUGCUGCACUGCUUCUG | 597 | CAGAAGCAGUGCAICAUCA | 3321-3339 | 3321 |
| 109 | UGAUGCUGCACUGCUUCUN | 598 | NAGAAGCAGUGCAICAUCA | 3321-3339 | 3321 |
| 110 | NGAUGCUGCACUGCUUCUG | 599 | CAGAAGCAGUGCAICAUCN | 3321-3339 | 3321 |
| 111 | NGAUGCUGCACUGCUUCUN | 600 | NAGAAGCAGUGCAICAUCN | 3321-3339 | 3321 |
| 112 | GUAGUCGCAGAACAGAGGG | 601 | CCCUCUGUUCUGCGACUAC | 3530-3548 | 3530 |
| 113 | UUAGUCGCAGAACAGAGGG | 602 | CCCUCUGUUCUGCGACUAA | 3530-3548 | 3530 |
| 114 | UUAGUCGCAGAACAGAGGN | 603 | NCCUCUGUUCUGCGACUAA | 3530-3548 | 3530 |
| 115 | NUAGUCGCAGAACAGAGGG | 604 | CCCUCUGUUCUGCGACUAN | 3530-3548 | 3530 |
| 116 | NUAGUCGCAGAACAGAGGN | 605 | NCCUCUGUUCUGCGACUAN | 3530-3548 | 3530 |
| 117 | UUAGUCGCAGAACAGAGGG | 606 | CCCUCUGUUCUGCIACUAA | 3530-3548 | 3530 |
| 118 | UUAGUCGCAGAACAGAGGN | 607 | NCCUCUGUUCUGCIACUAA | 3530-3548 | 3530 |
| 119 | NUAGUCGCAGAACAGAGGG | 608 | CCCUCUGUUCUGCIACUAN | 3530-3548 | 3530 |
| 120 | NUAGUCGCAGAACAGAGGN | 609 | NCCUCUGUUCUGCIACUAN | 3530-3548 | 3530 |
| 121 | AGUAGUCGCAGAACAGAGG | 610 | CCUCUGUUCUGCGACUACU | 3531-3549 | 3531 |
| 122 | AGUAGUCGCAGAACAGAGN | 611 | NCUCUGUUCUGCGACUACU | 3531-3549 | 3531 |
| 123 | UGUAGUCGCAGAACAGAGG | 612 | CCUCUGUUCUGCGACUACA | 3531-3549 | 3531 |
| 124 | UGUAGUCGCAGAACAGAGN | 613 | NCUCUGUUCUGCGACUACA | 3531-3549 | 3531 |
| 125 | NGUAGUCGCAGAACAGAGG | 614 | CCUCUGUUCUGCGACUACN | 3531-3549 | 3531 |
| 126 | NGUAGUCGCAGAACAGAGN | 615 | NCUCUGUUCUGCGACUACN | 3531-3549 | 3531 |
| 127 | AGUAGUCGCAGAACAGAGG | 616 | CCUCUGUUCUICGACUACU | 3531-3549 | 3531 |
| 128 | AGUAGUCGCAGAACAGAGN | 617 | NCUCUGUUCUICGACUACU | 3531-3549 | 3531 |
| 129 | UGUAGUCGCAGAACAGAGG | 618 | CCUCUGUUCUICGACUACA | 3531-3549 | 3531 |
| 130 | UGUAGUCGCAGAACAGAGN | 619 | NCUCUGUUCUICGACUACA | 3531-3549 | 3531 |
| 131 | NGUAGUCGCAGAACAGAGG | 620 | CCUCUGUUCUICGACUACN | 3531-3549 | 3531 |
| 132 | NGUAGUCGCAGAACAGAGN | 621 | NCUCUGUUCUICGACUACN | 3531-3549 | 3531 |
| 133 | GUAGUAGUCGCAGAACAGA | 622 | UCUGUUCUGCGACUACUAC | 3533-3551 | 3533 |
| 134 | UUAGUAGUCGCAGAACAGA | 623 | UCUGUUCUGCGACUACUAA | 3533-3551 | 3533 |
| 135 | NUAGUAGUCGCAGAACAGA | 624 | UCUGUUCUGCGACUACUAN | 3533-3551 | 3533 |
| 136 | NUAGUAGUCGCAGAACAGN | 625 | NCUGUUCUGCGACUACUAN | 3533-3551 | 3533 |
| 137 | UGUAGUAGUCGCAGAACAG | 626 | CUGUUCUGCGACUACUACA | 3534-3552 | 3534 |

TABLE 2-continued

MUC5AC RNAi Agent Antisense Strand and Sense Strand Core Stretch Base Sequences (N = any nucleobase; I = inosine (hypoxanthine nucleobase))

| SEQ ID NO:. | Antisense Strand Base Sequence (5' → 3') (Shown as an Unmodified Nucleotide Sequence) | SEQ ID NO:. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 138 | NGUAGUAGUCGCAGAACAG | 627 | CUGUUCUGCGACUACUACN | 3534-3552 | 3534 |
| 139 | NGUAGUAGUCGCAGAACAN | 628 | NUGUUCUGCGACUACUACN | 3534-3552 | 3534 |
| 140 | AUAGUUGUAGCAGAUGGGU | 629 | ACCCAUCUGCUACAACUAU | 5021-5039 | 5021 |
| 141 | AUAGUUGUAGCAGAUGGGN | 630 | NCCCAUCUGCUACAACUAU | 5021-5039 | 5021 |
| 142 | UUAGUUGUAGCAGAUGGGU | 631 | ACCCAUCUGCUACAACUAA | 5021-5039 | 5021 |
| 143 | UUAGUUGUAGCAGAUGGGN | 632 | NCCCAUCUGCUACAACUAA | 5021-5039 | 5021 |
| 144 | NUAGUUGUAGCAGAUGGGU | 633 | ACCCAUCUGCUACAACUAN | 5021-5039 | 5021 |
| 145 | NUAGUUGUAGCAGAUGGGN | 634 | NCCCAUCUGCUACAACUAN | 5021-5039 | 5021 |
| 146 | GUCCACGUCGAACCACUUU | 635 | AAAGUGGUUCGACGUGGAC | 5297-5315 | 5297 |
| 147 | UUCCACGUCGAACCACUUU | 636 | AAAGUGGUUCGACGUGGAA | 5297-5315 | 5297 |
| 148 | UUCCACGUCGAACCACUUN | 637 | NAAGUGGUUCGACGUGGAA | 5297-5315 | 5297 |
| 149 | NUCCACGUCGAACCACUUU | 638 | AAAGUGGUUCGACGUGGAN | 5297-5315 | 5297 |
| 150 | NUCCACGUCGAACCACUUN | 639 | NAAGUGGUUCGACGUGGAN | 5297-5315 | 5297 |
| 151 | UUCCACGUCGAACCACUUU | 640 | AAAGUGGUUCGACIUGGAA | 5297-5315 | 5297 |
| 152 | UUCCACGUCGAACCACUUN | 641 | NAAGUGGUUCGACIUGGAA | 5297-5315 | 5297 |
| 153 | NUCCACGUCGAACCACUUU | 642 | AAAGUGGUUCGACIUGGAN | 5297-5315 | 5297 |
| 154 | NUCCACGUCGAACCACUUN | 643 | NAAGUGGUUCGACIUGGAN | 5297-5315 | 5297 |
| 155 | GAAGUCCACGUCGAACCAC | 644 | GUGGUUCGACGUGGACUUC | 5300-5318 | 5300 |
| 156 | UAAGUCCACGUCGAACCAC | 645 | GUGGUUCGACGUGGACUUA | 5300-5318 | 5300 |
| 157 | UAAGUCCACGUCGAACCAN | 646 | NUGGUUCGACGUGGACUUA | 5300-5318 | 5300 |
| 158 | NAAGUCCACGUCGAACCAC | 647 | GUGGUUCGACGUGGACUUN | 5300-5318 | 5300 |
| 159 | NAAGUCCACGUCGAACCAN | 648 | NUGGUUCGACGUGGACUUN | 5300-5318 | 5300 |
| 160 | UAAGUCCACGUCGAACCAC | 649 | GUGGUUCGACGUGIACUUA | 5300-5318 | 5300 |
| 161 | UAAGUCCACGUCGAACCAN | 650 | NUGGUUCGACGUGIACUUA | 5300-5318 | 5300 |
| 162 | NAAGUCCACGUCGAACCAC | 651 | GUGGUUCGACGUGIACUUN | 5300-5318 | 5300 |
| 163 | NAAGUCCACGUCGAACCAN | 652 | NUGGUUCGACGUGIACUUN | 5300-5318 | 5300 |
| 164 | GGGAAGUCCACGUCGAACC | 653 | GGUUCGACGUGGACUUCCC | 5302-5320 | 5302 |
| 165 | UGGAAGUCCACGUCGAACC | 654 | GGUUCGACGUGGACUUCCA | 5302-5320 | 5302 |
| 166 | UGGAAGUCCACGUCGAACN | 655 | NGUUCGACGUGGACUUCCA | 5302-5320 | 5302 |
| 167 | NGGAAGUCCACGUCGAACC | 656 | GGUUCGACGUGGACUUCCN | 5302-5320 | 5302 |
| 168 | NGGAAGUCCACGUCGAACN | 657 | NGUUCGACGUGGACUUCCN | 5302-5320 | 5302 |
| 169 | UGGAAGUCCACGUCGAACC | 658 | GGUUCGACGUGIACUUCCA | 5302-5320 | 5302 |
| 170 | UGGAAGUCCACGUCGAACN | 659 | NGUUCGACGUGIACUUCCA | 5302-5320 | 5302 |
| 171 | NGGAAGUCCACGUCGAACC | 660 | GGUUCGACGUGIACUUCCN | 5302-5320 | 5302 |
| 172 | NGGAAGUCCACGUCGAACN | 661 | NGUUCGACGUGIACUUCCN | 5302-5320 | 5302 |

TABLE 2-continued

MUC5AC RNAi Agent Antisense Strand and Sense Strand Core Stretch Base Sequences (N = any nucleobase; I = inosine (hypoxanthine nucleobase))

| SEQ ID NO:. | Antisense Strand Base Sequence (5' → 3') (Shown as an Unmodified Nucleotide Sequence) | SEQ ID NO:. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 173 | AGAUGCUGGUCUUCUUGUC | 662 | GACAAGAAGACCAGCAUCU | 3090-3108 | 3090 |
| 174 | AGAUGCUGGUCUUCUUGUN | 663 | NACAAGAAGACCAGCAUCU | 3090-3108 | 3090 |
| 175 | UGAUGCUGGUCUUCUUGUC | 664 | GACAAGAAGACCAGCAUCA | 3090-3108 | 3090 |
| 176 | UGAUGCUGGUCUUCUUGUN | 665 | NACAAGAAGACCAGCAUCA | 3090-3108 | 3090 |
| 177 | NGAUGCUGGUCUUCUUGUC | 666 | GACAAGAAGACCAGCAUCN | 3090-3108 | 3090 |
| 178 | NGAUGCUGGUCUUCUUGUN | 667 | NACAAGAAGACCAGCAUCN | 3090-3108 | 3090 |
| 179 | AGAUGCUGGUCUUCUUGUC | 668 | GACAAGAAGACCAICAUCU | 3090-3108 | 3090 |
| 180 | AGAUGCUGGUCUUCUUGUN | 669 | NACAAGAAGACCAICAUCU | 3090-3108 | 3090 |
| 181 | UGAUGCUGGUCUUCUUGUC | 670 | GACAAGAAGACCAICAUCA | 3090-3108 | 3090 |
| 182 | UGAUGCUGGUCUUCUUGUN | 671 | NACAAGAAGACCAICAUCA | 3090-3108 | 3090 |
| 183 | NGAUGCUGGUCUUCUUGUC | 672 | GACAAGAAGACCAICAUCN | 3090-3108 | 3090 |
| 184 | NGAUGCUGGUCUUCUUGUN | 673 | NACAAGAAGACCAICAUCN | 3090-3108 | 3090 |
| 185 | GGUUGAUGAAGAUGCUGGU | 674 | ACCAGCAUCUUCAUCAACC | 3099-3117 | 3099 |
| 186 | UGUUGAUGAAGAUGCUGGN | 675 | NCCAGCAUCUUCAUCAACC | 3099-3117 | 3099 |
| 187 | NGUUGAUGAAGAUGCUGGU | 676 | ACCAGCAUCUUCAUCAACN | 3099-3117 | 3099 |
| 188 | NGUUGAUGAAGAUGCUGGN | 677 | NCCAGCAUCUUCAUCAACN | 3099-3117 | 3099 |
| 189 | AUGUUGUUGUAGGUUUCCU | 678 | AGGAAACCUACAACAACAU | 5347-5365 | 5347 |
| 190 | AUGUUGUUGUAGGUUUCCN | 679 | NGGAAACCUACAACAACAU | 5347-5365 | 5347 |
| 191 | UUGUUGUUGUAGGUUUCCU | 680 | AGGAAACCUACAACAACAA | 5347-5365 | 5347 |
| 192 | UUGUUGUUGUAGGUUUCCN | 681 | NGGAAACCUACAACAACAA | 5347-5365 | 5347 |
| 193 | NUGUUGUUGUAGGUUUCCN | 682 | NGGAAACCUACAACAACAN | 5347-5365 | 5347 |
| 194 | AUGAUGUUGUUGUAGGUUU | 683 | AAACCUACAACAACAUCAU | 5350-5368 | 5350 |
| 195 | AUGAUGUUGUUGUAGGUUN | 684 | NAACCUACAACAACAUCAU | 5350-5368 | 5350 |
| 196 | UUGAUGUUGUUGUAGGUUU | 685 | AAACCUACAACAACAUCAA | 5350-5368 | 5350 |
| 197 | UUGAUGUUGUUGUAGGUUN | 686 | NAACCUACAACAACAUCAA | 5350-5368 | 5350 |
| 198 | NUGAUGUUGUUGUAGGUUN | 687 | NAACCUACAACAACAUCAN | 5350-5368 | 5350 |
| 199 | UUGAUGAAGAUGCUGGUCU | 688 | AGACCAGCAUCUUCAUCAA | 3097-3115 | 3097 |
| 200 | UUGAUGAAGAUGCUGGUCN | 689 | NGACCAGCAUCUUCAUCAA | 3097-3115 | 3097 |
| 201 | NUGAUGAAGAUGCUGGUCU | 690 | AGACCAGCAUCUUCAUCAN | 3097-3115 | 3097 |
| 202 | NUGAUGAAGAUGCUGGUCN | 691 | NGACCAGCAUCUUCAUCAN | 3097-3115 | 3097 |
| 203 | UGAUCUGGUAGUUGUAGCA | 692 | UGCUACAACUACCAGAUCA | 4443-4461 | 4443 |
| 204 | UGAUCUGGUAGUUGUAGCN | 693 | NGCUACAACUACCAGAUCA | 4443-4461 | 4443 |
| 205 | NGAUCUGGUAGUUGUAGCA | 694 | UGCUACAACUACCAGAUCN | 4443-4461 | 4443 |
| 206 | NGAUCUGGUAGUUGUAGCN | 695 | NGCUACAACUACCAGAUCN | 4443-4461 | 4443 |
| 207 | UGAUCUGGUAGUUGUAGCN | 696 | NGCUACAACUACCAIAUCA | 4443-4461 | 4443 |

TABLE 2-continued

MUC5AC RNAi Agent Antisense Strand and Sense Strand Core Stretch Base Sequences (N = any nucleobase; I = inosine (hypoxanthine nucleobase))

| SEQ ID NO:. | Antisense Strand Base Sequence (5' → 3') (Shown as an Unmodified Nucleotide Sequence) | SEQ ID NO:. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 208 | NGAUCUGGUAGUUGUAGCA | 697 | UGCUACAACUACCAIAUCN | 4443-4461 | 4443 |
| 209 | NGAUCUGGUAGUUGUAGCN | 698 | NGCUACAACUACCAIAUCN | 4443-4461 | 4443 |
| 210 | UGAUCUGGUAGUUGUAGCN | 699 | NGCUACAACUACCAIAUCA | 4443-4461 | 4443 |
| 211 | CCCUGAUCUGGUAGUUGUA | 700 | UACAACUACCAGAUCAGGG | 4446-4464 | 4446 |
| 212 | UCCUGAUCUGGUAGUUGUA | 701 | UACAACUACCAGAUCAGGA | 4446-4464 | 4446 |
| 213 | NCCUGAUCUGGUAGUUGUA | 702 | UACAACUACCAGAUCAGGN | 4446-4464 | 4446 |
| 214 | UCCUGAUCUGGUAGUUGUN | 703 | NACAACUACCAGAUCAGGA | 4446-4464 | 4446 |
| 215 | NCCUGAUCUGGUAGUUGUN | 704 | NACAACUACCAGAUCAGGN | 4446-4464 | 4446 |
| 216 | CCCUGAUCUGGUAGUUGUA | 705 | UACAACUACCAGAUCAIGG | 4446-4464 | 4446 |
| 217 | UCCUGAUCUGGUAGUUGUA | 706 | UACAACUACCAGAUCAIGA | 4446-4464 | 4446 |
| 218 | NCCUGAUCUGGUAGUUGUA | 707 | UACAACUACCAGAUCAIGN | 4446-4464 | 4446 |
| 219 | UCCUGAUCUGGUAGUUGUN | 708 | NACAACUACCAGAUCAIGA | 4446-4464 | 4446 |
| 220 | NCCUGAUCUGGUAGUUGUN | 709 | NACAACUACCAGAUCAIGN | 4446-4464 | 4446 |
| 221 | UAGUUGUAGCAGAUGGGUG | 710 | CACCCAUCUGCUACAACUA | 5020-5038 | 5020 |
| 222 | NAGUUGUAGCAGAUGGGUG | 711 | CACCCAUCUGCUACAACUN | 5020-5038 | 5020 |
| 223 | UAGUUGUAGCAGAUGGGUN | 712 | NACCCAUCUGCUACAACUA | 5020-5038 | 5020 |
| 224 | NAGUUGUAGCAGAUGGGUN | 713 | NACCCAUCUGCUACAACUN | 5020-5038 | 5020 |
| 225 | GCAACACUGGAUGCGGAUC | 714 | GAUCCGCAUCCAGUGUUGC | 5042-5060 | 5042 |
| 226 | UCAACACUGGAUGCGGAUC | 715 | GAUCCGCAUCCAGUGUUGA | 5042-5060 | 5042 |
| 227 | NCAACACUGGAUGCGGAUC | 716 | GAUCCGCAUCCAGUGUUGA | 5042-5060 | 5042 |
| 228 | UCAACACUGGAUGCGGAUN | 717 | NAUCCGCAUCCAGUGUUGN | 5042-5060 | 5042 |
| 229 | NCAACACUGGAUGCGGAUN | 718 | NAUCCGCAUCCAGUGUUGN | 5042-5060 | 5042 |
| 230 | GCAACACUGGAUGCGGAUC | 719 | GAUCCGCAUCCAGUIUUGC | 5042-5060 | 5042 |
| 231 | UCAACACUGGAUGCGGAUC | 720 | GAUCCGCAUCCAGUIUUGA | 5042-5060 | 5042 |
| 232 | NCAACACUGGAUGCGGAUC | 721 | GAUCCGCAUCCAGUIUUGA | 5042-5060 | 5042 |
| 233 | UCAACACUGGAUGCGGAUN | 722 | NAUCCGCAUCCAGUIUUGN | 5042-5060 | 5042 |
| 234 | NCAACACUGGAUGCGGAUN | 723 | NAUCCGCAUCCAGUIUUGN | 5042-5060 | 5042 |
| 235 | GUGUUCGAUGCUCACCUCU | 724 | AGAGGUGAGCAUCGAACAC | 5441-5459 | 5441 |
| 236 | UUGUUCGAUGCUCACCUCU | 725 | AGAGGUGAGCAUCGAACAA | 5441-5459 | 5441 |
| 237 | NUGUUCGAUGCUCACCUCU | 726 | AGAGGUGAGCAUCGAACAN | 5441-5459 | 5441 |
| 238 | UUGUUCGAUGCUCACCUCN | 727 | NGAGGUGAGCAUCGAACAA | 5441-5459 | 5441 |
| 239 | NUGUUCGAUGCUCACCUCN | 728 | NGAGGUGAGCAUCGAACAN | 5441-5459 | 5441 |
| 240 | GUGUUCGAUGCUCACCUCU | 729 | AGAGGUGAGCAUCIAACAC | 5441-5459 | 5441 |
| 241 | UUGUUCGAUGCUCACCUCU | 730 | AGAGGUGAGCAUCIAACAA | 5441-5459 | 5441 |
| 242 | NUGUUCGAUGCUCACCUCU | 731 | AGAGGUGAGCAUCIAACAN | 5441-5459 | 5441 |

TABLE 2-continued

MUC5AC RNAi Agent Antisense Strand and Sense Strand Core Stretch Base Sequences (N = any nucleobase; I = inosine (hypoxanthine nucleobase)

| SEQ ID NO:. | Antisense Strand Base Sequence (5' → 3') (Shown as an Unmodified Nucleotide Sequence) | SEQ ID NO:. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 243 | UUGUUCGAUGCUCACCUCN | 732 | NGAGGUGAGCAUCIAACAA | 5441-5459 | 5441 |
| 244 | NUGUUCGAUGCUCACCUCN | 733 | NGAGGUGAGCAUCIAACAN | 5441-5459 | 5441 |
| 245 | CAUCUUGAAGGGUCCCUGC | 734 | GCAGGGACCCUUCAAGAUG | 5519-5537 | 5519 |
| 246 | UAUCUUGAAGGGUCCCUGC | 735 | GCAGGGACCCUUCAAGAUA | 5519-5537 | 5519 |
| 247 | NAUCUUGAAGGGUCCCUGC | 736 | GCAGGGACCCUUCAAGAUN | 5519-5537 | 5519 |
| 248 | UAUCUUGAAGGGUCCCUGN | 737 | NCAGGGACCCUUCAAGAUA | 5519-5537 | 5519 |
| 249 | NAUCUUGAAGGGUCCCUGN | 738 | NCAGGGACCCUUCAAGAUN | 5519-5537 | 5519 |
| 250 | UCGUAGUUGAGGCACAUCU | 739 | AGAUGUGCCUCAACUACGA | 5533-5551 | 5533 |
| 251 | NCGUAGUUGAGGCACAUCU | 740 | AGAUGUGCCUCAACUACGN | 5533-5551 | 5533 |
| 252 | UCGUAGUUGAGGCACAUCN | 741 | NGAUGUGCCUCAACUACGA | 5533-5551 | 5533 |
| 253 | NCGUAGUUGAGGCACAUCN | 742 | NGAUGUGCCUCAACUACGN | 5533-5551 | 5533 |
| 254 | UCGUAGUUGAGGCACAUCU | 743 | AGAUGUGCCUCAACUACIA | 5533-5551 | 5533 |
| 255 | NCGUAGUUGAGGCACAUCU | 744 | AGAUGUGCCUCAACUACIN | 5533-5551 | 5533 |
| 256 | UCGUAGUUGAGGCACAUCN | 745 | NGAUGUGCCUCAACUACIA | 5533-5551 | 5533 |
| 257 | NCGUAGUUGAGGCACAUCN | 746 | NGAUGUGCCUCAACUACIN | 5533-5551 | 5533 |
| 258 | CCUCGUAGUUGAGGCACAU | 747 | AUGUGCCUCAACUACGAGG | 5535-5553 | 5535 |
| 259 | UCUCGUAGUUGAGGCACAU | 748 | AUGUGCCUCAACUACGAGA | 5535-5553 | 5535 |
| 260 | NCUCGUAGUUGAGGCACAU | 749 | AUGUGCCUCAACUACGAGN | 5535-5553 | 5535 |
| 261 | UCUCGUAGUUGAGGCACAN | 750 | NUGUGCCUCAACUACGAGA | 5535-5553 | 5535 |
| 262 | NCUCGUAGUUGAGGCACAN | 751 | NUGUGCCUCAACUACGAGN | 5535-5553 | 5535 |
| 263 | CCUCGUAGUUGAGGCACAU | 752 | AUGUGCCUCAACUACIAGG | 5535-5553 | 5535 |
| 264 | UCUCGUAGUUGAGGCACAU | 753 | AUGUGCCUCAACUACIAGA | 5535-5553 | 5535 |
| 265 | NCUCGUAGUUGAGGCACAU | 754 | AUGUGCCUCAACUACIAGN | 5535-5553 | 5535 |
| 266 | UCUCGUAGUUGAGGCACAN | 755 | NUGUGCCUCAACUACIAGA | 5535-5553 | 5535 |
| 267 | NCUCGUAGUUGAGGCACAN | 756 | NUGUGCCUCAACUACIAGN | 5535-5553 | 5535 |
| 268 | CUUCAGGCAGGUCUCGCUG | 757 | CAGCGAGACCUGCCUGAAG | 1493-1511 | 1493 |
| 269 | UUUCAGGCAGGUCUCGCUG | 758 | CAGCGAGACCUGCCUGAAA | 1493-1511 | 1493 |
| 270 | NUUCAGGCAGGUCUCGCUG | 759 | CAGCGAGACCUGCCUGAAN | 1493-1511 | 1493 |
| 271 | UUUCAGGCAGGUCUCGCUN | 760 | NAGCGAGACCUGCCUGAAA | 1493-1511 | 1493 |
| 272 | NUUCAGGCAGGUCUCGCUN | 761 | NAGCGAGACCUGCCUGAAN | 1493-1511 | 1493 |
| 273 | GUCUGAAGAUGGUGACGUU | 762 | AACGUCACCAUCUUCAGAC | 1617-1635 | 1617 |
| 274 | UUCUGAAGAUGGUGACGUU | 763 | AACGUCACCAUCUUCAGAA | 1617-1635 | 1617 |
| 275 | NUCUGAAGAUGGUGACGUU | 764 | AACGUCACCAUCUUCAGAN | 1617-1635 | 1617 |
| 276 | UUCUGAAGAUGGUGACGUN | 765 | NACGUCACCAUCUUCAGAA | 1617-1635 | 1617 |
| 277 | NUCUGAAGAUGGUGACGUN | 766 | NACGUCACCAUCUUCAGAN | 1617-1635 | 1617 |

TABLE 2-continued

MUC5AC RNAi Agent Antisense Strand and Sense Strand Core Stretch Base Sequences (N = any nucleobase; I = inosine (hypoxanthine nucleobase)

| SEQ ID NO:. | Antisense Strand Base Sequence (5' → 3') (Shown as an Unmodified Nucleotide Sequence) | SEQ ID NO:. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 278 | GGUCUGAAGAUGGUGACGU | 767 | ACGUCACCAUCUUCAGACC | 1618-1636 | 1618 |
| 279 | UGUCUGAAGAUGGUGACGU | 768 | ACGUCACCAUCUUCAGACA | 1618-1636 | 1618 |
| 280 | NGUCUGAAGAUGGUGACGU | 769 | ACGUCACCAUCUUCAGACN | 1618-1636 | 1618 |
| 281 | UGUCUGAAGAUGGUGACGN | 770 | NCGUCACCAUCUUCAGACA | 1618-1636 | 1618 |
| 282 | NGUCUGAAGAUGGUGACGN | 771 | NCGUCACCAUCUUCAGACN | 1618-1636 | 1618 |
| 283 | GGUCUGAAGAUGGUGACGU | 772 | ACGUCACCAUCUUCAIACC | 1618-1636 | 1618 |
| 284 | UGUCUGAAGAUGGUGACGU | 773 | ACGUCACCAUCUUCAIACA | 1618-1636 | 1618 |
| 285 | NGUCUGAAGAUGGUGACGU | 774 | ACGUCACCAUCUUCAIACN | 1618-1636 | 1618 |
| 286 | UGUCUGAAGAUGGUGACGN | 775 | NCGUCACCAUCUUCAIACA | 1618-1636 | 1618 |
| 287 | NGUCUGAAGAUGGUGACGN | 776 | NCGUCACCAUCUUCAIACN | 1618-1636 | 1618 |
| 288 | CGGAAGUCAUCGGCCUGGA | 777 | UCCAGGCCGAUGACUUCCG | 1777-1795 | 1777 |
| 289 | UGGAAGUCAUCGGCCUGGA | 778 | UCCAGGCCGAUGACUUCCA | 1777-1795 | 1777 |
| 290 | NGGAAGUCAUCGGCCUGGA | 779 | UCCAGGCCGAUGACUUCCN | 1777-1795 | 1777 |
| 291 | UGGAAGUCAUCGGCCUGGN | 780 | NCCAGGCCGAUGACUUCCA | 1777-1795 | 1777 |
| 292 | NGGAAGUCAUCGGCCUGGN | 781 | NCCAGGCCGAUGACUUCCN | 1777-1795 | 1777 |
| 293 | CUUGAAGGUGUUGAAGAAG | 782 | CUUCUUCAACACCUUCAAG | 1832-1850 | 1832 |
| 294 | UUUGAAGGUGUUGAAGAAG | 783 | CUUCUUCAACACCUUCAAA | 1832-1850 | 1832 |
| 295 | NUUGAAGGUGUUGAAGAAG | 784 | CUUCUUCAACACCUUCAAN | 1832-1850 | 1832 |
| 296 | UUUGAAGGUGUUGAAGAAN | 785 | NUUCUUCAACACCUUCAAA | 1832-1850 | 1832 |
| 297 | NUUGAAGGUGUUGAAGAAN | 786 | NUUCUUCAACACCUUCAAN | 1832-1850 | 1832 |
| 298 | UGCAGUUCGAGUAGUAGGU | 787 | ACCUACUACUCGAACUGCA | 2001-2019 | 2001 |
| 299 | NGCAGUUCGAGUAGUAGGU | 788 | ACCUACUACUCGAACUGCN | 2001-2019 | 2001 |
| 300 | UGCAGUUCGAGUAGUAGGN | 789 | NCCUACUACUCGAACUGCA | 2001-2019 | 2001 |
| 301 | NGCAGUUCGAGUAGUAGGN | 790 | NCCUACUACUCGAACUGCN | 2001-2019 | 2001 |
| 302 | UGCAGUUCGAGUAGUAGGU | 791 | ACCUACUACUCGAACUICA | 2001-2019 | 2001 |
| 303 | NGCAGUUCGAGUAGUAGGU | 792 | ACCUACUACUCGAACUICN | 2001-2019 | 2001 |
| 304 | UGCAGUUCGAGUAGUAGGN | 793 | NCCUACUACUCGAACUICA | 2001-2019 | 2001 |
| 305 | NGCAGUUCGAGUAGUAGGN | 794 | NCCUACUACUCGAACUICN | 2001-2019 | 2001 |
| 306 | CUUGGAGCAGGUGGUCCCU | 795 | AGGGACCACCUGCUCCAAG | 2915-2933 | 2915 |
| 307 | UUUGGAGCAGGUGGUCCCU | 796 | AGGGACCACCUGCUCCAAA | 2915-2933 | 2915 |
| 308 | NUUGGAGCAGGUGGUCCCU | 797 | AGGGACCACCUGCUCCAAN | 2915-2933 | 2915 |
| 309 | UUUGGAGCAGGUGGUCCCN | 798 | NGGGACCACCUGCUCCAAA | 2915-2933 | 2915 |
| 310 | NUUGGAGCAGGUGGUCCCN | 799 | NGGGACCACCUGCUCCAAN | 2915-2933 | 2915 |
| 311 | UCUUGAUGGCCUUGGAGCA | 800 | UGCUCCAAGGCCAUCAAGA | 2925-2943 | 2925 |
| 312 | NCUUGAUGGCCUUGGAGCA | 801 | UGCUCCAAGGCCAUCAAGN | 2925-2943 | 2925 |

TABLE 2-continued

MUC5AC RNAi Agent Antisense Strand and Sense Strand Core Stretch Base Sequences (N = any nucleobase; I = inosine (hypoxanthine nucleobase)

| SEQ ID NO:. | Antisense Strand Base Sequence (5' → 3') (Shown as an Unmodified Nucleotide Sequence) | SEQ ID NO:. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 313 | UCUUGAUGGCCUUGGAGCN | 802 | NGCUCCAAGGCCAUCAAGA | 2925-2943 | 2925 |
| 314 | NCUUGAUGGCCUUGGAGCN | 803 | NGCUCCAAGGCCAUCAAGN | 2925-2943 | 2925 |
| 315 | CUGUCAUCGUGGUUCCACA | 804 | UGUGGAACCACGAUGACAG | 610-628 | 610 |
| 316 | UUGUCAUCGUGGUUCCACA | 805 | UGUGGAACCACGAUGACAA | 610-628 | 610 |
| 317 | NUGUCAUCGUGGUUCCACA | 806 | UGUGGAACCACGAUGACAN | 610-628 | 610 |
| 318 | UUGUCAUCGUGGUUCCACN | 807 | NGUGGAACCACGAUGACAA | 610-628 | 610 |
| 319 | NUGUCAUCGUGGUUCCACN | 808 | NGUGGAACCACGAUGACAN | 610-628 | 610 |
| 320 | CUGUCAUCGUGGUUCCACA | 809 | UGUGGAACCACGAUIACAG | 610-628 | 610 |
| 321 | UUGUCAUCGUGGUUCCACA | 810 | UGUGGAACCACGAUIACAA | 610-628 | 610 |
| 322 | NUGUCAUCGUGGUUCCACA | 811 | UGUGGAACCACGAUIACAN | 610-628 | 610 |
| 323 | UUGUCAUCGUGGUUCCACN | 812 | NGUGGAACCACGAUIACAA | 610-628 | 610 |
| 324 | NUGUCAUCGUGGUUCCACN | 813 | NGUGGAACCACGAUIACAN | 610-628 | 610 |
| 325 | ACAGAAGCAGAGGUCUUGC | 814 | GCAAGACCUCUGCUUCUGU | 923-941 | 923 |
| 326 | ACAGAAGCAGAGGUCUUGN | 815 | NCAAGACCUCUGCUUCUGU | 923-941 | 923 |
| 327 | UCAGAAGCAGAGGUCUUGC | 816 | GCAAGACCUCUGCUUCUGA | 923-941 | 923 |
| 328 | UCAGAAGCAGAGGUCUUGN | 817 | NCAAGACCUCUGCUUCUGA | 923-941 | 923 |
| 329 | ACAGAAGCAGAGGUCUUGC | 818 | GCAAGACCUCUGCUUCUIU | 923-941 | 923 |
| 330 | ACAGAAGCAGAGGUCUUGN | 819 | NCAAGACCUCUGCUUCUIU | 923-941 | 923 |
| 331 | UCAGAAGCAGAGGUCUUGC | 820 | GCAAGACCUCUGCUUCUIA | 923-941 | 923 |
| 332 | UCAGAAGCAGAGGUCUUGN | 821 | NCAAGACCUCUGCUUCUIA | 923-941 | 923 |
| 333 | GCAGUUGGUGCAGUCUGUG | 822 | CACAGACUGCACCAACUGC | 1277-1295 | 1277 |
| 334 | UCAGUUGGUGCAGUCUGUG | 823 | CACAGACUGCACCAACUGA | 1277-1295 | 1277 |
| 335 | NCAGUUGGUGCAGUCUGUG | 824 | CACAGACUGCACCAACUGA | 1277-1295 | 1277 |
| 336 | UCAGUUGGUGCAGUCUGUN | 825 | NACAGACUGCACCAACUGN | 1277-1295 | 1277 |
| 337 | NCAGUUGGUGCAGUCUGUN | 826 | NACAGACUGCACCAACUGN | 1277-1295 | 1277 |
| 338 | GCAGUUGGUGCAGUCUGUG | 827 | CACAGACUGCACCAACUIC | 1277-1295 | 1277 |
| 339 | UCAGUUGGUGCAGUCUGUG | 828 | CACAGACUGCACCAACUIA | 1277-1295 | 1277 |
| 340 | NCAGUUGGUGCAGUCUGUG | 829 | CACAGACUGCACCAACUIA | 1277-1295 | 1277 |
| 341 | UCAGUUGGUGCAGUCUGUN | 830 | NACAGACUGCACCAACUIN | 1277-1295 | 1277 |
| 342 | NCAGUUGGUGCAGUCUGUN | 831 | NACAGACUGCACCAACUIN | 1277-1295 | 1277 |
| 343 | GCAGUACAGUGAAGGCACU | 832 | AGUGCCUUCACUGUACUGC | 1446-1464 | 1446 |
| 344 | UCAGUACAGUGAAGGCACU | 833 | AGUGCCUUCACUGUACUGA | 1446-1464 | 1446 |
| 345 | NCAGUACAGUGAAGGCACU | 834 | AGUGCCUUCACUGUACUGN | 1446-1464 | 1446 |
| 346 | UCAGUACAGUGAAGGCACN | 835 | NGUGCCUUCACUGUACUGA | 1446-1464 | 1446 |
| 347 | NCAGUACAGUGAAGGCACN | 836 | NGUGCCUUCACUGUACUGN | 1446-1464 | 1446 |

TABLE 2-continued

MUC5AC RNAi Agent Antisense Strand and Sense Strand Core Stretch Base Sequences (N = any nucleobase; I = inosine (hypoxanthine nucleobase)

| SEQ ID NO:. | Antisense Strand Base Sequence (5' → 3') (Shown as an Unmodified Nucleotide Sequence) | SEQ ID NO:. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 348 | GCAGUACAGUGAAGGCACU | 837 | AGUGCCUUCACUGUACUIC | 1446-1464 | 1446 |
| 349 | UCAGUACAGUGAAGGCACU | 838 | AGUGCCUUCACUGUACUIA | 1446-1464 | 1446 |
| 350 | NCAGUACAGUGAAGGCACU | 839 | AGUGCCUUCACUGUACUIN | 1446-1464 | 1446 |
| 351 | UCAGUACAGUGAAGGCACN | 840 | NGUGCCUUCACUGUACUIA | 1446-1464 | 1446 |
| 352 | NCAGUACAGUGAAGGCACN | 841 | NGUGCCUUCACUGUACUIN | 1446-1464 | 1446 |
| 353 | UGCUGUUGAAGUUCCCACA | 842 | UGUGGGAACUUCAACAGCA | 1758-1776 | 1758 |
| 354 | NGCUGUUGAAGUUCCCACA | 843 | UGUGGGAACUUCAACAGCN | 1758-1776 | 1758 |
| 355 | UGCUGUUGAAGUUCCCACN | 844 | NGUGGGAACUUCAACAGCA | 1758-1776 | 1758 |
| 356 | NGCUGUUGAAGUUCCCACN | 845 | NGUGGGAACUUCAACAGCN | 1758-1776 | 1758 |
| 357 | UGCUGUUGAAGUUCCCACA | 846 | UGUGGGAACUUCAACAICA | 1758-1776 | 1758 |
| 358 | NGCUGUUGAAGUUCCCACA | 847 | UGUGGGAACUUCAACAICN | 1758-1776 | 1758 |
| 359 | UGCUGUUGAAGUUCCCACN | 848 | NGUGGGAACUUCAACAICA | 1758-1776 | 1758 |
| 360 | NGCUGUUGAAGUUCCCACN | 849 | NGUGGGAACUUCAACAICN | 1758-1776 | 1758 |
| 361 | GGAUGCUGUUGAAGUUCCC | 850 | GGGAACUUCAACAGCAUCC | 1761-1779 | 1761 |
| 362 | UGAUGCUGUUGAAGUUCCC | 851 | GGGAACUUCAACAGCAUCA | 1761-1779 | 1761 |
| 363 | NGAUGCUGUUGAAGUUCCC | 852 | GGGAACUUCAACAGCAUCN | 1761-1779 | 1761 |
| 364 | UGAUGCUGUUGAAGUUCCN | 853 | NGGAACUUCAACAGCAUCA | 1761-1779 | 1761 |
| 365 | NGAUGCUGUUGAAGUUCCN | 854 | NGGAACUUCAACAGCAUCN | 1761-1779 | 1761 |
| 366 | GGAUGCUGUUGAAGUUCCC | 855 | GGGAACUUCAACAICAUCC | 1761-1779 | 1761 |
| 367 | UGAUGCUGUUGAAGUUCCC | 856 | GGGAACUUCAACAICAUCA | 1761-1779 | 1761 |
| 368 | NGAUGCUGUUGAAGUUCCC | 857 | GGGAACUUCAACAICAUCN | 1761-1779 | 1761 |
| 369 | UGAUGCUGUUGAAGUUCCN | 858 | NGGAACUUCAACAICAUCA | 1761-1779 | 1761 |
| 370 | NGAUGCUGUUGAAGUUCCN | 859 | NGGAACUUCAACAICAUCN | 1761-1779 | 1761 |
| 371 | GGGUCUUGAAGGUGUUGAA | 860 | UUCAACACCUUCAAGACCC | 1836-1854 | 1836 |
| 372 | UGGUCUUGAAGGUGUUGAA | 861 | UUCAACACCUUCAAGACCA | 1836-1854 | 1836 |
| 373 | NGGUCUUGAAGGUGUUGAA | 862 | UUCAACACCUUCAAGACCN | 1836-1854 | 1836 |
| 374 | UGGUCUUGAAGGUGUUGAN | 863 | NUCAACACCUUCAAGACCA | 1836-1854 | 1836 |
| 375 | NGGUCUUGAAGGUGUUGAN | 864 | NUCAACACCUUCAAGACCN | 1836-1854 | 1836 |
| 376 | GGGUCUUGAAGGUGUUGAA | 865 | UUCAACACCUUCAAIACCC | 1836-1854 | 1836 |
| 377 | UGGUCUUGAAGGUGUUGAA | 866 | UUCAACACCUUCAAIACCA | 1836-1854 | 1836 |
| 378 | NGGUCUUGAAGGUGUUGAA | 867 | UUCAACACCUUCAAIACCN | 1836-1854 | 1836 |
| 379 | UGGUCUUGAAGGUGUUGAN | 868 | NUCAACACCUUCAAIACCA | 1836-1854 | 1836 |
| 380 | NGGUCUUGAAGGUGUUGAN | 869 | NUCAACACCUUCAAIACCN | 1836-1854 | 1836 |
| 381 | AAGCUGUUCCUGAUGUUGG | 870 | CCAACAUCAGGAACAGCUU | 1867-1885 | 1867 |
| 382 | AAGCUGUUCCUGAUGUUGN | 871 | NCAACAUCAGGAACAGCUU | 1867-1885 | 1867 |

TABLE 2-continued

MUC5AC RNAi Agent Antisense Strand and Sense Strand Core Stretch Base Sequences (N = any nucleobase; I = inosine (hypoxanthine nucleobase)

| SEQ ID NO:. | Antisense Strand Base Sequence (5' → 3') (Shown as an Unmodified Nucleotide Sequence) | SEQ ID NO:. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 383 | UAGCUGUUCCUGAUGUUGG | 872 | CCAACAUCAGGAACAGCUN | 1867-1885 | 1867 |
| 384 | UAGCUGUUCCUGAUGUUGN | 873 | NCAACAUCAGGAACAGCUU | 1867-1885 | 1867 |
| 385 | NAGCUGUUCCUGAUGUUGN | 874 | NCAACAUCAGGAACAGCUN | 1867-1885 | 1867 |
| 386 | AAGCUGUUCCUGAUGUUGG | 875 | CCAACAUCAGGAACAICUU | 1867-1885 | 1867 |
| 387 | AAGCUGUUCCUGAUGUUGN | 876 | NCAACAUCAGGAACAICUU | 1867-1885 | 1867 |
| 388 | UAGCUGUUCCUGAUGUUGG | 877 | CCAACAUCAGGAACAICUN | 1867-1885 | 1867 |
| 389 | UAGCUGUUCCUGAUGUUGN | 878 | NCAACAUCAGGAACAICUU | 1867-1885 | 1867 |
| 390 | NAGCUGUUCCUGAUGUUGN | 879 | NCAACAUCAGGAACAICUN | 1867-1885 | 1867 |
| 391 | ACAUGCAGUUCGAGUAGUA | 880 | UACUACUCGAACUGCAUGU | 2004-2022 | 2004 |
| 392 | ACAUGCAGUUCGAGUAGUN | 881 | NACUACUCGAACUGCAUGU | 2004-2022 | 2004 |
| 393 | UCAUGCAGUUCGAGUAGUA | 882 | UACUACUCGAACUGCAUGA | 2004-2022 | 2004 |
| 394 | UCAUGCAGUUCGAGUAGUN | 883 | NACUACUCGAACUGCAUGA | 2004-2022 | 2004 |
| 395 | NCAUGCAGUUCGAGUAGUN | 884 | NACUACUCGAACUGCAUGN | 2004-2022 | 2004 |
| 396 | GAAGCCAACACUGCAGGUG | 885 | CACCUGCAGUGUUGGCUUC | 2234-2252 | 2234 |
| 397 | UAAGCCAACACUGCAGGUG | 886 | CACCUGCAGUGUUGGCUUA | 2234-2252 | 2234 |
| 398 | NAAGCCAACACUGCAGGUG | 887 | CACCUGCAGUGUUGGCUUN | 2234-2252 | 2234 |
| 399 | UAAGCCAACACUGCAGGUN | 888 | NACCUGCAGUGUUGGCUUA | 2234-2252 | 2234 |
| 400 | NAAGCCAACACUGCAGGUN | 889 | NACCUGCAGUGUUGGCUUN | 2234-2252 | 2234 |
| 401 | GAAGCCAACACUGCAGGUG | 890 | CACCUGCAGUGUUGICUUC | 2234-2252 | 2234 |
| 402 | UAAGCCAACACUGCAGGUG | 891 | CACCUGCAGUGUUGICUUA | 2234-2252 | 2234 |
| 403 | NAAGCCAACACUGCAGGUG | 892 | CACCUGCAGUGUUGICUUN | 2234-2252 | 2234 |
| 404 | UAAGCCAACACUGCAGGUN | 893 | NACCUGCAGUGUUGICUUA | 2234-2252 | 2234 |
| 405 | NAAGCCAACACUGCAGGUN | 894 | NACCUGCAGUGUUGICUUN | 2234-2252 | 2234 |
| 406 | CUGUAACAGGUCAUGUCCA | 895 | UGGACAUGACCUGUUACAG | 2536-2554 | 2536 |
| 407 | UUGUAACAGGUCAUGUCCA | 896 | UGGACAUGACCUGUUACAA | 2536-2554 | 2536 |
| 408 | NUGUAACAGGUCAUGUCCA | 897 | UGGACAUGACCUGUUACAN | 2536-2554 | 2536 |
| 409 | UUGUAACAGGUCAUGUCCN | 898 | NGGACAUGACCUGUUACAA | 2536-2554 | 2536 |
| 410 | NUGUAACAGGUCAUGUCCN | 899 | NGGACAUGACCUGUUACAN | 2536-2554 | 2536 |
| 411 | CCGUUGAAGCUGUAGCUCU | 900 | AGAGCUACAGCUUCAACGG | 2797-2815 | 2797 |
| 412 | UCGUUGAAGCUGUAGCUCU | 901 | AGAGCUACAGCUUCAACGA | 2797-2815 | 2797 |
| 413 | NCGUUGAAGCUGUAGCUCU | 902 | AGAGCUACAGCUUCAACGN | 2797-2815 | 2797 |
| 414 | UCGUUGAAGCUGUAGCUCN | 903 | NGAGCUACAGCUUCAACGA | 2797-2815 | 2797 |
| 415 | NCGUUGAAGCUGUAGCUCN | 904 | NGAGCUACAGCUUCAACGN | 2797-2815 | 2797 |
| 416 | CCGUUGAAGCUGUAGCUCU | 905 | AGAGCUACAGCUUCAACIG | 2797-2815 | 2797 |
| 417 | UCGUUGAAGCUGUAGCUCU | 906 | AGAGCUACAGCUUCAACIA | 2797-2815 | 2797 |

TABLE 2-continued

MUC5AC RNAi Agent Antisense Strand and Sense Strand Core Stretch Base Sequences (N = any nucleobase; I = inosine (hypoxanthine nucleobase))

| SEQ ID NO:. | Antisense Strand Base Sequence (5' → 3') (Shown as an Unmodified Nucleotide Sequence) | SEQ ID NO:. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 418 | NCGUUGAAGCUGUAGCUCU | 907 | AGAGCUACAGCUUCAACIN | 2797-2815 | 2797 |
| 419 | UCGUUGAAGCUGUAGCUCN | 908 | NGAGCUACAGCUUCAACIA | 2797-2815 | 2797 |
| 420 | NCGUUGAAGCUGUAGCUCN | 909 | NGAGCUACAGCUUCAACIN | 2797-2815 | 2797 |
| 421 | CAGUACAGUGAAGGCACUG | 910 | CAGUGCCUUCACUGUACUG | 1445-1463 | 1445 |
| 422 | UAGUACAGUGAAGGCACUG | 911 | CAGUGCCUUCACUGUACUA | 1445-1463 | 1445 |
| 423 | UAGUACAGUGAAGGCACUN | 912 | NAGUGCCUUCACUGUACUA | 1445-1463 | 1445 |
| 424 | NAGUACAGUGAAGGCACUG | 913 | CAGUGCCUUCACUGUACUN | 1445-1463 | 1445 |
| 425 | NAGUACAGUGAAGGCACUN | 914 | NAGUGCCUUCACUGUACUN | 1445-1463 | 1445 |
| 426 | CUCGAAGCUGUUCCUGAUG | 915 | CAUCAGGAACAGCUUCGAG | 1871-1889 | 1871 |
| 427 | UUCGAAGCUGUUCCUGAUG | 916 | CAUCAGGAACAGCUUCGAA | 1871-1889 | 1871 |
| 428 | UUCGAAGCUGUUCCUGAUN | 917 | NAUCAGGAACAGCUUCGAA | 1871-1889 | 1871 |
| 429 | NUCGAAGCUGUUCCUGAUG | 918 | CAUCAGGAACAGCUUCGAN | 1871-1889 | 1871 |
| 430 | NUCGAAGCUGUUCCUGAUN | 919 | NAUCAGGAACAGCUUCGAN | 1871-1889 | 1871 |
| 431 | CUCGAAGCUGUUCCUGAUG | 920 | CAUCAGGAACAGCUUCIAG | 1871-1889 | 1871 |
| 432 | UUCGAAGCUGUUCCUGAUG | 921 | CAUCAGGAACAGCUUCIAA | 1871-1889 | 1871 |
| 433 | UUCGAAGCUGUUCCUGAUN | 922 | NAUCAGGAACAGCUUCIAA | 1871-1889 | 1871 |
| 434 | NUCGAAGCUGUUCCUGAUG | 923 | CAUCAGGAACAGCUUCIAN | 1871-1889 | 1871 |
| 435 | NUCGAAGCUGUUCCUGAUN | 924 | NAUCAGGAACAGCUUCIAN | 1871-1889 | 1871 |
| 436 | UCUUGUUCAGGCAAAUCAG | 925 | CUGAUUUGCCUGAACAAGA | 4992-5010 | 4992 |
| 437 | UCUUGUUCAGGCAAAUCAN | 926 | NUGAUUUGCCUGAACAAGA | 4992-5010 | 4992 |
| 438 | NCUUGUUCAGGCAAAUCAG | 927 | CUGAUUUGCCUGAACAAGN | 4992-5010 | 4992 |
| 439 | NCUUGUUCAGGCAAAUCAN | 928 | NUGAUUUGCCUGAACAAGN | 4992-5010 | 4992 |
| 440 | UCACCAAAGUGGUUGUCCU | 929 | AGGACAACCACUUUGGUGA | 6798-6816 | 6798 |
| 441 | UCACCAAAGUGGUUGUCCN | 930 | NGGACAACCACUUUGGUGA | 6798-6816 | 6798 |
| 442 | NCACCAAAGUGGUUGUCCU | 931 | AGGACAACCACUUUGGUGN | 6798-6816 | 6798 |
| 443 | NCACCAAAGUGGUUGUCCN | 932 | NGGACAACCACUUUGGUGN | 6798-6816 | 6798 |
| 444 | UCACCAAAGUGGUUGUCCU | 933 | AGGACAACCACUUUIGUGA | 6798-6816 | 6798 |
| 445 | UCACCAAAGUGGUUGUCCN | 934 | NGGACAACCACUUUIGUGA | 6798-6816 | 6798 |
| 446 | NCACCAAAGUGGUUGUCCU | 935 | AGGACAACCACUUUIGUGN | 6798-6816 | 6798 |
| 447 | NCACCAAAGUGGUUGUCCN | 936 | NGGACAACCACUUUIGUGN | 6798-6816 | 6798 |
| 448 | GAGCAGAGGUUGUUCUGGU | 937 | ACCAGAACAACCUCUGCUC | 8739-8757 | 8739 |
| 449 | UAGCAGAGGUUGUUCUGGU | 938 | ACCAGAACAACCUCUGCUA | 8739-8757 | 8739 |
| 450 | UAGCAGAGGUUGUUCUGGN | 939 | NCCAGAACAACCUCUGCUA | 8739-8757 | 8739 |
| 451 | NAGCAGAGGUUGUUCUGGU | 940 | ACCAGAACAACCUCUGCUN | 8739-8757 | 8739 |
| 452 | NAGCAGAGGUUGUUCUGGN | 941 | NCCAGAACAACCUCUGCUN | 8739-8757 | 8739 |

TABLE 2-continued

MUC5AC RNAi Agent Antisense Strand and Sense Strand Core Stretch Base Sequences (N = any nucleobase; I = inosine (hypoxanthine nucleobase)

| SEQ ID NO:. | Antisense Strand Base Sequence (5' → 3') (Shown as an Unmodified Nucleotide Sequence) | SEQ ID NO:. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 453 | GAGCAGAGGUUGUUCUGGU | 942 | ACCAGAACAACCUCUICUC | 8739-8757 | 8739 |
| 454 | UAGCAGAGGUUGUUCUGGU | 943 | ACCAGAACAACCUCUICUA | 8739-8757 | 8739 |
| 455 | UAGCAGAGGUUGUUCUGGN | 944 | NCCAGAACAACCUCUICUA | 8739-8757 | 8739 |
| 456 | NAGCAGAGGUUGUUCUGGU | 945 | ACCAGAACAACCUCUICUN | 8739-8757 | 8739 |
| 457 | NAGCAGAGGUUGUUCUGGN | 946 | NCCAGAACAACCUCUICUN | 8739-8757 | 8739 |
| 458 | UAGAUUGUGCUGGUUGUAG | 947 | CUACAACCAGCACAAUCUC | 9310-9328 | 9310 |
| 459 | UAGAUUGUGCUGGUUGUAG | 948 | CUACAACCAGCACAAUCUA | 9310-9328 | 9310 |
| 460 | NAGAUUGUGCUGGUUGUAG | 949 | CUACAACCAGCACAAUCUN | 9310-9328 | 9310 |
| 461 | UAGAUUGUGCUGGUUGUAN | 950 | NUACAACCAGCACAAUCUA | 9310-9328 | 9310 |
| 462 | NAGAUUGUGCUGGUUGUAN | 951 | NUACAACCAGCACAAUCUN | 9310-9328 | 9310 |
| 463 | CAGAAGUUGUGCUGGUUGU | 952 | ACAACCAGCACAACUUCUG | 10206-10224 | 10206 |
| 464 | UAGAAGUUGUGCUGGUUGU | 953 | ACAACCAGCACAACUUCUA | 10206-10224 | 10206 |
| 465 | NAGAAGUUGUGCUGGUUGU | 954 | ACAACCAGCACAACUUCUN | 10206-10224 | 10206 |
| 466 | UAGAAGUUGUGCUGGUUGN | 955 | NCAACCAGCACAACUUCUA | 10206-10224 | 10206 |
| 467 | NAGAAGUUGUGCUGGUUGN | 956 | NCAACCAGCACAACUUCUN | 10206-10224 | 10206 |
| 468 | CUUGUCACCAAAGUGGUUG | 957 | CAACCACUUUGGUGACAAG | 11014-11032 | 11014 |
| 469 | UUUGUCACCAAAGUGGUUG | 958 | CAACCACUUUGGUGACAAA | 11014-11032 | 11014 |
| 470 | NUUGUCACCAAAGUGGUUG | 959 | CAACCACUUUGGUGACAAN | 11014-11032 | 11014 |
| 471 | UUUGUCACCAAAGUGGUUN | 960 | NAACCACUUUGGUGACAAA | 11014-11032 | 11014 |
| 472 | NUUGUCACCAAAGUGGUUN | 961 | NAACCACUUUGGUGACAAN | 11014-11032 | 11014 |
| 473 | CAGAGGUUGUGUUGGUUGU | 962 | ACAACCAACACAACUUCUG | 11361-11379 | 11361 |
| 474 | UAGAGGUUGUGUUGGUUGU | 963 | ACAACCAACACAACUUCUA | 11361-11379 | 11361 |
| 475 | NAGAGGUUGUGUUGGUUGU | 964 | ACAACCAACACAACUUCUN | 11361-11379 | 11361 |
| 476 | UAGAGGUUGUGUUGGUUGN | 965 | NCAACCAACACAACUUCUA | 11361-11379 | 11361 |
| 477 | NAGAGGUUGUGUUGGUUGN | 966 | NCAACCAACACAACUUCUN | 11361-11379 | 11361 |
| 478 | UCUAGUUGUAGGAGCAGAG | 967 | CUCUGCUCCUACAACUAGA | 12965-12983 | 12965 |
| 479 | GCUAGUUGUAGGAGCAGAG | 968 | CUCUGCUCCUACAACUAGC | 12965-12983 | 12965 |
| 480 | NCUAGUUGUAGGAGCAGAG | 969 | CUCUGCUCCUACAACUAGN | 12965-12983 | 12965 |
| 481 | UCUAGUUGUAGGAGCAGAN | 970 | NUCUGCUCCUACAACUAGA | 12965-12983 | 12965 |
| 482 | NCUAGUUGUAGGAGCAGAN | 971 | NUCUGCUCCUACAACUAGN | 12965-12983 | 12965 |
| 483 | UGGUUCAGGAACACUUCCC | 972 | GGGAAGUGUUCCUGAACCA | 1567-1585 | 1567 |
| 484 | NGGUUCAGGAACACUUCCC | 973 | GGGAAGUGUUCCUGAACCN | 1567-1585 | 1567 |
| 485 | UGGUUCAGGAACACUUCCN | 974 | NGGAAGUGUUCCUGAACCA | 1567-1585 | 1567 |
| 486 | NGGUUCAGGAACACUUCCN | 975 | NGGAAGUGUUCCUGAACCN | 1567-1585 | 1567 |
| 487 | UGGUUCAGGAACACUUCCC | 976 | GGGAAGUGUUCCUIAACCA | 1567-1585 | 1567 |

TABLE 2-continued

MUC5AC RNAi Agent Antisense Strand and Sense Strand Core Stretch Base Sequences (N = any nucleobase; I = inosine (hypoxanthine nucleobase))

| SEQ ID NO:. | Antisense Strand Base Sequence (5' → 3') (Shown as an Unmodified Nucleotide Sequence) | SEQ ID NO:. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 488 | NGGUUCAGGAACACUUCCC | 977 | GGGAAGUGUUCCUIAACCN | 1567-1585 | 1567 |
| 489 | UGGUUCAGGAACACUUCCN | 978 | NGGAAGUGUUCCUIAACCA | 1567-1585 | 1567 |
| 490 | NGGUUCAGGAACACUUCCN | 979 | NGGAAGUGUUCCUIAACCN | 1567-1585 | 1567 |
| 491 | GAUGUCGUCGAAGUUCCCA | 980 | UGGGAACUUCGACGACAUC | 3155-3173 | 3155 |
| 492 | UAUGUCGUCGAAGUUCCCA | 981 | UGGGAACUUCGACGACAUA | 3155-3173 | 3155 |
| 493 | NAUGUCGUCGAAGUUCCCA | 982 | UGGGAACUUCGACGACAUN | 3155-3173 | 3155 |
| 494 | UAUGUCGUCGAAGUUCCCN | 983 | NGGGAACUUCGACGACAUA | 3155-3173 | 3155 |
| 495 | NAUGUCGUCGAAGUUCCCN | 984 | NGGGAACUUCGACGACAUN | 3155-3173 | 3155 |
| 496 | GAUGUCGUCGAAGUUCCCA | 985 | UGGGAACUUCGACIACAUC | 3155-3173 | 3155 |
| 497 | UAUGUCGUCGAAGUUCCCA | 986 | UGGGAACUUCGACIACAUA | 3155-3173 | 3155 |
| 498 | NAUGUCGUCGAAGUUCCCA | 987 | UGGGAACUUCGACIACAUN | 3155-3173 | 3155 |
| 499 | UAUGUCGUCGAAGUUCCCN | 988 | NGGGAACUUCGACIACAUA | 3155-3173 | 3155 |
| 500 | NAUGUCGUCGAAGUUCCCN | 989 | NGGGAACUUCGACIACAUN | 3155-3173 | 3155 |
| 501 | AUUUCUGCCAAGAGGAGGU | 990 | ACCUCCUCUUGGCAGAAAU | 6777-6795 | 6777 |
| 502 | AUUUCUGCCAAGAGGAGGN | 991 | NCCUCCUCUUGGCAGAAAU | 6777-6795 | 6777 |
| 503 | UUUUCUGCCAAGAGGAGGU | 992 | ACCUCCUCUUGGCAGAAAA | 6777-6795 | 6777 |
| 504 | UUUUCUGCCAAGAGGAGGN | 993 | NCCUCCUCUUGGCAGAAAA | 6777-6795 | 6777 |
| 505 | NUUUCUGCCAAGAGGAGGN | 994 | NCCUCCUCUUGGCAGAAAN | 6777-6795 | 6777 |
| 506 | AUUUCUGCCAAGAGGAGGU | 995 | ACCUCCUCUUGICAGAAAU | 6777-6795 | 6777 |
| 507 | AUUUCUGCCAAGAGGAGGN | 996 | NCCUCCUCUUGICAGAAAU | 6777-6795 | 6777 |
| 508 | UUUUCUGCCAAGAGGAGGU | 997 | ACCUCCUCUUGICAGAAAA | 6777-6795 | 6777 |
| 509 | UUUUCUGCCAAGAGGAGGN | 998 | NCCUCCUCUUGICAGAAAA | 6777-6795 | 6777 |
| 510 | NUUUCUGCCAAGAGGAGGN | 999 | NCCUCCUCUUGICAGAAAN | 6777-6795 | 6777 |
| 511 | UGUUGUUGAAGAUGAUCUC | 1000 | GAGAUCAUCUUCAACAACA | 15051-15069 | 15051 |
| 512 | UGUUGUUGAAGAUGAUCUN | 1001 | NAGAUCAUCUUCAACAACA | 15051-15069 | 15051 |
| 513 | NGUUGUUGAAGAUGAUCUC | 1002 | GAGAUCAUCUUCAACAACN | 15051-15069 | 15051 |
| 514 | NGUUGUUGAAGAUGAUCUN | 1003 | NAGAUCAUCUUCAACAACN | 15051-15069 | 15051 |
| 515 | UGUUGUUGUAGGUUUCCUU | 1004 | AAGGAAACCUACAACAACA | 5346-5364 | 5346 |
| 516 | NGUUGUUGUAGGUUUCCUU | 1005 | AAGGAAACCUACAACAACN | 5346-5364 | 5346 |
| 517 | UGUUGUUGUAGGUUUCCUN | 1006 | NAGGAAACCUACAACAACA | 5346-5364 | 5346 |
| 518 | NGUUGUUGUAGGUUUCCUN | 1007 | NAGGAAACCUACAACAACN | 5346-5364 | 5346 |
| 519 | AUCUUGUCCUCAUCAAAGA | 1008 | UCUUUGAUGAGGACAAGAU | 3694-3712 | 3694 |
| 520 | AUCUUGUCCUCAUCAAAGN | 1009 | NCUUUGAUGAGGACAAGAU | 3694-3712 | 3694 |
| 521 | NUCUUGUCCUCAUCAAAGN | 1010 | NCUUUGAUGAGGACAAGAN | 3694-3712 | 3694 |
| 522 | UUCUUGUCCUCAUCAAAGA | 1011 | UCUUUGAUGAGGACAAGAA | 3694-3712 | 3694 |

TABLE 2-continued

MUC5AC RNAi Agent Antisense Strand and Sense Strand Core Stretch Base Sequences (N = any nucleobase; I = inosine (hypoxanthine nucleobase))

| SEQ ID NO:. | Antisense Strand Base Sequence (5' → 3') (Shown as an Unmodified Nucleotide Sequence) | SEQ ID NO:. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 523 | UUCUUGUCCUCAUCAAAGN | 1012 | NCUUUGAUGAGGACAAGAA | 3694-3712 | 3694 |
| 524 | GCAUCUUGUCCUCAUCAAA | 1013 | UUUGAUGAGGACAAGAUGC | 3696-3714 | 3696 |
| 525 | UCAUCUUGUCCUCAUCAAA | 1014 | UUUGAUGAGGACAAGAUGA | 3696-3714 | 3696 |
| 526 | UCAUCUUGUCCUCAUCAAN | 1015 | NUUGAUGAGGACAAGAUGA | 3696-3714 | 3696 |
| 527 | NCAUCUUGUCCUCAUCAAA | 1016 | UUUGAUGAGGACAAGAUGN | 3696-3714 | 3696 |
| 528 | NCAUCUUGUCCUCAUCAAN | 1017 | NUUGAUGAGGACAAGAUGN | 3696-3714 | 3696 |
| 529 | GCUAGUUGUAGGAGCAGAG | 1018 | CUCUGCUCCUACAACUAGC | 6998-7016 | 6998 |
| 530 | UCUAGUUGUAGGAGCAGAG | 1019 | CUCUGCUCCUACAACUAGA | 6998-7016 | 6998 |
| 531 | NCUAGUUGUAGGAGCAGAG | 1020 | CUCUGCUCCUACAACUAGN | 6998-7016 | 6998 |
| 532 | UCUAGUUGUAGGAGCAGAN | 1021 | NUCUGCUCCUACAACUAGA | 6998-7016 | 6998 |
| 533 | NCUAGUUGUAGGAGCAGAN | 1022 | NUCUGCUCCUACAACUAGN | 6998-7016 | 6998 |
| 534 | UAGUUGUAGAAGCAGAGGU | 1023 | ACCUCUGCUUCUACAACUA | 7980-7998 | 7980 |
| 535 | NAGUUGUAGAAGCAGAGGU | 1024 | ACCUCUGCUUCUACAACUN | 7980-7998 | 7980 |
| 536 | UAGUUGUAGAAGCAGAGGN | 1025 | NCCUCUGCUUCUACAACUA | 7980-7998 | 7980 |
| 537 | NAGUUGUAGAAGCAGAGGN | 1026 | NCCUCUGCUUCUACAACUN | 7980-7998 | 7980 |
| 538 | CAGAAGUUGUGCUGGUUAU | 1027 | AUAACCAGCACAACUUCUG | 8448-8466 | 8448 |
| 539 | UAGAAGUUGUGCUGGUUAU | 1028 | AUAACCAGCACAACUUCUA | 8448-8466 | 8448 |
| 540 | NAGAAGUUGUGCUGGUUAU | 1029 | AUAACCAGCACAACUUCUN | 8448-8466 | 8448 |
| 541 | UAGAAGUUGUGCUGGUUAN | 1030 | NUAACCAGCACAACUUCUA | 8448-8466 | 8448 |
| 542 | NAGAAGUUGUGCUGGUUAN | 1031 | NUAACCAGCACAACUUCUN | 8448-8466 | 8448 |
| 543 | CCAACACUGCAGGUGAUGU | 1032 | ACAUCACCUGCAGUGUUGG | 2230-2248 | 2230 |
| 544 | UCAACACUGCAGGUGAUGU | 1033 | ACAUCACCUGCAGUGUUGA | 2230-2248 | 2230 |
| 545 | NCAACACUGCAGGUGAUGU | 1034 | ACAUCACCUGCAGUGUUGN | 2230-2248 | 2230 |
| 546 | UCAACACUGCAGGUGAUGN | 1035 | NCAUCACCUGCAGUGUUGA | 2230-2248 | 2230 |
| 547 | NCAACACUGCAGGUGAUGN | 1036 | NCAUCACCUGCAGUGUUGN | 2230-2248 | 2230 |
| 548 | CCAACACUGCAGGUGAUGU | 1037 | ACAUCACCUGCAGUIUUGG | 2230-2248 | 2230 |
| 549 | UCAACACUGCAGGUGAUGU | 1038 | ACAUCACCUGCAGUIUUGA | 2230-2248 | 2230 |
| 550 | NCAACACUGCAGGUGAUGU | 1039 | ACAUCACCUGCAGUIUUGN | 2230-2248 | 2230 |
| 551 | UCAACACUGCAGGUGAUGN | 1040 | NCAUCACCUGCAGUIUUGA | 2230-2248 | 2230 |
| 552 | NCAACACUGCAGGUGAUGN | 1041 | NCAUCACCUGCAGUIUUGN | 2230-2248 | 2230 |
| 553 | CAUCUUGUCCUCAUCAAAG | 1042 | CUUUGAUGAGGACAAGAUG | 3695-3713 | 3695 |
| 554 | UAUCUUGUCCUCAUCAAAG | 1043 | CUUUGAUGAGGACAAGAUA | 3695-3713 | 3695 |
| 555 | NAUCUUGUCCUCAUCAAAG | 1044 | CUUUGAUGAGGACAAGAUN | 3695-3713 | 3695 |
| 556 | UAUCUUGUCCUCAUCAAAN | 1045 | NUUUGAUGAGGACAAGAUA | 3695-3713 | 3695 |
| 557 | NAUCUUGUCCUCAUCAAAN | 1046 | NUUUGAUGAGGACAAGAUN | 3695-3713 | 3695 |

TABLE 2-continued

MUC5AC RNAi Agent Antisense Strand and Sense Strand Core Stretch Base Sequences (N = any nucleobase; I = inosine (hypoxanthine nucleobase))

| SEQ ID NO:. | Antisense Strand Base Sequence (5' → 3') (Shown as an Unmodified Nucleotide Sequence) | SEQ ID NO:. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 558 | GUCGUGUGGUAGAUGACGU | 1047 | ACGUCAUCUACCACACGAC | 3910-3928 | 3910 |
| 559 | UUCGUGUGGUAGAUGACGU | 1048 | ACGUCAUCUACCACACGAA | 3910-3928 | 3910 |
| 560 | NUCGUGUGGUAGAUGACGU | 1049 | ACGUCAUCUACCACACGAN | 3910-3928 | 3910 |
| 561 | UUCGUGUGGUAGAUGACGN | 1050 | NCGUCAUCUACCACACGAA | 3910-3928 | 3910 |
| 562 | NUCGUGUGGUAGAUGACGN | 1051 | NCGUCAUCUACCACACGAN | 3910-3928 | 3910 |
| 563 | GUCGUGUGGUAGAUGACGU | 1052 | ACGUCAUCUACCACACIAC | 3910-3928 | 3910 |
| 564 | UUCGUGUGGUAGAUGACGU | 1053 | ACGUCAUCUACCACACIAA | 3910-3928 | 3910 |
| 565 | NUCGUGUGGUAGAUGACGU | 1054 | ACGUCAUCUACCACACIAN | 3910-3928 | 3910 |
| 566 | UUCGUGUGGUAGAUGACGN | 1055 | NCGUCAUCUACCACACIAA | 3910-3928 | 3910 |
| 567 | NUCGUGUGGUAGAUGACGN | 1056 | NCGUCAUCUACCACACIAN | 3910-3928 | 3910 |

The MUC5AC RNAi agent sense strands and antisense strands that comprise or consist of the nucleotide sequences in Table 2 can be modified nucleotides or unmodified nucleotides. In some embodiments, the MUC5AC RNAi agents having the sense and antisense strand sequences that comprise or consist of any of the nucleotide sequences in Table 2 are all or substantially all modified nucleotides.

In some embodiments, the antisense strand of a MUC5AC RNAi agent disclosed herein comprises at least 15 contiguous nucleotides differing by 0, 1, 2, or 3 nucleotides from any of the antisense strand sequences in Table 2. In some embodiments, the sense strand of a MUC5AC RNAi agent disclosed herein comprises at least 15 contiguous nucleotides differing by 0, 1, 2, or 3 nucleotides from any of the sense strand sequences in Table 2.

As used herein, each N listed in a sequence disclosed in Table 2 may be independently selected from any and all nucleobases (including those found on both modified and unmodified nucleotides). In some embodiments, an N nucleotide listed in a sequence disclosed in Table 2 has a nucleobase that is complementary to the N nucleotide at the corresponding position on the other strand. In some embodiments, an N nucleotide listed in a sequence disclosed in Table 2 has a nucleobase that is not complementary to the N nucleotide at the corresponding position on the other strand. In some embodiments, an N nucleotide listed in a sequence disclosed in Table 2 has a nucleobase that is the same as the N nucleotide at the corresponding position on the other strand. In some embodiments, an N nucleotide listed in a sequence disclosed in Table 2 has a nucleobase that is different from the N nucleotide at the corresponding position on the other strand.

Certain modified MUC5AC RNAi agent sense and antisense strands are provided in Table 3, Table 4, Table 5, Table 6, Table 7, and Table 11. Certain modified MUC5AC RNAi agent antisense strands, as well as their underlying unmodified nucleobase sequences, are provided in Table 3. Certain modified MUC5AC RNAi agent sense strands, as well as their underlying unmodified nucleobase sequences, are provided in Tables 4, 5, and 6. In forming MUC5AC RNAi agents, each of the nucleotides in each of the underlying base sequences listed in Tables 3, 4, 5, 6, and 7, as well as in Table 2, above, can be a modified nucleotide.

The MUC5AC RNAi agents described herein are formed by annealing an antisense strand with a sense strand. A sense strand containing a sequence listed in Table 2, Table 4, Table 5, Table 6, Table 7, or Table 11 can be hybridized to any antisense strand containing a sequence listed in Table 2, Table 3, or Table 11, provided the two sequences have a region of at least 85% complementarity over a contiguous 16, 17, 18, 19, 20, or 21 nucleotide sequence.

In some embodiments, a MUC5AC RNAi agent antisense strand comprises a nucleotide sequence of any of the sequences in Table 2 or Table 3.

In some embodiments, a MUC5AC RNAi agent comprises or consists of a duplex having the nucleobase sequences of the sense strand and the antisense strand of any of the sequences in Table 2, Table 3, Table 4, Table 5, Table 6, Table 7, or Table 11.

Examples of antisense strands containing modified nucleotides are provided in Table 3. Examples of sense strands containing modified nucleotides are provided in Tables 4, 5 and 6.

As used in Tables 3, 4, 5, 6, 7, and 11, the following notations are used to indicate modified nucleotides, targeting groups, and linking groups:

A=adenosine-3'-phosphate
C=cytidine-3'-phosphate
G=guanosine-3'-phosphate
U=uridine-3'-phosphate
I=inosine-3'-phosphate
a=2'-O-methyladenosine-3'-phosphate
as =2'-O-methyladenosine-3'-phosphorothioate
c=2'-O-methylcytidine-3'-phosphate
cs=2'-O-methylcytidine-3'-phosphorothioate
g=2'-O-methylguanosine-3'-phosphate
gs=2'-O-methylguanosine-3'-phosphorothioate
i=2'-O-methylinosine-3'-phosphate is=2'-O-methylinosine-3'-phosphorothioate
t=2'-O-methyl-5-methyluridine-3'-phosphate
ts=2'-O-methyl-5-methyluridine-3'-phosphorothioate
u=2'-O-methyluridine-3'-phosphate
us=2'-O-methyluridine-3'-phosphorothioate
Af=2'-fluoroadenosine-3'-phosphate
Afs=2'-fluoroadenosine-3'-phosporothioate
Cf=2'-fluorocytidine-3'-phosphate
Cfs=2'-fluorocytidine-3'-phosphorothioate
Gf=2'-fluoroguanosine-3'-phosphate
Gfs=2'-fluoroguanosine-3'-phosphorothioate
Tf=2'-fluoro-5'-methyluridine-3'-phosphate
Tfs=2'-fluoro-5'-methyluridine-3'-phosphorothioate
Uf=2'-fluorouridine-3'-phosphate
Ufs=2'-fluorouridine-3'-phosphorothioate
dT=2'-deoxythymidine-3'-phosphate
$A_{UNA}$=2',3'-seco-adenosine-3'-phosphate
$A_{UNAS}$=2',3'-seco-adenosine-3'-phosphorothioate
$C_{UNA}$=2',3'-seco-cytidine-3'-phosphate
$C_{UNAS}$=2',3'-seco-cytidine-3'-phosphorothioate
$G_{UNA}$=2',3'-seco-guanosine-3'-phosphate
$G_{UNAS}$=2',3'-seco-guanosine-3'-phosphorothioate
$U_{UNA}$=2',3'-seco-uridine-3'-phosphate
$U_{UNAS}$=2',3'-seco-uridine-3'-phosphorothioate
a_2N=see Table 12
a_2Ns=see Table 12
(invAb)=inverted abasic deoxyribonucleotide-5'-phosphate, see Table 12
(invAb)s=inverted abasic deoxyribonucleotide-5'-phosphorothioate, see Table 12
s=phosphorothioate linkage
p=terminal phosphate (as synthesized)
vpdN=vinyl phosphonate deoxyribonucleotide
cPrpa=5'-cyclopropyl phosphonate-2'-O-methyladenosine-3'-phosphate (see Table 12)
cPrpas=5'-cyclopropyl phosphonate-2'-O-methyladenosine-3'-phosphorothioate (see Table 12)
cPrpu=5'-cyclopropyl phosphonate-2'-O-methyluridine-3'-phosphate (see Table 12)
cPrpus=5'-cyclopropyl phosphonate-2'-O-methyluridine-3'-phosphorothioate (see Table 12)
(Alk-SS-C6)=see Table 12
(C6-SS-Alk)=see Table 12
(C6-SS-C6)=see Table 12
(6-SS-6)=see Table 12
(C6-SS-Alk-Me)=see Table 12
(NH2-C6)=see Table 12
(TriAlk14)=see Table 12
(TriAlk14)s=see Table 12
—C6-=see Table 12
—C6s-=see Table 12
-L6-C6-=see Table 12
-L6-C6s-=see Table 12
Alk-cyHex-=see Table 12
Alk-cyHexs-=see Table 12
(TA14)=see Table 12 (structure of (TriAlk14)s after conjugation)
(TA14)s=see Table 12 (structure of (TriAlk14)s after conjugation)

As the person of ordinary skill in the art would readily understand, unless otherwise indicated by the sequence (such as, for example, by a phosphorothioate linkage "s"), when present in an oligonucleotide, the nucleotide monomers are mutually linked by 5'-3'-phosphodiester bonds. As the person of ordinary skill in the art would clearly understand, the inclusion of a phosphorothioate linkage as shown in the modified nucleotide sequences disclosed herein replaces the phosphodiester linkage typically present in oligonucleotides. Further, the person of ordinary skill in the art would readily understand that the terminal nucleotide at the 3' end of a given oligonucleotide sequence would typically have a hydroxyl (—OH) group at the respective 3' position of the given monomer instead of a phosphate moiety ex vivo. Additionally, for the embodiments disclosed herein, when viewing the respective strand 5'→3', the inverted abasic residues are inserted such that the 3' position of the deoxyribose is linked at the 3' end of the preceding monomer on the respective strand (see, e.g., Table 12). Moreover, as the person of ordinary skill would readily understand and appreciate, while the phosphorothioate chemical structures depicted herein typically show the anion on the sulfur atom, the inventions disclosed herein encompass all phosphorothioate tautomers (e.g., where the sulfur atom has a double-bond and the anion is on an oxygen atom). Unless expressly indicated otherwise herein, such understandings of the person of ordinary skill in the art are used when describing the MUC5AC RNAi agents and compositions of MUC5AC RNAi agents disclosed herein.

Certain examples of targeting groups and linking groups used with the MUC5AC RNAi agents disclosed herein are included in the chemical structures provided below in Table 12. Each sense strand and/or antisense strand disclosed herein can have any targeting groups or linking groups listed herein, as well as other targeting or linking groups, conjugated to the 5' and/or 3' end of the sequence.

TABLE 3

MUC5AC RNAi Agent Antisense Strand Sequences

| AS Strand ID | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM10579-AS | usUfsusGfaUfgGfcCfuUfgGfaGfcAfgGfsu | 1057 | UUUGAUGGCCUUGGAGCAGGU | 1517 |
| AM10581-AS | asAfsusCfuUfgAfuGfgCfcUfuGfgAfgCfsa | 1058 | AAUCUUGAUGGCCUUGGAGCA | 1518 |
| AM10583-AS | usUfsusGfaAfcUfcGfgGfgCfuGfaGfgUfsu | 1059 | UUUGAACUCGGGGCUGAGGUU | 1519 |
| AM10585-AS | usGfsasUfgCfuGfcAfcUfgCfuUfcUfgGfsg | 1060 | UGAUGCUGCACUGCUUCUGGG | 1520 |
| AM10587-AS | usUfsasGfuCfgCfaGfaAfcAfgAfgGfgCfsa | 1061 | UUAGUCGCAGAACAGAGGGCA | 1521 |
| AM10589-AS | asGfsusAfgUfcGfcAfgAfaCfaGfaGfgGfsc | 1062 | AGUAGUCGCAGAACAGAGGGC | 1522 |
| AM10591-AS | usUfsasGfuAfgUfcGfcAfgAfaCfaGfaGfsg | 1063 | UUAGUAGUCGCAGAACAGAGG | 1523 |

TABLE 3-continued

MUC5AC RNAi Agent Antisense Strand Sequences

| AS Strand ID | Modified Antisense Strand (5'→3') | SEQ ID NO. | Underlying Base Sequence (5'→3') (Shown as an Un-modified Nucleotide Sequence) | SEQ ID NO. |
|---|---|---|---|---|
| AM10593-AS | usGfsusAfgUfaGfuCfgCfaGfaAfcAfgAfsg | 1064 | UGUAGUAGUCGCAGAACAGAG | 1524 |
| AM10595-AS | usUfsgsUfaGfuAfgUfcGfcAfgAfaCfaGfsc | 1065 | UUGUAGUAGUCGCAGAACAGC | 1525 |
| AM10597-AS | asUfsasGfuUfgUfaGfcAfgAfuGfgGfuGfsg | 1066 | AUAGUUGUAGCAGAUGGGUGG | 1526 |
| AM10599-AS | usUfscsCfaCfgUfcGfaAfcCfaCfuUfuGfsc | 1067 | UUCCACGUCGAACCACUUUGC | 1527 |
| AM10601-AS | usAfsasGfuCfcAfcGfuCfgAfaCfcAfcUfsc | 1068 | UAAGUCCACGUCGAACCACUC | 1528 |
| AM10603-AS | usGfsgsAfaGfuCfcAfcGfuCfgAfaCfcAfsc | 1069 | UGGAAGUCCACGUCGAACCAC | 1529 |
| AM10605-AS | usGfsgsAfaGfU$_{UNA}$CfcAfcGfuCfgAfaCfcAfsc | 1070 | UGGAAGUCCACGUCGAACCAC | 1529 |
| AM10739-AS | cPrpasAfsgsGfuCfuUfgUfaGfuGfgAfaGfcUfsg | 1071 | AAGGUCUUGUAGUGGAAGCUG | 1530 |
| AM10741-AS | cPrpasAfsgsGfuCfU$_{UNA}$UfgUfaGfuGfgAfaGfcUfsg | 1072 | AAGGUCUUGUAGUGGAAGCUG | 1530 |
| AM10743-AS | cPrpusAfscsCfaGfuGfcUfgAfgCfaUfaCfuUfsc | 1073 | UACCAGUGCUGAGCAUACUUC | 1531 |
| AM10744-AS | cPrpusAfscsCfaGfU$_{UNA}$GfcUfgAfgCfaUfaCfuUfsc | 1074 | UACCAGUGCUGAGCAUACUUC | 1531 |
| AM10747-AS | cPrpusUfsusGfaAfgguguUfgAfaGfaAfgGfsc | 1075 | UUUGAAGGUGUUGAAGAAGGC | 1532 |
| AM10764-AS | asGfsasUfgCfuGfgUfcUfuCfuUfgUfcCfsc | 1076 | AGAUGCUGGUCUUCUUGUCCC | 1533 |
| AM10766-AS | usGfsusUfgAfuGfaAfgAfuGfcUfgGfuCfsc | 1077 | UGUUGAUGAAGAUGCUGGUCC | 1534 |
| AM10768-AS | usUfscsUfuGfuUfcAfgGfcAfaAfuCfaGfsc | 1078 | UUCUUGUUCAGGCAAAUCAGC | 1535 |
| AM10770-AS | asUfsgsUfuGfuUfgUfaGfgUfuUfcCfuUfsg | 1079 | AUGUUGUUGUAGGUUUCCUUG | 1536 |
| AM10772-AS | asUfsgsAfuGfuUfgUfuGfuAfgGfuUfuCfsc | 1080 | AUGAUGUUGUUGUAGGUUUCC | 1537 |
| AM10790-AS | usUfsgsAfuGfaAfgAfuGfcUfgGfuCfuUfsc | 1081 | UUGAUGAAGAUGCUGGUCUUC | 1538 |
| AM10792-AS | usGfsasUfcUfgGfuAfgUfuGfuAfgCfaGfsc | 1082 | UGAUCUGGUAGUUGUAGCAGC | 1539 |
| AM10794-AS | usCfscsUfgAfuCfuGfgUfaGfuUfgUfaGfsc | 1083 | UCCUGAUCUGGUAGUUGUAGC | 1540 |
| AM10796-AS | usAfsgsUfuGfuAfgCfaGfaUfgGfgUfgGfsg | 1084 | UAGUUGUAGCAGAUGGGUGGG | 1541 |
| AM10798-AS | usCfsasAfcAfcUfgGfaUfgCfgGfaUfcUfsc | 1085 | UCAACACUGGAUGCGGAUCUC | 1542 |
| AM10800-AS | usUfsgsUfuCfgAfuGfcUfcAfcCfuCfuGfsg | 1086 | UUGUUCGAUGCUCACCUCUGG | 1543 |
| AM10802-AS | usAfsusCfuUfgAfaGfgGfuCfcCfuGfcUfsg | 1087 | UAUCUUGAAGGGUCCCUGCUG | 1544 |
| AM10804-AS | usCfsgsUfaGfuUfgAfgGfcAfcAfuCfuUfsg | 1088 | UCGUAGUUGAGGCACAUCUUG | 1545 |
| AM10806-AS | usCfsusCfgUfaGfuUfgAfgGfcAfcAfuCfsc | 1089 | UCUCGUAGUUGAGGCACAUCC | 1546 |
| AM10808-AS | asAfsgsGfuCfuUfgUfaGfuGfgAfaGfcUfsg | 1090 | AAGGUCUUGUAGUGGAAGCUG | 1530 |
| AM10810-AS | usUfsusCfaGfgCfaGfgUfcUfcGfcUfgUfsc | 1091 | UUUCAGGCAGGUCUCGCUGUC | 1547 |
| AM10812-AS | usUfscsUfgAfaGfaUfgGfuGfaCfgUfuGfsg | 1092 | UUCUGAAGAUGGUGACGUUGG | 1548 |
| AM10814-AS | usGfsusCfuGfaAfgAfuGfgUfgAfcGfuUfsg | 1093 | UGUCUGAAGAUGGUGACGUUG | 1549 |
| AM10816-AS | usGfsgsAfaGfU$_{UNA}$CfaUfcGfgCfcUfgGfaUfsg | 1094 | UGGAAGUCAUCGGCCUGGAUG | 1550 |
| AM10818-AS | usUfsusGfaAfgguguUfgAfaGfaAfgGfsc | 1095 | UUUGAAGGUGUUGAAGAAGGC | 1532 |
| AM10821-AS | usGfscsAfgUfuCfgAfgUfaGfuAfgGfuUfsc | 1096 | UGCAGUUCGAGUAGUAGGUUC | 1551 |
| AM10823-AS | usUfsusGfgAfgCfaGfgUfgGfuCfcCfuGfsu | 1097 | UUUGGAGCAGGUGGUCCCUGU | 1552 |
| AM10825-AS | usCfsusUfgAfuGfgCfcUfuGfgAfgCfaGfsg | 1098 | UCUUGAUGGCCUUGGAGCAGG | 1553 |
| AM10827-AS | usUfsgsUfcAfuCfgUfgGfuUfcCfaCfaUfsg | 1099 | UUGUCAUCGUGGUUCCACAUG | 1554 |

TABLE 3-continued

MUC5AC RNAi Agent Antisense Strand Sequences

| AS Strand ID | Modified Antisense Strand (5'→3') | SEQ ID NO. | Underlying Base Sequence (5'→3') (Shown as an Un-modified Nucleotide Sequence) | SEQ ID NO. |
|---|---|---|---|---|
| AM10829-AS | asCfsasGfaAfgCfaGfaGfgUfcUfuGfcCfsu | 1100 | ACAGAAGCAGAGGUCUUGCCU | 1555 |
| AM10831-AS | usCfsasGfuUfgGfuGfcAfgUfcUfgUfgGfsa | 1101 | UCAGUUGGUGCAGUCUGUGGA | 1556 |
| AM10833-AS | usCfsasGfuAfcAfgUfgAfaGfgCfaCfuGfsc | 1102 | UCAGUACAGUGAAGGCACUGC | 1557 |
| AM10835-AS | usGfscsUfgUfuGfaAfgUfuCfcCfaCfaGfsc | 1103 | UGCUGUUGAAGUUCCCACAGC | 1558 |
| AM10837-AS | usGfsasUfgCfuGfuUfgAfaGfuUfcCfcAfsc | 1104 | UGAUGCUGUUGAAGUUCCCAC | 1559 |
| AM10839-AS | usGfsgsUfcUfuGfaAfgGfuGfuUfgAfaGfsc | 1105 | UGGUCUUGAAGGUGUUGAAGC | 1560 |
| AM10841-AS | asAfsgsCfuGfuUfcCfuGfaUfgUfuGfgGfsg | 1106 | AAGCUGUUCCUGAUGUUGGGG | 1561 |
| AM10843-AS | asCfsasUfgCfaGfuUfcGfaGfuAfgUfaGfsg | 1107 | ACAUGCAGUUCGAGUAGUAGG | 1562 |
| AM10845-AS | usAfsasGfcCfaAfcAfcUfgCfaGfgUfgAfsc | 1108 | UAAGCCAACACUGCAGGUGAC | 1563 |
| AM10847-AS | usUfsgsUfaAfcAfgGfuCfaUfgUfcCfaGfsc | 1109 | UUGUAACAGGUCAUGUCCAGC | 1564 |
| AM10849-AS | usCfsgsUfuGfaAfgCfuGfuAfgCfuCfuGfsc | 1110 | UCGUUGAAGCUGUAGCUCUGC | 1565 |
| AM11065-AS | usAfscsCfaGfU$_{UNA}$GfcUfgAfgCfaUfaCfuUfsc | 1111 | UACCAGUGCUGAGCAUACUUC | 1531 |
| AM11264-AS | cPrpusGfsgsAfuCfuCfaUfaGfuUfgUfaGfcAfsg | 1112 | UGGAUCUCAUAGUUGUAGCAG | 1566 |
| AM11266-AS | cPrpusGfsgsAfuCfU$_{UNA}$CfaUfaGfuUfgUfaGfcAfsg | 1113 | UGGAUCUCAUAGUUGUAGCAG | 1566 |
| AM11268-AS | cPrpusGfsusCfaAfaCfcAfcUfuGfgUfcCfaGfsg | 1114 | UGUCAAACCACUUGGUCCAGG | 1567 |
| AM11271-AS | cPrpusUfsgsUfuGfuUfgAfaGfaUfgAfuCfuCfsg | 1115 | UUGUUGUUGAAGAUGAUCUCG | 1568 |
| AM11272-AS | cPrpusUfsgsUfuguugaaGfaUfgAfucucsg | 1116 | UUGUUGUUGAAGAUGAUCUCG | 1568 |
| AM11275-AS | usAfsgsUfaCfaGfuGfaAfgGfcAfcUfgCfsu | 1117 | UAGUACAGUGAAGGCACUGCU | 1569 |
| AM11277-AS | usUfscsGfaAfgCfuGfuUfcCfuGfaUfgUfsc | 1118 | UUCGAAGCUGUUCCUGAUGUC | 1570 |
| AM11279-AS | usCfsusUfgUfuCfaGfgCfaAfaUfcAfgCfsc | 1119 | UCUUGUUCAGGCAAAUCAGCC | 1571 |
| AM11281-AS | usCfsasCfcAfaAfgUfgGfuUfgUfcCfuGfsg | 1120 | UCACCAAAGUGGUUGUCCUGG | 1572 |
| AM11283-AS | usAfsgsCfaGfaGfgUfuGfuUfcUfgGfuUfsg | 1121 | UAGCAGAGGUUGUUCUGGUUG | 1573 |
| AM11285-AS | usAfsgsAfuUfgUfgCfuGfgUfuGfuAfgCfsg | 1122 | UAGAUUGUGCUGGUUGUAGCG | 1574 |
| AM11287-AS | usAfsgsAfaGfuUfgUfgCfuGfgUfuGfuGfsg | 1123 | UAGAAGUUGUGCUGGUUGUGG | 1575 |
| AM11289-AS | usUfsusGfuCfaCfcAfaAfgUfgGfuUfgUfsc | 1124 | UUUGUCACCAAAGUGGUUGUC | 1576 |
| AM11291-AS | usAfsgsAfgGfuUfgUfgUfuGfgUfuGfuAfsg | 1125 | UAGAGGUUGUGUUGGUUGUAG | 1577 |
| AM11293-AS | usCfsusAfgUfuGfuAfgGfaGfcAfgAfgGfsu | 1126 | UCUAGUUGUAGGAGCAGAGGU | 1578 |
| AM11401-AS | cPrpusUfsgsUfaGfuAfgUfcGfcAfgAfaCfaGfsc | 1127 | UUGUAGUAGUCGCAGAACAGC | 1525 |
| AM11403-AS | usUfsgsUfaGfuAfgUfcAfcAfgAfaCfaGfsc | 1128 | UUGUAGUAGUCACAGAACAGC | 1579 |
| AM11404-AS | cPrpusUfsgsUfaGfuAfgUfcAfcAfgAfaCfaGfsc | 1129 | UUGUAGUAGUCACAGAACAGC | 1579 |
| AM11405-AS | cPrpusUfsgsuaguagucAfcAfgAfacagsc | 1130 | UUGUAGUAGUCACAGAACAGC | 1579 |
| AM11462-AS | cPrpusCfsasuaguuguaGfcAfcAfugggsu | 1131 | UCAUAGUUGUAGCACAUGGGU | 1580 |
| AM11464-AS | cPrpusGfsusUfgUfuGfaAfgAfuGfaUfcUfgGfsu | 1132 | UGUUGUUGAAGAUGAUCUGGU | 1581 |
| AM11465-AS | cPrpusGfsusuguugaagAfuGfaUfcuggsu | 1133 | UGUUGUUGAAGAUGAUCUGGU | 1581 |
| AM11467-AS | cPrpusGfsusUfgAfaGfuUfaCfcAfcAfgAfgCfsc | 1134 | UGUUGAAGUUACCACAGAGCC | 1582 |
| AM11469-AS | cPrpusAfscsUfuUfuCfaUfuCfuCfcAfcGfcUfsc | 1135 | UACUUUUCAUUCUCCACGCUC | 1583 |
| AM11471-AS | cPrpusAfsgsCfaUfaCfuUfuUfcAfuUfcUfcCfsc | 1136 | UAGCAUACUUUUCAUUCUCCC | 1584 |

TABLE 3-continued

MUC5AC RNAi Agent Antisense Strand Sequences

| AS Strand ID | Modified Antisense Strand (5'→3') | SEQ ID NO. | Underlying Base Sequence (5'→3') (Shown as an Un-modified Nucleotide Sequence) | SEQ ID NO. |
|---|---|---|---|---|
| AM11473-AS | cPrpusCfsasUfaCfaUfgCfaGfuUfcGfaGfaAfsg | 1137 | UCAUACAUGCAGUUCGAGAAG | 1585 |
| AM11475-AS | cPrpusGfsusCfaUfaCfaUfgCfaGfuUfcGfaGfsc | 1138 | UGUCAUACAUGCAGUUCGAGC | 1586 |
| AM11477-AS | cPrpusUfsgsUfcAfuAfcAfuGfcAfgUfuCfgAfsg | 1139 | UUGUCAUACAUGCAGUUCGAG | 1587 |
| AM11479-AS | cPrpusUfsasGfuAfgUfcAfcAfgAfaCfaGfuGfsg | 1140 | UUAGUAGUCACAGAACAGUGG | 1588 |
| AM11481-AS | cPrpusGfsusAfgUfaGfuCfaCfaGfaAfcAfgUfsg | 1141 | UGUAGUAGUCACAGAACAGUG | 1589 |
| AM11495-AS | cPrpusUfsgsUfaGfuAfgUfcicAfgAfaCfaGfsc | 1142 | UUGUAGUAGUCICAGAACAGC | 1590 |
| AM11496-AS | cPrpusUfsgsUfaGfuAfgUfcgcAfgAfaCfaGfsc | 1143 | UUGUAGUAGUCGCAGAACAGC | 1525 |
| AM11498-AS | asCfsasUfgCfaGfuUfcGfaGfaAfgAfaGfsg | 1144 | ACAUGCAGUUCGAGAAGAAGG | 1591 |
| AM11499-AS | cPrpasCfsasUfgCfaGfuUfcGfaGfaAfgAfaGfsg | 1145 | ACAUGCAGUUCGAGAAGAAGG | 1591 |
| AM11740-AS | cPrpasUfsasGfuUfgUfaGfcAfcAfuGfgGfuGfsg | 1146 | AUAGUUGUAGCACAUGGGUGG | 1592 |
| AM11741-AS | cPrpasUfsasguuguagcAfcAfuGfggugsg | 1147 | AUAGUUGUAGCACAUGGGUGG | 1592 |
| AM11742-AS | cPrpusGfsgsaucucauaGfuUfgUfagcasg | 1148 | UGGAUCUCAUAGUUGUAGCAG | 1566 |
| AM11745-AS | cPrpusUfsgsuuguugaaGfaUfgAfucucsg | 1149 | UUGUUGUUGAAGAUGAUCUCG | 1568 |
| AM11821-AS | cPrpusGfsusAfguagucaCfaGfaAfcagusg | 1150 | UGUAGUAGUCACAGAACAGUG | 1589 |
| AM11823-AS | cPrpusGfsusaguagucaCfaGfaAfcagusg | 1151 | UGUAGUAGUCACAGAACAGUG | 1589 |
| AM11825-AS | cPrpusGfsusaguagucaCfaGfaAfcagusc | 1152 | UGUAGUAGUCACAGAACAGUG | 1593 |
| AM11971-AS | usGfsgsUfuCfaGfgAfaCfaCfuUfcCfcCfsa | 1153 | UGGUUCAGGAACACUUCCCCA | 1594 |
| AM11973-AS | usCfsasAfcAfcUfgCfaGfgUfgAfuGfuCfsc | 1154 | UCAACACUGCAGGUGAUGUCC | 1595 |
| AM11975-AS | usAfsusGfuCfgUfcGfaAfgUfuCfcCfaCfsa | 1155 | UAUGUCGUCGAAGUUCCCACA | 1596 |
| AM11977-AS | usAfsusCfuUfgUfcCfuCfaUfcAfaAfgAfsc | 1156 | UAUCUUGUCCUCAUCAAAGAC | 1597 |
| AM11979-AS | usUfscsGfuGfuGfgUfaGfaUfgAfcGfuCfsc | 1157 | UUCGUGUGGUAGAUGACGUCC | 1598 |
| AM11982-AS | asUfsusUfcUfgCfcAfaGfaGfgAfgGfuGfsc | 1158 | AUUUCUGCCAAGAGGAGGUGC | 1599 |
| AM11984-AS | usGfsusUfgUfuGfaAfgAfuGfaUfcUfcGfsu | 1159 | UGUUGUUGAAGAUGAUCUCGU | 1600 |
| AM11986-AS | usUfsgsUfuguugaaGfaUfgAfucucsg | 1160 | UUGUUGUUGAAGAUGAUCUCG | 1568 |
| AM12158-AS | usGfsusUfgUfuGfuAfgGfuUfuCfcUfuGfsc | 1161 | UGUUGUUGUAGGUUUCCUUGC | 1601 |
| AM12159-AS | cPrpusGfsusUfgUfuGfuAfgGfuUfuCfcUfuGfsc | 1162 | UGUUGUUGUAGGUUUCCUUGC | 1601 |
| AM12161-AS | usGfsusuguuguagGfuUfuCfcuugsc | 1163 | UGUUGUUGUAGGUUUCCUUGC | 1601 |
| AM12162-AS | cPrpusGfsusuguuguagGfuUfuCfcuugsc | 1164 | UGUUGUUGUAGGUUUCCUUGC | 1601 |
| AM12163-AS | cPrpusUfscsUfuGfuUfcAfgGfcAfaAfuCfaGfsc | 1165 | UUCUUGUUCAGGCAAAUCAGC | 1535 |
| AM12165-AS | usUfscsuuguucagGfcAfaAfucagsc | 1166 | UUCUUGUUCAGGCAAAUCAGC | 1535 |
| AM12166-AS | cPrpusUfscsuuguucagGfcAfaAfucagsc | 1167 | UUCUUGUUCAGGCAAAUCAGC | 1535 |
| AM12167-AS | cPrpusUfscsuugU$_{UNA}$UcagGfcAfaAfucagsc | 1168 | UUCUUGUUCAGGCAAAUCAGC | 1535 |
| AM12169-AS | cPrpusCfsusUfgUfuCfaGfgCfaAfaUfcAfgCfsc | 1169 | UCUUGUUCAGGCAAAUCAGCC | 1571 |
| AM12171-AS | usCfsusuguucaggCfaAfaUfcagcsc | 1170 | UCUUGUUCAGGCAAAUCAGCC | 1571 |
| AM12172-AS | cPrpusCfsusuguucaggCfaAfaUfcagcsc | 1171 | UCUUGUUCAGGCAAAUCAGCC | 1571 |
| AM12173-AS | cPrpusGfsusUfgAfuGfaAfgAfuGfcUfgGfuCfsc | 1172 | UGUUGAUGAAGAUGCUGGUCC | 1534 |
| AM12175-AS | usGfsusugaugaagAfuGfcUfggucsc | 1173 | UGUUGAUGAAGAUGCUGGUCC | 1534 |

TABLE 3-continued

| MUC5AC RNAi Agent Antisense Strand Sequences | | | | |
|---|---|---|---|---|
| AS Strand ID | Modified Antisense Strand (5'→3') | SEQ ID NO. | Underlying Base Sequence (5'→3') (Shown as an Unmodified Nucleotide Sequence) | SEQ ID NO. |
| AM12176-AS | cPrpusGfsusugaugaagAfuGfcUfggucsc | 1174 | UGUUGAUGAAGAUGCUGGUCC | 1534 |
| AM12177-AS | cPrpusGfsusugaU$_{UNA}$gaagAfuGfcUfggucsc | 1175 | UGUUGAUGAAGAUGCUGGUCC | 1534 |
| AM12178-AS | cPrpusUfsgsUfugU$_{UNA}$UgaaGfaUfgAfucucsg | 1176 | UUGUUGUUGAAGAUGAUCUCG | 1568 |
| AM12180-AS | cPrpusUfsgsUfuguU$_{UNA}$gaaGfaUfgAfucucsg | 1177 | UUGUUGUUGAAGAUGAUCUCG | 1568 |
| AM12181-AS | cPrpusUfsgsUfU$_{UNA}$guugaaGfaUfgAfucucsg | 1178 | UUGUUGUUGAAGAUGAUCUCG | 1568 |
| AM12182-AS | cPrpusUfsgsiuguugaaGfaUfgAfucucsg | 1179 | UUGIUGUUGAAGAUGAUCUCG | 1602 |
| AM12189-AS | asUfscsUfuGfuCfcUfcAfuCfaAfaGfaUfsg | 1180 | AUCUUGUCCUCAUCAAAGAUG | 1603 |
| AM12191-AS | usCfsasUfcUfuGfuCfcUfcAfuCfaAfaGfsc | 1181 | UCAUCUUGUCCUCAUCAAAGC | 1604 |
| AM12193-AS | usCfsusAfgUfuGfuAfgGfaGfcAfgAfgAfsc | 1182 | UCUAGUUGUAGGAGCAGAGAC | 1605 |
| AM12195-AS | usAfsgsUfuGfuAfgAfaGfcAfgAfgGfuUfsg | 1183 | UAGUUGUAGAAGCAGAGGUUG | 1606 |
| AM12197-AS | usAfsgsAfaGfuUfgUfgCfuGfgUfuAfuAfsg | 1184 | UAGAAGUUGUGCUGGUUAUAG | 1607 |
| AM12516-AS | usUfsgsuaguagucGfcAfgAfacagsc | 1185 | UUGUAGUAGUCGCAGAACAGC | 1525 |
| AM12519-AS | usUfsgsuagU$_{UNA}$agucGfcAfgAfacagsc | 1186 | UUGUAGUAGUCGCAGAACAGC | 1525 |
| AM12608-AS | usUfscsuuguucagGfcAfaAfucagsg | 1187 | UUCUUGUUCAGGCAAAUCAGG | 1608 |
| AM12609-AS | usUfscsuuGfuucagGfcAfaAfucagsc | 1188 | UUCUUGUUCAGGCAAAUCAGC | 1535 |
| AM12610-AS | usUfscsUfuguucagGfcAfaAfucagsc | 1189 | UUCUUGUUCAGGCAAAUCAGC | 1535 |
| AM12611-AS | usUfscsuuguU$_{UNA}$cagGfcAfaAfucagsc | 1190 | UUCUUGUUCAGGCAAAUCAGC | 1535 |
| AM12612-AS | cPrpuUfcuuguucagGfcAfaAfucagsc | 1191 | UUCUUGUUCAGGCAAAUCAGC | 1535 |
| AM08569-AS | usGfsgsAfuCfuCfaUfaGfuUfgUfaGfcAfsg | 1716 | UGGAUCUCAUAGUUGUAGCAG | 1566 |
| AM07104-AS | usUfsgsUfuGfuUfgAfaGfaUfgAfuCfuCfsg | 1717 | UUGUUGUUGAAGAUGAUCUCG | 1568 |

TABLE 4

| MUC5AC Agent Sense Strand Sequences (Shown Without Linkers, Conjugates, or Capping Moieties) | | | | |
|---|---|---|---|---|
| Strand ID | Modified Sense Strand (5'→3') | SEQ ID NO. | Underlying Base Sequence (5'→3') (Shown as an Unmodified Nucleotide Sequence) | SEQ ID NO. |
| AM10578-SS-NL | asccugcucCfAfAfgiccaucaaa | 1192 | ACCUGCUCCAAGICCAUCAAA | 1609 |
| AM10580-SS-NL | usgcuccaaGfGfCfcaucaagauu | 1193 | UGCUCCAAGGCCAUCAAGAUU | 1610 |
| AM10582-SS-NL | asaccucagCfUfCfcgaguucaaa | 1194 | AACCUCAGCUCCGAGUUCAAA | 1611 |
| AM10584-SS-NL | csccagaagCfAfGfugcaicauca | 1195 | CCCAGAAGCAGUGCAICAUCA | 1612 |
| AM10586-SS-NL | usgcccucuGfUfUfcugciacuaa | 1196 | UGCCCUCUGUUCUGCIACUAA | 1613 |
| AM10588-SS-NL | gscccucugUfUfCfuicgacuacu | 1197 | GCCCUCUGUUCUICGACUACU | 1614 |
| AM10590-SS-NL | cscucuguuCfUfGfcgacuacuaa | 1198 | CCUCUGUUCUGCGACUACUAA | 1615 |
| AM10592-SS-NL | csucuguucUfGfCfgacuacuaca | 1199 | CUCUGUUCUGCGACUACUACA | 1616 |
| AM10594-SS-NL | gscuguucuGfCfGfacuacuacaa | 1200 | GCUGUUCUGCGACUACUACAA | 1617 |
| AM10596-SS-NL | cscacccauCfUfGfcuacaacuau | 1201 | CCACCCAUCUGCUACAACUAU | 1618 |
| AM10598-SS-NL | gscaaagugGfUfUfcgaciuggaa | 1202 | GCAAAGUGGUUCGACIUGGAA | 1619 |

TABLE 4-continued

MUC5AC Agent Sense Strand Sequences (Shown Without Linkers, Conjugates, or Capping Moieties)

| Strand ID | Modified Sense Strand (5'→3') | SEQ ID NO. | Underlying Base Sequence (5'→3') (Shown as an Un-modified Nucleotide Sequence) | SEQ ID NO. |
|---|---|---|---|---|
| AM10600-SS-NL | gsagugguuCfGfAfcgugiacuua | 1203 | GAGUGGUUCGACGUGIACUUA | 1620 |
| AM10602-SS-NL | gsugguucgAfCfGfugiacuucca | 1204 | GUGGUUCGACGUGIACUUCCA | 1621 |
| AM10604-SS-NL | gsugguucgAfCfGfuggacuucca | 1205 | GUGGUUCGACGUGGACUUCCA | 1622 |
| AM10738-SS-NL | csagcuuccAfCfUfacaaiaccuu | 1206 | CAGCUUCCACUACAAIACCUU | 1623 |
| AM10740-SS-NL | csagcuuccAfCfUfacaagaccuu | 1207 | CAGCUUCCACUACAAGACCUU | 1624 |
| AM10742-SS-NL | gsa_2NaguaugCfUfCfagcacugiua | 1208 | G($A^{2N}$)AGUAUGCUCAGCACUGIUA | 1625 |
| AM10745-SS-NL | gsa_2NaguaugCfUfCfaguacugiua | 1209 | G($A^{2N}$)AGUAUGCUCAGUACUGIUA | 1626 |
| AM10746-SS-NL | gsccuucuuCfAfAfcaccuucaaa | 1210 | GCCUUCUUCAACACCUUCAAA | 1627 |
| AM10748-SS-NL | gsccuucuuCfAfAfcaucuucaaa | 1211 | GCCUUCUUCAACAUCUUCAAA | 1628 |
| AM10749-SS-NL | gsccuucuuCfAfAfcacuuucaaa | 1212 | GCCUUCUUCAACACUUUCAAA | 1629 |
| AM10763-SS-NL | gsggacaagAfAfGfaccaicaucu | 1213 | GGGACAAGAAGACCAICAUCU | 1630 |
| AM10765-SS-NL | gsgaccagcAfUfCfuucaucaaca | 1214 | GGACCAGCAUCUUCAUCAACA | 1631 |
| AM10767-SS-NL | gscugauuuGfCfCfugaacaagaa | 1215 | GCUGAUUUGCCUGAACAAGAA | 1632 |
| AM10769-SS-NL | csa_2NaggaaaCfCfUfacaacaacau | 1216 | C($A^{2N}$)AGGAAACCUACAACAACAU | 1633 |
| AM10771-SS-NL | gsgaaaccuAfCfAfacaacaucau | 1217 | GGAAACCUACAACAACAUCAU | 1634 |
| AM10789-SS-NL | gsa_2NagaccaGfCfAfucuucaucaa | 1218 | G($A^{2N}$)AGACCAGCAUCUUCAUCAA | 1635 |
| AM10791-SS-NL | gscugcuacAfAfCfuaccaiauca | 1219 | GCUGCUACAACUACCAIAUCA | 1636 |
| AM10793-SS-NL | gscuacaacUfAfCfcagaucaiga | 1220 | GCUACAACUACCAGAUCAIGA | 1637 |
| AM10795-SS-NL | csccacccaUfCfUfgcuacaacua | 1221 | CCCACCCAUCUGCUACAACUA | 1638 |
| AM10797-SS-NL | gsagauccgCfAfUfccaguiuuga | 1222 | GAGAUCCGCAUCCAGUIUUGA | 1639 |
| AM10799-SS-NL | cscagagguGfAfGfcauciaacaa | 1223 | CCAGAGGUGAGCAUCIAACAA | 1640 |
| AM10801-SS-NL | csagcagggAfCfCfcuucaagaua | 1224 | CAGCAGGGACCCUUCAAGAUA | 1641 |
| AM10803-SS-NL | csa_2NagauguGfCfCfucaacuacia | 1225 | C($A^{2N}$)AGAUGUGCCUCAACUACIA | 1642 |
| AM10805-SS-NL | gsgaugugcCfUfCfaacuaciaga | 1226 | GGAUGUGCCUCAACUACIAGA | 1643 |
| AM10807-SS-NL | csagcuuccAfCfUfacaaiaccuu | 1227 | CAGCUUCCACUACAAIACCUU | 1623 |
| AM10809-SS-NL | gsacagcgaGfAfCfcugcuugaaa | 1228 | GACAGCGAGACCUGCUUGAAA | 1644 |
| AM10811-SS-NL | cscaacgucAfCfCfaucuucagaa | 1229 | CCAACGUCACCAUCUUCAGAA | 1645 |
| AM10813-SS-NL | csa_2NacgucaCfCfAfucuucaiaca | 1230 | C($A^{2N}$)ACGUCACCAUCUUCAIACA | 1646 |
| AM10815-SS-NL | csauccaggCfCfGfaugacuucca | 1231 | CAUCCAGGCCGAUGACUUCCA | 1647 |
| AM10817-SS-NL | gsccuucuuCfAfAfcaccuucaaa | 1232 | GCCUUCUUCAACACCUUCAAA | 1627 |
| AM10819-SS-NL | gsa_2NaguaugCfUfCfagcacugiua | 1233 | G($A^{2N}$)AGUAUGCUCAGCACUGIUA | 1625 |
| AM10820-SS-NL | gsa_2NaccuacUfAfCfucgaacuica | 1234 | G($A^{2N}$)ACCUACUACUCGAACUICA | 1648 |
| AM10822-SS-NL | ascagggacCfAfCfcugcuucaaa | 1235 | ACAGGGACCACCUGCUUCAAA | 1649 |
| AM10824-SS-NL | cscugcuccAfAfGfgcuaucaaga | 1236 | CCUGCUCCAAGGCUAUCAAGA | 1650 |
| AM10826-SS-NL | csa_2NuguggaAfCfCfacgauiacaa | 1237 | C($A^{2N}$)UGUGGAACCACGAUIACAA | 1651 |
| AM10828-SS-NL | asggcaagaCfCfUfcugcuucuiu | 1238 | AGGCAAGACCUCUGCUUCUIU | 1652 |

TABLE 4-continued

MUC5AC Agent Sense Strand Sequences (Shown Without Linkers, Conjugates, or Capping Moieties)

| Strand ID | Modified Sense Strand (5'→3') | SEQ ID NO. | Underlying Base Sequence (5'→3') (Shown as an Unmodified Nucleotide Sequence) | SEQ ID NO. |
|---|---|---|---|---|
| AM10830-SS-NL | usccacagaCfUfGfcaccaacuia | 1239 | UCCACAGACUGCACCAACUIA | 1653 |
| AM10832-SS-NL | gscagugccUfUfCfacuguacuia | 1240 | GCAGUGCCUUCACUGUACUIA | 1654 |
| AM10834-SS-NL | gscugugggAfAfCfuucaacaica | 1241 | GCUGUGGGAACUUCAACAICA | 1655 |
| AM10836-SS-NL | gsugggaacUfUfCfaacaicauca | 1242 | GUGGGAACUUCAACAICAUCA | 1656 |
| AM10838-SS-NL | gscuucaacAfCfCfuucaaiacca | 1243 | GCUUCAACACCUUCAAIACCA | 1657 |
| AM10840-SS-NL | cscccaacaUfCfAfggaacaicuu | 1244 | CCCCAACAUCAGGAACAICUU | 1658 |
| AM10842-SS-NL | cscuacuacUfCfGfaacuicaugu | 1245 | CCUACUACUCGAACUICAUGU | 1659 |
| AM10844-SS-NL | gsucaccugCfAfGfuguugicuua | 1246 | GUCACCUGCAGUGUUGICUUA | 1660 |
| AM10846-SS-NL | gscuggacaUfGfAfccuguuacaa | 1247 | GCUGGACAUGACCUGUUACAA | 1661 |
| AM10848-SS-NL | gscagagcuAfCfAfgcuucaacia | 1248 | GCAGAGCUACAGCUUCAACIA | 1662 |
| AM11066-SS-NL | gsa_2NaguaugCfUfCfaguacugiua | 1249 | G($A^{2N}$)AGUAUGCUCAGUACUGIUA | 1626 |
| AM11263-SS-NL | csugcuacaAfCfUfaugagaucca | 1250 | CUGCUACAACUAUGAGAUCCA | 1663 |
| AM11265-SS-NL | csugcuacaAfCfUfaugaiaucca | 1251 | CUGCUACAACUAUGAIAUCCA | 1664 |
| AM11267-SS-NL | cscuggaccAfAfGfugguuugaca | 1252 | CCUGGACCAAGUGGUUUGACA | 1665 |
| AM11269-SS-NL | cscuggaccAfAfGfugguuuiaca | 1253 | CCUGGACCAAGUGGUUUIACA | 1666 |
| AM11270-SS-NL | csgagaucaUfCfUfucaacaacaa | 1254 | CGAGAUCAUCUUCAACAACAA | 1667 |
| AM11274-SS-NL | asgcagugcCfUfUfcacuguacua | 1255 | AGCAGUGCCUUCACUGUACUA | 1668 |
| AM11276-SS-NL | gsacaucagGfAfAfcagcuuciaa | 1256 | GACAUCAGGAACAGCUUCIAA | 1669 |
| AM11278-SS-NL | gsgcugauuUfGfCfcugaacaaga | 1257 | GGCUGAUUUGCCUGAACAAGA | 1670 |
| AM11280-SS-NL | cscaggacaAfCfCfacuuuiguga | 1258 | CCAGGACAACCACUUUIGUGA | 1671 |
| AM11282-SS-NL | csaaccagaAfCfAfaccucuicua | 1259 | CAACCAGAACAACCUCUICUA | 1672 |
| AM11284-SS-NL | csgcuacaaCfCfAfgcacaaucua | 1260 | CGCUACAACCAGCACAAUCUA | 1673 |
| AM11286-SS-NL | cscacaaccAfGfCfacaacuucua | 1261 | CCACAACCAGCACAACUUCUA | 1674 |
| AM11288-SS-NL | gsacaaccaCfUfUfuggugacaaa | 1262 | GACAACCACUUUGGUGACAAA | 1675 |
| AM11290-SS-NL | csuacaaccAfAfCfacaacuucua | 1263 | CUACAACCAACACAACUUCUA | 1676 |
| AM11292-SS-NL | ascc ucugcUfCfCfuacaacuaga | 1264 | ACCUCUGCUCCUACAACUAGA | 1677 |
| AM11400-SS-NL | gscuguucuGfCfGfacuacuacaa | 1265 | GCUGUUCUGCGACUACUACAA | 1617 |
| AM11402-SS-NL | gscuguucuGfUfGfacuacuacaa | 1266 | GCUGUUCUGUGACUACUACAA | 1678 |
| AM11463-SS-NL | asccagaucAfUfCfuucaacaaca | 1267 | ACCAGAUCAUCUUCAACAACA | 1679 |
| AM11466-SS-NL | gsgcucuguGfGfUfaacuucaaca | 1268 | GGCUCUGUGGUAACUUCAACA | 1680 |
| AM11468-SS-NL | gsagcguggAfGfAfaugaaaagua | 1269 | GAGCGUGGAGAAUGAAAAGUA | 1681 |
| AM11470-SS-NL | gsgggagaauGfAfAfaaguaugcua | 1270 | GGGAGAAUGAAAAGUAUGCUA | 1682 |
| AM11472-SS-NL | csuucucgaAfCfUfgcauguauga | 1271 | CUUCUCGAACUGCAUGUAUGA | 1683 |
| AM11474-SS-NL | gscucgaacUfGfCfauguaugaca | 1272 | GCUCGAACUGCAUGUAUGACA | 1684 |
| AM11476-SS-NL | csucgaacuGfCfAfuguaugacaa | 1273 | CUCGAACUGCAUGUAUGACAA | 1685 |
| AM11478-SS-NL | cscacuguuCfUfGfugacuacuaa | 1274 | CCACUGUUCUGUGACUACUAA | 1686 |
| AM11480-SS-NL | csacuguucUfGfUfgacuacuaca | 1275 | CACUGUUCUGUGACUACUACA | 1687 |

TABLE 4-continued

MUC5AC Agent Sense Strand Sequences (Shown Without Linkers, Conjugates, or Capping Moieties)

| Strand ID | Modified Sense Strand (5'→3') | SEQ ID NO. | Underlying Base Sequence (5'→3') (Shown as an Unmodified Nucleotide Sequence) | SEQ ID NO. |
|---|---|---|---|---|
| AM11497-SS-NL | cscuucuucUfCfGfaacuicaugu | 1276 | CCUUCUUCUCGAACUICAUGU | 1688 |
| AM11739-SS-NL | cscacccauGfUfGfcuacaacuau | 1277 | CCACCCAUGUGCUACAACUAU | 1689 |
| AM11743-SS-NL | csugcuaCfaAfcUfaugaiaucca | 1278 | CUGCUACAACUAUGAIAUCCA | 1664 |
| AM11744-SS-NL | csgagauCfaUfcUfucaacaacaa | 1279 | CGAGAUCAUCUUCAACAACAA | 1667 |
| AM11822-SS-NL | csacuguUfcUfgUfgacuacuaca | 1280 | CACUGUUCUGUGACUACUACA | 1687 |
| AM11824-SS-NL | gsacuguUfcUfgUfgacuacuaca | 1281 | GACUGUUCUGUGACUACUACA | 1690 |
| AM11970-SS-NL | usggggaagUfGfUfuccuiaacca | 1282 | UGGGGAAGUGUUCCUIAACCA | 1691 |
| AM11972-SS-NL | gsgacaucaCfCfUfgcaguiuuga | 1283 | GGACAUCACCUGCAGUIUUGA | 1692 |
| AM11974-SS-NL | usgugggaaCfUfUfcgaciacaua | 1284 | UGUGGGAACUUCGACIACAUA | 1693 |
| AM11976-SS-NL | gsucuuugaUfGfAfggacaagaua | 1285 | GUCUUUGAUGAGGACAAGAUA | 1694 |
| AM11978-SS-NL | gsgacgucaUfCfUfaccacaciaa | 1286 | GGACGUCAUCUACCACACIAA | 1695 |
| AM11980-SS-NL | csugcuacaAfCfUfaugaiaucca | 1287 | CUGCUACAACUAUGAIAUCCA | 1664 |
| AM11981-SS-NL | gscaccuccUfCfUfugicagaaau | 1288 | GCACCUCCUCUUGICAGAAAU | 1696 |
| AM11983-SS-NL | ascgagaucAfUfCfuucaacaaca | 1289 | ACGAGAUCAUCUUCAACAACA | 1697 |
| AM11985-SS-NL | csgagaucaUfCfUfucaacaacaa | 1290 | CGAGAUCAUCUUCAACAACAA | 1667 |
| AM12157-SS-NL | gscaaggaaAfCfCfuacaacaaca | 1291 | GCAAGGAAACCUACAACAACA | 1698 |
| AM12160-SS-NL | gscaaggAfaAfcCfuacaacaaca | 1292 | GCAAGGAAACCUACAACAACA | 1698 |
| AM12164-SS-NL | gscugauUfuGfcCfugaacaagaa | 1293 | GCUGAUUUGCCUGAACAAGAA | 1632 |
| AM12168-SS-NL | gscugauUfuGfcCfuga_2Nacaagaa | 1294 | GCUGAUUUGCCUG($A^{2N}$)ACAAGAA | 1699 |
| AM12170-SS-NL | gsgcugaUfuUfgCfcugaacaaga | 1295 | GGCUGAUUUGCCUGAACAAGA | 1670 |
| AM12174-SS-NL | gsgaccaGfcAfuCfuucaucaaca | 1296 | GGACCAGCAUCUUCAUCAACA | 1631 |
| AM12179-SS-NL | csgagaucaUfCfUfuca_2Nacaacaa | 1297 | CGAGAUCAUCUUC($A^{2N}$)ACAACAA | 1700 |
| AM12188-SS-NL | csaucuuugAfUfGfaggacaagau | 1298 | CAUCUUUGAUGAGGACAAGAU | 1701 |
| AM12190-SS-NL | gscuuugauGfAfGfgacaagauga | 1299 | GCUUUGAUGAGGACAAGAUGA | 1702 |
| AM12192-SS-NL | gsucucugcUfCfCfuacaacuaga | 1300 | GUCUCUGCUCCUACAACUAGA | 1703 |
| AM12194-SS-NL | csaaccucuGfCfUfucuacaacua | 1301 | CAACCUCUGCUUCUACAACUA | 1704 |
| AM12196-SS-NL | csua_2NuaaccAfGfCfacaacuucua | 1302 | CU($A^{2N}$)UAACCAGCACAACUUCUA | 1705 |
| AM12198-SS-NL | csuauaaccAfGfCfacaacuucua | 1303 | CUAUAACCAGCACAACUUCUA | 1706 |
| AM12515-SS-NL | gscuguucuGfcGfaCfuacuacaa | 1304 | GCUGUUCUGCGACUACUACAA | 1617 |
| AM12517-SS-NL | gscuguuCfuGfcGfacuacuacaa | 1305 | GCUGUUCUGCGACUACUACAA | 1617 |
| AM12518-SS-NL | gscuguucuGfcGfacuacuacaa | 1306 | GCUGUUCUGCGACUACUACAA | 1617 |
| AM12520-SS-NL | gscuguuuuGfcGfacuacuacaa | 1307 | GCUGUUUUGCGACUACUACAA | 1707 |
| AM12521-SS-NL | gscuguucuGfcGfauuacuacaa | 1308 | GCUGUUCUGCGAUUACUACAA | 1708 |
| AM12522-SS-NL | gscuguucuGfcGfacuauuacaa | 1309 | GCUGUUCUGCGACUAUUACAA | 1709 |
| AM12523-SS-NL | gscuguucuGfcGfAfcuacuacaa | 1310 | GCUGUUCUGCGACUACUACAA | 1617 |
| AM12605-SS-NL | gscugauuuGfcCfugaacaagaa | 1311 | GCUGAUUUGCCUGAACAAGAA | 1632 |

TABLE 4-continued

MUC5AC Agent Sense Strand Sequences (Shown Without Linkers, Conjugates, or Capping Moieties)

| Strand ID | Modified Sense Strand (5'→3') | SEQ ID NO. | Underlying Base Sequence (5'→3') (Shown as an Unmodified Nucleotide Sequence) | SEQ ID NO. |
|---|---|---|---|---|
| AM12606-SS-NL | gscugauuuGfcCfuGfaacaagaa | 1312 | GCUGAUUUGCCUGAACAAGAA | 1632 |
| AM12607-SS-NL | cscugauUfuGfcCfugaacaagaa | 1313 | CCUGAUUUGCCUGAACAAGAA | 1710 |
| AM12715-SS-NL | csgagaucaUfCfUfucaacaacaa | 1314 | CGAGAUCAUCUUCAACAACAA | 1667 |
| AM13074-SS-NL | gscugauUfuGfcCfugaacaagaa | 1315 | GCUGAUUUGCCUGAACAAGAA | 1632 |
| AM14080-SS-NL | gscuguucuGfCfGfacuacuacaa | 1316 | GCUGUUCUGCGACUACUACAA | 1617 |
| AM14081-SS-NL | gscugguucuGfCfGfacuacuacaa | 1317 | GCUGGUUCUGCGACUACUACAA | 1711 |
| AM14084-SS-NL | gscguucuGfCfGfacuacuacaa | 1318 | GCGUUCUGCGACUACUACAA | 1712 |

($A^{2N}$) = 2-aminoadenine-containing nucleotide; 1 = hypoxanthine (inosine) nucleotide
**For the constructs in Table 4 above, a capping moiety, such as for example, (InvAb) or s(InvAb), or a conjugate is typically located at the 3' end of the modified sense strand sequence shown (see, e.g., Table 5, below).

TABLE 5

MUC5AC Agent Sense Strand Sequences (Shown With TriAlk14 Linker (see Table 12 for structure information)).

| Strand ID | Modified Sense Strand (5' → 3') | SEQ ID NO. | Underlying Base Sequence (5' → 3') (Shown as an Unmodified Nucleotide Sequence) | SEQ ID NO. |
|---|---|---|---|---|
| AM10578-SS | (TriAlk14)accugcucCfAfAfgiccaucaaas(invAb) | 1319 | ACCUGCUCCAAGICCAUCAAA | 1609 |
| AM10580-SS | (TriAlk14)ugcuccaaGfGfCfcaucaagauus(invAb) | 1320 | UGCUCCAAGGCCAUCAAGAUU | 1610 |
| AM10582-SS | (TriAlk14)aaccucagCfUfCfcgaguucaaas(invAb) | 1321 | AACCUCAGCUCCGAGUUCAAA | 1611 |
| AM10584-SS | (TriAlk14)cccagaagCfAfGfugcaicaucas(invAb) | 1322 | CCCAGAAGCAGUGCAICAUCA | 1612 |
| AM10586-SS | (TriAlk14)ugcccucuGfUfUfcugciacuaas(invAb) | 1323 | UGCCCUCUGUUCUGCIACUAA | 1613 |
| AM10588-SS | (TriAlk14)gcccucugUfUfCfuicgacuacus(invAb) | 1324 | GCCCUCUGUUCUICGACUACU | 1614 |
| AM10590-SS | (TriAlk14)ccucuguuCfUfGfcgacuacuaas(invAb) | 1325 | CCUCUGUUCUGCGACUACUAA | 1615 |
| AM10592-SS | (TriAlk14)cucuguucUfGfCfgacuacuacas(invAb) | 1326 | CUCUGUUCUGCGACUACUACA | 1616 |
| AM10594-SS | (TriAlk14)gcuguucuGfCfGfacuacuacaas(invAb) | 1327 | GCUGUUCUGCGACUACUACAA | 1617 |
| AM10596-SS | (TriAlk14)ccacccauCfUfGfcuacaacuaus(invAb) | 1328 | CCACCCAUCUGCUACAACUAU | 1618 |
| AM10598-SS | (TriAlk14)gcaaagugGfUfUfcgaciuggaas(invAb) | 1329 | GCAAAGUGGUUCGACIUGGAA | 1619 |
| AM10600-SS | (TriAlk14)gagugguuCfGfAfcgugiacuuas(invAb) | 1330 | GAGUGGUUCGACGUGIACUUA | 1620 |
| AM10602-SS | (TriAlk14)gugguucgAfCfGfugiacuuccas(invAb) | 1331 | GUGGUUCGACGUGIACUUCCA | 1621 |
| AM10604-SS | (TriAlk14)gugguucgAfCfGfuggacuuccas(invAb) | 1332 | GUGGUUCGACGUGGACUUCCA | 1622 |
| AM10738-SS | (TriAlk14)csagcuuccAfCfUfacaaiaccuus(invAb) | 1333 | CAGCUUCCACUACAAIACCUU | 1623 |
| AM10740-SS | (TriAlk14)csagcuuccAfCfUfacaagaccuus(invAb) | 1334 | CAGCUUCCACUACAAGACCUU | 1624 |
| AM10742-SS | (TriAlk14)gsa_2NaguaugCfUfCfagcacugiuas(invAb) | 1335 | G($A^{2N}$)AGUAUGCUCAGCACUGIUA | 1625 |
| AM10745-SS | (TriAlk14)gsa_2NaguaugCfUfCfaguacugiuas(invAb) | 1336 | G($A^{2N}$)AGUAUGCUCAGUACUGIUA | 1626 |
| AM10746-SS | (TriAlk14)gsccuucuuCfAfAfcaccuucaaas(invAb) | 1337 | GCCUUCUUCAACACCUUCAAA | 1627 |
| AM10748-SS | (TriAlk14)gsccuucuuCfAfAfcaucuucaaas(invAb) | 1338 | GCCUUCUUCAACAUCUUCAAA | 1628 |
| AM10749-SS | (TriAlk14)gsccuucuuCfAfAfcacuuucaaas(invAb) | 1339 | GCCUUCUUCAACACUUUCAAA | 1629 |
| AM10763-SS | (TriAlk14)gggacaagAfAfGfaccaicaucus(invAb) | 1340 | GGGACAAGAAGACCAICAUCU | 1630 |

TABLE 5-continued

MUC5AC Agent Sense Strand Sequences (Shown With TriAlk14 Linker (see Table 12 for structure information)).

| Strand ID | Modified Sense Strand (5' → 3') | SEQ ID NO. | Underlying Base Sequence (5' → 3') (Shown as an Unmodified Nucleotide Sequence) | SEQ ID NO. |
|---|---|---|---|---|
| AM10765-SS | (TriAlk14)ggaccagcAfUfCfuucaucaacas(invAb) | 1341 | GGACCAGCAUCUUCAUCAACA | 1631 |
| AM10767-SS | (TriAlk14)gcugauuuGfCfCfugaacaagaas(invAb) | 1342 | GCUGAUUUGCCUGAACAAGAA | 1632 |
| AM10769-SS | (TriAlk14)ca_2NaggaaaCfCfUfacaacaacaus(invAb) | 1343 | C($A^{2N}$)AGGAAACCUACAACAACAU | 1633 |
| AM10771-SS | (TriAlk14)ggaaaccuAfCfAfacaacaucaus(invAb) | 1344 | GGAAACCUACAACAACAUCAU | 1634 |
| AM10789-SS | (TriAlk14)ga_2NagaccaGfCfAfucuucaucaas(invAb) | 1345 | G($A^{2N}$)AGACCAGCAUCUUCAUCAA | 1635 |
| AM10791-SS | (TriAlk14)gcugcuacAfAfCfuaccaiaucas(invAb) | 1346 | GCUGCUACAACUACCAIAUCA | 1636 |
| AM10793-SS | (TriAlk14)gcuacaacUfAfCfcagaucaigas(invAb) | 1347 | GCUACAACUACCAGAUCAIGA | 1637 |
| AM10795-SS | (TriAlk14)cccacccaUfCfUfgcuacaacuas(invAb) | 1348 | CCCACCCAUCUGCUACAACUA | 1638 |
| AM10797-SS | (TriAlk14)gagauccgCfAfUfccaguiuugas(invAb) | 1349 | GAGAUCCGCAUCCAGUIUUGA | 1639 |
| AM10799-SS | (TriAlk14)ccagagguGfAfGfcauciaacaas(invAb) | 1350 | CCAGAGGUGAGCAUCIAACAA | 1640 |
| AM10801-SS | (TriAlk14)cagcagggAfCfCfcuucaagauas(invAb) | 1351 | CAGCAGGGACCCUUCAAGAUA | 1641 |
| AM10803-SS | (TriAlk14)ca_2NagauguGfCfCfucaacuacias(invAb) | 1352 | C($A^{2N}$)AGAUGUGCCUCAACUACIA | 1642 |
| AM10805-SS | (TriAlk14)ggaugugcCfUfCfaacuaciagas(invAb) | 1353 | GGAUGUGCCUCAACUACIAGA | 1643 |
| AM10807-SS | (TriAlk14)cagcuuccAfCfUfacaaiaccuus(invAb) | 1354 | CAGCUUCCACUACAAIACCUU | 1623 |
| AM10809-SS | (TriAlk14)gacagcgaGfAfCfcugcuugaaas(invAb) | 1355 | GACAGCGAGACCUGCUUGAAA | 1644 |
| AM10811-SS | (TriAlk14)ccaacgucAfCfCfaucuucagaas(invAb) | 1356 | CCAACGUCACCAUCUUCAGAA | 1645 |
| AM10813-SS | (TriAlk14)ca_2NacgucaCfCfAfucuucaiacas(invAb) | 1357 | C($A^{2N}$)ACGUCACCAUCUUCAIACA | 1646 |
| AM10815-SS | (TriAlk14)cauccaggCfCfGfaugacuuccas(invAb) | 1358 | CAUCCAGGCCGAUGACUUCCA | 1647 |
| AM10817-SS | (TriAlk14)gccuucuuCfAfAfcaccuucaaas(invAb) | 1359 | GCCUUCUUCAACACCUUCAAA | 1627 |
| AM10819-SS | (TriAlk14)ga_2NaguaugCfUfCfagcacugiuas(invAb) | 1360 | G($A^{2N}$)AGUAUGCUCAGCACUGIUA | 1625 |
| AM10820-SS | (TriAlk14)ga_2NaccuacUfAfCfucgaacuicas(invAb) | 1361 | G($A^{2N}$)ACCUACUACUCGAACUICA | 1648 |
| AM10822-SS | (TriAlk14)acagggacCfAfCfcugcuucaaas(invAb) | 1362 | ACAGGGACCACCUGCUUCAAA | 1649 |
| AM10824-SS | (TriAlk14)ccugcuccAfAfGfgcuaucaagas(invAb) | 1363 | CCUGCUCCAAGGCUAUCAAGA | 1650 |
| AM10826-SS | (TriAlk14)ca_2NuguggaAfCfCfacgauiacaas(invAb) | 1364 | C($A^{2N}$)UGUGGAACCACGAUIACAA | 1651 |
| AM10828-SS | (TriAlk14)aggcaagaCfCfUfcugcuucuius(invAb) | 1365 | AGGCAAGACCUCUGCUUCUIU | 1652 |
| AM10830-SS | (TriAlk14)uccacagaCfUfGfcaccaacuias(invAb) | 1366 | UCCACAGACUGCACCAACUIA | 1653 |
| AM10832-SS | (TriAlk14)gcagugccUfUfCfacuguacuias(invAb) | 1367 | GCAGUGCCUUCACUGUACUIA | 1654 |
| AM10834-SS | (TriAlk14)gcuguggGAfAfCfuucaacaicas(invAb) | 1368 | GCUGUGGGAACUUCAACAICA | 1655 |
| AM10836-SS | (TriAlk14)gugggaacUfUfCfaacaicaucas(invAb) | 1369 | GUGGGAACUUCAACAICAUCA | 1656 |
| AM10838-SS | (TriAlk14)gcuucaacAfCfCfuucaaiaccas(invAb) | 1370 | GCUUCAACACCUUCAAIACCA | 1657 |
| AM10840-SS | (TriAlk14)ccccaacaUfCfAfggaacaicuus(invAb) | 1371 | CCCCAACAUCAGGAACAICUU | 1658 |
| AM10842-SS | (TriAlk14)ccuacuacUfCfGfaacuicaugus(invAb) | 1372 | CCUACUACUCGAACUICAUGU | 1659 |
| AM10844-SS | (TriAlk14)gucaccugCfAfGfuguugicuuas(invAb) | 1373 | GUCACCUGCAGUGUUGICUUA | 1660 |
| AM10846-SS | (TriAlk14)gcuggacaUfGfAfccuguuacaas(invAb) | 1374 | GCUGGACAUGACCUGUUACAA | 1661 |
| AM10848-SS | (TriAlk14)gcagagcuAfCfAfgcuucaacias(invAb) | 1375 | GCAGAGCUACAGCUUCAACIA | 1662 |

TABLE 5-continued

MUC5AC Agent Sense Strand Sequences (Shown With TriAlk14 Linker (see Table 12 for structure information)).

| Strand ID | Modified Sense Strand (5' → 3') | SEQ ID NO. | Underlying Base Sequence (5' → 3') (Shown as an Unmodified Nucleotide Sequence) | SEQ ID NO. |
|---|---|---|---|---|
| AM11066-SS | (TriAlk14)ga_2NaguaugCfUfCfaguacugiuas(invAb) | 1376 | G(A$^{2N}$)AGUAUGCUCAGUACUGIUA | 1626 |
| AM11263-SS | (TriAlk14)csugcuacaAfCfUfaugagauccas(invAb) | 1377 | CUGCUACAACUAUGAGAUCCA | 1663 |
| AM11265-SS | (TriAlk14)csugcuacaAfCfUfaugaiauccas(invAb) | 1378 | CUGCUACAACUAUGAIAUCCA | 1664 |
| AM11267-SS | (TriAlk14)cscuggaccAfAfGfugguuugacas(invAb) | 1379 | CCUGGACCAAGUGGUUUGACA | 1665 |
| AM11269-SS | (TriAlk14)cscuggaccAfAfGfugguuuiacas(invAb) | 1380 | CCUGGACCAAGUGGUUUIACA | 1666 |
| AM11270-SS | (TriAlk14)csgagaucaUfCfUfucaacaacaas(invAb) | 1381 | CGAGAUCAUCUUCAACAACAA | 1667 |
| AM11274-SS | (TriAlk14)agcagugcCfUfUfcacuguacuas(invAb) | 1382 | AGCAGUGCCUUCACUGUACUA | 1668 |
| AM11276-SS | (TriAlk14)gacaucagGfAfAfcagcuuciaas(invAb) | 1383 | GACAUCAGGAACAGCUUCIAA | 1669 |
| AM11278-SS | (TriAlk14)ggcugauuUfGfCfcugaacaagas(invAb) | 1384 | GGCUGAUUUGCCUGAACAAGA | 1670 |
| AM11280-SS | (TriAlk14)ccaggacaAfCfCfacuuuigugas(invAb) | 1385 | CCAGGACAACCACUUUIGUGA | 1671 |
| AM11282-SS | (TriAlk14)caaccagaAfCfAfaccucuicuas(invAb) | 1386 | CAACCAGAACAACCUCUICUA | 1672 |
| AM11284-SS | (TriAlk14)cgcuacaaCfCfAfgcacaaucuas(invAb) | 1387 | CGCUACAACCAGCACAAUCUA | 1673 |
| AM11286-SS | (TriAlk14)ccacaaccAfGfCfacaacuucuas(invAb) | 1388 | CCACAACCAGCACAACUUCUA | 1674 |
| AM11288-SS | (TriAlk14)gacaaccaCfUfUfuggugacaaas(invAb) | 1389 | GACAACCACUUUGGUGACAAA | 1675 |
| AM11290-SS | (TriAlk14)cuacaaccAfAfCfacaacuucuas(invAb) | 1390 | CUACAACCAACACAACUUCUA | 1676 |
| AM11292-SS | (TriAlk14)accucugcUfCfCfuacaacuagas(invAb) | 1391 | ACCUCUGCUCCUACAACUAGA | 1677 |
| AM11400-SS | (TriAlk14)gscuguucuGfCfGfacuacuacaas(invAb) | 1392 | GCUGUUCUGCGACUACUACAA | 1617 |
| AM11402-SS | (TriAlk14)gscuguucuGfUfGfacuacuacaas(invAb) | 1393 | GCUGUUCUGUGACUACUACAA | 1678 |
| AM11463-SS | (TriAlk14)asccagaucAfUfCfuucaacaacas(invAb) | 1394 | ACCAGAUCAUCUUCAACAACA | 1679 |
| AM11466-SS | (TriAlk14)gsgcucuguGfGfUfaacuucaacas(invAb) | 1395 | GGCUCUGUGGUAACUUCAACA | 1680 |
| AM11468-SS | (TriAlk14)gsagcguggAfGfAfaugaaaaguas(invAb) | 1396 | GAGCGUGGAGAAUGAAAAGUA | 1681 |
| AM11470-SS | (TriAlk14)gsggagaauGfAfAfaaguaugcuas(invAb) | 1397 | GGGAGAAUGAAAAGUAUGCUA | 1682 |
| AM11472-SS | (TriAlk14)csuucucgaAfCfUfgcauguaugas(invAb) | 1398 | CUUCUCGAACUGCAUGUAUGA | 1683 |
| AM11474-SS | (TriAlk14)gscucgaacUfGfCfauguaugacas(invAb) | 1399 | GCUCGAACUGCAUGUAUGACA | 1684 |
| AM11476-SS | (TriAlk14)csucgaacuGfCfAfuguaugacaas(invAb) | 1400 | CUCGAACUGCAUGUAUGACAA | 1685 |
| AM11478-SS | (TriAlk14)cscacuguuCfUfGfugacuacuaas(invAb) | 1401 | CCACUGUUCUGUGACUACUAA | 1686 |
| AM11480-SS | (TriAlk14)csacuguucUfGfUfgacuacuacas(invAb) | 1402 | CACUGUUCUGUGACUACUACA | 1687 |
| AM11497-SS | (TriAlk14)cscuucuucUfCfGfaacuicaugus(invAb) | 1403 | CCUUCUUCUCGAACUICAUGU | 1688 |
| AM11739-SS | (TriAlk14)cscacccauGfUfGfcuacaacuaus(invAb) | 1404 | CCACCCAUGUGCUACAACUAU | 1689 |
| AM11743-SS | (TriAlk14)csugcuaCfaAfcUfaugaiauccas(invAb) | 1405 | CUGCUACAACUAUGAIAUCCA | 1664 |
| AM11744-SS | (TriAlk14)csgagauCfaUfcUfucaacaacaas(invAb) | 1406 | CGAGAUCAUCUUCAACAACAA | 1667 |
| AM11822-SS | (TriAlk14)csacuguUfcUfgUfgacuacuacas(invAb) | 1407 | CACUGUUCUGUGACUACUACA | 1687 |
| AM11824-SS | (TriAlk14)gsacuguUfcUfgUfgacuacuacas(invAb) | 1408 | GACUGUUCUGUGACUACUACA | 1690 |
| AM11970-SS | (TriAlk14)uggggaagUfGfUfuccuiaaccas(invAb) | 1409 | UGGGGAAGUGUUCCUIAACCA | 1691 |
| AM11972-SS | (TriAlk14)ggacaucaCfCfUfgcaguiuugas(invAb) | 1410 | GGACAUCACCUGCAGUIUUGA | 1692 |
| AM11974-SS | (TriAlk14)ugugggaaCfUfUfcgaciacauas(invAb) | 1411 | UGUGGGAACUUCGACIACAUA | 1693 |

TABLE 5-continued

MUC5AC Agent Sense Strand Sequences (Shown With TriAlk14 Linker (see Table 12 for structure information)).

| Strand ID | Modified Sense Strand (5' → 3') | SEQ ID NO. | Underlying Base Sequence (5' → 3') (Shown as an Unmodified Nucleotide Sequence) | SEQ ID NO. |
|---|---|---|---|---|
| AM11976-SS | (TriAlk14)gucuuugaUfGfAfggacaagauas(invAb) | 1412 | GUCUUUGAUGAGGACAAGAUA | 1694 |
| AM11978-SS | (TriAlk14)ggacgucaUfCfUfaccacaciaas(invAb) | 1413 | GGACGUCAUCUACCACACIAA | 1695 |
| AM11980-SS | (TriAlk14)cugcuacaAfCfUfaugaiauccas(invAb) | 1414 | CUGCUACAACUAUGAIAUCCA | 1664 |
| AM11981-SS | (TriAlk14)gcaccuccUfCfUfugicagaaaus(invAb) | 1415 | GCACCUCCUCUUGICAGAAAU | 1696 |
| AM11983-SS | (TriAlk14)acgagaucAfUfCfuucaacaacas(invAb) | 1416 | ACGAGAUCAUCUUCAACAACA | 1697 |
| AM11985-SS | (TriAlk14)cgagaucaUfCfUfucaacaacaas(invAb) | 1417 | CGAGAUCAUCUUCAACAACAA | 1667 |
| AM12157-SS | (TriAlk14)gcaaggaaAfCfCfuacaacaacas(invAb) | 1418 | GCAAGGAAACCUACAACAACA | 1698 |
| AM12160-SS | (TriAlk14)gcaaggAfaAfcCfuacaacaacas(invAb) | 1419 | GCAAGGAAACCUACAACAACA | 1698 |
| AM12164-SS | (TriAlk14)gcugauUfuGfcCfugaacaagaas(invAb) | 1420 | GCUGAUUUGCCUGAACAAGAA | 1632 |
| AM12168-SS | (TriAlk14)gcugauUfuGfcCfuga_2Nacaagaas(invAb) | 1421 | GCUGAUUUGCCUG($A^{2N}$)ACAAGAA | 1699 |
| AM12170-SS | (TriAlk14)ggcugaUfuUfgCfcugaacaagas(invAb) | 1422 | GGCUGAUUUGCCUGAACAAGA | 1670 |
| AM12174-SS | (TriAlk14)ggaccaGfcAfuCfuucaucaacas(invAb) | 1423 | GGACCAGCAUCUUCAUCAACA | 1631 |
| AM12179-SS | (TriAlk14)csgagaucaUfCfUfuca_2Nacaacaas(invAb) | 1424 | CGAGAUCAUCUUC($A^{2N}$)ACAACAA | 1700 |
| AM12188-SS | (TriAlk14)caucuuugAfUfGfaggacaagaus(invAb) | 1425 | CAUCUUUGAUGAGGACAAGAU | 1701 |
| AM12190-SS | (TriAlk14)gcuuugauGfAfGfgacaagaugas(invAb) | 1426 | GCUUUGAUGAGGACAAGAUGA | 1702 |
| AM12192-SS | (TriAlk14)gucucugcUfCfCfuacaacuagas(invAb) | 1427 | GUCUCUGCUCCUACAACUAGA | 1703 |
| AM12194-SS | (TriAlk14)caaccucuGfCfUfucuacaacuas(invAb) | 1428 | CAACCUCUGCUUCUACAACUA | 1704 |
| AM12196-SS | (TriAlk14)cua_2NuaaccAfGfCfacaacuucuas(invAb) | 1429 | CU($A^{2N}$)UAACCAGCACAACUUCUA | 1705 |
| AM12198-SS | (TriAlk14)cuauaaccAfGfCfacaacuucuas(invAb) | 1430 | CUAUAACCAGCACAACUUCUA | 1706 |
| AM12515-SS | (TriAlk14)gcuguucuGfcGfaCfuacuacaas(invAb) | 1431 | GCUGUUCUGCGACUACUACAA | 1617 |
| AM12517-SS | (TriAlk14)gcuguuCfuGfcGfacuacuacaas(invAb) | 1432 | GCUGUUCUGCGACUACUACAA | 1617 |
| AM12518-SS | (TriAlk14)gcuguucuGfcGfacuacuacaas(invAb) | 1433 | GCUGUUCUGCGACUACUACAA | 1617 |
| AM12520-SS | (TriAlk14)gcuguuuuGfcGfacuacuacaas(invAb) | 1434 | GCUGUUUUGCGACUACUACAA | 1707 |
| AM12521-SS | (TriAlk14)gcuguucuGfcGfauuacuacaas(invAb) | 1435 | GCUGUUCUGCGAUUACUACAA | 1708 |
| AM12522-SS | (TriAlk14)gcuguucuGfcGfacuauuacaas(invAb) | 1436 | GCUGUUCUGCGACUAUUACAA | 1709 |
| AM12523-SS | (TriAlk14)gcuguucuGfcGfAfcuacuacaas(invAb) | 1437 | GCUGUUCUGCGACUACUACAA | 1617 |
| AM12605-SS | (TriAlk14)gcugauuuGfcCfugaacaagaas(invAb) | 1438 | GCUGAUUUGCCUGAACAAGAA | 1632 |
| AM12606-SS | (TriAlk14)gcugauuuGfcCfuGfaacaagaas(invAb) | 1439 | GCUGAUUUGCCUGAACAAGAA | 1632 |
| AM12607-SS | (TriAlk14)ccugauUfuGfcCfugaacaagaas(invAb) | 1440 | CCUGAUUUGCCUGAACAAGAA | 1710 |
| AM13074-SS | (TriAlk14)gscugauUfuGfcCfugaacaagaas(invAb) | 1441 | GCUGAUUUGCCUGAACAAGAA | 1632 |
| AM14080-SS | (TriAlk14)gscuguucuGfCfGfacuacuacaa(invAb) | 1442 | GCUGUUCUGCGACUACUACAA | 1617 |
| AM14081-SS | (TriAlk14)gscugguucuGfCfGfacuacuacaas(invAb) | 1443 | GCUGGUUCUGCGACUACUACAA | 1711 |
| AM14084-SS | (TriAlk14)gscguucuGfCfGfacuacuacaas(invAb) | 1444 | GCGUUCUGCGACUACUACAA | 1712 |

($A^{2N}$) = 2-aminoadenine-containing nucleotide;
I = hypoxanthine (inosine) nucleotide

TABLE 6

Nucleotide Sequences With End Caps Shown For Certain MUC5AC RNAi Agents Tested In Vitro.

| Strand ID | Modified Sense Strand (5' → 3') | SEQ ID NO. | Underlying Base Sequence (5' → 3') (Shown as an Unmodified Nucleotide Sequence) | SEQ ID NO. |
|---|---|---|---|---|
| AM10594-SS-S | (invAb)sgcuguucuGfCfGfacuacuacaas(invAb) | 1445 | GCUGUUCUGCGACUACUACAA | 1617 |
| AM10600-SS-S | (invAb)sgagugguuCfGfAfcgugiacuuas(invAb) | 1446 | GAGUGGUUCGACGUGIACUUA | 1620 |
| AM10765-SS-S | (invAb)sggaccagcAfUfCfuucaucaacas(invAb) | 1447 | GGACCAGCAUCUUCAUCAACA | 1631 |
| AM10767-SS-S | (invAb)sgcugauuuGfCfCfugaacaagaas(invAb) | 1448 | GCUGAUUUGCCUGAACAAGAA | 1632 |
| AM10769-SS-S | (invAb)sca_2NaggaaaCfCfUfacaacaacaus(invAb) | 1449 | C($A^{2N}$)AGGAAACCUACAACAACAU | 1633 |
| AM10771-SS-S | (invAb)sggaaaccuAfCfAfacaacaucaus(invAb) | 1450 | GGAAACCUACAACAACAUCAU | 1634 |
| AM10791-SS-S | (invAb)sgcugcuacAfAfCfuaccaiaucas(invAb) | 1451 | GCUGCUACAACUACCAIAUCA | 1636 |
| AM10793-SS-S | (invAb)sgcuacaacUfAfCfcagaucaigas(invAb) | 1452 | GCUACAACUACCAGAUCAIGA | 1637 |
| AM10795-SS-S | (invAb)scccacccaUfCfUfgcuacaacuas(invAb) | 1453 | CCCACCCAUCUGCUACAACUA | 1638 |
| AM10797-SS-S | (invAb)sgagauccgCfAfUfccaguiuugas(invAb) | 1454 | GAGAUCCGCAUCCAGUIUUGA | 1639 |
| AM10799-SS-S | (invAb)sccagagguGfAfGfcauciaacaas(invAb) | 1455 | CCAGAGGUGAGCAUCIAACAA | 1640 |
| AM10801-SS-S | (invAb)scagcagggAfCfCfcuucaagauas(invAb) | 1456 | CAGCAGGGACCCUUCAAGAUA | 1641 |
| AM10803-SS-S | (invAb)sca_2NagauguGfCfCfucaacuacias(invAb) | 1457 | C($A^{2N}$)AGAUGUGCCUCAACUACIA | 1642 |
| AM10813-SS-S | (invAb)sca_2NacgucaCfCfAfucuucaiacas(invAb) | 1458 | C($A^{2N}$)ACGUCACCAUCUUCAIACA | 1646 |
| AM10820-SS-S | (invAb)sga_2NaccuacUfAfCfucgaacuicas(invAb) | 1459 | G($A^{2N}$)ACCUACUACUCGAACUICA | 1648 |
| AM10826-SS-S | (invAb)sca_2NuguggaAfCfCfacgauiacaas(invAb) | 1460 | C($A^{2N}$)UGUGGAACCACGAUIACAA | 1651 |
| AM10828-SS-S | (invAb)saggcaagaCfCfUfcugcuucuius(invAb) | 1461 | AGGCAAGACCUCUGCUUCUIU | 1652 |
| AM10832-SS-S | (invAb)sgcagugccUfUfCfacuguacuias(invAb) | 1462 | GCAGUGCCUUCACUGUACUIA | 1654 |
| AM10836-SS-S | (invAb)sgugggaacUfUfCfaacaicaucas(invAb) | 1463 | GUGGGAACUUCAACAICAUCA | 1656 |
| AM10840-SS-S | (invAb)sccccaacaUfCfAfggaacaicuus(invAb) | 1464 | CCCCAACAUCAGGAACAICUU | 1658 |
| AM10842-SS-S | (invAb)sccuacuacUfCfGfaacuicaugus(invAb) | 1465 | CCUACUACUCGAACUICAUGU | 1659 |
| AM10844-SS-S | (invAb)sgucaccugCfAfGfuguugicuuas(invAb) | 1466 | GUCACCUGCAGUGUUGICUUA | 1660 |
| AM10846-SS-S | (invAb)sgcuggacaUfGfAfccuguuacaas(invAb) | 1467 | GCUGGACAUGACCUGUUACAA | 1661 |
| AM10848-SS-S | (invAb)sgcagagcuAfCfAfgcuucaacias(invAb) | 1468 | GCAGAGCUACAGCUUCAACIA | 1662 |
| AM11274-SS-S | (invAb)sagcagugcCfUfUfcacuguacuas(invAb) | 1469 | AGCAGUGCCUUCACUGUACUA | 1668 |
| AM11276-SS-S | (invAb)sgacaucagGfAfAfcagcuuciaas(invAb) | 1470 | GACAUCAGGAACAGCUUCIAA | 1669 |
| AM11278-SS-S | (invAb)sggcugauuUfGfCfcugaacaagas(invAb) | 1471 | GGCUGAUUUGCCUGAACAAGA | 1670 |
| AM11280-SS-S | (invAb)sccaggacaAfCfCfacuuuigugas(invAb) | 1472 | CCAGGACAACCACUUUIGUGA | 1671 |
| AM11286-SS-S | (invAb)sccacaaccAfGfCfacaacuucuas(invAb) | 1473 | CCACAACCAGCACAACUUCUA | 1674 |
| AM11288-SS-S | (invAb)sgacaaccaCfUfUfuggugacaaas(invAb) | 1474 | GACAACCACUUUGGUGACAAA | 1675 |
| AM11292-SS-S | (invAb)saccucugcUfCfCfuacaacuagas(invAb) | 1475 | ACCUCUGCUCCUACAACUAGA | 1677 |
| AM11978-SS-S | (invAb)sggacgucaUfCfUfaccacaciaas(invAb) | 1476 | GGACGUCAUCUACCACACIAA | 1695 |
| AM11980-SS-S | (invAb)scugcuacaAfCfUfaugaiauccas(invAb) | 1477 | CUGCUACAACUAUGAIAUCCA | 1664 |
| AM11983-SS-S | (invAb)sacgagaucAfUfCfuucaacaacas(invAb) | 1478 | ACGAGAUCAUCUUCAACAACA | 1697 |
| AM11985-SS-S | (invAb)scgagaucaUfCfUfucaacaacaas(invAb) | 1479 | CGAGAUCAUCUUCAACAACAA | 1667 |
| AM12164-SS-S | (invAb)sgcugauUfuGfcCfugaacaagaas(invAb) | 1480 | GCUGAUUUGCCUGAACAAGAA | 1632 |

TABLE 6-continued

Nucleotide Sequences With End Caps Shown For Certain MUC5AC RNAi Agents Tested In Vitro.

| Strand ID | Modified Sense Strand (5' → 3') | SEQ ID NO. | Underlying Base Sequence (5' → 3') (Shown as an Unmodified Nucleotide Sequence) | SEQ ID NO. |
|---|---|---|---|---|
| AM12168-SS-S | (invAb)sgcugauUfuGfcCfuga_2Nacaagaas(invAb) | 1481 | GCUGAUUUGCCUG(AN)ACAAGAA | 1699 |
| AM12170-SS-S | (invAb)sggcugaUfuUfgCfcugaacaagas(invAb) | 1482 | GGCUGAUUUGCCUGAACAAGA | 1670 |

($A^{2N}$) = 2-aminoadenine-containing nucleotide;
I = hypoxanthine (inosine) nucleotide

TABLE 7

Figure 1:
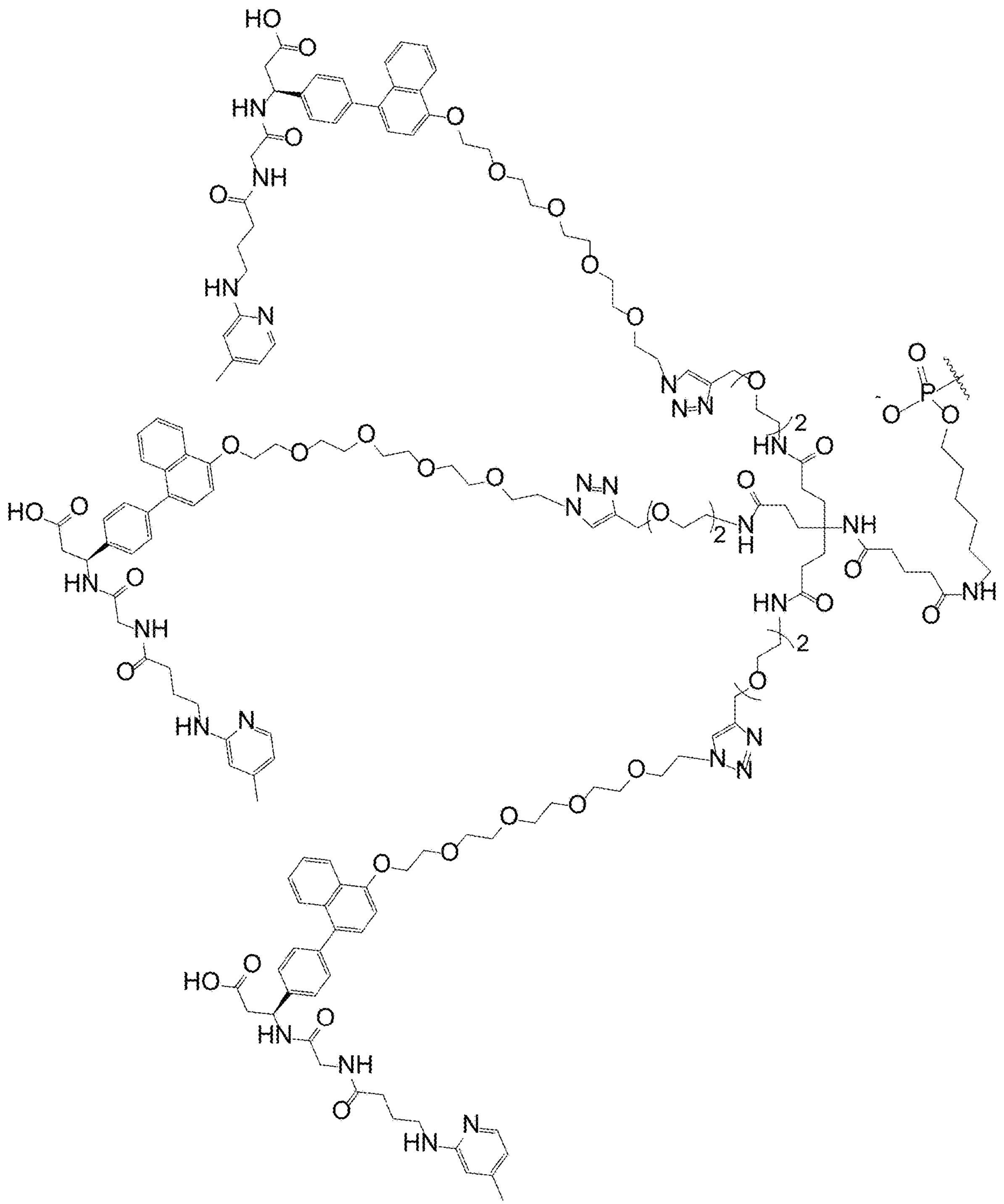
FIG. 1. Chemical structure representation of the tridentate αvβ6 epithelial cell targeting ligand referred to herein as Tri-SM6.1-αvβ6-(TA14).

MUC5AC Agent Sense Strand Sequences (Shown with Targeting Ligand Conjugate. The structure of αvβ6-SM6.1 is shown in Table 12, and the structure of Tri-SM6.1- αvβ6-(TA14) is shown in FIG. 1.)

| Strand ID | Modified Sense Strand (5' → 3') | SEQ ID NO. | Corresponding Sense Strand AM Number Without Linker or Conjugate (See Table 4) |
|---|---|---|---|
| CS000387 | Tri-SM6.1-avb6-(TA14)gsa_2NaguaugCfUfCfaguacugiuas(invAb) | 1483 | AM10745-SS |
| CS000517 | Tri-SM6.1-avb6-(TA14)ascccauguGfCfUfacaacuaugas(invAb) | 1484 | AM09492-SS |
| CS000519 | Tri-SM6.1-avb6-(TA14)cscauacagCfAfGfuacaguuacas(invAb) | 1485 | AM09657-SS |
| CS000521 | Tri-SM6.1-avb6-(TA14)csugcuacaAfCfUfaugagauccas(invAb) | 1486 | AM11263-SS |
| CS000523 | Tri-SM6.1-avb6-(TA14)csugcuacaAfCfUfaugaiauccas(invAb) | 1487 | AM11265-SS |
| CS000525 | Tri-SM6.1-avb6-(TA14)cscuggaccAfAfGfugguuugacas(invAb) | 1488 | AM11267-SS |
| CS000527 | Tri-SM6.1-avb6-(TA14)cscuggaccAfAfGfugguuuiacas(invAb) | 1489 | AM11269-SS |
| CS000528 | Tri-SM6.1-avb6-(TA14)csgagaucaUfCfUfucaacaacaas(invAb) | 1490 | AM11270-SS |
| CS000578 | Tri-SM6.1-avb6-(TA14)gscuguucuGfCfGfacuacuacaas(invAb) | 1491 | AM11400-SS |
| CS000583 | Tri-SM6.1-avb6-(TA14)gscuguucuGfUfGfacuacuacaas(invAb) | 1492 | AM11402-SS |
| CS000608 | Tri-SM6.1-avb6-(TA14)asccagaucAfUfCfuucaacaacas(invAb) | 1493 | AM11463-SS |
| CS000612 | Tri-SM6.1-avb6-(TA14)gsgcucuguGfGfUfaacuucaacas(invAb) | 1494 | AM11466-SS |
| CS000614 | Tri-SM6.1-avb6-(TA14)gsagcguggAfGfAfaugaaaaguas(invAb) | 1495 | AM11468-SS |
| CS000616 | Tri-SM6.1-avb6-(TA14)gsggagaauGfAfAfaaguaugcuas(invAb) | 1496 | AM11470-SS |
| CS000618 | Tri-SM6.1-avb6-(TA14)csuucucgaAfCfUfgcauguaugas(invAb) | 1497 | AM11472-SS |
| CS000620 | Tri-SM6.1-avb6-(TA14)gscucgaacUfGfCfauguaugacas(invAb) | 1498 | AM11474-SS |
| CS000622 | Tri-SM6.1-avb6-(TA14)csucgaacuGfCfAfuguaugacaas(invAb) | 1499 | AM11476-SS |
| CS000624 | Tri-SM6.1-avb6-(TA14)cscacuguuCfUfGfugacuacuaas(invAb) | 1500 | AM11478-SS |
| CS000626 | Tri-SM6.1-avb6-(TA14)csacuguucUfGfUfgacuacuacas(invAb) | 1501 | AM11480-SS |
| CS000665 | Tri-SM6.1-avb6-(TA14)cscuucuucUfCfGfaacuicaugus(invAb) | 1502 | AM11497-SS |
| CS001001 | Tri-SM6.1-avb6-(TA14)csagcuuccAfCfUfacaaiaccuus(invAb) | 1503 | AM10738-SS |
| CS001003 | Tri-SM6.1-avb6-(TA14)csagcuuccAfCfUfacaagaccuus(invAb) | 1504 | AM10740-SS |
| CS001005 | Tri-SM6.1-avb6-(TA14)gsa_2NaguaugCfUfCfagcacugiuas(invAb) | 1505 | AM10742-SS |
| CS001007 | Tri-SM6.1-avb6-(TA14)gsccuucuuCfAfAfcaccuucaaas(invAb) | 1506 | AM10746-SS |

TABLE 7-continued

MUC5AC Agent Sense Strand Sequences (Shown with Targeting Ligand Conjugate. The structure of αvβ6-SM6.1 is shown in Table 12, and the structure of Tri-SM6.1- αvβ6-(TA14) is shown in FIG. 1.)

| Strand ID | Modified Sense Strand (5' → 3') | SEQ ID NO. | Corresponding Sense Strand AM Number Without Linker or Conjugate (See Table 4) |
|---|---|---|---|
| CS001009 | Tri-SM6.1-avb6-(TA14)gsccuucuuCfAfAfcaucuucaaas(invAb) | 1507 | AM10748-SS |
| CS001010 | Tri-SM6.1-avb6-(TA14)gsccuucuuCfAfAfcacuuucaaas(invAb) | 1508 | AM10749-SS |
| CS001036 | Tri-SM6.1-avb6-(TA14)cscacccauGfUfGfcuacaacuaus(invAb) | 1509 | AM11739-SS |
| CS001040 | Tri-SM6.1-avb6-(TA14)csugcuaCfaAfcUfaugaiauccas(invAb) | 1510 | AM11743-SS |
| CS001041 | Tri-SM6.1-avb6-(TA14)csgagauCfaUfcUfucaacaacaas(invAb) | 1511 | AM11744-SS |
| CS001401 | Tri-SM6.1-avb6-(TA14)csgagaucaUfCfUfuca_2Nacaacaas(invAb) | 1512 | AM12179-SS |
| CS001644 | Tri-SM6.1-avb6-(TA14)gscugauUfuGfcCfugaacaagaas(invAb) | 1513 | AM13074-SS |
| CS002194 | Tri-SM6.1-avb6-(TA14)gscuguucuGfCfGfacuacuacaa(invAb) | 1514 | AM14080-SS |
| CS002195 | Tri-SM6.1-avb6-(TA14)gscugguucuGfCfGfacuacuacaas(invAb) | 1515 | AM14081-SS |
| CS002196 | Tri-SM6.1-avb6-(TA14)gscguucuGfCfGfacuacuacaas(invAb) | 1516 | AM14084-SS |

The MUC5AC RNAi agents disclosed herein are formed by annealing an antisense strand with a sense strand. A sense strand containing a sequence listed in Table 2, Table 4, Table 5, Table 6, or Table 7 can be hybridized to any antisense strand containing a sequence listed in Table 2 or Table 3, provided the two sequences have a region of at least 85% complementarity over a contiguous 16, 17, 18, 19, 20, or 21 nucleotide sequence.

As shown in Table 5 above, certain of the example MUC5AC RNAi agent nucleotide sequences are shown to further include reactive linking groups at one or both of the 5' terminal end and the 3' terminal end of the sense strand. For example, many of the MUC5AC RNAi agent sense strand sequences shown in Table 5 above have a (TriAlk14) linking group at the 5' end of the nucleotide sequence. Other linking groups, such as an (NH2-C6) linking group or a a (6-SS-6) or (C6-SS-C6) linking group, may be present as well or alternatively in certain embodiments. Such reactive linking groups are positioned to facilitate the linking of targeting ligands, targeting groups, and/or PK/PD modulators to the MUC5AC RNAi agents disclosed herein. Linking or conjugation reactions are well known in the art and provide for formation of covalent linkages between two molecules or reactants. Suitable conjugation reactions for use in the scope of the inventions herein include, but are not limited to, amide coupling reaction, Michael addition reaction, hydrazone formation reaction, inverse-demand Diels-Alder cycloaddition reaction, oxime ligation, and Copper (I)-catalyzed or strain-promoted azide-alkyne cycloaddition reaction cycloaddition reaction.

In some embodiments, targeting ligands, such as the integrin targeting ligands shown in the examples and figures disclosed herein, can be synthesized as activated esters, such as tetrafluorophenyl (TFP) esters, which can be displaced by a reactive amino group (e.g., $NH_2$—$C_6$) to attach the targeting ligand to the MUC5AC RNAi agents disclosed herein. In some embodiments, targeting ligands are synthesized as azides, which can be conjugated to a propargyl (e.g., TriAlk14) or DBCO group, for example, via Copper (I)-catalyzed or strain-promoted azide-alkyne cycloaddition reaction.

Additionally, the nucleotide sequences can be synthesized with a dT nucleotide at the 3' terminal end of the sense strand, followed by (3'→5') a linker (e.g., C6-SS-C6). The linker can, in some embodiments, facilitate the linkage to additional components, such as, for example, a PK/PD modulator or one or more targeting ligands. The disulfide bond of C6-SS-C6 can then be reduced, removing the dT from the molecule, which can then facilitate the conjugation of the desired PK/PD modulator. The terminal dT nucleotide would therefore not be a part of the fully conjugated construct.

In some embodiments, the antisense strand of a MUC5AC RNAi agent disclosed herein differs by 0, 1, 2, or 3 nucleotides from any of the antisense strand sequences in Table 3 or Table 11. In some embodiments, the sense strand of a MUC5AC RNAi agent disclosed herein differs by 0, 1, 2, or 3 nucleotides from any of the sense strand sequences in Table 4, Table 5, Table 6, Table 7, or Table 11.

In some embodiments, a MUC5AC RNAi agent antisense strand comprises a nucleotide sequence of any of the sequences in Table 2 or Table 3. In some embodiments, a MUC5AC RNAi agent antisense strand comprises the sequence of nucleotides (from 5' end→3' end) 1-17, 2-17, 1-18, 2-18, 1-19, 2-19, 1-20, 2-20, 1-21, 2-21, 1-22, 2-22, 1-23, 2-23, 1-24, or 2-24 of any of the sequences in Table 2, Table 3, or Table 11. In certain embodiments, a MUC5AC RNAi agent antisense strand comprises or consists of a modified sequence of any one of the modified sequences in Table 3 or Table 11.

In some embodiments, a MUC5AC RNAi agent sense strand comprises the nucleotide sequence of any of the sequences in Table 2 or Table 4. In some embodiments, a MUC5AC RNAi agent sense strand comprises the sequence of nucleotides (from 5' end→3' end) 1-17, 2-17, 3-17, 4-17, 1-18, 2-18, 3-18, 4-18, 1-19, 2-19, 3-19, 4-19, 1-20, 2-20, 3-20, 4-20, 1-21, 2-21, 3-21, 4-21, 1-22, 2-22, 3-22, 4-22, 1-23, 2-23, 3-23, 4-23, 1-24, 2-24, 3-24, or 4-24, of any of the sequences in Table 2, Table 4, Table 5, Table 6, Table 7, or Table 11. In certain embodiments, a MUC5AC RNAi agent sense strand comprises or consists of a modified sequence of any one of the modified sequences in Table 3 or Table 11.

For the RNAi agents disclosed herein, the nucleotide at position 1 of the antisense strand (from 5' end→3' end) can be perfectly complementary to a MUC5AC gene, or can be non-complementary to a MUC5AC gene. In some embodiments, the nucleotide at position 1 of the antisense strand (from 5' end→3' end) is a U, A, or dT (or a modified version of U, A or dT). In some embodiments, the nucleotide at position 1 of the antisense strand (from 5' end→3' end) forms an A:U or U:A base pair with the sense strand.

In some embodiments, a MUC5AC RNAi agent antisense strand comprises the sequence of nucleotides (from 5' end→3' end) 2-18 or 2-19 of any of the antisense strand sequences in Table 2, Table 3, or Table 11. In some embodiments, a MUC5AC RNAi sense strand comprises the sequence of nucleotides (from 5' end→3' end) 1-17 or 1-18 of any of the sense strand sequences in Table 2, Table 4, Table 5, Table 6, Table 7, or Table 11.

In some embodiments, a MUC5AC RNAi agent includes (i) an antisense strand comprising the sequence of nucleotides (from 5' end→3' end) 2-18 or 2-19 of any of the antisense strand sequences in Table 2, Table 3, or Table 11, and (ii) a sense strand comprising the sequence of nucleotides (from 5' end→3' end) 1-17 or 1-18 of any of the sense strand sequences in Table 2, Table 4, Table 5, Table 6, Table 7, or Table 11.

A sense strand containing a sequence listed in Table 2 or Table 4 can be hybridized to any antisense strand containing a sequence listed in Table 2 or Table 3 provided the two sequences have a region of at least 85% complementarity over a contiguous 16, 17, 18, 19, 20, or 21 nucleotide sequence. In some embodiments, the MUC5AC RNAi agent has a sense strand consisting of the modified sequence of any of the modified sequences in Table 4, Table 5, Table 6, Table 7, or Table 11, and an antisense strand consisting of the modified sequence of any of the modified sequences in Table 3 or Table 11. Certain representative sequence pairings are exemplified by the Duplex ID Nos. shown in Tables 8A, 8B, 8C, 9, 10A and 10B.

In some embodiments, a MUC5AC RNAi agent comprises, consists of, or consists essentially of a duplex represented by any one of the Duplex ID Nos. presented herein. In some embodiments, a MUC5AC RNAi agent consists of any of the Duplex ID Nos. presented herein. In some embodiments, a MUC5AC RNAi agent comprises the sense strand and antisense strand nucleotide sequences of any of the Duplex ID Nos. presented herein. In some embodiments, a MUC5AC RNAi agent comprises the sense strand and antisense strand nucleotide sequences of any of the Duplex ID Nos. presented herein and a targeting group, linking group, and/or other non-nucleotide group wherein the targeting group, linking group, and/or other non-nucleotide group is covalently linked (i.e., conjugated) to the sense strand or the antisense strand. In some embodiments, a MUC5AC RNAi agent includes the sense strand and antisense strand modified nucleotide sequences of any of the Duplex ID Nos. presented herein. In some embodiments, a MUC5AC RNAi agent comprises the sense strand and antisense strand modified nucleotide sequences of any of the Duplex ID Nos. presented herein and a targeting group, linking group, and/or other non-nucleotide group, wherein the targeting group, linking group, and/or other non-nucleotide group is covalently linked to the sense strand or the antisense strand.

In some embodiments, a MUC5AC RNAi agent comprises an antisense strand and a sense strand having the nucleotide sequences of any of the antisense strand/sense strand duplexes of Tables 2, 8A, 8B, 8C, 9, 10A, 10B, or 11, and comprises a targeting group. In some embodiments, a MUC5AC RNAi agent comprises an antisense strand and a sense strand having the nucleotide sequences of any of the antisense strand/sense strand duplexes of Tables 2, 8A, 8B, 8C, 9, 10A, 10B, or 11, and comprises one or more αvβ6 integrin targeting ligands.

In some embodiments, a MUC5AC RNAi agent comprises an antisense strand and a sense strand having the nucleotide sequences of any of the antisense strand/sense strand duplexes of Tables 2, 8A, 8B, 8C, 9, 10A, 10B, or 11, and comprises a targeting group that is an integrin targeting ligand. In some embodiments, a MUC5AC RNAi agent comprises an antisense strand and a sense strand having the nucleotide sequences of any of the antisense strand/sense strand duplexes of Tables 2, 8A, 8B, 8C, 9, 10A, 10B, or 11, and comprises one or more αvβ6 integrin targeting ligands or clusters of αvβ6 integrin targeting ligands (e.g., a tridentate αvβ6 integrin targeting ligand).

In some embodiments, a MUC5AC RNAi agent comprises an antisense strand and a sense strand having the modified nucleotide sequences of any of the antisense strand/sense strand duplexes of Tables 8A, 8B, 8C, 9, 10A, 10B, and 11.

In some embodiments, a MUC5AC RNAi agent comprises an antisense strand and a sense strand having the modified nucleotide sequences of any of the antisense strand/sense strand duplexes of Tables 8A, 8B, 8C, 9, 10A, 10B, and 11, and comprises an integrin targeting ligand.

In some embodiments, a MUC5AC RNAi agent comprises, consists of, or consists essentially of any of the duplexes of Tables 8A, 8B, 8C, 9, 10A, 10B, and 11.

TABLE 8A

MUC5AC RNAi Agent Duplexes with Corresponding Sense and Antisense Strand ID Numbers and Sequence ID numbers for the modified and unmodified nucleotide sequences. (Shown without Linking Agents or Conjugates)

| Duplex | AS ID | AS modified SEQ ID NO: | AS unmodified SEQ ID NO: | SS ID | SS modified SEQ ID NO: | SS unmodified SEQ ID NO: |
|---|---|---|---|---|---|---|
| AD07626 | AM10579-AS | 1057 | 1517 | AM10578-SS-NL | 1192 | 1609 |
| AD07627 | AM10581-AS | 1058 | 1518 | AM10580-SS-NL | 1193 | 1610 |
| AD07628 | AM10583-AS | 1059 | 1519 | AM10582-SS-NL | 1194 | 1611 |
| AD07629 | AM10585-AS | 1060 | 1520 | AM10584-SS-NL | 1195 | 1612 |

TABLE 8A-continued

MUC5AC RNAi Agent Duplexes with Corresponding Sense and Antisense Strand ID Numbers and Sequence ID numbers for the modified and unmodified nucleotide sequences. (Shown without Linking Agents or Conjugates)

| Duplex | AS ID | AS modified SEQ ID NO: | AS unmodified SEQ ID NO: | SS ID | SS modified SEQ ID NO: | SS unmodified SEQ ID NO: |
|---|---|---|---|---|---|---|
| AD07630 | AM10587-AS | 1061 | 1521 | AM10586-SS-NL | 1196 | 1613 |
| AD07631 | AM10589-AS | 1062 | 1522 | AM10588-SS-NL | 1197 | 1614 |
| AD07632 | AM10591-AS | 1063 | 1523 | AM10590-SS-NL | 1198 | 1615 |
| AD07633 | AM10593-AS | 1064 | 1524 | AM10592-SS-NL | 1199 | 1616 |
| AD07634 | AM10595-AS | 1065 | 1525 | AM10594-SS-NL | 1200 | 1617 |
| AD07635 | AM10597-AS | 1066 | 1526 | AM10596-SS-NL | 1201 | 1618 |
| AD07636 | AM10599-AS | 1067 | 1527 | AM10598-SS-NL | 1202 | 1619 |
| AD07637 | AM10601-AS | 1068 | 1528 | AM10600-SS-NL | 1203 | 1620 |
| AD07638 | AM10603-AS | 1069 | 1529 | AM10602-SS-NL | 1204 | 1621 |
| AD07639 | AM10605-AS | 1070 | 1529 | AM10604-SS-NL | 1205 | 1622 |
| AD07716 | AM10739-AS | 1071 | 1530 | AM10738-SS-NL | 1206 | 1623 |
| AD07717 | AM10741-AS | 1072 | 1530 | AM10740-SS-NL | 1207 | 1624 |
| AD07718 | AM10743-AS | 1073 | 1531 | AM10742-SS-NL | 1208 | 1625 |
| AD07719 | AM10744-AS | 1074 | 1531 | AM10742-SS-NL | 1208 | 1625 |
| AD07720 | AM10743-AS | 1073 | 1531 | AM10745-SS-NL | 1209 | 1626 |
| AD07721 | AM10747-AS | 1075 | 1532 | AM10746-SS-NL | 1210 | 1627 |
| AD07722 | AM10747-AS | 1075 | 1532 | AM10748-SS-NL | 1211 | 1628 |
| AD07723 | AM10747-AS | 1075 | 1532 | AM10749-SS-NL | 1212 | 1629 |
| AD07731 | AM10764-AS | 1076 | 1533 | AM10763-SS-NL | 1213 | 1630 |
| AD07732 | AM10766-AS | 1077 | 1534 | AM10765-SS-NL | 1214 | 1631 |
| AD07733 | AM10768-AS | 1078 | 1535 | AM10767-SS-NL | 1215 | 1632 |
| AD07734 | AM10770-AS | 1079 | 1536 | AM10769-SS-NL | 1216 | 1633 |
| AD07735 | AM10772-AS | 1080 | 1537 | AM10771-SS-NL | 1217 | 1634 |
| AD07744 | AM10790-AS | 1081 | 1538 | AM10789-SS-NL | 1218 | 1635 |
| AD07745 | AM10792-AS | 1082 | 1539 | AM10791-SS-NL | 1219 | 1636 |
| AD07746 | AM10794-AS | 1083 | 1540 | AM10793-SS-NL | 1220 | 1637 |
| AD07747 | AM10796-AS | 1084 | 1541 | AM10795-SS-NL | 1221 | 1638 |
| AD07748 | AM10798-AS | 1085 | 1542 | AM10797-SS-NL | 1222 | 1639 |
| AD07749 | AM10800-AS | 1086 | 1543 | AM10799-SS-NL | 1223 | 1640 |
| AD07750 | AM10802-AS | 1087 | 1544 | AM10801-SS-NL | 1224 | 1641 |
| AD07751 | AM10804-AS | 1088 | 1545 | AM10803-SS-NL | 1225 | 1642 |
| AD07752 | AM10806-AS | 1089 | 1546 | AM10805-SS-NL | 1226 | 1643 |
| AD07753 | AM10808-AS | 1090 | 1530 | AM10807-SS-NL | 1227 | 1623 |
| AD07754 | AM10810-AS | 1091 | 1547 | AM10809-SS-NL | 1228 | 1644 |
| AD07755 | AM10812-AS | 1092 | 1548 | AM10811-SS-NL | 1229 | 1645 |
| AD07756 | AM10814-AS | 1093 | 1549 | AM10813-SS-NL | 1230 | 1646 |
| AD07757 | AM10816-AS | 1094 | 1550 | AM10815-SS-NL | 1231 | 1647 |
| AD07758 | AM10818-AS | 1095 | 1532 | AM10817-SS-NL | 1232 | 1627 |
| AD07760 | AM10821-AS | 1096 | 1551 | AM10820-SS-NL | 1234 | 1648 |
| AD07761 | AM10823-AS | 1097 | 1552 | AM10822-SS-NL | 1235 | 1649 |
| AD07762 | AM10825-AS | 1098 | 1553 | AM10824-SS-NL | 1236 | 1650 |
| AD07763 | AM10827-AS | 1099 | 1554 | AM10826-SS-NL | 1237 | 1651 |
| AD07764 | AM10829-AS | 1100 | 1555 | AM10828-SS-NL | 1238 | 1652 |
| AD07765 | AM10831-AS | 1101 | 1556 | AM10830-SS-NL | 1239 | 1653 |
| AD07766 | AM10833-AS | 1102 | 1557 | AM10832-SS-NL | 1240 | 1654 |
| AD07767 | AM10835-AS | 1103 | 1558 | AM10834-SS-NL | 1241 | 1655 |
| AD07768 | AM10837-AS | 1104 | 1559 | AM10836-SS-NL | 1242 | 1656 |
| AD07769 | AM10839-AS | 1105 | 1560 | AM10838-SS-NL | 1243 | 1657 |
| AD07770 | AM10841-AS | 1106 | 1561 | AM10840-SS-NL | 1244 | 1658 |
| AD07771 | AM10843-AS | 1107 | 1562 | AM10842-SS-NL | 1245 | 1659 |
| AD07772 | AM10845-AS | 1108 | 1563 | AM10844-SS-NL | 1246 | 1660 |
| AD07773 | AM10847-AS | 1109 | 1564 | AM10846-SS-NL | 1247 | 1661 |
| AD07774 | AM10849-AS | 1110 | 1565 | AM10848-SS-NL | 1248 | 1662 |
| AD07941 | AM11065-AS | 1111 | 1531 | AM10819-SS-NL | 1233 | 1625 |
| AD08083 | AM11264-AS | 1112 | 1566 | AM11263-SS-NL | 1250 | 1663 |
| AD08084 | AM11264-AS | 1112 | 1566 | AM11265-SS-NL | 1251 | 1664 |
| AD08085 | AM11266-AS | 1113 | 1566 | AM11263-SS-NL | 1250 | 1663 |
| AD08086 | AM11268-AS | 1114 | 1567 | AM11267-SS-NL | 1252 | 1665 |
| AD08087 | AM11268-AS | 1114 | 1567 | AM11269-SS-NL | 1253 | 1666 |
| AD08088 | AM11271-AS | 1115 | 1568 | AM11270-SS-NL | 1254 | 1667 |
| AD08089 | AM11272-AS | 1116 | 1568 | AM11270-SS-NL | 1254 | 1667 |
| AD08094 | AM11275-AS | 1117 | 1569 | AM11274-SS-NL | 1255 | 1668 |
| AD08095 | AM11277-AS | 1118 | 1570 | AM11276-SS-NL | 1256 | 1669 |
| AD08096 | AM11279-AS | 1119 | 1571 | AM11278-SS-NL | 1257 | 1670 |
| AD08097 | AM11281-AS | 1120 | 1572 | AM11280-SS-NL | 1258 | 1671 |
| AD08098 | AM11283-AS | 1121 | 1573 | AM11282-SS-NL | 1259 | 1672 |
| AD08099 | AM11285-AS | 1122 | 1574 | AM11284-SS-NL | 1260 | 1673 |
| AD08100 | AM11287-AS | 1123 | 1575 | AM11286-SS-NL | 1261 | 1674 |
| AD08101 | AM11289-AS | 1124 | 1576 | AM11288-SS-NL | 1262 | 1675 |
| AD08102 | AM11291-AS | 1125 | 1577 | AM11290-SS-NL | 1263 | 1676 |
| AD08103 | AM11293-AS | 1126 | 1578 | AM11292-SS-NL | 1264 | 1677 |
| AD08173 | AM10595-AS | 1065 | 1525 | AM11400-SS-NL | 1265 | 1617 |

TABLE 8A-continued

MUC5AC RNAi Agent Duplexes with Corresponding Sense and Antisense Strand ID Numbers and Sequence ID numbers for the modified and unmodified nucleotide sequences. (Shown without Linking Agents or Conjugates)

| Duplex | AS ID | AS modified SEQ ID NO: | AS unmodified SEQ ID NO: | SS ID | SS modified SEQ ID NO: | SS unmodified SEQ ID NO: |
|---|---|---|---|---|---|---|
| AD08174 | AM11401-AS | 1127 | 1525 | AM11400-SS-NL | 1265 | 1617 |
| AD08175 | AM11403-AS | 1128 | 1579 | AM11402-SS-NL | 1266 | 1678 |
| AD08176 | AM11404-AS | 1129 | 1579 | AM11402-SS-NL | 1266 | 1678 |
| AD08177 | AM11405-AS | 1130 | 1579 | AM11402-SS-NL | 1266 | 1678 |
| AD08224 | AM11464-AS | 1132 | 1581 | AM11463-SS-NL | 1267 | 1679 |
| AD08225 | AM11465-AS | 1133 | 1581 | AM11463-SS-NL | 1267 | 1679 |
| AD08226 | AM11467-AS | 1134 | 1582 | AM11466-SS-NL | 1268 | 1680 |
| AD08227 | AM11469-AS | 1135 | 1583 | AM11468-SS-NL | 1269 | 1681 |
| AD08228 | AM11471-AS | 1136 | 1584 | AM11470-SS-NL | 1270 | 1682 |
| AD08229 | AM11473-AS | 1137 | 1585 | AM11472-SS-NL | 1271 | 1683 |
| AD08230 | AM11475-AS | 1138 | 1586 | AM11474-SS-NL | 1272 | 1684 |
| AD08231 | AM11477-AS | 1139 | 1587 | AM11476-SS-NL | 1273 | 1685 |
| AD08232 | AM11479-AS | 1140 | 1588 | AM11478-SS-NL | 1274 | 1686 |
| AD08233 | AM11481-AS | 1141 | 1589 | AM11480-SS-NL | 1275 | 1687 |
| AD08243 | AM11495-AS | 1142 | 1590 | AM11400-SS-NL | 1265 | 1617 |
| AD08244 | AM11496-AS | 1143 | 1525 | AM11400-SS-NL | 1265 | 1617 |
| AD08245 | AM11498-AS | 1144 | 1591 | AM11497-SS-NL | 1276 | 1688 |
| AD08246 | AM11499-AS | 1145 | 1591 | AM11497-SS-NL | 1276 | 1688 |
| AD08420 | AM11742-AS | 1148 | 1566 | AM11265-SS-NL | 1251 | 1664 |
| AD08421 | AM11742-AS | 1148 | 1566 | AM11263-SS-NL | 1250 | 1663 |
| AD08422 | AM11742-AS | 1148 | 1566 | AM11743-SS-NL | 1278 | 1664 |
| AD08423 | AM11272-AS | 1116 | 1568 | AM11744-SS-NL | 1279 | 1667 |
| AD08424 | AM11745-AS | 1149 | 1568 | AM11744-SS-NL | 1279 | 1667 |
| AD08468 | AM11821-AS | 1150 | 1589 | AM11480-SS-NL | 1275 | 1687 |
| AD08469 | AM11823-AS | 1151 | 1589 | AM11822-SS-NL | 1280 | 1687 |
| AD08470 | AM11825-AS | 1152 | 1593 | AM11824-SS-NL | 1281 | 1690 |
| AD08564 | AM11971-AS | 1153 | 1594 | AM11970-SS-NL | 1282 | 1691 |
| AD08565 | AM11973-AS | 1154 | 1595 | AM11972-SS-NL | 1283 | 1692 |
| AD08566 | AM11975-AS | 1155 | 1596 | AM11974-SS-NL | 1284 | 1693 |
| AD08567 | AM11977-AS | 1156 | 1597 | AM11976-SS-NL | 1285 | 1694 |
| AD08568 | AM11979-AS | 1157 | 1598 | AM11978-SS-NL | 1286 | 1695 |
| AD08569 | AM07100-AS | 1716 | 1566 | AM11980-SS-NL | 1287 | 1664 |
| AD08570 | AM11982-AS | 1158 | 1599 | AM11981-SS-NL | 1288 | 1696 |
| AD08571 | AM11984-AS | 1159 | 1600 | AM11983-SS-NL | 1289 | 1697 |
| AD08572 | AM07104-AS | 1717 | 1568 | AM11985-SS-NL | 1290 | 1667 |
| AD08573 | AM11986-AS | 1160 | 1568 | AM11985-SS-NL | 1290 | 1667 |
| AD08662 | AM12158-AS | 1161 | 1601 | AM12157-SS-NL | 1291 | 1698 |
| AD08663 | AM12159-AS | 1162 | 1601 | AM12157-SS-NL | 1291 | 1698 |
| AD08664 | AM12161-AS | 1163 | 1601 | AM12160-SS-NL | 1292 | 1698 |
| AD08665 | AM12162-AS | 1164 | 1601 | AM12160-SS-NL | 1292 | 1698 |
| AD08666 | AM12163-AS | 1165 | 1535 | AM10767-SS-NL | 1215 | 1632 |
| AD08667 | AM12165-AS | 1166 | 1535 | AM12164-SS-NL | 1293 | 1632 |
| AD08668 | AM12166-AS | 1167 | 1535 | AM12164-SS-NL | 1293 | 1632 |
| AD08669 | AM12167-AS | 1168 | 1535 | AM12164-SS-NL | 1293 | 1632 |
| AD08670 | AM12167-AS | 1168 | 1535 | AM12168-SS-NL | 1294 | 1699 |
| AD08671 | AM12169-AS | 1169 | 1571 | AM11278-SS-NL | 1257 | 1670 |
| AD08672 | AM12171-AS | 1170 | 1571 | AM12170-SS-NL | 1295 | 1670 |
| AD08673 | AM12172-AS | 1171 | 1571 | AM12170-SS-NL | 1295 | 1670 |
| AD08674 | AM12173-AS | 1172 | 1534 | AM10765-SS-NL | 1214 | 1631 |
| AD08675 | AM12175-AS | 1173 | 1534 | AM12174-SS-NL | 1296 | 1631 |
| AD08676 | AM12176-AS | 1174 | 1534 | AM12174-SS-NL | 1296 | 1631 |
| AD08677 | AM12177-AS | 1175 | 1534 | AM12174-SS-NL | 1296 | 1631 |
| AD08678 | AM12178-AS | 1176 | 1568 | AM11270-SS-NL | 1254 | 1667 |
| AD08679 | AM12178-AS | 1176 | 1568 | AM12179-SS-NL | 1297 | 1700 |
| AD08680 | AM12180-AS | 1177 | 1568 | AM11270-SS-NL | 1254 | 1667 |
| AD08681 | AM12181-AS | 1178 | 1568 | AM11270-SS-NL | 1254 | 1667 |
| AD08682 | AM12182-AS | 1179 | 1602 | AM11270-SS-NL | 1254 | 1667 |
| AD08687 | AM12189-AS | 1180 | 1603 | AM12188-SS-NL | 1298 | 1701 |
| AD08688 | AM12191-AS | 1181 | 1604 | AM12190-SS-NL | 1299 | 1702 |
| AD08689 | AM12193-AS | 1182 | 1605 | AM12192-SS-NL | 1300 | 1703 |
| AD08690 | AM12195-AS | 1183 | 1606 | AM12194-SS-NL | 1301 | 1704 |
| AD08691 | AM12197-AS | 1184 | 1607 | AM12196-SS-NL | 1302 | 1705 |
| AD08692 | AM12197-AS | 1184 | 1607 | AM12198-SS-NL | 1303 | 1706 |
| AD08889 | AM11401-AS | 1127 | 1525 | AM10594-SS-NL | 1200 | 1617 |
| AD08890 | AM12516-AS | 1185 | 1525 | AM12515-SS-NL | 1304 | 1617 |
| AD08891 | AM12516-AS | 1185 | 1525 | AM12517-SS-NL | 1305 | 1617 |
| AD08892 | AM12516-AS | 1185 | 1525 | AM12518-SS-NL | 1306 | 1617 |
| AD08893 | AM12519-AS | 1186 | 1525 | AM12518-SS-NL | 1306 | 1617 |
| AD08894 | AM12516-AS | 1185 | 1525 | AM12520-SS-NL | 1307 | 1707 |
| AD08895 | AM12516-AS | 1185 | 1525 | AM12521-SS-NL | 1308 | 1708 |
| AD08896 | AM12516-AS | 1185 | 1525 | AM12522-SS-NL | 1309 | 1709 |
| AD08897 | AM12516-AS | 1185 | 1525 | AM12523-SS-NL | 1310 | 1617 |

TABLE 8A-continued

MUC5AC RNAi Agent Duplexes with Corresponding Sense and Antisense Strand ID Numbers and Sequence ID numbers for the modified and unmodified nucleotide sequences. (Shown without Linking Agents or Conjugates)

| Duplex | AS ID | AS modified SEQ ID NO: | AS unmodified SEQ ID NO: | SS ID | SS modified SEQ ID NO: | SS unmodified SEQ ID NO: |
|---|---|---|---|---|---|---|
| AD08951 | AM12165-AS | 1166 | 1535 | AM12605-SS-NL | 1311 | 1632 |
| AD08952 | AM12165-AS | 1166 | 1535 | AM12606-SS-NL | 1312 | 1632 |
| AD08953 | AM12608-AS | 1187 | 1608 | AM12607-SS-NL | 1313 | 1710 |
| AD08954 | AM12609-AS | 1188 | 1535 | AM12164-SS-NL | 1293 | 1632 |
| AD08955 | AM12610-AS | 1189 | 1535 | AM12164-SS-NL | 1293 | 1632 |
| AD08956 | AM12611-AS | 1190 | 1535 | AM12164-SS-NL | 1293 | 1632 |
| AD08957 | AM12612-AS | 1191 | 1535 | AM12164-SS-NL | 1293 | 1632 |
| AD09240 | AM12165-AS | 1166 | 1535 | AM13074-SS-NL | 1315 | 1632 |
| AD09241 | AM12612-AS | 1191 | 1535 | AM13074-SS-NL | 1315 | 1632 |
| AD09863 | AM11401-AS | 1127 | 1525 | AM14080-SS-NL | 1316 | 1617 |
| AD09864 | AM11401-AS | 1127 | 1525 | AM14081-SS-NL | 1317 | 1711 |
| AD09865 | AM11401-AS | 1127 | 1525 | AM14084-SS-NL | 1318 | 1712 |

TABLE 8B

MUC5AC RNAi Agent Duplexes with Corresponding Sense and Antisense Strand ID Numbers and Sequence ID numbers for the modified and unmodified nucleotide sequences.)

| Duplex | AS ID | AS modified SEQ ID NO: | AS unmodified SEQ ID NO: | SS ID | SS modified SEQ ID NO: | SS unmodified SEQ ID NO: |
|---|---|---|---|---|---|---|
| AD07626 | AM10579-AS | 1057 | 1517 | AM10578-SS | 1319 | 1609 |
| AD07627 | AM10581-AS | 1058 | 1518 | AM10580-SS | 1320 | 1610 |
| AD07628 | AM10583-AS | 1059 | 1519 | AM10582-SS | 1321 | 1611 |
| AD07629 | AM10585-AS | 1060 | 1520 | AM10584-SS | 1322 | 1612 |
| AD07630 | AM10587-AS | 1061 | 1521 | AM10586-SS | 1323 | 1613 |
| AD07631 | AM10589-AS | 1062 | 1522 | AM10588-SS | 1324 | 1614 |
| AD07632 | AM10591-AS | 1063 | 1523 | AM10590-SS | 1325 | 1615 |
| AD07633 | AM10593-AS | 1064 | 1524 | AM10592-SS | 1326 | 1616 |
| AD07634 | AM10595-AS | 1065 | 1525 | AM10594-SS | 1327 | 1617 |
| AD07635 | AM10597-AS | 1066 | 1526 | AM10596-SS | 1328 | 1618 |
| AD07636 | AM10599-AS | 1067 | 1527 | AM10598-SS | 1329 | 1619 |
| AD07637 | AM10601-AS | 1068 | 1528 | AM10600-SS | 1330 | 1620 |
| AD07638 | AM10603-AS | 1069 | 1529 | AM10602-SS | 1331 | 1621 |
| AD07639 | AM10605-AS | 1070 | 1529 | AM10604-SS | 1332 | 1622 |
| AD07716 | AM10739-AS | 1071 | 1530 | AM10738-SS | 1333 | 1623 |
| AD07717 | AM10741-AS | 1072 | 1530 | AM10740-SS | 1334 | 1624 |
| AD07718 | AM10743-AS | 1073 | 1531 | AM10742-SS | 1335 | 1625 |
| AD07719 | AM10744-AS | 1074 | 1531 | AM10742-SS | 1335 | 1625 |
| AD07720 | AM10743-AS | 1073 | 1531 | AM10745-SS | 1336 | 1626 |
| AD07721 | AM10747-AS | 1075 | 1532 | AM10746-SS | 1337 | 1627 |
| AD07722 | AM10747-AS | 1075 | 1532 | AM10748-SS | 1338 | 1628 |
| AD07723 | AM10747-AS | 1075 | 1532 | AM10749-SS | 1339 | 1629 |
| AD07731 | AM10764-AS | 1076 | 1533 | AM10763-SS | 1340 | 1630 |
| AD07732 | AM10766-AS | 1077 | 1534 | AM10765-SS | 1341 | 1631 |
| AD07733 | AM10768-AS | 1078 | 1535 | AM10767-SS | 1342 | 1632 |
| AD07734 | AM10770-AS | 1079 | 1536 | AM10769-SS | 1343 | 1633 |
| AD07735 | AM10772-AS | 1080 | 1537 | AM10771-SS | 1344 | 1634 |
| AD07744 | AM10790-AS | 1081 | 1538 | AM10789-SS | 1345 | 1635 |
| AD07745 | AM10792-AS | 1082 | 1539 | AM10791-SS | 1346 | 1636 |
| AD07746 | AM10794-AS | 1083 | 1540 | AM10793-SS | 1347 | 1637 |
| AD07747 | AM10796-AS | 1084 | 1541 | AM10795-SS | 1348 | 1638 |
| AD07748 | AM10798-AS | 1085 | 1542 | AM10797-SS | 1349 | 1639 |
| AD07749 | AM10800-AS | 1086 | 1543 | AM10799-SS | 1350 | 1640 |
| AD07750 | AM10802-AS | 1087 | 1544 | AM10801-SS | 1351 | 1641 |
| AD07751 | AM10804-AS | 1088 | 1545 | AM10803-SS | 1352 | 1642 |
| AD07752 | AM10806-AS | 1089 | 1546 | AM10805-SS | 1353 | 1643 |
| AD07753 | AM10808-AS | 1090 | 1530 | AM10807-SS | 1354 | 1623 |
| AD07754 | AM10810-AS | 1091 | 1547 | AM10809-SS | 1355 | 1644 |
| AD07755 | AM10812-AS | 1092 | 1548 | AM10811-SS | 1356 | 1645 |
| AD07756 | AM10814-AS | 1093 | 1549 | AM10813-SS | 1357 | 1646 |
| AD07757 | AM10816-AS | 1094 | 1550 | AM10815-SS | 1358 | 1647 |
| AD07758 | AM10818-AS | 1095 | 1532 | AM10817-SS | 1359 | 1627 |
| AD07760 | AM10821-AS | 1096 | 1551 | AM10820-SS | 1361 | 1648 |
| AD07761 | AM10823-AS | 1097 | 1552 | AM10822-SS | 1362 | 1649 |
| AD07762 | AM10825-AS | 1098 | 1553 | AM10824-SS | 1363 | 1650 |
| AD07763 | AM10827-AS | 1099 | 1554 | AM10826-SS | 1364 | 1651 |
| AD07764 | AM10829-AS | 1100 | 1555 | AM10828-SS | 1365 | 1652 |

TABLE 8B-continued

MUC5AC RNAi Agent Duplexes with Corresponding Sense and Antisense Strand ID Numbers and Sequence ID numbers for the modified and unmodified nucleotide sequences.)

| Duplex | AS ID | AS modified SEQ ID NO: | AS unmodified SEQ ID NO: | SS ID | SS modified SEQ ID NO: | SS unmodified SEQ ID NO: |
|---|---|---|---|---|---|---|
| AD07765 | AM10831-AS | 1101 | 1556 | AM10830-SS | 1366 | 1653 |
| AD07766 | AM10833-AS | 1102 | 1557 | AM10832-SS | 1367 | 1654 |
| AD07767 | AM10835-AS | 1103 | 1558 | AM10834-SS | 1368 | 1655 |
| AD07768 | AM10837-AS | 1104 | 1559 | AM10836-SS | 1369 | 1656 |
| AD07769 | AM10839-AS | 1105 | 1560 | AM10838-SS | 1370 | 1657 |
| AD07770 | AM10841-AS | 1106 | 1561 | AM10840-SS | 1371 | 1658 |
| AD07771 | AM10843-AS | 1107 | 1562 | AM10842-SS | 1372 | 1659 |
| AD07772 | AM10845-AS | 1108 | 1563 | AM10844-SS | 1373 | 1660 |
| AD07773 | AM10847-AS | 1109 | 1564 | AM10846-SS | 1374 | 1661 |
| AD07774 | AM10849-AS | 1110 | 1565 | AM10848-SS | 1375 | 1662 |
| AD07941 | AM11065-AS | 1111 | 1531 | AM10819-SS | 1360 | 1625 |
| AD08083 | AM11264-AS | 1112 | 1566 | AM11263-SS | 1377 | 1663 |
| AD08084 | AM11264-AS | 1112 | 1566 | AM11265-SS | 1378 | 1664 |
| AD08085 | AM11266-AS | 1113 | 1566 | AM11263-SS | 1377 | 1663 |
| AD08086 | AM11268-AS | 1114 | 1567 | AM11267-SS | 1379 | 1665 |
| AD08087 | AM11268-AS | 1114 | 1567 | AM11269-SS | 1380 | 1666 |
| AD08088 | AM11271-AS | 1115 | 1568 | AM11270-SS | 1381 | 1667 |
| AD08089 | AM11272-AS | 1116 | 1568 | AM11270-SS | 1381 | 1667 |
| AD08094 | AM11275-AS | 1117 | 1569 | AM11274-SS | 1382 | 1668 |
| AD08095 | AM11277-AS | 1118 | 1570 | AM11276-SS | 1383 | 1669 |
| AD08096 | AM11279-AS | 1119 | 1571 | AM11278-SS | 1384 | 1670 |
| AD08097 | AM11281-AS | 1120 | 1572 | AM11280-SS | 1385 | 1671 |
| AD08098 | AM11283-AS | 1121 | 1573 | AM11282-SS | 1386 | 1672 |
| AD08099 | AM11285-AS | 1122 | 1574 | AM11284-SS | 1387 | 1673 |
| AD08100 | AM11287-AS | 1123 | 1575 | AM11286-SS | 1388 | 1674 |
| AD08101 | AM11289-AS | 1124 | 1576 | AM11288-SS | 1389 | 1675 |
| AD08102 | AM11291-AS | 1125 | 1577 | AM11290-SS | 1390 | 1676 |
| AD08103 | AM11293-AS | 1126 | 1578 | AM11292-SS | 1391 | 1677 |
| AD08173 | AM10595-AS | 1065 | 1525 | AM11400-SS | 1392 | 1617 |
| AD08174 | AM11401-AS | 1127 | 1525 | AM11400-SS | 1392 | 1617 |
| AD08175 | AM11403-AS | 1128 | 1579 | AM11402-SS | 1393 | 1678 |
| AD08176 | AM11404-AS | 1129 | 1579 | AM11402-SS | 1393 | 1678 |
| AD08177 | AM11405-AS | 1130 | 1579 | AM11402-SS | 1393 | 1678 |
| AD08224 | AM11464-AS | 1132 | 1581 | AM11463-SS | 1394 | 1679 |
| AD08225 | AM11465-AS | 1133 | 1581 | AM11463-SS | 1394 | 1679 |
| AD08226 | AM11467-AS | 1134 | 1582 | AM11466-SS | 1395 | 1680 |
| AD08227 | AM11469-AS | 1135 | 1583 | AM11468-SS | 1396 | 1681 |
| AD08228 | AM11471-AS | 1136 | 1584 | AM11470-SS | 1397 | 1682 |
| AD08229 | AM11473-AS | 1137 | 1585 | AM11472-SS | 1398 | 1683 |
| AD08230 | AM11475-AS | 1138 | 1586 | AM11474-SS | 1399 | 1684 |
| AD08231 | AM11477-AS | 1139 | 1587 | AM11476-SS | 1400 | 1685 |
| AD08232 | AM11479-AS | 1140 | 1588 | AM11478-SS | 1401 | 1686 |
| AD08233 | AM11481-AS | 1141 | 1589 | AM11480-SS | 1402 | 1687 |
| AD08243 | AM11495-AS | 1142 | 1590 | AM11400-SS | 1392 | 1617 |
| AD08244 | AM11496-AS | 1143 | 1525 | AM11400-SS | 1392 | 1617 |
| AD08245 | AM11498-AS | 1144 | 1591 | AM11497-SS | 1403 | 1688 |
| AD08246 | AM11499-AS | 1145 | 1591 | AM11497-SS | 1403 | 1688 |
| AD08420 | AM11742-AS | 1148 | 1566 | AM11265-SS | 1378 | 1664 |
| AD08421 | AM11742-AS | 1148 | 1566 | AM11263-SS | 1377 | 1663 |
| AD08422 | AM11742-AS | 1148 | 1566 | AM11743-SS | 1405 | 1664 |
| AD08423 | AM11272-AS | 1116 | 1568 | AM11744-SS | 1406 | 1667 |
| AD08424 | AM11745-AS | 1149 | 1568 | AM11744-SS | 1406 | 1667 |
| AD08468 | AM11821-AS | 1150 | 1589 | AM11480-SS | 1402 | 1687 |
| AD08469 | AM11823-AS | 1151 | 1589 | AM11822-SS | 1407 | 1687 |
| AD08470 | AM11825-AS | 1152 | 1593 | AM11824-SS | 1408 | 1690 |
| AD08564 | AM11971-AS | 1153 | 1594 | AM11970-SS | 1409 | 1691 |
| AD08565 | AM11973-AS | 1154 | 1595 | AM11972-SS | 1410 | 1692 |
| AD08566 | AM11975-AS | 1155 | 1596 | AM11974-SS | 1411 | 1693 |
| AD08567 | AM11977-AS | 1156 | 1597 | AM11976-SS | 1412 | 1694 |
| AD08568 | AM11979-AS | 1157 | 1598 | AM11978-SS | 1413 | 1695 |
| AD08569 | AM07100-AS | 1716 | 1566 | AM11980-SS | 1414 | 1664 |
| AD08570 | AM11982-AS | 1158 | 1599 | AM11981-SS | 1415 | 1696 |
| AD08571 | AM11984-AS | 1159 | 1600 | AM11983-SS | 1416 | 1697 |
| AD08572 | AM07104-AS | 1717 | 1568 | AM11985-SS | 1417 | 1667 |
| AD08573 | AM11986-AS | 1160 | 1568 | AM11985-SS | 1417 | 1667 |
| AD08662 | AM12158-AS | 1161 | 1601 | AM12157-SS | 1418 | 1698 |
| AD08663 | AM12159-AS | 1162 | 1601 | AM12157-SS | 1418 | 1698 |
| AD08664 | AM12161-AS | 1163 | 1601 | AM12160-SS | 1419 | 1698 |
| AD08665 | AM12162-AS | 1164 | 1601 | AM12160-SS | 1419 | 1698 |
| AD08666 | AM12163-AS | 1165 | 1535 | AM10767-SS | 1342 | 1632 |
| AD08667 | AM12165-AS | 1166 | 1535 | AM12164-SS | 1420 | 1632 |
| AD08668 | AM12166-AS | 1167 | 1535 | AM12164-SS | 1420 | 1632 |
| AD08669 | AM12167-AS | 1168 | 1535 | AM12164-SS | 1420 | 1632 |

TABLE 8B-continued

MUC5AC RNAi Agent Duplexes with Corresponding Sense and Antisense Strand ID Numbers and Sequence ID numbers for the modified and unmodified nucleotide sequences.)

| Duplex | AS ID | AS modified SEQ ID NO: | AS unmodified SEQ ID NO: | SS ID | SS modified SEQ ID NO: | SS unmodified SEQ ID NO: |
|---|---|---|---|---|---|---|
| AD08670 | AM12167-AS | 1168 | 1535 | AM12168-SS | 1421 | 1699 |
| AD08671 | AM12169-AS | 1169 | 1571 | AM11278-SS | 1384 | 1670 |
| AD08672 | AM12171-AS | 1170 | 1571 | AM12170-SS | 1422 | 1670 |
| AD08673 | AM12172-AS | 1171 | 1571 | AM12170-SS | 1422 | 1670 |
| AD08674 | AM12173-AS | 1172 | 1534 | AM10765-SS | 1341 | 1631 |
| AD08675 | AM12175-AS | 1173 | 1534 | AM12174-SS | 1423 | 1631 |
| AD08676 | AM12176-AS | 1174 | 1534 | AM12174-SS | 1423 | 1631 |
| AD08677 | AM12177-AS | 1175 | 1534 | AM12174-SS | 1423 | 1631 |
| AD08678 | AM12178-AS | 1176 | 1568 | AM11270-SS | 1381 | 1667 |
| AD08679 | AM12178-AS | 1176 | 1568 | AM12179-SS | 1424 | 1700 |
| AD08680 | AM12180-AS | 1177 | 1568 | AM11270-SS | 1381 | 1667 |
| AD08681 | AM12181-AS | 1178 | 1568 | AM11270-SS | 1381 | 1667 |
| AD08682 | AM12182-AS | 1179 | 1602 | AM11270-SS | 1381 | 1667 |
| AD08687 | AM12189-AS | 1180 | 1603 | AM12188-SS | 1425 | 1701 |
| AD08688 | AM12191-AS | 1181 | 1604 | AM12190-SS | 1426 | 1702 |
| AD08689 | AM12193-AS | 1182 | 1605 | AM12192-SS | 1427 | 1703 |
| AD08690 | AM12195-AS | 1183 | 1606 | AM12194-SS | 1428 | 1704 |
| AD08691 | AM12197-AS | 1184 | 1607 | AM12196-SS | 1429 | 1705 |
| AD08692 | AM12197-AS | 1184 | 1607 | AM12198-SS | 1430 | 1706 |
| AD08889 | AM11401-AS | 1127 | 1525 | AM10594-SS | 1327 | 1617 |
| AD08890 | AM12516-AS | 1185 | 1525 | AM12515-SS | 1431 | 1617 |
| AD08891 | AM12516-AS | 1185 | 1525 | AM12517-SS | 1432 | 1617 |
| AD08892 | AM12516-AS | 1185 | 1525 | AM12518-SS | 1433 | 1617 |
| AD08893 | AM12519-AS | 1186 | 1525 | AM12518-SS | 1433 | 1617 |
| AD08894 | AM12516-AS | 1185 | 1525 | AM12520-SS | 1434 | 1707 |
| AD08895 | AM12516-AS | 1185 | 1525 | AM12521-SS | 1435 | 1708 |
| AD08896 | AM12516-AS | 1185 | 1525 | AM12522-SS | 1436 | 1709 |
| AD08897 | AM12516-AS | 1185 | 1525 | AM12523-SS | 1437 | 1617 |
| AD08951 | AM12165-AS | 1166 | 1535 | AM12605-SS | 1438 | 1632 |
| AD08952 | AM12165-AS | 1166 | 1535 | AM12606-SS | 1439 | 1632 |
| AD08953 | AM12608-AS | 1187 | 1608 | AM12607-SS | 1440 | 1710 |
| AD08954 | AM12609-AS | 1188 | 1535 | AM12164-SS | 1420 | 1632 |
| AD08955 | AM12610-AS | 1189 | 1535 | AM12164-SS | 1420 | 1632 |
| AD08956 | AM12611-AS | 1190 | 1535 | AM12164-SS | 1420 | 1632 |
| AD08957 | AM12612-AS | 1191 | 1535 | AM12164-SS | 1420 | 1632 |
| AD09240 | AM12165-AS | 1166 | 1535 | AM13074-SS | 1441 | 1632 |
| AD09241 | AM12612-AS | 1191 | 1535 | AM13074-SS | 1441 | 1632 |
| AD09863 | AM11401-AS | 1127 | 1525 | AM14080-SS | 1442 | 1617 |
| AD09864 | AM11401-AS | 1127 | 1525 | AM14081-SS | 1443 | 1711 |
| AD09865 | AM11401-AS | 1127 | 1525 | AM14084-SS | 1444 | 1712 |

TABLE 8C

MUC5AC RNAi Agent Duplexes with Corresponding Sense and Antisense Strand ID Numbers and Sequence ID numbers for certain modified and unmodified nucleotide sequences tested in vitro.

| Duplex | AS ID | AS modified SEQ ID NO: | AS unmodified SEQ ID NO: | SS ID | SS modified SEQ ID NO: | SS unmodified SEQ ID NO: |
|---|---|---|---|---|---|---|
| AD07634 | AM10595-AS | 1065 | 1525 | AM10594-SS-S | 1445 | 1617 |
| AD07637 | AM10601-AS | 1068 | 1528 | AM10600-SS-S | 1446 | 1620 |
| AD07732 | AM10766-AS | 1077 | 1534 | AM10765-SS-S | 1447 | 1631 |
| AD07733 | AM10768-AS | 1078 | 1535 | AM10767-SS-S | 1448 | 1632 |
| AD07734 | AM10770-AS | 1079 | 1536 | AM10769-SS-S | 1449 | 1633 |
| AD07735 | AM10772-AS | 1080 | 1537 | AM10771-SS-S | 1450 | 1634 |
| AD07745 | AM10792-AS | 1082 | 1539 | AM10791-SS-S | 1451 | 1636 |
| AD07746 | AM10794-AS | 1083 | 1540 | AM10793-SS-S | 1452 | 1637 |
| AD07747 | AM10796-AS | 1084 | 1541 | AM10795-SS-S | 1453 | 1638 |
| AD07748 | AM10798-AS | 1085 | 1542 | AM10797-SS-S | 1454 | 1639 |
| AD07749 | AM10800-AS | 1086 | 1543 | AM10799-SS-S | 1455 | 1640 |
| AD07750 | AM10802-AS | 1087 | 1544 | AM10801-SS-S | 1456 | 1641 |
| AD07751 | AM10804-AS | 1088 | 1545 | AM10803-SS-S | 1457 | 1642 |
| AD07756 | AM10814-AS | 1093 | 1549 | AM10813-SS-S | 1458 | 1646 |
| AD07760 | AM10821-AS | 1096 | 1551 | AM10820-SS-S | 1459 | 1648 |
| AD07763 | AM10827-AS | 1099 | 1554 | AM10826-SS-S | 1460 | 1651 |
| AD07764 | AM10829-AS | 1100 | 1555 | AM10828-SS-S | 1461 | 1652 |
| AD07766 | AM10833-AS | 1102 | 1557 | AM10832-SS-S | 1462 | 1654 |

TABLE 8C-continued

MUC5AC RNAi Agent Duplexes with Corresponding Sense and Antisense Strand ID Numbers and Sequence ID numbers for certain modified and unmodified nucleotide sequences tested in vitro.

| Duplex | AS ID | AS modified SEQ ID NO: | AS unmodified SEQ ID NO: | SS ID | SS modified SEQ ID NO: | SS unmodified SEQ ID NO: |
|---|---|---|---|---|---|---|
| AD07768 | AM10837-AS | 1104 | 1559 | AM10836-SS-S | 1463 | 1656 |
| AD07770 | AM10841-AS | 1106 | 1561 | AM10840-SS-S | 1464 | 1658 |
| AD07771 | AM10843-AS | 1107 | 1562 | AM10842-SS-S | 1465 | 1659 |
| AD07772 | AM10845-AS | 1108 | 1563 | AM10844-SS-S | 1466 | 1660 |
| AD07773 | AM10847-AS | 1109 | 1564 | AM10846-SS-S | 1467 | 1661 |
| AD07774 | AM10849-AS | 1110 | 1565 | AM10848-SS-S | 1468 | 1662 |
| AD08094 | AM11275-AS | 1117 | 1569 | AM11274-SS-S | 1469 | 1668 |
| AD08095 | AM11277-AS | 1118 | 1570 | AM11276-SS-S | 1470 | 1669 |
| AD08096 | AM11279-AS | 1119 | 1571 | AM11278-SS-S | 1471 | 1670 |
| AD08097 | AM11281-AS | 1120 | 1572 | AM11280-SS-S | 1472 | 1671 |
| AD08100 | AM11287-AS | 1123 | 1575 | AM11286-SS-S | 1473 | 1674 |
| AD08101 | AM11289-AS | 1124 | 1576 | AM11288-SS-S | 1474 | 1675 |
| AD08103 | AM11293-AS | 1126 | 1578 | AM11292-SS-S | 1475 | 1677 |
| AD08568 | AM11979-AS | 1157 | 1598 | AM11978-SS-S | 1476 | 1695 |
| AD08569 | AM07100-AS | 1716 | 1566 | AM11980-SS-S | 1477 | 1664 |
| AD08571 | AM11984-AS | 1159 | 1600 | AM11983-SS-S | 1478 | 1697 |
| AD08572 | AM07104-AS | 1717 | 1568 | AM11985-SS-S | 1479 | 1667 |
| AD08573 | AM11986-AS | 1160 | 1568 | AM11985-SS-S | 1479 | 1667 |
| AD08666 | AM12163-AS | 1165 | 1535 | AM10767-SS-S | 1448 | 1632 |
| AD08667 | AM12165-AS | 1166 | 1535 | AM12164-SS-S | 1480 | 1632 |
| AD08668 | AM12166-AS | 1167 | 1535 | AM12164-SS-S | 1480 | 1632 |
| AD08669 | AM12167-AS | 1168 | 1535 | AM12164-SS-S | 1480 | 1632 |
| AD08670 | AM12167-AS | 1168 | 1535 | AM12168-SS-S | 1481 | 1699 |
| AD08671 | AM12169-AS | 1169 | 1571 | AM11278-SS-S | 1471 | 1670 |
| AD08672 | AM12171-AS | 1170 | 1571 | AM12170-SS-S | 1482 | 1670 |
| AD08673 | AM12172-AS | 1171 | 1571 | AM12170-SS-S | 1482 | 1670 |

TABLE 9

MUC5AC RNAi Agent Conjugated Duplexes with Corresponding Sense and Antisense Strand ID Numbers and Sequence ID numbers for the modified and unmodified nucleotide sequences. (Shown with Targeting Ligand Conjugates)

| Duplex | AS ID | AS modified SEQ ID NO: | AS unmodified SEQ ID NO: | SS ID | SS modified SEQ ID NO: | SS unmodified SEQ ID NO: |
|---|---|---|---|---|---|---|
| AC000313 | AM10743-AS | 1073 | 1531 | CS000387 | 1483 | 1626 |
| AC000431 | AM11264-AS | 1112 | 1566 | CS000521 | 1486 | 1663 |
| AC000432 | AM11264-AS | 1112 | 1566 | CS000523 | 1487 | 1664 |
| AC000433 | AM11266-AS | 1113 | 1566 | CS000521 | 1486 | 1663 |
| AC000434 | AM11268-AS | 1114 | 1567 | CS000525 | 1488 | 1665 |
| AC000435 | AM11268-AS | 1114 | 1567 | CS000527 | 1489 | 1666 |
| AC000436 | AM11271-AS | 1115 | 1568 | CS000528 | 1490 | 1667 |
| AC000437 | AM11272-AS | 1116 | 1568 | CS000528 | 1490 | 1667 |
| AC000480 | AM11401-AS | 1127 | 1525 | CS000578 | 1491 | 1617 |
| AC000482 | AM10595-AS | 1065 | 1525 | CS000578 | 1491 | 1617 |
| AC000483 | AM11495-AS | 1142 | 1590 | CS000578 | 1491 | 1617 |
| AC000484 | AM11496-AS | 1143 | 1525 | CS000578 | 1491 | 1617 |
| AC000485 | AM11403-AS | 1128 | 1579 | CS000583 | 1492 | 1678 |
| AC000486 | AM11404-AS | 1129 | 1579 | CS000583 | 1492 | 1678 |
| AC000487 | AM11405-AS | 1130 | 1579 | CS000583 | 1492 | 1678 |
| AC000502 | AM11462-AS | 1131 | 1580 | CS000517 | 1484 | 1718 |
| AC000504 | AM11464-AS | 1132 | 1581 | CS000608 | 1493 | 1679 |
| AC000505 | AM11465-AS | 1133 | 1581 | CS000608 | 1493 | 1679 |
| AC000506 | AM11467-AS | 1134 | 1582 | CS000612 | 1494 | 1680 |
| AC000507 | AM11469-AS | 1135 | 1583 | CS000614 | 1495 | 1681 |
| AC000508 | AM11471-AS | 1136 | 1584 | CS000616 | 1496 | 1682 |
| AC000509 | AM11473-AS | 1137 | 1585 | CS000618 | 1497 | 1683 |
| AC000510 | AM11475-AS | 1138 | 1586 | CS000620 | 1498 | 1684 |
| AC000511 | AM11477-AS | 1139 | 1587 | CS000622 | 1499 | 1685 |
| AC000512 | AM11479-AS | 1140 | 1588 | CS000624 | 1500 | 1686 |
| AC000513 | AM11481-AS | 1141 | 1589 | CS000626 | 1501 | 1687 |
| AC000805 | AM10739-AS | 1071 | 1530 | CS001001 | 1503 | 1623 |
| AC000806 | AM10741-AS | 1072 | 1530 | CS001003 | 1504 | 1624 |
| AC000807 | AM10743-AS | 1073 | 1531 | CS001005 | 1505 | 1625 |
| AC000808 | AM10744-AS | 1074 | 1531 | CS001005 | 1505 | 1625 |
| AC000809 | AM10747-AS | 1075 | 1532 | CS001007 | 1506 | 1627 |
| AC000810 | AM10747-AS | 1075 | 1532 | CS001009 | 1507 | 1628 |

TABLE 9-continued

MUC5AC RNAi Agent Conjugated Duplexes with Corresponding Sense and Antisense Strand ID Numbers and Sequence ID numbers for the modified and unmodified nucleotide sequences. (Shown with Targeting Ligand Conjugates)

| Duplex | AS ID | AS modified SEQ ID NO: | AS unmodified SEQ ID NO: | SS ID | SS modified SEQ ID NO: | SS unmodified SEQ ID NO: |
|---|---|---|---|---|---|---|
| AC000811 | AM10747-AS | 1075 | 1532 | CS001010 | 1508 | 1629 |
| AC001128 | AM12178-AS | 1176 | 1568 | CS000528 | 1490 | 1667 |
| AC001129 | AM12178-AS | 1176 | 1568 | CS001401 | 1512 | 1700 |
| AC001130 | AM12180-AS | 1177 | 1568 | CS000528 | 1490 | 1667 |
| AC001131 | AM12181-AS | 1178 | 1568 | CS000528 | 1490 | 1667 |
| AC000832 | AM11742-AS | 1148 | 1566 | CS000523 | 1487 | 1664 |
| AC000833 | AM11742-AS | 1148 | 1566 | CS000521 | 1486 | 1663 |
| AC000834 | AM11742-AS | 1148 | 1566 | CS001040 | 1510 | 1664 |
| AC000835 | AM11272-AS | 1116 | 1568 | CS001041 | 1511 | 1667 |
| AC000836 | AM11745-AS | 1149 | 1568 | CS001041 | 1511 | 1667 |
| AC001305 | AM12165-AS | 1166 | 1535 | CS001644 | 1513 | 1632 |
| AC001306 | AM12612-AS | 1191 | 1535 | CS001644 | 1513 | 1632 |
| AC001708 | AM11401-AS | 1127 | 1525 | CS002194 | 1514 | 1617 |
| AC001709 | AM11401-AS | 1127 | 1525 | CS002195 | 1515 | 1711 |
| AC001710 | AM11401-AS | 1127 | 1525 | CS002196 | 1516 | 1712 |

TABLE 10A

Conjugate Duplex ID Numbers Referencing Position Targeted On MUC5AC (MUC5AC) Gene

| Duplex | AS ID | SS ID | Targeted MUC5AC Gene Position (Of SEQ ID NO: 1) |
|---|---|---|---|
| AC000313 | AM10743-AS | CS000387 | 1921 |
| AC000431 | AM11264-AS | CS000521 | 5029 |
| AC000432 | AM11264-AS | CS000523 | 5029 |
| AC000433 | AM11266-AS | CS000521 | 5029 |
| AC000434 | AM11268-AS | CS000525 | 9729 |
| AC000435 | AM11268-AS | CS000527 | 9729 |
| AC000436 | AM11271-AS | CS000528 | 15052 |
| AC000437 | AM11272-AS | CS000528 | 15052 |
| AC000480 | AM11401-AS | CS000578 | 3535 |
| AC000482 | AM10595-AS | CS000578 | 3535 |
| AC000483 | AM11495-AS | CS000578 | 3535 |
| AC000484 | AM11496-AS | CS000578 | 3535 |
| AC000485 | AM11403-AS | CS000583 | 3535 |
| AC000486 | AM11404-AS | CS000583 | 3535 |
| AC000487 | AM11405-AS | CS000583 | 3535 |
| AC000502 | AM11462-AS | CS000517 | N/A (murine-specific) |
| AC000504 | AM11464-AS | CS000608 | N/A (murine-specific) |
| AC000505 | AM11465-AS | CS000608 | N/A (murine-specific) |
| AC000506 | AM11467-AS | CS000612 | N/A (murine-specific) |
| AC000507 | AM11469-AS | CS000614 | N/A (murine-specific) |
| AC000508 | AM11471-AS | CS000616 | N/A (murine-specific) |
| AC000509 | AM11473-AS | CS000618 | N/A (murine-specific) |
| AC000510 | AM11475-AS | CS000620 | N/A (murine-specific) |
| AC000511 | AM11477-AS | CS000622 | N/A (murine-specific) |
| AC000512 | AM11479-AS | CS000624 | N/A (murine-specific) |
| AC000513 | AM11481-AS | CS000626 | N/A (murine-specific) |
| AC000805 | AM10739-AS | CS001001 | 304 |
| AC000806 | AM10741-AS | CS001003 | 304 |
| AC000807 | AM10743-AS | CS001005 | 1921 |
| AC000808 | AM10744-AS | CS001005 | 1921 |
| AC000809 | AM10747-AS | CS001007 | 1832 |
| AC000810 | AM10747-AS | CS001009 | 1832 |
| AC000811 | AM10747-AS | CS001010 | 1832 |
| AC001128 | AM12178-AS | CS000528 | 15052 |
| AC001129 | AM12178-AS | CS001401 | 15052 |
| AC001130 | AM12180-AS | CS000528 | 15052 |
| AC001131 | AM12181-AS | CS000528 | 15052 |
| AC000832 | AM11742-AS | CS000523 | 5029 |
| AC000833 | AM11742-AS | CS000521 | 5029 |
| AC000834 | AM11742-AS | CS001040 | 5029 |
| AC000835 | AM11272-AS | CS001041 | 15052 |
| AC000836 | AM11745-AS | CS001041 | 15052 |
| AC001305 | AM12165-AS | CS001644 | 4993 |
| AC001306 | AM12612-AS | CS001644 | 4993 |

TABLE 10A-continued

Conjugate Duplex ID Numbers Referencing Position Targeted On MUC5AC (MUC5AC) Gene

| Duplex | AS ID | SS ID | Targeted MUC5AC Gene Position (Of SEQ ID NO: 1) |
|---|---|---|---|
| AC001708 | AM11401-AS | CS002194 | 3535 |
| AC001709 | AM11401-AS | CS002195 | 3535 |
| AC001710 | AM11401-AS | CS002196 | 3535 |

TABLE 10B

Conjugate ID Numbers and Corresponding AD Duplex Numbers, Referencing Position Targeted On MUC5AC (MUC5AC) Gene

| AC Duplex Number | Corresponding AD Duplex Number | Targeted MUC5AC Gene Position (Of SEQ ID NO: 1) |
|---|---|---|
| AC000313 | AD07720 | 1921 |
| AC000431 | AD08083 | 5029 |
| AC000432 | AD08084 | 5029 |
| AC000433 | AD08085 | 5029 |
| AC000434 | AD08086 | 9729 |
| AC000435 | AD08087 | 9729 |
| AC000436 | AD08088 | 15052 |
| AC000437 | AD08089 | 15052 |
| AC000480 | AD08174 | 3535 |
| AC000482 | AD08173 | 3535 |
| AC000483 | AD08243 | 3535 |
| AC000484 | AD08244 | 3535 |
| AC000485 | AD08175 | 3535 |
| AC000486 | AD08176 | 3535 |
| AC000487 | AD08177 | 3535 |
| AC000502 | AD08222 | N/A (murine-specific) |
| AC000503 | AD08223 | N/A (murine-specific) |
| AC000504 | AD08224 | N/A (murine-specific) |
| AC000505 | AD08225 | N/A (murine-specific) |
| AC000506 | AD08226 | N/A (murine-specific) |
| AC000507 | AD08227 | N/A (murine-specific) |
| AC000508 | AD08228 | N/A (murine-specific) |
| AC000509 | AD08229 | N/A (murine-specific) |
| AC000510 | AD08230 | N/A (murine-specific) |
| AC000511 | AD08231 | N/A (murine-specific) |
| AC000512 | AD08232 | N/A (murine-specific) |
| AC000513 | AD08233 | N/A (murine-specific) |
| AC000805 | AD07716 | 304 |
| AC000806 | AD07717 | 304 |

TABLE 10B-continued

| Conjugate ID Numbers and Corresponding AD Duplex Numbers, Referencing Position Targeted On MUC5AC (MUC5AC) Gene | | |
|---|---|---|
| AC Duplex Number | Corresponding AD Duplex Number | Targeted MUC5AC Gene Position (Of SEQ ID NO: 1) |
| AC000807 | AD07718 | 1921 |
| AC000808 | AD07719 | 1921 |
| AC000809 | AD07721 | 1832 |
| AC000810 | AD07722 | 1832 |
| AC000811 | AD07723 | 1832 |
| AC001128 | AD08678 | 15052 |
| AC001129 | AD08679 | 15052 |
| AC001130 | AD08680 | 15052 |
| AC001131 | AD08681 | 15052 |
| AC000832 | AD08420 | 5029 |
| AC000833 | AD08421 | 5029 |
| AC000834 | AD08422 | 5029 |
| AC000835 | AD08423 | 15052 |
| AC000836 | AD08424 | 15052 |
| AC001305 | AD09240 | 4993 |
| AC001306 | AD09241 | 4993 |
| AC001708 | AD09863 | 3535 |
| AC001709 | AD09864 | 3535 |
| AC001710 | AD09865 | 3535 |

TABLE 11

Conjugate ID Numbers With Chemically Modified Antisense and Sense Strands (including Linkers and Conjugates)

| AC ID Number | Sense Strand (Fully Modified with Conjugated Targeting Ligand) (5' → 3') | SEQ ID NO. | Antisense Strand (5' → 3') | SEQ ID NO. |
|---|---|---|---|---|
| AC000313 | Tri-SM6.1-avb6-(TA14)gsa_2NaguaugCfUfCfaguacugiuas(invAb) | 1483 | cPrpusAfscsCfaGfuGfcUfgAfgCfaUfaCfuUfsc | 1073 |
| AC000431 | Tri-SM6.1-avb6-(TA14)csugcuacaAfCfUfaugagauccas(invAb) | 1486 | cPrpusGfsgsAfuCfuCfaUfaGfuUfgUfaGfcAfsg | 1112 |
| AC000432 | Tri-SM6.1-avb6-(TA14)csugcuacaAfCfUfaugaiauccas(invAb) | 1487 | cPrpusGfsgsAfuCfuCfaUfaGfuUfgUfaGfcAfsg | 1112 |
| AC000433 | Tri-SM6.1-avb6-(TA14)csugcuacaAfCfUfaugagauccas(invAb) | 1486 | cPrpusGfsgsAfuCfUuNACfaUfaGfuUfgUfaGfcAfsg | 1113 |
| AC000434 | Tri-SM6.1-avb6-(TA14)cscuggaccAfAfGfugguuugacas(invAb) | 1488 | cPrpusGfsusCfaAfaCfcAfcUfuGfgUfcCfaGfsg | 1114 |
| AC000435 | Tri-SM6.1-avb6-(TA14)cscuggaccAfAfGfugguuuiacas(invAb) | 1489 | cPrpusGfsusCfaAfaCfcAfcUfuGfgUfcCfaGfsg | 1114 |
| AC000436 | Tri-SM6.1-avb6-(TA14)csgagaucaUfCfUfucaacaacaas(invAb) | 1490 | cPrpusUfsgsUfuGfuUfgAfaGfaUfgAfuCfuCfsg | 1115 |
| AC000437 | Tri-SM6.1-avb6-(TA14)csgagaucaUfCfUfucaacaacaas(invAb) | 1490 | cPrpusUfsgsUfuguugaaGfaUfgAfucucsg | 1116 |
| AC000480 | Tri-SM6.1-avb6-(TA14)gscuguucuGfCfGfacuacuacaas(invAb) | 1491 | cPrpusUfsgsUfaGfuAfgUfcGfcAfgAfaCfaGfsc | 1127 |
| AC000482 | Tri-SM6.1-avb6-(TA14)gscuguucuGfCfGfacuacuacaas(invAb) | 1491 | usUfsgsUfaGfuAfgUfcGfcAfgAfaCfaGfsc | 1065 |
| AC000483 | Tri-SM6.1-avb6-(TA14)gscuguucuGfCfGfacuacuacaas(invAb) | 1491 | cPrpusUfsgsUfaGfuAfgUfcicAfgAfaCfaGfsc | 1142 |
| AC000484 | Tri-SM6.1-avb6-(TA14)gscuguucuGfCfGfacuacuacaas(invAb) | 1491 | cPrpusUfsgsUfaGfuAfgUfcgcAfgAfaCfaGfsc | 1143 |
| AC000485 | Tri-SM6.1-avb6-(TA14)gscuguucuGfUfGfacuacuacaas(invAb) | 1492 | usUfsgsUfaGfuAfgUfcAfcAfgAfaCfaGfsc | 1128 |
| AC000486 | Tri-SM6.1-avb6-(TA14)gscuguucuGfUfGfacuacuacaas(invAb) | 1492 | cPrpusUfsgsUfaGfuAfgUfcAfcAfgAfaCfaGfsc | 1129 |
| AC000487 | Tri-SM6.1-avb6-(TA14)gscuguucuGfUfGfacuacuacaas(invAb) | 1492 | cPrpusUfsgsuaguagucAfcAfgAfacagsc | 1130 |
| AC000502 | Tri-SM6.1-avb6-(TA14)ascccauguGfCfUfacaacuaugas(invAb) | 1484 | cPrpusCfsasuaguuguaGfcAfcAfugggsu | 1131 |
| AC000503 | Tri-SM6.1-avb6-(TA14)asccagaucAfUfCfuucaacaacas(invAb) | 1493 | usGfsusUfgUfuGfaAfgAfuGfaUfcUfgGfsu | 1715 |
| AC000504 | Tri-SM6.1-avb6-(TA14)asccagaucAfUfCfuucaacaacas(invAb) | 1493 | cPrpusGfsusUfgUfuGfaAfgAfuGfaUfcUfgGfsu | 1132 |
| AC000505 | Tri-SM6.1-avb6-(TA14)asccagaucAfUfCfuucaacaacas(invAb) | 1493 | cPrpusGfsusuguugaagAfuGfaUfcuggsu | 1133 |
| AC000506 | Tri-SM6.1-avb6-(TA14)gsgcucuguGfGfUfaacuucaacas(invAb) | 1494 | cPrpusGfsusUfgAfaGfuUfaCfcAfcAfgAfgCfsc | 1134 |
| AC000507 | Tri-SM6.1-avb6-(TA14)gsagcguggAfGfAfaugaaaaguas(invAb) | 1495 | cPrpusAfscsUfuUfuCfaUfuCfuCfcAfcGfcUfsc | 1135 |
| AC000508 | Tri-SM6.1-avb6-(TA14)gsggagaauGfAfAfaaguaugcuas(invAb) | 1496 | cPrpusAfsgsCfaUfaCfuUfuUfcAfuUfcUfcCfsc | 1136 |
| AC000509 | Tri-SM6.1-avb6-(TA14)csuucucgaAfCfUfgcauguaugas(invAb) | 1497 | cPrpusCfsasUfaCfaUfgCfaGfuUfcGfaGfaAfsg | 1137 |

TABLE 11-continued

| Conjugate ID Numbers With Chemically Modified Antisense and Sense Strands (including Linkers and Conjugates) | | | | |
|---|---|---|---|---|
| AC ID Number | Sense Strand (Fully Modified with Conjugated Targeting Ligand) (5' → 3') | SEQ ID NO. | Antisense Strand (5' → 3') | SEQ ID NO. |
| AC000510 | Tri-SM6.1-avb6-(TA14)gscucgaacUfGfCfauguaugacas(invAb) | 1498 | cPrpusGfsusCfaUfaCfaUfgCfaGfuUfcGfaGfsc | 1138 |
| AC000511 | Tri-SM6.1-avb6-(TA14)csucgaacuGfCfAfuguaugacaas(invAb) | 1499 | cPrpusUfsgsUfcAfuAfcAfuGfcAfgUfuCfgAfsg | 1139 |
| AC000512 | Tri-SM6.1-avb6-(TA14)cscacuguuCfUfGfugacuacuaas(invAb) | 1500 | cPrpusUfsasGfuAfgUfcAfcAfgAfaCfaGfuGfsg | 1140 |
| AC000513 | Tri-SM6.1-avb6-(TA14)csacuguucUfGfUfgacuacuacas(invAb) | 1501 | cPrpusGfsusAfgUfaGfuCfaCfaGfaAfcAfgUfsg | 1141 |
| AC000805 | Tri-SM6.1-avb6-(TA14)csagcuuccAfCfUfacaaiaccuus(invAb) | 1503 | cPrpasAfsgsGfuCfuUfgUfaGfuGfgAfaGfcUfsg | 1071 |
| AC000806 | Tri-SM6.1-avb6-(TA14)csagcuuccAfCfUfacaagaccuus(invAb) | 1504 | cPrpasAfsgsGfuCfUuNAUfgUfaGfuGfgAfaGfcUfsg | 1072 |
| AC000807 | Tri-SM6.1-avb6-(TA14)gsa_2NaguaugCfUfCfagcacugiuas(invAb) | 1505 | cPrpusAfscsCfaGfuGfcUfgAfgCfaUfaCfuUfsc | 1073 |
| AC000808 | Tri-SM6.1-avb6-(TA14)gsa_2NaguaugCfUfCfagcacugiuas(invAb) | 1505 | cPrpusAfscsCfaGfUuNAGfcUfgAfgCfaUfaCfuUfsc | 1074 |
| AC000809 | Tri-SM6.1-avb6-(TA14)gsccuucuuCfAfAfcaccuucaaas(invAb) | 1506 | cPrpusUfsusGfaAfgguguUfgAfaGfaAfgGfsc | 1075 |
| AC000810 | Tri-SM6.1-avb6-(TA14)gsccuucuuCfAfAfcaucuucaaas(invAb) | 1507 | cPrpusUfsusGfaAfgguguUfgAfaGfaAfgGfsc | 1075 |
| AC000811 | Tri-SM6.1-avb6-(TA14)gsccuucuuCfAfAfcacuuucaaas(invAb) | 1508 | cPrpusUfsusGfaAfgguguUfgAfaGfaAfgGfsc | 1075 |
| AC000832 | Tri-SM6.1-avb6-(TA14)csugcuacaAfCfUfaugaiauccas(invAb) | 1487 | cPrpusGfsgsaucucauaGfuUfgUfagcasg | 1148 |
| AC000833 | Tri-SM6.1-avb6-(TA14)csugcuacaAfCfUfaugagauccas(invAb) | 1486 | cPrpusGfsgsaucucauaGfuUfgUfagcasg | 1148 |
| AC000834 | Tri-SM6.1-avb6-(TA14)csugcuaCfaAfcUfaugaiauccas(invAb) | 1510 | cPrpusGfsgsaucucauaGfuUfgUfagcasg | 1148 |
| AC000835 | Tri-SM6.1-avb6-(TA14)csgagauCfaUfcUfucaacaacaas(invAb) | 1511 | cPrpusUfsgsUfuguugaaGfaUfgAfucucsg | 1116 |
| AC000836 | Tri-SM6.1-avb6-(TA14)csgagauCfaUfcUfucaacaacaas(invAb) | 1511 | cPrpusUfsgsuuguugaaGfaUfgAfucucsg | 1149 |
| AC001128 | Tri-SM6.1-avb6-(TA14)csgagaucaUfCfUfucaacaacaas(invAb) | 1490 | cPrpusUfsgsUfugUuNAUgaaGfaUfgAfucucsg | 1176 |
| AC001129 | Tri-SM6.1-avb6-(TA14)csgagaucaUfCfUfuca_2Nacaacaas(invAb) | 1512 | cPrpusUfsgsUfugUuNAUgaaGfaUfgAfucucsg | 1176 |
| AC001130 | Tri-SM6.1-avb6-(TA14)csgagaucaUfCfUfucaacaacaas(invAb) | 1490 | cPrpusUfsgsUfuguUuNAgaaGfaUfgAfucucsg | 1177 |
| AC001131 | Tri-SM6.1-avb6-(TA14)csgagaucaUfCfUfucaacaacaas(invAb) | 1490 | cPrpusUfsgsUfUuNAguugaaGfaUfgAfucucsg | 1178 |
| AC001305 | Tri-SM6.1-avb6-(TA14)gscugauUfuGfcCfugaacaagaas(invAb) | 1513 | usUfscsuuguucagGfcAfaAfucagsc | 1166 |
| AC001306 | Tri-SM6.1-avb6-(TA14)gscugauUfuGfcCfugaacaagaas(invAb) | 1513 | cPrpuUfcuuguucagGfcAfaAfucagsc | 1191 |

TABLE 11-continued

| Conjugate ID Numbers With Chemically Modified Antisense and Sense Strands (including Linkers and Conjugates) | | | | |
|---|---|---|---|---|
| AC ID Number | Sense Strand (Fully Modified with Conjugated Targeting Ligand) (5' → 3') | SEQ ID NO. | Antisense Strand (5' → 3') | SEQ ID NO. |
| AC001708 | Tri-SM6.1-avb6-(TA14)gscuguucuGfCfGfacuacuacaa(invAb) | 1514 | cPrpusUfsgsUfaGfuAfgUfcGfcAfgAfaCfaGfsc | 1127 |
| AC001709 | Tri-SM6.1-avb6-(TA14)gscugguucuGfCfGfacuacuacaas(invAb) | 1515 | cPrpusUfsgsUfaGfuAfgUfcGfcAfgAfaCfaGfsc | 1127 |
| AC001710 | Tri-SM6.1-avb6-(TA14)gscguucuGfCfGfacuacuacaas(invAb) | 1516 | cPrpusUfsgsUfaGfuAfgUfcGfcAfgAfaCfaGfsc | 1127 |

In some embodiments, a MUC5AC RNAi agent is prepared or provided as a salt, mixed salt, or a free-acid. In some embodiments, a MUC5AC RNAi agent is prepared or provided as a pharmaceutically acceptable salt. In some embodiments, a MUC5AC RNAi agent is prepared or provided as a pharmaceutically acceptable sodium or potassium salt The RNAi agents described herein, upon delivery to a cell expressing an MUC5AC gene, inhibit or knockdown expression of one or more MUC5AC genes in vivo and/or in vitro.

Targeting Groups, Linking Groups, Pharmacokinetic/Pharmacodynamic (PK/PD) Modulators, and Delivery Vehicles In some embodiments, a MUC5AC RNAi agent contains or is conjugated to one or more non-nucleotide groups including, but not limited to, a targeting group, a linking group, a pharmacokinetic/pharmacodynamic (PK/PD) modulator, a delivery polymer, or a delivery vehicle. The non-nucleotide group can enhance targeting, delivery, or attachment of the RNAi agent. The non-nucleotide group can be covalently linked to the 3' and/or 5' end of either the sense strand and/or the antisense strand. In some embodiments, a MUC5AC RNAi agent contains a non-nucleotide group linked to the 3' and/or 5' end of the sense strand. In some embodiments, a non-nucleotide group is linked to the 5' end of a MUC5AC RNAi agent sense strand. A non-nucleotide group can be linked directly or indirectly to the RNAi agent via a linker/linking group. In some embodiments, a non-nucleotide group is linked to the RNAi agent via a labile, cleavable, or reversible bond or linker.

In some embodiments, a non-nucleotide group enhances the pharmacokinetic or biodistribution properties of an RNAi agent or conjugate to which it is attached to improve cell- or tissue-specific distribution and cell-specific uptake of the conjugate. In some embodiments, a non-nucleotide group enhances endocytosis of the RNAi agent.

Targeting groups or targeting moieties enhance the pharmacokinetic or biodistribution properties of a conjugate or RNAi agent to which they are attached to improve cell-specific (including, in some cases, organ specific) distribution and cell-specific (or organ specific) uptake of the conjugate or RNAi agent. A targeting group can be monovalent, divalent, trivalent, tetravalent, or have higher valency for the target to which it is directed. Representative targeting groups include, without limitation, compounds with affinity to cell surface molecule, cell receptor ligands, hapten, antibodies, monoclonal antibodies, antibody fragments, and antibody mimics with affinity to cell surface molecules. In some embodiments, a targeting group is linked to an RNAi agent using a linker, such as a PEG linker or one, two, or three abasic and/or ribitol (abasic ribose) residues, which in some instances can serve as linkers.

A targeting group, with or without a linker, can be attached to the 5' or 3' end of any of the sense and/or antisense strands disclosed in Tables 2, 3, 4, 5, 6, 7, and 11. A linker, with or without a targeting group, can be attached to the 5' or 3' end of any of the sense and/or antisense strands disclosed in Tables 2, 3, 4, 5, 6, 7, and 11.

The MUC5AC RNAi agents described herein can be synthesized having a reactive group, such as an amino group (also referred to herein as an amine), at the 5'-terminus and/or the 3'-terminus. The reactive group can be used subsequently to attach a targeting moiety using methods typical in the art.

For example, in some embodiments, the MUC5AC RNAi agents disclosed herein can be synthesized having an $NH_2$-$C_6$ group at the 5'-terminus of the sense strand of the RNAi agent. The terminal amino group subsequently can be reacted to form a conjugate with, for example, a group that includes an αvβ6 integrin targeting ligand. In some embodiments, the MUC5AC RNAi agents disclosed herein are synthesized having one or more alkyne groups at the 5'-terminus of the sense strand of the RNAi agent. The terminal alkyne group(s) can subsequently be reacted to form a conjugate with, for example, a group that includes an αvβ6 integrin targeting ligand.

In some embodiments, a targeting group comprises an integrin targeting ligand. In some embodiments, an integrin targeting ligand is an αvβ6 integrin targeting ligand. The use of an αvβ6 integrin targeting ligand facilitates cell-specific targeting to cells having αvβ6 on its respective surface, and binding of the integrin targeting ligand can facilitate entry of the therapeutic agent, such as an RNAi agent, to which it is linked, into cells such as epithelial cells, including pulmonary epithelial cells and renal epithelial cells. Integrin targeting ligands can be monomeric or monovalent (e.g., having a single integrin targeting moiety) or multimeric or multivalent (e.g., having multiple integrin targeting moieties). The targeting group can be attached to the 3' and/or 5' end of the RNAi oligonucleotide using methods known in the art. The preparation of targeting groups, such as αvβ6 integrin targeting ligands, is described, for example, in International Patent Application Publication No. WO 2018/085415 and in International Patent Application Publication No. WO 2019/089765, the contents of each of which are incorporated herein in its entirety.

In some embodiments, targeting groups are linked to the MUC5AC RNAi agents without the use of an additional linker. In some embodiments, the targeting group is designed having a linker readily present to facilitate the linkage to a MUC5AC RNAi agent. In some embodiments, when two or more RNAi agents are included in a composition, the two or more RNAi agents can be linked to their respective targeting groups using the same linkers. In some embodiments, when two or more RNAi agents are included in a composition, the two or more RNAi agents are linked to their respective targeting groups using different linkers.

In some embodiments, a linking group is conjugated to the RNAi agent. The linking group facilitates covalent linkage of the agent to a targeting group, pharmacokinetic modulator, delivery polymer, or delivery vehicle. The linking group can be linked to the 3' and/or the 5' end of the RNAi agent sense strand or antisense strand. In some embodiments, the linking group is linked to the RNAi agent sense strand. In some embodiments, the linking group is conjugated to the 5' or 3' end of an RNAi agent sense strand. In some embodiments, a linking group is conjugated to the 5' end of an RNAi agent sense strand. Examples of linking groups, include but are not limited to: C6-SS-C6, 6-SS-6, reactive groups such a primary amines (e.g., NH2-C6) and alkynes, alkyl groups, abasic residues/nucleotides, amino acids, tri-alkyne functionalized groups, ribitol, and/or PEG groups. Examples of certain linking groups are provided in Table 12.

A linker or linking group is a connection between two atoms that links one chemical group (such as an RNAi agent) or segment of interest to another chemical group (such as a targeting group, pharmacokinetic modulator, or delivery polymer) or segment of interest via one or more covalent bonds. A labile linkage contains a labile bond. A linkage can optionally include a spacer that increases the distance between the two joined atoms. A spacer may further add flexibility and/or length to the linkage. Spacers include, but are not be limited to, alkyl groups, alkenyl groups, alkynyl groups, aryl groups, aralkyl groups, aralkenyl groups, and aralkynyl groups; each of which can contain one or more heteroatoms, heterocycles, amino acids, nucleotides, and saccharides. Spacer groups are well known in the art and the preceding list is not meant to limit the scope of the description. In some embodiments, a MUC5AC RNAi agent is conjugated to a polyethylene glycol (PEG) moiety, or to a hydrophobic group having 12 or more carbon atoms, such as a cholesterol or palmitoyl group.

In some embodiments, a MUC5AC RNAi agent is linked to one or more pharmacokinetic/pharmacodynamic (PK/PD) modulators. PK/PD modulators can increase circulation time of the conjugated drug and/or increase the activity of the RNAi agent through improved cell receptor binding, improved cellular uptake, and/or other means. Various PK/PD modulators suitable for use with RNAi agents are known in the art. In some embodiments, the PK/PD modulatory can be cholesterol or cholesteryl derivatives, or in some circumstances a PK/PD modulator can be comprised of alkyl groups, alkenyl groups, alkynyl groups, aryl groups, aralkyl groups, aralkenyl groups, or aralkynyl groups, each of which may be linear, branched, cyclic, and/or substituted or unsubstituted. In some embodiments, the location of attachment for these moieties is at the 5' or 3' end of the sense strand, at the 2' position of the ribose ring of any given nucleotide of the sense strand, and/or attached to the phosphate or phosphorothioate backbone at any position of the sense strand.

Any of the MUC5AC RNAi agent nucleotide sequences listed in Tables 2, 3, 4, 5, 6, 7, and 11, whether modified or unmodified, can contain 3' and/or 5' targeting group(s), linking group(s), and/or PK/PD modulator(s). Any of the MUC5AC RNAi agent sequences listed in Tables 3, 4, 5, 6, 7, and 11, or are otherwise described herein, which contain a 3' or 5' targeting group, linking group, and/or PK/PD modulator can alternatively contain no 3' or 5' targeting group, linking group, or PK/PD modulator, or can contain a different 3' or 5' targeting group, linking group, or pharmacokinetic modulator including, but not limited to, those depicted in Table 12. Any of the MUC5AC RNAi agent duplexes listed in Tables 8A, 8B, 8C, 9, 10A, 10B, and 11, whether modified or unmodified, can further comprise a targeting group or linking group, including, but not limited to, those depicted in Table 11, and the targeting group or linking group can be attached to the 3' or 5' terminus of either the sense strand or the antisense strand of the MUC5AC RNAi agent duplex.

Examples of certain modified nucleotides, capping moieties, and linking groups are provided in Table 12.

TABLE 12

Structures Representing Various Modified Nucleotides, Capping Moieties, and Linking Groups (wherein ⌇ indicates the point of connection)

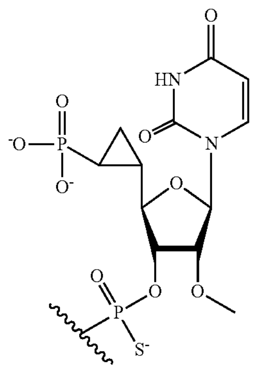

cPrpus

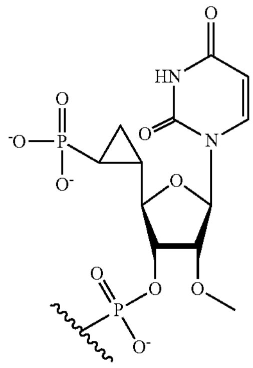

cPrpu

TABLE 12-continued
Structures Representing Various Modified Nucleotides, Capping Moieties, and Linking Groups (wherein ⌇indicates the point of connection)
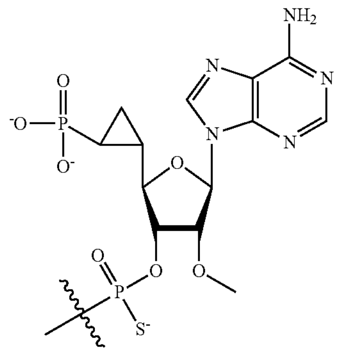
cPrpas
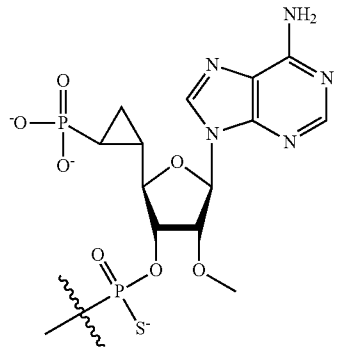
cPrpa
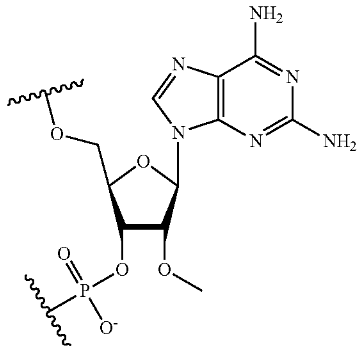
a_2N
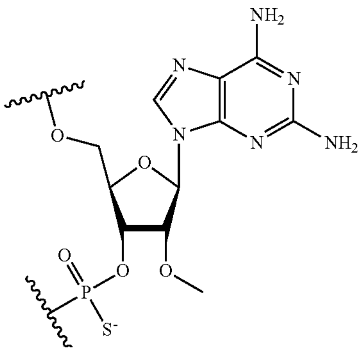
a_2Ns TABLE 12-continued Structures Representing Various Modified Nucleotides, Capping Moieties, and Linking Groups (wherein ⌇indicates the point of connection)

When positioned internally:

linkage towards 5′ end

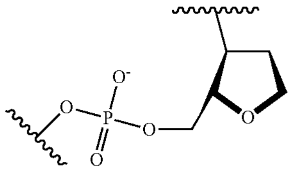

linkage towards 3′ end (invAb)

When positioned internally:

linkage towards 5′ end

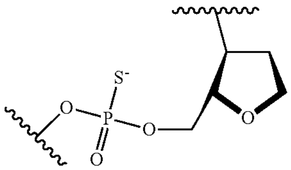

linkage towards 3′ end (invAb)s

When positioned at the 3' terminal end:

linkage towards 5′ end

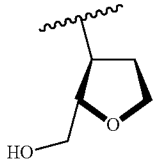

(invAb)

When positioned at the 3' terminal end:

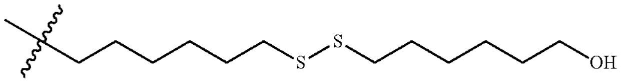

linkage towards 5′ end (C6-SS-C6)

When positioned internally:

linkage towards 5′ end linkage towards 3′ end

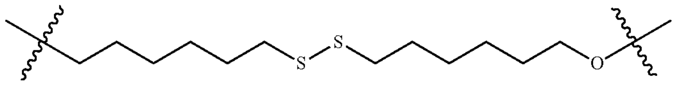

(C6-SS-C6)

TABLE 12-continued
| Structures Representing Various Modified Nucleotides, Capping Moieties, and Linking Groups (wherein ⌇indicates the point of connection) |
| --- |
| When positioned at the 3' terminal end: |
| 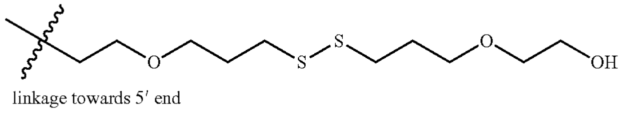 [SMILES: *CCOCCCSSCCCOCCO] |
| (6-SS-6) |
| When positioned internally: |
| 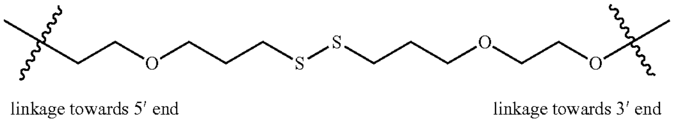 [SMILES: *CCOCCCSSCCCOCCO*] |
| (6-SS-6) |
| 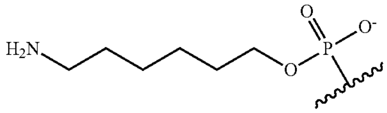 [SMILES: *P(=O)([O-])OCCCCCCN] |
| (NH2-C6) |
| 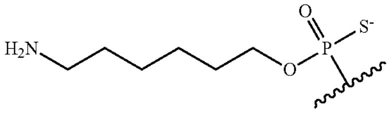 [SMILES: *P(=O)([S-])OCCCCCCN] |
| (NH2-C6)s |
| 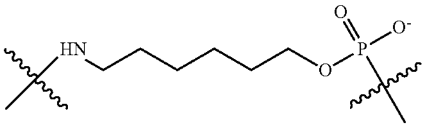 [SMILES: *NCCCCCCOP(*)(=O)[O-]] |
| -C6- |
| 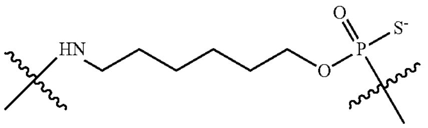 |
| -C6s- |
| 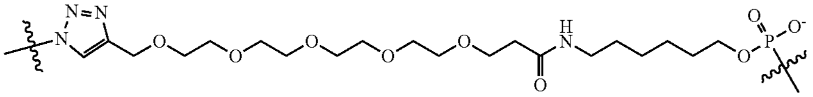 [SMILES: *n1cc(COCCOCCOCCOCCOCCC(=O)NCCCCCCOP(*)(=O)[O-])nn1] |
| -L6-C6- |
| 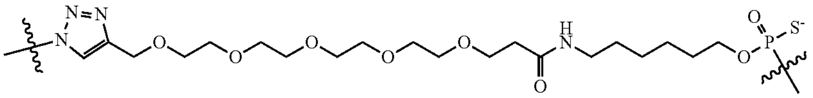 [SMILES: *n1cc(COCCOCCOCCOCCOCCC(=O)NCCCCCCOP(*)(=O)[S-])nn1] |
| -L6-C6s- |

TABLE 12-continued
Structures Representing Various Modified Nucleotides, Capping Moieties, and Linking Groups (wherein ⌇indicates the point of connection)
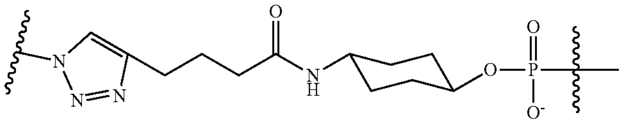 [SMILES: *n1cc(CCCC(=O)NC2CCC(OP(*)(=O)[O-])CC2)nn1]
-Alk-cyHex-
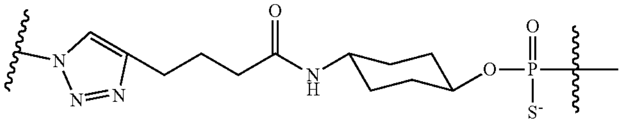 [SMILES: *n1cc(CCCC(=O)NC2CCC(OP(*)(=O)[S-])CC2)nn1]
-Alk-cyHexs-
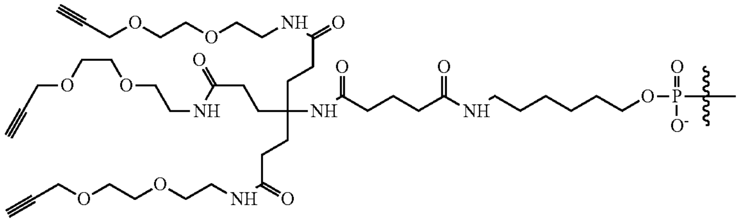 [SMILES: *P(=O)([O-])OCCCCCCNC(=O)CCCC(=O)NC(CCC(=O)NCCOCCOCC#C)(CCC(=O)NCCOCCOCC#C)CCC(=O)NCCOCCOCC#C]
(TriAlk14)
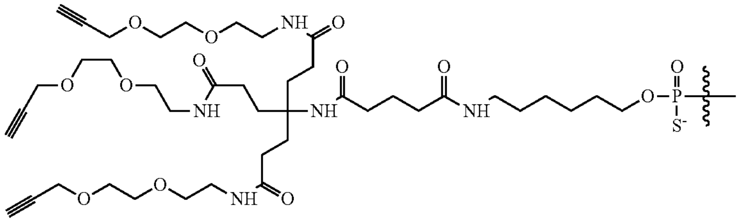 [SMILES: *P(=O)([S-])OCCCCCCNC(=O)CCCC(=O)NC(CCC(=O)NCCOCCOCC#C)(CCC(=O)NCCOCCOCC#C)CCC(=O)NCCOCCOCC#C]
(TriAlk14)s
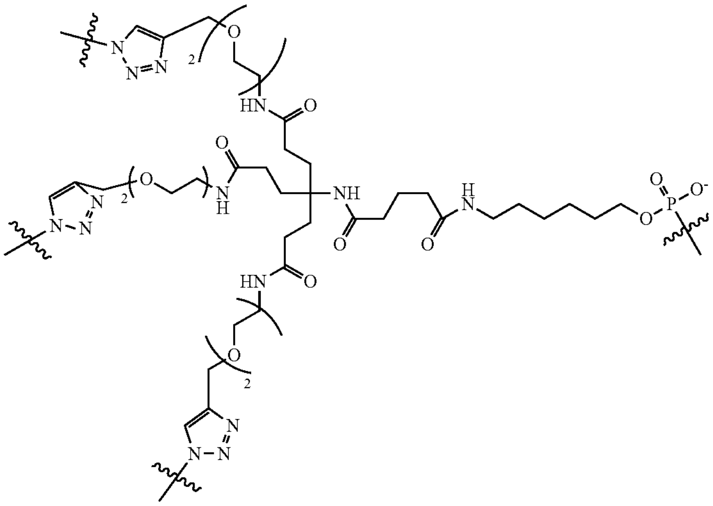
(TA14)

TABLE 12-continued

Structures Representing Various Modified Nucleotides, Capping Moieties, and Linking Groups (wherein ⌇ indicates the point of connection)

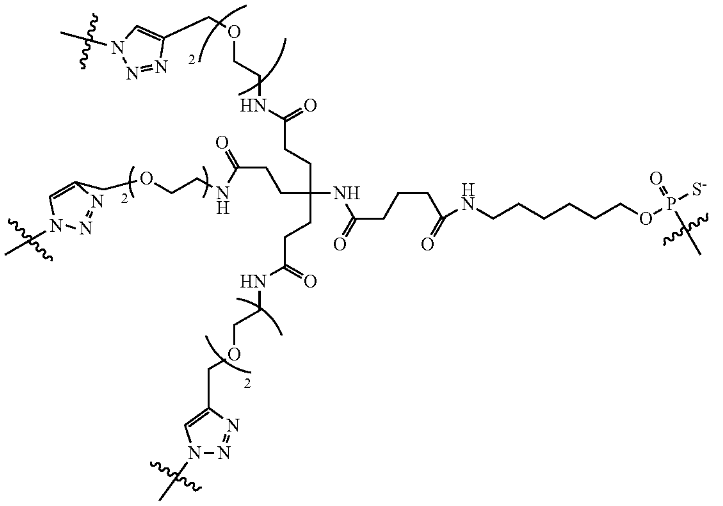

(TA14)s

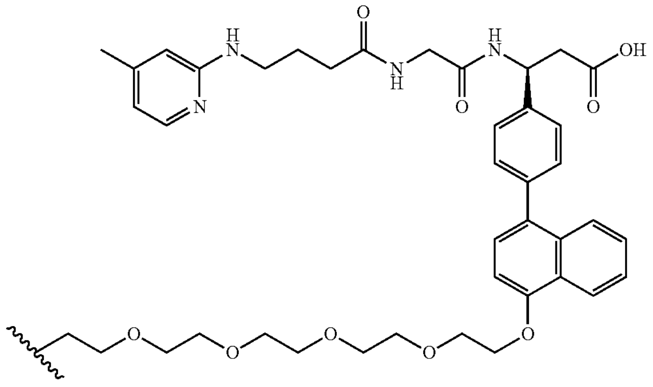 [SMILES: *CCOCCOCCOCCOCCOc1ccc(-c2ccc([C@H](CC(=O)O)NC(=O)CNC(=O)CCCNc3cc(C)ccn3)cc2)c2ccccc12]

SM6.1-αvβ6

Alternatively, other linking groups known in the art may be used. In many instances, linking groups can be commercially acquired or alternatively, are incorporated into commercially available nucleotide phosphoramidites. (See, e.g., International Patent Application Publication No. WO 2019/161213, which is incorporated herein by reference in its entirety).

In some embodiments, a MUC5AC RNAi agent is delivered without being conjugated to a targeting ligand or pharmacokinetic/pharmacodynamic (PK/PD) modulator (referred to as being "naked" or a "naked RNAi agent").

In some embodiments, a MUC5AC RNAi agent is conjugated to a targeting group, a linking group, a PK modulator, and/or another non-nucleotide group to facilitate delivery of the MUC5AC RNAi agent to the cell or tissue of choice, for example, to an epithelial cell in vivo. In some embodiments, a MUC5AC RNAi agent is conjugated to a targeting group wherein the targeting group includes an integrin targeting ligand. In some embodiments, the integrin targeting ligand is an αvβ6 integrin targeting ligand. In some embodiments, a targeting group includes one or more αvβ6 integrin targeting ligands.

In some embodiments, a delivery vehicle may be used to deliver an RNAi agent to a cell or tissue. A delivery vehicle is a compound that improves delivery of the RNAi agent to a cell or tissue. A delivery vehicle can include, or consist of, but is not limited to: a polymer, such as an amphipathic polymer, a membrane active polymer, a peptide, a melittin peptide, a melittin-like peptide (MLP), a lipid, a reversibly modified polymer or peptide, or a reversibly modified membrane active polyamine.

In some embodiments, the RNAi agents can be combined with lipids, nanoparticles, polymers, liposomes, micelles, DPCs or other delivery systems available in the art for nucleic acid delivery. The RNAi agents can also be chemically conjugated to targeting groups, lipids (including, but not limited to cholesteryl and cholesteryl derivatives), encapsulating in nanoparticles, liposomes, micelles, conjugating to polymers or DPCs (see, for example WO 2000/053722, WO 2008/022309, WO 2011/104169, and WO 2012/083185, WO 2013/032829, WO 2013/158141, each of which is incorporated herein by reference), by iontophoresis, or by incorporation into other delivery vehicles or systems available in the art such as hydrogels, cyclodextrins, biodegradable nanocapsules, bioadhesive microspheres, or proteinaceous vectors. In some embodiments the RNAi agents can be conjugated to antibodies having affinity for pulmonary epithelial cells. In some embodiments, the RNAi agents can be linked to targeting ligands that have affinity for pulmonary epithelial cells or receptors present on pulmonary epithelial cells.

Pharmaceutical Compositions and Formulations

The MUC5AC RNAi agents disclosed herein can be prepared as pharmaceutical compositions or formulations (also referred to herein as "medicaments"). In some embodiments, pharmaceutical compositions include at least one MUC5AC RNAi agent. These pharmaceutical compositions are particularly useful in the inhibition of the expression of MUC5AC mRNA in a target cell, a group of cells, a tissue, or an organism. The pharmaceutical compositions can be used to treat a subject having a disease, disorder, or condition that would benefit from reduction in the level of the target mRNA, or inhibition in expression of the target gene. The pharmaceutical compositions can be used to treat a subject at risk of developing a disease or disorder that would benefit from reduction of the level of the target mRNA or an inhibition in expression the target gene. In one embodiment, the method includes administering a MUC5AC RNAi agent linked to a targeting ligand as described herein, to a subject to be treated. In some embodiments, one or more pharmaceutically acceptable excipients (including vehicles, carriers, diluents, and/or delivery polymers) are added to the pharmaceutical compositions that include a MUC5AC RNAi agent, thereby forming a pharmaceutical formulation or medicament suitable for in vivo delivery to a subject, including a human.

The pharmaceutical compositions that include a MUC5AC RNAi agent and methods disclosed herein decrease the level of the target mRNA in a cell, group of cells, group of cells, tissue, organ, or subject, including by administering to the subject a therapeutically effective amount of a herein described MUC5AC RNAi agent, thereby inhibiting the expression of MUC5AC mRNA in the subject. In some embodiments, the subject has been previously identified or diagnosed as having a disease or disorder that can be mediated at least in part by a reduction in MUC5AC expression. In some embodiments, the subject has been previously diagnosed with having one or more mucoobstructive lung diseases, such as asthma, CF, COPD, NCFB, PCD. In some embodiments the mucoobstructive lung disease is severe asthma.

In some embodiments the subject has been previously diagnosed with having interstitial lung diseases, cancer (such as lung adenocarcinomas, pancreatic cancer, salivary gland carcinoma, breast cancer, cholangiocarcinoma, ovarian cancer, and other tumors), respiratory infections (such as respiratory syncytial virus, influenza, rhinovirus), otitis media, inflammatory bowel disease, gallstone disease, allergic rhinitis, chronic rhinosinusitis or nasal polyposis.

Embodiments of the present disclosure include pharmaceutical compositions for delivering a MUC5AC RNAi agent to a pulmonary epithelial cell in vivo. Such pharmaceutical compositions can include, for example, a MUC5AC RNAi agent conjugated to a targeting group that comprises an integrin targeting ligand. In some embodiments, the integrin targeting ligand is comprised of an $\alpha v\beta 6$ integrin ligand.

In some embodiments, the described pharmaceutical compositions including a MUC5AC RNAi agent are used for treating or managing clinical presentations in a subject that would benefit from the inhibition of expression of MUC5AC. In some embodiments, a therapeutically or prophylactically effective amount of one or more of pharmaceutical compositions is administered to a subject in need of such treatment. In some embodiments, administration of any of the disclosed MUC5AC RNAi agents can be used to decrease the number, severity, and/or frequency of symptoms of a disease in a subject.

In some embodiments, the described MUC5AC RNAi agents are optionally combined with one or more additional (i.e., second, third, etc.) therapeutics. A second therapeutic can be another MUC5AC RNAi agent (e.g., a MUC5AC RNAi agent that targets a different sequence within a MUC5AC gene). In some embodiments, a second therapeutic can be an RNAi agent that targets the MUC5AC gene. An additional therapeutic can also be a small molecule drug, antibody, antibody fragment, and/or aptamer. The MUC5AC RNAi agents, with or without the one or more additional therapeutics, can be combined with one or more excipients to form pharmaceutical compositions.

The described pharmaceutical compositions that include a MUC5AC RNAi agent can be used to treat at least one symptom in a subject having a disease or disorder that would benefit from reduction or inhibition in expression of MUC5AC mRNA. In some embodiments, the subject is administered a therapeutically effective amount of one or more pharmaceutical compositions that include a MUC5AC RNAi agent thereby treating the symptom. In other embodiments, the subject is administered a prophylactically effective amount of one or more MUC5AC RNAi agents, thereby preventing or inhibiting the at least one symptom.

In some embodiments, one or more of the described MUC5AC RNAi agents are administered to a mammal in a pharmaceutically acceptable carrier or diluent. In some embodiments, the mammal is a human.

The route of administration is the path by which a MUC5AC RNAi agent is brought into contact with the body. In general, methods of administering drugs, oligonucleotides, and nucleic acids, for treatment of a mammal are well known in the art and can be applied to administration of the compositions described herein. The MUC5AC RNAi agents disclosed herein can be administered via any suitable route in a preparation appropriately tailored to the particular route. Thus, in some embodiments, the herein described pharmaceutical compositions are administered via inhalation, intranasal administration, intratracheal administration, or oropharyngeal aspiration administration. In some embodiments, the pharmaceutical compositions can be administered by injection, for example, intravenously, intramuscularly, intracutaneously, subcutaneously, intraarticularly, intraocularly, or intraperitoneally, or topically.

The pharmaceutical compositions including a MUC5AC RNAi agent described herein can be delivered to a cell, group of cells, tissue, or subject using oligonucleotide delivery technologies known in the art. In general, any suitable method recognized in the art for delivering a nucleic acid molecule (in vitro or in vivo) can be adapted for use with the compositions described herein. For example, delivery can be by local administration, (e.g., direct injection, implantation, or topical administering), systemic administration, or subcutaneous, intravenous, intraperitoneal, or parenteral routes, including intracranial (e.g., intraventricular, intraparenchymal and intrathecal), intramuscular, transdermal, airway (aerosol), nasal, oral, rectal, or topical (including buccal and sublingual) administration. In some embodiments, the compositions are administered via inhalation, intranasal administration, oropharyngeal aspiration administration, or intratracheal administration. For example, in some embodiments, it is desired that the MUC5AC RNAi agents described herein inhibit the expression of an MUC5AC gene in the pulmonary epithelium, for which administration via inhalation (e.g., by an inhaler device, such as a metered-dose inhaler, or a nebulizer such as a jet or vibrating mesh nebulizer, or a soft mist inhaler) is particularly suitable and advantageous.

In some embodiments, the pharmaceutical compositions described herein comprise one or more pharmaceutically acceptable excipients. The pharmaceutical compositions described herein are formulated for administration to a subject.

As used herein, a pharmaceutical composition or medicament includes a pharmacologically effective amount of at least one of the described therapeutic compounds and one or more pharmaceutically acceptable excipients. Pharmaceutically acceptable excipients (excipients) are substances other than the Active Pharmaceutical Ingredient (API, therapeutic product, e.g., MUC5AC RNAi agent) that are intentionally included in the drug delivery system. Excipients do not exert or are not intended to exert a therapeutic effect at the intended dosage. Excipients can act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, detergents, dextran, dextrose, diluents, disintegrants, emulsifiers, extenders, fillers, flavors, glidants, humectants, lubricants, oils, polymers, preservatives, saline, salts, solvents, sugars, surfactants, suspending agents, sustained release matrices, sweeteners, thickening agents, tonicity agents, vehicles, water-repelling agents, and wetting agents.

Pharmaceutical compositions suitable for injectable use include sterile aqueous solutions (where water-soluble) or dispersions and sterile powders for the extemporaneous preparation of sterile injectable solutions or dispersion. For intravenous administration, suitable carriers include physiological saline, bacteriostatic water, Cremophor® ELTM (BASF, Parsippany, NJ) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

Formulations suitable for inhalation administration can be prepared by incorporating the active compound in the desired amount in an appropriate solvent, followed by sterile filtration. In general, formulations for inhalation administration are sterile solutions at physiological pH and have low viscosity (<5 cP). Salts may be added to the formulation to balance tonicity. In some cases, surfactants or co-solvents can be added to increase active compound solubility and improve aerosol characteristics. In some cases, excipients can be added to control viscosity in order to ensure size and distribution of nebulized droplets.

In some embodiments, pharmaceutical formulations that include the MUC5AC RNAi agents disclosed herein suitable for inhalation administration can be prepared in water for injection (sterile water), isotonic saline (0.9% saline), or an aqueous sodium phosphate buffer (for example, the MUC5AC RNAi agent formulated in 0.5 mM sodium phosphate monobasic, 0.5 mM sodium phosphate dibasic, in water).

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

The MUC5AC RNAi agents can be formulated in compositions in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the therapeutic effect to be achieved, and the limitations inherent in the art of compounding such an active compound for the treatment of individuals.

A pharmaceutical composition can contain other additional components commonly found in pharmaceutical compositions. Such additional components include, but are not limited to: anti-pruritics, astringents, local anesthetics, or anti-inflammatory agents (e.g., antihistamine, diphenhydramine, etc.). It is also envisioned that cells, tissues, or isolated organs that express or comprise the herein defined RNAi agents may be used as "pharmaceutical compositions." As used herein, "pharmacologically effective amount," "therapeutically effective amount," or simply "effective amount" refers to that amount of an RNAi agent to produce a pharmacological, therapeutic, or preventive result.

In some embodiments, the methods disclosed herein further comprise the step of administering a second therapeutic or treatment in addition to administering an RNAi agent disclosed herein. In some embodiments, the second therapeutic is another MUC5AC RNAi agent (e.g., a MUC5AC RNAi agent that targets a different sequence within the MUC5AC target). In other embodiments, the second therapeutic can be a small molecule drug, an antibody, an antibody fragment, and/or an aptamer.

In some embodiments, described herein are compositions that include a combination or cocktail of at least two MUC5AC RNAi agents having different sequences. In some embodiments, the two or more MUC5AC RNAi agents are each separately and independently linked to targeting groups. In some embodiments, the two or more MUC5AC RNAi agents are each linked to targeting groups that include or consist of integrin targeting ligands. In some embodiments, the two or more MUC5AC RNAi agents are each linked to targeting groups that include or consist of αvβ6 integrin targeting ligands.

Described herein are compositions for delivery of MUC5AC RNAi agents to pulmonary epithelial cells. Furthermore, compositions for delivery of MUC5AC RNAi agents to cells, including renal epithelial cells and/or epithelial cells in the GI or reproductive tract and/or and ocular surface epithelial cells in the eye, in vivo, are generally described herein.

Generally, an effective amount of a MUC5AC RNAi agent disclosed herein will be in the range of from about 0.0001 to about 20 mg/kg of body weight/pulmonary deposited dose (PDD), e.g., from about 0.001 to about 5 mg/kg of body weight/pulmonary deposited dose. In some embodiments, an effective amount of a MUC5AC RNAi agent will be in the range of from about 0.01 mg/kg to about 3.0 mg/kg of body weight per pulmonary deposited dose. In some embodiments, an effective amount of a MUC5AC RNAi agent will be in the range of from about 0.03 mg/kg to about 2.0 mg/kg of body weight per pulmonary deposited dose. In some embodiments, an effective amount of a MUC5AC RNAi agent will be in the range of from about 0.01 to about 1.0 mg/kg of pulmonary deposited dose per body weight. In some embodiments, an effective amount of a MUC5AC RNAi agent will be in the range of from about 0.25 to about 1.0 mg/kg of pulmonary deposited dose per body weight. In some embodiments, an effective amount of a MUC5AC RNAi agent will be in the range of from about 0.25 mg/kg of pulmonary deposited dose per body weight. In some embodiments, an effective amount of a MUC5AC RNAi agent will be in the range of from about 0.50 mg/kg of pulmonary deposited dose per body weight. In some embodiments, an effective amount of a MUC5AC RNAi agent will be in the range of from about 1.0 mg/kg of pulmonary deposited dose per body weight. Calculating the pulmonary deposited dose (PDD) is done in accordance with methods known in the art. (See Wolff R. K., Dorato M. A., Toxicologic Testing of Inhaled Pharmaceutical Aerosols, Crit Rev Toxicol., 1993; 23(4):343-369; Tepper et al., International J. Toxicology, 2016, vol. 35(4):376-392). A comparable and alternatively acceptable method of calculating dose that is well known in the art, especially for human subjects, is determining the respirable delivered dose (RDD). RDD refers to the amount of drug contained in droplets of a size suitable for penetration into the lungs. Generally, an effective amount of a MUC5AC RNAi agent disclosed herein will be in the range of from about 0.001 to about 5 mg respirable delivered dose (RDD)/kg body weight.

For clinical applications, the amount of MUC5AC RNAi agent needed to be loaded into the delivery device of choice (e.g., a nebulizer) that is required to produce such RDDs in human subjects will depend upon the delivery device used (see, for example, Hatley RHM, Byrne SM, Variability in delivered dose and respirable delivered dose from nebulizers: are current regulatory testing guidelines sufficient to produce meaningful information?, Med Devices, 2017, 10:17-28). Some lower efficient nebulizers, for example, RDD is approximately 15%-25% of the dose loaded into the nebulizer. For other more efficient devices, for example, RDD is approximately 50%, approximately 60%, or even higher than 60% of the dose loaded into the nebulizer. In some embodiments, a fixed dose of, for example, approximately 5 mg, approximately 10 gm, approximately 20 mg, approximately 25 mg, approximately 50 mg, approximately 75 mg, approximately 100 mg, approximately 150 mg, approximately 200 mg, approximately 250 mg, or approximately 300 mg of MUC5AC RNAi agent may be loaded into the respective device of choice, which will produce an RDD from about 0.001 to about 5 mg/kg of body weight per dose. The amount desired or required to be administered will also likely depend on such variables as the overall health status of the patient, the relative biological efficacy of the compound delivered, the formulation of the drug, the presence and types of excipient in the formulation, and the route of administration. Also, it is to be understood that the initial dosage administered can be increased beyond the above upper level to rapidly achieve the desired blood-level or tissue-level, or the initial dosage can be smaller than the optimum. In various embodiments, a dose may be administered daily, weekly, bi-weekly, tri-weekly, once monthly, once quarterly (i.e. once every three months), or once every six months. In various embodiments, a dose may be administered at other intervals contained within the range provided above.

For treatment of disease or for formation of a medicament or composition for treatment of a disease, the pharmaceutical compositions described herein including a MUC5AC RNAi agent can be combined with an excipient or with a second therapeutic agent or treatment including, but not limited to: a second or other RNAi agent, a small molecule drug, an antibody, an antibody fragment, peptide, and/or an aptamer.

The described MUC5AC RNAi agents, when added to pharmaceutically acceptable excipients or adjuvants, can be packaged into kits, containers, packs, or dispensers. The pharmaceutical compositions described herein can be packaged in dry powder or aerosol inhalers, other metered-dose inhalers, nebulizers, pre-filled syringes, or vials.

Methods of Treatment and Inhibition of MUC5AC Expression

The MUC5AC RNAi agents disclosed herein can be used to treat a subject (e.g., a human or other mammal) having a disease or disorder that would benefit from administration of the RNAi agent. In some embodiments, the RNAi agents disclosed herein can be used to treat a subject (e.g., a human) that would benefit from a reduction and/or inhibition in expression of MUC5AC mRNA and/or a reduction in MUC5AC receptor levels.

In some embodiments, the RNAi agents disclosed herein can be used to treat a subject (e.g., a human) having a disease or disorder for which the subject would benefit from reduction in MUC5AC receptors, including but not limited to, mucoobstructive lung diseases (such as asthma, CF, COPD, NCFB, PCD), allergic bronchopulmonary aspergillosis, interstitial lung diseases, cancer (such as lung adenocarcinomas, pancreatic cancer, salivary gland carcinoma, breast cancer, cholangiocarcinoma, ovarian cancer, and other tumors), respiratory infections (such as respiratory syncytial virus, influenza, rhinovirus), otitis media, inflammatory bowel disease, gallstone disease, allergic rhinitis, chronic rhinosinusitis and nasal polyposis. In some embodiments the pulmonary diseases is severe asthma. Treatment of a subject can include therapeutic and/or prophylactic treatment. The subject is administered a therapeutically effective amount of any one or more MUC5AC RNAi agents described herein. The subject can be a human, patient, or human patient. The subject may be an adult, adolescent, child, or infant. Administration of a pharmaceutical composition described herein can be to a human being or animal.

Increased membrane MUC5AC activity is known to promote mucoobstruction tissues. In some embodiments, the described MUC5AC RNAi agents are used to treat at least one symptom mediated at least in part by a reduction in MUC5AC levels, in a subject. The subject is administered a therapeutically effective amount of any one or more of the described MUC5AC RNAi agents. In some embodiments, the subject is administered a prophylactically effective amount of any one or more of the described RNAi agents, thereby treating the subject by preventing or inhibiting the at least one symptom.

In certain embodiments, the present disclosure provides methods for treatment of diseases, disorders, conditions, or pathological states mediated at least in part by MUC5AC gene expression, in a patient in need thereof, wherein the methods include administering to the patient any of the MUC5AC RNAi agents described herein.

In some embodiments, the MUC5AC RNAi agents are used to treat or manage a clinical presentation or pathological state in a subject, wherein the clinical presentation or pathological state is mediated at least in part by a reduction in MUC5AC expression. The subject is administered a therapeutically effective amount of one or more of the MUC5AC RNAi agents or MUC5AC RNAi agent-containing compositions described herein. In some embodiments, the method comprises administering a composition comprising a MUC5AC RNAi agent described herein to a subject to be treated.

In a further aspect, the disclosure features methods of treatment (including prophylactic or preventative treatment) of diseases or symptoms that may be addressed by a reduction in MUC5AC receptor levels, the methods comprising administering to a subject in need thereof a MUC5AC RNAi agent that includes an antisense strand comprising the sequence of any of the sequences in Table 2, Table 3, or Table 11. Also described herein are compositions for use in such methods.

The described MUC5AC RNAi agents and/or compositions that include MUC5AC RNAi agents can be used in methods for therapeutic treatment of disease or conditions caused by enhanced or elevated MUC5AC protein or MUC5AC gene expression. Such methods include administration of a MUC5AC RNAi agent as described herein to a subject, e.g., a human or animal subject.

In another aspect, the disclosure provides methods for the treatment (including prophylactic treatment) of a pathological state (such as a condition or disease) mediated at least in part by MUC5AC expression, wherein the methods include administering to a subject a therapeutically effective amount of an RNAi agent that includes an antisense strand comprising the sequence of any of the sequences in Table 2, Table 3, or Table 11.

In some embodiments, methods for inhibiting expression of an MUC5AC gene are disclosed herein, wherein the methods include administering to a cell an RNAi agent that includes an antisense strand comprising the sequence of any of the sequences in Table 2, Table 3, or Table 11.

In some embodiments, methods for the treatment (including prophylactic treatment) of a pathological state mediated at least in part by MUC5AC expression are disclosed herein, wherein the methods include administering to a subject a therapeutically effective amount of an RNAi agent that includes a sense strand comprising the sequence of any of the sequences in Table 2, Table 4, Table 5, Table 6, Table 7, or Table 11.

In some embodiments, methods for inhibiting expression of an MUC5AC gene are disclosed herein, wherein the methods comprise administering to a cell an RNAi agent that includes a sense strand comprising the sequence of any of the sequences in Table 2, Table 4, Table 5, Table 6, Table 7, or Table 11.

In some embodiments, methods for the treatment (including prophylactic treatment) of a pathological state mediated at least in part by MUC5AC expression are disclosed herein, wherein the methods include administering to a subject a therapeutically effective amount of an RNAi agent that includes a sense strand comprising the sequence of any of the sequences in Table 4, Table 5, Table 6, Table 7, or Table 11, and an antisense strand comprising the sequence of any of the sequences in Table 3 or Table 11.

In some embodiments, methods for inhibiting expression of a MUC5AC gene are disclosed herein, wherein the methods include administering to a cell an RNAi agent that includes a sense strand comprising the sequence of any of the sequences in Table 4, Table 5, Table 6, Table 7, or Table 11, and an antisense strand comprising the sequence of any of the sequences in Table 3 or Table 11.

In some embodiments, methods of inhibiting expression of a MUC5AC gene are disclosed herein, wherein the methods include administering to a subject a MUC5AC RNAi agent that includes a sense strand consisting of the nucleobase sequence of any of the sequences in Table 4, Table 5, Table 6, Table 7, or Table 11, and the antisense strand consisting of the nucleobase sequence of any of the sequences in Table 3 or Table 11. In other embodiments, disclosed herein are methods of inhibiting expression of a MUC5AC gene, wherein the methods include administering to a subject a MUC5AC RNAi agent that includes a sense strand consisting of the modified sequence of any of the modified sequences in Table 4, Table 5, Table 6, Table 7, or Table 11, and the antisense strand consisting of the modified sequence of any of the modified sequences in Table 3 or Table 11.

In some embodiments, methods for inhibiting expression of an MUC5AC gene in a cell are disclosed herein, wherein the methods include administering one or more MUC5AC RNAi agents comprising a duplex structure of one of the duplexes set forth in Tables 8A, 8B, 8C, 9, 10A, 10B, and 11.

In some embodiments, the quantity or amount of MUC5AC protein and/or MUC5AC mRNA in certain pulmonary epithelial cells of subject to whom a described MUC5AC RNAi agent is administered is reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater than 99%, relative to the subject prior to being administered the MUC5AC RNAi agent or to a subject not receiving the MUC5AC RNAi agent. In some embodiments, MUC5AC protein levels in certain epithelial cells of a subject to whom a described MUC5AC RNAi agent is administered is reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater than 99%, relative to the subject prior to being administered the MUC5AC RNAi agent or to a subject not receiving the MUC5AC RNAi agent. The gene expression level, protein level, and/or mRNA level in the subject may be reduced in a cell, group of cells, and/or tissue of the subject. In some embodiments, the MUC5AC mRNA levels in certain epithelial cells subject to whom a described MUC5AC RNAi agent has been administered is reduced by at least about 30%, 35%, 40%, 45%, 50%, 55%, 60%, 65%, 70%, 75%, 80%, 85%, 90%, 95%, or 98% relative to the subject prior to being administered the MUC5AC RNAi agent or to a subject not receiving the MUC5AC RNAi agent.

A reduction in MUC5AC mRNA and MUC5AC protein levels can be assessed by any methods known in the art. Reduction or decrease in MUC5AC mRNA and/or MUC5AC protein levels are collectively referred to herein as a decrease in, reduction of, or inhibition of MUC5AC gene expression. The Examples set forth herein illustrate known methods for assessing inhibition of MUC5AC.

Cells, Tissues, Organs, and Non-Human Organisms

Cells, tissues, organs, and non-human organisms that include at least one of the MUC5AC RNAi agents described herein are contemplated. The cell, tissue, organ, or non-human organism is made by delivering the RNAi agent to the cell, tissue, organ, or non-human organism.

Additional Illustrative Embodiments

Provided here are certain additional illustrative embodiments of the disclosed technology. These embodiments are illustrative only and do not limit the scope of the present disclosure or of the claims attached hereto.

Embodiment 1. An RNAi agent for inhibiting expression of a Mucin 5AC gene, comprising: an antisense strand comprising at least 17 contiguous nucleotides differing by 0 or 1 nucleotides from any one of the sequences provided in Table 2 or Table 3; and a sense strand comprising a nucleotide sequence that is at least partially complementary to the antisense strand Embodiment 2. The RNAi agent of Embodiment 1, wherein the antisense strand comprises nucleotides 2-18 of any one of the sequences provided in Table 2 or Table 3.

Embodiment 3. The RNAi agent of Embodiment 1 or Embodiment 2, wherein the sense strand comprises a nucleotide sequence of at least 17 contiguous nucleotides differing by 0 or 1 nucleotides from any one of the sequences provided in Table 2 or Table 4, and wherein the sense strand has a region of at least 85% complementarity over the 17 contiguous nucleotides to the antisense strand.

Embodiment 4. The RNAi agent of any one of Embodiments 1-3, wherein at least one nucleotide of the RNAi agent is a modified nucleotide or includes a modified internucleoside linkage.

Embodiment 5. The RNAi agent of any one of Embodiments 1-4, wherein all or substantially all of the nucleotides are modified nucleotides.

Embodiment 6. The RNAi agent of any one of Embodiments 4-5, wherein the modified nucleotide is selected from the group consisting of: 2'-O-methyl nucleotide, 2'-fluoro nucleotide, 2'-deoxy nucleotide, 2',3'-seco nucleotide mimic, locked nucleotide, 2'-F-arabino nucleotide, 2'-methoxyethyl nucleotide, abasic nucleotide, ribitol, inverted nucleotide, inverted 2'-O-methyl nucleotide, inverted 2'-deoxy nucleotide, 2'-amino-modified nucleotide, 2'-alkyl-modified nucleotide, morpholino nucleotide, vinyl phosphonate-containing nucleotide, cyclopropyl phosphonate-containing nucleotide, and 3'-O-methyl nucleotide.

Embodiment 7. The RNAi agent of Embodiment 5, wherein all or substantially all of the nucleotides are modified with 2'-O-methyl nucleotides, 2'-fluoro nucleotides, or combinations thereof.

Embodiment 8. The RNAi agent of any one of Embodiments 1-7, wherein the antisense strand comprises the nucleotide sequence of any one of the modified antisense strand sequences provided in Table 3 or Table 11.

Embodiment 9. The RNAi agent of any one of Embodiments 1-8, wherein the sense strand comprises the nucleotide sequence of any one of the modified sense strand sequences provided in Table 4 or Table 11.

Embodiment 10. The RNAi agent of Embodiment 1, wherein the antisense strand comprises the nucleotide sequence of any one of the modified antisense strand sequences provided in Table 3 or Table 11, and the sense strand comprises the nucleotide sequence of any one of the modified sense strand sequences provided in Table 4 or Table 11.

Embodiment 11. The RNAi agent of any one of Embodiments 1-10, wherein the sense strand is between 18 and 30 nucleotides in length, and the antisense strand is between 18 and 30 nucleotides in length.

Embodiment 12. The RNAi agent of Embodiment 11, wherein the sense strand and the antisense strand are each between 18 and 27 nucleotides in length.

Embodiment 13. The RNAi agent of Embodiment 12, wherein the sense strand and the antisense strand are each between 18 and 24 nucleotides in length.

Embodiment 14. The RNAi agent of Embodiment 13, wherein the sense strand and the antisense strand are each 21 nucleotides in length.

Embodiment 15. The RNAi agent of Embodiment 14, wherein the RNAi agent has two blunt ends.

Embodiment 16. The RNAi agent of any one of Embodiments 1-15, wherein the sense strand comprises one or two terminal caps.

Embodiment 17. The RNAi agent of any one of Embodiments 1-16, wherein the sense strand comprises one or two inverted abasic residues.

Embodiment 18. The RNAi agent of Embodiment 1, wherein the RNAi agent is comprised of a sense strand and an antisense strand that form a duplex having the structure of any one of the duplexes in Table 8A, Table 8B, Table 8C, Table 9, Table 10A, or Table 10B.

Embodiment 19. The RNAi agent of Embodiment 18, wherein all or substantially all of the nucleotides are modified nucleotides.

Embodiment 20. The RNAi agent of Embodiment 1, wherein the antisense strand consists of, consists essentially of, or comprises a nucleotide sequence that differs by 0 or 1 nucleotides from one of the following nucleotide sequences (5'→3'):

(SEQ ID NO: 79)
UUGUAGUAGUCGCAGAACA;
or (SEQ ID NO: 83)
UUCUUGUUCAGGCAAAUCA.

Embodiment 21. The RNAi agent of Embodiment 1, wherein the antisense strand consists of, consists essentially of, or comprises a nucleotide sequence that differs by 0 or 1 nucleotides from one of the following nucleotide sequences (5'→3'):

(SEQ ID NO: 1525)
UUGUAGUAGUCGCAGAACAGC;
or (SEQ ID NO: 1535)
UUCUUGUUCAGGCAAAUCAGC.

Embodiment 22. The RNAi agent of Embodiment 1, wherein the sense strand consists of, consists essentially of, or comprises a nucleotide sequence that differs by 0 or 1 nucleotides from one of the following nucleotide sequences (5'→3'):

(SEQ ID NO: 568)
UGUUCUGCGACUACUACAA;
or (SEQ ID NO: 572)
UGAUUUGCCUGAACAAGAA.

Embodiment 23. The RNAi agent of Embodiment 20, 21, or 22, wherein all or substantially all of the nucleotides are modified nucleotides Embodiment 24. The RNAi agent of Embodiment 1, wherein the antisense strand comprises, consists of, or consists essentially of a modified nucleotide sequence that differs by 0 or 1 nucleotides from one of the following nucleotide sequences (5'→3'):

(SEQ ID NO: 1127)
cPrpusUfsgsUfaGfuAfgUfcGfcAfgAfaCfaGfsc;

(SEQ ID NO: 1065)
usUfsgsUfaGfuAfgUfcGfcAfgAfaCfaGfsc;

(SEQ ID NO: 1166)
usUfscsuuguucagGfcAfaAfucagsc;
or (SEQ ID NO: 1191)
cPrpuUfcuuguucagGfcAfaAfucagsc;

wherein a, c, g, and u represent 2'-O-methyl adenosine, 2'-O-methyl cytidine, 2'-O-methyl guanosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; cPrpu represents a 5'-cyclopropyl phosphonate-2'-O-methyl uridine; s represents a phosphorothioate linkage; and wherein all or substantially all of the nucleotides on the sense strand are modified nucleotides.

Embodiment 25. The RNAi agent of Embodiment 1, wherein the sense strand comprises, consists of, or consists essentially of a modified nucleotide sequence that differs by 0 or 1 nucleotides from one of the following nucleotide sequences (5'→3'):

(SEQ ID NO: 1265)
gscuguucuGfCfGfacuacuacaa;
or (SEQ ID NO: 1315)
gscugauUfuGfcCfugaacaagaa;

wherein a, c, g, and u represent 2'-O-methyl adenosine, 2'-O-methyl cytidine, 2'-O-methyl guanosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; and s represents a phosphorothioate linkage; and wherein all or substantially all of the nucleotides on the antisense strand are modified nucleotides.

Embodiment 26. The RNAi agent of any one of Embodiments 20-25, wherein the sense strand further includes inverted abasic residues at the 3' terminal end of the nucleotide sequence, at the 5' end of the nucleotide sequence, or at both.

Embodiment 27. The RNAi agent of any one of Embodiments 1-26, wherein the RNAi agent is linked to a targeting ligand.

Embodiment 28. The RNAi agent of Embodiment 27, wherein the targeting ligand has affinity for a cell receptor expressed on an epithelial cell.

Embodiment 29. The RNAi agent of Embodiment 28, wherein the targeting ligand comprises an integrin targeting ligand.

Embodiment 30. The RNAi agent of Embodiment 29, wherein the integrin targeting ligand is an αvβ6 integrin targeting ligand.

Embodiment 31. The RNAi agent of Embodiment 30, wherein the targeting ligand comprises the structure:

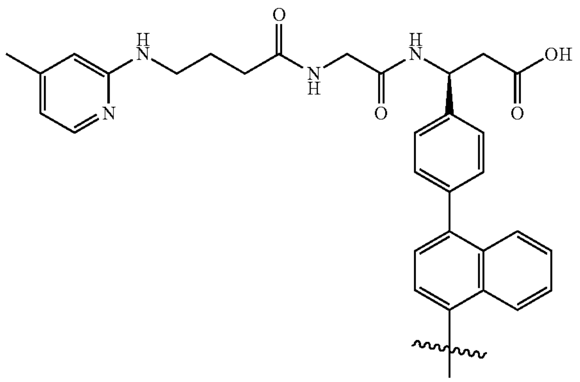 [SMILES: *c1ccc(-c2ccc([C@H](CC(=O)O)NC(=O)CNC(=O)CCCNc3cc(C)ccn3)cc2)c2ccccc12]

or a pharmaceutically acceptable salt thereof, or

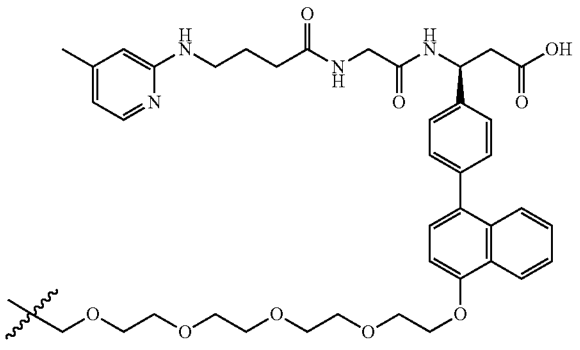 [SMILES: *COCCOCCOCCOCCOc1ccc(-c2ccc([C@H](CC(=O)O)NC(=O)CNC(=O)CCCNc3cc(C)ccn3)cc2)c2ccccc12]

or a pharmaceutically acceptable salt thereof, wherein ⌇ indicates the point of connection to the RNAi agent.

Embodiment 32. The RNAi agent of any one of Embodiments 27-30, wherein RNAi agent is conjugated to a targeting ligand having the following structure:

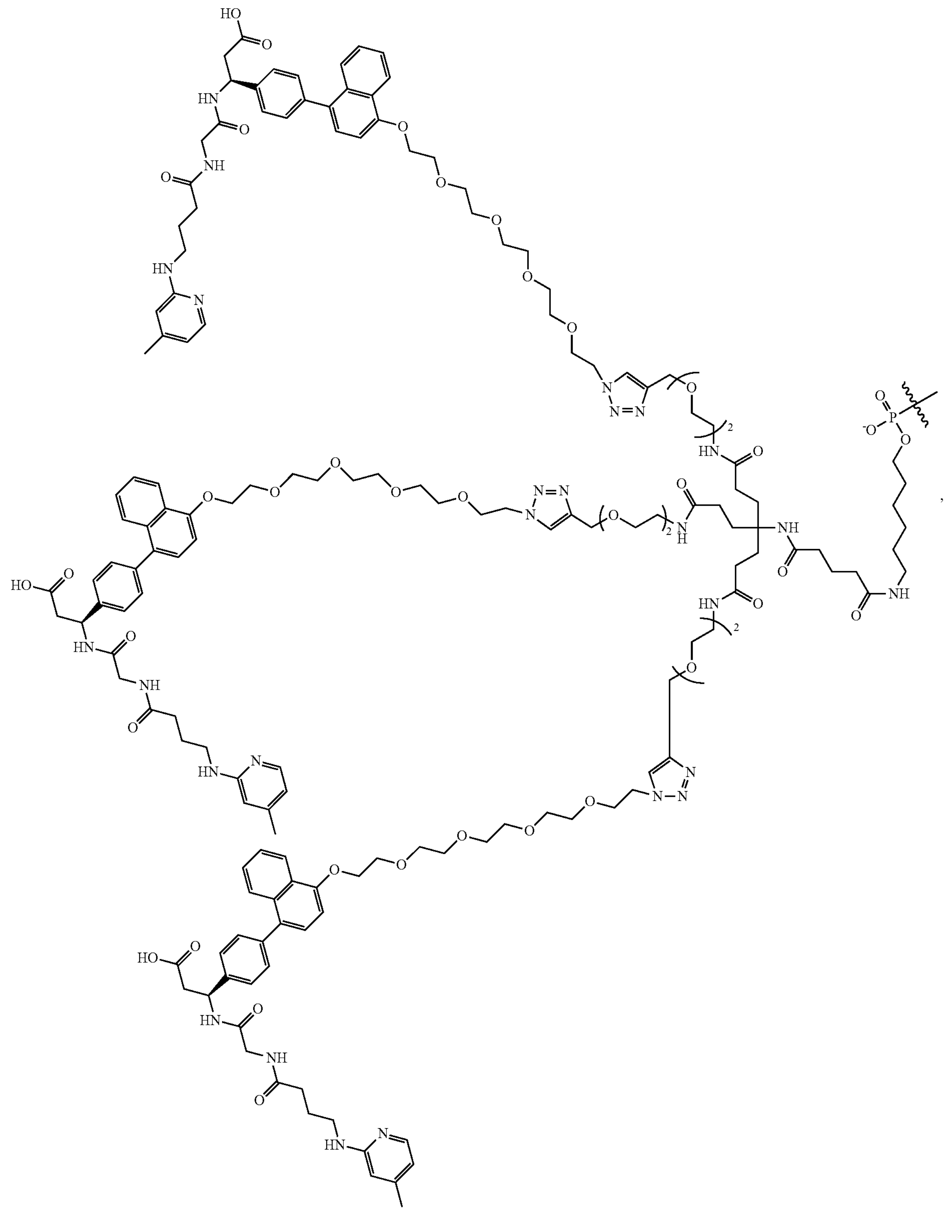
,
or a pharmaceutically acceptable salt thereof, wherein indicates the point of connection to the RNAi agent.

Embodiment 33. The RNAi agent of any one of Embodiments 27-30, wherein the targeting ligand has the following structure:

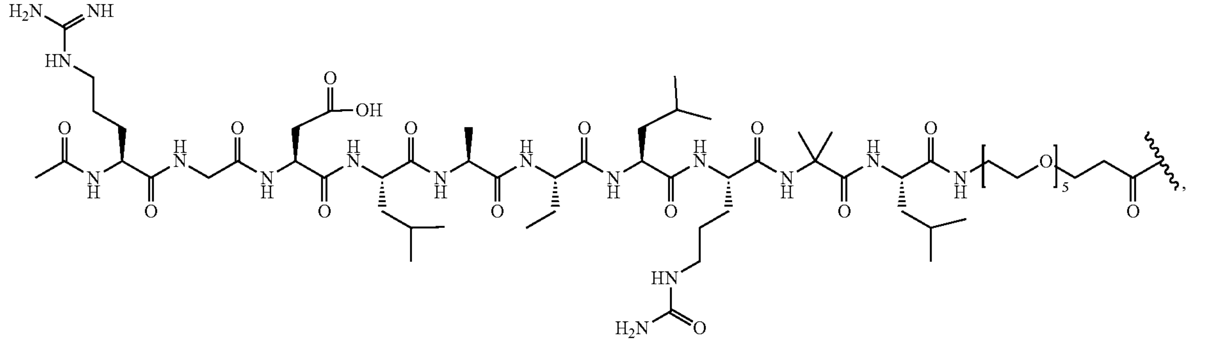

or a pharmaceutically acceptable salt thereof, wherein ⌇ indicates the point of connection to the RNAi agent.

Embodiment 34. The RNAi agent of any one of Embodiments 27-33, wherein the targeting ligand is conjugated to the sense strand.

Embodiment 35. The RNAi agent of Embodiment 34, wherein the targeting ligand is conjugated to the 5' terminal end of the sense strand.

Embodiment 36. A composition comprising the RNAi agent of any one of Embodiments 1-35, wherein the composition further comprises a pharmaceutically acceptable excipient.

Embodiment 37. The composition of Embodiment 36, further comprising a second RNAi agent capable of inhibiting the expression of Mucin 5AC gene expression.

Embodiment 38. The composition of any one of Embodiments 36-37, further comprising one or more additional therapeutics.

Embodiment 39. The composition of any one of Embodiments 36-38, wherein the composition is formulated for administration by inhalation.

Embodiment 40. The composition of Embodiment 39, wherein the composition is delivered by a metered-dose inhaler, jet nebulizer, vibrating mesh nebulizer, or soft mist inhaler.

Embodiment 41. The composition of any of Embodiments 36-40, wherein the RNAi agent is a sodium salt.

Embodiment 42. The composition of any of Embodiments 36-41, wherein the pharmaceutically acceptable excipient is water for injection.

Embodiment 43. The composition of any of Embodiments 36-42, wherein the pharmaceutically acceptable excipient is isotonic saline.

Embodiment 44. A method for inhibiting expression of a MUC5AC gene in a cell, the method comprising introducing into a cell an effective amount of an RNAi agent of any one of Embodiments 1-35 or the composition of any one of Embodiments 36-43.

Embodiment 45. The method of Embodiment 44, wherein the cell is within a subject.

Embodiment 46. The method of Embodiment 45, wherein the subject is a human subject.

Embodiment 47. The method of any one of claims 44-46, wherein following the administration of the RNAi agent the Mucin 5AC gene expression is inhibited by at least about 30%.

Embodiment 48. A method of treating one or more symptoms or diseases associated with MUC5AC protein levels, the method comprising administering to a human subject in need thereof a therapeutically effective amount of the composition of any one of Embodiments 36-43.

Embodiment 49. The method of Embodiment 48, wherein the disease is a mucoobstructive lung disease.

Embodiment 50. The method of Embodiment 49, wherein the mucoobstructive lung disease is asthma (including severe asthma), cystic fibrosis (CF), bronchiectasis (NCFB), or chronic obstructive pulmonary disease (COPD).

Embodiment 51. The method of Embodiment 50, wherein the disease is asthma (including severe asthma).

Embodiment 52. The method of Embodiment 48, wherein the disease is cancer.

Embodiment 53. The method of Embodiment 52, wherein the cancer is lung adenocarcinoma, pancreatic cancer, salivary gland carcinoma, breast cancer, cholangiocarcinoma, or ovarian cancer.

Embodiment 54. The method of any one of Embodiments 44-53, wherein the RNAi agent is administered at a pulmonary deposited dose (PDD) of about 0.01 mg/kg to about 5.0 mg/kg of body weight of the subject.

Embodiment 55. The method of any one of Embodiments 44-53, wherein the RNAi agent is administered at a pulmonary deposited dose (PDD) of about 0.1 mg/kg to about 2.0 mg/kg of body weight of the subject.

Embodiment 56. The method of any one of Embodiments 44-53, wherein the RNAi agent is administered at a respirable delivered dose (RDD) of about 0.01 mg/kg to about 5.0 mg/kg of body weight of the subject.

Embodiment 57. The method of any one of Embodiments 44-53, wherein the RNAi agent is administered at a respirable delivered dose (RDD) of about 0.1 mg/kg to about 2.0 mg/kg of body weight of the subject.

Embodiment 58. The method of any of Embodiments 44-57, wherein the RNAi agent is administered in two or more doses.

Embodiment 59. Use of the RNAi agent of any one of Embodiments 1-35, for the treatment of a disease, disorder, or symptom that is mediated at least in part by Mucin 5AC protein levels.

Embodiment 60. Use of the composition according to any one of Embodiments 36-43, for the treatment of a disease, disorder, or symptom that is mediated at least in part by Mucin 5AC gene expression.

Embodiment 61. Use of the composition according to any one of Embodiments 36-43, for the manufacture of a medicament for treatment of a disease, disorder, or symptom that is mediated at least in part by Mucin 5AC gene expression.

Embodiment 62. The use of any one of Embodiments 59-61, wherein the disease is asthma (including severe asthma).

Embodiment 63. A method of making an RNAi agent of any one of Embodiments 1-35, comprising annealing a sense strand and an antisense strand to form a double-stranded ribonucleic acid molecule.

Embodiment 64. The method of Embodiment 63, wherein the sense strand comprises a targeting ligand.

Embodiment 65. The method of Embodiment 64, comprising conjugating a targeting ligand to the sense strand.

Embodiment 66. An RNAi agent for inhibiting expression of a Mucin 5AC gene, comprising:

an antisense strand comprising at least 15 contiguous nucleotides differing by 0, 1, 2, or 3 nucleotides from any one of the sequences provided in Table 2, Table 3, or Table 11; and a sense strand comprising a nucleotide sequence that is at least partially complementary to the antisense strand.

Embodiment 67. An RNAi agent for inhibiting expression of a Mucin 5AC (MUC5AC) gene, comprising:

an antisense strand comprising at least 15 contiguous nucleotides differing by 0, 1, 2, or 3 nucleotides from any one of the sequences disclosed in Table 2 or Table 3; and a sense strand comprising a nucleotide sequence that is at least partially complementary to the antisense strand.

Embodiment 68. An RNAi agent for inhibiting expression of a Mucin 5AC (MUC5AC) gene, comprising:

a sense strand comprising at least 15 contiguous nucleotides differing by 0, 1, 2, or 3 nucleotides from a stretch of the same length of nucleotides of SEQ ID NO:1; and an antisense strand comprising a nucleotide sequence that is at least partially complementary to the sense strand.

Embodiment 69. An inhibitor of a MUC5AC gene comprising an antisense nucleotide sequence having at least 15 contiguous nucleotides differing by 0, 1, 2, or 3 nucleotides that are complementary to any of the target nucleotide sequences in Table 1.

Embodiment 70. An RNAi agent comprising (i) an antisense strand comprising a nucleotide sequence having at least 15 contiguous nucleotides differing by 0, 1, 2, or 3 nucleotides from any of the nucleotide sequences in Table 2, Table 3 or Table 11, and (ii) a sense strand at least partially complementary to the antisense strand.

Embodiment 71. An RNAi agent comprising (i) an antisense strand comprising, consisting of, or consisting essentially of a nucleotide sequence from any of the antisense strand nucleotide sequences in Table 2, Table 3 or Table 11, and (ii) a sense strand comprising, consisting of, or consisting essentially of a nucleotide sequence from any of the sense strand nucleotide sequences in Table 2, Table 4, Table 5, Table 6, Table 7, or Table 11.

Embodiment 72. An RNAi agent comprising an antisense strand and sense strand annealed to form a duplex, wherein the duplex has the structure of any of the duplexes set forth in Table 8A, Table 8B, Table 8C, Table 9, Table 10, or Table 11.

Embodiment 73. An RNAi agent for inhibiting expression of a Mucin 5AC gene, comprising:

an antisense strand comprising at least 17 contiguous nucleotides differing by 0 or 1 nucleotides from any one of the sequences provided in Table 2 or Table 3; and a sense strand comprising a nucleotide sequence that is at least partially complementary to the antisense strand, wherein optionally all or substantially all of the nucleotides of the sense strand and the antisense strand modified nucleotides, and wherein the sense strand is optionally linked to a targeting ligand.

The above provided embodiments and items are now illustrated with the following, non-limiting examples.

EXAMPLES

Example 1. Synthesis of MUC5AC RNAi Agents

MUC5AC RNAi agent duplexes disclosed herein were synthesized in accordance with the following:

A. Synthesis. The sense and antisense strands of the MUC5AC RNAi agents were synthesized according to phosphoramidite technology on solid phase used in oligonucleotide synthesis. Depending on the scale, a MerMade96E® (Bioautomation), a MerMade12® (Bioautomation), or an OP Pilot 100 (GE Healthcare) was used. Syntheses were performed on a solid support made of controlled pore glass (CPG, 500 Å or 600 Å, obtained from Prime Synthesis, Aston, PA, USA). All RNA and 2'-modified RNA phosphoramidites were purchased from Thermo Fisher Scientific (Milwaukee, WI, USA). Specifically, the 2'-O-methyl phosphoramidites that were used included the following: (5'-O-dimethoxytrityl-$N^6$-(benzoyl)-2'-O-methyl-adenosine-3'-O-(2-cyanoethyl-N,N-diisopropylamino) phosphoramidite, 5'-O-dimethoxy-trityl-$N^4$-(acetyl)-2'-O-methyl-cytidine-3'-O-(2-cyanoethyl-N,N-diisopropyl-amino) phosphoramidite, (5'-O-dimethoxytrityl-$N^2$-(isobutyryl)-2'-O-methyl-guanosine-3'-O-(2-cyanoethyl-N,N-diisopropylamino) phosphoramidite, and 5'-O-dimethoxytrityl-2'-O-methyl-uridine-3'-O-(2-cyanoethyl-N,N-diisopropylamino) phosphoramidite. The 2'-deoxy-2'-fluoro-phosphoramidites carried the same protecting groups as the 2'-O-methyl RNA amidites. 5'-dimethoxytrityl-2'-O-methyl-inosine-3'-O-(2-cyanoethyl-N,N-diisopropylamino) phosphoramidites were purchased from Glen Research (Virginia). The inverted abasic (3'-O-dimethoxytrityl-2'-deoxy-ribose-5'-O-(2-cyanoethyl-N,N-diisopropylamino) phosphoramidites were purchased from ChemGenes (Wilmington, MA, USA). The following UNA phosphoramidites were used: 5'-(4,4'-Dimethoxytrityl)-N6-(benzoyl)-2',3'-seco-adenosine, 2'-benzoyl-3'-[(2-cyanoethyl)-(N,N-diisopropyl)]-phosphoramidite, 5'-(4,4'-Dimethoxytrityl)-N-acetyl-2',3'-seco-cytosine, 2'-benzoyl-3'-[(2-cyanoethyl)-(N,N-diisopropyl)]-phosphoramidite, 5'-(4,4'-Dimethoxytrityl)-N-isobutyryl-2',3'-seco-guanosine, 2'-benzoyl-3'-[(2-cyanoethyl)-(N,N-diisopropyl)]-phosphoramidite, and 5'-(4,4'-Dimethoxy-trityl)-2',3'-seco-uridine, 2'-benzoyl-3'-[(2-cyanoethyl)-(N,N-diisopropyl)]-phosphoramidite. TFA aminolink phosphoramidites were also commercially purchased (ThermoFisher). Linker L6 was purchased as propargyl-PEG5-NHS from BroadPharm (catalog #BP-20907) and coupled to the $NH_2$-$C_6$ group from an aminolink phosphoramidite to form -L6-C6-, using standard coupling conditions. The linker Alk-cyHex was similarly commercially purchased from Lumiprobe (alkyne phosphoramidite, 5'-terminal) as a propargyl-containing compound phosphoramidite compound to form the linker -Alk-cyHex-. In each case, phosphorothioate linkages were introduced as specified using the conditions set forth herein. The cyclopropyl phosphonate phosphoramidites were synthesized in accordance with International Patent Application Publication No. WO 2017/214112 (see also Altenhofer et. al., Chem. Communications (Royal Soc. Chem.), 57(55):6808-6811 (2021)).

Tri-alkyne-containing phosphoramidites were dissolved in anhydrous dichloromethane or anhydrous acetonitrile (50 mM), while all other amidites were dissolved in anhydrous acetonitrile (50 mM) and molecular sieves (3 Å) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 10 minutes (RNA), 90 seconds (2' O-Me), and 60 seconds (2' F). In order to introduce phosphorothioate linkages, a 100 mM solution of 3-phenyl 1,2,4-dithiazoline-5-one (POS, obtained from PolyOrg, Inc., Leominster, MA, USA) in anhydrous acetonitrile was employed.

Alternatively, tri-alkyne moieties were introduced post-synthetically (see section E, below). For this route, the sense strand was functionalized with a 5' and/or 3' terminal nucleotide containing a primary amine. TFA aminolink phosphoramidite was dissolved in anhydrous acetonitrile (50 mM) and molecular sieves (3 Å) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 10 minutes (RNA), 90 seconds (2' O-Me), and 60 seconds (2' F). In order to introduce phosphorothioate linkages, a 100 mM solution of 3-phenyl 1,2,4-dithiazoline-5-one (POS, obtained from PolyOrg, Inc., Leominster, MA, USA) in anhydrous acetonitrile was employed.

B. Cleavage and deprotection of support bound oligomer. After finalization of the solid phase synthesis, the dried solid support was treated with a 1:1 volume solution of 40 wt. % methylamine in water and 28% to 31% ammonium hydroxide solution (Aldrich) for 1.5 hours at 30° C. The solution was evaporated and the solid residue was reconstituted in water (see below).

C. Purification. Crude oligomers were purified by anionic exchange HPLC using a TSKgel SuperQ-5PW 13 μm column and Shimadzu LC-8 system. Buffer A was 20 mM Tris, 5 mM EDTA, pH 9.0 and contained 20% Acetonitrile and buffer B was the same as buffer A with the addition of 1.5 M sodium chloride. UV traces at 260 nm were recorded. Appropriate fractions were pooled then run on size exclusion HPLC using a GE Healthcare XK 16/40 column packed with Sephadex G-25 fine with a running buffer of 100 mM ammonium bicarbonate, pH 6.7 and 20% Acetonitrile or filtered water. Alternatively, pooled fractions were desalted and exchanged into an appropriate buffer or solvent system via tangential flow filtration.

D. Annealing. Complementary strands were mixed by combining equimolar RNA solutions (sense and antisense) in 1×PBS (Phosphate-Buffered Saline, 1×, Corning, Cellgro) to form the RNAi agents. Some RNAi agents were lyophilized and stored at −15 to −25° C. Duplex concentration was determined by measuring the solution absorbance on a UV-Vis spectrometer in 1×PBS. The solution absorbance at 260 nm was then multiplied by a conversion factor (0.050 mg/(mL·cm)) and the dilution factor to determine the duplex concentration.

E. Conjugation of Tri-alkyne linker. In some embodiments a tri-alkyne linker is conjugated to the sense strand of the RNAi agent on resin as a phosphoramidite (see Example 1G for the synthesis of an example tri-alkyne linker phosphoramidite and Example 1A for the conjugation of the phosphoramidite.). In other embodiments, a tri-alkyne linker may be conjugated to the sense strand following cleavage from the resin, described as follows: either prior to or after annealing, in some embodiments, the 5' or 3' amine functionalized sense strand is conjugated to a tri-alkyne linker. An example tri-alkyne linker structure that can be used in forming the constructs disclosed herein is as follows:

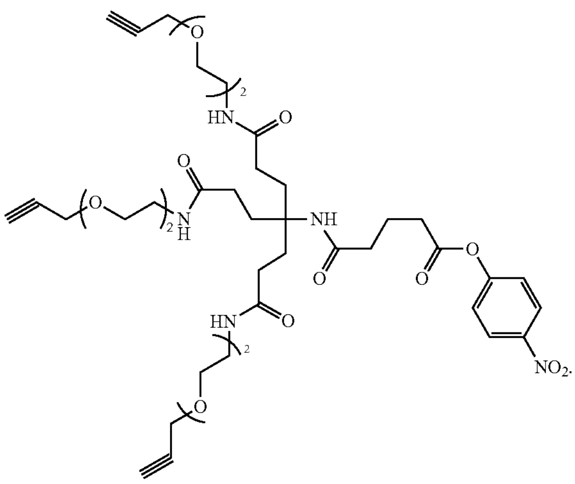

To conjugate the tri-alkyne linker to the annealed duplex, amine-functionalized duplex was dissolved in 90% DMSO/10% $H_2O$, at ~50-70 mg/mL. 40 equivalents triethylamine was added, followed by 3 equivalents tri-alkyne-PNP. Once complete, the conjugate was precipitated twice in a solvent system of 1×phosphate buffered saline/acetonitrile (1:14 ratio), and dried.

F. Synthesis of Targeting Ligand SM6.1

((S)-3-(4-(4-((14-azido-3,6,9,12-tetraoxatetradecyl)oxy)naphthalen-1-yl)phenyl)-3-(2-(4-((4-methylpyridin-2-yl)amino)butanamido)acetamido)propanoic acid)

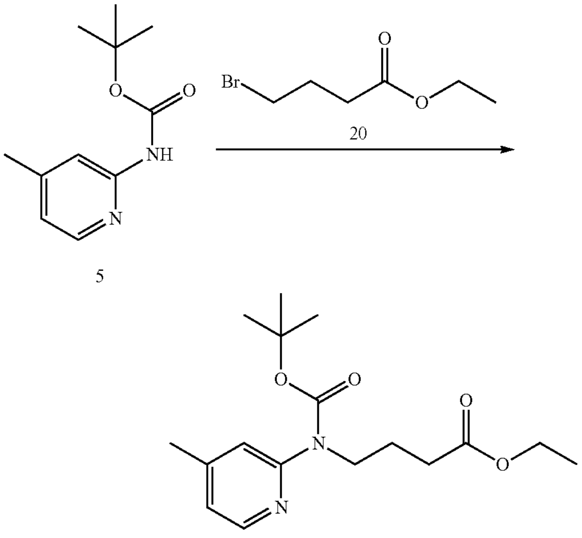

5

20

21

Compound 5 (tert-Butyl(4-methylpyridin-2-yl)carbamate) (0.501 g, 2.406 mmol, 1 equiv.) was dissolved in DMF (17 mL). To the mixture was added NaH (0.116 mg, 3.01 mmol, 1.25 eq, 60% dispersion in oil) The mixture stirred for 10 min before adding Compound 20 (Ethyl 4-Bromobutyrate (0.745 g, 3.82 mmol, 0.547 mL)) (Sigma 167118). After 3 hours the reaction was quenched with ethanol (18 mL) and concentrated. The concentrate was dissolved in DCM (50 mL) and washed with saturated aq. NaCl solution (1×50 mL), dried over $Na_2SO_4$, filtered and concentrated. The product was purified on silica column, gradient 0-5% Methanol in DCM.

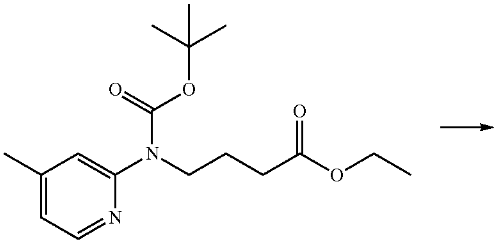

21

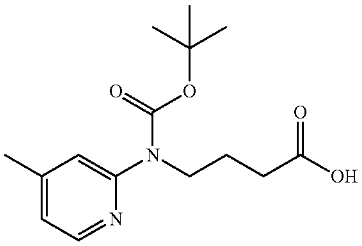

22

Compound 21 was dissolved (0.80 g, 2.378 mmol) in 100 mL of Acetone: 0.1 M NaOH [1:1]. The reaction was monitored by TLC (5% ethyl acetate in hexane). The organics were concentrated away, and the residue was acidified to pH 3-4 with 0.3 M Citric Acid (40 mL). The product was extracted with DCM (3×75 mL). The organics were pooled, dried over $Na_2SO_4$, filtered and concentrated. The product was used without further purification.

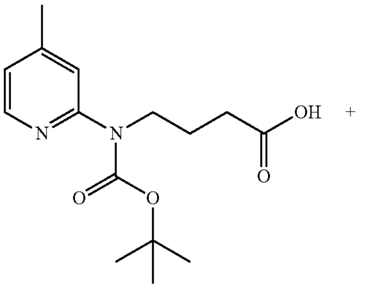

22

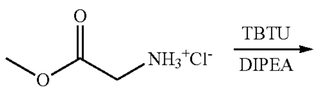

45

-continued

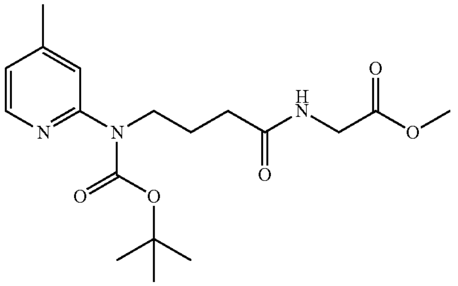

60

To a solution of Compound 22 (1.1 g, 3.95 mmol, 1 equiv.), Compound 45 (595 mg, 4.74 mmol, 1.2 equiv.), and TBTU (1.52 g, 4.74 mmol, 1.2 equiv.) in anhydrous DMF (10 mL) was added diisopropylethylamine (2.06 mL, 11.85 mmol, 3 equiv.) at 0° C. The reaction mixture was warmed to room temperature and stirred 3 hours. The reaction was quenched by saturated $NaHCO_3$ solution (10 mL). The aqueous phase was extracted with ethyl acetate (3×10 mL) and the organic phase was combined, dried over anhydrous $Na_2SO_4$, and concentrated. The product was separated by CombiFlash® using silica gel as the stationary phase. LC-MS: calculated [M+H]+ 366.20, found 367.

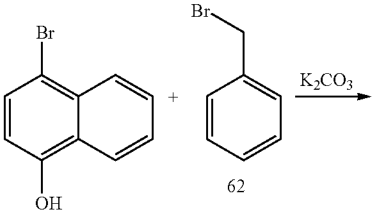

61

62

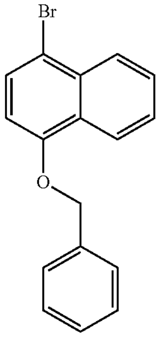

63

To a solution of compound 61 (2 g, 8.96 mmol, 1 equiv.), and compound 62 (2.13 mL, 17.93 mmol, 2 equiv.) in anhydrous DMF (10 mL) was added $K_2CO_3$ (2.48 g, 17.93 mmol, 2 equiv.) at 0° C. The reaction mixture was warmed to room temperature and stirred overnight. The reaction was quenched by water (10 mL). The aqueous phase was extracted with ethyl acetate (3×10 mL) and the organic phase was combined, dried over anhydrous $Na_2SO_4$, and concentrated. The product was separated by CombiFlash® using silica gel as the stationary phase.

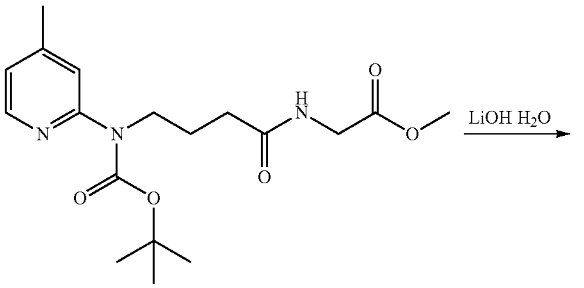

60

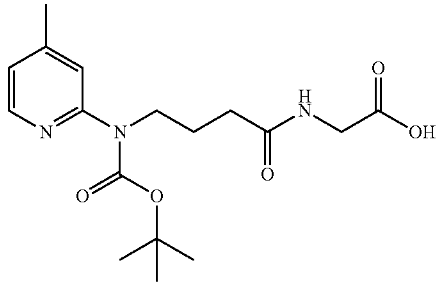

64

To a solution of compound 60 (1.77 g, 4.84 mmol, 1 equiv.) in THF (5 mL) and $H_2O$ (5 mL) was added lithium hydroxide monohydrate (0.61 g, 14.53 mmol, 3 equiv.) portion-wise at 0° C. The reaction mixture was warmed to room temperature. After stirring at room temperature for 3 hours, the reaction mixture was acidified by HCl (6 N) to pH 3.0. The aqueous phase was extracted with ethyl acetate (3×20 mL) and the organic layer was combined, dried over $Na_2SO_4$, and concentrated. LC-MS: calculated [M+H]+ 352.18, found 352.

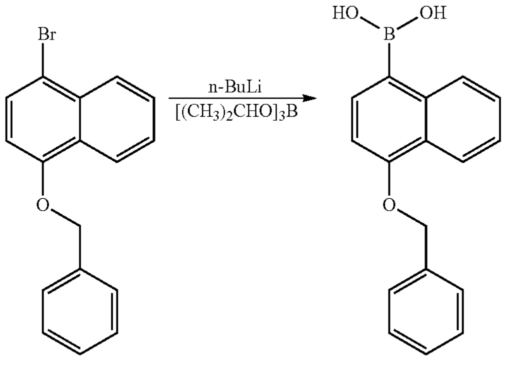

63 65

To a solution of compound 63 (1.88 g, 6.0 mmol, 1.0 equiv.) in anhydrous THF (20 mL) was added n-BuLi in hexane (3.6 mL, 9.0 mmol, 1.5 equiv.) drop-wise at −78° C. The reaction was kept at −78° C. for another 1 hour. Triisopropylborate (2.08 mL, 9.0 mmol, 1.5 equiv.) was then added into the mixture at −78° C. The reaction was then warmed up to room temperature and stirred for another 1 hour. The reaction was quenched by saturated $NH_4Cl$ solution (20 mL) and the pH was adjusted to 3. The aqueous phase was extracted with EtOAc (3×20 mL) and the organic phase was combined, dried over $Na_2SO_4$, and concentrated.

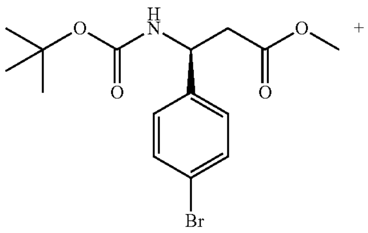

12

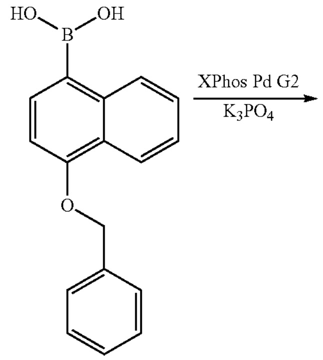

65

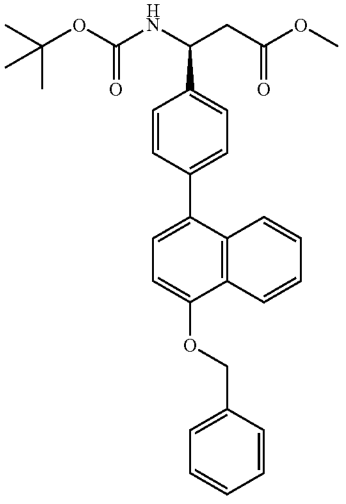

66

Compound 12 (300 mg, 0.837 mmol, 1.0 equiv.), Compound 65 (349 mg, 1.256 mmol, 1.5 equiv.), XPhos Pd G2 (13 mg, 0.0167 mmol, 0.02 equiv.), and $K_3PO_4$ (355 mg, 1.675 mmol, 2.0 equiv.) were mixed in a round-bottom flask. The flask was sealed with a screw-cap septum, and then evacuated and backfilled with nitrogen (this process was repeated a total of 3 times). Then, THF (8 mL) and water (2 mL) were added via syringe. The mixture was bubbled with nitrogen for 20 min and the reaction was kept at room temperature for overnight. The reaction was quenched with water (10 mL), and the aqueous phase was extracted with ethyl acetate (3×10 mL). The organic phase was dried over $Na_2SO_4$, concentrated, and purified via CombiFlash® using silica gel as the stationary phase and was eluted with 15% EtOAc in hexane. LC-MS: calculated [M+H]+ 512.24, found 512.56.

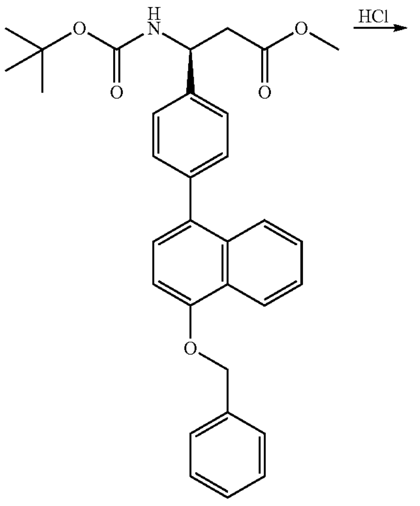

66

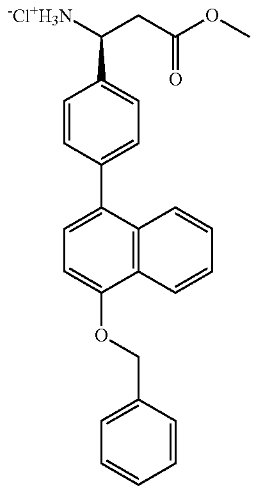

67

Compound 66 (858 mg, 1.677 mmol, 1.0 equiv.) was cooled by ice bath. HCl in dioxane (8.4 mL, 33.54 mmol, 20 equiv.) was added into the flask. The reaction was warmed to room temperature and stirred for another 1 hr. The solvent was removed by rotary evaporator and the product was directly used without further purification. LC-MS: calculated [M+H]+ 412.18, found 412.46.

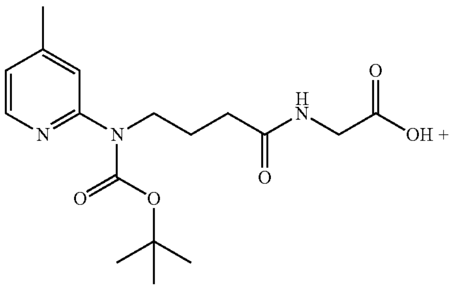

64

-continued

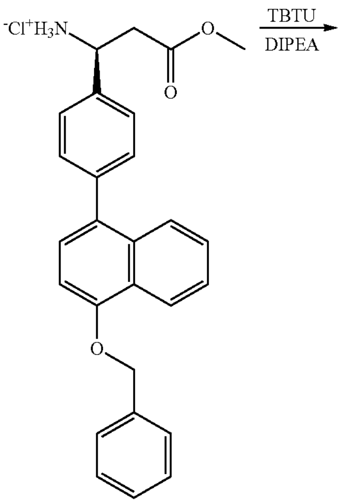

67

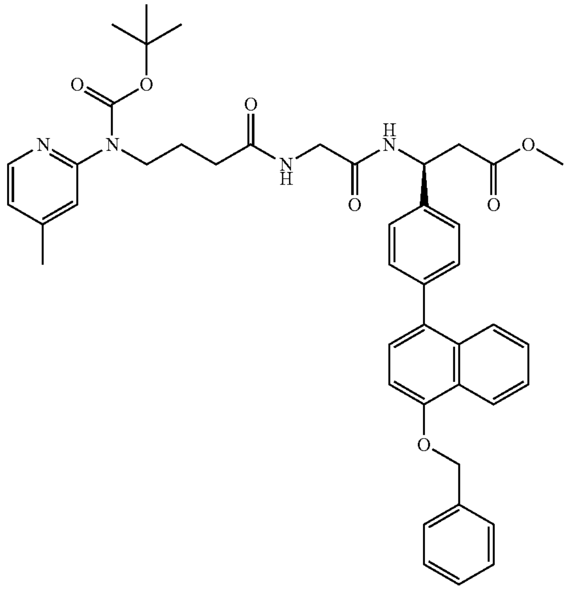

68

To a solution of compound 64 (500 mg, 1.423 mmol, 1 equiv.), compound 67 (669 mg, 1.494 mmol, 1.05 equiv.), and TBTU (548 mg, 0.492 mmol, 1.2 equiv.) in anhydrous DMF (15 mL) was added diisopropylethylamine (0.744 mL, 4.268 mmol, 3 equiv.) at 0° C. The reaction mixture was warmed to room temperature and stirred for another 1 hr. The reaction was quenched by saturated $NaHCO_3$ aqueous solution (10 mL) and the product was extracted with ethyl acetate (3x20 mL). The organic phase was combined, dried over $Na_2SO_4$, and concentrated. The product was purified by CombiFlash® using silica gel as the stationary phase and was eluted with 3-4% methanol in DCM. The yield was 96.23%. LC-MS: calculated [M+H]+ 745.35, found 746.08.

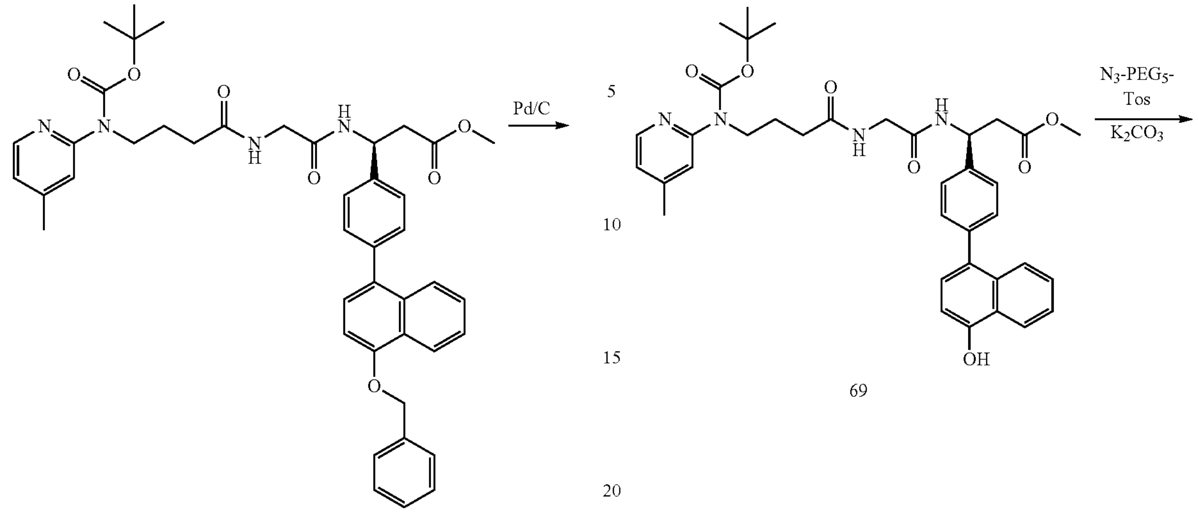

68 69

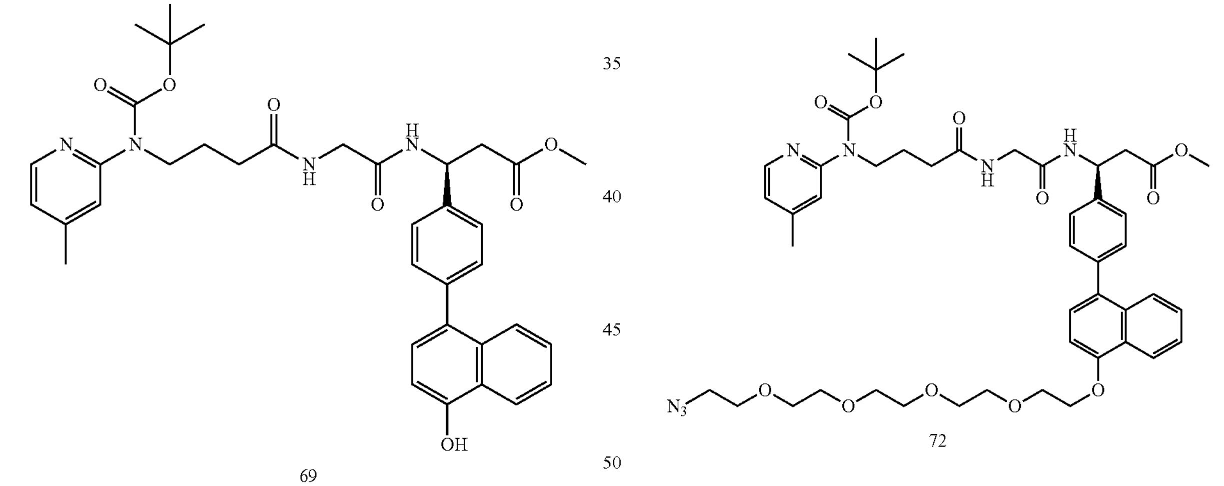

69 72

To a solution of compound 68 (1.02 g, 1.369 mmol, 1 equiv.) in ethyl acetate (10 mL) was added 10% Pd/C (0.15 g, 50% $H_2O$) at room temperature. The reaction mixture was warmed to room temperature and the reaction was monitored by LC-MS. The reaction was kept at room temperature overnight. The solids were filtered through Celite® and the solvent was removed by rotary evaporator. The product was directly used without further purification. LC-MS: [M+H]+ 655.31, found 655.87.

To a solution of compound 69 (100 mg, 0.152 mmol, 1 equiv.) and azido-$PEG_5$-OTs (128 mg, 0.305 mmol, 2 equiv.) in anhydrous DMF (2 mL) was added $K_2CO_3$ (42 mg, 0.305 mmol, 2 equiv.) at 0° C. The reaction mixture was stirred for 6 hours at 80° C. The reaction was quenched by saturated $NaHCO_3$ solution and the aqueous layer was extracted with ethyl acetate (3×10 mL). The organic phase was combined, dried over $Na_2SO_4$, and concentrated. LC-MS: calculated [M+H]+ 900.40, found 901.46.

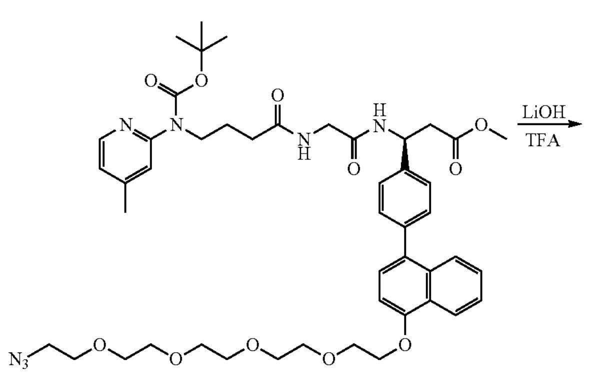

72

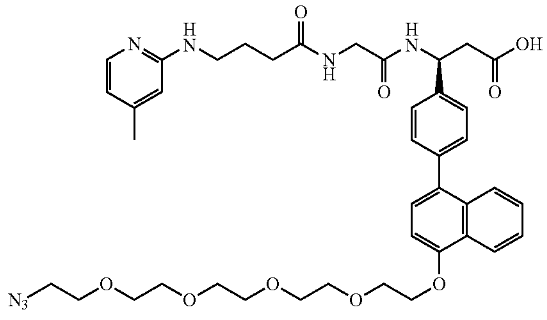

•TFA

Structure 6.1b

To a solution of compound 72 (59 mg, 0.0656 mmol, 1.0 equiv.) in THF (2 mL) and water (2 mL) was added lithium hydroxide (5 mg, 0.197 mmol, 3.0 equiv.) at room temperature. The mixture was stirred at room temperature for another 1 hr. The pH was adjusted to 3.0 by HCl (6N) and the aqueous phase was extracted with EtOAc (3×10 mL). The organic phase was combined, dried over $Na_2SO_4$, and concentrated. TFA (0.5 mL) and DCM (0.5 mL) was added into the residue and the mixture was stirred at room temperature for another 3 hr. The solvent was removed by rotary evaporator. LC-MS: calculated [M+H]+ 786.37, found 786.95.

G. Synthesis of TriAlk 14

TriAlk14 and (TriAlk14)s as shown in Table 12, above, may be synthesized using the synthetic route shown below. Compound 14 may be added to the sense strand as a phosphoramidite using standard oligonucleotide synthesis techniques, or compound 22 may be conjugated to the sense strand comprising an amine in an amide coupling reaction.

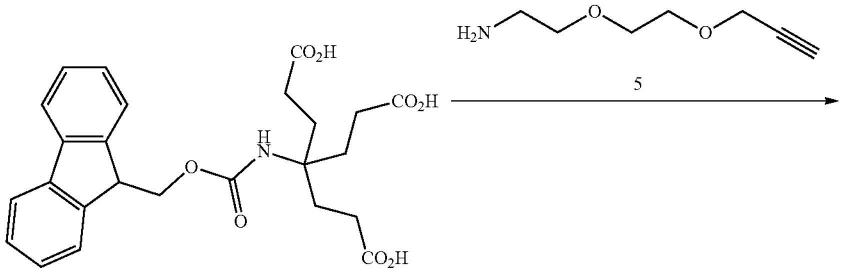

4

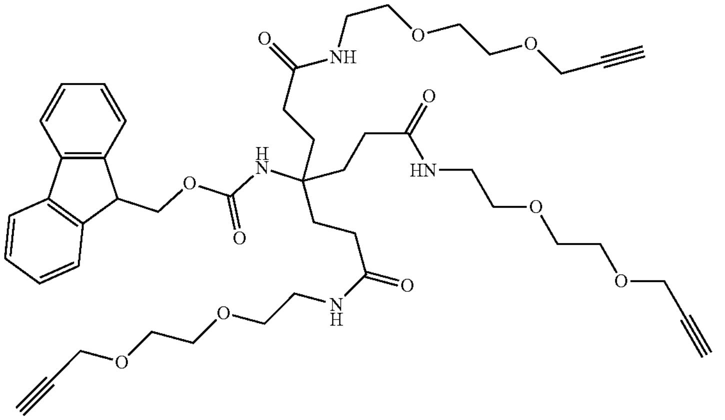

6

To a 3-L jacketed reactor was added 500 mL DCM and 4 (75.0 g, 0.16 mol). The internal temperature of the reaction was cooled to 0° C. and TBTU (170.0 g, 0.53 mol) was added. The suspension was then treated with the amine 5 (75.5 g, 0.53 mol) dropwise keeping the internal temperature less than 5° C. The reaction was then treated with DIPEA (72.3 g, 0.56 mol) slowly, keeping the internal temperature less than 5° C. After the addition was complete, the reaction was warmed up to 23° C. over 1 hour, and allowed to stir for 3 hours. A 10% kicker charge of all three reagents were added and allowed to stir an additional 3 hours. The reaction was deemed complete when <1% of 4 remained. The reaction mixture was washed with saturated ammonium chloride solution (2×500 mL) and once with saturated sodium bicarbonate solution (500 mL). The organic layer was then dried over sodium sulfate and concentrated to an oil. The mass of the crude oil was 188 g which contained 72% 6 by QNMR. The crude oil was carried to the next step. Calculated mass for $C_{46}H_{60}N_4O_{11}$=845.0 m/z. Found [M+H]=846.0.

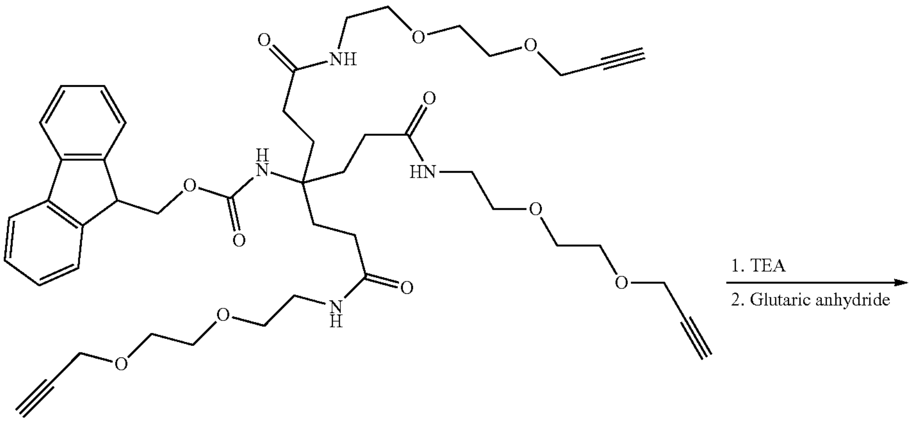

6

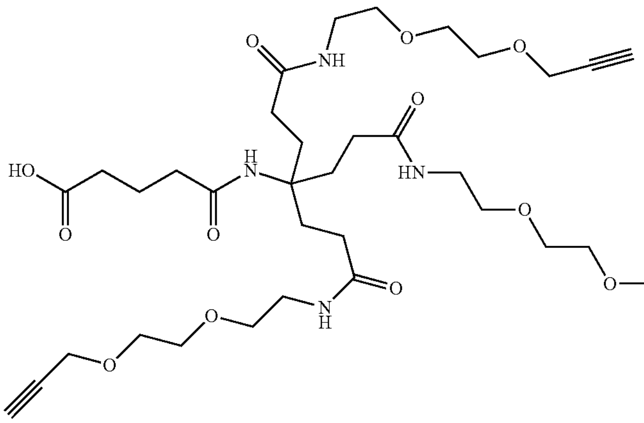

8

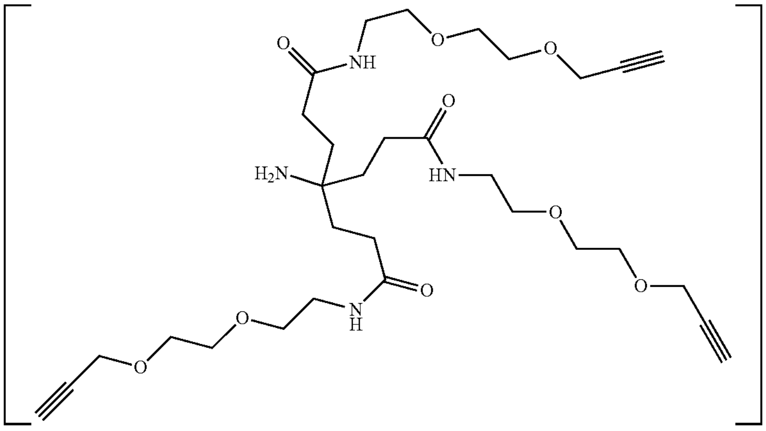

7

Figure 2:
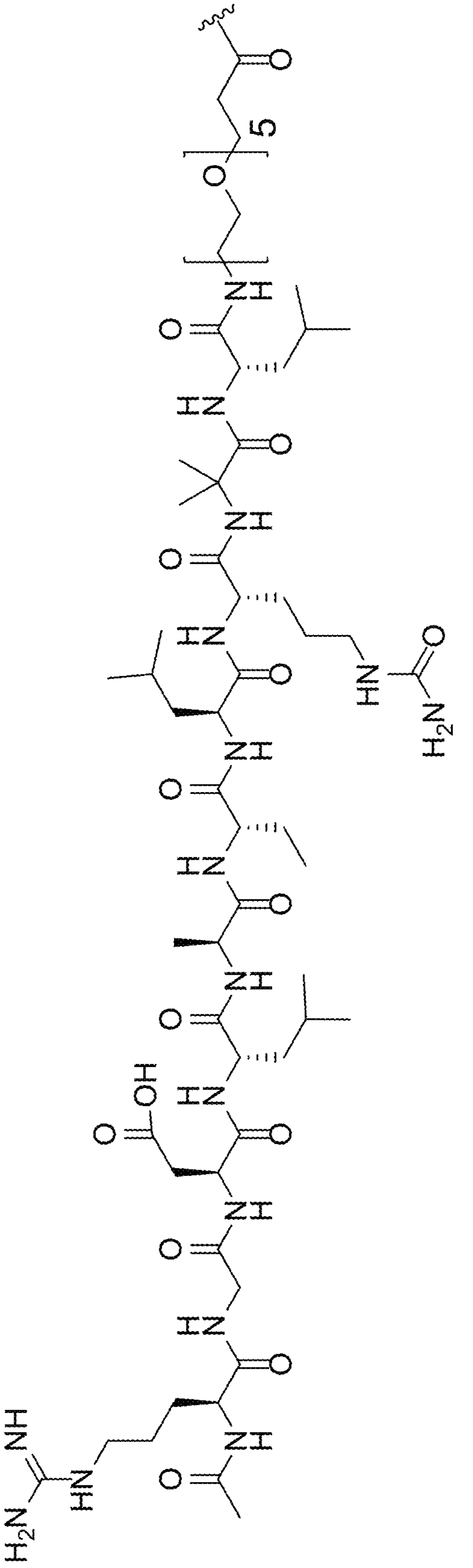
FIG. 2. Chemical structure representation of the peptide αvβ6 epithelial cell targeting ligand referred to herein as αvβ6-pep1 (SEQ ID NO: 1719).

The 121.2 g of crude oil containing 72 wt % compound 6 (86.0 g, 0.10 mol) was dissolved in DMF (344 mL) and treated with TEA (86 mL, 20 v/v %), keeping the internal temperature below 23° C. The formation of dibenzofulvene (DBF) relative to the consumption of Fmoc-amine 6 was monitored via HPLC method 1 (FIG. 2) and the reaction was complete within 10 hours. To the solution was added glutaric anhydride (12.8 g, 0.11 mol) and the intermediate amine 7 was converted to compound 8 within 2 hours. Upon completion, the DMF and TEA were removed at 30° C. under reduced pressure resulting in 100 g of a crude oil. Due to the high solubility of compound 7 in water, an aqueous workup could not be used, and chromatography is the only way to remove DBF, TMU, and glutaric anhydride. The crude oil (75 g) was purified on a Teledyne ISCO Combi-Flash® purification system in three portions. The crude oil (25 g) was loaded onto a 330 g silica column and eluted from 0-20% methanol/DCM over 30 minutes resulting in 42 g of compound 8 (54% yield over 3 steps). Calculated mass for $C_{36}H_{55}N_4O_{12}$=736.4 m/z. Found [M+H]=737.0.

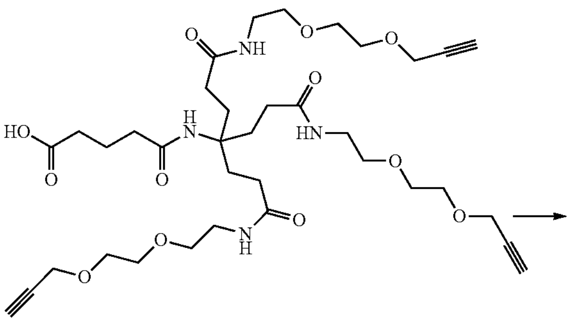

8

-continued

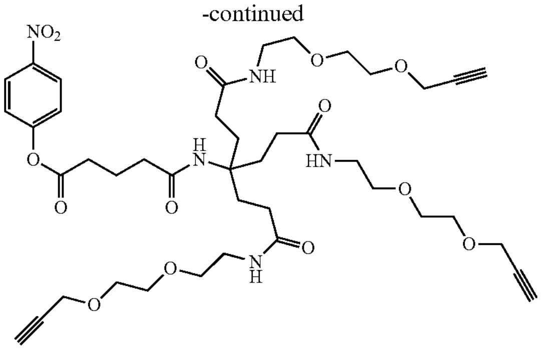

9

Compound 22

Compound 8 (42.0 g, 0.057 mol) was co-stripped with 10 volumes of acetonitrile prior to use to remove any residual methanol from chromatography solvents. The oil was redissolved in DMF (210 mL) and cooled to 0° C. The solution was treated with 4-nitrophenol (8.7 g, 0.063 moL) followed by EDC-hydrochloride (12.0 g, 0.063 mol) and found to reach completion within 10 hours. The solution was cooled to 0° C. and 10 volumes ethyl acetate was added followed by 10 volumes saturated ammonium chloride solution, keeping the internal temperature below 15° C. The layers were allowed to separate and the ethyl acetate layer was washed with brine. The combined aqueous layers were extracted twice with 5 volumes ethyl acetate. The combined organic layers were dried over sodium sulfate and concentrated to an oil. The crude oil (55 g) was purified on a Teledyne ISCO Combi-Flash® purification system in three portions. The crude oil (25 g) was loaded onto a 330 g silica column and eluted from 0-10% methanol/DCM over 30 minutes resulting in 22 g of pure 9 (Compound 22) (50% yield). Calculated mass for $C_{42}H_{59}N_5O_{14}$=857.4 m/z. Found [M+H]=858.0.

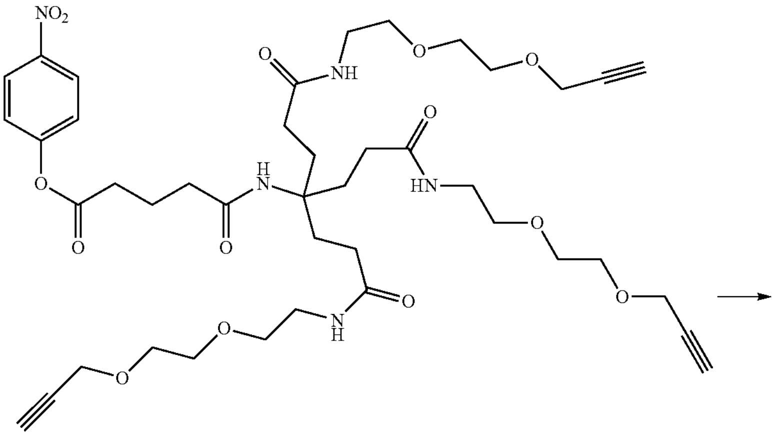

9

-continued

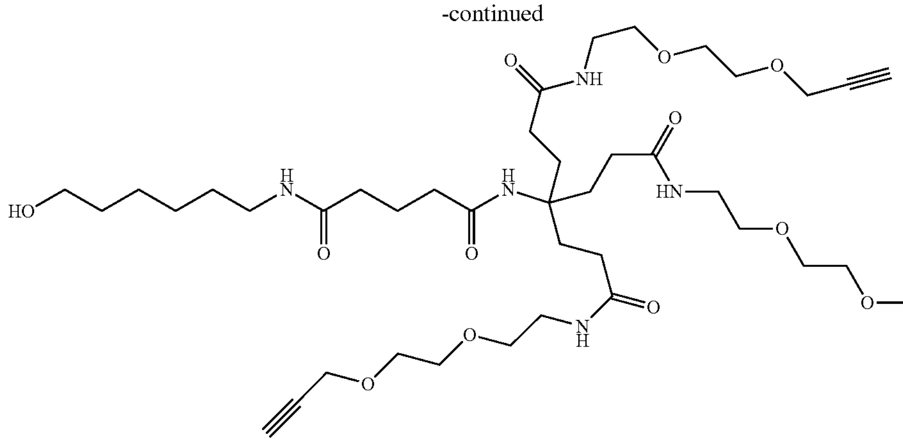

10

A solution of ester 9 (49.0 g, 57.1 mmol) and 6-amino-1-hexanol (7.36 g, 6.28 mmol) in dichloromethane (3 volumes) was treated with triethylamine (11.56 g, 111.4 mmol) dropwise. The reaction was monitored by observing the disappearance of compound 9 on HPLC Method 1 and was found to be complete in 10 minutes. The crude reaction mixture was diluted with 5 volumes dichloromethane and washed with saturated ammonium chloride (5 volumes) and brine (5 volumes). The organic layer was dried over sodium sulfate and concentrated to an oil. The crude oil was purified on a Teledyne ISCO Combi-Flash® purification system using a 330 g silica column. The 4-nitrophenol was eluted with 100% ethyl acetate and 10 was flushed from the column using 20% methanol/DCM resulting in a colorless oil (39 g, 81% yield). Calculated mass for $C_{42}H_{69}N_5O_{12}$=836.0 m/z. Found [M+H]=837.0.

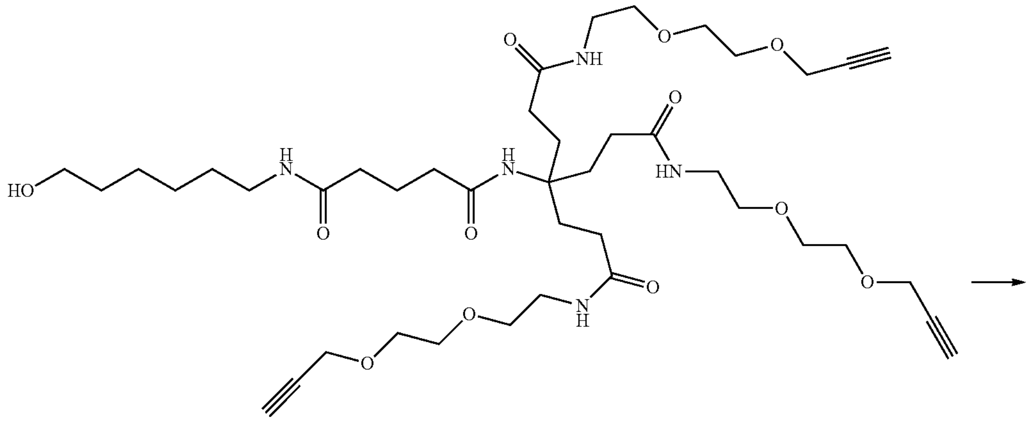

10

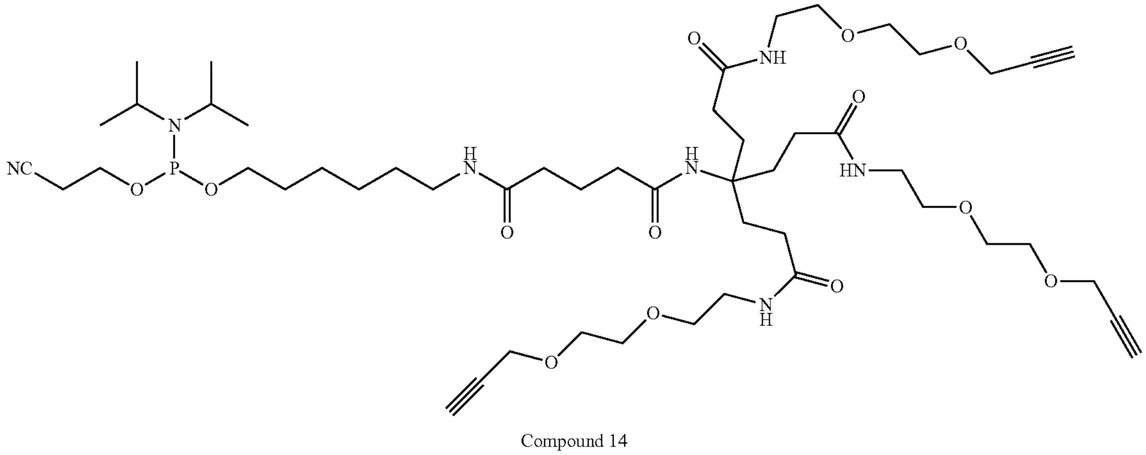

Compound 14

Alcohol 10 was co-stripped twice with 10 volumes of acetonitrile to remove any residual methanol from chromatography solvents and once more with dry dichloromethane (KF<60 ppm) to remove trace water. The alcohol 10 (2.30 g, 2.8 mmol) was dissolved in 5 volumes dry dichloromethane (KF<50 ppm) and treated with diisopropylammonium tetrazolide (188 mg, 1.1 mmol). The solution was cooled to 0° C. and treated with 2-cyanoethyl N,N,N',N'-tetraisopropylphosphoramidite (1.00 g, 3.3 mmol) dropwise. The solution was removed from ice-bath and stirred at 20° C. The reaction was found to be complete within 3-6 hours. The reaction mixture was cooled to 0° C. and treated with 10 volumes of a 1:1 solution of saturated ammonium bicarbonate/brine and then warmed to ambient over 1 minute and allowed to stir an additional 3 minutes at 20° C. The biphasic mixture was transferred to a separatory funnel and 10 volumes of dichloromethane was added. The organic layer was separated and washed with 10 volumes of saturated sodium bicarbonate solution to hydrolyze unreacted bis-phosphorous reagent. The organic layer was dried over sodium sulfate and concentrated to an oil resulting in 3.08 g of 94 wt % Compound 14. Calculated mass for $C_{51}H_{86}N_7O_{13}P$=1035.6 m/z. Found [M+H]=1036.

H. Conjugation of Targeting Ligands. Either prior to or after annealing, the 5' or 3' tridentate alkyne functionalized sense strand is conjugated to targeting ligands. The following example describes the conjugation of targeting ligands to the annealed duplex: Stock solutions of 0.5M Tris(3-hydroxypropyltriazolylmethyl)amine (THPTA), 0.5M of Cu(II) sulfate pentahydrate ($Cu(II)SO_4 \cdot 5H_2O$) and 2M solution of sodium ascorbate were prepared in deionized water. A 75 mg/mL solution in DMSO of targeting ligand was made. In a 1.5 mL centrifuge tube containing tri-alkyne functionalized duplex (3 mg, 75 µL, 40 mg/mL in deionized water, ~15,000 g/mol), 25 µL of 1M Hepes pH 8.5 buffer is added. After vortexing, 35 µL of DMSO was added and the solution is vortexed. Targeting ligand was added to the reaction (6 equivalents/duplex, 2 equivalents/alkyne, ~15 µL) and the solution is vortexed. Using pH paper, pH was checked and confirmed to be pH ~8. In a separate 1.5 mL centrifuge tube, 50 µL of 0.5M THPTA was mixed with 10 uL of 0.5M $Cu(II)SO_4 \cdot 5H_2O$, vortexed, and incubated at room temp for 5 min. After 5 min, THPTA/Cu solution (7.2 µL, 6 equivalents 5:1 THPTA:Cu) was added to the reaction vial, and vortexed. Immediately afterwards, 2M ascorbate (5 µL, 50 equivalents per duplex, 16.7 per alkyne) was added to the reaction vial and vortexed. Once the reaction was complete (typically complete in 0.5-1 h), the reaction was immediately purified by non-denaturing anion exchange chromatography.

Example 2. In Vitro Testing of MUC5AC RNAi Agents

Certain chemically modified candidate sequence duplexes shown Table 8C above (with the antisense strand sequence set forth in Table 3 and the nucleotide and end cap portion of the sense strand found in Table 6), were tested in vitro. The MUC5AC RNAi agents were prepared in accordance with the procedures set forth in Example 1.

Evaluation of MUC5AC RNAi agents in vitro was performed by transfection of A549 cells, a human lung epithelial cell line. Cells were plated at ~7,500 cells per well in 96-well format, and each of the RNAi agent duplexes shown in Table 12 was transfected at three concentrations (10 nM, 1 nM, and 0.1 nM), using LipoFectamine RNAiMax (Thermo Fisher) transfection reagent. Relative expression of each of the MUC5AC RNAi agents was determined by qRT-PCR by comparing the expression levels of MUC5AC mRNA to an endogenous control, and normalized to untreated A549 cells ($\Delta\Delta C_T$ analysis), as shown in Table 12.

Table 13, below, lists the AD duplex number for the sequence being examined, as well as in parenthesis the gene position being targeted by that particular RNAi agent. Thus, for example, for Duplex ID AD08101, average relative expression at 1 nM of 0.377 shows MUC5AC gene knockdown of 62.3%, and average relative expression at 0.1 nM shows inhibition of 53.0% (0.470) normalized to untreated wells (mock control).

TABLE 13

In Vitro Testing of MUC5AC RNAi Agents.

| Duplex ID No. | Avg. Rel. Exp. 10 nM | High (error) | Low (error) | Avg. Rel. Exp. 1 nM | High (error) | Low (error) | Avg. Rel. Exp. 0.1 nM | High (error) | Low (error) |
|---|---|---|---|---|---|---|---|---|---|
| AD08101 (11014_1) | 0.230 | 0.042 | 0.051 | 0.377 | 0.049 | 0.056 | 0.470 | 0.056 | 0.064 |
| AD08666 (4993_2) | 0.258 | 0.047 | 0.058 | 0.394 | 0.068 | 0.082 | 0.474 | 0.102 | 0.131 |
| AD08668 (4993_4) | 0.228 | 0.052 | 0.068 | 0.401 | 0.065 | 0.078 | 0.554 | 0.181 | 0.270 |
| AD07732 (3099_1) | 0.240 | 0.057 | 0.075 | 0.427 | 0.083 | 0.103 | 0.527 | 0.087 | 0.105 |
| AD08100 (10206_1) | 0.286 | 0.031 | 0.035 | 0.382 | 0.048 | 0.054 | 0.550 | 0.081 | 0.096 |
| AD08103 (12965_1) | 0.198 | 0.063 | 0.092 | 0.439 | 0.079 | 0.097 | 0.656 | 0.086 | 0.099 |
| AD07734 (5347_1) | 0.186 | 0.047 | 0.062 | 0.515 | 0.089 | 0.107 | 0.614 | 0.085 | 0.099 |
| AD07634 (3535_1) | 0.161 | 0.025 | 0.030 | 0.423 | 0.046 | 0.051 | 0.769 | 0.129 | 0.154 |
| AD08671 (4992_2) | 0.353 | 0.047 | 0.054 | 0.416 | 0.078 | 0.096 | 0.588 | 0.068 | 0.077 |
| AD07763 (610_1) | 0.138 | 0.034 | 0.046 | 0.432 | 0.065 | 0.077 | 0.826 | 0.149 | 0.182 |
| AD08667 (4993_3) | 0.293 | 0.056 | 0.069 | 0.427 | 0.051 | 0.057 | 0.677 | 0.151 | 0.195 |
| AD07733 (4993_1) | 0.253 | 0.031 | 0.036 | 0.501 | 0.084 | 0.102 | 0.655 | 0.123 | 0.152 |

TABLE 13-continued

In Vitro Testing of MUC5AC RNAi Agents.

| Duplex ID No. | Avg. Rel. Exp. 10 nM | High (error) | Low (error) | Avg. Rel. Exp. 1 nM | High (error) | Low (error) | Avg. Rel. Exp. 0.1 nM | High (error) | Low (error) |
|---|---|---|---|---|---|---|---|---|---|
| AD08669 (4993_5) | 0.302 | 0.037 | 0.042 | 0.461 | 0.057 | 0.065 | 0.658 | 0.083 | 0.094 |
| AD08673 (4992_4) | 0.369 | 0.061 | 0.073 | 0.468 | 0.060 | 0.069 | 0.624 | 0.070 | 0.079 |
| AD07774 (2797_1) | 0.182 | 0.053 | 0.074 | 0.565 | 0.088 | 0.104 | 0.860 | 0.099 | 0.112 |
| AD07735 (5350_1) | 0.288 | 0.037 | 0.043 | 0.565 | 0.097 | 0.117 | 0.774 | 0.071 | 0.078 |
| AD08670 (4993_6) | 0.360 | 0.033 | 0.036 | 0.513 | 0.072 | 0.084 | 0.814 | 0.198 | 0.261 |
| AD07637 (5300_1) | 0.539 | 0.061 | 0.069 | 0.606 | 0.057 | 0.063 | 0.674 | 0.051 | 0.055 |
| AD08571 (15051_1) | 0.250 | 0.039 | 0.047 | 0.612 | 0.046 | 0.050 | 0.978 | 0.089 | 0.099 |
| AD08572 (15052_7) | 0.389 | 0.052 | 0.059 | 0.688 | 0.080 | 0.091 | 0.819 | 0.098 | 0.112 |
| AD08568 (3910_1) | 0.448 | 0.069 | 0.082 | 0.661 | 0.080 | 0.091 | 0.789 | 0.082 | 0.092 |
| AD08569 (5029_9) | 0.282 | 0.034 | 0.038 | 0.666 | 0.096 | 0.113 | 0.978 | 0.046 | 0.048 |
| AD08573 (15052_8) | 0.398 | 0.027 | 0.029 | 0.736 | 0.069 | 0.076 | 0.814 | 0.118 | 0.138 |
| AD08096 (4992_1) | 0.359 | 0.040 | 0.045 | 0.621 | 0.076 | 0.086 | 1.008 | 0.080 | 0.087 |
| AD08672 (4992_3) | 0.432 | 0.052 | 0.059 | 0.669 | 0.057 | 0.063 | 0.925 | 0.040 | 0.042 |
| AD07756 (1618_1) | 0.372 | 0.064 | 0.078 | 0.693 | 0.053 | 0.058 | 1.082 | 0.146 | 0.169 |
| AD07773 (2536_1) | 0.446 | 0.042 | 0.046 | 0.837 | 0.117 | 0.136 | 0.935 | 0.153 | 0.183 |
| AD07760 (2001_1) | 0.379 | 0.059 | 0.070 | 0.806 | 0.141 | 0.171 | 1.096 | 0.151 | 0.175 |
| AD07771 (2004_1) | 0.389 | 0.032 | 0.035 | 0.872 | 0.093 | 0.104 | 1.205 | 0.161 | 0.185 |
| Mock Control | 1.000 | 0.164 | 0.197 | 1.000 | 0.164 | 0.197 | 1.000 | 0.164 | 0.197 |

Example 3. In Vitro Testing of MUC5AC RNAi Agents

Certain chemically modified candidate sequence duplexes shown Table 8C above (with the antisense strand sequence set forth in Table 3 and the nucleotide and end cap portion of the sense strand found in Table 6), were tested in vitro. The MUC5AC RNAi agents were prepared in accordance with the procedures set forth in Example 1.

Evaluation of MUC5AC RNAi agents in vitro was performed by transfection of A549 cells, a human lung epithelial cell line. Cells were plated at ~7,500 cells per well in 96-well format, and each of the RNAi agent duplexes shown in Table 12 was transfected at three concentrations (10 nM, 1 nM, and 0.1 nM), using LipoFectamine RNAiMax (Thermo Fisher) transfection reagent. Relative expression of each of the MUC5AC RNAi agents was determined by qRT-PCR by comparing the expression levels of MUC5AC mRNA to an endogenous control, and normalized to untreated A549 cells ($\Delta\Delta C_T$ analysis), as shown in Table 12.

Table 14, below, lists the AD duplex number for the sequence being examined, as well as in parenthesis the gene position being targeted by that particular RNAi agent. Thus, for example, for Duplex ID AD07733, αaverage relative expression at 1 nM of 0.192 shows MUC5AC gene knockdown of % 80.8%, and αaverage relative expression at 0.1 nM shows inhibition of 66.4% (0.336) normalized to untreated wells (mock control).

TABLE 14

In Vitro Testing of MUC5AC RNAi Agents.

| Duplex ID No. | Avg. Rel. Exp. 10 nM | High (error) | Low (error) | Avg. Rel. Exp. 1 nM | High (error) | Low (error) | Avg. Rel. Exp. 0.1 nM | High (error) | Low (error) |
|---|---|---|---|---|---|---|---|---|---|
| AD07733 (4993_1) | 0.156 | 0.047 | 0.067 | 0.192 | 0.030 | 0.035 | 0.336 | 0.024 | 0.026 |
| AD08096 (4992_1) | 0.171 | 0.022 | 0.026 | 0.275 | 0.035 | 0.040 | 0.406 | 0.027 | 0.028 |
| AD07767 (1758_1) | 0.140 | 0.019 | 0.022 | 0.195 | 0.097 | 0.193 | 0.536 | 0.226 | 0.392 |
| AD08103 (12965_1) | 0.197 | 0.057 | 0.080 | 0.276 | 0.042 | 0.050 | 0.409 | 0.046 | 0.052 |
| AD08098 (8739_1) | 0.172 | 0.032 | 0.039 | 0.259 | 0.076 | 0.109 | 0.466 | 0.042 | 0.046 |

TABLE 14-continued

In Vitro Testing of MUC5AC RNAi Agents.

| Duplex ID No. | Avg. Rel. Exp. 10 nM | High (error) | Low (error) | Avg. Rel. Exp. 1 nM | High (error) | Low (error) | Avg. Rel. Exp. 0.1 nM | High (error) | Low (error) |
|---|---|---|---|---|---|---|---|---|---|
| AD07763 (610_1) | 0.094 | 0.024 | 0.032 | 0.293 | 0.033 | 0.037 | 0.514 | 0.026 | 0.027 |
| AD08100 (10206_1) | 0.242 | 0.046 | 0.056 | 0.260 | 0.051 | 0.064 | 0.417 | 0.041 | 0.045 |
| AD08101 (11014_1) | 0.236 | 0.054 | 0.071 | 0.322 | 0.044 | 0.052 | 0.364 | 0.039 | 0.043 |
| AD07751 (5533_1) | 0.161 | 0.058 | 0.091 | 0.335 | 0.051 | 0.061 | 0.536 | 0.035 | 0.037 |
| AD07634 (3535_1) | 0.159 | 0.034 | 0.043 | 0.385 | 0.035 | 0.039 | 0.507 | 0.061 | 0.069 |
| AD07770 (1867_1) | 0.114 | 0.022 | 0.028 | 0.377 | 0.041 | 0.046 | 0.599 | 0.059 | 0.066 |
| AD07747 (5020_1) | 0.347 | 0.057 | 0.069 | 0.330 | 0.042 | 0.049 | 0.413 | 0.033 | 0.036 |
| AD07749 (5441_1) | 0.365 | 0.061 | 0.073 | 0.337 | 0.017 | 0.018 | 0.464 | 0.060 | 0.068 |
| AD08095 (1871_1) | 0.204 | 0.024 | 0.027 | 0.380 | 0.064 | 0.077 | 0.624 | 0.046 | 0.049 |
| AD08097 (6798_1) | 0.364 | 0.056 | 0.066 | 0.384 | 0.068 | 0.083 | 0.511 | 0.061 | 0.069 |
| AD07750 (5519_1) | 0.432 | 0.063 | 0.074 | 0.240 | 0.073 | 0.105 | 0.589 | 0.056 | 0.062 |
| AD07774 (2797_1) | 0.168 | 0.031 | 0.038 | 0.432 | 0.072 | 0.087 | 0.679 | 0.040 | 0.042 |
| AD07732 (3099_1) | 0.352 | 0.056 | 0.067 | 0.402 | 0.147 | 0.231 | 0.535 | 0.154 | 0.217 |
| AD07764 (923_1) | 0.424 | 0.080 | 0.099 | 0.431 | 0.051 | 0.057 | 0.505 | 0.048 | 0.052 |
| AD07771 (2004_1) | 0.367 | 0.064 | 0.077 | 0.493 | 0.090 | 0.109 | 0.597 | 0.078 | 0.090 |
| AD07748 (5042_1) | 0.518 | 0.131 | 0.176 | 0.413 | 0.078 | 0.095 | 0.559 | 0.068 | 0.077 |
| AD07768 (1761_1) | 0.278 | 0.039 | 0.046 | 0.561 | 0.084 | 0.099 | 0.728 | 0.041 | 0.043 |
| AD07756 (1618_1) | 0.522 | 0.081 | 0.096 | 0.464 | 0.081 | 0.099 | 0.708 | 0.052 | 0.056 |
| AD07772 (2234_1) | 0.476 | 0.055 | 0.062 | 0.588 | 0.057 | 0.063 | 0.654 | 0.070 | 0.078 |
| AD07773 (2536_1) | 0.498 | 0.039 | 0.043 | 0.596 | 0.060 | 0.067 | 0.672 | 0.055 | 0.060 |
| AD07746 (4446_1) | 0.578 | 0.058 | 0.065 | 0.671 | 0.086 | 0.099 | 0.740 | 0.052 | 0.056 |
| AD08094 (1445_1) | 0.646 | 0.056 | 0.061 | 0.721 | 0.071 | 0.079 | 0.762 | 0.076 | 0.084 |
| AD07766 (1446_1) | 0.760 | 0.103 | 0.119 | 0.806 | 0.067 | 0.072 | 0.793 | 0.082 | 0.092 |
| AD07745 (4443_1) | 0.902 | 0.194 | 0.247 | 0.840 | 0.088 | 0.098 | 0.821 | 0.049 | 0.052 |
| Mock Control | 1.000 | 0.109 | 0.122 | 1.000 | 0.109 | 0.122 | 1.000 | 0.109 | 0.122 |

Example 4. House Dust Mite (HDM) Induced Allergic Asthma Model

To study the properties of certain MUC5AC RNAi agents in vivo, the house dust mite (HDM) induced allergic asthma mouse model was used. To induce mouse Muc5ac expression, female Balb/c mice (6-8 weeks in age) were administered 50 μg house dust mite protein acquired commercially in 25 μL of isotonic saline intranasally using a pipette for 5 consecutive days. 72 hours after the fifth daily dose, mice were euthanized and whole lungs were harvested for mRNA expression analysis. Compared to unchallenged, naïve mice, relative expression of mouse Muc5ac mRNA in HDM challenged mice is shown to increase approximately 100 fold.

Example 5. In Vivo Intratracheal Administration of MUC5AC RNAi Agents in the HDM Model The HDM induced allergic asthma mouse model described in Example 4, above, was used. The following Table 15 sets forth the dosing Groups:

TABLE 15

| MUC5AC RNAi Agent and Dosing for Example 5. | | | | | |
|---|---|---|---|---|---|
| GROUP | IT Dose Administered | Study Days IT Administered | IN Dose Administered | Study Days IN Dose Administered | Animals Per Group |
| 1 | No treatment | N/A | No treatment | N/A | 6 |
| 2 | No treatment | N/A | Saline | Days 8-12 | 6 |
| 3 | Saline | 1, 3, 5, and 8 | Saline | Days 8-12 | 3 |
| 4 | No treatment | N/A | HDM | Days 8-12 | 6 |
| 5 | Saline | 1, 3, 5, and 8 | HDM | Days 8-12 | 4 |
| 6 | 5.0 mg/kg Tri-SM6.1-αvβ6-AD07022 | 1, 3, 5, and 8 | HDM | Days 8-12 | 4 |
| 7 | 5.0 mg/kg Tri-SM6.1-αvβ6-AD07720 | 1, 3, 5, and 8 | HDM | Days 8-12 | 5 |
| 8 | 5.0 mg/kg Tri-SM6.1-αvβ6-AD07719 | 1, 3, 5, and 8 | HDM | Days 8-12 | 5 |

As noted in Table 15 above, the mice in Group 1 received no treatment throughout. For the mice in Groups 3, 5, 6, 7 and 8, on study days 1, 3, 5, and 8, female Balb/c mice were administered a single dose of 50 microliters via a microsprayer device (Penn Century, Philadelphia, PA) suitable for intratracheal (IT) administration of isotonic saline or 5.0 mg/kg the respective MUC5AC RNAi agent formulated in isotonic saline as noted in Table 15.

As shown in Table 15, each of the MUC5AC RNAi agents (Groups 6, 7 and 8) were conjugated to a tridentate small molecule αvβ6 epithelial cell targeting ligand (Tri-SM6.1, see FIG. 1) at the 5' terminal end of the sense strand.

The chemically modified sequences for MUC5AC RNAi agents AD07720 and AD07719 (Groups 7 and 8) are shown in Table 7B (showing duplex), Table 3 (showing respective antisense strand), and Table 5 (showing respective sense strand with linker but without tridentate small molecule αvβ6 epithelial cell targeting ligand (Tri-SM6.1).

AD07022 has mouse-specific sequences that do not have homology with the human MUC5AC gene, and were chemically modified as follows:

```
Tri-SM6.1-αvβ6-AD07022
Modified Sense Strand (5' → 3'):
                                    (SEQ ID NO: 1714)
Tri-SM6.1-αvβ6-(TA14)cscauacagCfAfGfuacaguuacas

(invAb)

Modified Antisense Strand (5' → 3'):
                                    (SEQ ID NO: 1713)
cPrpusGfsusAfaCfuGfuAfcUfgCfuGfuAfuGfsg
```

On each of Days 8 through 12, the mice in Groups 2 through 8 were administered a single dose intranasally (IN) using a pipette with 25 microliters of isotonic saline (Groups 2 and 3) or 50 micrograms of house dust mite formulated in isotonic saline (referred to in Table 15 as HDM).

Mice were sacrificed on study day 15, and total RNA was isolated from both lungs following collection and homogenization. Mouse Muc5ac mRNA expression was quantitated by probe-based quantitative PCR, normalized to mouse beta-actin expression, and expressed as fraction of vehicle control group (geometric mean, +/−95% confidence interval).

TABLE 16

| Average Relative Mouse MUC5AC mRNA at Sacrifice (Day 15) in Example 5 | | | |
|---|---|---|---|
| Group ID | Average Relative mMuc5AC mRNA | Low (error) | High (error) |
| Group 1 (No Treatment) | 1.000 | 0.213 | 0.270 |
| Group 2 (IN Saline) | 1.941 | 0.638 | 0.951 |
| Group 3 (IT Saline & IN Saline) | 1.706 | 0.532 | 0.774 |
| Group 4 (IN HDM) | 117.876 | 26.269 | 33.801 |
| Group 5 (IT Saline & IN HDM) | 95.585 | 21.822 | 28.277 |
| Group 6 (IT 5 mg/kg Tri-SM6.1-αvβ6-AD07022 & IN HDM) | 13.444 | 3.410 | 4.569 |
| Group 7 (IT 5 mg/kg Tri-SM6.1-αvβ6-AD07720 & IN HDM) | 71.812 | 16.633 | 21.647 |
| Group 8 (IT 5 mg/kg Tri-SM6.1-αvβ6-AD07719 & IN HDM) | 90.537 | 27.214 | 38.910 |

The data were normalized to the non-treatment group (Group 1). As shown in the data in Table 16 above, the HDM mouse model performed as expected with respect to promoting an increase in MUC5AC expression after exposure to HDM. The data show that Groups 7 and 8, which each had nucleotide sequences targeting position 1921 of the MUC5AC gene and has homology to both the human and mouse gene transcript, provided only a very minimal reduction in MUC5AC protein compared to the HDM model mice of Groups 4 and 5 with no RNAi agent, indicating only a minimal amount of inhibition for these specific RNAi agents. Alternatively, the mouse-specific RNAi agent of AD07022 (Group 6) showed a substantial reduction in Muc5ac mouse mRNA levels (only 13.444) compared to the groups where HDM was administered without a MUC5AC RNAi agent.

Example 6. In Vivo Intratracheal Administration of MUC5AC RNAi Agents in the HDM Model The HDM induced allergic asthma mouse model described in Example 4, above, was used. The following Table 17 sets forth the dosing Groups:

TABLE 17

MUC5AC RNAi Agent and Dosing for Example 6.

| GROUP | IT Dose Administered | Study Days IT Administered | IN Dose Administered | Study Days IN Dose Administered | Animals Per Group | Targeted Gene Position |
|---|---|---|---|---|---|---|
| 1 | Saline | 1, 3, 5, and 8 | Saline | Days 8-12 | 6 | N/A |
| 2 | Saline | 1, 3, 5, and 8 | HDM | Days 8-12 | 5 | N/A |
| 3 | 5.0 mg/kg Tri-SM6.1-αvβ6-AD07022 | 1, 3, 5, and 8 | HDM | Days 8-12 | 6 | Mouse-specific |
| 4 | 5.0 mg/kg Tri-SM6.1-αvβ6-AD08083 | 1, 3, 5, and 8 | HDM | Days 8-12 | 5 | 5029 |
| 5 | 5.0 mg/kg Tri-SM6.1-αvβ6-AD08084 | 1, 3, 5, and 8 | HDM | Days 8-12 | 5 | 5029 |
| 6 | 5.0 mg/kg Tri-SM6.1-αvβ6-AD08085 | 1, 3, 5, and 8 | HDM | Days 8-12 | 4 | 5029 |
| 7 | 5.0 mg/kg Tri-SM6.1-αvβ6-AD08086 | 1, 3, 5, and 8 | HDM | Days 8-12 | 5 | 9729 |
| 8 | 5.0 mg/kg Tri-SM6.1-αvβ6-AD08087 | 1, 3, 5, and 8 | HDM | Days 8-12 | 6 | 9729 |
| 9 | 5.0 mg/kg Tri-SM6.1-αvβ6-AD08088 | 1, 3, 5, and 8 | HDM | Days 8-12 | 5 | 15052 |
| 10 | 5.0 mg/kg Tri-SM6.1-αvβ6-AD08089 | 1, 3, 5, and 8 | HDM | Days 8-12 | 5 | 15052 |
| 11 | 5.0 mg/kg Tri-SM6.1-αvβ6-AD07022 | 1 and 8 | HDM | Days 8-12 | 5 | Mouse-specific |

For the mice in Groups 1-10, on study days 1, 3, 5, and 8, female Balb/c mice were administered a single dose of 50 microliters via a microsprayer device (Penn Century, Philadelphia, PA) suitable for intratracheal (IT) administration of isotonic saline or 5.0 mg/kg of the respective MUC5AC RNAi agent formulated in isotonic saline as noted in Table 17. For the mice in Group 11, the MUC5AC RNAi agent was administered only on days 1 and 8.

As shown in Table 17, each of the MUC5AC RNAi agents (Groups 3-11) were conjugated to a tridentate small molecule αvβ6 epithelial cell targeting ligand (Tri-SM6.1, see FIG. 1) at the 5' terminal end of the sense strand. The chemically modified sequences for MUC5AC RNAi agents AD08083, AD08084, AD08085, AD08086, AD08087, AD08088, and AD08089 (Groups 4 through 10) are shown in Table 7B (showing duplex), Table 3 (showing respective antisense strand), and Table 5 (showing respective sense strand with linker but without tridentate small molecule αvβ6 epithelial cell targeting ligand (Tri-SM6.1)).

AD07022 has mouse-specific sequences that do not have homology with the human MUC5AC gene, and were chemically modified as shown above in Example 5.

On each of Days 8 through 12, the mice were administered a single dose intranasally (IN) using a pipette with 25 microliters of isotonic saline (Group 2) or 50 micrograms of house dust mite formulated in isotonic saline (referred to in Table 17 as HDM).

Mice were sacrificed on study day 15, and total RNA was isolated from both lungs following collection and homogenization. Mouse Muc5ac mRNA expression was quantitated by probe-based quantitative PCR, normalized to mouse beta-actin expression, and expressed as fraction of vehicle control group (geometric mean, +/−95% confidence interval).

TABLE 18

Average Relative Mouse MUC5AC mRNA at Sacrifice (Day 15) in Example 6

| Group ID | Average Relative mMuc5ac mRNA | Low (error) | High (error) |
|---|---|---|---|
| Group 1 (IT Saline & IN Saline) | 1.000 | 0.305 | 0.440 |
| Group 2 (IT Saline & IN HDM) | 115.127 | 17.128 | 20.122 |
| Group 3 (IT 5 mg/kg Tri-SM6.1-αvβ6-AD07022 & IN HDM) | 19.053 | 6.287 | 9.383 |
| Group 4 (IT 5 mg/kg Tri-SM6.1-αvβ6-AD08083 & IN HDM) | 35.333 | 13.193 | 21.054 |
| Group 5 (IT 5 mg/kg Tri-SM6.1-αvβ6-AD08084 & IN HDM) | 26.634 | 12.943 | 25.180 |
| Group 6 (IT 5 mg/kg Tri-SM6.1-αvβ6-AD08085 & IN HDM) | 34.602 | 3.503 | 3.897 |
| Group 7 (IT 5 mg/kg Tri-SM6.1-αvβ6-AD08086 & IN HDM) | 55.475 | 15.377 | 21.273 |
| Group 8 (IT 5 mg/kg Tri-SM6.1-αvβ6-AD08087 & IN HDM) | 66.631 | 19.703 | 27.976 |
| Group 9 (IT 5 mg/kg Tri-SM6.1-αvβ6-AD08088 & IN HDM) | 26.879 | 4.505 | 5.412 |
| Group 10 (IT 5 mg/kg Tri-SM6.1-αvβ6-AD08089 & IN HDM) | 14.903 | 2.441 | 2.919 |
| Group 11 (IT 5 mg/kg Tri-SM6.1-αvβ6-AD07022 & IN HDM) | 14.457 | 6.005 | 10.271 |

The data were normalized to the IT and IN saline-only dosed group (Group 1). As shown in the data in Table 18 above, the HDM mouse model performed as expected with respect to promoting an increase in MUC5AC expression after exposure to HDM. The data show that Groups 7 and 8, which both had nucleotide sequences targeting position 9729 of the MUC5AC gene and has homology to both the human and mouse gene transcript, provided only a moderate reduction in MUC5AC protein compared to the HDM model mice of Group 2 with no RNAi agent, indicating only a moderate amount of inhibition for these specific RNAi agents. Alternatively, the remaining MUC5AC RNAi agents tested (targeting gene position 5029 in Groups 4-6 and gene position 15052 in Groups 9 and 10) each showed substantial inhibition compared to Group 2, as did the mouse-specific MUC5AC RNAi agent of AD07022 (Group 6).

Example 7. In Vivo Intratracheal Administration of MUC5AC RNAi Agents in Rats The HDM induced allergic asthma mouse model described in Example 4, above, was used. The following Table 19 sets forth certain dosing Groups included in the study:

TABLE 19

MUC5AC RNAi Agent and Dosing for Example 7.

| GROUP | IT Dose Administered | Study Days IT Administered | IN Dose Administered | Study Days IN Dose Administered | Animals Per Group | Targeted Gene Position |
|---|---|---|---|---|---|---|
| 1 | Saline | 1, 3, 5, and 8 | Saline | Days 8-12 | 6 | N/A |
| 2 | Saline | 1, 3, 5, and 8 | HDM | Days 8-12 | 6 | N/A |
| 3 | 5.0 mg/kg Tri-SM6.1-αvβ6-AD07022 | 1, 3, 5, and 8 | HDM | Days 8-12 | 5 | Mouse-Specific |
| 4 | 5.0 mg/kg Tri-SM6.1-αvβ6-AD08173 | 1, 3, 5, and 8 | HDM | Days 8-12 | 6 | 3535 |
| 5 | 5.0 mg/kg Tri-SM6.1-αvβ6-AD08174 | 1, 3, 5, and 8 | HDM | Days 8-12 | 6 | 3535 |
| 6 | 5.0 mg/kg Tri-SM6.1-αvβ6-AD08243 | 1, 3, 5, and 8 | HDM | Days 8-12 | 6 | 3535 |
| 7 | 5.0 mg/kg Tri-SM6.1-αvβ6-AD08244 | 1, 3, 5, and 8 | HDM | Days 8-12 | 6 | 3535 |
| 8 | 5.0 mg/kg Tri-SM6.1-αvβ6-AD08175 | 1, 3, 5, and 8 | HDM | Days 8-12 | 6 | 3535 |
| 9 | 5.0 mg/kg Tri-SM6.1-αvβ6-AD08176 | 1, 3, 5, and 8 | HDM | Days 8-12 | 6 | 3535 |
| 10 | 5.0 mg/kg Tri-SM6.1-αvβ6-AD08177 | 1, 3, 5, and 8 | HDM | Days 8-12 | 6 | 3535 |

For the mice in Groups 1-5, on study days 1, 3, 5, and 8, female Balb/c mice were administered a single dose of 50 microliters via a microsprayer device (Penn Century, Philadelphia, PA) suitable for intratracheal (IT) administration of isotonic saline or 5.0 mg/kg the respective MUC5AC RNAi agent formulated in isotonic saline as noted in Table 19.

As shown in Table 19, each of the MUC5AC RNAi agents (Groups 3-5) were conjugated to a tridentate small molecule αvβ6 epithelial cell targeting ligand (Tri-SM6.1, see FIG. 1) at the 5' terminal end of the sense strand. The chemically modified sequences for MUC5AC RNAi agents AD08173 and AD08174 (Groups 4 and 5) are shown in Table 7B (showing duplex), Table 3 (showing respective antisense strand), and Table 5 (showing respective sense strand with linker but without tridentate small molecule αvβ6 epithelial cell targeting ligand (Tri-SM6.1)). Each of the MUC5AC RNAi agents with sequences targeting position 3535 have a mismatch in what is understood to be an important location from the mouse gene, and therefore it is expected that the MUC5AC RNAi agents would show little to no inhibitory activity in view of the mismatch.

AD07022 has mouse-specific sequences that do not have homology with the human MUC5AC gene, and were chemically modified as shown above in Example 5.

On each of Days 8 through 12, the mice were administered a single dose intranasally (IN) using a pipette with 25 microliters of isotonic saline (Group 1 only) or 50 micrograms of house dust mite formulated in isotonic saline (referred to in Table 19 as HDM).

Mice were sacrificed on study day 15, and total RNA was isolated from both lungs following collection and homogenization. Mouse Muc5ac mRNA expression was quantitated by probe-based quantitative PCR, normalized to mouse beta-actin expression, and expressed as fraction of vehicle control group (geometric mean, +/−95% confidence interval).

TABLE 20

Average Relative Mouse MUC5AC mRNA at Sacrifice (Day 15) in Example 7

| Group ID | Average Relative mMuc5ac mRNA | Low (error) | High (error) |
|---|---|---|---|
| Group 1 (IT Saline & IN Saline) | 1.000 | 0.197 | 0.245 |
| Group 2 (IT Saline & IN HDM) | 132.247 | 31.248 | 40.917 |
| Group 3 (IT 5 mg/kg Tri-SM6.1-αvβ6-AD07022 & IN HDM) | 13.139 | 2.426 | 2.975 |
| Group 4 (IT 5 mg/kg Tri-SM6.1-αvβ6-AD08173 & IN HDM) | 96.522 | 13.056 | 15.098 |
| Group 5 (IT 5 mg/kg Tri-SM6.1-αvβ6-AD08174 & IN HDM) | 57.983 | 15.132 | 20.476 |
| Group 6 (IT 5 mg/kg Tri-SM6.1-αvβ6-AD08243 & IN HDM) | 55.592 | 8.761 | 10.400 |
| Group 7 (IT 5 mg/kg Tri-SM6.1-αvβ6-AD08244 & IN HDM) | 75.149 | 17.661 | 23.087 |
| Group 8 (IT 5 mg/kg Tri-SM6.1-αvβ6-AD08175 & IN HDM) | 75.420 | 10.876 | 12.708 |
| Group 9 (IT 5 mg/kg Tri-SM6.1-αvβ6-AD08176 & IN HDM) | 72.203 | 12.062 | 14.482 |
| Group 10 (IT 5 mg/kg Tri-SM6.1-αvβ6-AD08177 & IN HDM) | 67.222 | 12.063 | 14.701 |

The data were normalized to the IT and IN saline-only dosed group (Group 1). As noted above, given the nature of the mismatch to the mouse gene for the MUC5AC RNAi agents in Groups 4 and 5 (targeting position 3535 of the human gene), minimal inhibition is expected. As shown in the data in Table 20 above, the HDM mouse model performed as expected with respect to promoting an increase in MUC5AC expression after exposure to HDM, as shown in Groups 1 and 2. Unexpectedly, the MUC5AC RNAi agents targeting position 3535 still showed moderate levels of inhibition despite the mismatch to the mouse gene, indicating that MUC5AC RNAi agents targeting this position may be viable as human therapeutic candidates.

Example 8. In Vivo Intratracheal Administration of MUC5AC RNAi Agents in the HDM Model The HDM induced allergic asthma mouse model described in Example 4, above, was used. The following Table 17 sets forth the dosing Groups:

TABLE 21

MUC5AC RNAi Agent and Dosing for Example 8.

| GROUP | IT Dose Administered | Study Days IT Administered | IN Dose Administered | Study Days IN Dose Administered | Animals Per Group | Targeted Gene Position |
|---|---|---|---|---|---|---|
| 1 | Saline | 1 and 7 | Saline | Days 7-11 | 6 | N/A |
| 2 | Saline | 1 and 7 | HDM | Days 7-11 | 6 | N/A |
| 3 | 5.0 mg/kg Tri-SM6.1-αvβ6-AD07022 | 1, 2, 4 and 7 | HDM | Days 7-11 | 6 | Mouse-specific |
| 4 | 5.0 mg/kg Tri-SM6.1-αvβ6-AD07022 | 1 and 7 | HDM | Days 7-11 | 6 | Mouse-specific |
| 5 | 2.5 mg/kg Tri-SM6.1-αvβ6-AD07022 | 1 and 7 | HDM | Days 7-11 | 6 | Mouse-specific |
| 6 | 1.0 mg/kg Tri-SM6.1-αvβ6-AD07022 | 1 and 7 | HDM | Days 7-11 | 6 | Mouse-specific |
| 7 | 5.0 mg/kg Tri-SM6.1-αvβ6-AD08089 | 1, 2, 4 and 7 | HDM | Days 7-11 | 6 | 15052 |
| 8 | 5.0 mg/kg Tri-SM6.1-αvβ6-AD08089 | 1 and 7 | HDM | Days 7-11 | 6 | 15052 |
| 9 | 2.5 mg/kg Tri-SM6.1-αvβ6-AD08089 | 1 and 7 | HDM | Days 7-11 | 6 | 15052 |
| 10 | 1.0 mg/kg Tri-SM6.1-αvβ6-AD08089 | 1 and 7 | HDM | Days 7-11 | 6 | 15052 |
| 11 | 1.0 mg/kg Tri-SM6.1-αvβ6-AD08089 | 1 | HDM | Days 7-11 | 6 | 15052 |

Female Balb/c mice were administered a single dose of 50 microliters via a microsprayer device (Penn Century, Philadelphia, PA) suitable for intratracheal (IT) administration of isotonic saline or an MUC5AC RNAi agent formulated in isotonic saline, on the dates and at the concentrations set forth in Table 21 above.

As shown in Table 21, each of the MUC5AC RNAi agents (Groups 3-11) were conjugated to a tridentate small molecule αvβ6 epithelial cell targeting ligand (see FIG. 1) at the 5' terminal end of the sense strand. The chemically modified sequences for MUC5AC RNAi agents AD08089 is shown in Table 7B (showing duplex), Table 3 (showing respective antisense strand), and Table 5 (showing respective sense strand with linker but without tridentate small molecule αvβ6 epithelial cell targeting ligand).

AD07022 has mouse-specific sequences that do not have homology with the human MUC5AC gene, and were chemically modified as shown above in Example 5.

On each of Days 7 through 11, the mice were administered a single dose intranasally (IN) using a pipette with 25 microliters of isotonic saline (Group 1) or 50 micrograms of house dust mite formulated in isotonic saline (referred to in Table 21 as HDM).

Mice were sacrificed on study day 14, and total RNA was isolated from both lungs following collection and homogenization. Mouse Muc5ac mRNA expression was quantitated by probe-based quantitative PCR, normalized to mouse beta-actin expression, and expressed as fraction of vehicle control group (geometric mean, +/−95% confidence interval).

TABLE 22

Average Relative Mouse MUC5AC mRNA at Sacrifice (Day 14) in Example 8

| Group ID | Average Relative mMuc5ac mRNA | Low (error) | High (error) |
|---|---|---|---|
| Group 1 (IT Saline & IN Saline) | 1.000 | 0.315 | 0.459 |
| Group 2 (IT Saline & IN HDM) | 112.848 | 44.187 | 72.623 |
| Group 3 (IT 5.0 mg/kg Tri-SM6.1-αvβ6-AD07022 (days 1, 2, 4, & 7) & IN HDM) | 12.455 | 3.896 | 5.669 |
| Group 4 (IT 5.0 mg/kg Tri-SM6.1-αvβ6-AD07022 (days 1 & 7) & IN HDM) | 16.521 | 4.908 | 6.982 |
| Group 5 (IT 2.5 mg/kg Tri-SM6.1-αvβ6-AD07022 & IN HDM) | 26.846 | 5.096 | 6.290 |
| Group 6 (IT 1.0 mg/kg Tri-SM6.1-αvβ6-AD07022 & IN HDM) | 26.521 | 9.295 | 14.311 |
| Group 7 (IT 5.0 mg/kg Tri-SM6.1-αvβ6-AD08089 (days 1, 2, 4, & 7) & IN HDM) | 10.978 | 3.101 | 4.322 |
| Group 8 (IT 5.0 mg/kg Tri-SM6.1-αvβ6-AD08089 (days 1 & 7) & IN HDM) | 17.629 | 6.752 | 10.944 |
| Group 9 (IT 2.5 mg/kg Tri-SM6.1-αvβ6-AD08089 & IN HDM) | 17.746 | 4.647 | 6.296 |

TABLE 22-continued

| Average Relative Mouse MUC5AC mRNA at Sacrifice (Day 14) in Example 8 | | | |
|---|---|---|---|
| Group ID | Average Relative mMuc5ac mRNA | Low (error) | High (error) |
| Group 10 (IT 1.0 mg/kg Tri-SM6.1-αvβ6-AD08089 & IN HDM) | 21.106 | 4.109 | 5.103 |
| Group 11 (IT 1.0 mg/kg Tri-SM6.1-αvβ6-AD08089 (day 1 only) & IN HDM) | 42.413 | 14.428 | 21.868 |

The data were normalized to the IT and IN saline-only dosed group (Group 1). As shown in the data in Table 22 above, the HDM mouse model performed as expected with respect to promoting an increase in MUC5AC expression after exposure to HDM. The data show that AD08089, which has nucleotide sequences targeting position 15052 of the MUC5AC gene and has homology to both the human and mouse gene transcript, provided substantial inhibition of MUC5AC and was generally comparable to the highly active mouse-specific MUC5AC RNAi agent of AD07022.

Example 9. In Vivo Inhaled Aerosolized Administration of MUC5AC RNAi Agents in Cynomolgus Monkeys On study day 1, male cynomolgus monkeys were administered a single dose on each of days 1, 8, and 15 at 1 mg/kg pulmonary deposited dose (PDD) of the MUC5AC RNAi agent AC001305 or AC001306. Using a vibrating mesh nebulizer (Aeroneb Solo), aerosol was delivered to restrained, anesthetized monkeys intubated intratracheally. Intubated animals were connected to a ventilator, which was used to control respiratory minute volume. Test article aerosol was generated via an Aeroneb Solo mesh nebulizer connected in-line with the exposure system. Exposures times were determined from aerosol trials in which the efficiency of the system was determined by placing a filter at the end of the endotracheal tube, collecting the aerosol during the course of the exposure. The MUC5AC RNAi agent was conjugated to a tridentate small molecule αvβ6 epithelial cell targeting ligand (see FIG. 1) at the 5' terminal end of the sense strand, formulated in isotonic saline. The chemically modified sequences for MUC5AC RNAi agents AC001305 and AC001306 are shown in Table 11. The antisense strand sequence of AC001305 is also shown as AM12165 in Table 3, and the antisense strand sequence of AC001306 is also shown as AM12166 in Table 3, both of which target position 4993 of the MUC5AC gene.

The dosing groups were as described in the following Table 23:

TABLE 23

| MUC5AC RNAi Agent and Dosing for Example 9 Group ID |
|---|
| Group 1 (isotonic saline on Days 1, 8, 15 |
| Group 2 (1.0 mg/kg pulmonary deposited dose AC001305 on Days 1, 8, 15 |
| Group 3 (1.0 mg/kg pulmonary deposited dose AC001306 on Days 1, 8, 15 |

Two (2) monkeys were dosed per group. Monkeys were sacrificed on study day 22, and total RNA was isolated from lung samples following collection and homogenization. The data in Table 24, below, shows mRNA expression sampled from the distal left caudal lobe. Cynomolgus monkey MUC5AC mRNA expression was quantitated by probe-based quantitative PCR, normalized to Cynomolgus monkey beta-actin expression, and expressed as fraction of vehicle control group (geometric mean, +/−95% confidence interval).

TABLE 24A

| Cynomolgus Monkey Mucosal Tissue Muc5ac mRNA Relative Expression at Sacrifice in Example 9 | | | |
|---|---|---|---|
| Group ID | Relative cMuc5ac mRNA Expression (n = 2) | Low (error) | High (error) |
| Group 1 (isotonic saline) | 1.000 | 0.386 | 0.628 |
| Group 2 (1.0 mg/kg deposited dose AC001305 on Days 1, 8, 15) | 0.034 | 0.010 | 0.015 |
| Group 3 (1.0 mg/kg deposited dose AC001306 on Days 1, 8, 15 | 0.171 | 0.085 | 0.169 |

TABLE 24B

| Cynomolgus Monkey Right Cranial Hilar Muc5ac mRNA Relative Expression at Sacrifice in Example 9 | | | |
|---|---|---|---|
| Group ID | Relative cMuc5ac mRNA Expression (n = 2) | Low (error) | High (error) |
| Group 1 (isotonic saline) | 1.000 | 0.708 | 2.421 |
| Group 2 (1.0 mg/kg deposited dose AC001305 on Days 1, 8, 15) | 0.034 | 0.010 | 0.015 |
| Group 3 (1.0 mg/kg deposited dose AC001306 on Days 1, 8, 15 | 0.180 | 0.089 | 0.174 |

TABLE 24C

| Cynomolgus Monkey Right Cranial Mid Airway Muc5ac mRNA Relative Expression at Sacrifice in Example 9 | | | |
|---|---|---|---|
| Group ID | Relative cMuc5ac mRNA Expression (n = 2) | Low (error) | High (error) |
| Group 1 (isotonic saline) | 1.000 | 0.489 | 0.956 |
| Group 2 (1.0 mg/kg deposited dose AC001305 on Days 1, 8, 15) | 0.162 | 0.099 | 0.256 |
| Group 3 (1.0 mg/kg deposited dose AC001306 on Days 1, 8, 15 | 0.077 | 0.041 | 0.086 |

As reported in Tables 24A, 24B, and 24C above, the MUC5AC RNAi agents AC001305 and AC001306 both demonstrated Muc5ac mRNA knockdown in mucosal tissue, right cranial hilar, and right cranial mid airway.

Example 10. Aerosolized Administration of MUC5AC RNAi Agents in Sheep

Sheep exposed to inhaled *ascaris* antigen exhibit responses typical of allergic asthma, including an acute phase response (AR), late phase response (LR), and airway hyperreactivity (AHR) as shown by Abraham et. al. (Am Rev Respir Dis., 1983), and the model has been shown to respond well to standard of care therapies (Caniga, et. al., J Inflamm., 2013). Accordingly, the model may be used to determine the impact of sheep Muc5ac (sMuc5ac) mRNA silencing on airway mechanics and AHR upon treatment with MUC5AC RNAi agents. Test article delivery to intubated sheep, airway mechanics assessments detecting changes in pulmonary resistance ($R_L$) following challenge with *Ascaris suum* antigen, and AHR assessments by performing cumulative concentration response curves to inhaled carbachol were performed according to published procedures (Abraham et. al., J Clin Invest., 1994).

Two (2) *ascaris*-sensitive sheep with previously established responses to *Ascaris suum* challenge were administered 1 mg/kg pulmonary deposited dose levels of AC000480 on days 1, 8 and 15. The chemical structure of AC000480 is shown, for example, in Table 11 and is designed to target position 3535 on the MUC5AC gene. On day 21, AHR was assessed by determining the cumulative carbachol concentration (in breath units, BU) that increased $R_L$ to 400% over the post-1×PBS value ($PC_{400}$). On day 22, sheep were challenged with *Ascaris suum* extract, and $R_L$ was monitored out to 8 hours post-challenge. On day 23, AHR was again assessed in the same manner as on day 21. To monitor duration of effect, sheep were again challenged with *Ascaris suum* extract on day 51, bracketed on day 50 and day 52 with assessments of AHR.

TABLE 25

Airway Mechanics Results

| | | Control Trial (no treatment) | | | | Drug Trial: Day 22 | | | | Drug Trial: Day 51 | | | |
|---|---|---|---|---|---|---|---|---|---|---|---|---|---|
| | | Animal # | | | | Animal # | | | | Animal # | | | |
| Timepoint | | 2489 | 2497 | Mean | S.D. | 2489 | 2497 | Mean | S.D. | 2489 | 2497 | Mean | S.D. |
| Baseline | RL | 0.99 | 0.99 | 0.99 | 0.00 | 1.00 | 1.00 | 1.00 | 0.00 | 1.00 | 1.00 | 1.00 | 0.00 |
| Post-Ascaris | RL | 6.66 | 6.62 | 6.64 | 0.03 | 4.28 | 5.21 | 4.75 | 0.66 | 6.35 | 6.38 | 6.37 | 0.02 |
| | % | 573% | 569% | 571% | 3% | 328% | 421% | 375% | 66% | 535% | 538% | 537% | 2% |
| 1 h | RL | 4.51 | 4.40 | 4.46 | 0.08 | 2.35 | 3.59 | 2.97 | 0.88 | 4.60 | 4.61 | 4.61 | 0.01 |
| | % | 356% | 344% | 350% | 8% | 135% | 259% | 197% | 88% | 360% | 361% | 361% | 1% |
| 2 h | RL | 2.53 | 2.57 | 2.55 | 0.03 | 1.81 | 1.66 | 1.74 | 0.11 | 2.42 | 2.64 | 2.53 | 0.16 |
| | % | 156% | 160% | 158% | 3% | 81% | 66% | 74% | 11% | 142% | 164% | 153% | 16% |
| 3 h | RL | 1.55 | 1.53 | 1.54 | 0.01 | 1.37 | 1.36 | 1.37 | 0.01 | 1.68 | 1.62 | 1.65 | 0.04 |
| | % | 57% | 55% | 56% | 1% | 37% | 36% | 37% | 1% | 68% | 62% | 65% | 4% |
| 4 h | RL | 1.06 | 1.21 | 1.14 | 0.11 | 1.05 | 1.09 | 1.07 | 0.03 | 1.05 | 1.07 | 1.06 | 0.01 |
| | % | 7% | 22% | 15% | 11% | 5% | 9% | 7% | 3% | 5% | 7% | 6% | 1% |
| 5 h | RL | 1.52 | 1.66 | 1.59 | 0.10 | 1.14 | 1.19 | 1.17 | 0.04 | 1.64 | 1.55 | 1.60 | 0.06 |
| | % | 54% | 68% | 61% | 10% | 14% | 19% | 17% | 4% | 64% | 55% | 60% | 6% |
| 6 h | RL | 2.13 | 2.09 | 2.11 | 0.03 | 1.28 | 1.34 | 1.31 | 0.04 | 2.07 | 2.18 | 2.13 | 0.08 |
| | % | 115% | 111% | 113% | 3% | 28% | 34% | 31% | 4% | 107% | 118% | 113% | 8% |
| 6.5 h | RL | 2.26 | 2.21 | 2.24 | 0.04 | 1.51 | 1.49 | 1.50 | 0.01 | 2.22 | 2.26 | 2.24 | 0.03 |
| | % | 128% | 123% | 126% | 4% | 51% | 49% | 50% | 1% | 122% | 126% | 124% | 3% |
| 7 h | RL | 2.32 | 2.26 | 2.29 | 0.04 | 1.39 | 1.40 | 1.40 | 0.01 | 2.37 | 2.29 | 2.33 | 0.06 |
| | % | 134% | 128% | 131% | 4% | 39% | 40% | 40% | 1% | 137% | 129% | 133% | 6% |
| 7.5 h | RL | 2.12 | 2.16 | 2.14 | 0.03 | 1.27 | 1.35 | 1.31 | 0.06 | 2.32 | 2.05 | 2.19 | 0.19 |
| | % | 114% | 118% | 116% | 3% | 27% | 35% | 31% | 6% | 132% | 105% | 119% | 19% |
| 8 h | RL | 2.08 | 2.03 | 2.06 | 0.04 | 1.16 | 1.28 | 1.22 | 0.08 | 2.12 | 2.13 | 2.13 | 0.01 |
| | % | 110% | 105% | 108% | 4% | 16% | 28% | 22% | 8% | 112% | 113% | 113% | 1% |

TABLE 26

AHR Results

| | BU Carbachol to Produce PC400 | |
|---|---|---|
| Sheep # | 24 h pre-ascaris | 24 h post Ascaris |
| Control Trial | | |
| 2489 | 24 | 13 |
| 2497 | 31 | 13 |
| Drug Trial: Day 22 | | |
| 2489 | 25 | 26 |
| 2497 | 26 | 25 |
| Drug Trial: Day 51 | | |
| 2489 | 26 | 13 |
| 2497 | 29 | 12 |

As shown in Table 25, treatment with AC000480 resulted in attenuation of AR as well as LR upon challenge on day 22. For example, untreated sheep display a mean LR increase of 126% in $R_L$ at 6.5 h compared to baseline, where AC000480 treated sheep on day 22 challenge show a more attenuated LR increase of 50% in $R_L$ at 6.5 h compared to baseline. In addition, 24 h after the day 22 *ascaris* challenge both AC000480 treated sheep showed no signs of *ascaris* induced airway hyperresponsiveness, as shown by equivalent number of carbachol breath units required to produce $PC_{400}$. In contrast, in the control trial without AC000480 treatment, sheep required approximately half the amount of carbachol breath units to induce $PC_{400}$ post-*ascaris* challenge, signifying airway hyperresponsiveness.

With no additional dosing after day 15, sheep returned to baseline airway mechanics and AHR upon the day 51 *ascaris* challenge.

Example 11. Aerosolized Administration of MUC5AC RNAi Agents in Sheep

The sheep model of allergic asthma airway inflammation described in example 10, above, was used. Three (3) *ascaris* sensitive sheep with previously established responses to *Ascaris suum* challenge were administered 1 mg/kg pulmonary deposited dose levels of AC000482 on days 1, 8 and 15. The chemical structure of AC000482 is shown, for example, in Table 11 and is designed to target position 3535 on the MUC5AC gene. On day 21, AHR was assessed by determining the cumulative carbachol concentration (in breath units, BU) that increased $R_L$ to 400% over the post-1×PBS value ($PC_{400}$). On day 22, sheep were challenged with *Ascaris suum* extract, and $R_L$ was monitored out to 8 h post-challenge. On day 23, AHR was again assessed as on day 21.

As shown in Table 27, treatment with AC000482 resulted in minimal attenuation of AR but robust attenuation of LR upon challenge on day 22. For example, untreated sheep display a mean LR increase of 1210% in $R_L$ at 6.5 h compared to baseline, where AC000482 treated sheep on day 22 challenge show a more attenuated LR increase of 56% in $R_L$ at 6.5 h compared to baseline. In addition, 24 h after the day 22 *ascaris* challenge all AC000482 treated sheep showed no signs of *ascaris* induced airway hyperresponsiveness, as shown by equivalent number of carbachol breath units required to produce $PC_{400}$. In contrast, in the control trial without AC000482 treatment, sheep required approximately half the amount of carbachol breath units to induce $PC_{400}$ post-*ascaris* challenge, signifying airway hyperresponsiveness.

TABLE 27

Airway Mechanics Results

| | | Control (no treatment) | | | | | Drug Trial: Day 22 | | | | |
|---|---|---|---|---|---|---|---|---|---|---|---|
| | | Animal # | | | Mean | | Animal # | | | Mean | |
| Timepoint | | 2485 | 2515 | 2535 | Mean | S.D. | 2485 | 2515 | 2535 | Mean | S.D. |
| Baseline | RL | 0.99 | 1.00 | 1.00 | 1.00 | 0.01 | 1.00 | 1.00 | 1.00 | 1.00 | 0.00 |
| Post- | RL | 6.43 | 6.94 | 6.89 | 6.75 | 0.28 | 5.49 | 6.44 | 6.09 | 6.01 | 0.48 |
| Ascaris | % | 549% | 594% | 589% | 577% | 24% | 449% | 544% | 509% | 501% | 48% |
| 1 h | RL | 4.10 | 4.67 | 4.40 | 4.39 | 0.29 | 4.68 | 4.27 | 4.10 | 4.35 | 0.30 |
| | % | 314% | 367% | 340% | 340% | 26% | 368% | 327% | 310% | 335% | 30% |
| 2 h | RL | 2.62 | 2.51 | 2.64 | 2.59 | 0.07 | 2.81 | 2.10 | 2.05 | 2.32 | 0.43 |
| | % | 165% | 151% | 164% | 160% | 8% | 181% | 110% | 105% | 132% | 43% |
| 3 h | RL | 1.65 | 1.46 | 1.58 | 1.56 | 0.10 | 1.53 | 1.37 | 1.31 | 1.40 | 0.11 |
| | % | 67% | 46% | 58% | 57% | 10% | 53% | 37% | 31% | 40% | 11% |
| 4 h | RL | 1.08 | 1.09 | 1.05 | 1.07 | 0.02 | 1.09 | 1.05 | 1.04 | 1.06 | 0.03 |
| | % | 9% | 9% | 5% | 8% | 2% | 9% | 5% | 4% | 6% | 3% |
| 5 h | RL | 1.57 | 1.53 | 1.57 | 1.56 | 0.02 | 1.27 | 1.15 | 1.18 | 1.20 | 0.06 |
| | % | 59% | 53% | 57% | 56% | 3% | 27% | 15% | 18% | 20% | 6% |
| 6 h | RL | 1.87 | 2.10 | 2.03 | 2.00 | 0.12 | 1.42 | 1.32 | 1.23 | 1.32 | 0.10 |
| | % | 89% | 110% | 103% | 101% | 11% | 42% | 32% | 23% | 32% | 10% |
| 6.5 h | RL | 2.16 | 2.30 | 2.15 | 2.20 | 0.08 | 1.66 | 1.55 | 1.46 | 1.56 | 0.10 |
| | % | 118% | 130% | 115% | 121% | 8% | 66% | 55% | 46% | 56% | 10% |
| 7 h | RL | 2.20 | 2.21 | 2.23 | 2.21 | 0.02 | 1.54 | 1.41 | 1.34 | 1.43 | 0.10 |
| | % | 122% | 121% | 123% | 122% | 1% | 54% | 41% | 34% | 43% | 10% |
| 7.5 h | RL | 2.27 | 2.11 | 2.19 | 2.19 | 0.08 | 1.33 | 1.24 | 1.18 | 1.25 | 0.08 |
| | % | 129% | 111% | 119% | 120% | 9% | 33% | 24% | 18% | 25% | 8% |
| 8 h | RL | 2.10 | 2.06 | 2.14 | 2.10 | 0.04 | 1.25 | 1.16 | 1.23 | 1.21 | 0.05 |
| | % | 112% | 106% | 114% | 111% | 4% | 25% | 16% | 23% | 21% | 5% |

TABLE 28

AHR results

| | BU Carbachol to Produce PC400 | |
|---|---|---|
| Sheep # | 24 h pre-ascaris | 24 h post Ascaris |
| Control Trial | | |
| 2485 | 13 | 6 |
| 2515 | 22 | 12 |
| 2535 | 14 | 6 |
| Drug Trial: Day 22 | | |
| 2485 | 13 | 12 |
| 2515 | 24 | 24 |
| 2535 | 11 | 11 |

Example 12. Aerosolized Administration of MUC5AC RNAi Agents in Sheep

The sheep model of allergic asthma airway inflammation described in example 10, above, was used. Six (6) *ascaris* sensitive sheep with previously established responses to *Ascaris suum* challenge were administered either 0.5 mg/kg pulmonary deposited dose levels of AC000482 (n=3) of 0.25 mg/kg pulmonary deposited dose levels of AC000482 on days 1, 8 and 15. On day 21, AHR was assessed by determining the cumulative carbachol concentration (in breath units, BU) that increased $R_L$ to 400% over the post-1×PBS value ($PC_{400}$). On day 22, sheep were challenged with *Ascaris suum* extract, and $R_L$ was monitored out to 8 h post-challenge. On day 23, AHR was again assessed as on day 21.

TABLE 29

Airway mechanics results, 0.5 mg/kg dose level

| | | Control (no treatment) | | | | | Drug Trial: Day 22 | | | | |
|---|---|---|---|---|---|---|---|---|---|---|---|
| | | Animal # | | | Mean | | Animal # | | | Mean | |
| Timepoint | | 2489 | 2497 | 2520 | Mean | S.D. | 2489 | 2497 | 2520 | Mean | S.D. |
| Baseline | RL | 0.99 | 0.99 | 0.99 | 0.99 | 0.00 | 1.00 | 1.00 | 1.00 | 1.00 | 0.00 |
| Post- | RL | 6.66 | 6.62 | 7.37 | 6.88 | 0.42 | 6.23 | 6.38 | 7.10 | 6.57 | 0.47 |
| Ascaris | % | 573% | 569% | 644% | 595% | 43% | 523% | 538% | 610% | 557% | 47% |
| 1 h | RL | 4.51 | 4.40 | 4.49 | 4.47 | 0.06 | 4.15 | 4.06 | 4.33 | 4.18 | 0.14 |
| | % | 356% | 344% | 354% | 351% | 6% | 315% | 306% | 333% | 318% | 14% |
| 2 h | RL | 2.53 | 2.57 | 2.37 | 2.49 | 0.11 | 2.25 | 2.31 | 2.10 | 2.22 | 0.11 |
| | % | 156% | 160% | 139% | 152% | 11% | 125% | 131% | 110% | 122% | 11% |
| 3 h | RL | 1.55 | 1.53 | 1.53 | 1.54 | 0.01 | 1.41 | 1.46 | 1.35 | 1.41 | 0.06 |
| | % | 57% | 55% | 55% | 55% | 1% | 41% | 46% | 35% | 41% | 6% |
| 4 h | RL | 1.06 | 1.21 | 1.12 | 1.13 | 0.08 | 1.07 | 1.02 | 1.04 | 1.04 | 0.03 |
| | % | 7% | 22% | 13% | 14% | 8% | 7% | 2% | 4% | 4% | 3% |
| 5 h | RL | 1.52 | 1.66 | 1.54 | 1.57 | 0.08 | 1.21 | 1.33 | 1.38 | 1.31 | 0.09 |
| | % | 54% | 68% | 56% | 59% | 8% | 21% | 33% | 38% | 31% | 9% |
| 6 h | RL | 2.13 | 2.09 | 2.03 | 2.08 | 0.05 | 1.46 | 1.56 | 1.52 | 1.51 | 0.05 |
| | % | 115% | 111% | 105% | 110% | 5% | 46% | 56% | 52% | 51% | 5% |
| 6.5 h | RL | 2.26 | 2.21 | 2.21 | 2.23 | 0.03 | 1.68 | 1.72 | 1.67 | 1.69 | 0.03 |
| | % | 128% | 123% | 123% | 125% | 3% | 68% | 72% | 67% | 69% | 3% |
| 7 h | RL | 2.32 | 2.26 | 2.30 | 2.29 | 0.03 | 1.62 | 1.68 | 1.61 | 1.64 | 0.04 |
| | % | 134% | 128% | 132% | 132% | 3% | 62% | 68% | 61% | 64% | 4% |
| 7.5 h | RL | 2.12 | 2.16 | 2.20 | 2.16 | 0.04 | 1.30 | 1.41 | 1.48 | 1.40 | 0.09 |
| | % | 114% | 118% | 122% | 118% | 4% | 30% | 41% | 48% | 40% | 9% |
| 8 h | RL | 2.08 | 2.03 | 2.12 | 2.08 | 0.05 | 1.25 | 1.26 | 1.13 | 1.21 | 0.07 |
| | % | 110% | 105% | 114% | 110% | 5% | 25% | 26% | 13% | 21% | 7% |

TABLE 30

Airway mechanics results, 0.25 mg/kg dose level

| | | Control (no treatment) | | | | | Drug Trial: Day 22 | | | | |
|---|---|---|---|---|---|---|---|---|---|---|---|
| | | Animal # | | | Mean | | Animal # | | | Mean | |
| Timepoint | | 2457 | 2517 | 2539 | Mean | S.D. | 2457 | 2517 | 2539 | Mean | S.D. |
| Baseline | RL | 1.00 | 1.01 | 1.00 | 1.00 | 0.01 | 1.00 | 1.00 | 1.00 | 1.00 | 0.00 |
| Post- | RL | 6.63 | 7.29 | 6.03 | 6.65 | 0.63 | 6.50 | 7.03 | 6.26 | 6.60 | 0.39 |
| Ascaris | % | 563% | 622% | 503% | 563% | 59% | 550% | 603% | 526% | 560% | 39% |
| 1 h | RL | 4.15 | 4.26 | 4.50 | 4.30 | 0.18 | 4.09 | 4.10 | 4.11 | 4.10 | 0.01 |
| | % | 315% | 322% | 350% | 329% | 19% | 309% | 310% | 311% | 310% | 1% |
| 2 h | RL | 2.73 | 2.47 | 2.59 | 2.60 | 0.13 | 2.23 | 2.33 | 2.46 | 2.34 | 0.12 |
| | % | 173% | 145% | 159% | 159% | 14% | 123% | 133% | 146% | 134% | 12% |
| 3 h | RL | 1.54 | 1.37 | 1.62 | 1.51 | 0.13 | 1.45 | 1.27 | 1.54 | 1.42 | 0.14 |
| | % | 54% | 36% | 62% | 51% | 14% | 45% | 27% | 54% | 42% | 14% |
| 4 h | RL | 1.17 | 1.08 | 1.03 | 1.09 | 0.07 | 1.07 | 1.03 | 1.04 | 1.05 | 0.02 |
| | % | 17% | 7% | 3% | 9% | 7% | 7% | 3% | 4% | 5% | 2% |
| 5 h | RL | 1.69 | 1.61 | 1.29 | 1.53 | 0.21 | 1.43 | 1.21 | 1.32 | 1.32 | 0.11 |
| | % | 69% | 59% | 29% | 52% | 21% | 43% | 21% | 32% | 32% | 11% |
| 6 h | RL | 2.04 | 2.14 | 2.26 | 2.15 | 0.11 | 1.62 | 1.51 | 1.57 | 1.57 | 0.06 |
| | % | 104% | 112% | 126% | 114% | 11% | 62% | 51% | 57% | 57% | 6% |
| 6.5 h | RL | 2.18 | 2.36 | 2.14 | 2.23 | 0.12 | 1.87 | 1.78 | 1.83 | 1.83 | 0.05 |
| | % | 118% | 134% | 114% | 122% | 10% | 87% | 78% | 83% | 83% | 5% |
| 7 h | RL | 2.12 | 2.52 | 2.30 | 2.31 | 0.20 | 1.93 | 1.89 | 1.86 | 1.89 | 0.04 |
| | % | 112% | 150% | 130% | 131% | 19% | 93% | 89% | 86% | 89% | 4% |
| 7.5 h | RL | 2.17 | 2.35 | 2.21 | 2.24 | 0.09 | 1.74 | 1.67 | 1.68 | 1.70 | 0.04 |
| | % | 117% | 133% | 121% | 124% | 8% | 74% | 67% | 68% | 70% | 4% |
| 8 h | RL | 2.18 | 2.30 | 2.17 | 2.22 | 0.07 | 1.52 | 1.45 | 1.55 | 1.51 | 0.05 |
| | % | 118% | 128% | 117% | 121% | 6% | 52% | 45% | 55% | 51% | 5% |

TABLE 31

| AHR results, 0.5 mg/kg dose level | | |
|---|---|---|
| | BU Carbachol to Produce PC400 | |
| Sheep # | 24 h pre-ascaris | 24 h post Ascaris |
| Control Trial | | |
| 2489 | 24 | 13 |
| 2497 | 31 | 13 |
| 2520 | 26 | 13 |
| Drug Trial: Day 22 | | |
| 2489 | 26 | 25 |
| 2497 | 26 | 24 |
| 2520 | 27 | 25 |

TABLE 32

| AHR results, 0.25 mg/kg dose level | | |
|---|---|---|
| | BU Carbachol to Produce PC400 | |
| Sheep # | 24 h pre-ascaris | 24 h post Ascaris |
| Control Trial | | |
| 2457 | 10 | 6 |
| 2517 | 28 | 13 |
| 2539 | 13 | 6 |
| Drug Trial: Day 22 | | |
| 2457 | 13 | 11 |
| 2517 | 26 | 25 |
| 2539 | 14 | 13 |

As shown in Table 29, treatment with AC000482 at 0.5 mg/kg dose level resulted in minimal attenuation of AR but robust attenuation of LR upon challenge on day 22. For example, untreated sheep display a mean LR increase of 125% in $R_L$ at 6.5 h compared to baseline, where AC000482 treated sheep on day 22 challenge show a more attenuated LR increase of 69% in $R_L$ at 6.5 h compared to baseline. In addition, 24 h after the day 22 *ascaris* challenge all AC000482 treated sheep showed no signs of *ascaris* induced airway hyperresponsiveness, as shown by similar number of carbachol breath units required to produce $PC_{400}$. In contrast, in the control trial without AC000482 treatment, sheep required approximately half the amount of carbachol breath units to induce $PC_{400}$ post-*ascaris* challenge, signifying airway hyperresponsiveness.

As shown in Table 30, treatment with AC000482 at 0.25 mg/kg dose level resulted in minimal attenuation of AR but robust attenuation of LR upon challenge on day 22. For example, untreated sheep display a mean LR increase of 122% in $R_L$ at 6.5 h compared to baseline, where AC000482 treated sheep on day 22 challenge show a more attenuated LR increase of 83% in $R_L$ at 6.5 h compared to baseline. In addition, 24 h after the day 22 *ascaris* challenge all AC000482 treated sheep showed no signs of *ascaris* induced airway hyperresponsiveness, as shown by similar number of carbachol breath units required to produce $PC_{400}$. In contrast, in the control trial without AC000482 treatment, sheep required approximately half the amount of carbachol breath units to induce $PC_{400}$ post-*ascaris* challenge, signifying airway hyperresponsiveness.

Collectively, the results demonstrate dose-responsive impacts of AC000482 treatment on airway mechanics following *ascaris* challenge. The results show that even at the lowest dose of AC000482, the impact on the late phase response is still substantial enough to block airway hyperresponsiveness 24 h post challenge.

Example 13. Aerosolized Administration of MUC5AC RNAi Agents in Sheep

The sheep model of allergic asthma airway inflammation described in example 10, above, was used. Six (6) *ascaris* sensitive sheep with previously established responses to *Ascaris suum* challenge were administered, on days 1, 8 and 15, with either 1.0 mg/kg pulmonary deposited dose levels of AC000480 or 1.0 mg/kg pulmonary deposited dose of a negative control siRNA conjugate that included the same targeting ligand but is unable to load into the RISC complex and therefore is unable to mediate RNA interference gene silencing. On day 21, AHR was assessed by determining the cumulative carbachol concentration (in breath units, BU) that increased $R_L$ to 400% over the post-1×PBS value ($PC_{400}$). On day 22, sheep were challenged with *Ascaris suum* extract, and $R_L$ was monitored out to 8 h post-challenge. On day 23, AHR was again assessed as on day 21. Sheep dosed with AC000480 attenuated allergen-induced late-phase reaction and airway hyperresponsiveness in a dose dependent manner, while similar exposure of the negative control conjugate did not attenuate allergen-induced changes in airway mechanics.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. An RNAi agent for inhibiting expression of a Mucin 5AC gene, comprising:

an antisense strand comprising the nucleobase sequence (SEQ ID NO: 79)
UUGUAGUAGUCGCAGAACA;

and a sense strand comprising a nucleotide sequence that is at least partially complementary to the antisense strand.

2. The RNAi agent of claim 1, wherein at least one nucleotide of the RNAi agent is a modified nucleotide or includes a modified internucleoside linkage.

3. The RNAi agent of claim 2, wherein the modified nucleotide is selected from the group consisting of: 2'-O-methyl nucleotide, 2'-fluoro nucleotide, 2'-deoxy nucleotide, 2',3'-seco nucleotide mimic, locked nucleotide, 2'-F-arabino nucleotide, 2'-methoxyethyl nucleotide, abasic nucleotide, ribitol, inverted nucleotide, inverted 2'-O-methyl nucleotide, inverted 2'-deoxy nucleotide, 2'-amino-modified nucleotide, 2'-alkyl-modified nucleotide, morpholino nucleotide, vinyl phosphonate-containing nucleotide, cyclopropyl phosphonate-containing nucleotide, and 3'-O-methyl nucleotide.

4. The RNAi agent of claim 1, wherein the sense strand comprises the nucleobase sequence (SEQ ID NO: 568)
UGUUCUGCGACUACUACAA.

5. The RNAi agent of claim 1, wherein the sense strand is between 18 and 30 nucleotides in length, and the antisense strand is between 18 and 30 nucleotides in length.

6. The RNAi agent of claim 1, wherein the sense strand comprises one or two inverted abasic residues.

7. The RNAi agent of claim 1, wherein the antisense strand consists of consists essentially of, or comprises the nucleobase sequence (5'→3'):

(SEQ ID NO: 1525)
UUGUAGUAGUCGCAGAACAGC.

8. The RNAi agent of claim 1, wherein the antisense strand comprises, consists of, or consists essentially of a modified nucleotide sequence selected from one of the following nucleotide sequences (5'→3'):

(SEQ ID NO: 1127)
cPrpusUfsgsUfaGfuAfgUfcGfcAfgAfaCfaGfsc;

(SEQ ID NO: 1065)
usUfsgsUfaGfuAfgUfcGfcAfgAfaCfaGfsc;

wherein a, c, g, and u represent 2'-O-methyl adenosine, 2'-O-methyl cytidine, 2'-O-methyl guanosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; cPrpu represents a 5'-cyclopropyl phosphonate-2'-O-methyl uridine; s represents a phosphorothioate linkage; and wherein all of the nucleotides on the sense strand are modified nucleotides.

9. The RNAi agent of claim 1, wherein the sense strand comprises, consists of, or consists essentially of the modified nucleotide sequence (5'→3'):

(SEQ ID NO: 1265)
gscuguucuGfCfGfacuacuacaa;

wherein a, c, g, and u represent 2'-O-methyl adenosine, 2'-O-methyl cytidine, 2'-O-methyl guanosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; and s represents a phosphorothioate linkage; and wherein all of the nucleotides on the antisense strand are modified nucleotides.

10. The RNAi agent of claim 1, wherein the RNAi agent is linked to a targeting ligand.

11. The RNAi agent of claim 10, wherein the targeting ligand comprises the structure:

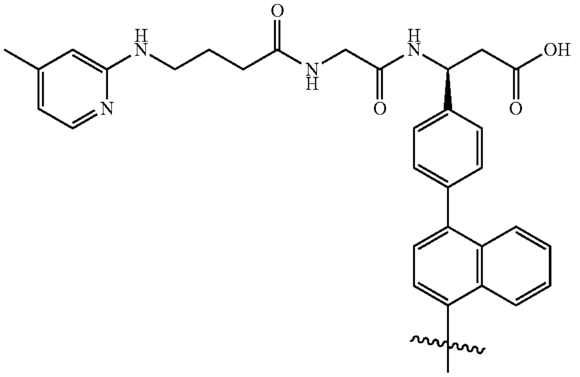 [SMILES: *c1ccc(-c2ccc([C@H](CC(=O)O)NC(=O)CNC(=O)CCCNc3cc(C)ccn3)cc2)c2ccccc12]

or a pharmaceutically acceptable salt thereof, or

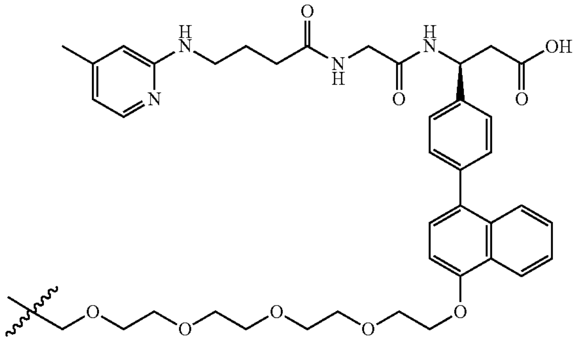 [SMILES: *COCCOCCOCCOCCOc1ccc(-c2ccc([C@H](CC(=O)O)NC(=O)CNC(=O)CCCNc3cc(C)ccn3)cc2)c2ccccc12]

or a pharmaceutically acceptable salt thereof, wherein ⌇ indicates the point of connection to the RNAi agent.

12. The RNAi agent of claim 10, wherein the RNAi agent is conjugated to a targeting ligand having the following structure:

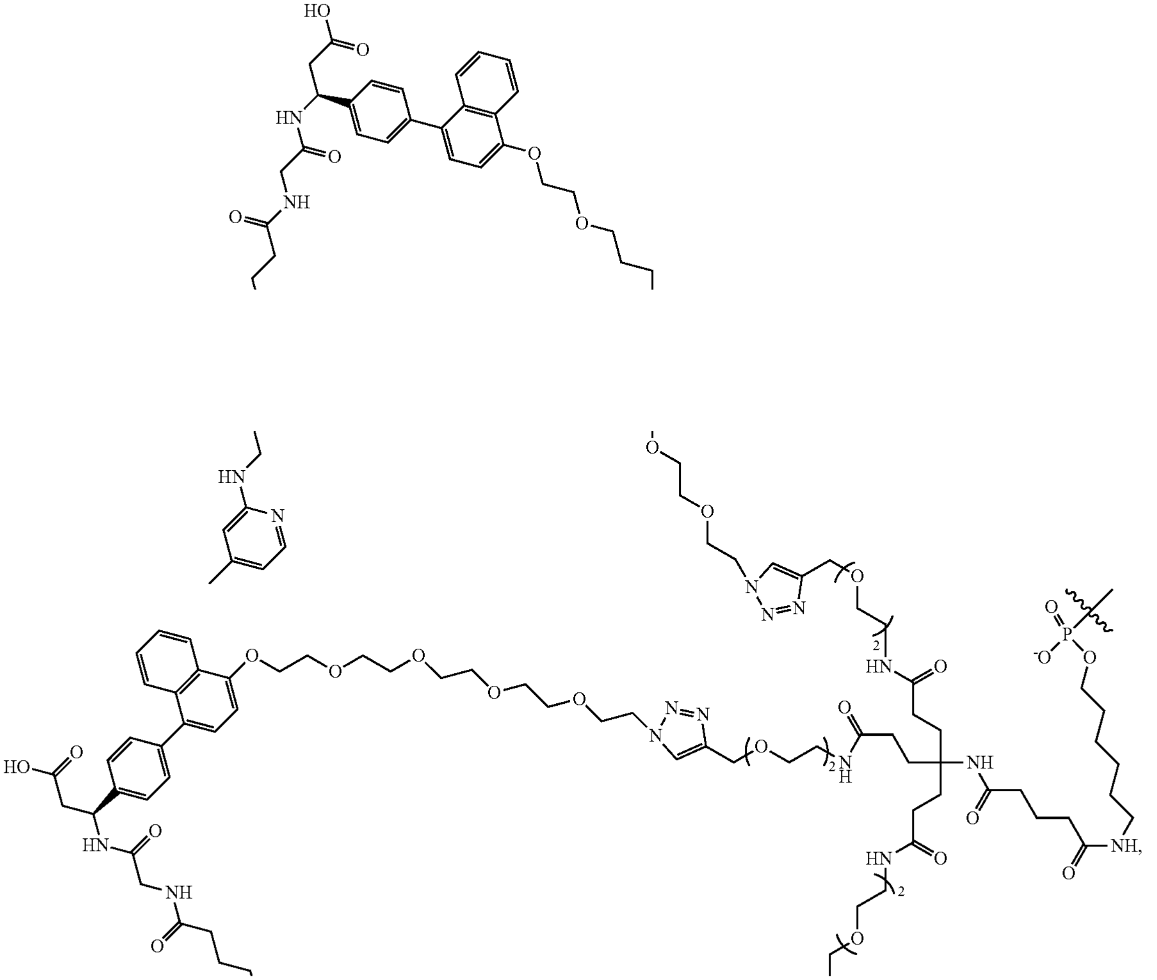

-continued

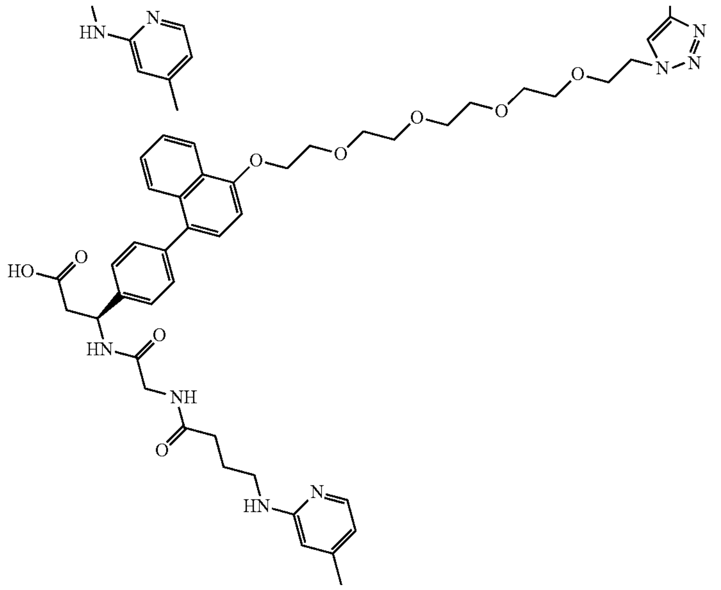

or a pharmaceutically acceptable salt thereof, wherein ⌇ indicates the point of connection to the RNAi agent.

13. A method for inhibiting expression of a MUC5AC gene in a cell, the method comprising introducing into a cell an effective amount of an RNAi agent of claim 1.

14. The method of claim 13, wherein the cell is within a subject.

15. The method of claim 14, wherein the RNAi agent is administered at a pulmonary deposited dose (PDD) of 0.01 mg/kg to 5.0 mg/kg of body weight of the subject.

16. The method of claim 14, wherein the RNAi agent is administered at a respirable delivered dose (RDD) of 0.01 mg/kg to 5.0 mg/kg of body weight of the subject.

17. The RNAi agent of claim 1, wherein the sense strand consists of the structure (5'→3'): Tri-SM6.1-αvβ6-(TA14) gscuguucuGfCfGfacuacuacaas(invAb) (SEQ ID NO:1491), and the antisense strand consists of the structure (5'→3'): cPrpusUfsgsUfaGfuAfgUfcGfcAfgAfaCfaGfsc (SEQ ID NO: 1127);

wherein a, c, g, and u represent 2'-O-methyl adenosine, 2'-O-methyl cytidine, 2'-O-methyl guanosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; s represents a phosphorothioate linkage; (invAb) represents an inverted abasic residue, and Tri-SM6.1-αvβ6-(TA14) represents:

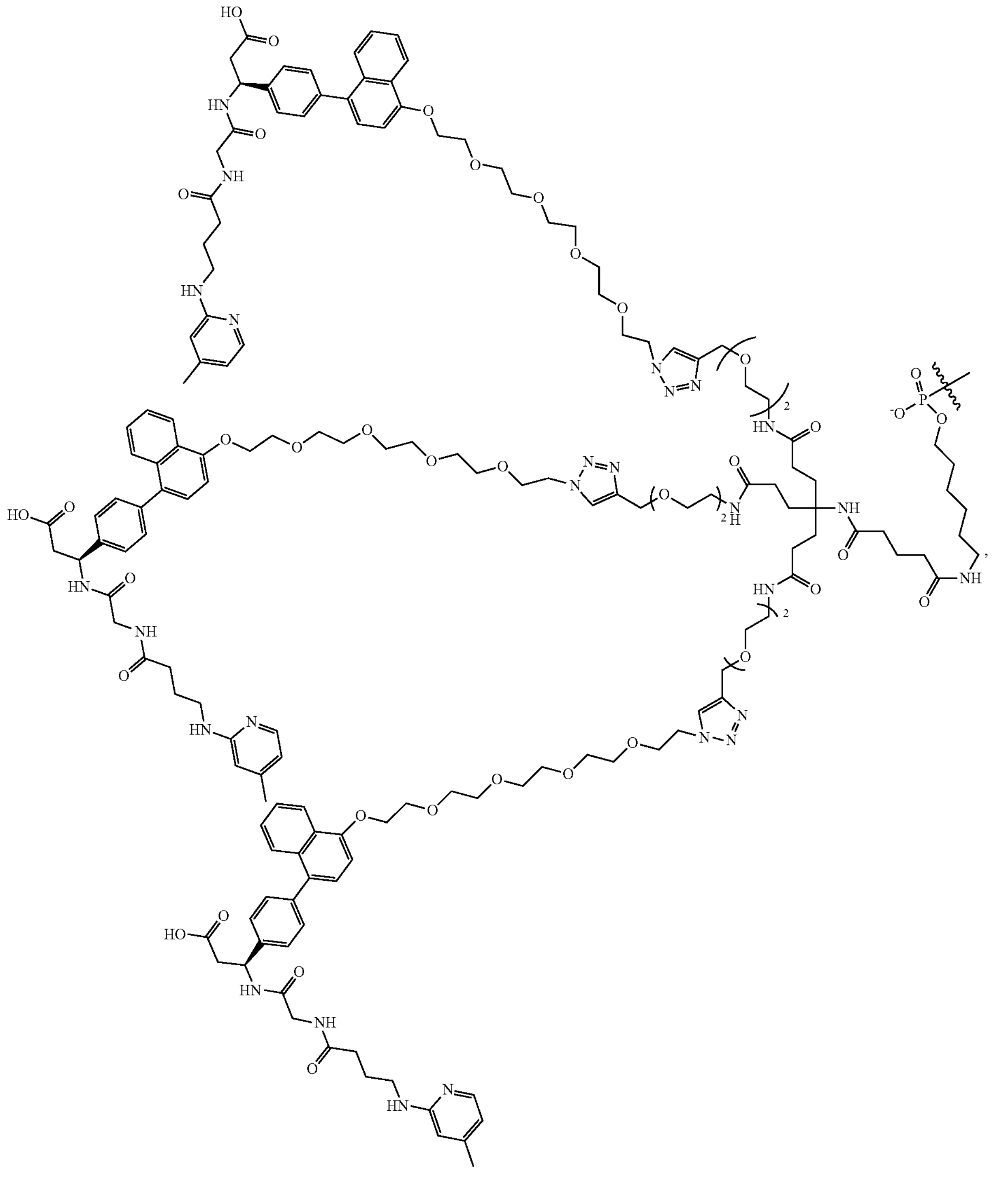

or a pharmaceutically acceptable salt thereof.

18. The RNAi agent of claim 1, wherein the sense strand consists of the structure (5'→3'): Tri-SM6.1-αvβ6-(TA14) gscuguucuGfCfGfacuacuacaas(invAb) (SEQ ID NO:1491), and the antisense strand consists of the structure (5'→3'): usUfsgsUfaGfuAfgUfcGfcAfgAfaCfaGfsc (SEQ ID NO: 1065);

wherein a, c, g, and u represent 2'-O-methyl adenosine, 2'-O-methyl cytidine, 2'-O-methyl guanosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; s represents a phosphorothioate linkage; (invAb) represents an inverted abasic residue, and Tri-SM6.1-αvβ6-(TA14) represents:

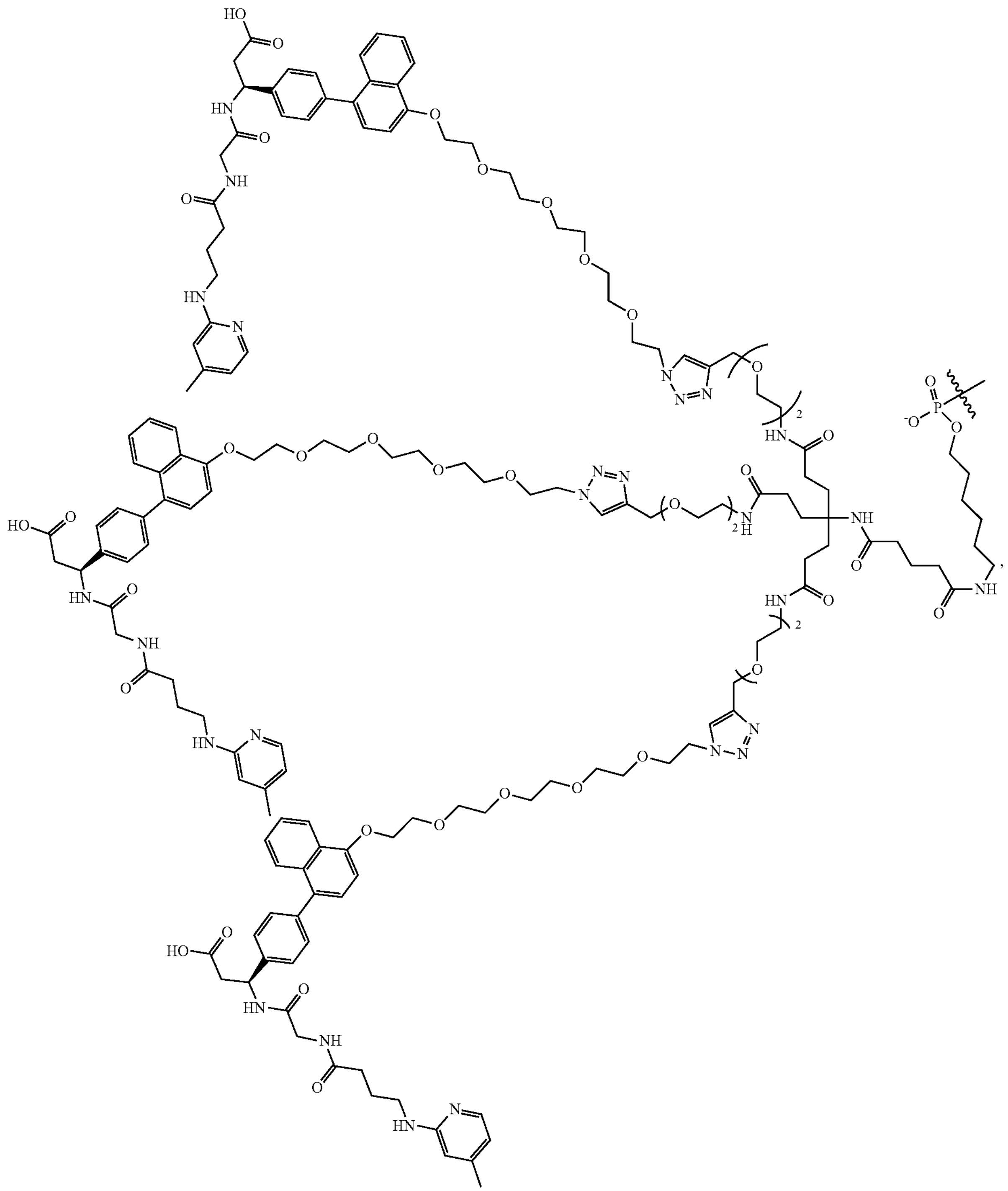
or a pharmaceutically acceptable salt thereof.
* * * * *

SEQUENCE LISTING

```
<160> NUMBER OF SEQ ID NOS: 1719

<210> SEQ ID NO 1
<211> LENGTH: 17448
<212> TYPE: DNA
<213> ORGANISM: Homo Sapiens
<220> FEATURE:
<223> OTHER INFORMATION: Homo sapiens mucin 5AC, oligomeric mucus/gel-
      forming (MUC5AC) gene transcript, GenBank NM_001304359.2

<400> SEQUENCE: 1

ctcagaggct gctgagggac agggcactct tccccgccgt ccacacaatg agtgttggcc     60
```

```
ggaggaagct ggccctgctc tgggccctgg ctctcgctct ggcctgcacc cggcatacag    120
gccatgccca ggatggctcc tccgaatcca gctacaagca ccaccctgcc ctctctccta    180
tcgcccgggg gcccagcggg gtcccgctcc gtggggcgac tgtcttccca tctctgagga    240
ccatccctgt ggtacgagcc tccaacccgg cgcacaacgg gcgggtgtgc agcacctggg    300
gcagcttcca ctacaagacc ttcgacggcg acgtcttccg cttccccggc ctctgcaact    360
acgtgttctc cgagcactgc ggtgccgcct acgaggattt taacatccag ctacgccgca    420
gccaggagtc agcggccccc acgctgagca gggtcctcat gaaggtggat ggcgtggtca    480
tccagctgac caagggctcc gtcctggtca acggccaccc ggtcctgctg cccttcagcc    540
agtctggggt cctcattcag cagagcagca gctacaccaa ggtggaggcc aggctgggcc    600
ttgtcctcat gtggaaccac gatgacagcc tgctgctgga gctggacacc aaatacgcca    660
acaagacctg tgggctctgt ggggacttca acgggatgcc cgtggtcagc gagctcctct    720
cccacaacac caagctgaca cccatggaat tcgggaacct gcagaagatg gacgacccca    780
cggaccagtg tcaggaccct gtccctgaac ccccgaggaa ctgctccact ggctttggca    840
tctgtgagga gctcctgcac ggccagctgt tctctggctg cgtggccctg gtggacgtcg    900
gcagctacct ggaggcttgc aggcaagacc tctgcttctg tgaagacacc gacctgctca    960
gctgcgtctg ccacaccctt gccgagtact cccggcagtg cacccatgca ggggggttgc   1020
cccaggactg gcggggccct gacttctgcc cccagaagtg ccccaacaac atgcagtacc   1080
acgagtgccg ctccccctgc gcagacacct gctccaacca ggagcactcc cgggcctgtg   1140
aggaccactg tgtggccggc tgcttctgcc ctgaggggac ggtgcttgac gacatcggcc   1200
agaccggctg tgtccctgtg tcaaagtgtg cctgcgtcta caacggggct gcctatgccc   1260
caggggccac ctactccaca gactgcacca actgcacctg ctccggaggc cggtggagct   1320
gccaggaggt tccatgcccg ggtacctgct ctgtgcttgg aggtgcccac ttctcaacgt   1380
ttgacgggaa gcaatacacg gtgcacggcg actgcagcta tgtgctgacc aagccctgtg   1440
acagcagtgc cttcactgta ctggctgagc tgcgcaggtg cgggctgacg gacagcgaga   1500
cctgcctgaa gagcgtgaca ctgagcctgg atggggcgca gacggtggtg gtgatcaagg   1560
ccagtgggga agtgttcctg aaccagatct acacccagct gcccatctct gcagccaacg   1620
tcaccatctt cagaccctca accttcttca tcatcgccca gaccagcctg ggcctgcagc   1680
tgaacctgca gctggtgccc accatgcagc tgttcatgca gctggcgccc aagctccgtg   1740
ggcagacctg cggtctctgt gggaacttca acagcatcca ggccgatgac ttccggaccc   1800
tcagtggggt ggtggaggcc accgctgcgg ccttcttcaa caccttcaag acccaggccg   1860
cctgccccaa catcaggaac agcttcgagg acccctgctc tctgagcgtg gagaatgaga   1920
agtatgctca gcactggtgc tcgcagctga ccgatgccga cggccccttc ggccggtgcc   1980
atgctgccgt gaagccggga acctactact cgaactgcat gtttgacacc tgcaactgtg   2040
agcggagcga ggactgcctg tgcgccgcgc tgtcctccta cgtgcacgcc tgtgccgcca   2100
agggcgtgca gctcggcggc tggagggacg gcgtctgcac gaagcctatg accacttgcc   2160
ccaagtcaat gacgtaccac taccatgtca gcacctgcca gcccacctgc cgctccctga   2220
gcgaggggga catcacctgc agtgttggct tcatccccgt ggatggctgc atctgtccca   2280
agggcacctt cctggacgac acgggcaagt gtgtgcaggc cagcaactgt ccctgctacc   2340
acagaggctc catgatcccc aatggggagt cggtgcacga cagcggggct atctgcacct   2400
```

-continued gcacacatgg gaagctgagc tgcatcggag gccaagcccc cgccccagtg tgtgctgcgc 2460
ccatggtgtt ctttgactgc cgaaatgcca cgcccgggga cacaggggct ggctgtcaga 2520
agagctgcca cacactggac atgacctgtt acagccccca gtgtgtgcct ggctgcgtgt 2580
gccccgacgg gctggtggcg gacggcgagg gcggctgcat cactgcggag gactgcccct 2640
gcgtgcacaa tgaggccagc taccgggccg gccagaccat ccgggtgggc tgcaacacct 2700
gcacctgtga cagcaggatg tggcggtgca cagatgaccc ctgcctggcc acctgcgccg 2760
tgtacgggga cggccactac ctcaccttcg acggacagag ctacagcttc aacggagact 2820
gcgagtacac gctggtgcag aaccactgtg gcgggaaaga cagcacccag gactcctttc 2880
gtgttgtcac cgagaacgtc ccctgcggca ccacagggac cacctgctcc aaggccatca 2940
agatttttcct gggggggcttc gagctgaagc taagccatgg gaaggtggag gtgatcggga 3000
cggacgagag ccaggaggtg ccatacacca tccggcagat gggcatctac ctggtggtgg 3060
acaccgacat tggcctggtg ctgctgtggg acaagaagac cagcatcttc atcaacctca 3120
gccccgagtt caagggcagg gtctgcggcc tgtgtgggaa cttcgacgac atcgccgtta 3180
atgactttgc cacgcggagc cggtctgtgg tgggggacgt gctggagttt gggaacagct 3240
ggaagctctc cccctcctgc ccagatgccc tggcgcccaa ggacccctgc acggccaacc 3300
ccttccgcaa gtcctgggcc cagaagcagt gcagcatcct ccacggcccc accttcgccg 3360
cctgccacgc acacgtggag ccggccaggt actacgaggc ctgcgtgaac gacgcgtgcg 3420
cctgcgactc cgggggtgac tgcgagtgct tctgcacggc tgtggccgcc tacgcccagg 3480
cctgccatga agtaggcctg tgtgtgtcct ggcggacccc gagcatctgc cctctgttct 3540
gcgactacta caaccccgaa ggccagtgcg agtggcacta ccagccctgc ggggtgccct 3600
gcctgcgcac ctgccggaac ccccgtggag actgcctgcg ggacgtccgg ggcctggaag 3660
gctgctaccc caagtgccca ccagaggctc ccatctttga tgaggacaag atgcagtgtg 3720
tggccacctg cccaaccccg cctctgccac cacggtgcca cgtccatggg aagtcctacc 3780
ggccaggtgc agtggtgccc tcggacaaga actgccagtc ctgcctttgt acggagcgcg 3840
gcgtggagtg cacctacaaa gctgaggcct gtgtctgcac ctacaatgga cagcgcttcc 3900
acccagggga cgtcatctac cacacgacgg atggcacggg tggctgcatc tccgcccgct 3960
gcggggccaa cggcaccatt gagaggaggg tctacccctg cagcccccacc accccctgtcc 4020
ccccaaccac cttctccttc tccacacccc cgcttgtcgt gagctccacg cacaccccca 4080
gcaatggccc aagcagcgcg cacacaggcc ctccgagcag cgcctggccc accacagcag 4140
gcacttctcc caggacgagg ctgcccacag cctctgcctc actgccgccg gtctgtgggg 4200
aaaagtgcct gtggtcgcca tggatggatg tcagccgccc tggacggggc acggacagcg 4260
gtgacttcga cacactggag aacctccgcg cccatgggta ccgggtgtgc gaatcaccca 4320
ggtcggtgga gtgccgagct gaggacgccc ccggagtgcc gctccgagcc ctggggcagc 4380
gtgtgcagtg cagcccggat gtggggctga cctgtcgtaa cagggagcag gcatcggggc 4440
tctgctacaa ctaccagatc agggtccagt gctgcacgcc cctaccctgc tccacctcta 4500
gcagtccagc ccagaccact cctccaacta cctccaagac cactgaaacc cgggcctcag 4560
gctcctcagc tcccagcagc acacctggca ccgtgtctct ctctacagcc aggacgacac 4620
ctgccccagg taccgctacc tctgtcaaaa aaactttctc aactcccagc cctccgccag 4680
tgccggcaac atcaacatca tccatgtcga ccacggcccc ggggacctct gtggtctcca 4740
gcaagcccac ccccacggag cccagcacat cctcctgcct gcaggagctt tgcacctgga 4800

```
ccgagtggat cgatggcagc taccctgctc ctggaataaa tggtggagat tttgacacat   4860
ttcaaaattt gagagacgaa ggatacacat tctgtgaaag tcctcgaagc gtgcagtgcc   4920
gggcagagag cttccccaac acgccgctgg cagacctggg gcaggacgtc atctgcagcc   4980
acacagaggg gctgatttgc ctgaacaaga accagctccc acccatctgc tacaactatg   5040
agatccgcat ccagtgttgc gagacggtga acgtgtgcag agacatcacc agactgccaa   5100
agaccgtcgc aacgacacgg ccgactccac atccaaccgg agctcagacc cagaccacct   5160
tcaccacaca catgccctcg gcctccacag agcaacccac ggcaacctcc aggggtgggc   5220
ccacagcaac cagcgtcaca cagggcaccc acaccacact agtcaccaga aactgtcatc   5280
cccggtgcac ctggacaaag tggttcgacg tggacttccc gtcccccgga ccccatggtg   5340
gagacaagga aacctacaac aacatcatca ggagtgggga aaaaatctgc cgccgacctg   5400
aggagatcac caggctccag tgccgagcca agagccaccc agaggtgagc atcgaacacc   5460
tgggccaggt ggtgcagtgc agccgggaag agggcctggt gtgccggaac caggaccagc   5520
agggaccctt caagatgtgc ctcaactacg aggtgcgtgt gctctgctgc gagaccccca   5580
gaggctgcca catgacctcc acacctggct ccacctctag cagtccagcc cagaccactc   5640
cttcaacaac ctccaagacc actgaaaccc aggcctcagg ctcctcagcc cccagcagca   5700
cacctggcac cgtgtctctc tctacagcca ggacgacacc tgccccaggt accgctacct   5760
ctgtcaaaaa aactttctca actcccagcc ctccgccagt gccggcaaca tcaacatcat   5820
ccatgtcgac cacggccccg gggacctctg tggtctccag caagcccacc cccacggagc   5880
ccagcacatc ctcctgcctg caggagcttt gcacctggac cgagtggatt gatggcagct   5940
accctgctcc tggaataaat ggtggagatt ttgacacatt tcaaaatttg agagacgaag   6000
gatacacatt ctgtgaaagt cctcgaagcg tgcagtgccg ggcagagagc ttccccaaca   6060
cgccgctggc agacctgggg caggacgtca tctgcagcca cacagagggg ctgatttgcc   6120
tgaacaagaa ccagctccca cccatctgct acaactatga gatccgcatc cagtgttgcg   6180
agacggtgaa cgtgtgcaga gacatcacca gaccgccaaa gaccgtcgca acgacacggc   6240
cgactccaca tccaaccgga gctcagaccc agaccacctt caccacacac atgccctcgg   6300
cctccacaga gcaacccacg gcaacctcca ggggtgggcc cacagcaacc agcgtcacac   6360
agggcaccca caccacacca gtcaccagaa actgtcatcc ccggtgcacc tggacaacgt   6420
ggttcgacgt ggacttcccg tcccccggac cccatggtgg agacaaggaa acctacaaca   6480
acatcatcag gagtggggaa aaaatctgcc gccgacctga ggagatcacc aggctccagt   6540
gccgagccaa gagccaccca gaggtgagca tcgaacacct gggccaggtg gtgcagtgca   6600
gccgggaaga gggcctggtg tgccggaacc aggaccagca gggacccttc aagatgtgcc   6660
tcaactacga ggtgcgtgtg ctctgctgcg agacccccaa aggctgcccc gtgacctcca   6720
cacctgtgac agctcctagc acccctagtg ggagagccac cagcccaact cagagcacct   6780
cctcttggca gaaatccagg acaaccactt tggtgacaac cagcacaacc tccactccac   6840
agaccagtac aacctatgcc catacaacca gcacaacctc tgctcctaca gccagaacaa   6900
cctctgctcc tacaaccaga acaacctctg cctctccagc cagcacaacc tctggtcctg   6960
gaaatactcc cagccctgtt cctaccacca gcacaatctc tgctcctaca actagcataa   7020
cctctgcccc tacaaccagc acaacctctg cccctacaag cagcacaacc tctggtcctg   7080
gaactactcc cagccctgtt cctaccacca gcataacctc tgcccctaca accagcacaa   7140
```

cctctgctcc tacaaccagc acaacctctg cccgtacaag cagcacaacc tctgccacta 7200
ccaccagcag aatctctggt cctgaaacta ctcccagccc tgttcctacc accagcacaa 7260
cctctgccac tacaaccagc acaacctcag ctcctacaac cagcacaacc tctgccccta 7320
caagcagcac aacctccagt ccacagacca gcacaacctc ggctcctaca accagcacaa 7380
cttctggtcc tggaactacc ccaagccctg ttcccacgac cagcacaacc tctgccccta 7440
caacaagaac aacttctgct cctaaaagca gcacaacctc tgccgctaca accagcacaa 7500
cctctggtcc tgaaactact cctagacctg ttcctaccac cagcacaacc tcttctccta 7560
caaccagcac aacctctgct cctacaacca gcacaacctc tgcttctaca accagcacaa 7620
cctctggtgc tggaactact cccagccctg ttcccaccac cagcacaacc tctgctccta 7680
caaccagcac aacctctgcc cctataagca gcacaacctc tgccactaca accagcacaa 7740
cctctggtcc tggaactact cccagccctg ttcctaccac gagcacaacc tctgctccta 7800
caaccagcac aacctctggt cctggaacta ctcccagtgc tgttcccacc accagcataa 7860
cctctgcacc tacaaccagc acaaactctg cccctataag cagcacaacc tctgccacta 7920
caaccagcag aatctctggt cctgaaacta ctcccagccc tgttcctacc gccagcacaa 7980
cctctgcttc tacaactagc acaacctctg gtcctggaac tactcccagc cctgttccta 8040
ccaccagcac aatctctgtt cctaccacca gcacaacttc tgcttctaca accagcacaa 8100
cctctgcttc tacaaccagc acaacctctg gtcctggaac tactcccagc cctgttccca 8160
ccaccagcac aacctctgct cccacaacaa gcacaacctc tgcccctaca accagcacaa 8220
tctcggcccc aacaaccagc acaacctctg ccactacaac cagcacgacc tctgctccta 8280
cacccagaag aacctcagcc cctacaacca gcacaatctc tgcctctacc accagcacaa 8340
cctctgcgac tacaaccagc acaacctctg ctactacaac cagcacaatc tctgccccta 8400
caaccagcac aactttgtct cctacaacca gcacaacctc tactactata accagcacaa 8460
cttctgcccc tataagcagc acaacttcca caccacagac cagcacaact tcggctccta 8520
caaccagcac aacttctggt cctggaacta cttcaagccc tgttcccacc accagcacaa 8580
cctctgcccc tacaaccagc acaacctctg cccctacaac cagaacaacc tctgtcccta 8640
caagcagcac aacctccact gctacaacca gcacaacctc tggccctgga actactccca 8700
gccctgttcc caccaccagt acaacctctg ctcctacaac cagaacaacc tctgctccta 8760
caaccagcac aacctctgcc cctacaacca gcacaacctc tgcccctaca agcagcacaa 8820
cctcagctac tacaaccagc acaatctctg ttcctacaac cagcacaact tctgttcctg 8880
gaactactcc cagccctgtt cctaccacca gcacaatctc tgttcctacc accagcacaa 8940
cttctgcttc tacaaccagc acaacctctg gtcctggaac tactcccagc cctgttccca 9000
ccaccagcac aacctctgct cccacaacaa gcacaacctc tgcccctaca accagcacaa 9060
tctcggcccc aacaaccagc acaccctctg cccctacaac cagcacaacc ttagctccta 9120
caaccagcac aacctctgcc cctacaacca gcacaacctc taccccctaca agcagcacaa 9180
cctcctctcc acagaccagc acaacctcgg cttctaccac cagcataact tctggtcctg 9240
gaactacccc aagccctgtt cccaccacca gcacaacctc tgctcctaca accagcacaa 9300
cctctgccgc tacaaccagc acaatctcgg ccccaacaac cagcacaacg tctgctccta 9360
caaccagcac aacctctgcc tctacagcca gcaaaacctc tggtcttgga actactccca 9420
gccctattcc taccaccagc acaacctctc ctcctacaac cagcacaact tctgcctcta 9480
cagccagcaa aacctctggt cctggaacca ctcccagccc tgttcccacc accagcacaa 9540

```
tctttgctcc tagaaccagc accacttctg cctctacaac cagcacaacc cctggtcctg   9600
gaaccactcc cagccccgtt cccaccacca gcacagcctc tgtttcaaag accagcacaa   9660
gccatgtttc catatccaag acaacccact cccaaccagt caccagagac tgtcatctcc   9720
ggtgcacctg gaccaagtgg tttgacatag acttcccatc ccctggaccc cacggcgggg   9780
acaaggaaac ctacaacaac atcatcagga gtggggaaaa aatctgccgc cgacctgagg   9840
agatcaccag gctccagtgc cgagccgaga gccacccgga ggtgagcatt gaacacctgg   9900
gccaggtggt gcagtgcagc cgtgaagagg gcctggtgtg ccggaaccag gaccagcagg   9960
gacccttcaa gatgtgcctc aactacgagg tgcgtgtgct ctgctgcgag accccctaaag  10020
gttgccccgt gacctccaca cctgtgacag ctcctagcac ccctagtggg agagccacca  10080
gcccaactca gagcacttcc tcttggcaga aatccaggac aaccactttg gtgacaacca  10140
gcacaacctc cactccacag accagcacaa cctctgctcc tacaaccagc acaacctctg  10200
ctcccacaac cagcacaact tctgccccta caaccagcac aacctccact ccacagacca  10260
gcatatcctc tgcccctaca agcagcacaa cctcggctcc tacaagcagc acaatctctg  10320
ctcgtacaac cagcataatc tctgccccta caaccagcac aacctcttcc cctacaacca  10380
gcacaacctc tgctactaca accagcacaa cctctgcccc tacaagcagc acaacctcca  10440
ctccacagac cagcaaaacc tcagctgcta caagcagcac aacctccggt tctggaacta  10500
ctcccagccc tgttaccacc accagcacag cctctgtttc aaagaccagc acaagccatg  10560
tttctgtatc caagacaacc cactcccaac cagtcaccag agactgtcat ccccggtgca  10620
cctggaccaa atggtttgat gtggactttc catcccctgg accccacggt ggggacaagg  10680
aaacctacaa caacatcatc aggagtgggg aaaaaatctg ccgccgacct gaggagatca  10740
ccaggctcca gtgccgagcc aagagccacc cggaggtgag catcgaacac ctgggccagg  10800
tggtgcagtg cagccgcgaa gagggcctgg tgtgccggaa ccaggaccag cagggaccct  10860
tcaagatgtg cctcaactac gaggtgcgtg tgctttgctg cgagaccccc aaaggctgcc  10920
ccgtgacctc cacatctgtg acagctccta gcacccctag tgggagagcc accagcccaa  10980
ctcagagcac ctcctcttgg cagaaatcca ggacaaccac tttggtgaca agcagcataa  11040
cctccactac acagaccagc acaacctctg cccctacaac tagcacaacc cctgcttcta  11100
tacccagcac aacctctgcc ccaacaacca gcacaacctc tgctcccaca acgagcacaa  11160
cttctgcccc tacaaccagc acaacctcca ctccacagac caccacatcc tctgccccta  11220
caagcagcac aacctcggct cctaccacca gcacaatctc tgcccctaca accagcacaa  11280
tctctgcccc tacaaccagc acaacctctg ctcccacagc cagcacaacg tcagctccta  11340
cgagcacttc ctcggctcct acaaccaaca caacctctgc ccctacaact agcactacct  11400
ctgctcccat aaccagcaca atctctgccc ctacaaccag cacaacctcc actccacaga  11460
ccagcacaat ctcttcccct acaaccagca caacctccac tccgcagacc agcacaacct  11520
cttcccctac aactagcaca acctcagctc ctacaaccag cacaacttct gcccctacaa  11580
ccagcacaac ctccactcca cagaccagca tatcctctgc ccctacaagc agcacaacct  11640
ctgctcctac agccagcaca atctctgccc ctacaaccag cacaacctct ttccatacaa  11700
ccagcacaac ctctcccccct acaagcagca caagctccac tccacagacc agcaaaacct  11760
cagctgctac aagcagcaca acctccggtt ctggaactac tcccagcccc gttcccacca  11820
ccagcacagc ctctgtttca aagaccagca caagccatgt ttctgtatcc aagacaaccc  11880
```

```
actcccaacc agtcaccaga gactgtcatc cccggtgcac ctggaccaag tggtttgacg  11940
tggactttcc atcccctgga ccccacggtg gggacaagga aacctacaac aacatcatca  12000
ggagtgggga aaaaatctgc cgccgacctg aggagatcac caggctccag tgccgagccg  12060
agagccaccc ggaggtgagc atcgaacacc tgggccaggt ggtgcagtgc agccgggaag  12120
agggcctggt gtgccggaac caggaccagc agggaccctt caagatgtgc ctcaactacg  12180
aggtgcgtgt gctctgctgc gagacccccca aaggctgccc cgtgacctcc acacctgtga  12240
cagctcctag caccctagt gggagagcca ccagcccaac tcagagcact tcctcttggc  12300
agaaatccag gacaaccact ttggtgacaa ccagcacaac ctccactcca cagaccagca  12360
caacctctgc ccctacaacc agcacaatcc ctgcttctac acccagcaca acctctgccc  12420
ctacaaccag cacaacctct gcccctacaa ccagcacgac ctcagctcct acacacagaa  12480
cgacttctgg tcctacaacc agcacaacct tggctcctac aaccagcaca acctctgctc  12540
caacaaccag cacaaactct gctcctacaa ccagcacaat ctctgcctct acaaccagca  12600
caatctctgc ccctacaacc agcacaatct cttcccctac aagcagcaca acctccactc  12660
cacagaccag caaaacctca gctgctacaa gcagcacaac ctccggttct ggaactactc  12720
caagccctgt tcccaccacc agcacaacct ctgcctctac aaccagcaca acttctgctc  12780
ctacaaccag cacaacctct ggtcctggaa ctactccaag ccctgttccc agcaccagta  12840
caacctctgc tgctacaacc agcacaacct ctgctcctac aaccagaaca acatctgctc  12900
ctacaagcag catgacctct ggtcctggaa ctactcccag ccctgttccc accaccagca  12960
caacctctgc tcctacaact agcacaacct ctggtcctgg aactactccc agccctgttc  13020
ccaccaccag cacaacctct gctcctataa ccagcacaac ctctggtcct ggaagtactc  13080
ccagccctgt tcccaccacc agcacaacct ctgctcctac aaccagcaca acctctgcct  13140
ctacagccag cacaacctct ggtcctggaa ctactcccag ccctgttccc accaccagca  13200
caacctctgc tcctacaacc agaacaacct ctgcctctac agccagcaca acctctggtc  13260
ctggaagtac tcccagccct gttcccacca ccagcacaac ctctgctcct acaaccagaa  13320
caacccctgc ctctacagcc agcacaacct ctggtcctgg aactactccc agccctgttc  13380
ccaccacaag cacaacctct gcttctacaa ccagcacaat ctctctccct acaaccagca  13440
caacctctgc tcctataacc agcatgacct ctggtcctgg aactactccc agccctgttc  13500
ccaccaccag cacaacctct gctcctacaa ccagcacaac ctctgcctct acagccagca  13560
caacctctgg tcctggaact actcccagcc ctgttcccac caccagcaca acctctgctc  13620
ctacaaccag cacaacctct gcctctacag ccagcacaac ctctggtcct ggaacttctc  13680
tcagccctgt tcccaccacg agcacaacct ctgctcctac aactagcaca acctctggtc  13740
ctggaactac tcccagccct gttcccacca ccagcacaac ctctgctcct acaaccagca  13800
cgacctctgg tcctggaact actcccagcc ccgttcccac caccagcaca acccctgttt  13860
caaagaccag cacaagccat ctttctgtat ccaagacaac ccactcccaa ccagtcacca  13920
gtgactgtca tcctctgtgc gcctggacaa agtggttcga cgtggacttc ccatcccctg  13980
gaccccacgg cggggacaag gaaacctaca acaacatcat caggagtggg gaaaaaatct  14040
gccgccgacc tgaggagatc accaggctcc agtgccgagc cgagagccac ccggaggtga  14100
acattgaaca cctgggtcag gtggtgcagt gcagccgtga agagggcctg gtgtgccgga  14160
accaggacca gcagggaccc ttcaagatgt gcctcaacta cgaggtgcgc gtgctctgct  14220
gcgagacccc cagaggctgc ccggtgacct ctgtgacccc atatgggact tctcctacca  14280
```

atgctctgta tccttccctg tctacttcca tggtatccgc ctccgtggca tccacctctg 14340
tggcatccag ctctgtggca tccagctctg tggcttactc cacccaaacc tgcttctgca 14400
acgtggctga ccggctctac cctgcaggat ccaccatata ccgccacaga gacctcgctg 14460
gccattgcta ttatgccctg tgtagccagg actgccaagt ggtcagaggg gttgacagtg 14520
actgtccgtc caccacgctg cctcctgccc cagccacgtc cccttcaata tccacctccg 14580
agcccgtcac tgagctggga tgcccaaatg cggttccccc cagaaagaaa ggtgagacct 14640
gggccacacc caactgctcc gaggccacct gtgagggcaa caacgtcatc tccctgcgcc 14700
cgcgcacgtg cccgagggtg gagaagccca cttgtgccaa cggctacccg gctgtgaagg 14760
tggctgacca agatggctgc tgccatcact accagtgcca gtgtgtgtgc agcggctggg 14820
gtgaccccca ctacatcacc ttcgacggca cctactacac cttcctggac aactgcacgt 14880
acgtgctggt gcagcagatt gtgcccgtgt atggccactt ccgcgtgctc gtcgacaact 14940
acttctgcgg tgcggaggac gggctctcct gcccgaggtc catcatcctg gagtaccacc 15000
aggaccgcgt ggtgctgacc cgcaagccag tccacggggt gatgacaaac gagatcatct 15060
tcaacaacaa ggtggtcagc cccggcttcc ggaaaaacgg catcgtggtc tcgcgcatcg 15120
gcgtcaagat gtacgcgacc atcccggagc tgggagtcca ggtcatgttc tccggcctca 15180
tcttctccgt ggaggtgccc ttcagcaagt ttgccaacaa caccgagggc cagtgcggca 15240
cttgcaccaa cgacaggaag gatgagtgcc gcacgcctag gggacggtg gtcgcttcct 15300
gctccgagat gtccggcctc tggaacgtga gcatacccga ccagccagcc tgccaccggc 15360
ctcacccgac gcccaccacg gtcgggccca ccacagttgg gtctaccacg gtcgggccca 15420
ccacagttgg gtctaccacg gtcgggccca ccacaccgcc tgctccgtgc ctgccatcac 15480
ccatctgcca gctgattctg agcaaggtct ttgagccgtg ccacactgtg atccccccac 15540
tgctgttcta tgagggctgc gtctttgacc ggtgccacat gacggacctg gatgtggtgt 15600
gctccagcct ggagctgtac gcggcactct gtgcgtccca cgacatctgc atcgattgga 15660
gaggccggac cggccacatg tgcccattca cctgcccagc cgacaaggtg taccagccct 15720
gcggcccgag caacccctcc tactgctacg ggaatgacag cgccagcctc ggggctctgc 15780
cggaggccgg ccccatcacc gaaggctgct tctgtccgga gggcatgacc ctcttcagca 15840
ccagtgccca agtctgcgtg cccacgggct gccccaggtg tctggggccc cacggagagc 15900
cggtgaaggt gggccacacc gtcggcatgg actgccagga gtgcacgtgt gaggcggcca 15960
cgtggacgct gacctgccga cccaagctct gcccgctgcc ccctgcctgc cccctgcccg 16020
gcttcgtgcc tgtgcctgca gccccacagg ccggccagtg ctgcccccag tacagctgcg 16080
cctgcaacac cagccgctgc cccgcgcccg tgggctgtcc tgagggcgcc cgcgcgatcc 16140
cgacctacca ggagggggcc tgctgcccag tccaaaactg cagctggaca gtgtgcagca 16200
tcaacgggac cctgtaccag cccggcgccg tggtctcctc gagcctgtgc gaaacctgca 16260
ggtgtgagct gccgggtggc cccccatcgg acgcgtttgt ggtcagctgt gagacccaga 16320
tctgcaacac acactgccct gtgggcttcg agtaccagga gcagagcggg cagtgctgtg 16380
gcacctgtgt gcaggtcgcc tgtgtcacca acaccagcaa gagccccgcc cacctcttct 16440
accccggcga gacctggtca gacgcaggga accactgtgt gacccaccag tgtgagaagc 16500
accaggatgg gctcgtggtg gtcaccacga agaaggcgtg ccccccgctc agctgttctc 16560
tggacgaggc ccgcatgagc aaggacggct gctgccgctt ctgcccgccg cccccgcccc 16620

-continued

```
cgtaccagaa ccagtcgacc tgtgctgtgt accataggag cctgatcatc cagcagcagg  16680

gctgcagctc ctcggagccc gtgcgcctgg cttactgccg ggggaactgt ggggacagct  16740

cttccatgta ctcgctcgag ggcaacacgg tggagcacag gtgccagtgc tgccaggagc  16800

tgcggacctc gctgaggaat gtgaccctgc actgcaccga cggctccagc cgggccttca  16860

gctacaccga ggtggaagag tgcggctgca tgggccggcg gtgccctgcg ccgggcgaca  16920

cccagcactc ggaggaggcg gaacccgagc ccagccagga ggcagagagt gggagctggg  16980

agagaggcgt cccagtgtcc cccatgcact gaccagcact gccgccctcc tgacctccaa  17040

ggagaacctc ccatatgtcc tctgagctcg gcttccaagg ccagtggaac ttgtgcccct  17100

gtccaggcgg ctgcagcttt gaacacactg tccacgcccg ctttcttgtg gagggtgtgg  17160

gctatgggtc acctgctgcc tggaggaggg gcccttaccc accccgcctg cagccacctc  17220

tcaggaccag ccccggggct ggccgagctc ctctggccat gcatccagcc tgctgttctg  17280

gggacgtgag catcacctga gggtctcagg aatgacgctt ggacatggtg atcagctgcc  17340

tggtggctgc aggaggaaga acctcactcc tacctcagcc ctcagcctgc gctcccctcc  17400

tcagtacacg gccaatctgt tgcataaata cacttgagca ttttgcaa              17448


<210> SEQ ID NO 2
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target
      sequence

<400> SEQUENCE: 2

gcuuccacua caagaccuu                                               19


<210> SEQ ID NO 3
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target
      sequence

<400> SEQUENCE: 3

uguggaacca cgaugacag                                               19


<210> SEQ ID NO 4
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target
      sequence

<400> SEQUENCE: 4

gcaagaccuc ugcuucugu                                               19


<210> SEQ ID NO 5
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target
      sequence

<400> SEQUENCE: 5

cacagacugc accaacugc                                               19
```

<210> SEQ ID NO 6
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 6
cagugccuuc acuguacug 19

<210> SEQ ID NO 7
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 7
agugccuuca cuguacugc 19

<210> SEQ ID NO 8
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 8
cagcgagacc ugccugaag 19

<210> SEQ ID NO 9
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 9
gggaaguguu ccugaacca 19

<210> SEQ ID NO 10
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 10
aacgucacca ucuucagac 19

<210> SEQ ID NO 11
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 11
acgucaccau cuucagacc 19

-continued

<210> SEQ ID NO 12
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target
sequence

<400> SEQUENCE: 12
ugugggaacu ucaacagca 19

<210> SEQ ID NO 13
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target
sequence

<400> SEQUENCE: 13
gggaacuuca acagcaucc 19

<210> SEQ ID NO 14
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target
sequence

<400> SEQUENCE: 14
uccaggccga ugacuuccg 19

<210> SEQ ID NO 15
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target
sequence

<400> SEQUENCE: 15
cuucuucaac accuucaag 19

<210> SEQ ID NO 16
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target
sequence

<400> SEQUENCE: 16
uucaacaccu ucaagaccc 19

<210> SEQ ID NO 17
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target
sequence

<400> SEQUENCE: 17
ccaacaucag gaacagcuu 19

<210> SEQ ID NO 18
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 18
caucaggaac agcuucgag 19

<210> SEQ ID NO 19
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 19
aguaugcuca gcacuggug 19

<210> SEQ ID NO 20
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 20
accuacuacu cgaacugca 19

<210> SEQ ID NO 21
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 21
uacuacucga acugcaugu 19

<210> SEQ ID NO 22
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 22
acaucaccug caguguugg 19

<210> SEQ ID NO 23
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 23
caccugcagu guuggcuuc 19

<210> SEQ ID NO 24

<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 24
uggacaugac cuguuacag 19

<210> SEQ ID NO 25
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 25
agagcuacag cuucaacgg 19

<210> SEQ ID NO 26
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 26
agggaccacc ugcuccaag 19

<210> SEQ ID NO 27
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 27
cugcuccaag gccaucaag 19

<210> SEQ ID NO 28
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 28
ugcuccaagg ccaucaaga 19

<210> SEQ ID NO 29
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 29
cuccaaggcc aucaagauu 19

<210> SEQ ID NO 30
<211> LENGTH: 19

<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 30
gacaagaaga ccagcaucu 19

<210> SEQ ID NO 31
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 31
agaccagcau cuucaucaa 19

<210> SEQ ID NO 32
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 32
accagcaucu ucaucaacc 19

<210> SEQ ID NO 33
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 33
ccucagcccc gaguucaag 19

<210> SEQ ID NO 34
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 34
ugggaacuuc gacgacauc 19

<210> SEQ ID NO 35
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 35
cagaagcagu gcagcaucc 19

<210> SEQ ID NO 36
<211> LENGTH: 19
<212> TYPE: RNA

<213> ORGANISM: Artificial sequence
<220> FEATURE:
<223> OTHER INFORMATION: MUC5AC 19-mer gene transcript (mRNA) target
sequence

<400> SEQUENCE: 36
caggccugcc augaaguuu 19

<210> SEQ ID NO 37
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target
sequence

<400> SEQUENCE: 37
cccucuguuc ugcgacuac 19

<210> SEQ ID NO 38
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target
sequence

<400> SEQUENCE: 38
ccucuguucu gcgacuacu 19

<210> SEQ ID NO 39
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target
sequence

<400> SEQUENCE: 39
ucuguucugc gacuacuac 19

<210> SEQ ID NO 40
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target
sequence

<400> SEQUENCE: 40
cuguucugcg acuacuaca 19

<210> SEQ ID NO 41
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target
sequence

<400> SEQUENCE: 41
uguucugcga cuacuacaa 19

<210> SEQ ID NO 42
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target
sequence

<400> SEQUENCE: 42
ucuuugauga ggacaagau 19

<210> SEQ ID NO 43
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target
sequence

<400> SEQUENCE: 43
cuuugaugag gacaagaug 19

<210> SEQ ID NO 44
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target
sequence

<400> SEQUENCE: 44
uuugaugagg acaagaugc 19

<210> SEQ ID NO 45
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target
sequence

<400> SEQUENCE: 45
acgucaucua ccacacgac 19

<210> SEQ ID NO 46
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target
sequence

<400> SEQUENCE: 46
ugcuacaacu accagauca 19

<210> SEQ ID NO 47
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target
sequence

<400> SEQUENCE: 47
uacaacuacc agaucaggg 19

<210> SEQ ID NO 48
<211> LENGTH: 19
<212> TYPE: RNA
<213> ORGANISM: Artificial sequence
<220> FEATURE:

<223> OTHER INFORMATION: MUC5AC 19-mer gene transcript (mRNA) target sequence

<400> SEQUENCE: 48
cugauuugcc ugaacaaga 19

<210> SEQ ID NO 49
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 49
ugauuugccu gaacaagaa 19

<210> SEQ ID NO 50
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 50
cacccaucug cuacaacua 19

<210> SEQ ID NO 51
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 51
acccaucugc uacaacuau 19

<210> SEQ ID NO 52
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 52
ugcuacaacu augagaucc 19

<210> SEQ ID NO 53
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 53
gcuacaacua ugagauccg 19

<210> SEQ ID NO 54
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 54
gauccgcauc caguguugc 19

<210> SEQ ID NO 55
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 55
aaagugguuc gacguggac 19

<210> SEQ ID NO 56
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 56
gugguucgac guggacuuc 19

<210> SEQ ID NO 57
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 57
gguucgacgu ggacuuccc 19

<210> SEQ ID NO 58
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 58
aaggaaaccu acaacaaca 19

<210> SEQ ID NO 59
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 59
aggaaaccua caacaacau 19

<210> SEQ ID NO 60
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 60
aaaccuacaa caacaucau 19

<210> SEQ ID NO 61
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 61
agaggugagc aucgaacac 19

<210> SEQ ID NO 62
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 62
gcagggaccc uucaagaug 19

<210> SEQ ID NO 63
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 63
agaugugccu caacuacga 19

<210> SEQ ID NO 64
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 64
augugccuca acuacgagg 19

<210> SEQ ID NO 65
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 65
accuccucuu ggcagaaau 19

<210> SEQ ID NO 66
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 66
aggacaacca cuuugguga 19

<210> SEQ ID NO 67
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 67
cucugcuccu acaacuagc 19

<210> SEQ ID NO 68
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 68
accucugcuu cuacaacua 19

<210> SEQ ID NO 69
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 69
auaaccagca caacuucug 19

<210> SEQ ID NO 70
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 70
accagaacaa ccucugcuc 19

<210> SEQ ID NO 71
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 71
cuacaaccag cacaaucuc 19

<210> SEQ ID NO 72
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 72
uggaccaagu gguuugaca 19

<210> SEQ ID NO 73
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 73
acaaccagca caacuucug 19

<210> SEQ ID NO 74
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 74
caaccacuuu ggugacaag 19

<210> SEQ ID NO 75
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 75
acaaccaaca caacuucug 19

<210> SEQ ID NO 76
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 76
cucugcuccu acaacuagc 19

<210> SEQ ID NO 77
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 77
gagaucaucu ucaacaaca 19

<210> SEQ ID NO 78
<211> LENGTH: 19
<212> TYPE: RNA
<213> ORGANISM: Artificial sequence
<220> FEATURE:
<223> OTHER INFORMATION: MUC5AC 19-mer gene transcript (mRNA) target sequence

<400> SEQUENCE: 78
agaucaucuu caacaacaa 19

<210> SEQ ID NO 79
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 79
uuguaguagu cgcagaaca 19

<210> SEQ ID NO 80
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 80
nuguaguagu cgcagaaca 19

<210> SEQ ID NO 81
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 81
uuguaguagu cgcagaacn 19

<210> SEQ ID NO 82
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 82
nuguaguagu cgcagaacn 19

<210> SEQ ID NO 83
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 83
uucuuguuca ggcaaauca 19

<210> SEQ ID NO 84
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1
<223> OTHER INFORMATION: n = any nucleobase

<400> SEQUENCE: 84
nucuuguuca ggcaaauca 19

<210> SEQ ID NO 85
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 19
<223> OTHER INFORMATION: n = any nucleobase

<400> SEQUENCE: 85
uucuuguuca ggcaaaucn 19

<210> SEQ ID NO 86
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 86
nucuuguuca ggcaaaucn 19

<210> SEQ ID NO 87
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 87
cuugauggcc uuggagcag 19

<210> SEQ ID NO 88
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 88
uuugauggcc uuggagcag 19

<210> SEQ ID NO 89

<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 89
nuugauggcc uuggagcag 19

<210> SEQ ID NO 90
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 90
uuugauggcc uuggagcan 19

<210> SEQ ID NO 91
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 91
nuugauggcc uuggagcan 19

<210> SEQ ID NO 92
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 92
aaucuugaug gccuuggag 19

<210> SEQ ID NO 93
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 93
aaucuugaug gccuuggan 19

<210> SEQ ID NO 94
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 94
uaucuugaug gccuuggag 19

<210> SEQ ID NO 95
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 19
<223> OTHER INFORMATION: n = any nucleobase

<400> SEQUENCE: 95
uaucuugaug gccuuggan 19

<210> SEQ ID NO 96
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1
<223> OTHER INFORMATION: n = any nucleobase

<400> SEQUENCE: 96
naucuugaug gccuuggag 19

<210> SEQ ID NO 97
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 97
naucuugaug gccuuggan 19

<210> SEQ ID NO 98
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 98
cuugaacucg gggcugagg 19

<210> SEQ ID NO 99

<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 99
uuugaacucg gggcugagg 19

<210> SEQ ID NO 100
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 100
nuugaacucg gggcugagg 19

<210> SEQ ID NO 101
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 101
uuugaacucg gggcugagn 19

<210> SEQ ID NO 102
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 102
nuugaacucg gggcugagn 19

<210> SEQ ID NO 103
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 103
ggaugcugca cugcuucug 19

<210> SEQ ID NO 104
<211> LENGTH: 19
<212> TYPE: RNA

<213> ORGANISM: Artificial sequence
<220> FEATURE:
<223> OTHER INFORMATION: RNAi agent antisense strand 19-mer core base sequence

<400> SEQUENCE: 104
ugaugcugca cugcuucug 19

<210> SEQ ID NO 105
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 105
ngaugcugca cugcuucug 19

<210> SEQ ID NO 106
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 106
ugaugcugca cugcuucun 19

<210> SEQ ID NO 107
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 107
ngaugcugca cugcuucun 19

<210> SEQ ID NO 108
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 108
ugaugcugca cugcuucug 19

<210> SEQ ID NO 109
<211> LENGTH: 19
<212> TYPE: RNA
<213> ORGANISM: Artificial sequence
<220> FEATURE:

<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 109
ugaugcugca cugcuucun 19

<210> SEQ ID NO 110
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 110
ngaugcugca cugcuucug 19

<210> SEQ ID NO 111
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 111
ngaugcugca cugcuucun 19

<210> SEQ ID NO 112
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 112
guagucgcag aacagaggg 19

<210> SEQ ID NO 113
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 113
uuagucgcag aacagaggg 19

<210> SEQ ID NO 114
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 114
uuagucgcag aacagaggn 19

<210> SEQ ID NO 115
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 115
nuagucgcag aacagaggg 19

<210> SEQ ID NO 116
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 116
nuagucgcag aacagaggn 19

<210> SEQ ID NO 117
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 117
uuagucgcag aacagaggg 19

<210> SEQ ID NO 118
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 118
uuagucgcag aacagaggn 19

<210> SEQ ID NO 119
<211> LENGTH: 19
<212> TYPE: RNA
<213> ORGANISM: Artificial sequence
<220> FEATURE:

<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 119
nuagucgcag aacagaggg 19

<210> SEQ ID NO 120
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 120
nuagucgcag aacagaggn 19

<210> SEQ ID NO 121
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 121
aguagucgca gaacagagg 19

<210> SEQ ID NO 122
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 122
aguagucgca gaacagagn 19

<210> SEQ ID NO 123
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 123
uguagucgca gaacagagg 19

<210> SEQ ID NO 124
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 124
uguagucgca gaacagagn 19

<210> SEQ ID NO 125
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 125
nguagucgca gaacagagg 19

<210> SEQ ID NO 126
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 126
nguagucgca gaacagagn 19

<210> SEQ ID NO 127
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 127
aguagucgca gaacagagg 19

<210> SEQ ID NO 128
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 128
aguagucgca gaacagagn 19

<210> SEQ ID NO 129
<211> LENGTH: 19
<212> TYPE: RNA
<213> ORGANISM: Artificial sequence
<220> FEATURE:

<223> OTHER INFORMATION: RNAi agent antisense strand 19-mer core base sequence

<400> SEQUENCE: 129
uguagucgca gaacagagg 19

<210> SEQ ID NO 130
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 130
uguagucgca gaacagagn 19

<210> SEQ ID NO 131
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 131
nguagucgca gaacagagg 19

<210> SEQ ID NO 132
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 132
nguagucgca gaacagagn 19

<210> SEQ ID NO 133
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 133
guaguagucg cagaacaga 19

<210> SEQ ID NO 134
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 134
uuaguagucg cagaacaga 19

<210> SEQ ID NO 135
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 135
nuaguagucg cagaacaga 19

<210> SEQ ID NO 136
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 136
nuaguagucg cagaacagn 19

<210> SEQ ID NO 137
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 137
uguaguaguc gcagaacag 19

<210> SEQ ID NO 138
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 138
nguaguaguc gcagaacag 19

<210> SEQ ID NO 139
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 139
nguaguaguc gcagaacan 19

<210> SEQ ID NO 140
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 140
auaguuguag cagaugggu 19

<210> SEQ ID NO 141
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 141
auaguuguag cagaugggn 19

<210> SEQ ID NO 142
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 142
uuaguuguag cagaugggu 19

<210> SEQ ID NO 143
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 143
uuaguuguag cagaugggn 19

<210> SEQ ID NO 144
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 144
nuaguuguag cagaugggu 19

<210> SEQ ID NO 145
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 145
nuaguuguag cagaugggn 19

<210> SEQ ID NO 146
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 146
guccacgucg aaccacuuu 19

<210> SEQ ID NO 147
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 147
uuccacgucg aaccacuuu 19

<210> SEQ ID NO 148
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 148
uuccacgucg aaccacuun 19

<210> SEQ ID NO 149
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 149
nuccacgucg aaccacuuu 19

<210> SEQ ID NO 150
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 150
nuccacgucg aaccacuun 19

<210> SEQ ID NO 151
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 151
uuccacgucg aaccacuuu 19

<210> SEQ ID NO 152
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 152
uuccacgucg aaccacuun 19

<210> SEQ ID NO 153
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 153
nuccacgucg aaccacuuu 19

<210> SEQ ID NO 154
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 154
nuccacgucg aaccacuun 19

<210> SEQ ID NO 155
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 155
gaaguccacg ucgaaccac 19

<210> SEQ ID NO 156
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 156
uaaguccacg ucgaaccac 19

<210> SEQ ID NO 157
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 157
uaaguccacg ucgaaccan 19

<210> SEQ ID NO 158
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 158
naaguccacg ucgaaccac 19

<210> SEQ ID NO 159
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 159
naaguccacg ucgaaccan 19

<210> SEQ ID NO 160
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 160
uaaguccacg ucgaaccac 19

<210> SEQ ID NO 161
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 161
uaaguccacg ucgaaccan 19

<210> SEQ ID NO 162
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 162
naaguccacg ucgaaccac 19

<210> SEQ ID NO 163
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 163
naaguccacg ucgaaccan 19

<210> SEQ ID NO 164
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 164
gggaagucca cgucgaacc 19

<210> SEQ ID NO 165
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 165
uggaagucca cgucgaacc 19

<210> SEQ ID NO 166
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 166
uggaagucca cgucgaacn 19

<210> SEQ ID NO 167
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 167
nggaagucca cgucgaacc 19

<210> SEQ ID NO 168
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 168
nggaagucca cgucgaacn 19

<210> SEQ ID NO 169
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 169
uggaagucca cgucgaacc 19

<210> SEQ ID NO 170
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 170
uggaagucca cgucgaacn 19

<210> SEQ ID NO 171
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 171
nggaagucca cgucgaacc 19

<210> SEQ ID NO 172
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 172
nggaagucca cgucgaacn 19

<210> SEQ ID NO 173
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 173
agaugcuggu cuucuuguc 19

<210> SEQ ID NO 174
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 174
agaugcuggu cuucuugun 19

<210> SEQ ID NO 175
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 175
ugaugcuggu cuucuuguc 19

<210> SEQ ID NO 176
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 19
<223> OTHER INFORMATION: n = any nucleobase

<400> SEQUENCE: 176
ugaugcuggu cuucuugun 19

<210> SEQ ID NO 177
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1
<223> OTHER INFORMATION: n = any nucleobase

<400> SEQUENCE: 177
ngaugcuggu cuucuuguc 19

<210> SEQ ID NO 178
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 178
ngaugcuggu cuucuugun 19

<210> SEQ ID NO 179
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 179
agaugcuggu cuucuuguc 19

<210> SEQ ID NO 180
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 180
agaugcuggu cuucuugun 19

<210> SEQ ID NO 181
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 181
ugaugcuggu cuucuuguc 19

<210> SEQ ID NO 182
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 182
ugaugcuggu cuucuugun 19

<210> SEQ ID NO 183
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 183
ngaugcuggu cuucuuguc 19

<210> SEQ ID NO 184
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 184
ngaugcuggu cuucuugun 19

<210> SEQ ID NO 185
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 185
gguugaugaa gaugcuggu 19

<210> SEQ ID NO 186
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 19
<223> OTHER INFORMATION: n = any nucleobase

<400> SEQUENCE: 186
uguugaugaa gaugcuggn 19

<210> SEQ ID NO 187
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1
<223> OTHER INFORMATION: n = any nucleobase

<400> SEQUENCE: 187
nguugaugaa gaugcuggu 19

<210> SEQ ID NO 188
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 188
nguugaugaa gaugcuggn 19

<210> SEQ ID NO 189
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 189
auguuguugu agguuuccu 19

<210> SEQ ID NO 190
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 190
auguuguugu agguuuccn 19

<210> SEQ ID NO 191
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 191
uuguuguugu agguuuccu 19

<210> SEQ ID NO 192
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 192
uuguuguugu agguuuccn 19

<210> SEQ ID NO 193
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 193
nuguuguugu agguuuccn 19

<210> SEQ ID NO 194
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 194
augauguugu uguagguuu 19

<210> SEQ ID NO 195
<211> LENGTH: 19

<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 195
augauguugu uguagguun 19

<210> SEQ ID NO 196
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 196
uugauguugu uguagguuu 19

<210> SEQ ID NO 197
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 197
uugauguugu uguagguun 19

<210> SEQ ID NO 198
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 198
nugauguugu uguagguun 19

<210> SEQ ID NO 199
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 199
uugaugaaga ugcuggucu 19

<210> SEQ ID NO 200
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 200
uugaugaaga ugcuggucn 19

<210> SEQ ID NO 201
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 201
nugaugaaga ugcuggucu 19

<210> SEQ ID NO 202
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 202
nugaugaaga ugcuggucn 19

<210> SEQ ID NO 203
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 203
ugaucuggua guuguagca 19

<210> SEQ ID NO 204
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 204
ugaucuggua guuguagcn 19

<210> SEQ ID NO 205
<211> LENGTH: 19

<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 205
ngaucuggua guuguagca 19

<210> SEQ ID NO 206
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 206
ngaucuggua guuguagcn 19

<210> SEQ ID NO 207
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 207
ugaucuggua guuguagcn 19

<210> SEQ ID NO 208
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 208
ngaucuggua guuguagca 19

<210> SEQ ID NO 209
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 209
ngaucuggua guuguagcn 19

<210> SEQ ID NO 210
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 210
ugaucuggua guuguagcn 19

<210> SEQ ID NO 211
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 211
cccugaucug guaguugua 19

<210> SEQ ID NO 212
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 212
uccugaucug guaguugua 19

<210> SEQ ID NO 213
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 213
nccugaucug guaguugua 19

<210> SEQ ID NO 214
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 214
uccugaucug guaguugun 19

<210> SEQ ID NO 215
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 215
nccugaucug guaguugun 19

<210> SEQ ID NO 216
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 216
cccugaucug guaguugua 19

<210> SEQ ID NO 217
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 217
uccugaucug guaguugua 19

<210> SEQ ID NO 218
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 218
nccugaucug guaguugua 19

<210> SEQ ID NO 219
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 219
uccugaucug guaguugun 19

<210> SEQ ID NO 220
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 220
nccugaucug guaguugun 19

<210> SEQ ID NO 221
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 221
uaguuguagc agaugggug 19

<210> SEQ ID NO 222
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 222
naguuguagc agaugggug 19

<210> SEQ ID NO 223
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 223
uaguuguagc agaugggun 19

<210> SEQ ID NO 224
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 224
naguuguagc agaugggun 19

<210> SEQ ID NO 225
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 225
gcaacacugg augcggauc 19

<210> SEQ ID NO 226
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 226
ucaacacugg augcggauc 19

<210> SEQ ID NO 227
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1
<223> OTHER INFORMATION: n = any nucleobase

<400> SEQUENCE: 227
ncaacacugg augcggauc 19

<210> SEQ ID NO 228
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 19
<223> OTHER INFORMATION: n = any nucleobase

<400> SEQUENCE: 228
ucaacacugg augcggaun 19

<210> SEQ ID NO 229
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 229
ncaacacugg augcggaun 19

<210> SEQ ID NO 230
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 230
gcaacacugg augcggauc 19

<210> SEQ ID NO 231
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 231
ucaacacugg augcggauc 19

<210> SEQ ID NO 232
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 232
ncaacacugg augcggauc 19

<210> SEQ ID NO 233
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 233
ucaacacugg augcggaun 19

<210> SEQ ID NO 234
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 234
ncaacacugg augcggaun 19

<210> SEQ ID NO 235
<211> LENGTH: 19

<212> TYPE: RNA
<213> ORGANISM: Artificial sequence
<220> FEATURE:
<223> OTHER INFORMATION: RNAi agent antisense strand 19-mer core base sequence

<400> SEQUENCE: 235
guguucgaug cucaccucu 19

<210> SEQ ID NO 236
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 236
uuguucgaug cucaccucu 19

<210> SEQ ID NO 237
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 237
nuguucgaug cucaccucu 19

<210> SEQ ID NO 238
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 238
uuguucgaug cucaccucn 19

<210> SEQ ID NO 239
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 239
nuguucgaug cucaccucn 19

<210> SEQ ID NO 240
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 240
guguucgaug cucaccucu 19

<210> SEQ ID NO 241
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 241
uuguucgaug cucaccucu 19

<210> SEQ ID NO 242
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 242
nuguucgaug cucaccucu 19

<210> SEQ ID NO 243
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 19
<223> OTHER INFORMATION: n = any nucleobase

<400> SEQUENCE: 243
uuguucgaug cucaccucn 19

<210> SEQ ID NO 244
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 244
nuguucgaug cucaccucn 19

<210> SEQ ID NO 245
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 245
caucuugaag ggucccugc 19

<210> SEQ ID NO 246
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 246
uaucuugaag ggucccugc 19

<210> SEQ ID NO 247
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1
<223> OTHER INFORMATION: n = any nucleobase

<400> SEQUENCE: 247
naucuugaag ggucccugc 19

<210> SEQ ID NO 248
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 19
<223> OTHER INFORMATION: n = any nucleobase

<400> SEQUENCE: 248
uaucuugaag ggucccugn 19

<210> SEQ ID NO 249
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 249
naucuugaag ggucccugn 19

<210> SEQ ID NO 250
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 250
ucguaguuga ggcacaucu 19

<210> SEQ ID NO 251
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1
<223> OTHER INFORMATION: n = any nucleobase

<400> SEQUENCE: 251
ncguaguuga ggcacaucu 19

<210> SEQ ID NO 252
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 19
<223> OTHER INFORMATION: n = any nucleobase

<400> SEQUENCE: 252
ucguaguuga ggcacaucn 19

<210> SEQ ID NO 253
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 253
ncguaguuga ggcacaucn 19

<210> SEQ ID NO 254
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 254
ucguaguuga ggcacaucu 19

<210> SEQ ID NO 255
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1

<223> OTHER INFORMATION: n = any nucleobase

<400> SEQUENCE: 255
ncguaguuga ggcacaucu 19

<210> SEQ ID NO 256
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 256
ucguaguuga ggcacaucn 19

<210> SEQ ID NO 257
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 257
ncguaguuga ggcacaucn 19

<210> SEQ ID NO 258
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 258
ccucguaguu gaggcacau 19

<210> SEQ ID NO 259
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 259
ucucguaguu gaggcacau 19

<210> SEQ ID NO 260
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 260
ncucguaguu gaggcacau 19

<210> SEQ ID NO 261
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 261
ucucguaguu gaggcacan 19

<210> SEQ ID NO 262
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 262
ncucguaguu gaggcacan 19

<210> SEQ ID NO 263
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 263
ccucguaguu gaggcacau 19

<210> SEQ ID NO 264
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 264
ucucguaguu gaggcacau 19

<210> SEQ ID NO 265
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 265
ncucguaguu gaggcacau 19

<210> SEQ ID NO 266
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 266
ucucguaguu gaggcacan 19

<210> SEQ ID NO 267
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 267
ncucguaguu gaggcacan 19

<210> SEQ ID NO 268
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 268
cuucaggcag gucucgcug 19

<210> SEQ ID NO 269
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 269
uuucaggcag gucucgcug 19

<210> SEQ ID NO 270
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 270
nuucaggcag gucucgcug 19

```
<210> SEQ ID NO 271
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 19
<223> OTHER INFORMATION: n = any nucleobase

<400> SEQUENCE: 271

uuucaggcag gucucgcun                                                    19


<210> SEQ ID NO 272
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 272

nuucaggcag gucucgcun                                                    19


<210> SEQ ID NO 273
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 273

gucugaagau ggugacguu                                                    19


<210> SEQ ID NO 274
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 274

uucugaagau ggugacguu                                                    19


<210> SEQ ID NO 275
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 275

nucugaagau ggugacguu                                                    19


<210> SEQ ID NO 276
```

<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 276
uucugaagau ggugacgun 19

<210> SEQ ID NO 277
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 277
nucugaagau ggugacgun 19

<210> SEQ ID NO 278
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 278
ggucugaaga uggugacgu 19

<210> SEQ ID NO 279
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 279
ugucugaaga uggugacgu 19

<210> SEQ ID NO 280
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 280
ngucugaaga uggugacgu 19

<210> SEQ ID NO 281
<211> LENGTH: 19
<212> TYPE: RNA

<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 281
ugucugaaga uggugacgn 19

<210> SEQ ID NO 282
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 282
ngucugaaga uggugacgn 19

<210> SEQ ID NO 283
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 283
ggucugaaga uggugacgu 19

<210> SEQ ID NO 284
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 284
ugucugaaga uggugacgu 19

<210> SEQ ID NO 285
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 285
ngucugaaga uggugacgu 19

<210> SEQ ID NO 286
<211> LENGTH: 19
<212> TYPE: RNA
<213> ORGANISM: Artificial sequence
<220> FEATURE:

<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 286
ugucugaaga uggugacgn 19

<210> SEQ ID NO 287
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 287
ngucugaaga uggugacgn 19

<210> SEQ ID NO 288
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 288
cggaagucau cggccugga 19

<210> SEQ ID NO 289
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 289
uggaagucau cggccugga 19

<210> SEQ ID NO 290
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 290
nggaagucau cggccugga 19

<210> SEQ ID NO 291
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 291
uggaagucau cggccuggn 19

<210> SEQ ID NO 292
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 292
nggaagucau cggccuggn 19

<210> SEQ ID NO 293
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 293
cuugaaggug uugaagaag 19

<210> SEQ ID NO 294
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 294
uuugaaggug uugaagaag 19

<210> SEQ ID NO 295
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 295
nuugaaggug uugaagaag 19

<210> SEQ ID NO 296
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 296
uuugaaggug uugaagaan 19

<210> SEQ ID NO 297
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 297
nuugaaggug uugaagaan 19

<210> SEQ ID NO 298
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 298
ugcaguucga guaguaggu 19

<210> SEQ ID NO 299
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 299
ngcaguucga guaguaggu 19

<210> SEQ ID NO 300
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 300
ugcaguucga guaguaggn 19

<210> SEQ ID NO 301
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 301
ngcaguucga guaguaggn 19

<210> SEQ ID NO 302
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 302
ugcaguucga guaguaggu 19

<210> SEQ ID NO 303
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 303
ngcaguucga guaguaggu 19

<210> SEQ ID NO 304
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 304
ugcaguucga guaguaggn 19

<210> SEQ ID NO 305
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 305
ngcaguucga guaguaggn 19

<210> SEQ ID NO 306
<211> LENGTH: 19
<212> TYPE: RNA
<213> ORGANISM: Artificial sequence
<220> FEATURE:

```
<223> OTHER INFORMATION: RNAi agent antisense strand 19-mer core base
      sequence

<400> SEQUENCE: 306

cuuggagcag gugguccccu                                                    19

<210> SEQ ID NO 307
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 307

uuuggagcag gugguccccu                                                    19

<210> SEQ ID NO 308
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 308

nuuggagcag gugguccccu                                                    19

<210> SEQ ID NO 309
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 19
<223> OTHER INFORMATION: n = any nucleobase

<400> SEQUENCE: 309

uuuggagcag guggucccn                                                     19

<210> SEQ ID NO 310
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 310

nuuggagcag guggucccn                                                     19

<210> SEQ ID NO 311
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
```

<400> SEQUENCE: 311
ucuugauggc cuuggagca 19

<210> SEQ ID NO 312
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 312
ncuugauggc cuuggagca 19

<210> SEQ ID NO 313
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 313
ucuugauggc cuuggagcn 19

<210> SEQ ID NO 314
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 314
ncuugauggc cuuggagcn 19

<210> SEQ ID NO 315
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 315
cugucaucgu gguuccaca 19

<210> SEQ ID NO 316
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 316
uugucaucgu gguuccaca 19

<210> SEQ ID NO 317
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 317
nugucaucgu gguuccaca 19

<210> SEQ ID NO 318
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 318
uugucaucgu gguuccacn 19

<210> SEQ ID NO 319
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 319
nugucaucgu gguuccacn 19

<210> SEQ ID NO 320
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 320
cugucaucgu gguuccaca 19

<210> SEQ ID NO 321
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 321
uugucaucgu gguuccaca 19

<210> SEQ ID NO 322
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 322
nugucaucgu gguuccaca 19

<210> SEQ ID NO 323
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 323
uugucaucgu gguuccacn 19

<210> SEQ ID NO 324
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 324
nugucaucgu gguuccacn 19

<210> SEQ ID NO 325
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 325
acagaagcag aggucuugc 19

<210> SEQ ID NO 326
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 326
acagaagcag aggucuugn 19

<210> SEQ ID NO 327
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 327
ucagaagcag aggucuugc 19

<210> SEQ ID NO 328
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 328
ucagaagcag aggucuugn 19

<210> SEQ ID NO 329
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 329
acagaagcag aggucuugc 19

<210> SEQ ID NO 330
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 330
acagaagcag aggucuugn 19

<210> SEQ ID NO 331
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 331
ucagaagcag aggucuugc 19

<210> SEQ ID NO 332
<211> LENGTH: 19

<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 332
ucagaagcag aggucuugn 19

<210> SEQ ID NO 333
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 333
gcaguuggug cagucugug 19

<210> SEQ ID NO 334
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 334
ucaguuggug cagucugug 19

<210> SEQ ID NO 335
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 335
ncaguuggug cagucugug 19

<210> SEQ ID NO 336
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 336
ucaguuggug cagucugun 19

<210> SEQ ID NO 337
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 337
ncaguuggug cagucugun 19

<210> SEQ ID NO 338
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 338
gcaguuggug cagucugug 19

<210> SEQ ID NO 339
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 339
ucaguuggug cagucugug 19

<210> SEQ ID NO 340
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 340
ncaguuggug cagucugug 19

<210> SEQ ID NO 341
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 19
<223> OTHER INFORMATION: n = any nucleobase

<400> SEQUENCE: 341
ucaguuggug cagucugun 19

<210> SEQ ID NO 342
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 342
ncaguuggug cagucugun 19

<210> SEQ ID NO 343
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 343
gcaguacagu gaaggcacu 19

<210> SEQ ID NO 344
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 344
ucaguacagu gaaggcacu 19

<210> SEQ ID NO 345
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 345
ncaguacagu gaaggcacu 19

<210> SEQ ID NO 346
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 346
ucaguacagu gaaggcacn 19

<210> SEQ ID NO 347
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:

<221> NAME/KEY: modified_base
<222> LOCATION: 1, 19
<223> OTHER INFORMATION: n = any nucleobase

<400> SEQUENCE: 347
ncaguacagu gaaggcacn 19

<210> SEQ ID NO 348
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 348
gcaguacagu gaaggcacu 19

<210> SEQ ID NO 349
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 349
ucaguacagu gaaggcacu 19

<210> SEQ ID NO 350
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 350
ncaguacagu gaaggcacu 19

<210> SEQ ID NO 351
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 351
ucaguacagu gaaggcacn 19

<210> SEQ ID NO 352
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19

<223> OTHER INFORMATION: n = any nucleobase

<400> SEQUENCE: 352
ncaguacagu gaaggcacn 19

<210> SEQ ID NO 353
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 353
ugcuguugaa guucccaca 19

<210> SEQ ID NO 354
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 354
ngcuguugaa guucccaca 19

<210> SEQ ID NO 355
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 355
ugcuguugaa guucccacn 19

<210> SEQ ID NO 356
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 356
ngcuguugaa guucccacn 19

<210> SEQ ID NO 357
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 357
ugcuguugaa guucccaca 19

<210> SEQ ID NO 358
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 358
ngcuguugaa guucccaca 19

<210> SEQ ID NO 359
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 359
ugcuguugaa guucccacn 19

<210> SEQ ID NO 360
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 360
ngcuguugaa guucccacn 19

<210> SEQ ID NO 361
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 361
ggaugcuguu gaaguuccc 19

<210> SEQ ID NO 362
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 362
ugaugcuguu gaaguuccc 19

<210> SEQ ID NO 363
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 363
ngaugcuguu gaaguuccc 19

<210> SEQ ID NO 364
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 364
ugaugcuguu gaaguuccn 19

<210> SEQ ID NO 365
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 365
ngaugcuguu gaaguuccn 19

<210> SEQ ID NO 366
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 366
ggaugcuguu gaaguuccc 19

<210> SEQ ID NO 367
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 367
ugaugcuguu gaaguuccc 19

<210> SEQ ID NO 368
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 368
ngaugcuguu gaaguuccc 19

<210> SEQ ID NO 369
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 369
ugaugcuguu gaaguuccn 19

<210> SEQ ID NO 370
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 370
ngaugcuguu gaaguuccn 19

<210> SEQ ID NO 371
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 371
gggucuugaa gguguugaa 19

<210> SEQ ID NO 372
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 372
uggucuugaa gguguugaa 19

<210> SEQ ID NO 373

<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1
<223> OTHER INFORMATION: n = any nucleobase

<400> SEQUENCE: 373
nggucuugaa gguguugaa 19

<210> SEQ ID NO 374
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 19
<223> OTHER INFORMATION: n = any nucleobase

<400> SEQUENCE: 374
uggucuugaa gguguugan 19

<210> SEQ ID NO 375
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 375
nggucuugaa gguguugan 19

<210> SEQ ID NO 376
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 376
gggucuugaa gguguugaa 19

<210> SEQ ID NO 377
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 377
uggucuugaa gguguugaa 19

<210> SEQ ID NO 378
<211> LENGTH: 19
<212> TYPE: RNA

<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 378
nggucuugaa gguguugaa 19

<210> SEQ ID NO 379
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 379
uggucuugaa gguguugan 19

<210> SEQ ID NO 380
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 380
nggucuugaa gguguugan 19

<210> SEQ ID NO 381
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 381
aagcuguucc ugauguugg 19

<210> SEQ ID NO 382
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 382
aagcuguucc ugauguugn 19

<210> SEQ ID NO 383

<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 383
uagcuguucc ugauguugg 19

<210> SEQ ID NO 384
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 384
uagcuguucc ugauguugn 19

<210> SEQ ID NO 385
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 385
nagcuguucc ugauguugn 19

<210> SEQ ID NO 386
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 386
aagcuguucc ugauguugg 19

<210> SEQ ID NO 387
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 387
aagcuguucc ugauguugn 19

<210> SEQ ID NO 388
<211> LENGTH: 19
<212> TYPE: RNA

<213> ORGANISM: Artificial sequence
<220> FEATURE:
<223> OTHER INFORMATION: RNAi agent antisense strand 19-mer core base sequence

<400> SEQUENCE: 388
uagcuguucc ugauguugg 19

<210> SEQ ID NO 389
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 389
uagcuguucc ugauguugn 19

<210> SEQ ID NO 390
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 390
nagcuguucc ugauguugn 19

<210> SEQ ID NO 391
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 391
acaugcaguu cgaguagua 19

<210> SEQ ID NO 392
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 392
acaugcaguu cgaguagun 19

<210> SEQ ID NO 393
<211> LENGTH: 19
<212> TYPE: RNA
<213> ORGANISM: Artificial sequence
<220> FEATURE:

<223> OTHER INFORMATION: RNAi agent antisense strand 19-mer core base
      sequence

<400> SEQUENCE: 393
ucaugcaguu cgaguagua 19

<210> SEQ ID NO 394
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 19
<223> OTHER INFORMATION: n = any nucleobase

<400> SEQUENCE: 394
ucaugcaguu cgaguagun 19

<210> SEQ ID NO 395
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 395
ncaugcaguu cgaguagun 19

<210> SEQ ID NO 396
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 396
gaagccaaca cugcaggug 19

<210> SEQ ID NO 397
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 397
uaagccaaca cugcaggug 19

<210> SEQ ID NO 398
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 398
naagccaaca cugcaggug 19

<210> SEQ ID NO 399
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 399
uaagccaaca cugcaggun 19

<210> SEQ ID NO 400
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 400
naagccaaca cugcaggun 19

<210> SEQ ID NO 401
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 401
gaagccaaca cugcaggug 19

<210> SEQ ID NO 402
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 402
uaagccaaca cugcaggug 19

<210> SEQ ID NO 403
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 403
naagccaaca cugcaggug 19

<210> SEQ ID NO 404
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 404
uaagccaaca cugcaggun 19

<210> SEQ ID NO 405
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 405
naagccaaca cugcaggun 19

<210> SEQ ID NO 406
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 406
cuguaacagg ucaugucca 19

<210> SEQ ID NO 407
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 407
uuguaacagg ucaugucca 19

<210> SEQ ID NO 408
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 408
nuguaacagg ucaugucca 19

<210> SEQ ID NO 409
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 409
uuguaacagg ucauguccn 19

<210> SEQ ID NO 410
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 410
nuguaacagg ucauguccn 19

<210> SEQ ID NO 411
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 411
ccguugaagc uguagcucu 19

<210> SEQ ID NO 412
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 412
ucguugaagc uguagcucu 19

<210> SEQ ID NO 413
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 413
ncguugaagc uguagcucu 19

<210> SEQ ID NO 414
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 414
ucguugaagc uguagcucn 19

<210> SEQ ID NO 415
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 415
ncguugaagc uguagcucn 19

<210> SEQ ID NO 416
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 416
ccguugaagc uguagcucu 19

<210> SEQ ID NO 417
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 417
ucguugaagc uguagcucu 19

<210> SEQ ID NO 418
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 418
ncguugaagc uguagcucu 19

<210> SEQ ID NO 419
<211> LENGTH: 19

<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 419
ucguugaagc uguagcucn 19

<210> SEQ ID NO 420
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 420
ncguugaagc uguagcucn 19

<210> SEQ ID NO 421
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 421
caguacagug aaggcacug 19

<210> SEQ ID NO 422
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 422
uaguacagug aaggcacug 19

<210> SEQ ID NO 423
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 423
uaguacagug aaggcacun 19

<210> SEQ ID NO 424
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 424
naguacagug aaggcacug 19

<210> SEQ ID NO 425
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 425
naguacagug aaggcacun 19

<210> SEQ ID NO 426
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 426
cucgaagcug uuccugaug 19

<210> SEQ ID NO 427
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 427
uucgaagcug uuccugaug 19

<210> SEQ ID NO 428
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 428
uucgaagcug uuccugaun 19

<210> SEQ ID NO 429
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 429
nucgaagcug uuccugaug 19

<210> SEQ ID NO 430
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 430
nucgaagcug uuccugaun 19

<210> SEQ ID NO 431
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 431
cucgaagcug uuccugaug 19

<210> SEQ ID NO 432
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 432
uucgaagcug uuccugaug 19

<210> SEQ ID NO 433
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 19
<223> OTHER INFORMATION: n = any nucleobase

<400> SEQUENCE: 433
uucgaagcug uuccugaun 19

<210> SEQ ID NO 434
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:

<221> NAME/KEY: modified_base
<222> LOCATION: 1
<223> OTHER INFORMATION: n = any nucleobase

<400> SEQUENCE: 434
nucgaagcug uuccugaug 19

<210> SEQ ID NO 435
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 435
nucgaagcug uuccugaun 19

<210> SEQ ID NO 436
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 436
ucuuguucag gcaaaucag 19

<210> SEQ ID NO 437
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 437
ucuuguucag gcaaaucan 19

<210> SEQ ID NO 438
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 438
ncuuguucag gcaaaucag 19

<210> SEQ ID NO 439
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 439
ncuuguucag gcaaaucan 19

<210> SEQ ID NO 440
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 440
ucaccaaagu gguuguccu 19

<210> SEQ ID NO 441
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 19
<223> OTHER INFORMATION: n = any nucleobase

<400> SEQUENCE: 441
ucaccaaagu gguuguccn 19

<210> SEQ ID NO 442
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1
<223> OTHER INFORMATION: n = any nucleobase

<400> SEQUENCE: 442
ncaccaaagu gguuguccu 19

<210> SEQ ID NO 443
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 443
ncaccaaagu gguuguccn 19

<210> SEQ ID NO 444
<211> LENGTH: 19
<212> TYPE: RNA
<213> ORGANISM: Artificial sequence

```
-continued

<220> FEATURE:
<223> OTHER INFORMATION: RNAi agent antisense strand 19-mer core base
      sequence

<400> SEQUENCE: 444

ucaccaaagu gguuguccu                                                      19

<210> SEQ ID NO 445
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 19
<223> OTHER INFORMATION: n = any nucleobase

<400> SEQUENCE: 445

ucaccaaagu gguuguccn                                                      19

<210> SEQ ID NO 446
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 446

ncaccaaagu gguuguccu                                                      19

<210> SEQ ID NO 447
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 447

ncaccaaagu gguuguccn                                                      19

<210> SEQ ID NO 448
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 448

gagcagaggu uguucuggu                                                      19

<210> SEQ ID NO 449
<211> LENGTH: 19
<212> TYPE: RNA
<213> ORGANISM: Artificial sequence
<220> FEATURE:
<223> OTHER INFORMATION: RNAi agent antisense strand 19-mer core base
```

sequence

<400> SEQUENCE: 449
uagcagaggu uguucuggu 19

<210> SEQ ID NO 450
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 450
uagcagaggu uguucuggn 19

<210> SEQ ID NO 451
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 451
nagcagaggu uguucuggu 19

<210> SEQ ID NO 452
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 452
nagcagaggu uguucuggn 19

<210> SEQ ID NO 453
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 453
gagcagaggu uguucuggu 19

<210> SEQ ID NO 454
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 454
uagcagaggu uguucuggu 19

<210> SEQ ID NO 455
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 455
uagcagaggu uguucuggn 19

<210> SEQ ID NO 456
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 456
nagcagaggu uguucuggu 19

<210> SEQ ID NO 457
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 457
nagcagaggu uguucuggn 19

<210> SEQ ID NO 458
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 458
uagauugugc ugguuguag 19

<210> SEQ ID NO 459
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 459
uagauugugc ugguuguag 19

<210> SEQ ID NO 460
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 460
nagauugugc ugguuguag 19

<210> SEQ ID NO 461
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 461
uagauugugc ugguuguan 19

<210> SEQ ID NO 462
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 462
nagauugugc ugguuguan 19

<210> SEQ ID NO 463
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 463
cagaaguugu gcugguugu 19

<210> SEQ ID NO 464
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 464
uagaaguugu gcugguugu 19

<210> SEQ ID NO 465
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 465
nagaaguugu gcugguugu 19

<210> SEQ ID NO 466
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 466
uagaaguugu gcugguugn 19

<210> SEQ ID NO 467
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 467
nagaaguugu gcugguugn 19

<210> SEQ ID NO 468
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 468
cuugucacca aagugguug 19

<210> SEQ ID NO 469
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 469
uuugucacca aagugguug 19

<210> SEQ ID NO 470

```
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 470

nuugucacca aagugguug                                                    19

<210> SEQ ID NO 471
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 19
<223> OTHER INFORMATION: n = any nucleobase

<400> SEQUENCE: 471

uuugucacca aagugguun                                                    19

<210> SEQ ID NO 472
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 472

nuugucacca aagugguun                                                    19

<210> SEQ ID NO 473
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 473

cagagguugu guugguugu                                                    19

<210> SEQ ID NO 474
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 474

uagagguugu guugguugu                                                    19

<210> SEQ ID NO 475
<211> LENGTH: 19
<212> TYPE: RNA
```

<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 475
nagagguugu guugguugu 19

<210> SEQ ID NO 476
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 476
uagagguugu guugguugn 19

<210> SEQ ID NO 477
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 477
nagagguugu guugguugn 19

<210> SEQ ID NO 478
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 478
ucuaguugua ggagcagag 19

<210> SEQ ID NO 479
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 479
gcuaguugua ggagcagag 19

<210> SEQ ID NO 480
<211> LENGTH: 19
<212> TYPE: RNA
<213> ORGANISM: Artificial sequence
<220> FEATURE:

<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 480
ncuaguugua ggagcagag 19

<210> SEQ ID NO 481
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 481
ucuaguugua ggagcagan 19

<210> SEQ ID NO 482
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 482
ncuaguugua ggagcagan 19

<210> SEQ ID NO 483
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 483
ugguucagga acacuuccc 19

<210> SEQ ID NO 484
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 484
ngguucagga acacuuccc 19

<210> SEQ ID NO 485
<211> LENGTH: 19
<212> TYPE: RNA

```
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 19
<223> OTHER INFORMATION: n = any nucleobase

<400> SEQUENCE: 485

ugguucagga acacuuccn                                                19


<210> SEQ ID NO 486
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 486

ngguucagga acacuuccn                                                19


<210> SEQ ID NO 487
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 487

ugguucagga acacuuccc                                                19


<210> SEQ ID NO 488
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 488

ngguucagga acacuuccc                                                19


<210> SEQ ID NO 489
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 19
<223> OTHER INFORMATION: n = any nucleobase

<400> SEQUENCE: 489

ugguucagga acacuuccn                                                19


<210> SEQ ID NO 490
```

<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 490
ngguucagga acacuuccn 19

<210> SEQ ID NO 491
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 491
gaugucgucg aaguuccca 19

<210> SEQ ID NO 492
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 492
uaugucgucg aaguuccca 19

<210> SEQ ID NO 493
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 493
naugucgucg aaguuccca 19

<210> SEQ ID NO 494
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 494
uaugucgucg aaguucccn 19

<210> SEQ ID NO 495
<211> LENGTH: 19
<212> TYPE: RNA

<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 495
naugucgucg aaguucccn 19

<210> SEQ ID NO 496
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 496
gaugucgucg aaguuccca 19

<210> SEQ ID NO 497
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 497
uaugucgucg aaguuccca 19

<210> SEQ ID NO 498
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 498
naugucgucg aaguuccca 19

<210> SEQ ID NO 499
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 499
uaugucgucg aaguucccn 19

<210> SEQ ID NO 500
<211> LENGTH: 19
<212> TYPE: RNA
<213> ORGANISM: Artificial sequence
<220> FEATURE:

<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 500
naugucgucg aaguucccn 19

<210> SEQ ID NO 501
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 501
auuucugcca agaggaggu 19

<210> SEQ ID NO 502
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 19
<223> OTHER INFORMATION: n = any nucleobase

<400> SEQUENCE: 502
auuucugcca agaggaggn 19

<210> SEQ ID NO 503
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 503
uuuucugcca agaggaggu 19

<210> SEQ ID NO 504
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 19
<223> OTHER INFORMATION: n = any nucleobase

<400> SEQUENCE: 504
uuuucugcca agaggaggn 19

<210> SEQ ID NO 505
<211> LENGTH: 19
<212> TYPE: RNA
<213> ORGANISM: Artificial sequence
<220> FEATURE:
<223> OTHER INFORMATION: RNAi agent antisense strand 19-mer core base
sequence <220> FEATURE:
<221> NAME/KEY: modified_base
<222> LOCATION: 1, 19
<223> OTHER INFORMATION: n = any nucleobase

<400> SEQUENCE: 505
nuuucugcca agaggaggn 19

<210> SEQ ID NO 506
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 506
auuucugcca agaggaggu 19

<210> SEQ ID NO 507
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 19
<223> OTHER INFORMATION: n = any nucleobase

<400> SEQUENCE: 507
auuucugcca agaggaggn 19

<210> SEQ ID NO 508
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 508
uuuucugcca agaggaggu 19

<210> SEQ ID NO 509
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 19
<223> OTHER INFORMATION: n = any nucleobase

<400> SEQUENCE: 509
uuuucugcca agaggaggn 19

<210> SEQ ID NO 510
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 510
nuuucugcca agaggaggn 19

<210> SEQ ID NO 511
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 511
uguuguugaa gaugaucuc 19

<210> SEQ ID NO 512
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 512
uguuguugaa gaugaucun 19

<210> SEQ ID NO 513
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 513
nguuguugaa gaugaucuc 19

<210> SEQ ID NO 514
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 514
nguuguugaa gaugaucun 19

<210> SEQ ID NO 515
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 515
uguuguugua gguuuccuu 19

<210> SEQ ID NO 516
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 516
nguuguugua gguuuccuu 19

<210> SEQ ID NO 517
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 517
uguuguugua gguuuccun 19

<210> SEQ ID NO 518
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 518
nguuguugua gguuuccun 19

<210> SEQ ID NO 519
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 519
aucuuguccu caucaaaga 19

<210> SEQ ID NO 520
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 520
aucuuguccu caucaaagn 19

<210> SEQ ID NO 521
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 521
nucuuguccu caucaaagn 19

<210> SEQ ID NO 522
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 522
uucuuguccu caucaaaga 19

<210> SEQ ID NO 523
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 523
uucuuguccu caucaaagn 19

<210> SEQ ID NO 524
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 524
gcaucuuguc cucaucaaa 19

<210> SEQ ID NO 525
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 525
ucaucuuguc cucaucaaa 19

<210> SEQ ID NO 526
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 526
ucaucuuguc cucaucaan 19

<210> SEQ ID NO 527
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 527
ncaucuuguc cucaucaaa 19

<210> SEQ ID NO 528
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 528
ncaucuuguc cucaucaan 19

<210> SEQ ID NO 529
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 529
gcuaguugua ggagcagag 19

<210> SEQ ID NO 530
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 530
ucuaguugua ggagcagag 19

<210> SEQ ID NO 531
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 531
ncuaguugua ggagcagag 19

<210> SEQ ID NO 532
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 532
ucuaguugua ggagcagan 19

<210> SEQ ID NO 533
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 533
ncuaguugua ggagcagan 19

<210> SEQ ID NO 534
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 534
uaguuguaga agcagaggu 19

<210> SEQ ID NO 535
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 535
naguuguaga agcagaggu 19

<210> SEQ ID NO 536
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 536
uaguuguaga agcagaggn 19

<210> SEQ ID NO 537
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 537
naguuguaga agcagaggn 19

<210> SEQ ID NO 538
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 538
cagaaguugu gcugguuau 19

<210> SEQ ID NO 539
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 539
uagaaguugu gcugguuau 19

<210> SEQ ID NO 540
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 540
nagaaguugu gcugguuau 19

<210> SEQ ID NO 541
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 541
uagaaguugu gcugguuan 19

<210> SEQ ID NO 542
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 542
nagaaguugu gcugguuan 19

<210> SEQ ID NO 543
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 543
ccaacacugc aggugaugu 19

<210> SEQ ID NO 544
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 544
ucaacacugc aggugaugu 19

<210> SEQ ID NO 545
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 545
ncaacacugc aggugaugu 19

<210> SEQ ID NO 546
<211> LENGTH: 19

<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19
<223> OTHER INFORMATION: n = any nucleobase

<400> SEQUENCE: 546
ucaacacugc aggugaugn 19

<210> SEQ ID NO 547
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 547
ncaacacugc aggugaugn 19

<210> SEQ ID NO 548
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 548
ccaacacugc aggugaugu 19

<210> SEQ ID NO 549
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 549
ucaacacugc aggugaugu 19

<210> SEQ ID NO 550
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 550
ncaacacugc aggugaugu 19

<210> SEQ ID NO 551
<211> LENGTH: 19
<212> TYPE: RNA
<213> ORGANISM: Artificial sequence

```
<220> FEATURE:
<223> OTHER INFORMATION: RNAi agent antisense strand 19-mer core base
      sequence
<220> FEATURE:
<221> NAME/KEY: modified_base
<222> LOCATION: 19
<223> OTHER INFORMATION: n = any nucleobase

<400> SEQUENCE: 551

ucaacacugc aggugaugn                                                  19


<210> SEQ ID NO 552
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 552

ncaacacugc aggugaugn                                                  19


<210> SEQ ID NO 553
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 553

caucuugucc ucaucaaag                                                  19


<210> SEQ ID NO 554
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 554

uaucuugucc ucaucaaag                                                  19


<210> SEQ ID NO 555
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 555

naucuugucc ucaucaaag                                                  19


<210> SEQ ID NO 556
<211> LENGTH: 19
<212> TYPE: RNA
<213> ORGANISM: Artificial sequence
<220> FEATURE:
<223> OTHER INFORMATION: RNAi agent antisense strand 19-mer core base
```

sequence
<220> FEATURE:
<221> NAME/KEY: modified_base
<222> LOCATION: 19
<223> OTHER INFORMATION: n = any nucleobase

<400> SEQUENCE: 556
uaucuugucc ucaucaaan 19

<210> SEQ ID NO 557
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 557
naucuugucc ucaucaaan 19

<210> SEQ ID NO 558
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 558
gucguguggu agaugacgu 19

<210> SEQ ID NO 559
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 559
uucguguggu agaugacgu 19

<210> SEQ ID NO 560
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 560
nucguguggu agaugacgu 19

<210> SEQ ID NO 561
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:

<221> NAME/KEY: modified_base
<222> LOCATION: 19
<223> OTHER INFORMATION: n = any nucleobase

<400> SEQUENCE: 561
uucguguggu agaugacgn 19

<210> SEQ ID NO 562
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 562
nucguguggu agaugacgn 19

<210> SEQ ID NO 563
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 563
gucguguggu agaugacgu 19

<210> SEQ ID NO 564
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 564
uucguguggu agaugacgu 19

<210> SEQ ID NO 565
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 565
nucguguggu agaugacgu 19

<210> SEQ ID NO 566
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 19

<223> OTHER INFORMATION: n = any nucleobase

<400> SEQUENCE: 566
uucguguggu agaugacgn 19

<210> SEQ ID NO 567
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 567
nucguguggu agaugacgn 19

<210> SEQ ID NO 568
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 568
uguucugcga cuacuacaa 19

<210> SEQ ID NO 569
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 19
<223> OTHER INFORMATION: n = any nucleobase

<400> SEQUENCE: 569
uguucugcga cuacuacan 19

<210> SEQ ID NO 570
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1
<223> OTHER INFORMATION: n = any nucleobase

<400> SEQUENCE: 570
nguucugcga cuacuacaa 19

<210> SEQ ID NO 571
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:

<221> NAME/KEY: modified_base
<222> LOCATION: 1, 19
<223> OTHER INFORMATION: n = any nucleobase

<400> SEQUENCE: 571
nguucugcga cuacuacan 19

<210> SEQ ID NO 572
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 572
ugauuugccu gaacaagaa 19

<210> SEQ ID NO 573
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 573
ugauuugccu gaacaagan 19

<210> SEQ ID NO 574
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 574
ngauuugccu gaacaagaa 19

<210> SEQ ID NO 575
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 575
ngauuugccu gaacaagan 19

<210> SEQ ID NO 576
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 576
cugcuccaag gccaucaag 19

<210> SEQ ID NO 577
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 577
cugcuccaag gccaucaaa 19

<210> SEQ ID NO 578
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 578
cugcuccaag gccaucaan 19

<210> SEQ ID NO 579
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 579
nugcuccaag gccaucaaa 19

<210> SEQ ID NO 580
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 580
nugcuccaag gccaucaan 19

<210> SEQ ID NO 581
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 581
cuccaaggcc aucaagauu 19

<210> SEQ ID NO 582
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 582
nuccaaggcc aucaagauu 19

<210> SEQ ID NO 583
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 583
cuccaaggcc aucaagaua 19

<210> SEQ ID NO 584
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 584
nuccaaggcc aucaagaua 19

<210> SEQ ID NO 585
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 585
cuccaaggcc aucaagaun 19

<210> SEQ ID NO 586
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19

<223> OTHER INFORMATION: n = any nucleobase

<400> SEQUENCE: 586
nuccaaggcc aucaagaun 19

<210> SEQ ID NO 587
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 587
ccucagcccc gaguucaag 19

<210> SEQ ID NO 588
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 588
ccucagcccc gaguucaaa 19

<210> SEQ ID NO 589
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 589
ccucagcccc gaguucaan 19

<210> SEQ ID NO 590
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 590
ncucagcccc gaguucaaa 19

<210> SEQ ID NO 591
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 591
ncucagcccc gaguucaan 19

<210> SEQ ID NO 592
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 592
cagaagcagu gcagcaucc 19

<210> SEQ ID NO 593
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 593
cagaagcagu gcagcauca 19

<210> SEQ ID NO 594
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 594
cagaagcagu gcagcaucn 19

<210> SEQ ID NO 595
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 595
nagaagcagu gcagcauca 19

<210> SEQ ID NO 596
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 596
nagaagcagu gcagcaucn 19

<210> SEQ ID NO 597
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 14
<223> OTHER INFORMATION: n = hypoxanthine (inosine)

<400> SEQUENCE: 597
cagaagcagu gcancauca 19

<210> SEQ ID NO 598
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 14
<223> OTHER INFORMATION: n = hypoxanthine (inosine)

<400> SEQUENCE: 598
nagaagcagu gcancauca 19

<210> SEQ ID NO 599
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 14
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 599
cagaagcagu gcancaucn 19

<210> SEQ ID NO 600
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 14
<223> OTHER INFORMATION: n = hypoxanthine (inosine)

<400> SEQUENCE: 600
nagaagcagu gcancaucn 19

<210> SEQ ID NO 601
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 601
cccucuguuc ugcgacuac 19

<210> SEQ ID NO 602
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 602
cccucuguuc ugcgacuaa 19

<210> SEQ ID NO 603
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 603
nccucuguuc ugcgacuaa 19

<210> SEQ ID NO 604
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 604
cccucuguuc ugcgacuan 19

<210> SEQ ID NO 605
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 605
nccucuguuc ugcgacuan 19

<210> SEQ ID NO 606
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 14
<223> OTHER INFORMATION: n = hypoxanthine (inosine)

<400> SEQUENCE: 606
cccucuguuc ugcnacuaa 19

<210> SEQ ID NO 607
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 14
<223> OTHER INFORMATION: n = hypoxanthine (inosine)

<400> SEQUENCE: 607
nccucuguuc ugcnacuaa 19

<210> SEQ ID NO 608
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 14
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 608
cccucuguuc ugcnacuan 19

<210> SEQ ID NO 609
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 14
<223> OTHER INFORMATION: n = hypoxanthine (inosine)

<400> SEQUENCE: 609
nccucuguuc ugcnacuan 19

<210> SEQ ID NO 610
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 610
ccucuguucu gcgacuacu 19

<210> SEQ ID NO 611
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 611
ncucuguucu gcgacuacu 19

<210> SEQ ID NO 612
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 612
ccucuguucu gcgacuaca 19

<210> SEQ ID NO 613
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 613
ncucuguucu gcgacuaca 19

<210> SEQ ID NO 614
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 614
ccucuguucu gcgacuacn 19

<210> SEQ ID NO 615
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 615
ncucuguucu gcgacuacn 19

<210> SEQ ID NO 616
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 11
<223> OTHER INFORMATION: n = hypoxanthine (inosine)

<400> SEQUENCE: 616
ccucuguucu ncgacuacu 19

<210> SEQ ID NO 617
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 11
<223> OTHER INFORMATION: n = hypoxanthine (inosine)

<400> SEQUENCE: 617
ncucuguucu ncgacuacu 19

<210> SEQ ID NO 618
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 11
<223> OTHER INFORMATION: n = hypoxanthine (inosine)

<400> SEQUENCE: 618
ccucuguucu ncgacuaca 19

<210> SEQ ID NO 619
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 11
<223> OTHER INFORMATION: n = hypoxanthine (inosine)

<400> SEQUENCE: 619
ncucuguucu ncgacuaca 19

<210> SEQ ID NO 620
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 11
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 620
ccucuguucu ncgacuacn 19

<210> SEQ ID NO 621
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 11
<223> OTHER INFORMATION: n = hypoxanthine (inosine)

<400> SEQUENCE: 621
ncucuguucu ncgacuacn 19

<210> SEQ ID NO 622
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 622
ucuguucugc gacuacuac 19

<210> SEQ ID NO 623
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 623
ucuguucugc gacuacuaa 19

<210> SEQ ID NO 624
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 624
ucuguucugc gacuacuan 19

<210> SEQ ID NO 625
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 625
ncuguucugc gacuacuan 19

<210> SEQ ID NO 626
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 626
cuguucugcg acuacuaca 19

<210> SEQ ID NO 627
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 627
cuguucugcg acuacuacn 19

<210> SEQ ID NO 628
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 628
nuguucugcg acuacuacn 19

<210> SEQ ID NO 629
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 629
acccaucugc uacaacuau 19

<210> SEQ ID NO 630
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 630
ncccaucugc uacaacuau 19

<210> SEQ ID NO 631
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 631
acccaucugc uacaacuaa 19

<210> SEQ ID NO 632
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 632
ncccaucugc uacaacuaa 19

<210> SEQ ID NO 633
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 633
acccaucugc uacaacuan 19

<210> SEQ ID NO 634
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 634
ncccaucugc uacaacuan 19

<210> SEQ ID NO 635
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 635
aaagugguuc gacguggac 19

<210> SEQ ID NO 636
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 636
aaagugguuc gacguggaa 19

<210> SEQ ID NO 637
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 637
naagugguuc gacguggaa 19

<210> SEQ ID NO 638
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 638
aaagugguuc gacguggan 19

<210> SEQ ID NO 639
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 639
naagugguuc gacguggan 19

<210> SEQ ID NO 640
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 14
<223> OTHER INFORMATION: n = hypoxanthine (inosine)

<400> SEQUENCE: 640
aaagugguuc gacnuggaa 19

<210> SEQ ID NO 641
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 14
<223> OTHER INFORMATION: n = hypoxanthine (inosine)

<400> SEQUENCE: 641
naagugguuc gacnuggaa 19

<210> SEQ ID NO 642
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 14
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 642
aaagugguuc gacnuggan 19

<210> SEQ ID NO 643

<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 14
<223> OTHER INFORMATION: n = hypoxanthine (inosine)

<400> SEQUENCE: 643
naagugguuc gacnuggan 19

<210> SEQ ID NO 644
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 644
gugguucgac guggacuuc 19

<210> SEQ ID NO 645
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 645
gugguucgac guggacuua 19

<210> SEQ ID NO 646
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 646
nugguucgac guggacuua 19

<210> SEQ ID NO 647
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 647
gugguucgac guggacuun 19

<210> SEQ ID NO 648
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 648
nugguucgac guggacuun 19

<210> SEQ ID NO 649
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 14
<223> OTHER INFORMATION: n = hypoxanthine (inosine)

<400> SEQUENCE: 649
gugguucgac gugnacuua 19

<210> SEQ ID NO 650
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 14
<223> OTHER INFORMATION: n = hypoxanthine (inosine)

<400> SEQUENCE: 650
nugguucgac gugnacuua 19

<210> SEQ ID NO 651
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 14
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 651
gugguucgac gugnacuun 19

<210> SEQ ID NO 652
<211> LENGTH: 19

```
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 14
<223> OTHER INFORMATION: n = hypoxanthine (inosine)

<400> SEQUENCE: 652

nugguucgac gugnacuun                                                      19

<210> SEQ ID NO 653
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 653

gguucgacgu ggacuuccc                                                      19

<210> SEQ ID NO 654
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 654

gguucgacgu ggacuucca                                                      19

<210> SEQ ID NO 655
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1
<223> OTHER INFORMATION: n = any nucleobase

<400> SEQUENCE: 655

nguucgacgu ggacuucca                                                      19

<210> SEQ ID NO 656
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 656

gguucgacgu ggacuuccn                                                      19
```

<210> SEQ ID NO 657
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 657
nguucgacgu ggacuuccn 19

<210> SEQ ID NO 658
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 12
<223> OTHER INFORMATION: n = hypoxanthine (inosine)

<400> SEQUENCE: 658
gguucgacgu gnacuucca 19

<210> SEQ ID NO 659
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 12
<223> OTHER INFORMATION: n = hypoxanthine (inosine)

<400> SEQUENCE: 659
nguucgacgu gnacuucca 19

<210> SEQ ID NO 660
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 12
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 660
gguucgacgu gnacuuccn 19

<210> SEQ ID NO 661
<211> LENGTH: 19
<212> TYPE: RNA

<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 12
<223> OTHER INFORMATION: n = hypoxanthine (inosine)

<400> SEQUENCE: 661
nguucgacgu gnacuuccn 19

<210> SEQ ID NO 662
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 662
gacaagaaga ccagcaucu 19

<210> SEQ ID NO 663
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 663
nacaagaaga ccagcaucu 19

<210> SEQ ID NO 664
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 664
gacaagaaga ccagcauca 19

<210> SEQ ID NO 665
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 665
nacaagaaga ccagcauca 19

<210> SEQ ID NO 666

<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 666
gacaagaaga ccagcaucn 19

<210> SEQ ID NO 667
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 667
nacaagaaga ccagcaucn 19

<210> SEQ ID NO 668
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 14
<223> OTHER INFORMATION: n = hypoxanthine (inosine)

<400> SEQUENCE: 668
gacaagaaga ccancaucu 19

<210> SEQ ID NO 669
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 14
<223> OTHER INFORMATION: n = hypoxanthine (inosine)

<400> SEQUENCE: 669
nacaagaaga ccancaucu 19

<210> SEQ ID NO 670
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:

<221> NAME/KEY: modified_base
<222> LOCATION: 14
<223> OTHER INFORMATION: n = hypoxanthine (inosine)

<400> SEQUENCE: 670
gacaagaaga ccancauca 19

<210> SEQ ID NO 671
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 14
<223> OTHER INFORMATION: n = hypoxanthine (inosine)

<400> SEQUENCE: 671
nacaagaaga ccancauca 19

<210> SEQ ID NO 672
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 14
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 672
gacaagaaga ccancaucn 19

<210> SEQ ID NO 673
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 14
<223> OTHER INFORMATION: n = hypoxanthine (inosine)

<400> SEQUENCE: 673
nacaagaaga ccancaucn 19

<210> SEQ ID NO 674
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 674
accagcaucu ucaucaacc 19

<210> SEQ ID NO 675
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1
<223> OTHER INFORMATION: n = any nucleobase

<400> SEQUENCE: 675
nccagcaucu ucaucaacc 19

<210> SEQ ID NO 676
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 19
<223> OTHER INFORMATION: n = any nucleobase

<400> SEQUENCE: 676
accagcaucu ucaucaacn 19

<210> SEQ ID NO 677
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 677
nccagcaucu ucaucaacn 19

<210> SEQ ID NO 678
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 678
aggaaaccua caacaacau 19

<210> SEQ ID NO 679
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1
<223> OTHER INFORMATION: n = any nucleobase

<400> SEQUENCE: 679
nggaaaccua caacaacau 19

<210> SEQ ID NO 680
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 680
aggaaaccua caacaacaa 19

<210> SEQ ID NO 681
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 681
nggaaaccua caacaacaa 19

<210> SEQ ID NO 682
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 682
nggaaaccua caacaacan 19

<210> SEQ ID NO 683
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 683
aaaccuacaa caacaucau 19

<210> SEQ ID NO 684
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 684
naaccuacaa caacaucau 19

<210> SEQ ID NO 685
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 685
aaaccuacaa caacaucaa 19

<210> SEQ ID NO 686
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 686
naaccuacaa caacaucaa 19

<210> SEQ ID NO 687
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 687
naaccuacaa caacaucan 19

<210> SEQ ID NO 688
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 688
agaccagcau cuucaucaa 19

<210> SEQ ID NO 689
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 689
ngaccagcau cuucaucaa 19

<210> SEQ ID NO 690
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 690
agaccagcau cuucaucan 19

<210> SEQ ID NO 691
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 691
ngaccagcau cuucaucan 19

<210> SEQ ID NO 692
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 692
ugcuacaacu accagauca 19

<210> SEQ ID NO 693
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 693
ngcuacaacu accagauca 19

<210> SEQ ID NO 694
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 694
ugcuacaacu accagaucn 19

<210> SEQ ID NO 695
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 695
ngcuacaacu accagaucn 19

<210> SEQ ID NO 696
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 15
<223> OTHER INFORMATION: n = hypoxanthine (inosine)

<400> SEQUENCE: 696
ngcuacaacu accanauca 19

<210> SEQ ID NO 697
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 697
ugcuacaacu accanaucn 19

<210> SEQ ID NO 698
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 15

<223> OTHER INFORMATION: n = hypoxanthine (inosine)

<400> SEQUENCE: 698
ngcuacaacu accanaucn 19

<210> SEQ ID NO 699
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 15
<223> OTHER INFORMATION: n = hypoxanthine (inosine)

<400> SEQUENCE: 699
ngcuacaacu accanauca 19

<210> SEQ ID NO 700
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 700
uacaacuacc agaucaggg 19

<210> SEQ ID NO 701
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 701
uacaacuacc agaucagga 19

<210> SEQ ID NO 702
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 702
uacaacuacc agaucaggn 19

<210> SEQ ID NO 703
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:

<221> NAME/KEY: modified_base
<222> LOCATION: 1
<223> OTHER INFORMATION: n = any nucleobase

<400> SEQUENCE: 703
nacaacuacc agaucagga 19

<210> SEQ ID NO 704
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 704
nacaacuacc agaucaggn 19

<210> SEQ ID NO 705
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 17
<223> OTHER INFORMATION: n = hypoxanthine (inosine)

<400> SEQUENCE: 705
uacaacuacc agaucangg 19

<210> SEQ ID NO 706
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 17
<223> OTHER INFORMATION: n = hypoxanthine (inosine)

<400> SEQUENCE: 706
uacaacuacc agaucanga 19

<210> SEQ ID NO 707
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 17
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 707
uacaacuacc agaucangn 19

<210> SEQ ID NO 708
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 17
<223> OTHER INFORMATION: n = hypoxanthine (inosine)

<400> SEQUENCE: 708
nacaacuacc agaucanga 19

<210> SEQ ID NO 709
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 17
<223> OTHER INFORMATION: n = hypoxanthine (inosine)

<400> SEQUENCE: 709
nacaacuacc agaucangn 19

<210> SEQ ID NO 710
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 710
cacccaucug cuacaacua 19

<210> SEQ ID NO 711
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 711
cacccaucug cuacaacun 19

<210> SEQ ID NO 712
<211> LENGTH: 19
<212> TYPE: RNA
<213> ORGANISM: Artificial sequence
<220> FEATURE:

<223> OTHER INFORMATION: RNAi agent sense strand 19-mer core base
      sequence
<220> FEATURE:
<221> NAME/KEY: modified_base
<222> LOCATION: 1
<223> OTHER INFORMATION: n = any nucleobase

<400> SEQUENCE: 712
nacccaucug cuacaacua 19

<210> SEQ ID NO 713
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 713
nacccaucug cuacaacun 19

<210> SEQ ID NO 714
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 714
gauccgcauc caguguugc 19

<210> SEQ ID NO 715
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 715
gauccgcauc caguguuga 19

<210> SEQ ID NO 716
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 716
gauccgcauc caguguuga 19

<210> SEQ ID NO 717
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 717
nauccgcauc caguguugn 19

<210> SEQ ID NO 718
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 718
nauccgcauc caguguugn 19

<210> SEQ ID NO 719
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = hypoxanthine (inosine)

<400> SEQUENCE: 719
gauccgcauc cagunuugc 19

<210> SEQ ID NO 720
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = hypoxanthine (inosine)

<400> SEQUENCE: 720
gauccgcauc cagunuuga 19

<210> SEQ ID NO 721
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = hypoxanthine (inosine)

<400> SEQUENCE: 721
gauccgcauc cagunuuga 19

<210> SEQ ID NO 722
<211> LENGTH: 19
<212> TYPE: RNA
<213> ORGANISM: Artificial sequence
<220> FEATURE:

<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 15
<223> OTHER INFORMATION: n = hypoxanthine (inosine)

<400> SEQUENCE: 722
nauccgcauc cagunuugn 19

<210> SEQ ID NO 723
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 15
<223> OTHER INFORMATION: n = hypoxanthine (inosine)

<400> SEQUENCE: 723
nauccgcauc cagunuugn 19

<210> SEQ ID NO 724
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 724
agaggugagc aucgaacac 19

<210> SEQ ID NO 725
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 725
agaggugagc aucgaacaa 19

<210> SEQ ID NO 726
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 726
agaggugagc aucgaacan 19

<210> SEQ ID NO 727
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 727
ngaggugagc aucgaacaa 19

<210> SEQ ID NO 728
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 728
ngaggugagc aucgaacan 19

<210> SEQ ID NO 729
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 14
<223> OTHER INFORMATION: n = hypoxanthine (inosine)

<400> SEQUENCE: 729
agaggugagc aucnaacac 19

<210> SEQ ID NO 730
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 14
<223> OTHER INFORMATION: n = hypoxanthine (inosine)

<400> SEQUENCE: 730
agaggugagc aucnaacaa 19

<210> SEQ ID NO 731
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 14

<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 731
agaggugagc aucnaacan 19

<210> SEQ ID NO 732
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 14
<223> OTHER INFORMATION: n = hypoxanthine (inosine)

<400> SEQUENCE: 732
ngaggugagc aucnaacaa 19

<210> SEQ ID NO 733
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 14
<223> OTHER INFORMATION: n = hypoxanthine (inosine)

<400> SEQUENCE: 733
ngaggugagc aucnaacan 19

<210> SEQ ID NO 734
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 734
gcagggaccc uucaagaug 19

<210> SEQ ID NO 735
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 735
gcagggaccc uucaagaua 19

<210> SEQ ID NO 736
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 736
gcagggaccc uucaagaun 19

<210> SEQ ID NO 737
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 737
ncagggaccc uucaagaua 19

<210> SEQ ID NO 738
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 738
ncagggaccc uucaagaun 19

<210> SEQ ID NO 739
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 739
agaugugccu caacuacga 19

<210> SEQ ID NO 740
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 740
agaugugccu caacuacgn 19

<210> SEQ ID NO 741
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 741
ngaugugccu caacuacga 19

<210> SEQ ID NO 742
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 742
ngaugugccu caacuacgn 19

<210> SEQ ID NO 743
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 18
<223> OTHER INFORMATION: n = hypoxanthine (inosine)

<400> SEQUENCE: 743
agaugugccu caacuacna 19

<210> SEQ ID NO 744
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 18
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 744
agaugugccu caacuacnn 19

<210> SEQ ID NO 745
<211> LENGTH: 19
<212> TYPE: RNA
<213> ORGANISM: Artificial sequence
<220> FEATURE:

<223> OTHER INFORMATION: RNAi agent sense strand 19-mer core base
      sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 18
<223> OTHER INFORMATION: n = hypoxanthine (inosine)

<400> SEQUENCE: 745
ngaugugccu caacuacna 19

<210> SEQ ID NO 746
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 18
<223> OTHER INFORMATION: n = hypoxanthine (inosine)

<400> SEQUENCE: 746
ngaugugccu caacuacnn 19

<210> SEQ ID NO 747
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 747
augugccuca acuacgagg 19

<210> SEQ ID NO 748
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 748
augugccuca acuacgaga 19

<210> SEQ ID NO 749
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 749
augugccuca acuacgagn 19

<210> SEQ ID NO 750
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 750
nugugccuca acuacgaga 19

<210> SEQ ID NO 751
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 751
nugugccuca acuacgagn 19

<210> SEQ ID NO 752
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 16
<223> OTHER INFORMATION: n = hypoxanthine (inosine)

<400> SEQUENCE: 752
augugccuca acuacnagg 19

<210> SEQ ID NO 753
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 16
<223> OTHER INFORMATION: n = hypoxanthine (inosine)

<400> SEQUENCE: 753
augugccuca acuacnaga 19

<210> SEQ ID NO 754
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 16

<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 754
augugccuca acuacnagn 19

<210> SEQ ID NO 755
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 16
<223> OTHER INFORMATION: n = hypoxanthine (inosine)

<400> SEQUENCE: 755
nugugccuca acuacnaga 19

<210> SEQ ID NO 756
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 16
<223> OTHER INFORMATION: n = hypoxanthine (inosine)

<400> SEQUENCE: 756
nugugccuca acuacnagn 19

<210> SEQ ID NO 757
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 757
cagcgagacc ugccugaag 19

<210> SEQ ID NO 758
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 758
cagcgagacc ugccugaaa 19

<210> SEQ ID NO 759
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 759
cagcgagacc ugccugaan 19

<210> SEQ ID NO 760
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 760
nagcgagacc ugccugaaa 19

<210> SEQ ID NO 761
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 761
nagcgagacc ugccugaan 19

<210> SEQ ID NO 762
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 762
aacgucacca ucuucagac 19

<210> SEQ ID NO 763
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 763
aacgucacca ucuucagaa 19

<210> SEQ ID NO 764
<211> LENGTH: 19

<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 764
aacgucacca ucuucagan 19

<210> SEQ ID NO 765
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 765
nacgucacca ucuucagaa 19

<210> SEQ ID NO 766
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 766
nacgucacca ucuucagan 19

<210> SEQ ID NO 767
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 767
acgucaccau cuucagacc 19

<210> SEQ ID NO 768
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 768
acgucaccau cuucagaca 19

<210> SEQ ID NO 769
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 769
acgucaccau cuucagacn 19

<210> SEQ ID NO 770
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1
<223> OTHER INFORMATION: n = any nucleobase

<400> SEQUENCE: 770
ncgucaccau cuucagaca 19

<210> SEQ ID NO 771
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 771
ncgucaccau cuucagacn 19

<210> SEQ ID NO 772
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 16
<223> OTHER INFORMATION: n = hypoxanthine (inosine)

<400> SEQUENCE: 772
acgucaccau cuucanacc 19

<210> SEQ ID NO 773
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 16
<223> OTHER INFORMATION: n = hypoxanthine (inosine)

<400> SEQUENCE: 773
acgucaccau cuucanaca 19

<210> SEQ ID NO 774
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 16
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 774
acgucaccau cuucanacn 19

<210> SEQ ID NO 775
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 16
<223> OTHER INFORMATION: n = hypoxanthine (inosine)

<400> SEQUENCE: 775
ncgucaccau cuucanaca 19

<210> SEQ ID NO 776
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 16
<223> OTHER INFORMATION: n = hypoxanthine (inosine)

<400> SEQUENCE: 776
ncgucaccau cuucanacn 19

<210> SEQ ID NO 777
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 777
uccaggccga ugacuuccg 19

<210> SEQ ID NO 778

<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 778
uccaggccga ugacuucca 19

<210> SEQ ID NO 779
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 19
<223> OTHER INFORMATION: n = any nucleobase

<400> SEQUENCE: 779
uccaggccga ugacuuccn 19

<210> SEQ ID NO 780
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1
<223> OTHER INFORMATION: n = any nucleobase

<400> SEQUENCE: 780
nccaggccga ugacuucca 19

<210> SEQ ID NO 781
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 781
nccaggccga ugacuuccn 19

<210> SEQ ID NO 782
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 782
cuucuucaac accuucaag 19

<210> SEQ ID NO 783
<211> LENGTH: 19
<212> TYPE: RNA

```
<213> ORGANISM: Artificial sequence
<220> FEATURE:
<223> OTHER INFORMATION: RNAi agent sense strand 19-mer core base
      sequence

<400> SEQUENCE: 783

cuucuucaac accuucaaa                                                19


<210> SEQ ID NO 784
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 784

cuucuucaac accuucaan                                                19


<210> SEQ ID NO 785
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1
<223> OTHER INFORMATION: n = any nucleobase

<400> SEQUENCE: 785

nuucuucaac accuucaaa                                                19


<210> SEQ ID NO 786
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 786

nuucuucaac accuucaan                                                19


<210> SEQ ID NO 787
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 787

accuacuacu cgaacugca                                                19


<210> SEQ ID NO 788
<211> LENGTH: 19
<212> TYPE: RNA
<213> ORGANISM: Artificial sequence
<220> FEATURE:
```

<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 788
accuacuacu cgaacugcn 19

<210> SEQ ID NO 789
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1
<223> OTHER INFORMATION: n = any nucleobase

<400> SEQUENCE: 789
nccuacuacu cgaacugca 19

<210> SEQ ID NO 790
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 790
nccuacuacu cgaacugcn 19

<210> SEQ ID NO 791
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 17
<223> OTHER INFORMATION: n = hypoxanthine (inosine)

<400> SEQUENCE: 791
accuacuacu cgaacunca 19

<210> SEQ ID NO 792
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 17
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 792
accuacuacu cgaacuncn 19

<210> SEQ ID NO 793
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 17
<223> OTHER INFORMATION: n = hypoxanthine (inosine)

<400> SEQUENCE: 793
nccuacuacu cgaacunca 19

<210> SEQ ID NO 794
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 17
<223> OTHER INFORMATION: n = hypoxanthine (inosine)

<400> SEQUENCE: 794
nccuacuacu cgaacuncn 19

<210> SEQ ID NO 795
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 795
agggaccacc ugcuccaag 19

<210> SEQ ID NO 796
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 796
agggaccacc ugcuccaaa 19

<210> SEQ ID NO 797
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 797
agggaccacc ugcuccaan 19

<210> SEQ ID NO 798
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 798
ngggaccacc ugcuccaaa 19

<210> SEQ ID NO 799
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 799
ngggaccacc ugcuccaan 19

<210> SEQ ID NO 800
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 800
ugcuccaagg ccaucaaga 19

<210> SEQ ID NO 801
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 801
ugcuccaagg ccaucaagn 19

<210> SEQ ID NO 802
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 802
ngcuccaagg ccaucaaga 19

<210> SEQ ID NO 803
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 803
ngcuccaagg ccaucaagn 19

<210> SEQ ID NO 804
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 804
uguggaacca cgaugacag 19

<210> SEQ ID NO 805
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 805
uguggaacca cgaugacaa 19

<210> SEQ ID NO 806
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 806
uguggaacca cgaugacan 19

<210> SEQ ID NO 807
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 807
nguggaacca cgaugacaa 19

<210> SEQ ID NO 808
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 808
nguggaacca cgaugacan 19

<210> SEQ ID NO 809
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = hypoxanthine (inosine)

<400> SEQUENCE: 809
uguggaacca cgaunacag 19

<210> SEQ ID NO 810
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = hypoxanthine (inosine)

<400> SEQUENCE: 810
uguggaacca cgaunacaa 19

<210> SEQ ID NO 811
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 811
uguggaacca cgaunacan 19

<210> SEQ ID NO 812
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 15
<223> OTHER INFORMATION: n = hypoxanthine (inosine)

<400> SEQUENCE: 812
nguggaacca cgaunacaa 19

<210> SEQ ID NO 813
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 15
<223> OTHER INFORMATION: n = hypoxanthine (inosine)

<400> SEQUENCE: 813
nguggaacca cgaunacan 19

<210> SEQ ID NO 814
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 814
gcaagaccuc ugcuucugu 19

<210> SEQ ID NO 815
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 815
ncaagaccuc ugcuucugu 19

<210> SEQ ID NO 816
<211> LENGTH: 19
<212> TYPE: RNA

```
<213> ORGANISM: Artificial sequence
<220> FEATURE:
<223> OTHER INFORMATION: RNAi agent sense strand 19-mer core base
      sequence

<400> SEQUENCE: 816

gcaagaccuc ugcuucuga                                                19


<210> SEQ ID NO 817
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1
<223> OTHER INFORMATION: n = any nucleobase

<400> SEQUENCE: 817

ncaagaccuc ugcuucuga                                                19


<210> SEQ ID NO 818
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 18
<223> OTHER INFORMATION: n = hypoxanthine (inosine)

<400> SEQUENCE: 818

gcaagaccuc ugcuucunu                                                19


<210> SEQ ID NO 819
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 18
<223> OTHER INFORMATION: n = hypoxanthine (inosine)

<400> SEQUENCE: 819

ncaagaccuc ugcuucunu                                                19


<210> SEQ ID NO 820
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 18
<223> OTHER INFORMATION: n = hypoxanthine (inosine)

<400> SEQUENCE: 820
```

gcaagaccuc ugcuucuna 19

<210> SEQ ID NO 821
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 18
<223> OTHER INFORMATION: n = hypoxanthine (inosine)

<400> SEQUENCE: 821
ncaagaccuc ugcuucuna 19

<210> SEQ ID NO 822
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 822
cacagacugc accaacugc 19

<210> SEQ ID NO 823
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 823
cacagacugc accaacuga 19

<210> SEQ ID NO 824
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 824
cacagacugc accaacuga 19

<210> SEQ ID NO 825
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 825
nacagacugc accaacugn 19

<210> SEQ ID NO 826
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 826
nacagacugc accaacugn 19

<210> SEQ ID NO 827
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 18
<223> OTHER INFORMATION: n = hypoxanthine (inosine)

<400> SEQUENCE: 827
cacagacugc accaacunc 19

<210> SEQ ID NO 828
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 18
<223> OTHER INFORMATION: n = hypoxanthine (inosine)

<400> SEQUENCE: 828
cacagacugc accaacuna 19

<210> SEQ ID NO 829
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 18
<223> OTHER INFORMATION: n = hypoxanthine (inosine)

<400> SEQUENCE: 829
cacagacugc accaacuna 19

<210> SEQ ID NO 830
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19

<223> OTHER INFORMATION: n = any nucleobase
<220> FEATURE:
<221> NAME/KEY: modified_base
<222> LOCATION: 18
<223> OTHER INFORMATION: n = hypoxanthine (inosine)

<400> SEQUENCE: 830
nacagacugc accaacunn 19

<210> SEQ ID NO 831
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 18
<223> OTHER INFORMATION: n = hypoxanthine (inosine)

<400> SEQUENCE: 831
nacagacugc accaacunn 19

<210> SEQ ID NO 832
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 832
agugccuuca cuguacugc 19

<210> SEQ ID NO 833
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 833
agugccuuca cuguacuga 19

<210> SEQ ID NO 834
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 834
agugccuuca cuguacugn 19

<210> SEQ ID NO 835
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1
<223> OTHER INFORMATION: n = any nucleobase

<400> SEQUENCE: 835
ngugccuuca cuguacuga 19

<210> SEQ ID NO 836
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 836
ngugccuuca cuguacugn 19

<210> SEQ ID NO 837
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 18
<223> OTHER INFORMATION: n = hypoxanthine (inosine)

<400> SEQUENCE: 837
agugccuuca cuguacunc 19

<210> SEQ ID NO 838
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 18
<223> OTHER INFORMATION: n = hypoxanthine (inosine)

<400> SEQUENCE: 838
agugccuuca cuguacuna 19

<210> SEQ ID NO 839
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase
<220> FEATURE:
<221> NAME/KEY: modified_base
<222> LOCATION: 18
<223> OTHER INFORMATION: n = hypoxanthine (inosine)

<400> SEQUENCE: 839
agugccuuca cuguacunn 19

<210> SEQ ID NO 840
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 18
<223> OTHER INFORMATION: n = hypoxanthine (inosine)

<400> SEQUENCE: 840
ngugccuuca cuguacuna 19

<210> SEQ ID NO 841
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 18
<223> OTHER INFORMATION: n = hypoxanthine (inosine)

<400> SEQUENCE: 841
ngugccuuca cuguacunn 19

<210> SEQ ID NO 842
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 842
ugugggaacu ucaacagca 19

<210> SEQ ID NO 843
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 843
ugugggaacu ucaacagcn 19

<210> SEQ ID NO 844

<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 844
ngugggaacu ucaacagca 19

<210> SEQ ID NO 845
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 845
ngugggaacu ucaacagcn 19

<210> SEQ ID NO 846
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 17
<223> OTHER INFORMATION: n = hypoxanthine (inosine)

<400> SEQUENCE: 846
ugugggaacu ucaacanca 19

<210> SEQ ID NO 847
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 17
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 847
ugugggaacu ucaacancn 19

<210> SEQ ID NO 848
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:

<221> NAME/KEY: modified_base
<222> LOCATION: 1
<223> OTHER INFORMATION: n = any nucleobase
<220> FEATURE:
<221> NAME/KEY: modified_base
<222> LOCATION: 17
<223> OTHER INFORMATION: n = hypoxanthine (inosine)

<400> SEQUENCE: 848
ngugggaacu ucaacanca 19

<210> SEQ ID NO 849
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 17
<223> OTHER INFORMATION: n = hypoxanthine (inosine)

<400> SEQUENCE: 849
ngugggaacu ucaacancn 19

<210> SEQ ID NO 850
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 850
gggaacuuca acagcaucc 19

<210> SEQ ID NO 851
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 851
gggaacuuca acagcauca 19

<210> SEQ ID NO 852
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 852
gggaacuuca acagcaucn 19

<210> SEQ ID NO 853
<211> LENGTH: 19

<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1
<223> OTHER INFORMATION: n = any nucleobase

<400> SEQUENCE: 853
nggaacuuca acagcauca 19

<210> SEQ ID NO 854
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 854
nggaacuuca acagcaucn 19

<210> SEQ ID NO 855
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 14
<223> OTHER INFORMATION: n = hypoxanthine (inosine)

<400> SEQUENCE: 855
gggaacuuca acancaucc 19

<210> SEQ ID NO 856
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 14
<223> OTHER INFORMATION: n = hypoxanthine (inosine)

<400> SEQUENCE: 856
gggaacuuca acancauca 19

<210> SEQ ID NO 857
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 14
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 857
gggaacuuca acancaucn 19

<210> SEQ ID NO 858
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 14
<223> OTHER INFORMATION: n = hypoxanthine (inosine)

<400> SEQUENCE: 858
nggaacuuca acancauca 19

<210> SEQ ID NO 859
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 14
<223> OTHER INFORMATION: n = hypoxanthine (inosine)

<400> SEQUENCE: 859
nggaacuuca acancaucn 19

<210> SEQ ID NO 860
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 860
uucaacaccu ucaagaccc 19

<210> SEQ ID NO 861
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 861
uucaacaccu ucaagacca 19

<210> SEQ ID NO 862
<211> LENGTH: 19
<212> TYPE: RNA

<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 862
uucaacaccu ucaagaccn 19

<210> SEQ ID NO 863
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1
<223> OTHER INFORMATION: n = any nucleobase

<400> SEQUENCE: 863
nucaacaccu ucaagacca 19

<210> SEQ ID NO 864
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 864
nucaacaccu ucaagaccn 19

<210> SEQ ID NO 865
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 15
<223> OTHER INFORMATION: n = hypoxanthine (inosine)

<400> SEQUENCE: 865
uucaacaccu ucaanaccc 19

<210> SEQ ID NO 866
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 15
<223> OTHER INFORMATION: n = hypoxanthine (inosine)

<400> SEQUENCE: 866
uucaacaccu ucaanacca 19

<210> SEQ ID NO 867
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 867
uucaacaccu ucaanaccn 19

<210> SEQ ID NO 868
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 15
<223> OTHER INFORMATION: n = hypoxanthine (inosine)

<400> SEQUENCE: 868
nucaacaccu ucaanacca 19

<210> SEQ ID NO 869
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 15
<223> OTHER INFORMATION: n = hypoxanthine (inosine)

<400> SEQUENCE: 869
nucaacaccu ucaanaccn 19

<210> SEQ ID NO 870
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 870
ccaacaucag gaacagcuu 19

<210> SEQ ID NO 871
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 871
ncaacaucag gaacagcuu 19

<210> SEQ ID NO 872
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 872
ccaacaucag gaacagcun 19

<210> SEQ ID NO 873
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 873
ncaacaucag gaacagcuu 19

<210> SEQ ID NO 874
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 874
ncaacaucag gaacagcun 19

<210> SEQ ID NO 875
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 16
<223> OTHER INFORMATION: n = hypoxanthine (inosine)

<400> SEQUENCE: 875
ccaacaucag gaacancuu 19

<210> SEQ ID NO 876
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 16
<223> OTHER INFORMATION: n = hypoxanthine (inosine)

<400> SEQUENCE: 876
ncaacaucag gaacancuu 19

<210> SEQ ID NO 877
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 16
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 877
ccaacaucag gaacancun 19

<210> SEQ ID NO 878
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 16
<223> OTHER INFORMATION: n = hypoxanthine (inosine)

<400> SEQUENCE: 878
ncaacaucag gaacancuu 19

<210> SEQ ID NO 879
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19

<223> OTHER INFORMATION: n = any nucleobase
<220> FEATURE:
<221> NAME/KEY: modified_base
<222> LOCATION: 16
<223> OTHER INFORMATION: n = hypoxanthine (inosine)

<400> SEQUENCE: 879
ncaacaucag gaacancun 19

<210> SEQ ID NO 880
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 880
uacuacucga acugcaugu 19

<210> SEQ ID NO 881
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 881
nacuacucga acugcaugu 19

<210> SEQ ID NO 882
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 882
uacuacucga acugcauga 19

<210> SEQ ID NO 883
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 883
nacuacucga acugcauga 19

<210> SEQ ID NO 884
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:

<221> NAME/KEY: modified_base
<222> LOCATION: 1, 19
<223> OTHER INFORMATION: n = any nucleobase

<400> SEQUENCE: 884
nacuacucga acugcaugn 19

<210> SEQ ID NO 885
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 885
caccugcagu guuggcuuc 19

<210> SEQ ID NO 886
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 886
caccugcagu guuggcuua 19

<210> SEQ ID NO 887
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 887
caccugcagu guuggcuun 19

<210> SEQ ID NO 888
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 888
naccugcagu guuggcuua 19

<210> SEQ ID NO 889
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19

<223> OTHER INFORMATION: n = any nucleobase

<400> SEQUENCE: 889
naccugcagu guuggcuun 19

<210> SEQ ID NO 890
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = hypoxanthine (inosine)

<400> SEQUENCE: 890
caccugcagu guugncuuc 19

<210> SEQ ID NO 891
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = hypoxanthine (inosine)

<400> SEQUENCE: 891
caccugcagu guugncuua 19

<210> SEQ ID NO 892
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 892
caccugcagu guugncuun 19

<210> SEQ ID NO 893
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 15
<223> OTHER INFORMATION: n = hypoxanthine (inosine)

<400> SEQUENCE: 893
naccugcagu guugncuua 19

<210> SEQ ID NO 894
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 15
<223> OTHER INFORMATION: n = hypoxanthine (inosine)

<400> SEQUENCE: 894
naccugcagu guugncuun 19

<210> SEQ ID NO 895
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 895
uggacaugac cuguuacag 19

<210> SEQ ID NO 896
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 896
uggacaugac cuguuacaa 19

<210> SEQ ID NO 897
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 897
uggacaugac cuguuacan 19

<210> SEQ ID NO 898
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 898
nggacaugac cuguuacaa 19

<210> SEQ ID NO 899
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 899
nggacaugac cuguuacan 19

<210> SEQ ID NO 900
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 900
agagcuacag cuucaacgg 19

<210> SEQ ID NO 901
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 901
agagcuacag cuucaacga 19

<210> SEQ ID NO 902
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 902
agagcuacag cuucaacgn 19

<210> SEQ ID NO 903
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 903
ngagcuacag cuucaacga 19

<210> SEQ ID NO 904
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 904
ngagcuacag cuucaacgn 19

<210> SEQ ID NO 905
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 18
<223> OTHER INFORMATION: n = hypoxanthine (inosine)

<400> SEQUENCE: 905
agagcuacag cuucaacng 19

<210> SEQ ID NO 906
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 18
<223> OTHER INFORMATION: n = hypoxanthine (inosine)

<400> SEQUENCE: 906
agagcuacag cuucaacna 19

<210> SEQ ID NO 907
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 18
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 907
agagcuacag cuucaacnn 19

<210> SEQ ID NO 908
<211> LENGTH: 19
<212> TYPE: RNA

<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 18
<223> OTHER INFORMATION: n = hypoxanthine (inosine)

<400> SEQUENCE: 908
ngagcuacag cuucaacna 19

<210> SEQ ID NO 909
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 18
<223> OTHER INFORMATION: n = hypoxanthine (inosine)

<400> SEQUENCE: 909
ngagcuacag cuucaacnn 19

<210> SEQ ID NO 910
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 910
cagugccuuc acuguacug 19

<210> SEQ ID NO 911
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 911
cagugccuuc acuguacua 19

<210> SEQ ID NO 912
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1
<223> OTHER INFORMATION: n = any nucleobase

<400> SEQUENCE: 912
nagugccuuc acuguacua 19

<210> SEQ ID NO 913
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 913
cagugccuuc acuguacun 19

<210> SEQ ID NO 914
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 914
nagugccuuc acuguacun 19

<210> SEQ ID NO 915
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 915
caucaggaac agcuucgag 19

<210> SEQ ID NO 916
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 916
caucaggaac agcuucgaa 19

<210> SEQ ID NO 917
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 917
naucaggaac agcuucgaa 19

<210> SEQ ID NO 918
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 918
caucaggaac agcuucgan 19

<210> SEQ ID NO 919
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 919
naucaggaac agcuucgan 19

<210> SEQ ID NO 920
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 17
<223> OTHER INFORMATION: n = hypoxanthine (inosine)

<400> SEQUENCE: 920
caucaggaac agcuucnag 19

<210> SEQ ID NO 921
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 17
<223> OTHER INFORMATION: n = hypoxanthine (inosine)

<400> SEQUENCE: 921
caucaggaac agcuucnaa 19

<210> SEQ ID NO 922
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1

<223> OTHER INFORMATION: n = any nucleobase
<220> FEATURE:
<221> NAME/KEY: modified_base
<222> LOCATION: 17
<223> OTHER INFORMATION: n = hypoxanthine (inosine)

<400> SEQUENCE: 922
naucaggaac agcuucnaa 19

<210> SEQ ID NO 923
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 17
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 923
caucaggaac agcuucnan 19

<210> SEQ ID NO 924
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 17
<223> OTHER INFORMATION: n = hypoxanthine (inosine)

<400> SEQUENCE: 924
naucaggaac agcuucnan 19

<210> SEQ ID NO 925
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 925
cugauuugcc ugaacaaga 19

<210> SEQ ID NO 926
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 926
nugauuugcc ugaacaaga 19

<210> SEQ ID NO 927
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 927
cugauuugcc ugaacaagn 19

<210> SEQ ID NO 928
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 928
nugauuugcc ugaacaagn 19

<210> SEQ ID NO 929
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 929
aggacaacca cuuugguga 19

<210> SEQ ID NO 930
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 930
nggacaacca cuuugguga 19

<210> SEQ ID NO 931
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 931
aggacaacca cuuuggugn 19

<210> SEQ ID NO 932
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 932
nggacaacca cuuuggugn 19

<210> SEQ ID NO 933
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = hypoxanthine (inosine)

<400> SEQUENCE: 933
aggacaacca cuuunguga 19

<210> SEQ ID NO 934
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 15
<223> OTHER INFORMATION: n = hypoxanthine (inosine)

<400> SEQUENCE: 934
nggacaacca cuuunguga 19

<210> SEQ ID NO 935
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 935
aggacaacca cuuungugn 19

<210> SEQ ID NO 936
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 15
<223> OTHER INFORMATION: n = hypoxanthine (inosine)

<400> SEQUENCE: 936
nggacaacca cuuungugn 19

<210> SEQ ID NO 937
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 937
accagaacaa ccucugcuc 19

<210> SEQ ID NO 938
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 938
accagaacaa ccucugcua 19

<210> SEQ ID NO 939
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 939
nccagaacaa ccucugcua 19

<210> SEQ ID NO 940
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 940
accagaacaa ccucugcun 19

<210> SEQ ID NO 941
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 941
nccagaacaa ccucugcun 19

<210> SEQ ID NO 942
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 16
<223> OTHER INFORMATION: n = hypoxanthine (inosine)

<400> SEQUENCE: 942
accagaacaa ccucuncuc 19

<210> SEQ ID NO 943
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 16
<223> OTHER INFORMATION: n = hypoxanthine (inosine)

<400> SEQUENCE: 943
accagaacaa ccucuncua 19

<210> SEQ ID NO 944
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 16
<223> OTHER INFORMATION: n = hypoxanthine (inosine)

<400> SEQUENCE: 944
nccagaacaa ccucuncua 19

<210> SEQ ID NO 945
<211> LENGTH: 19

<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 16
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 945
accagaacaa ccucuncun 19

<210> SEQ ID NO 946
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 16
<223> OTHER INFORMATION: n = hypoxanthine (inosine)

<400> SEQUENCE: 946
nccagaacaa ccucuncun 19

<210> SEQ ID NO 947
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 947
cuacaaccag cacaaucuc 19

<210> SEQ ID NO 948
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 948
cuacaaccag cacaaucua 19

<210> SEQ ID NO 949
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 949
cuacaaccag cacaaucun 19

<210> SEQ ID NO 950
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 950
nuacaaccag cacaaucua 19

<210> SEQ ID NO 951
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 951
nuacaaccag cacaaucun 19

<210> SEQ ID NO 952
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 952
acaaccagca caacuucug 19

<210> SEQ ID NO 953
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 953
acaaccagca caacuucua 19

<210> SEQ ID NO 954
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 954
acaaccagca caacuucun 19

```
<210> SEQ ID NO 955
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1
<223> OTHER INFORMATION: n = any nucleobase

<400> SEQUENCE: 955

ncaaccagca caacuucua                                                19


<210> SEQ ID NO 956
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 956

ncaaccagca caacuucun                                                19


<210> SEQ ID NO 957
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 957

caaccacuuu ggugacaag                                                19


<210> SEQ ID NO 958
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 958

caaccacuuu ggugacaaa                                                19


<210> SEQ ID NO 959
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 959

caaccacuuu ggugacaan                                                19
```

<210> SEQ ID NO 960
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 960
naaccacuuu ggugacaaa 19

<210> SEQ ID NO 961
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 961
naaccacuuu ggugacaan 19

<210> SEQ ID NO 962
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 962
acaaccaaca caacuucug 19

<210> SEQ ID NO 963
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 963
acaaccaaca caacuucua 19

<210> SEQ ID NO 964
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 964
acaaccaaca caacuucun 19

<210> SEQ ID NO 965
<211> LENGTH: 19

<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 965
ncaaccaaca caacuucua 19

<210> SEQ ID NO 966
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 966
ncaaccaaca caacuucun 19

<210> SEQ ID NO 967
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 967
cucugcuccu acaacuaga 19

<210> SEQ ID NO 968
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 968
cucugcuccu acaacuagc 19

<210> SEQ ID NO 969
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 969
cucugcuccu acaacuagn 19

<210> SEQ ID NO 970
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 970
nucugcuccu acaacuaga 19

<210> SEQ ID NO 971
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 971
nucugcuccu acaacuagn 19

<210> SEQ ID NO 972
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 972
gggaaguguu ccugaacca 19

<210> SEQ ID NO 973
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 973
gggaaguguu ccugaaccn 19

<210> SEQ ID NO 974
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 974
nggaaguguu ccugaacca 19

<210> SEQ ID NO 975
<211> LENGTH: 19

<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 975
nggaaguguu ccugaaccn 19

<210> SEQ ID NO 976
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 14
<223> OTHER INFORMATION: n = hypoxanthine (inosine)

<400> SEQUENCE: 976
gggaaguguu ccunaacca 19

<210> SEQ ID NO 977
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 14
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 977
gggaaguguu ccunaaccn 19

<210> SEQ ID NO 978
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 14
<223> OTHER INFORMATION: n = hypoxanthine (inosine)

<400> SEQUENCE: 978
nggaaguguu ccunaacca 19

<210> SEQ ID NO 979
<211> LENGTH: 19
<212> TYPE: RNA
<213> ORGANISM: Artificial sequence
<220> FEATURE:

<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 14
<223> OTHER INFORMATION: n = hypoxanthine (inosine)

<400> SEQUENCE: 979
nggaaguguu ccunaaccn 19

<210> SEQ ID NO 980
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 980
ugggaacuuc gacgacauc 19

<210> SEQ ID NO 981
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 981
ugggaacuuc gacgacaua 19

<210> SEQ ID NO 982
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 982
ugggaacuuc gacgacaun 19

<210> SEQ ID NO 983
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 983
ngggaacuuc gacgacaua 19

<210> SEQ ID NO 984
<211> LENGTH: 19
<212> TYPE: RNA

<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 984
ngggaacuuc gacgacaun 19

<210> SEQ ID NO 985
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 14
<223> OTHER INFORMATION: n = hypoxanthine (inosine)

<400> SEQUENCE: 985
ugggaacuuc gacnacauc 19

<210> SEQ ID NO 986
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 14
<223> OTHER INFORMATION: n = hypoxanthine (inosine)

<400> SEQUENCE: 986
ugggaacuuc gacnacaua 19

<210> SEQ ID NO 987
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 14
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 987
ugggaacuuc gacnacaun 19

<210> SEQ ID NO 988
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1

<223> OTHER INFORMATION: n = any nucleobase
<220> FEATURE:
<221> NAME/KEY: modified_base
<222> LOCATION: 14
<223> OTHER INFORMATION: n = hypoxanthine (inosine)

<400> SEQUENCE: 988
ngggaacuuc gacnacaua 19

<210> SEQ ID NO 989
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 14
<223> OTHER INFORMATION: n = hypoxanthine (inosine)

<400> SEQUENCE: 989
ngggaacuuc gacnacaun 19

<210> SEQ ID NO 990
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 990
accuccucuu ggcagaaau 19

<210> SEQ ID NO 991
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 991
nccuccucuu ggcagaaau 19

<210> SEQ ID NO 992
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 992
accuccucuu ggcagaaaa 19

<210> SEQ ID NO 993
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1
<223> OTHER INFORMATION: n = any nucleobase

<400> SEQUENCE: 993
nccuccucuu ggcagaaaa 19

<210> SEQ ID NO 994
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 994
nccuccucuu ggcagaaan 19

<210> SEQ ID NO 995
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 12
<223> OTHER INFORMATION: n = hypoxanthine (inosine)

<400> SEQUENCE: 995
accuccucuu gncagaaau 19

<210> SEQ ID NO 996
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 12
<223> OTHER INFORMATION: n = hypoxanthine (inosine)

<400> SEQUENCE: 996
nccuccucuu gncagaaau 19

<210> SEQ ID NO 997
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 12
<223> OTHER INFORMATION: n = hypoxanthine (inosine)

<400> SEQUENCE: 997
accuccucuu gncagaaaa 19

<210> SEQ ID NO 998
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 12
<223> OTHER INFORMATION: n = hypoxanthine (inosine)

<400> SEQUENCE: 998
nccuccucuu gncagaaaa 19

<210> SEQ ID NO 999
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 12
<223> OTHER INFORMATION: n = hypoxanthine (inosine)

<400> SEQUENCE: 999
nccuccucuu gncagaaan 19

<210> SEQ ID NO 1000
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 1000
gagaucaucu ucaacaaca 19

<210> SEQ ID NO 1001
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 1001
nagaucaucu ucaacaaca 19

<210> SEQ ID NO 1002

<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 1002
gagaucaucu ucaacaacn 19

<210> SEQ ID NO 1003
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 1003
nagaucaucu ucaacaacn 19

<210> SEQ ID NO 1004
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 1004
aaggaaaccu acaacaaca 19

<210> SEQ ID NO 1005
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 1005
aaggaaaccu acaacaacn 19

<210> SEQ ID NO 1006
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 1006
naggaaaccu acaacaaca 19

<210> SEQ ID NO 1007
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 1007
naggaaaccu acaacaacn 19

<210> SEQ ID NO 1008
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 1008
ucuuugauga ggacaagau 19

<210> SEQ ID NO 1009
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 1009
ncuuugauga ggacaagau 19

<210> SEQ ID NO 1010
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 1010
ncuuugauga ggacaagan 19

<210> SEQ ID NO 1011
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 1011
ucuuugauga ggacaagaa 19

<210> SEQ ID NO 1012

<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 1012
ncuuugauga ggacaagaa 19

<210> SEQ ID NO 1013
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 1013
uuugaugagg acaagaugc 19

<210> SEQ ID NO 1014
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 1014
uuugaugagg acaagauga 19

<210> SEQ ID NO 1015
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 1015
nuugaugagg acaagauga 19

<210> SEQ ID NO 1016
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 1016
uuugaugagg acaagaugn 19

<210> SEQ ID NO 1017
<211> LENGTH: 19
<212> TYPE: RNA

<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 1017
nuugaugagg acaagaugn 19

<210> SEQ ID NO 1018
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 1018
cucugcuccu acaacuagc 19

<210> SEQ ID NO 1019
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 1019
cucugcuccu acaacuaga 19

<210> SEQ ID NO 1020
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 1020
cucugcuccu acaacuagn 19

<210> SEQ ID NO 1021
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 1021
nucugcuccu acaacuaga 19

<210> SEQ ID NO 1022
<211> LENGTH: 19
<212> TYPE: RNA
<213> ORGANISM: Artificial sequence
<220> FEATURE:

<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 1022
nucugcuccu acaacuagn 19

<210> SEQ ID NO 1023
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 1023
accucugcuu cuacaacua 19

<210> SEQ ID NO 1024
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 1024
accucugcuu cuacaacun 19

<210> SEQ ID NO 1025
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 1025
nccucugcuu cuacaacua 19

<210> SEQ ID NO 1026
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 1026
nccucugcuu cuacaacun 19

<210> SEQ ID NO 1027
<211> LENGTH: 19
<212> TYPE: RNA

<213> ORGANISM: Artificial sequence
<220> FEATURE:
<223> OTHER INFORMATION: RNAi agent sense strand 19-mer core base
      sequence

<400> SEQUENCE: 1027
auaaccagca caacuucug 19

<210> SEQ ID NO 1028
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 1028
auaaccagca caacuucua 19

<210> SEQ ID NO 1029
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 1029
auaaccagca caacuucun 19

<210> SEQ ID NO 1030
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1
<223> OTHER INFORMATION: n = any nucleobase

<400> SEQUENCE: 1030
nuaaccagca caacuucua 19

<210> SEQ ID NO 1031
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 1031
nuaaccagca caacuucun 19

<210> SEQ ID NO 1032
<211> LENGTH: 19
<212> TYPE: RNA
<213> ORGANISM: Artificial sequence
<220> FEATURE:

<223> OTHER INFORMATION: RNAi agent sense strand 19-mer core base sequence

<400> SEQUENCE: 1032
acaucaccug caguguugg 19

<210> SEQ ID NO 1033
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 1033
acaucaccug caguguuga 19

<210> SEQ ID NO 1034
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 1034
acaucaccug caguguugn 19

<210> SEQ ID NO 1035
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 1035
ncaucaccug caguguuga 19

<210> SEQ ID NO 1036
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 1036
ncaucaccug caguguugn 19

<210> SEQ ID NO 1037
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = hypoxanthine (inosine)

<400> SEQUENCE: 1037
acaucaccug cagunuugg 19

<210> SEQ ID NO 1038
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = hypoxanthine (inosine)

<400> SEQUENCE: 1038
acaucaccug cagunuuga 19

<210> SEQ ID NO 1039
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 1039
acaucaccug cagunuugn 19

<210> SEQ ID NO 1040
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 15
<223> OTHER INFORMATION: n = hypoxanthine (inosine)

<400> SEQUENCE: 1040
ncaucaccug cagunuuga 19

<210> SEQ ID NO 1041
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19

<223> OTHER INFORMATION: n = any nucleobase
<220> FEATURE:
<221> NAME/KEY: modified_base
<222> LOCATION: 15
<223> OTHER INFORMATION: n = hypoxanthine (inosine)

<400> SEQUENCE: 1041
ncaucaccug cagunuugn 19

<210> SEQ ID NO 1042
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 1042
cuuugaugag gacaagaug 19

<210> SEQ ID NO 1043
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 1043
cuuugaugag gacaagaua 19

<210> SEQ ID NO 1044
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 1044
cuuugaugag gacaagaun 19

<210> SEQ ID NO 1045
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 1045
nuuugaugag gacaagaua 19

<210> SEQ ID NO 1046
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:

<221> NAME/KEY: modified_base
<222> LOCATION: 1, 19
<223> OTHER INFORMATION: n = any nucleobase

<400> SEQUENCE: 1046
nuuugaugag gacaagaun 19

<210> SEQ ID NO 1047
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 1047
acgucaucua ccacacgac 19

<210> SEQ ID NO 1048
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 1048
acgucaucua ccacacgaa 19

<210> SEQ ID NO 1049
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 1049
acgucaucua ccacacgan 19

<210> SEQ ID NO 1050
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase

<400> SEQUENCE: 1050
ncgucaucua ccacacgaa 19

<210> SEQ ID NO 1051
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19

<223> OTHER INFORMATION: n = any nucleobase

<400> SEQUENCE: 1051
ncgucaucua ccacacgan 19

<210> SEQ ID NO 1052
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 17
<223> OTHER INFORMATION: n = hypoxanthine (inosine)

<400> SEQUENCE: 1052
acgucaucua ccacacnac 19

<210> SEQ ID NO 1053
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 17
<223> OTHER INFORMATION: n = hypoxanthine (inosine)

<400> SEQUENCE: 1053
acgucaucua ccacacnaa 19

<210> SEQ ID NO 1054
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 17
<223> OTHER INFORMATION: n = hypoxanthine (inosine)
<220> FEATURE:
<221> NAME/KEY: modified_base
<222> LOCATION: 19
<223> OTHER INFORMATION: n = any nucleobase

<400> SEQUENCE: 1054
acgucaucua ccacacnan 19

<210> SEQ ID NO 1055
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1
<223> OTHER INFORMATION: n = any nucleobase
<220> FEATURE:
<221> NAME/KEY: modified_base
<222> LOCATION: 17
<223> OTHER INFORMATION: n = hypoxanthine (inosine)

<400> SEQUENCE: 1055
ncgucaucua ccacacnaa 19

<210> SEQ ID NO 1056
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 17
<223> OTHER INFORMATION: n = hypoxanthine (inosine)

<400> SEQUENCE: 1056
ncgucaucua ccacacnan 19

<210> SEQ ID NO 1057
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1057
uuugauggcc uuggagcagg u 21

<210> SEQ ID NO 1058
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1058
aaucuugaug gccuuggagc a 21

<210> SEQ ID NO 1059
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1059
uuugaacucg gggcugaggu u 21

<210> SEQ ID NO 1060
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1060
ugaugcugca cugcuucugg g 21

<210> SEQ ID NO 1061
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1061
uuagucgcag aacagagggc a 21

<210> SEQ ID NO 1062
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1062
aguagucgca gaacagaggg c 21

<210> SEQ ID NO 1063
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1063
uuaguagucg cagaacagag g 21

<210> SEQ ID NO 1064
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1064
uguaguaguc gcagaacaga g 21

<210> SEQ ID NO 1065
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1065
uuguaguagu cgcagaacag c 21

<210> SEQ ID NO 1066
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1066
auaguuguag cagaugggug g 21

<210> SEQ ID NO 1067
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1067
uuccacgucg aaccacuuug c 21

<210> SEQ ID NO 1068

<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1068
uaaguccacg ucgaaccacu c 21

<210> SEQ ID NO 1069
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1069
uggaagucca cgucgaacca c 21

<210> SEQ ID NO 1070
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1070
uggaagucca cgucgaacca c 21

<210> SEQ ID NO 1071
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1071
aaggucuugu aguggaagcu g 21

<210> SEQ ID NO 1072
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1072
aaggucuugu aguggaagcu g 21

<210> SEQ ID NO 1073
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1073
uaccagugcu gagcauacuu c 21

<210> SEQ ID NO 1074
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1074

-continued uaccagugcu gagcauacuu c 21

<210> SEQ ID NO 1075
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1075
uuugaaggug uugaagaagg c 21

<210> SEQ ID NO 1076
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1076
agaugcuggu cuucuugucc c 21

<210> SEQ ID NO 1077
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1077
uguugaugaa gaugcugguc c 21

<210> SEQ ID NO 1078
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1078
uucuuguuca ggcaaaucag c 21

<210> SEQ ID NO 1079
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1079
auguuguugu agguuuccuu g 21

<210> SEQ ID NO 1080
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1080
augauguugu uguagguuuc c 21

<210> SEQ ID NO 1081
<211> LENGTH: 21
<212> TYPE: RNA

<213> ORGANISM: Artificial sequence
<220> FEATURE:
<223> OTHER INFORMATION: RNAi agent antisense strand modified sequence

<400> SEQUENCE: 1081
uugaugaaga ugcuggucuu c 21

<210> SEQ ID NO 1082
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1082
ugaucuggua guuguagcag c 21

<210> SEQ ID NO 1083
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1083
uccugaucug guaguuguag c 21

<210> SEQ ID NO 1084
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1084
uaguuguagc agaugggugg g 21

<210> SEQ ID NO 1085
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1085
ucaacacugg augcggaucu c 21

<210> SEQ ID NO 1086
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1086
uuguucgaug cucaccucug g 21

<210> SEQ ID NO 1087
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1087
uaucuugaag ggucccugcu g 21

<210> SEQ ID NO 1088
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1088
ucguaguuga ggcacaucuu g 21

<210> SEQ ID NO 1089
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1089
ucucguaguu gaggcacauc c 21

<210> SEQ ID NO 1090
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1090
aaggucuugu aguggaagcu g 21

<210> SEQ ID NO 1091
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1091
uuucaggcag gucucgcugu c 21

<210> SEQ ID NO 1092
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1092
uucugaagau ggugacguug g 21

<210> SEQ ID NO 1093
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1093
ugucugaaga uggugacguu g 21

<210> SEQ ID NO 1094
<211> LENGTH: 21
<212> TYPE: RNA
<213> ORGANISM: Artificial sequence
<220> FEATURE:

```
<223> OTHER INFORMATION: RNAi agent antisense strand modified sequence

<400> SEQUENCE: 1094

uggaagucau cggccuggau g                                            21

<210> SEQ ID NO 1095
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1095

uuugaaggug uugaagaagg c                                            21

<210> SEQ ID NO 1096
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1096

ugcaguucga guaguagguu c                                            21

<210> SEQ ID NO 1097
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1097

uuuggagcag guggucccug u                                            21

<210> SEQ ID NO 1098
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1098

ucuugauggc cuuggagcag g                                            21

<210> SEQ ID NO 1099
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1099

uugucaucgu gguuccacau g                                            21

<210> SEQ ID NO 1100
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1100

acagaagcag aggucuugcc u                                            21
```

-continued

<210> SEQ ID NO 1101
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1101
ucaguuggug cagucugugg a 21

<210> SEQ ID NO 1102
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1102
ucaguacagu gaaggcacug c 21

<210> SEQ ID NO 1103
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1103
ugcuguugaa guucccacag c 21

<210> SEQ ID NO 1104
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1104
ugaugcuguu gaaguuccca c 21

<210> SEQ ID NO 1105
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1105
uggucuugaa gguguugaag c 21

<210> SEQ ID NO 1106
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1106
aagcuguucc ugauguuggg g 21

<210> SEQ ID NO 1107
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1107
acaugcaguu cgaguaguag g 21

<210> SEQ ID NO 1108
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1108
uaagccaaca cugcagguga c 21

<210> SEQ ID NO 1109
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1109
uuguaacagg ucauguccag c 21

<210> SEQ ID NO 1110
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1110
ucguugaagc uguagcucug c 21

<210> SEQ ID NO 1111
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1111
uaccagugcu gagcauacuu c 21

<210> SEQ ID NO 1112
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1112
uggaucucau aguuguagca g 21

<210> SEQ ID NO 1113
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1113
uggaucucau aguuguagca g 21

<210> SEQ ID NO 1114
<211> LENGTH: 21

<212> TYPE: RNA
<213> ORGANISM: Artificial sequence
<220> FEATURE:
<223> OTHER INFORMATION: RNAi agent antisense strand modified sequence

<400> SEQUENCE: 1114
ugucaaacca cuugguccag g 21

<210> SEQ ID NO 1115
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1115
uuguuguuga agaugaucuc g 21

<210> SEQ ID NO 1116
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1116
uuguuguuga agaugaucuc g 21

<210> SEQ ID NO 1117
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1117
uaguacagug aaggcacugc u 21

<210> SEQ ID NO 1118
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1118
uucgaagcug uuccugaugu c 21

<210> SEQ ID NO 1119
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1119
ucuuguucag gcaaaucagc c 21

<210> SEQ ID NO 1120
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1120
ucaccaaagu gguuguccug g 21

<210> SEQ ID NO 1121
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1121
uagcagaggu uguucugguu g 21

<210> SEQ ID NO 1122
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1122
uagauugugc ugguuguagc g 21

<210> SEQ ID NO 1123
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1123
uagaaguugu gcugguugug g 21

<210> SEQ ID NO 1124
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1124
uuugucacca aagugguugu c 21

<210> SEQ ID NO 1125
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1125
uagagguugu guugguugua g 21

<210> SEQ ID NO 1126
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1126
ucuaguugua ggagcagagg u 21

<210> SEQ ID NO 1127
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1127
uuguaguagu cgcagaacag c 21

<210> SEQ ID NO 1128
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1128
uuguaguagu cacagaacag c 21

<210> SEQ ID NO 1129
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1129
uuguaguagu cacagaacag c 21

<210> SEQ ID NO 1130
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1130
uuguaguagu cacagaacag c 21

<210> SEQ ID NO 1131
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1131
ucauaguugu agcacauggg u 21

<210> SEQ ID NO 1132
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1132
uguuguugaa gaugaucugg u 21

<210> SEQ ID NO 1133
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1133
uguuguugaa gaugaucugg u 21

<210> SEQ ID NO 1134
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1134
uguugaaguu accacagagc c 21

<210> SEQ ID NO 1135
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1135
uacuuuucau ucuccacgcu c 21

<210> SEQ ID NO 1136
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1136
uagcauacuu uucauucucc c 21

<210> SEQ ID NO 1137
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1137
ucauacaugc aguucgagaa g 21

<210> SEQ ID NO 1138
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1138
ugucauacau gcaguucgag c 21

<210> SEQ ID NO 1139
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1139
uugucauaca ugcaguucga g 21

<210> SEQ ID NO 1140
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1140
uuaguaguca cagaacagug g 21

<210> SEQ ID NO 1141
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1141
uguaguaguc acagaacagu g 21

<210> SEQ ID NO 1142
<211> LENGTH: 21
<212> TYPE: RNA
<213> ORGANISM: Artificial sequence
<220> FEATURE:
<223> OTHER INFORMATION: RNAi agent antisense strand modified sequence
<220> FEATURE:
<221> NAME/KEY: modified_base
<222> LOCATION: 12
<223> OTHER INFORMATION: n = 2'-O-methylinosine-3'-phosphate

<400> SEQUENCE: 1142
uuguaguagu cncagaacag c 21

<210> SEQ ID NO 1143
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1143
uuguaguagu cgcagaacag c 21

<210> SEQ ID NO 1144
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1144
acaugcaguu cgagaagaag g 21

<210> SEQ ID NO 1145
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1145
acaugcaguu cgagaagaag g 21

<210> SEQ ID NO 1146
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1146
auaguuguag cacaugggug g 21

<210> SEQ ID NO 1147
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1147
auaguuguag cacaugggug g 21

<210> SEQ ID NO 1148
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1148
uggaucucau aguuguagca g 21

<210> SEQ ID NO 1149
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1149
uuguuguuga agaugaucuc g 21

<210> SEQ ID NO 1150
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1150
uguaguaguc acagaacagu g 21

<210> SEQ ID NO 1151
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1151
uguaguaguc acagaacagu g 21

<210> SEQ ID NO 1152
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1152
uguaguaguc acagaacagu c 21

<210> SEQ ID NO 1153
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1153
ugguucagga acacuucccc a 21

<210> SEQ ID NO 1154
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1154
ucaacacugc aggugauguc c 21

<210> SEQ ID NO 1155
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1155
uaugucgucg aaguucccac a 21

<210> SEQ ID NO 1156
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1156
uaucuugucc ucaucaaaga c 21

<210> SEQ ID NO 1157
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1157
uucguguggu agaugacguc c 21

<210> SEQ ID NO 1158
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1158
auuucugcca agaggaggug c 21

<210> SEQ ID NO 1159
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1159
uguuguugaa gaugaucucg u 21

<210> SEQ ID NO 1160
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1160
uuguuguuga agaugaucuc g 21

<210> SEQ ID NO 1161
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1161
uguuguugua gguuuccuug c 21

<210> SEQ ID NO 1162
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1162
uguuguugua gguuuccuug c 21

<210> SEQ ID NO 1163
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1163
uguuguugua gguuuccuug c 21

<210> SEQ ID NO 1164
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1164
uguuguugua gguuuccuug c 21

<210> SEQ ID NO 1165
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1165
uucuuguuca ggcaaaucag c 21

<210> SEQ ID NO 1166
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1166
uucuuguuca ggcaaaucag c 21

<210> SEQ ID NO 1167
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1167
uucuuguuca ggcaaaucag c 21

<210> SEQ ID NO 1168
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1168
uucuuguuca ggcaaaucag c 21

<210> SEQ ID NO 1169
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1169
ucuuguucag gcaaaucagc c 21

<210> SEQ ID NO 1170
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1170
ucuuguucag gcaaaucagc c 21

<210> SEQ ID NO 1171
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1171
ucuuguucag gcaaaucagc c 21

<210> SEQ ID NO 1172
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1172
uguugaugaa gaugcugguc c 21

<210> SEQ ID NO 1173

<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1173
uguugaugaa gaugcugguc c 21

<210> SEQ ID NO 1174
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1174
uguugaugaa gaugcugguc c 21

<210> SEQ ID NO 1175
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1175
uguugaugaa gaugcugguc c 21

<210> SEQ ID NO 1176
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1176
uuguuguuga agaugaucuc g 21

<210> SEQ ID NO 1177
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1177
uuguuguuga agaugaucuc g 21

<210> SEQ ID NO 1178
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1178
uuguuguuga agaugaucuc g 21

<210> SEQ ID NO 1179
<211> LENGTH: 21
<212> TYPE: RNA
<213> ORGANISM: Artificial sequence
<220> FEATURE:
<223> OTHER INFORMATION: RNAi agent antisense strand modified sequence
<220> FEATURE:
<221> NAME/KEY: modified_base
<222> LOCATION: 4
<223> OTHER INFORMATION: n = 2'-O-methylinosine-3'-phosphate

<400> SEQUENCE: 1179
uugnuguuga agaugaucuc g 21

<210> SEQ ID NO 1180
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1180
aucuuguccu caucaaagau g 21

<210> SEQ ID NO 1181
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1181
ucaucuuguc cucaucaaag c 21

<210> SEQ ID NO 1182
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1182
ucuaguugua ggagcagaga c 21

<210> SEQ ID NO 1183
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1183
uaguuguaga agcagagguu g 21

<210> SEQ ID NO 1184
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1184
uagaaguugu gcugguuaua g 21

<210> SEQ ID NO 1185
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1185
uuguaguagu cgcagaacag c 21

<210> SEQ ID NO 1186
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1186
uuguaguagu cgcagaacag c 21

<210> SEQ ID NO 1187
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1187
uucuuguuca ggcaaaucag g 21

<210> SEQ ID NO 1188
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1188
uucuuguuca ggcaaaucag c 21

<210> SEQ ID NO 1189
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1189
uucuuguuca ggcaaaucag c 21

<210> SEQ ID NO 1190
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1190
uucuuguuca ggcaaaucag c 21

<210> SEQ ID NO 1191
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1191
uucuuguuca ggcaaaucag c 21

<210> SEQ ID NO 1192
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 13
<223> OTHER INFORMATION: n = 2'-O-methylinosine-3'-phosphate

<400> SEQUENCE: 1192
accugcucca agnccaucaa a 21

<210> SEQ ID NO 1193
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1193
ugcuccaagg ccaucaagau u 21

<210> SEQ ID NO 1194
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1194
aaccucagcu ccgaguucaa a 21

<210> SEQ ID NO 1195
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1195
cccagaagca gugcancauc a 21

<210> SEQ ID NO 1196
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1196
ugcccucugu ucugcnacua a 21

<210> SEQ ID NO 1197
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 13
<223> OTHER INFORMATION: n = 2'-O-methylinosine-3'-phosphate

<400> SEQUENCE: 1197
gcccucuguu cuncgacuac u 21

<210> SEQ ID NO 1198
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1198
ccucuguucu gcgacuacua a 21

<210> SEQ ID NO 1199
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1199
cucuguucug cgacuacuac a 21

<210> SEQ ID NO 1200
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1200
gcuguucugc gacuacuaca a 21

<210> SEQ ID NO 1201
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1201
ccacccaucu gcuacaacua u 21

<210> SEQ ID NO 1202
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1202
gcaaaguggu ucgacnugga a 21

<210> SEQ ID NO 1203
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1203
gagugguucg acgugnacuu a 21

<210> SEQ ID NO 1204
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 14
<223> OTHER INFORMATION: n = 2'-O-methylinosine-3'-phosphate

<400> SEQUENCE: 1204
gugguucgac gugnacuucc a 21

<210> SEQ ID NO 1205
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1205
gugguucgac guggacuucc a 21

<210> SEQ ID NO 1206
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1206
cagcuuccac uacaanaccu u 21

<210> SEQ ID NO 1207
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1207
cagcuuccac uacaagaccu u 21

<210> SEQ ID NO 1208
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate
<220> FEATURE:
<221> NAME/KEY: modified_base
<222> LOCATION: 19
<223> OTHER INFORMATION: n = 2'-O-methylinosine-3'-phosphate

<400> SEQUENCE: 1208
gnaguaugcu cagcacugnu a 21

<210> SEQ ID NO 1209
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate
<220> FEATURE:
<221> NAME/KEY: modified_base
<222> LOCATION: 19
<223> OTHER INFORMATION: n = 2'-O-methylinosine-3'-phosphate

<400> SEQUENCE: 1209
gnaguaugcu caguacugnu a 21

<210> SEQ ID NO 1210
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1210
gccuucuuca acaccuucaa a 21

<210> SEQ ID NO 1211
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1211
gccuucuuca acaucuucaa a 21

<210> SEQ ID NO 1212
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1212
gccuucuuca acacuuucaa a 21

<210> SEQ ID NO 1213
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1213
gggacaagaa gaccancauc u 21

<210> SEQ ID NO 1214
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1214
ggaccagcau cuucaucaac a 21

<210> SEQ ID NO 1215
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1215
gcugauuugc cugaacaaga a 21

<210> SEQ ID NO 1216
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate

<400> SEQUENCE: 1216
cnaggaaacc uacaacaaca u 21

<210> SEQ ID NO 1217
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1217
ggaaaccuac aacaacauca u 21

<210> SEQ ID NO 1218
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate

<400> SEQUENCE: 1218
gnagaccagc aucuucauca a 21

<210> SEQ ID NO 1219
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 1219
gcugcuacaa cuaccanauc a 21

<210> SEQ ID NO 1220

<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 1220
gcuacaacua ccagaucang a 21

<210> SEQ ID NO 1221
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1221
cccacccauc ugcuacaacu a 21

<210> SEQ ID NO 1222
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 1222
gagauccgca uccagunuug a 21

<210> SEQ ID NO 1223
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1223
ccagagguga gcaucnaaca a 21

<210> SEQ ID NO 1224
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1224
cagcagggac ccuucaagau a 21

<210> SEQ ID NO 1225
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate
<220> FEATURE:
<221> NAME/KEY: modified_base
<222> LOCATION: 20
<223> OTHER INFORMATION: n = 2'-O-methylinosine-3'-phosphate

<400> SEQUENCE: 1225
cnagaugugc cucaacuacn a 21

<210> SEQ ID NO 1226
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 1226
ggaugugccu caacuacnag a 21

<210> SEQ ID NO 1227
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1227
cagcuuccac uacaanaccu u 21

<210> SEQ ID NO 1228
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1228
gacagcgaga ccugcuugaa a 21

<210> SEQ ID NO 1229
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1229
ccaacgucac caucuucaga a 21

<210> SEQ ID NO 1230
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate
<220> FEATURE:

<221> NAME/KEY: modified_base
<222> LOCATION: 18
<223> OTHER INFORMATION: n = 2'-O-methylinosine-3'-phosphate

<400> SEQUENCE: 1230
cnacgucacc aucuucanac a 21

<210> SEQ ID NO 1231
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1231
cauccaggcc gaugacuucc a 21

<210> SEQ ID NO 1232
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1232
gccuucuuca acaccuucaa a 21

<210> SEQ ID NO 1233
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate
<220> FEATURE:
<221> NAME/KEY: modified_base
<222> LOCATION: 19
<223> OTHER INFORMATION: n = 2'-O-methylinosine-3'-phosphate

<400> SEQUENCE: 1233
gnaguaugcu cagcacugnu a 21

<210> SEQ ID NO 1234
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate
<220> FEATURE:
<221> NAME/KEY: modified_base
<222> LOCATION: 19
<223> OTHER INFORMATION: n = 2'-O-methylinosine-3'-phosphate

<400> SEQUENCE: 1234
gnaccuacua cucgaacunc a 21

<210> SEQ ID NO 1235
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1235
acagggacca ccugcuucaa a 21

<210> SEQ ID NO 1236
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1236
ccugcuccaa ggcuaucaag a 21

<210> SEQ ID NO 1237
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate
<220> FEATURE:
<221> NAME/KEY: modified_base
<222> LOCATION: 17
<223> OTHER INFORMATION: n = 2'-O-methylinosine-3'-phosphate

<400> SEQUENCE: 1237
cnuguggaac cacgaunaca a 21

<210> SEQ ID NO 1238
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 1238
aggcaagacc ucugcuucun u 21

<210> SEQ ID NO 1239
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 1239
uccacagacu gcaccaacun a 21

<210> SEQ ID NO 1240
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20

<223> OTHER INFORMATION: n = 2'-O-methylinosine-3'-phosphate

<400> SEQUENCE: 1240
gcagugccuu cacuguacun a 21

<210> SEQ ID NO 1241
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 1241
gcugugggaa cuucaacanc a 21

<210> SEQ ID NO 1242
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1242
gugggaacuu caacancauc a 21

<210> SEQ ID NO 1243
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 1243
gcuucaacac cuucaanacc a 21

<210> SEQ ID NO 1244
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 1244
ccccaacauc aggaacancu u 21

<210> SEQ ID NO 1245
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1245
ccuacuacuc gaacuncaug u 21

<210> SEQ ID NO 1246
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 1246
gucaccugca guguugncuu a 21

<210> SEQ ID NO 1247
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1247
gcuggacaug accuguuaca a 21

<210> SEQ ID NO 1248
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 1248
gcagagcuac agcuucaacn a 21

<210> SEQ ID NO 1249
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate
<220> FEATURE:
<221> NAME/KEY: modified_base
<222> LOCATION: 19
<223> OTHER INFORMATION: n = 2'-O-methylinosine-3'-phosphate

<400> SEQUENCE: 1249
gnaguaugcu caguacugnu a 21

<210> SEQ ID NO 1250
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1250
cugcuacaac uaugagaucc a 21

<210> SEQ ID NO 1251
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1251
cugcuacaac uauganaucc a 21

<210> SEQ ID NO 1252
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1252
ccuggaccaa gugguuugac a 21

<210> SEQ ID NO 1253
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 1253
ccuggaccaa gugguuunac a 21

<210> SEQ ID NO 1254
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1254
cgagaucauc uucaacaaca a 21

<210> SEQ ID NO 1255
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1255
agcagugccu ucacuguacu a 21

<210> SEQ ID NO 1256
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 1256
gacaucagga acagcuucna a 21

<210> SEQ ID NO 1257
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1257
ggcugauuug ccugaacaag a 21

<210> SEQ ID NO 1258
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 1258
ccaggacaac cacuuungug a 21

<210> SEQ ID NO 1259
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 1259
caaccagaac aaccucuncu a 21

<210> SEQ ID NO 1260
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1260
cgcuacaacc agcacaaucu a 21

<210> SEQ ID NO 1261
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1261
ccacaaccag cacaacuucu a 21

<210> SEQ ID NO 1262

<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1262
gacaaccacu uuggugacaa a 21

<210> SEQ ID NO 1263
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1263
cuacaaccaa cacaacuucu a 21

<210> SEQ ID NO 1264
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1264
accucugcuc cuacaacuag a 21

<210> SEQ ID NO 1265
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1265
gcuguucugc gacuacuaca a 21

<210> SEQ ID NO 1266
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1266
gcuguucugu gacuacuaca a 21

<210> SEQ ID NO 1267
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1267
accagaucau cuucaacaac a 21

<210> SEQ ID NO 1268
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1268
ggcucugugg uaacuucaac a 21

<210> SEQ ID NO 1269
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1269
gagcguggag aaugaaaagu a 21

<210> SEQ ID NO 1270
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1270
gggagaauga aaaguaugcu a 21

<210> SEQ ID NO 1271
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1271
cuucucgaac ugcauguaug a 21

<210> SEQ ID NO 1272
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1272
gcucgaacug cauguaugac a 21

<210> SEQ ID NO 1273
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1273
cucgaacugc auguaugaca a 21

<210> SEQ ID NO 1274
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1274
ccacuguucu gugacuacua a 21

<210> SEQ ID NO 1275
<211> LENGTH: 21
<212> TYPE: RNA

<213> ORGANISM: Artificial sequence
<220> FEATURE:
<223> OTHER INFORMATION: RNAi agent sense strand modified sequence

<400> SEQUENCE: 1275
cacuguucug ugacuacuac a 21

<210> SEQ ID NO 1276
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1276
ccuucuucuc gaacuncaug u 21

<210> SEQ ID NO 1277
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1277
ccacccaugu gcuacaacua u 21

<210> SEQ ID NO 1278
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1278
cugcuacaac uauganaucc a 21

<210> SEQ ID NO 1279
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1279
cgagaucauc uucaacaaca a 21

<210> SEQ ID NO 1280
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1280
cacuguucug ugacuacuac a 21

<210> SEQ ID NO 1281
<211> LENGTH: 21

<212> TYPE: RNA
<213> ORGANISM: Artificial sequence
<220> FEATURE:
<223> OTHER INFORMATION: RNAi agent sense strand modified sequence

<400> SEQUENCE: 1281
gacuguucug ugacuacuac a 21

<210> SEQ ID NO 1282
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1282
uggggaagug uuccunaacc a 21

<210> SEQ ID NO 1283
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 1283
ggacaucacc ugcagunuug a 21

<210> SEQ ID NO 1284
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1284
ugugggaacu ucgacnacau a 21

<210> SEQ ID NO 1285
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1285
gucuuugaug aggacaagau a 21

<210> SEQ ID NO 1286
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19

<223> OTHER INFORMATION: n = 2'-O-methylinosine-3'-phosphate

<400> SEQUENCE: 1286
ggacgucauc uaccacacna a 21

<210> SEQ ID NO 1287
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1287
cugcuacaac uauganaucc a 21

<210> SEQ ID NO 1288
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 14
<223> OTHER INFORMATION: n = 2'-O-methylinosine-3'-phosphate

<400> SEQUENCE: 1288
gcaccuccuc uugncagaaa u 21

<210> SEQ ID NO 1289
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1289
acgagaucau cuucaacaac a 21

<210> SEQ ID NO 1290
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1290
cgagaucauc uucaacaaca a 21

<210> SEQ ID NO 1291
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1291
gcaaggaaac cuacaacaac a 21

<210> SEQ ID NO 1292
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1292
gcaaggaaac cuacaacaac a 21

<210> SEQ ID NO 1293
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1293
gcugauuugc cugaacaaga a 21

<210> SEQ ID NO 1294
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 14
<223> OTHER INFORMATION: n = 2'-O-methyl-2-aminoadenosine-3'-phosphate

<400> SEQUENCE: 1294
gcugauuugc cugnacaaga a 21

<210> SEQ ID NO 1295
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1295
ggcugauuug ccugaacaag a 21

<210> SEQ ID NO 1296
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1296
ggaccagcau cuucaucaac a 21

<210> SEQ ID NO 1297
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 14
<223> OTHER INFORMATION: n = 2'-O-methyl-2-aminoadenosine-3'-phosphate

<400> SEQUENCE: 1297
cgagaucauc uucnacaaca a 21

<210> SEQ ID NO 1298
<211> LENGTH: 21
<212> TYPE: RNA

<213> ORGANISM: Artificial sequence
<220> FEATURE:
<223> OTHER INFORMATION: RNAi agent sense strand modified sequence

<400> SEQUENCE: 1298
caucuuugau gaggacaaga u 21

<210> SEQ ID NO 1299
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1299
gcuuugauga ggacaagaug a 21

<210> SEQ ID NO 1300
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1300
gucucugcuc cuacaacuag a 21

<210> SEQ ID NO 1301
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1301
caaccucugc uucuacaacu a 21

<210> SEQ ID NO 1302
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 3
<223> OTHER INFORMATION: n = 2'-O-methyl-2-aminoadenosine-3'-phosphate

<400> SEQUENCE: 1302
cunuaaccag cacaacuucu a 21

<210> SEQ ID NO 1303
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1303
cuauaaccag cacaacuucu a 21

<210> SEQ ID NO 1304
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1304
gcuguucugc gacuacuaca a 21

<210> SEQ ID NO 1305
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1305
gcuguucugc gacuacuaca a 21

<210> SEQ ID NO 1306
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1306
gcuguucugc gacuacuaca a 21

<210> SEQ ID NO 1307
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1307
gcuguuuugc gacuacuaca a 21

<210> SEQ ID NO 1308
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1308
gcuguucugc gauuacuaca a 21

<210> SEQ ID NO 1309
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1309
gcuguucugc gacuauuaca a 21

<210> SEQ ID NO 1310
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1310
gcuguucugc gacuacuaca a 21

<210> SEQ ID NO 1311

<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1311
gcugauuugc cugaacaaga a 21

<210> SEQ ID NO 1312
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1312
gcugauuugc cugaacaaga a 21

<210> SEQ ID NO 1313
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1313
ccugauuugc cugaacaaga a 21

<210> SEQ ID NO 1314
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1314
cgagaucauc uucaacaaca a 21

<210> SEQ ID NO 1315
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1315
gcugauuugc cugaacaaga a 21

<210> SEQ ID NO 1316
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1316
gcuguucugc gacuacuaca a 21

<210> SEQ ID NO 1317
<211> LENGTH: 22
<212> TYPE: RNA
<213> ORGANISM: Artificial sequence
<220> FEATURE:
<223> OTHER INFORMATION: RNAi agent sense strand modified sequence

<400> SEQUENCE: 1317
gcugguucug cgacuacuac aa 22

<210> SEQ ID NO 1318
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 1318
gcguucugcg acuacuacaa 20

<210> SEQ ID NO 1319
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 13
<223> OTHER INFORMATION: n = 2'-O-methylinosine-3'-phosphate

<400> SEQUENCE: 1319
accugcucca agnccaucaa a 21

<210> SEQ ID NO 1320
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1320
ugcuccaagg ccaucaagau u 21

<210> SEQ ID NO 1321
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1321
aaccucagcu ccgaguucaa a 21

<210> SEQ ID NO 1322
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1322
cccagaagca gugcancauc a 21

<210> SEQ ID NO 1323
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:

<221> NAME/KEY: modified_base
<222> LOCATION: 16
<223> OTHER INFORMATION: n = 2'-O-methylinosine-3'-phosphate

<400> SEQUENCE: 1323
ugcccucugu ucugcnacua a 21

<210> SEQ ID NO 1324
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 13
<223> OTHER INFORMATION: n = 2'-O-methylinosine-3'-phosphate

<400> SEQUENCE: 1324
gcccucuguu cuncgacuac u 21

<210> SEQ ID NO 1325
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1325
ccucuguucu gcgacuacua a 21

<210> SEQ ID NO 1326
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1326
cucuguucug cgacuacuac a 21

<210> SEQ ID NO 1327
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1327
gcuguucugc gacuacuaca a 21

<210> SEQ ID NO 1328
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1328
ccacccaucu gcuacaacua u 21

<210> SEQ ID NO 1329
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1329
gcaaaguggu ucgacnugga a 21

<210> SEQ ID NO 1330
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1330
gagugguucg acgugnacuu a 21

<210> SEQ ID NO 1331
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 14
<223> OTHER INFORMATION: n = 2'-O-methylinosine-3'-phosphate

<400> SEQUENCE: 1331
gugguucgac gugnacuucc a 21

<210> SEQ ID NO 1332
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1332
gugguucgac guggacuucc a 21

<210> SEQ ID NO 1333
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1333
cagcuuccac uacaanaccu u 21

<210> SEQ ID NO 1334
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1334
cagcuuccac uacaagaccu u 21

<210> SEQ ID NO 1335
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2, 19
<223> OTHER INFORMATION: n = 2'-O-methylinosine-3'-phosphate

<400> SEQUENCE: 1335
gnaguaugcu cagcacugnu a 21

<210> SEQ ID NO 1336
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2, 19
<223> OTHER INFORMATION: n = 2'-O-methylinosine-3'-phosphate

<400> SEQUENCE: 1336
gnaguaugcu caguacugnu a 21

<210> SEQ ID NO 1337
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1337
gccuucuuca acaccuucaa a 21

<210> SEQ ID NO 1338
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1338
gccuucuuca acaucuucaa a 21

<210> SEQ ID NO 1339
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1339
gccuucuuca acacuuucaa a 21

<210> SEQ ID NO 1340
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1340
gggacaagaa gaccancauc u 21

<210> SEQ ID NO 1341
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1341
ggaccagcau cuucaucaac a 21

<210> SEQ ID NO 1342
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1342
gcugauuugc cugaacaaga a 21

<210> SEQ ID NO 1343
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate

<400> SEQUENCE: 1343
cnaggaaacc uacaacaaca u 21

<210> SEQ ID NO 1344
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1344
ggaaaccuac aacaacauca u 21

<210> SEQ ID NO 1345
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate

<400> SEQUENCE: 1345
gnagaccagc aucuucauca a 21

<210> SEQ ID NO 1346
<211> LENGTH: 21
<212> TYPE: RNA

<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 1346
gcugcuacaa cuaccanauc a 21

<210> SEQ ID NO 1347
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 1347
gcuacaacua ccagaucang a 21

<210> SEQ ID NO 1348
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1348
cccacccauc ugcuacaacu a 21

<210> SEQ ID NO 1349
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 1349
gagauccgca uccagunuug a 21

<210> SEQ ID NO 1350
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1350
ccagagguga gcaucnaaca a 21

<210> SEQ ID NO 1351
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1351
cagcagggac ccuucaagau a 21

<210> SEQ ID NO 1352
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate
<220> FEATURE:
<221> NAME/KEY: modified_base
<222> LOCATION: 20
<223> OTHER INFORMATION: n = 2'-O-methylinosine-3'-phosphate

<400> SEQUENCE: 1352
cnagaugugc cucaacuacn a 21

<210> SEQ ID NO 1353
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = n = 2'-O-methylinosine-3'-phosphate

<400> SEQUENCE: 1353
ggaugugccu caacuacnag a 21

<210> SEQ ID NO 1354
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = n = 2'-O-methylinosine-3'-phosphate

<400> SEQUENCE: 1354
cagcuuccac uacaanaccu u 21

<210> SEQ ID NO 1355
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1355
gacagcgaga ccugcuugaa a 21

<210> SEQ ID NO 1356
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1356
ccaacgucac caucuucaga a 21

<210> SEQ ID NO 1357
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate
<220> FEATURE:
<221> NAME/KEY: modified_base
<222> LOCATION: 18
<223> OTHER INFORMATION: n = 2'-O-methylinosine-3'-phosphate

<400> SEQUENCE: 1357
cnacgucacc aucuucanac a 21

<210> SEQ ID NO 1358
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1358
cauccaggcc gaugacuucc a 21

<210> SEQ ID NO 1359
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1359
gccuucuuca acaccuucaa a 21

<210> SEQ ID NO 1360
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate
<220> FEATURE:
<221> NAME/KEY: modified_base
<222> LOCATION: 19
<223> OTHER INFORMATION: n = 2'-O-methylinosine-3'-phosphate

<400> SEQUENCE: 1360
gnaguaugcu cagcacugnu a 21

<210> SEQ ID NO 1361
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate
<220> FEATURE:
<221> NAME/KEY: modified_base
<222> LOCATION: 19
<223> OTHER INFORMATION: n = 2'-O-methylinosine-3'-phosphate

<400> SEQUENCE: 1361
gnaccuacua cucgaacunc a 21

<210> SEQ ID NO 1362
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1362
acagggacca ccugcuucaa a 21

<210> SEQ ID NO 1363
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1363
ccugcuccaa ggcuaucaag a 21

<210> SEQ ID NO 1364
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate
<220> FEATURE:
<221> NAME/KEY: modified_base
<222> LOCATION: 17
<223> OTHER INFORMATION: n = 2'-O-methylinosine-3'-phosphate

<400> SEQUENCE: 1364
cnuguggaac cacgaunaca a 21

<210> SEQ ID NO 1365
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 1365
aggcaagacc ucugcuucun u 21

<210> SEQ ID NO 1366
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 1366
uccacagacu gcaccaacun a 21

<210> SEQ ID NO 1367
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 1367
gcagugccuu cacuguacun a 21

<210> SEQ ID NO 1368
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 1368
gcugugggaa cuucaacanc a 21

<210> SEQ ID NO 1369
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1369
gugggaacuu caacancauc a 21

<210> SEQ ID NO 1370
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 1370
gcuucaacac cuucaanacc a 21

<210> SEQ ID NO 1371
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 1371
ccccaacauc aggaacancu u 21

<210> SEQ ID NO 1372
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1372
ccuacuacuc gaacuncaug u 21

<210> SEQ ID NO 1373
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 1373
gucaccugca guguugncuu a 21

<210> SEQ ID NO 1374
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1374
gcuggacaug accuguuaca a 21

<210> SEQ ID NO 1375
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 1375
gcagagcuac agcuucaacn a 21

<210> SEQ ID NO 1376
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate
<220> FEATURE:
<221> NAME/KEY: modified_base
<222> LOCATION: 19

<223> OTHER INFORMATION: n = 2'-O-methylinosine-3'-phosphate

<400> SEQUENCE: 1376
gnaguaugcu caguacugnu a 21

<210> SEQ ID NO 1377
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1377
cugcuacaac uaugagaucc a 21

<210> SEQ ID NO 1378
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1378
cugcuacaac uauganaucc a 21

<210> SEQ ID NO 1379
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1379
ccuggaccaa gugguuugac a 21

<210> SEQ ID NO 1380
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 1380
ccuggaccaa gugguuunac a 21

<210> SEQ ID NO 1381
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1381
cgagaucauc uucaacaaca a 21

<210> SEQ ID NO 1382
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1382
agcagugccu ucacuguacu a 21

<210> SEQ ID NO 1383
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 1383
gacaucagga acagcuucna a 21

<210> SEQ ID NO 1384
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1384
ggcugauuug ccugaacaag a 21

<210> SEQ ID NO 1385
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 1385
ccaggacaac cacuuungug a 21

<210> SEQ ID NO 1386
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 1386
caaccagaac aaccucuncu a 21

<210> SEQ ID NO 1387
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1387
cgcuacaacc agcacaaucu a 21

<210> SEQ ID NO 1388
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1388
ccacaaccag cacaacuucu a 21

<210> SEQ ID NO 1389
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1389
gacaaccacu uuggugacaa a 21

<210> SEQ ID NO 1390
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1390
cuacaaccaa cacaacuucu a 21

<210> SEQ ID NO 1391
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1391
accucugcuc cuacaacuag a 21

<210> SEQ ID NO 1392
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1392
gcuguucugc gacuacuaca a 21

<210> SEQ ID NO 1393
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1393
gcuguucugu gacuacuaca a 21

<210> SEQ ID NO 1394
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1394
accagaucau cuucaacaac a 21

<210> SEQ ID NO 1395
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1395
ggcucugugg uaacuucaac a 21

<210> SEQ ID NO 1396
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1396
gagcguggag aaugaaaagu a 21

<210> SEQ ID NO 1397
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1397
gggagaauga aaaguaugcu a 21

<210> SEQ ID NO 1398
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1398
cuucucgaac ugcauguaug a 21

<210> SEQ ID NO 1399
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1399
gcucgaacug cauguaugac a 21

<210> SEQ ID NO 1400
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1400
cucgaacugc auguaugaca a 21

<210> SEQ ID NO 1401

<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1401
ccacuguucu gugacuacua a 21

<210> SEQ ID NO 1402
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1402
cacuguucug ugacuacuac a 21

<210> SEQ ID NO 1403
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1403
ccuucuucuc gaacuncaug u 21

<210> SEQ ID NO 1404
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1404
ccacccaugu gcuacaacua u 21

<210> SEQ ID NO 1405
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1405
cugcuacaac uauganaucc a 21

<210> SEQ ID NO 1406
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1406
cgagaucauc uucaacaaca a 21

<210> SEQ ID NO 1407
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1407
cacuguucug ugacuacuac a 21

<210> SEQ ID NO 1408
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1408
gacuguucug ugacuacuac a 21

<210> SEQ ID NO 1409
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1409
uggggaagug uuccunaacc a 21

<210> SEQ ID NO 1410
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 1410
ggacaucacc ugcagunuug a 21

<210> SEQ ID NO 1411
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1411
ugugggaacu ucgacnacau a 21

<210> SEQ ID NO 1412
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1412
gucuuugaug aggacaagau a 21

<210> SEQ ID NO 1413
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 1413
ggacgucauc uaccacacna a 21

<210> SEQ ID NO 1414
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1414
cugcuacaac uauganaucc a 21

<210> SEQ ID NO 1415
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 14
<223> OTHER INFORMATION: n = 2'-O-methylinosine-3'-phosphate

<400> SEQUENCE: 1415
gcaccuccuc uugncagaaa u 21

<210> SEQ ID NO 1416
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1416
acgagaucau cuucaacaac a 21

<210> SEQ ID NO 1417
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1417
cgagaucauc uucaacaaca a 21

<210> SEQ ID NO 1418
<211> LENGTH: 21

<212> TYPE: RNA
<213> ORGANISM: Artificial sequence
<220> FEATURE:
<223> OTHER INFORMATION: RNAi agent sense strand modified sequence

<400> SEQUENCE: 1418
gcaaggaaac cuacaacaac a 21

<210> SEQ ID NO 1419
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1419
gcaaggaaac cuacaacaac a 21

<210> SEQ ID NO 1420
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1420
gcugauuugc cugaacaaga a 21

<210> SEQ ID NO 1421
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 14
<223> OTHER INFORMATION: n = 2'-O-methyl-2-aminoadenosine-3'-phosphate

<400> SEQUENCE: 1421
gcugauuugc cugnacaaga a 21

<210> SEQ ID NO 1422
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1422
ggcugauuug ccugaacaag a 21

<210> SEQ ID NO 1423
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1423
ggaccagcau cuucaucaac a 21

<210> SEQ ID NO 1424
<211> LENGTH: 21
<212> TYPE: RNA
<213> ORGANISM: Artificial sequence
<220> FEATURE:

<223> OTHER INFORMATION: RNAi agent sense strand modified sequence
<220> FEATURE:
<221> NAME/KEY: modified_base
<222> LOCATION: 14
<223> OTHER INFORMATION: n = 2'-O-methyl-2-aminoadenosine-3'-phosphate

<400> SEQUENCE: 1424
cgagaucauc uucnacaaca a 21

<210> SEQ ID NO 1425
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1425
caucuuugau gaggacaaga u 21

<210> SEQ ID NO 1426
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1426
gcuuugauga ggacaagaug a 21

<210> SEQ ID NO 1427
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1427
gucucugcuc cuacaacuag a 21

<210> SEQ ID NO 1428
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1428
caaccucugc uucuacaacu a 21

<210> SEQ ID NO 1429
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 3
<223> OTHER INFORMATION: n = 2'-O-methyl-2-aminoadenosine-3'-phosphate

<400> SEQUENCE: 1429
cunuaaccag cacaacuucu a 21

<210> SEQ ID NO 1430
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1430
cuauaaccag cacaacuucu a 21

<210> SEQ ID NO 1431
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1431
gcuguucugc gacuacuaca a 21

<210> SEQ ID NO 1432
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1432
gcuguucugc gacuacuaca a 21

<210> SEQ ID NO 1433
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1433
gcuguucugc gacuacuaca a 21

<210> SEQ ID NO 1434
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1434
gcuguuuugc gacuacuaca a 21

<210> SEQ ID NO 1435
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1435
gcuguucugc gauuacuaca a 21

<210> SEQ ID NO 1436
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1436
gcuguucugc gacuauuaca a 21

<210> SEQ ID NO 1437
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1437
gcuguucugc gacuacuaca a 21

<210> SEQ ID NO 1438
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1438
gcugauuugc cugaacaaga a 21

<210> SEQ ID NO 1439
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1439
gcugauuugc cugaacaaga a 21

<210> SEQ ID NO 1440
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1440
ccugauuugc cugaacaaga a 21

<210> SEQ ID NO 1441
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1441
gcugauuugc cugaacaaga a 21

<210> SEQ ID NO 1442
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1442
gcuguucugc gacuacuaca a 21

<210> SEQ ID NO 1443
<211> LENGTH: 22
<212> TYPE: RNA
<213> ORGANISM: Artificial sequence
<220> FEATURE:
<223> OTHER INFORMATION: RNAi agent sense strand modified sequence

<400> SEQUENCE: 1443
gcugguucug cgacuacuac aa 22

<210> SEQ ID NO 1444
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 1444
gcguucugcg acuacuacaa 20

<210> SEQ ID NO 1445
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1445
gcuguucugc gacuacuaca a 21

<210> SEQ ID NO 1446
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1446
gagugguucg acgugnacuu a 21

<210> SEQ ID NO 1447
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1447
ggaccagcau cuucaucaac a 21

<210> SEQ ID NO 1448
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1448
gcugauuugc cugaacaaga a 21

<210> SEQ ID NO 1449
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2

<223> OTHER INFORMATION: n = 2'-O-methyl-2-aminoadenosine-3'-phosphate

<400> SEQUENCE: 1449
cnaggaaacc uacaacaaca u 21

<210> SEQ ID NO 1450
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1450
ggaaaccuac aacaacauca u 21

<210> SEQ ID NO 1451
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 1451
gcugcuacaa cuaccanauc a 21

<210> SEQ ID NO 1452
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 1452
gcuacaacua ccagaucang a 21

<210> SEQ ID NO 1453
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1453
cccacccauc ugcuacaacu a 21

<210> SEQ ID NO 1454
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 1454
gagauccgca uccagunuug a 21

<210> SEQ ID NO 1455
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1455
ccagagguga gcaucnaaca a 21

<210> SEQ ID NO 1456
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1456
cagcagggac ccuucaagau a 21

<210> SEQ ID NO 1457
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate
<220> FEATURE:
<221> NAME/KEY: modified_base
<222> LOCATION: 20
<223> OTHER INFORMATION: n = 2'-O-methylinosine-3'-phosphate

<400> SEQUENCE: 1457
cnagaugugc cucaacuacn a 21

<210> SEQ ID NO 1458
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate
<220> FEATURE:
<221> NAME/KEY: modified_base
<222> LOCATION: 18
<223> OTHER INFORMATION: n = 2'-O-methylinosine-3'-phosphate

<400> SEQUENCE: 1458
cnacgucacc aucuucanac a 21

<210> SEQ ID NO 1459
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate
<220> FEATURE:

<221> NAME/KEY: modified_base
<222> LOCATION: 19
<223> OTHER INFORMATION: n = 2'-O-methylinosine-3'-phosphate

<400> SEQUENCE: 1459
gnaccuacua cucgaacunc a 21

<210> SEQ ID NO 1460
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate
<220> FEATURE:
<221> NAME/KEY: modified_base
<222> LOCATION: 17
<223> OTHER INFORMATION: n = 2'-O-methylinosine-3'-phosphate

<400> SEQUENCE: 1460
cnuguggaac cacgaunaca a 21

<210> SEQ ID NO 1461
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 1461
aggcaagacc ucugcuucun u 21

<210> SEQ ID NO 1462
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 1462
gcagugccuu cacuguacun a 21

<210> SEQ ID NO 1463
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1463
gugggaacuu caacancauc a 21

<210> SEQ ID NO 1464
<211> LENGTH: 21

<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 1464
ccccaacauc aggaacancu u 21

<210> SEQ ID NO 1465
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1465
ccuacuacuc gaacuncaug u 21

<210> SEQ ID NO 1466
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 1466
gucaccugca guguugncuu a 21

<210> SEQ ID NO 1467
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1467
gcuggacaug accuguuaca a 21

<210> SEQ ID NO 1468
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 1468
gcagagcuac agcuucaacn a 21

<210> SEQ ID NO 1469
<211> LENGTH: 21
<212> TYPE: RNA
<213> ORGANISM: Artificial sequence
<220> FEATURE:

<223> OTHER INFORMATION: RNAi agent sense strand modified sequence

<400> SEQUENCE: 1469
agcagugccu ucacuguacu a 21

<210> SEQ ID NO 1470
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 1470
gacaucagga acagcuucna a 21

<210> SEQ ID NO 1471
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1471
ggcugauuug ccugaacaag a 21

<210> SEQ ID NO 1472
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 1472
ccaggacaac cacuuungug a 21

<210> SEQ ID NO 1473
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1473
ccacaaccag cacaacuucu a 21

<210> SEQ ID NO 1474
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1474
gacaaccacu uuggugacaa a 21

<210> SEQ ID NO 1475
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1475
accucugcuc cuacaacuag a 21

<210> SEQ ID NO 1476
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 1476
ggacgucauc uaccacacna a 21

<210> SEQ ID NO 1477
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1477
cugcuacaac uauganaucc a 21

<210> SEQ ID NO 1478
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1478
acgagaucau cuucaacaac a 21

<210> SEQ ID NO 1479
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1479
cgagaucauc uucaacaaca a 21

<210> SEQ ID NO 1480
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1480
gcugauuugc cugaacaaga a 21

<210> SEQ ID NO 1481
<211> LENGTH: 21
<212> TYPE: RNA

<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 14
<223> OTHER INFORMATION: n = 2'-O-methyl-2-aminoadenosine-3'-phosphate

<400> SEQUENCE: 1481
gcugauuugc cugnacaaga a 21

<210> SEQ ID NO 1482
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1482
ggcugauuug ccugaacaag a 21

<210> SEQ ID NO 1483
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate
<220> FEATURE:
<221> NAME/KEY: modified_base
<222> LOCATION: 19
<223> OTHER INFORMATION: n = 2'-O-methylinosine-3'-phosphate

<400> SEQUENCE: 1483
gnaguaugcu caguacugnu a 21

<210> SEQ ID NO 1484
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1484
acccaugugc uacaacuaug a 21

<210> SEQ ID NO 1485
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1485
ccauacagca guacaguuac a 21

<210> SEQ ID NO 1486
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1486
cugcuacaac uaugagaucc a 21

<210> SEQ ID NO 1487
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1487
cugcuacaac uauganaucc a 21

<210> SEQ ID NO 1488
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1488
ccuggaccaa gugguuugac a 21

<210> SEQ ID NO 1489
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 1489
ccuggaccaa gugguuunac a 21

<210> SEQ ID NO 1490
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1490
cgagaucauc uucaacaaca a 21

<210> SEQ ID NO 1491
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1491
gcuguucugc gacuacuaca a 21

<210> SEQ ID NO 1492
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1492
gcuguucugu gacuacuaca a 21

<210> SEQ ID NO 1493
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1493
accagaucau cuucaacaac a 21

<210> SEQ ID NO 1494
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1494
ggcucugugg uaacuucaac a 21

<210> SEQ ID NO 1495
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1495
gagcguggag aaugaaaagu a 21

<210> SEQ ID NO 1496
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1496
gggagaauga aaaguaugcu a 21

<210> SEQ ID NO 1497
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1497
cuucucgaac ugcauguaug a 21

<210> SEQ ID NO 1498
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1498
gcucgaacug cauguaugac a 21

<210> SEQ ID NO 1499
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1499
cucgaacugc auguaugaca a 21

<210> SEQ ID NO 1500
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1500
ccacuguucu gugacuacua a 21

<210> SEQ ID NO 1501
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1501
cacuguucug ugacuacuac a 21

<210> SEQ ID NO 1502
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1502
ccuucuucuc gaacuncaug u 21

<210> SEQ ID NO 1503
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1503
cagcuuccac uacaanaccu u 21

<210> SEQ ID NO 1504
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1504
cagcuuccac uacaagaccu u 21

<210> SEQ ID NO 1505
<211> LENGTH: 21
<212> TYPE: RNA

<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate
<220> FEATURE:
<221> NAME/KEY: modified_base
<222> LOCATION: 19
<223> OTHER INFORMATION: n = 2'-O-methylinosine-3'-phosphate

<400> SEQUENCE: 1505
gnaguaugcu cagcacugnu a 21

<210> SEQ ID NO 1506
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1506
gccuucuuca acaccuucaa a 21

<210> SEQ ID NO 1507
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1507
gccuucuuca acaucuucaa a 21

<210> SEQ ID NO 1508
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1508
gccuucuuca acacuuucaa a 21

<210> SEQ ID NO 1509
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1509
ccacccaugu gcuacaacua u 21

<210> SEQ ID NO 1510
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 1510
cugcuacaac uauganaucc a 21

<210> SEQ ID NO 1511
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1511
cgagaucauc uucaacaaca a 21

<210> SEQ ID NO 1512
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 14
<223> OTHER INFORMATION: n = 2'-O-methyl-2-aminoadenosine-3'-phosphate

<400> SEQUENCE: 1512
cgagaucauc uucnacaaca a 21

<210> SEQ ID NO 1513
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1513
gcugauuugc cugaacaaga a 21

<210> SEQ ID NO 1514
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 1514
gcuguucugc gacuacuaca a 21

<210> SEQ ID NO 1515
<211> LENGTH: 22
<212> TYPE: RNA
<213> ORGANISM: Artificial sequence
<220> FEATURE:
<223> OTHER INFORMATION: RNAi agent sense strand modified sequence

<400> SEQUENCE: 1515
gcugguucug cgacuacuac aa 22

<210> SEQ ID NO 1516
<211> LENGTH: 20
<212> TYPE: RNA
<213> ORGANISM: Artificial sequence
<220> FEATURE:
<223> OTHER INFORMATION: RNAi agent sense strand modified sequence

<400> SEQUENCE: 1516
gcguucugcg acuacuacaa 20

<210> SEQ ID NO 1517

<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1517
uuugauggcc uuggagcagg u 21

<210> SEQ ID NO 1518
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1518
aaucuugaug gccuuggagc a 21

<210> SEQ ID NO 1519
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1519
uuugaacucg gggcugaggu u 21

<210> SEQ ID NO 1520
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1520
ugaugcugca cugcuucugg g 21

<210> SEQ ID NO 1521
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1521
uuagucgcag aacagagggc a 21

<210> SEQ ID NO 1522
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1522
aguagucgca gaacagaggg c 21

<210> SEQ ID NO 1523
<211> LENGTH: 21

<212> TYPE: RNA
<213> ORGANISM: Artificial sequence
<220> FEATURE:
<223> OTHER INFORMATION: RNAi agent antisense strand underlying base sequence

<400> SEQUENCE: 1523
uuaguagucg cagaacagag g 21

<210> SEQ ID NO 1524
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1524
uguaguaguc gcagaacaga g 21

<210> SEQ ID NO 1525
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1525
uuguaguagu cgcagaacag c 21

<210> SEQ ID NO 1526
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1526
auaguuguag cagaugggug g 21

<210> SEQ ID NO 1527
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1527
uuccacgucg aaccacuuug c 21

<210> SEQ ID NO 1528
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1528
uaaguccacg ucgaaccacu c 21

<210> SEQ ID NO 1529
<211> LENGTH: 21
<212> TYPE: RNA

<213> ORGANISM: Artificial sequence
<220> FEATURE:
<223> OTHER INFORMATION: RNAi agent antisense strand underlying base sequence

<400> SEQUENCE: 1529
uggaagucca cgucgaacca c 21

<210> SEQ ID NO 1530
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1530
aaggucuugu aguggaagcu g 21

<210> SEQ ID NO 1531
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1531
uaccagugcu gagcauacuu c 21

<210> SEQ ID NO 1532
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1532
uuugaaggug uugaagaagg c 21

<210> SEQ ID NO 1533
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1533
agaugcuggu cuucuugucc c 21

<210> SEQ ID NO 1534
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1534
uguugaugaa gaugcugguc c 21

<210> SEQ ID NO 1535
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1535
uucuuguuca ggcaaaucag c                                              21

<210> SEQ ID NO 1536
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1536
auguuguugu agguuuccuu g                                              21

<210> SEQ ID NO 1537
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1537
augauguugu uguagguuuc c                                              21

<210> SEQ ID NO 1538
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1538
uugaugaaga ugcuggucuu c                                              21

<210> SEQ ID NO 1539
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1539
ugaucuggua guuguagcag c                                              21

<210> SEQ ID NO 1540
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1540
uccugaucug guaguuguag c                                              21

<210> SEQ ID NO 1541
<211> LENGTH: 21
<212> TYPE: RNA
<213> ORGANISM: Artificial sequence
<220> FEATURE:

<223> OTHER INFORMATION: RNAi agent antisense strand underlying base sequence

<400> SEQUENCE: 1541
uaguuguagc agaugggugg g 21

<210> SEQ ID NO 1542
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1542
ucaacacugg augcggaucu c 21

<210> SEQ ID NO 1543
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1543
uuguucgaug cucaccucug g 21

<210> SEQ ID NO 1544
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1544
uaucuugaag ggucccugcu g 21

<210> SEQ ID NO 1545
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1545
ucguaguuga ggcacaucuu g 21

<210> SEQ ID NO 1546
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1546
ucucguaguu gaggcacauc c 21

<210> SEQ ID NO 1547
<211> LENGTH: 21
<212> TYPE: RNA
<213> ORGANISM: Artificial sequence
<220> FEATURE:
<223> OTHER INFORMATION: RNAi agent antisense strand underlying base -continued

<400> SEQUENCE: 1547
uuucaggcag gucucgcugu c                                              21

<210> SEQ ID NO 1548
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1548
uucugaagau ggugacguug g                                              21

<210> SEQ ID NO 1549
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1549
ugucugaaga uggugacguu g                                              21

<210> SEQ ID NO 1550
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1550
uggaagucau cggccuggau g                                              21

<210> SEQ ID NO 1551
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1551
ugcaguucga guaguagguu c                                              21

<210> SEQ ID NO 1552
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1552
uuuggagcag guggucccug u                                              21

<210> SEQ ID NO 1553
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1553
ucuugauggc cuuggagcag g 21

<210> SEQ ID NO 1554
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1554
uugucaucgu gguuccacau g 21

<210> SEQ ID NO 1555
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1555
acagaagcag aggucuugcc u 21

<210> SEQ ID NO 1556
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1556
ucaguuggug cagucugugg a 21

<210> SEQ ID NO 1557
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1557
ucaguacagu gaaggcacug c 21

<210> SEQ ID NO 1558
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1558
ugcuguugaa guucccacag c 21

<210> SEQ ID NO 1559
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1559
ugaugcuguu gaaguuccca c                                              21

<210> SEQ ID NO 1560
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1560
uggucuugaa gguguugaag c                                              21

<210> SEQ ID NO 1561
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1561
aagcuguucc ugauguuggg g                                              21

<210> SEQ ID NO 1562
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1562
acaugcaguu cgaguaguag g                                              21

<210> SEQ ID NO 1563
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1563
uaagccaaca cugcagguga c                                              21

<210> SEQ ID NO 1564
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1564
uuguaacagg ucauguccag c                                              21

<210> SEQ ID NO 1565
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 1565
ucguugaagc uguagcucug c 21

<210> SEQ ID NO 1566
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1566
uggaucucau aguuguagca g 21

<210> SEQ ID NO 1567
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1567
ugucaaacca cuugguccag g 21

<210> SEQ ID NO 1568
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1568
uuguuguuga agaugaucuc g 21

<210> SEQ ID NO 1569
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1569
uaguacagug aaggcacugc u 21

<210> SEQ ID NO 1570
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1570
uucgaagcug uuccugaugu c 21

<210> SEQ ID NO 1571
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1571
ucuuguucag gcaaaucagc c 21

<210> SEQ ID NO 1572
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1572
ucaccaaagu gguuguccug g 21

<210> SEQ ID NO 1573
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1573
uagcagaggu uguucugguu g 21

<210> SEQ ID NO 1574
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1574
uagauugugc ugguuguagc g 21

<210> SEQ ID NO 1575
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1575
uagaaguugu gcugguugug g 21

<210> SEQ ID NO 1576
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1576
uuugucacca aagugguugu c 21

<210> SEQ ID NO 1577
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1577
uagagguugu guugguugua g 21

<210> SEQ ID NO 1578
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1578
ucuaguugua ggagcagagg u 21

<210> SEQ ID NO 1579
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1579
uuguaguagu cacagaacag c 21

<210> SEQ ID NO 1580
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1580
ucauaguugu agcacauggg u 21

<210> SEQ ID NO 1581
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1581
uguuguugaa gaugaucugg u 21

<210> SEQ ID NO 1582
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1582
uguugaaguu accacagagc c 21

<210> SEQ ID NO 1583
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1583
uacuuuucau ucuccacgcu c 21

<210> SEQ ID NO 1584
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 1584
uagcauacuu uucauucucc c 21

<210> SEQ ID NO 1585
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 1585
ucauacaugc aguucgagaa g 21

<210> SEQ ID NO 1586
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 1586
ugucauacau gcaguucgag c 21

<210> SEQ ID NO 1587
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 1587
uugucauaca ugcaguucga g 21

<210> SEQ ID NO 1588
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 1588
uuaguaguca cagaacagug g 21

<210> SEQ ID NO 1589
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 1589
uguaguaguc acagaacagu g 21

<210> SEQ ID NO 1590
<211> LENGTH: 21
<212> TYPE: RNA
<213> ORGANISM: Artificial sequence
<220> FEATURE:
<223> OTHER INFORMATION: RNAi agent antisense strand underlying base sequence
<220> FEATURE:
<221> NAME/KEY: modified_base
<222> LOCATION: 12
<223> OTHER INFORMATION: n = inosine (hypoxanthine)

<400> SEQUENCE: 1590
uuguaguagu cncagaacag c 21

<210> SEQ ID NO 1591
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1591
acaugcaguu cgagaagaag g 21

<210> SEQ ID NO 1592
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1592
auaguuguag cacaugggug g 21

<210> SEQ ID NO 1593
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1593
uguaguaguc acagaacagu c 21

<210> SEQ ID NO 1594
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1594
ugguucagga acacuucccc a 21

<210> SEQ ID NO 1595
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1595
ucaacacugc aggugauguc c 21

<210> SEQ ID NO 1596
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1596
uaugucgucg aaguucccac a 21

<210> SEQ ID NO 1597
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1597
uaucuugucc ucaucaaaga c 21

<210> SEQ ID NO 1598
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1598
uucguguggu agaugacguc c 21

<210> SEQ ID NO 1599
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1599
auuucugcca agaggaggug c 21

<210> SEQ ID NO 1600
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1600
uguuguugaa gaugaucucg u 21

<210> SEQ ID NO 1601
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1601
uguuguugua gguuuccuug c 21

<210> SEQ ID NO 1602
<211> LENGTH: 21
<212> TYPE: RNA
<213> ORGANISM: Artificial sequence
<220> FEATURE:
<223> OTHER INFORMATION: RNAi agent antisense strand underlying base sequence
<220> FEATURE:
<221> NAME/KEY: modified_base
<222> LOCATION: 4
<223> OTHER INFORMATION: n = inosine (hypoxanthine)

<400> SEQUENCE: 1602
uugnuguuga agaugaucuc g 21

<210> SEQ ID NO 1603
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1603
aucuuguccu caucaaagau g 21

<210> SEQ ID NO 1604
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1604
ucaucuuguc cucaucaaag c 21

<210> SEQ ID NO 1605
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1605
ucuaguugua ggagcagaga c 21

<210> SEQ ID NO 1606
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1606
uaguuguaga agcagagguu g 21

<210> SEQ ID NO 1607
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1607
uagaaguugu gcugguuaua g 21

<210> SEQ ID NO 1608
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 1608
uucuuguuca ggcaaaucag g 21

<210> SEQ ID NO 1609
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 13
<223> OTHER INFORMATION: n = inosine (hypoxanthine)

<400> SEQUENCE: 1609
accugcucca agnccaucaa a 21

<210> SEQ ID NO 1610
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1610
ugcuccaagg ccaucaagau u 21

<210> SEQ ID NO 1611
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1611
aaccucagcu ccgaguucaa a 21

<210> SEQ ID NO 1612
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 16
<223> OTHER INFORMATION: n = inosine (hypoxanthine)

<400> SEQUENCE: 1612
cccagaagca gugcancauc a 21

<210> SEQ ID NO 1613

```
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 16
<223> OTHER INFORMATION: n = inosine (hypoxanthine)

<400> SEQUENCE: 1613

ugcccucugu ucugcnacua a                                              21


<210> SEQ ID NO 1614
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 13
<223> OTHER INFORMATION: n = inosine (hypoxanthine)

<400> SEQUENCE: 1614

gcccucuguu cuncgacuac u                                              21


<210> SEQ ID NO 1615
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1615

ccucuguucu gcgacuacua a                                              21


<210> SEQ ID NO 1616
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1616

cucuguucug cgacuacuac a                                              21


<210> SEQ ID NO 1617
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1617

gcuguucugc gacuacuaca a                                              21


<210> SEQ ID NO 1618
<211> LENGTH: 21
<212> TYPE: RNA
<213> ORGANISM: Artificial sequence
<220> FEATURE:
<223> OTHER INFORMATION: RNAi agent sense strand underlying base
      sequence
```

<400> SEQUENCE: 1618
ccacccaucu gcuacaacua u 21

<210> SEQ ID NO 1619
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 16
<223> OTHER INFORMATION: n = inosine (hypoxanthine)

<400> SEQUENCE: 1619
gcaaaguggu ucgacnugga a 21

<210> SEQ ID NO 1620
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 16
<223> OTHER INFORMATION: n = inosine (hypoxanthine)

<400> SEQUENCE: 1620
gagugguucg acgugnacuu a 21

<210> SEQ ID NO 1621
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 14
<223> OTHER INFORMATION: n = inosine (hypoxanthine)

<400> SEQUENCE: 1621
gugguucgac gugnacuucc a 21

<210> SEQ ID NO 1622
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1622
gugguucgac guggacuucc a 21

<210> SEQ ID NO 1623
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 16
<223> OTHER INFORMATION: n = inosine (hypoxanthine)

<400> SEQUENCE: 1623
cagcuuccac uacaanaccu u 21

<210> SEQ ID NO 1624
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1624
cagcuuccac uacaagaccu u 21

<210> SEQ ID NO 1625
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 2
<223> OTHER INFORMATION: n = 2-aminoadenosine (2-aminoadenine)
<220> FEATURE:
<221> NAME/KEY: modified_base
<222> LOCATION: 19
<223> OTHER INFORMATION: n = inosine (hypoxanthine)

<400> SEQUENCE: 1625
gnaguaugcu cagcacugnu a 21

<210> SEQ ID NO 1626
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 2
<223> OTHER INFORMATION: n = 2-aminoadenosine (2-aminoadenine)
<220> FEATURE:
<221> NAME/KEY: modified_base
<222> LOCATION: 19
<223> OTHER INFORMATION: n = inosine (hypoxanthine)

<400> SEQUENCE: 1626
gnaguaugcu caguacugnu a 21

<210> SEQ ID NO 1627
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1627
gccuucuuca acaccuucaa a 21

<210> SEQ ID NO 1628
<211> LENGTH: 21
<212> TYPE: RNA

<213> ORGANISM: Artificial sequence
<220> FEATURE:
<223> OTHER INFORMATION: RNAi agent sense strand underlying base
sequence

<400> SEQUENCE: 1628
gccuucuuca acaucuucaa a 21

<210> SEQ ID NO 1629
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 1629
gccuucuuca acacuuucaa a 21

<210> SEQ ID NO 1630
<211> LENGTH: 21
<212> TYPE: RNA
<213> ORGANISM: Artificial sequence
<220> FEATURE:
<223> OTHER INFORMATION: RNAi agent sense strand underlying base
sequence
<220> FEATURE:
<221> NAME/KEY: modified_base
<222> LOCATION: 16
<223> OTHER INFORMATION: n = inosine (hypoxanthine)

<400> SEQUENCE: 1630
gggacaagaa gaccancauc u 21

<210> SEQ ID NO 1631
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 1631
ggaccagcau cuucaucaac a 21

<210> SEQ ID NO 1632
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 1632
gcugauuugc cugaacaaga a 21

<210> SEQ ID NO 1633
<211> LENGTH: 21
<212> TYPE: RNA
<213> ORGANISM: Artificial sequence
<220> FEATURE:
<223> OTHER INFORMATION: RNAi agent sense strand underlying base
sequence
<220> FEATURE:
<221> NAME/KEY: modified_base
<222> LOCATION: 2
<223> OTHER INFORMATION: n = 2-aminoadenosine (2-aminoadenine)

<400> SEQUENCE: 1633
cnaggaaacc uacaacaaca u 21

<210> SEQ ID NO 1634
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1634
ggaaaccuac aacaacauca u 21

<210> SEQ ID NO 1635
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 2
<223> OTHER INFORMATION: n = 2-aminoadenosine (2-aminoadenine)

<400> SEQUENCE: 1635
gnagaccagc aucuucauca a 21

<210> SEQ ID NO 1636
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 17
<223> OTHER INFORMATION: n = inosine (hypoxanthine)

<400> SEQUENCE: 1636
gcugcuacaa cuaccanauc a 21

<210> SEQ ID NO 1637
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 19
<223> OTHER INFORMATION: n = inosine (hypoxanthine)

<400> SEQUENCE: 1637
gcuacaacua ccagaucang a 21

<210> SEQ ID NO 1638
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1638
cccacccauc ugcuacaacu a 21

<210> SEQ ID NO 1639
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 17
<223> OTHER INFORMATION: n = inosine (hypoxanthine)

<400> SEQUENCE: 1639
gagauccgca uccagunuug a    21

<210> SEQ ID NO 1640
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 16
<223> OTHER INFORMATION: n = inosine (hypoxanthine)

<400> SEQUENCE: 1640
ccagagguga gcaucnaaca a    21

<210> SEQ ID NO 1641
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1641
cagcagggac ccuucaagau a    21

<210> SEQ ID NO 1642
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 2
<223> OTHER INFORMATION: n = 2-aminoadenosine (2-aminoadenine)
<220> FEATURE:
<221> NAME/KEY: modified_base
<222> LOCATION: 20
<223> OTHER INFORMATION: n = inosine (hypoxanthine)

<400> SEQUENCE: 1642
cnagaugugc cucaacuacn a    21

<210> SEQ ID NO 1643
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 18
<223> OTHER INFORMATION: n = inosine (hypoxanthine)

<400> SEQUENCE: 1643
ggaugugccu caacuacnag a 21

<210> SEQ ID NO 1644
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1644
gacagcgaga ccugcuugaa a 21

<210> SEQ ID NO 1645
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1645
ccaacgucac caucuucaga a 21

<210> SEQ ID NO 1646
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 2
<223> OTHER INFORMATION: n = 2-aminoadenosine (2-aminoadenine)
<220> FEATURE:
<221> NAME/KEY: modified_base
<222> LOCATION: 18
<223> OTHER INFORMATION: n = inosine (hypoxanthine)

<400> SEQUENCE: 1646
cnacgucacc aucuucanac a 21

<210> SEQ ID NO 1647
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1647
cauccaggcc gaugacuucc a 21

<210> SEQ ID NO 1648
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 2
<223> OTHER INFORMATION: n = 2-aminoadenosine (2-aminoadenine)

<220> FEATURE:
<221> NAME/KEY: modified_base
<222> LOCATION: 19
<223> OTHER INFORMATION: n = inosine (hypoxanthine)

<400> SEQUENCE: 1648
gnaccuacua cucgaacunc a 21

<210> SEQ ID NO 1649
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1649
acagggacca ccugcuucaa a 21

<210> SEQ ID NO 1650
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1650
ccugcuccaa ggcuaucaag a 21

<210> SEQ ID NO 1651
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 2
<223> OTHER INFORMATION: n = 2-aminoadenosine (2-aminoadenine)
<220> FEATURE:
<221> NAME/KEY: modified_base
<222> LOCATION: 17
<223> OTHER INFORMATION: n = inosine (hypoxanthine)

<400> SEQUENCE: 1651
cnuguggaac cacgaunaca a 21

<210> SEQ ID NO 1652
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 20
<223> OTHER INFORMATION: n = inosine (hypoxanthine)

<400> SEQUENCE: 1652
aggcaagacc ucugcuucun u 21

<210> SEQ ID NO 1653
<211> LENGTH: 21
<212> TYPE: RNA
<213> ORGANISM: Artificial sequence
<220> FEATURE:

<223> OTHER INFORMATION: RNAi agent sense strand underlying base
      sequence
<220> FEATURE:
<221> NAME/KEY: modified_base
<222> LOCATION: 20
<223> OTHER INFORMATION: n = inosine (hypoxanthine)

<400> SEQUENCE: 1653
uccacagacu gcaccaacun a 21

<210> SEQ ID NO 1654
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 20
<223> OTHER INFORMATION: n = inosine (hypoxanthine)

<400> SEQUENCE: 1654
gcagugccuu cacuguacun a 21

<210> SEQ ID NO 1655
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 19
<223> OTHER INFORMATION: n = inosine (hypoxanthine)

<400> SEQUENCE: 1655
gcugugggaa cuucaacanc a 21

<210> SEQ ID NO 1656
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 16
<223> OTHER INFORMATION: n = inosine (hypoxanthine)

<400> SEQUENCE: 1656
gugggaacuu caacancauc a 21

<210> SEQ ID NO 1657
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 17
<223> OTHER INFORMATION: n = inosine (hypoxanthine)

<400> SEQUENCE: 1657
gcuucaacac cuucaanacc a 21

<210> SEQ ID NO 1658
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 18
<223> OTHER INFORMATION: n = inosine (hypoxanthine)

<400> SEQUENCE: 1658
ccccaacauc aggaacancu u 21

<210> SEQ ID NO 1659
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 16
<223> OTHER INFORMATION: n = inosine (hypoxanthine)

<400> SEQUENCE: 1659
ccuacuacuc gaacuncaug u 21

<210> SEQ ID NO 1660
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 17
<223> OTHER INFORMATION: n = inosine (hypoxanthine)

<400> SEQUENCE: 1660
gucaccugca guguugncuu a 21

<210> SEQ ID NO 1661
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1661
gcuggacaug accuguuaca a 21

<210> SEQ ID NO 1662
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 20
<223> OTHER INFORMATION: n = inosine (hypoxanthine)

<400> SEQUENCE: 1662
gcagagcuac agcuucaacn a 21

<210> SEQ ID NO 1663
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1663
cugcuacaac uaugagaucc a 21

<210> SEQ ID NO 1664
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 16
<223> OTHER INFORMATION: n = inosine (hypoxanthine)

<400> SEQUENCE: 1664
cugcuacaac uauganaucc a 21

<210> SEQ ID NO 1665
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1665
ccuggaccaa gugguuugac a 21

<210> SEQ ID NO 1666
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 18
<223> OTHER INFORMATION: n = inosine (hypoxanthine)

<400> SEQUENCE: 1666
ccuggaccaa gugguuunac a 21

<210> SEQ ID NO 1667
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1667
cgagaucauc uucaacaaca a 21

<210> SEQ ID NO 1668
<211> LENGTH: 21
<212> TYPE: RNA

<213> ORGANISM: Artificial sequence
<220> FEATURE:
<223> OTHER INFORMATION: RNAi agent sense strand underlying base
sequence

<400> SEQUENCE: 1668
agcagugccu ucacuguacu a 21

<210> SEQ ID NO 1669
<211> LENGTH: 21
<212> TYPE: RNA
<213> ORGANISM: Artificial sequence
<220> FEATURE:
<223> OTHER INFORMATION: RNAi agent sense strand underlying base
sequence
<220> FEATURE:
<221> NAME/KEY: modified_base
<222> LOCATION: 19
<223> OTHER INFORMATION: n = inosine (hypoxanthine)

<400> SEQUENCE: 1669
gacaucagga acagcuucna a 21

<210> SEQ ID NO 1670
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 1670
ggcugauuug ccugaacaag a 21

<210> SEQ ID NO 1671
<211> LENGTH: 21
<212> TYPE: RNA
<213> ORGANISM: Artificial sequence
<220> FEATURE:
<223> OTHER INFORMATION: RNAi agent sense strand underlying base
sequence
<220> FEATURE:
<221> NAME/KEY: modified_base
<222> LOCATION: 17
<223> OTHER INFORMATION: n = inosine (hypoxanthine)

<400> SEQUENCE: 1671
ccaggacaac cacuuungug a 21

<210> SEQ ID NO 1672
<211> LENGTH: 21
<212> TYPE: RNA
<213> ORGANISM: Artificial sequence
<220> FEATURE:
<223> OTHER INFORMATION: RNAi agent sense strand underlying base
sequence
<220> FEATURE:
<221> NAME/KEY: modified_base
<222> LOCATION: 18
<223> OTHER INFORMATION: n = inosine (hypoxanthine)

<400> SEQUENCE: 1672
caaccagaac aaccucuncu a 21

<210> SEQ ID NO 1673
<211> LENGTH: 21
<212> TYPE: RNA
<213> ORGANISM: Artificial sequence
<220> FEATURE:

<223> OTHER INFORMATION: RNAi agent sense strand underlying base
      sequence

<400> SEQUENCE: 1673
cgcuacaacc agcacaaucu a                                               21

<210> SEQ ID NO 1674
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1674
ccacaaccag cacaacuucu a                                               21

<210> SEQ ID NO 1675
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1675
gacaaccacu uuggugacaa a                                               21

<210> SEQ ID NO 1676
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1676
cuacaaccaa cacaacuucu a                                               21

<210> SEQ ID NO 1677
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1677
accucugcuc cuacaacuag a                                               21

<210> SEQ ID NO 1678
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1678
gcuguucugu gacuacuaca a                                               21

<210> SEQ ID NO 1679
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1679
accagaucau cuucaacaac a 21

<210> SEQ ID NO 1680
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1680
ggcucugugg uaacuucaac a 21

<210> SEQ ID NO 1681
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1681
gagcguggag aaugaaaagu a 21

<210> SEQ ID NO 1682
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1682
gggagaauga aaaguaugcu a 21

<210> SEQ ID NO 1683
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1683
cuucucgaac ugcauguaug a 21

<210> SEQ ID NO 1684
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1684
gcucgaacug cauguaugac a 21

<210> SEQ ID NO 1685
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1685
cucgaacugc auguaugaca a 21

<210> SEQ ID NO 1686
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1686
ccacuguucu gugacuacua a 21

<210> SEQ ID NO 1687
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1687
cacuguucug ugacuacuac a 21

<210> SEQ ID NO 1688
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 16
<223> OTHER INFORMATION: n = inosine (hypoxanthine)

<400> SEQUENCE: 1688
ccuucuucuc gaacuncaug u 21

<210> SEQ ID NO 1689
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1689
ccacccaugu gcuacaacua u 21

<210> SEQ ID NO 1690
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1690
gacuguucug ugacuacuac a 21

<210> SEQ ID NO 1691
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 16
<223> OTHER INFORMATION: n = inosine (hypoxanthine)

<400> SEQUENCE: 1691
uggggaagug uuccunaacc a 21

<210> SEQ ID NO 1692
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 17
<223> OTHER INFORMATION: n = inosine (hypoxanthine)

<400> SEQUENCE: 1692
ggacaucacc ugcagunuug a 21

<210> SEQ ID NO 1693
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 16
<223> OTHER INFORMATION: n = inosine (hypoxanthine)

<400> SEQUENCE: 1693
ugugggaacu ucgacnacau a 21

<210> SEQ ID NO 1694
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 1694
gucuuugaug aggacaagau a 21

<210> SEQ ID NO 1695
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 19
<223> OTHER INFORMATION: n = inosine (hypoxanthine)

<400> SEQUENCE: 1695
ggacgucauc uaccacacna a 21

<210> SEQ ID NO 1696
<211> LENGTH: 21

<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 14
<223> OTHER INFORMATION: n = inosine (hypoxanthine)

<400> SEQUENCE: 1696
gcaccuccuc uugncagaaa u 21

<210> SEQ ID NO 1697
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1697
acgagaucau cuucaacaac a 21

<210> SEQ ID NO 1698
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1698
gcaaggaaac cuacaacaac a 21

<210> SEQ ID NO 1699
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 14
<223> OTHER INFORMATION: n = 2-aminoadenosine (2-aminoadenine)

<400> SEQUENCE: 1699
gcugauuugc cugnacaaga a 21

<210> SEQ ID NO 1700
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 14
<223> OTHER INFORMATION: n = 2-aminoadenosine (2-aminoadenine)

<400> SEQUENCE: 1700
cgagaucauc uucnacaaca a 21

<210> SEQ ID NO 1701
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 1701
caucuuugau gaggacaaga u 21

<210> SEQ ID NO 1702
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 1702
gcuuugauga ggacaagaug a 21

<210> SEQ ID NO 1703
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 1703
gucucugcuc cuacaacuag a 21

<210> SEQ ID NO 1704
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 1704
caaccucugc uucuacaacu a 21

<210> SEQ ID NO 1705
<211> LENGTH: 21
<212> TYPE: RNA
<213> ORGANISM: Artificial sequence
<220> FEATURE:
<223> OTHER INFORMATION: RNAi agent sense strand underlying base
sequence
<220> FEATURE:
<221> NAME/KEY: modified_base
<222> LOCATION: 3
<223> OTHER INFORMATION: n = 2-aminoadenosine (2-aminoadenine)

<400> SEQUENCE: 1705
cunuaaccag cacaacuucu a 21

<210> SEQ ID NO 1706
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 1706
cuauaaccag cacaacuucu a 21

<210> SEQ ID NO 1707

<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1707
gcuguuuugc gacuacuaca a 21

<210> SEQ ID NO 1708
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1708
gcuguucugc gauuacuaca a 21

<210> SEQ ID NO 1709
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1709
gcuguucugc gacuauuaca a 21

<210> SEQ ID NO 1710
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 1710
ccugauuugc cugaacaaga a 21

<210> SEQ ID NO 1711
<211> LENGTH: 22
<212> TYPE: RNA
<213> ORGANISM: Artificial sequence
<220> FEATURE:
<223> OTHER INFORMATION: RNAi agent sense strand underlying base sequence

<400> SEQUENCE: 1711
gcugguucug cgacuacuac aa 22

<210> SEQ ID NO 1712
<211> LENGTH: 20
<212> TYPE: RNA
<213> ORGANISM: Artificial sequence
<220> FEATURE:
<223> OTHER INFORMATION: RNAi agent sense strand underlying base sequence

<400> SEQUENCE: 1712
gcguucugcg acuacuacaa 20

<210> SEQ ID NO 1713
<211> LENGTH: 21

<212> TYPE: RNA
<213> ORGANISM: Artificial sequence
<220> FEATURE:
<223> OTHER INFORMATION: Mouse-specific antisense strand modified sequence

<400> SEQUENCE: 1713
uguaacugua cugcuguaug g 21

<210> SEQ ID NO 1714
<211> LENGTH: 21
<212> TYPE: RNA
<213> ORGANISM: Artificial sequence
<220> FEATURE:
<223> OTHER INFORMATION: Mouse-specific sense strand modified sequence

<400> SEQUENCE: 1714
ccauacagca guacaguuac a 21

<210> SEQ ID NO 1715
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1715
uguuguugaa gaugaucugg u 21

<210> SEQ ID NO 1716
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1716
uggaucucau aguuguagca g 21

<210> SEQ ID NO 1717
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 1717
uuguuguuga agaugaucuc g 21

<210> SEQ ID NO 1718
<211> LENGTH: 21
<212> TYPE: RNA
<213> ORGANISM: Artificial sequence
<220> FEATURE:
<223> OTHER INFORMATION: Mouse-specific sense strand underlying base sequence -continued

```
<400> SEQUENCE: 1718

uuguuguuga agaugaucuc g                                              21


<210> SEQ ID NO 1719
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 1719

Arg Gly Asp Leu Ala Xaa Leu Xaa Xaa Leu
1               5                   10
```